(12) United States Patent
Taniguchi et al.

(10) Patent No.: US 8,513,251 B2
(45) Date of Patent: *Aug. 20, 2013

(54) PYRIDAZINONE COMPOUNDS

(75) Inventors: Takahiko Taniguchi, Cambridge (GB); Jun Kunitomo, Kanagawa (JP)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/543,296

(22) Filed: Jul. 6, 2012

(65) Prior Publication Data

US 2012/0277430 A1    Nov. 1, 2012

Related U.S. Application Data

(62) Division of application No. 13/148,172, filed as application No. PCT/US2010/000307 on Feb. 4, 2010.

(60) Provisional application No. 61/202,207, filed on Feb. 5, 2009, provisional application No. 61/213,927, filed on Jul. 30, 2009.

(51) Int. Cl.
*A61K 31/50* (2006.01)
*A61K 31/501* (2006.01)
*C07D 401/00* (2006.01)

(52) U.S. Cl.
USPC ................... 514/252.05; 544/238

(58) Field of Classification Search
USPC ............ 544/224, 238; 514/252.01, 252.05
See application file for complete search history.

(56) References Cited

U.S. PATENT DOCUMENTS

| | | | |
|---|---|---|---|
| 5,059,599 | A | 10/1991 | Mouzin et al. |
| 5,877,175 | A | 3/1999 | Sargent et al. |
| 6,469,003 | B1 | 10/2002 | Gotoh et al. |
| 2004/0009988 | A1 | 1/2004 | Dodic |
| 2007/0060606 | A1 | 3/2007 | Robertson et al. |
| 2008/0207902 | A1 | 8/2008 | Kohno et al. |
| 2009/0163545 | A1 | 6/2009 | Goldfarb |
| 2010/0197651 | A1 | 8/2010 | Taniguchi et al. |
| 2012/0028951 | A1 | 2/2012 | Taniguchi et al. |
| 2012/0277204 | A1 | 11/2012 | Taniguchi et al. |
| 2012/0277431 | A1 | 11/2012 | Taniguchi et al. |

FOREIGN PATENT DOCUMENTS

| | | |
|---|---|---|
| WO | 2006/072828 | 7/2006 |
| WO | 2008/001182 | 1/2008 |
| WO | 2008/004117 | 1/2008 |
| WO | 2010/057121 | 5/2010 |
| WO | 2010/057126 | 5/2010 |
| WO | 2010/063610 | 6/2010 |

OTHER PUBLICATIONS

International Search Report and Written Opinion issued in PCT/US2010/000307.

Excerpt of Search Results of Commercial Database: 478077-64-4; 478077-63-3; 478077-62-2; 478077-61-1;478077-60-0; 478077-59-7; 478063-64-8;478063-63-7; 478063-62-6; 478063-61-5; 478063-60-4; 478063-59-1; 478063-58-0; 361343-72-8; 318498-11-2;318498-08-7; 318498-04-3; 318498-03-2; 318498-02-1; 318498-01-0; 318497-96-0; 318497-95-9; 318497-94-8; 1022754-82-0; 318498-12-3; 318498-10-1; 318498-09-8; 318498-07-6; 318498-06-5; 318498-05-4; 318497-99-3; 318497-98-2; 318497-91-1; 263252-38-6.

X. Zou et al., "Synthesis of Pyridazinone-Substituted 1,3,4-Thiadiazoles, -1,3,4-Oxadiazoles and -1,2,4-Triazoles", Journal of Heterocyclic Chemistry, vol. 38, No. 4, pp. 993-996, Jul.-Aug. 2001.
M. H. Mohamed et al., "Studies with Functionally Substituted N-Alkylazoles: The Reactivity of 1-(3,5-Dimethylpyrazol-1-yl)-Acetone Towards Electrophilic Reagents", Journal of Heterocyclic Chemistry, vol. 38, No. 3, pp. 685-689, May-Jun. 2001.
Weber et al., Psychopharmacology, 203: 723-735 (2009).
Schmidt et al., J. Pharmacol. & Experimen. Therap., vol. 325, No. 2, (2008).
Sotty et al., J. Neurochem., 109: 766-775 (2009).
Sharma et al., Indian J. Het. Chem., 16(1): 47-52 (2006).
Zou et al. (I), Chinese J. Chem., 23(8): 1120-1122 (2005).
Qi et al., Youji Huaxue, 24(6): 645-649 (2004).
Collier, Science of Synthesis, 13: 349-414 (2004).
Zou et al. (II), J. Chem. Res., Synopses, (5): 228-230 (2002).
Zou et al. (III), J. Agricult. & Food Chem., 50(13): 3757-3760 (2002).
Zou et al. (IV), J. Agricul. & Food Chem., 50(6): 1451-1454 (2002).
Zou et al. (V), J. Het. Chem., 38(4): 993-996 (2001).
Mohamed et al., J. Het. Chem., 38(3): 685-689 (2001).
Zou et al. (VI), Chinese Chemical Letters, 12(5): 419-420 (2001).
Plescia et al., J. Het. Chem., 18(2), 333-334 (1981).

(Continued)

*Primary Examiner* — Paul V. Ward
(74) *Attorney, Agent, or Firm* — Wenderoth, Lind & Ponack, L.L.P.

(57) ABSTRACT

The present invention provides a compound which has the effect of PDE inhibition, and which is useful as a medicament for preventing or treating schizophrenia or so on. A compound of formula ($I_0$), wherein R1 represents a substituent; R2 represents a hydrogen atom, or a substituent; R3 represents a hydrogen atom, or a substituent; Ring A represents an aromatic ring which can be substituted, and Ring B represents a 5-membered heteroaromatic ring which can be substituted, or a salt thereof.

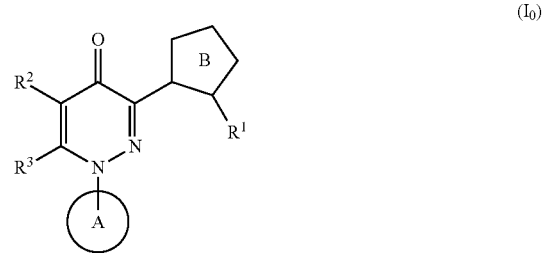

($I_0$)

1 Claim, 3 Drawing Sheets

(56) References Cited

OTHER PUBLICATIONS

Costa Rican Opposition dated Feb. 15, 2012 in corresponding Costa Rican Application No. 2011-0440, with English translation.
Halene et al., "PDE inhibitors in psychiatry—future options for dementia, depression and schizophrenia?", *Drug Discovery Today*, vol. 12, Nos. 19/20, pp. 870-878 (Oct. 2007) (USA).
Paris et al , "Inhibition of Alzheimer's β-Amyloid Induced Vasoactivity and Proinflammatory Response in Microglia by a cGMP-Dependent Mechanism", *Experimental Neurology*, vol. 157, Issue 1, pp. 211-221 (May 1999) (USA).
Laddha et al., "A new therapeutic approach in Parkinson's disease: Some novel quinazoline derivatives as dual selective phosphodiesterase 1 inhibitors and anti-inflammatory agents", *Bioorganic & Medicinal Chemistry*, vol. 17, pp. 6796-6802 (1999) (USA).
Snyder, "The adipocyte cGMP-inhibited cyclic nucleotide phosphodiesterase (PDE3B) as a target for lipolytic and thermogenic agents for the treatment of obesity", *Emerging Therapeutic Targets*, vol. 3(4), pp. 587-599 (1999) (UK).

PYRIDAZINONE COMPOUNDS

This is a divisional of Ser. No. 13/148,172, filed Oct. 20, 2011, which is a U.S. national stage of International Application No. PCT/US2010/000307 filed Feb. 4, 2010, which claims the benefit of U.S. provisional application Ser. No. 61/202,207 filed Feb. 5, 2009 and Ser. No. 61/213,927 filed Jul. 30, 2009.

TECHNICAL FIELD

The present invention relates to pyridazinone compounds.

BACKGROUND OF THE INVENTION

Phosphodiesterases (PDEs) are a superfamily of enzymes encoded by 21 genes and subdivided into 11 distinct families according to structural and functional properties. These enzymes metabolically inactivate the ubiquitous intracellular second messengers, cyclic adenosine monophosphate (cAMP) and cyclic guanosine monophosphate (cGMP); PDEs selectively catalyze the hydrolysis of the 3'-ester bond, forming the inactive 5'-monophosphate. On the basis of substrate specificity, the PDE families can be further classified into three groups: i) the cAMP-PDEs (PDE4, PDE7, PDE8), ii) the cGMP-PDEs (PDE5, PDE6 and PDE9), and iii) the dual-substrate PDEs (PDE1, PDE2, PDE3, PDE10 and PDE11).

The cAMP and cGMP are involved in the regulation of virtually every physiological process such as pro-inflammatory mediator production and action, ion channel function, muscle relaxation, learning and memory formation, differentiation, apoptosis; lipogenesis, glycogenolysis and gluconeogenesis. Especially, in neurons, these second messengers have important role in the regulation of synaptic transmission as well as in neuronal differentiation and survival (Nat. Rev. Drug Discov. 2006, vol. 5: 660-670). Regulation of these processes by cAMP and cGMP are accompanied by activation of protein kinase A (PKA) and protein kinase G (PKG), which in turn phosphorylate a variety of substrates, including transcription factors, ion channels and receptors that regulate a variety of physiological processes. Intracellular cAMP and cGMP concentrations seem to be temporally, spatially, and functionally compartmentalized by regulation of adenyl and guanyl cyclases in response to extracellular signaling and their degradation by PDEs (Circ. Res. 2007, vol. 100(7): 950-966). PDEs provide the only means of degrading the cyclic nucleotides cAMP and cGMP in cells, thus PDEs play an essential role in cyclic nucleotide signaling. Thereby, PDEs could be promising targets for various therapeutic drugs.

Phosphodiesterase 10A (PDE10A) was discovered in 1999 by three independent groups (Proc. Natl. Acad. Sci. USA 1999, vol. 96: 8991-8996, J. Biol. Chem. 1999, vol. 274: 18438-18445, Gene 1999, vol. 234: 109-117). Expression studies have shown that PDE10A has the most restricted distribution within the all known PDE families; the PDE10A mRNA is highly expressed only in brain and testes (Eur. J. Biochem. 1999, vol. 266: 1118-1127, J. Biol. Chem. 1999, vol. 274: 18438-18445). In the brain, mRNA and protein of PDE10A are highly enriched in medium spiny neurons (MSNs) of the striatum (Eur. J. Biochem. 1999, vol. 266: 1118-1127, Brain Res. 2003, vol. 985: 113-126). MSNs are classified into two groups: the MSN that express $D_1$ dopamine receptors responsible for a direct (striatonigral) pathway and the MSN that express $D_2$ dopamine receptors responsible for an indirect (striatopallidal) pathway. The function of direct pathway is to plan and execution, while indirect pathway is to act as a brake on behavioral activation. As PDE10A expresses in both MSNs, PDE10A inhibitors could activate both of these pathways. The antipsychotic efficacy of current medications, $D_2$ or $D_2/5\text{-}HT_{2A}$ antagonists, mainly derives from their activation of the indirect pathway in the striatum. As PDE10A inhibitors are able to activate this pathway, this suggests that PDE10A inhibitors are promising as antipsychotic drugs. The excessive $D_2$ receptor antagonism in the brain by $D_2$ antagonists causes problems of extrapyramidal side effects and hyperprolactinaemia. However the expression of PDE10A is limited to these striatal pathways in the brain, thus side effects by PDE10A inhibitors were expected to be weaker compared with current $D_2$ antagonists. Regarding hyperprolactinaemia, PDE10A inhibitors would produce no prolactin elevation due to lack of $D_2$ receptor antagonism in the pituitary. Moreover, the presence of PDE10A in a direct pathway makes it likely that PDE10A inhibition will have some advantage over current $D_2$ antagonists; the direct pathway is thought to promote desired action, and activation of this pathway by PDE10A inhibitors may counteract extrapyramidal symptoms induced by excessive $D_2$ receptor antagonism. In addition, activation of this pathway could facilitate striatal-thalamic outflow, promoting the execution of procedural strategies. Furthermore, enhancement of second messenger levels without blockade of dopamine and/or other neurotransmitter receptors may also provide therapeutic advantages with fewer adverse side-effects compared with current antipsychotics (e.g., hyperprolactinaemia and weight gain). This unique distribution and function in the brain indicates that PDE10A represents an important new target for the treatment of neurological and psychiatric disorders, in particular psychotic disorders like schizophrenia.

As a phosphodiesterase (PDE)10 inhibitor, a compound represented by the formula:

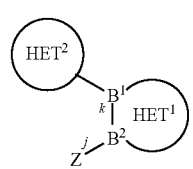

I wherein Z is

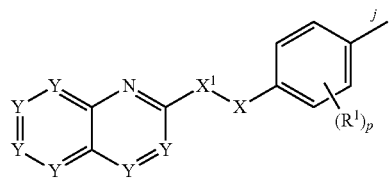

was disclosed in WO2006/072828 Pamphlet.

Further, as a phosphodiesterase (PDE)10 inhibitor, a compound represented by the general formula

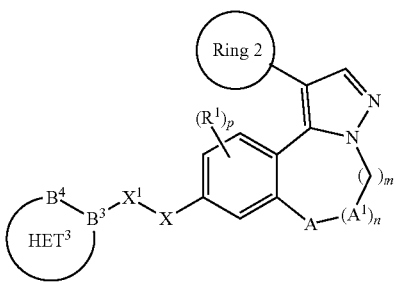

was also disclosed in WO2008/001182 Pamphlet.

SUMMARY OF INVENTION

Technical Problem

However, development of new phosphodiesterase (PDE) 10A inhibitors is further requested.

Solution to Problem

The present inventors discovered that a compound expressed by the formula ($I_o$) or a salt thereof (referred to as compound ($I_o$) in this specification) has a PDE 10A inhibitory action and after extensive investigation, completed the present invention.

Among the compounds ($I_o$), the compound represented by the formula (I) or a salt thereof (referred to as compound (I) in this specification) is a novel compound.

In this specification, the compound ($I_o$) including the compound (I) or a prodrug thereof is also referred to as the compound of the present invention.

That is, the present invention provides the following features.

[1]

A compound of formula (I):

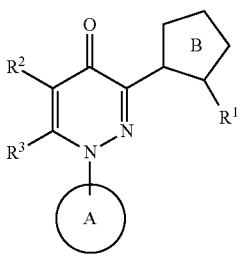

wherein
$R^1$ represents
a substituent,
$R^2$ represents
a hydrogen atom, or a substituent,
$R^3$ represents
a hydrogen atom, or a substituent,
Ring A represents
an aromatic ring which can be substituted, and
Ring B represents
a 5-membered heteroaromatic ring which can be substituted;

provided that the following compounds:

1-(2-chlorophenyl)-6-methyl-3-{5-thioxo-4-[3-(trifluoromethyl)phenyl]-4,5-dihydro-1H-1,2,4-triazol-3-yl}pyridazin-4(1H)-one, 1-(4-chlorophenyl)-3-[4-(2-fluorophenyl)-5-thioxo-4,5-dihydro-1H-1,2,4-triazol-3-yl]-6-methylpyridazin-4(1H)-one, 1-(4-chlorophenyl)-6-methyl-3-{5-thioxo-4-[3-(trifluoromethyl)phenyl]-4,5-dihydro-1H-1,2,4-triazol-3-yl}pyridazin-4(1H)-one, 1-(4-chlorophenyl)-3-[4-(2-fluorophenyl)-5-(methylsulfanyl)-4H-1,2,4-triazol-3-yl]-6-methylpyridazin-4(1H)-one, 1-(4-chlorophenyl)-6-methyl-3-{5-(methylsulfanyl)-4-[3-(trifluoromethyl)phenyl]-4H-1,2,4-triazol-3-yl}pyridazin-4(1H)-one, 1-(2-chlorophenyl)-6-methyl-3-{5-(methylsulfanyl)-4-[3-(trifluoromethyl)phenyl]-4H-1,2,4-triazol-3-yl}pyridazin-4(1H)-one, 3-(3,5-dimethyl-1H-pyrazol-1-yl)-1-phenylpyridazin-4(1H)-one, 1-(4-chlorophenyl)-3-{1-[3-chloro-5-(trifluoromethyl)pyridin-2-yl]-1H-pyrazol-5-yl}pyridazin-4(1H)-one, 3-[1-(2-fluorophenyl)-1H-pyrazol-5-yl]-1-[3-(trifluoromethyl)phenyl]pyridazin-4(1H)-one, 3-[1-(3-chlorophenyl)-1H-pyrazol-5-yl]-1-[3-(trifluoromethyl)phenyl]pyridazin-4(1H)-one, 3-[1-(4-methoxyphenyl)-1H-pyrazol-5-yl]-1-[3-(trifluoromethyl)phenyl]pyridazin-4(1H)-one, 3-(1-phenyl-1H-pyrazol-5-yl)-1-[3-(trifluoromethyl)phenyl]pyridazin-4(1H)-one, 3-[1-(3-nitrophenyl)-1H-pyrazol-5-yl]-1-[3-(trifluoromethyl)phenyl]pyridazin-4(1H-one, 3-[1-(1,1-dioxidotetrahydrothiophen-3-yl)-1H-pyrazol-5-yl]-1-[3-(trifluoromethyl)phenyl]pyridazin-4(1H)-one, 3-[1-(4-methylphenyl)-1H-pyrazol-5-yl]-1-phenylpyridazin-4(1H)-one, 3-[1-(4-chlorophenyl)-1H-pyrazol-5-yl]-1-phenylpyridazin-4(1H)-one, 3-(4-ethyl-5-thioxo-4,5-dihydro-1H-1,2,4-triazol-3-yl)-1-(4-methylphenyl)pyridazin-4(1H)-one, 1-(4-chlorophenyl)-3-{1-[3-chloro-5-(trifluoromethyl)pyridin-2-yl]-1H-pyrazol-3-yl}pyridazin-4(1H)-one, 3-[1-(2-fluorophenyl)-1H-pyrazol-3-yl]-1-[3-(trifluoromethyl)phenyl]pyridazin-4(1H)-one, 3-[1-(3-chlorophenyl)-1H-pyrazol-3-yl]-1-[3-(trifluoromethyl)phenyl]pyridazin-4(1H)-one, 3-[1-(3-methoxyphenyl)-1H-pyrazol-3-yl]-1-[3-(trifluoromethyl)phenyl]pyridazin-4(1H)-one, 3-(1-phenyl-1H-pyrazol-3-yl)-1-[3-(trifluoromethyl)phenyl]pyridazin-4(1H)-one, 3-[1-(3-nitrophenyl)-1H-pyrazol-3-yl]-1-[3-(trifluoromethyl)phenyl]pyridazin-4(1H)-one, 3-[1-(4-methylphenyl)-1H-pyrazol-3-yl]-1-phenylpyridazin-4(1H)-one, 3-[1-(4-chlorophenyl)-1H-pyrazol-3-yl]-1-phenylpyridazin-4(1H)-one, a compound of formula:

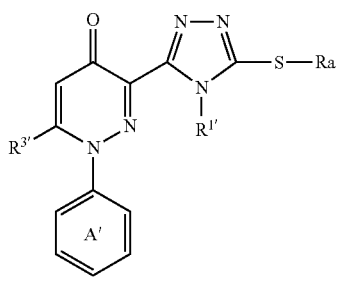

wherein

Ring A' is a benzene ring which can be substituted by one substituent selected from a halogen atom, and an alkyl group,
$R^{1'}$ is
(1) an ethyl group, or
(2) a phenyl group which can be substituted by one or more substituents selected from a fluorine atom, and a trifluoromethyl group,
$R^{3'}$ is a hydrogen atom, or a methyl group, and
Ra is a hydrogen atom, or a $C_{1-4}$ acyclic hydrocarbon group which can be substituted,
a compound of formula:

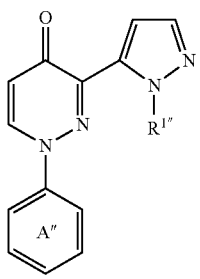

wherein
Ring A'' is a benzene ring which can be substituted by halogen, and
$R^{1''}$ is an acyl group
are excluded;
or a salt thereof.

[2]
The compound according to the above-mentioned [1], wherein
$R^2$ represents
a halogen atom, a hydroxy group, a $C_{1-10}$ alkyl group which can be substituted, or a $C_{1-10}$ alkoxy group which can be substituted.

[3]
The compound according to the above-mentioned [1] or [2], wherein
$R^2$ represents
a $C_{1-10}$ alkoxy group which can be substituted by one or more substituents selected from a halogen atom, a $C_{1-10}$ alkoxy group, and a $C_{3-7}$ cycloalkyl group.

[4]
The compound according to the above-mentioned [1] or [2], wherein
$R^2$ represents
a $C_{1-10}$ alkoxy group.

[5]
The compound according to any one of the above-mentioned [1] to [4], wherein
$R^1$ represents
a phenyl group which can be substituted by 1 to 5 substituents selected from a halogen atom, a $C_{1-10}$ alkyl group which can be substituted, and a $C_{1-10}$ alkoxy group which can be substituted.

[6]
The compound according to any one of the above-mentioned [1] to [5], wherein
$R^1$ represents
a phenyl group which can be substituted by 1 to 5 substituents selected from a halogen atom, a $C_{1-10}$ alkyl group, and a $C_{1-10}$ alkoxy group.

[7]
The compound according to any one of the above-mentioned [1] to [6], wherein
$R^1$ represents
a phenyl group which can be substituted by 1 to 5 halogen atoms.

[8]
The compound according to any one of the above-mentioned [1] to [7], wherein
$R^3$ represents
a hydrogen atom, or a $C_{1-10}$ alkoxy group which can be substituted.

[9]
The compound according to any one of the above-mentioned [1] to [8], wherein
$R^3$ represents
a hydrogen atom, or a $C_{1-10}$ alkoxy group.

[10]
The compound according to any one of the above-mentioned [1] to [9], wherein
$R^3$ represents
a hydrogen atom.

[11]
The compound according to any one of the above-mentioned [1] to [10], wherein
Ring A represents
a benzene ring which can be substituted by 1 to 5 substituents selected from
(1) a halogen atom,
(2) a $C_{1-10}$ alkyl group which can be substituted,
(3) a $C_{1-10}$ alkoxy group which can be substituted,
(4) a 4- to 6-membered heterocyclic group containing 0 or 1 oxygen atom, and 1 to 3 nitrogen atoms as heteroatoms which can be substituted,
(5) a $C_{1-10}$ alkylsulfonyl group which can be substituted,
(6) a $C_{3-7}$ cycloalkyl group which can be substituted,
(7) a cyano group,
(8) a carbamoyl group which can be substituted,
(9) a $C_{1-10}$ alkylsulfonyloxy group which can be substituted,
(10) a $C_{3-7}$ cycloalkyl-$C_{2-6}$ alkynyl group which can be substituted,
(11) a tetrahydropyranyl group which can be substituted,
(12) a dihydropyranyl group which can be substituted,
(13) a mono-($C_{1-10}$ alkyl-carbonyl)-amino group which can be substituted,
(14) a $C_{1-10}$ alkoxy-carbonyl group which can be substituted,
(15) a $C_{1-10}$ alkylsulfinyl group which can be substituted, and
(16) a $C_{1-10}$ alkylsulfanyl group which can be substituted.

[12]
The compound according to any one of the above-mentioned [1] to [11], wherein Ring A represents
a benzene ring which can be substituted by 1 to 5 substituents selected from
(1) a halogen atom,
(2) a $C_{1-10}$ alkyl group which can be substituted,
(3) a $C_{1-10}$ alkoxy group which can be substituted,
(4) a $C_{3-7}$ cycloalkyl group,
(5) a halogeno $C_{1-10}$ alkylsulfonyloxy group,
(6) a $C_{3-7}$ cycloalkyl-$C_{2-6}$ alkynyl group, and
(7) a 4- to 6-membered heterocyclic group containing 0 or 1 oxygen atom, and 1 to 3 nitrogen atoms as heteroatoms which can be substituted by one or more substituents selected from a halogen atom, a hydroxy group, an oxo group, a $C_{1-10}$ alkoxy-carbonyl group, a $C_{1-10}$ alkoxy group which can be substituted, and a $C_{1-10}$ alkyl group which can be substituted.

[13]
The compound according to any one of the above-mentioned [1] to [12], wherein
Ring A represents
a benzene ring which can be substituted by 1 to 5 substituents selected from
(1) a halogen atom,
(2) a $C_{1-10}$ alkyl group which can be substituted by 1 to 3 halogen atoms,
(3) a $C_{1-10}$ alkoxy group which can be substituted by 1 to 3 halogen atoms,
(4) a $C_{3-7}$ cycloalkyl group,
(5) a halogeno $C_{1-10}$ alkylsulfonyloxy group,
(6) a $C_{3-7}$ cycloalkyl-$C_{2-6}$ alkynyl group, and
(7) a 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen.

[14]
The compound according to any one of the above-mentioned [1] to [13], wherein
Ring A represents
a benzene ring which is substituted with
(1) (i) 1 or 2 halogen atoms, or (ii) one $C_{1-10}$ alkoxy group, and
(2) one 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen.

[15]
The compound according to the above-mentioned [14], wherein
the 4- to 6-membered heterocyclic group containing 0 or 1 oxygen atom, and 1 to 3 nitrogen atoms as heteroatoms represents
a morpholino group, a pyrrolyl group, a dihydropyrrolyl group, a pyrazolyl group, a dihydropyrazolyl group, a piperidyl group, an azetidinyl group, a pyrrolidinyl group, an oxazolidinyl group, an imidazolyl group or an imidazolidinyl group.

[16]
The compound according to any one of the above-mentioned [1] to [15], wherein
Ring B represents
an imidazole ring, a pyrazole ring, a triazole ring or a tetrazole ring, each of which can be further substituted with 1 to 3 substituents selected from a halogen atom, and a $C_{1-10}$ alkyl group which can be substituted by halogen.

[17]
The compound according to any one of the above-mentioned [1] to [16], wherein
Ring B represents
a pyrazole ring which can be further substituted with 1 to 3 substituents selected from a halogen atom, and a $C_{1-10}$ alkyl group which can be substituted by halogen.

[18]
The compound according to any one of the above-mentioned [1] to [17], wherein
Ring B represents
a pyrazole ring.

[19]
The compound according to the above-mentioned [2], wherein
$R^1$ represents
a phenyl group which can be substituted by 1 to 5 substituents selected from a halogen atom, a $C_{1-10}$ alkyl group which can be substituted, and a $C_{1-10}$ alkoxy group which can be substituted,
$R^2$ represents
a halogen atom, a hydroxy group, a $C_{1-10}$ alkyl group which can be substituted, or a $C_{1-10}$ alkoxy group which can be substituted,
$R^3$ represents
a hydrogen atom, or a $C_{1-10}$ alkoxy group which can be substituted,
Ring A represents
a benzene ring which can be substituted by 1 to 5 substituents selected from
(1) a halogen atom,
(2) a $C_{1-10}$ alkyl group which can be substituted,
(3) a $C_{1-10}$ alkoxy group which can be substituted,
(4) a 4- to 6-membered heterocyclic group containing 0 or 1 oxygen atom, and 1 to 3 nitrogen atoms as heteroatoms which can be substituted,
(5) a $C_{1-10}$ alkylsulfonyl group which can be substituted,
(6) a $C_{3-7}$ cycloalkyl group which can be substituted,
(7) a cyano group,
(8) a carbamoyl group which can be substituted,
(9) a $C_{1-10}$ alkylsulfonyloxy group which can be substituted,
(10) a $C_{3-7}$ cycloalkyl-$C_{2-6}$ alkynyl group which can be substituted,
(11) a tetrahydropyranyl group which can be substituted,
(12) a dihydropyranyl group which can be substituted,
(13) a mono-($C_{1-10}$ alkyl-carbonyl)-amino group which can be substituted,
(14) a $C_{1-10}$ alkoxy-carbonyl group which can be substituted,
(15) a $C_{1-10}$ alkylsulfinyl group which can be substituted, and
(16) a $C_{1-10}$ alkylsulfanyl group which can be substituted, and
Ring B represents
an imidazole ring, a pyrazole ring, a triazole ring or a tetrazole ring, each of which can be further substituted with 1 to 3 substituents selected from a halogen atom, and a $C_{1-10}$ alkyl group which can be substituted by halogen.

[20]
The compound according to the above-mentioned [19], wherein.
Ring A represents
a benzene ring which can be substituted by 1 to 5 substituents selected from (1) a halogen atom,
(2) a $C_{1-10}$ alkyl group which can be substituted,
(3) a $C_{1-10}$ alkoxy group which can be substituted,
(4) a $C_{3-7}$ cycloalkyl group,
(5) a halogeno $C_{1-10}$ alkylsulfonyloxy group,
(6) a $C_{3-7}$ cycloalkyl-$C_{2-6}$ alkynyl group, and
(7) a 4- to 6-membered heterocyclic group containing 0 or 1 oxygen atom; and 1 to 3 nitrogen atoms as heteroatoms which can be substituted by one or more substituents selected from a halogen atom, a hydroxy group, an oxo group, a $C_{1-10}$ alkoxy-carbonyl group, a $C_{1-10}$ alkoxy group which can be substituted, and a $C_{1-10}$ alkyl group which can be substituted.

[21]
The compound according to the above-mentioned [2], wherein
$R^1$ represents
a phenyl group which can be substituted by 1 to 5 substituents selected from a halogen atom, a $C_{1-10}$ alkyl group, and a $C_{1-10}$ alkoxy group,
$R^2$ represents
a $C_{1-10}$ alkoxy group which can be substituted by one or more substituents selected from a halogen atom, a $C_{1-10}$ alkoxy group, and a $C_{3-7}$ cycloalkyl group,
$R^3$ represents
a hydrogen atom, or a $C_{1-10}$ alkoxy group,
Ring A represents
a benzene ring which can be substituted by 1 to 5 substituents selected from
(1) a halogen atom,
(2) a $C_{1-10}$ alkyl group which can be substituted by 1 to 3 halogen atoms,
(3) a $C_{1-10}$ alkoxy group which can be substituted by 1 to 3 halogen atoms,
(4) a $C_{3-7}$ cycloalkyl group,
(5) a halogeno $C_{1-10}$ alkylsulfonyloxy group,
(6) a $C_{3-7}$ cycloalkyl-$C_{2-6}$ alkynyl group, and
(7) a 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen,
Ring B represents
a pyrazole ring which can be further substituted with 1 to 3 substituents selected from a halogen atom, and a $C_{1-10}$ alkyl group which can be substituted by halogen.

[22]
The compound according to the above-mentioned [2], wherein
$R^1$ represents
a phenyl group which can be substituted by 1 to 5 halogen atoms,
$R^2$ represents
a $C_{1-10}$ alkoxy group,
$R^3$ represents
a hydrogen atom,
Ring A represents
a benzene ring which is substituted with
(1) (i) 1 or 2 halogen atoms, or (ii) one $C_{1-10}$ alkoxy group, and
(2) one 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen,
Ring B represents
a pyrazole ring.

[23]
The compound according to the above-mentioned [22], wherein
the 4- to 6-membered heterocyclic group containing 0 or 1 oxygen atom, and 1 to 3 nitrogen atoms as heteroatoms represents
a morpholino group, a pyrrolyl group, a dihydropyrrolyl group, a pyrazolyl group, a dihydropyrazolyl group, a piperidyl group, an azetidinyl group, a pyrrolidinyl group, an oxazolidinyl group, an imidazolyl group or an imidazolidinyl group.

[24]
The compound according to the above-mentioned [1], wherein
$R^1$ represents
an aromatic group which can be substituted,
Ring A represents
an aromatic ring which is substituted with
(a) one substituent selected from
(1) a $C_{3-7}$ cycloalkyl group which can be substituted, and
(2) a 4- to 6-membered heterocyclic group containing 1 to 5 heteroatoms selected from a nitrogen atom, a sulfur atom, and an oxygen atom which can be substituted, and
(b) one or more further substituents.

[25]
The compound according to the above-mentioned [24], wherein
$R^1$ represents
a phenyl group which can be substituted,
$R^2$ represents
a hydrogen atom, a halogen atom, a hydroxy group, a $C_{1-10}$ alkyl group which can be substituted, or a $C_{1-10}$ alkoxy group which can be substituted,
$R^3$ represents
a hydrogen atom, or a $C_{1-10}$ alkoxy group which can be substituted,
Ring A represents
a benzene ring which
is substituted with one substituent selected from
(1) a $C_{3-7}$ cycloalkyl group which can be substituted,
(2) a dihydropyranyl group which can be substituted,
(3) a tetrahydropyranyl group which can be substituted, and
(4) a 4- to 6-membered heterocyclic group containing 0 or 1 oxygen atom, and 1 to 3 nitrogen atoms as heteroatoms which can be substituted,
and can be substituted by further substituents, and
Ring B represents
an imidazole ring, a pyrazole ring, a triazole ring, a tetrazole ring, an isoxazole ring, an 1,3-oxazole ring, a furan ring, or a thiophene ring, each of which can be substituted.

[26]
The compound according to the above-mentioned [25], wherein
the 4- to 6-membered heterocyclic group containing 0 or 1 oxygen atom, and 1 to 3 nitrogen atoms as heteroatoms represents
a morpholino group, a pyrrolyl group, a dihydropyrrolyl group, a pyrazolyl group, a dihydropyrazolyl group, a piperidyl group, an azetidinyl group, a pyrrolidinyl group, an oxazolidinyl group, an imidazolyl group, an imidazolidinyl group, an isoxazolyl group, a pyridyl group, a piperazinyl group, or a thiazolyl group.

[27]
The compound according to the above-mentioned [24], wherein
the further substituents are 1 to 4 substituents selected from
(1) a halogen atom,
(2) an oxo group,
(3) a hydroxy group,
(4) a $C_{1-10}$ alkyl group which can be substituted,
(5) a $C_{1-10}$ alkoxy group which can be substituted,
(6) a $C_{1-10}$ alkylsulfonyl group,
(7) a morpholin-4-yl sulfonyl group,
(8) a cyano group,
(9) a carbamoyl group,
(10) a halogeno $C_{1-10}$ alkylsulfonyloxy group,
(11) a $C_{3-7}$ cycloalkyl-$C_{2-6}$ alkynyl group,
(12) a di-$C_{1-10}$ alkyl-amino group,
(13) a mono-($C_{1-10}$ alkyl-carbonyl)-amino group,
(14) a $C_{1-10}$ alkoxy-carbonyl group,
(15) a phenoxy group,
(16) a $C_{1-10}$ alkylsulfinyl group,
(17) a benzimidazole-2-yloxy group, and
(18) a benzimidazole-2-yl sulfonyl group.

[28]
The compound according to the above-mentioned [24], wherein
$R^1$ represents
a phenyl group which can be substituted by 1 to 5 halogen atoms,
$R^2$ represents
a hydrogen atom or a $C_{1-10}$ alkoxy group,
$R^3$ represents
a hydrogen atom,
Ring A represents
a benzene ring,
which is substituted with one 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, halogeno $C_{1-10}$ alkoxy group, a $C_{1-10}$ alkoxy-carbonyl, and a $C_{1-10}$ alkyl group which can be substituted by halogen,
and which can be further substituted with 1 or 2 substituents selected from a halogen atom and a $C_{1-10}$ alkoxy group, and
Ring B represents
a pyrazole ring.

[29]
The compound according to the above-mentioned [28], wherein
the 4- to 6-membered heterocyclic group containing 0 or 1 oxygen atom, and 1 to 3 nitrogen atoms as heteroatoms represents
a morpholino group, a pyrrolyl group, a dihydropyrrolyl group, a pyrazolyl group, a dihydropyrazolyl group, a piperidyl group, an azetidinyl group, a pyrrolidinyl group, an oxazolidinyl group, an imidazolyl group or an imidazolidinyl group.

[30]
1-[2-fluoro-4-(3,3,4,4-tetrafluoropyrrolidin-1-yl)phenyl]-5-methoxy-3-(1-phenyl-1H-pyrazol-5-yl)pyridazin-4(1H)-one, or a salt thereof.

[31]
1-[2-fluoro-4-(2-oxopyrrolidin-1-yl)phenyl]-5-methoxy-3-(1-phenyl-1H-pyrazol-5-yl)pyridazin-4(1H)-one, or a salt thereof.

[32]
1-[4-(3,4-difluoro-1H-pyrrol-1-yl)-2-fluorophenyl]-5-methoxy-3-(1-phenyl-1H-pyrazol-5-yl)pyridazin-4(1H)-one, or a salt thereof.

[33]
1-[2-fluoro-4-(1H-pyrazol-1-yl)phenyl]-5-methoxy-3-(1-phenyl-1H-pyrazol-5-yl)pyridazin-4(1H)-one, or a salt thereof.

[34]
1-[4-(4-chloro-1H-pyrazol-1-yl)-2-fluorophenyl]-5-methoxy-3-(1-phenyl-1H-pyrazol-5-yl)pyridazin-4(1H)-one, or a salt thereof.

[35]
1-[2-fluoro-4-(2-oxo-1,3-oxazolidin-3-yl)phenyl]-5-methoxy-3-(1-phenyl-1H-pyrazol-5-yl)pyridazin-4(1H)-one, or a salt thereof

[36]
3-[1-(2-fluorophenyl)-1H-pyrazol-5-yl]-1-[2-fluoro-4-(1H-pyrazol-1-yl)phenyl]-5-methoxypyridazin-4(1H)-one, or a salt thereof.

[37]
3-[1-(3-chlorophenyl)-1H-pyrazol-5-yl]-1-[2-fluoro-4-(1H-pyrazol-1-yl)phenyl]-5-methoxypyridazin-4(1H)-one, or a salt thereof.

[38]
1-[4-(4,4-dimethyl-2-oxopyrrolidin-1-yl)-2-fluorophenyl]-5-methoxy-3-(1-phenyl-1H-pyrazol-5-yl)pyridazin-4(1H)-one, or a salt thereof.

[39]
1-[4-(5,5-dimethyl-2-oxo-1,3-oxazolidin-3-yl)-2-fluorophenyl]-5-methoxy-3-(1-phenyl-1H-pyrazol-5-yl)pyridazin-4(1H)-one, or a salt thereof.

[40]
5-methoxy-1-[2-methoxy-4-(1H-pyrazol-1-yl)phenyl]-3-(1-phenyl-1H-pyrazol-5-yl)pyridazin-4(1H)-one, or a salt thereof.

[41]
A prodrug of the compound according to according to any one of the above-mentioned [1] to [40]

[42]
A medicament comprising the compound according to according to any one of the above-mentioned [1] to [40] or a prodrug thereof.

[43]
A medicament comprising a compound of formula ($I_0$):

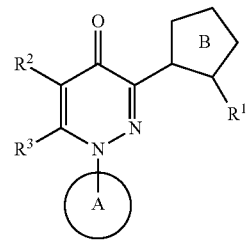

(I₀)

wherein
$R^1$ represents
a substituent,
$R^2$ represents
a hydrogen atom, or a substituent, R³ represents
a hydrogen atom, or a substituent,
Ring A represents
an aromatic ring which can be substituted, and
Ring B represents
a 5-membered heteroaromatic ring which can be substituted,
or a salt thereof, or a prodrug thereof.

[44]
The medicament according to the above-mentioned [43] which is an agent for inhibiting phosphodiesterase 10A.

[45]
The medicament according to the above-mentioned [43] which is for preventing or treating schizophrenia.

[46]
A method of preventing or treating schizophrenia comprising administrating an effective amount of a compound of formula ($I_0$):

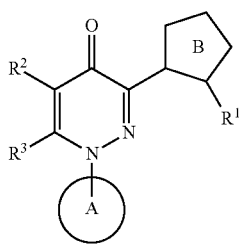

wherein
R¹ represents
a substituent,
R² represents
a hydrogen atom, or a substituent,
R³ represents
a hydrogen atom, or a substituent,
Ring A represents
an aromatic ring which can be substituted, and
Ring B represents
a 5-membered heteroaromatic ring which can be substituted,
or a salt thereof, or a prodrug thereof
to a mammal.

[47]
Use of a compound of formula ($I_0$):

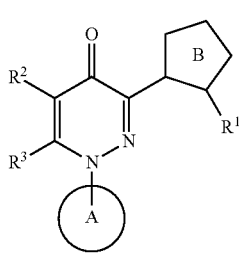

wherein
R¹ represents
a substituent,
R² represents
a hydrogen atom, or a substituent,
R³ represents
a hydrogen atom, or a substituent,
Ring A represents
an aromatic ring which can be substituted, and
Ring B represents
a 5-membered heteroaromatic ring which can be substituted,
or a salt thereof, or a prodrug thereof
as a medicament.

[48]
Use of a compound of formula ($I_0$):

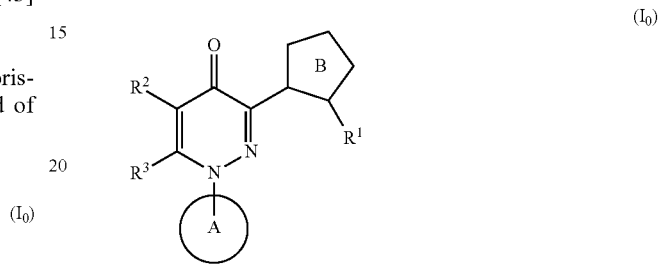

wherein
R¹ represents
a substituent,
R² represents
a hydrogen atom, or a substituent,
R³ represents
a hydrogen atom, or a substituent,
Ring A represents
an aromatic ring which can be substituted, and
Ring B represents
a 5-membered heteroaromatic ring which can be substituted,
or a salt thereof, or a prodrug thereof
in the manufacture of a medicament for preventing or treating schizophrenia.

Besides, the present invention also provides the following features.

[1']
A compound represented by the formula (I):

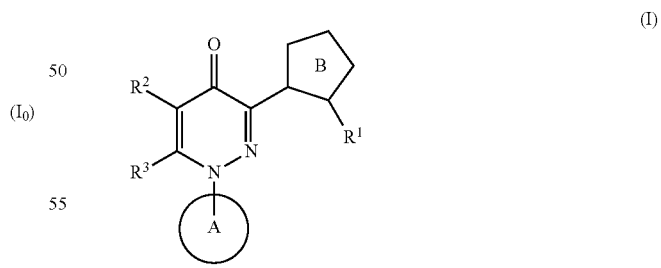

wherein
R¹ represents a substituent,
R² represents a hydrogen atom or a substituent,
R³ represents a hydrogen atom or a substituent,
Ring A represents an aromatic ring which can be substituted, and
Ring B represents a 5-membered aromatic heterocyclic ring which can be substituted;

provided that the following compounds are excluded:
a compound represented by the formula:

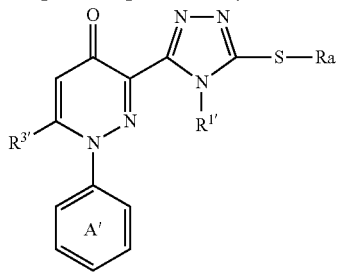

wherein
Ring A' represents a benzene ring which can be substituted by one substituent selected from halogen and alkyl,
$R^{1'}$ represents (1) ethyl or (2) phenyl which can be substituted by one or more substituents selected from fluorine and trifluoromethyl,
$R^{3'}$ represents hydrogen or methyl, and
Ra represents a hydrogen atom or a $C_{1-4}$ acyclic hydrocarbon group which can be substituted; and
a compound represented by the formula:

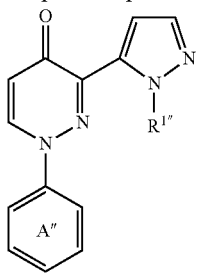

wherein
Ring A" represents a benzene ring which can be substituted by halogen, and
$R^{1''}$ represents an acyl group;
or a salt thereof.

[2']
A prodrug of the compound described as in the above-mentioned [1'].

[3']
A medicament comprising the compound described as in the above-mentioned [1'] or the prodrug thereof.

[4']
A medicament comprising a compound represented by the formula $(I_o)$:

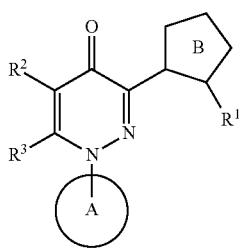

(I₀)

wherein
$R^1$ represents a substituent,
$R^2$ represents a hydrogen atom or a substituent,
$R^3$ represents a hydrogen atom or a substituent,
Ring A represents an aromatic ring which can be substituted, and
Ring B represents a 5-membered aromatic heterocyclic ring which can be substituted,
or a salt thereof.

[5']
The medicament described as in the above-mentioned [4'] which is an agent for inhibiting phosphodiesterase 10A.

[6']
The medicament described as in the above-mentioned [4'] which is for preventing or treating schizophrenia.

[7']
A method for preventing or treating schizophrenia which comprises administering an effective amount of a compound represented by the formula $(I_o)$:

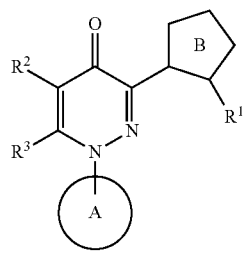

(I₀)

wherein
$R^1$ represents a substituent,
$R^2$ represents a hydrogen atom or a substituent,
$R^3$ represents a hydrogen atom or a substituent,
Ring A represents an aromatic ring which can be substituted, and
Ring B represents a 5-membered aromatic heterocyclic ring which can be substituted,
or a salt thereof.

[8']
Use of a compound represented by the formula $(I_o)$:

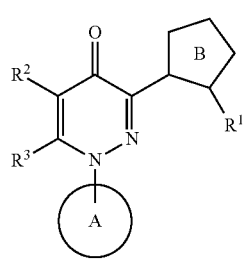

(I₀)

wherein
$R^1$ represents a substituent,
$R^2$ represents a hydrogen atom or a substituent,
$R^3$ represents a hydrogen atom or a substituent,
Ring A represents an aromatic ring which can be substituted, and
Ring B represents a 5-membered aromatic heterocyclic ring which can be substituted,
or a salt thereof
as a medicament.

[9']
Use of a compound represented by the formula (I$_o$):

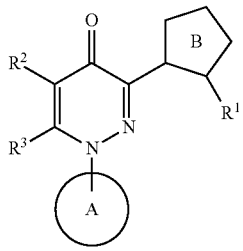

wherein
R$^1$ represents a substituent,
R$^2$ represents a hydrogen atom or a substituent,
R$^3$ represents a hydrogen atom or a substituent,
Ring A represents an aromatic ring which can be substituted, and
Ring B represents a 5-membered aromatic heterocyclic ring which can be substituted,
or a salt thereof
in the manufacture of a medicament for preventing or treating schizophrenia.

Advantageous Effects of Invention

The compound of the present invention has a PDE inhibitory activity and is useful as a drug for preventing or treating schizophrenia, etc.

DETAILED DESCRIPTION OF THE INVENTION

Figure 1A:
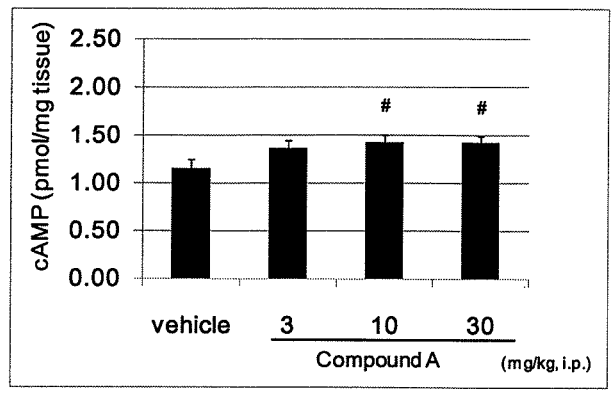
FIG. 1. Graphs showing dose-dependent elevation of cAMP (FIG. 1A) and cGMP (FIG. 1B) contents in the mouse striatum by compound A. All data were represented as means plus the standard errors of the means (n=5-7) and analyzed using a williams' test with significance set at #P<0.025. The phrase (mg/kg, i.p.) means (milligram per kilogram, intraperitoneal treatment). The phrase (pmol/mg tissue) means (picomole per milligram tissue).

The present invention will be explained in detail below.

Unless otherwise specifically stated, in this specification, examples of the "halogen" include fluorine, chlorine, bromine and iodine.

Unless otherwise specifically stated, in this specification, the phrase "can be halogenated" or the term "halogeno" means that one or more (e.g., 1 to 3) halogen atoms can be present as substituents.

Unless otherwise specifically stated, in this specification, examples of the "alkyl (group)" include $C_{1-10}$ alkyl (group).

Unless otherwise specifically stated, in this specification, examples of the "$C_{1-10}$ alkyl (group)" include methyl, ethyl, propyl, isopropyl, butyl, isobutyl, sec-butyl, tert-butyl, pentyl, isopentyl, neopentyl, and hexyl.

Unless otherwise specifically stated, in this specification, the term "$C_{1-10}$ alkyl (group) that can be halogenated" means $C_{1-10}$ alkyl (group) which can be substituted by halogen, and examples thereof include trifluoromethyl.

Unless otherwise specifically stated, in this specification, examples of the "alkenyl (group)" include $C_{2-6}$ alkenyl (group).

Unless otherwise specifically stated, in this specification, examples of the "$C_{2-6}$ alkenyl (group)" include vinyl, 1-propen-1-yl, 2-propen-1-yl, isopropenyl, 2-buten-1-yl, 4-penten-1-yl, and 5-hexen-1-yl.

Unless otherwise specifically stated, in this specification, examples of the "alkynyl (group)" include $C_{2-6}$ alkynyl (group).

Examples of "$C_{2-6}$ alkynyl (group)" include ethynyl, 1-propyn-1-yl, 2-propyn-1-yl, 4-pentyn-1-yl, and 5-hexyn-1-yl.

Unless otherwise specifically stated, in this specification, examples of the "$C_{3-7}$ cycloalkyl-$C_{2-5}$ alkynyl (group)" include cyclopropylethynyl.

Unless otherwise specifically stated, in this specification, examples of the "$C_{3-7}$ cycloalkyl (group)" include cyclopropyl, cyclobutyl, cyclopentyl, and cyclohexyl.

Unless otherwise specifically stated, in this specification, examples of the "$C_{6-14}$ aryl (group)" include phenyl, 1-naphthyl, 2-naphthyl, 2-biphenylyl, 3-biphenylyl, 4-biphenylyl, and 2-anthryl.

Unless otherwise specifically stated, in this specification, examples of "$C_{7-16}$ aralkyl (group)" include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylmethyl, 3-biphenylmethyl, and 4-biphenylmethyl.

Unless otherwise specifically stated, in this specification, examples of "$C_{6-14}$ aryl-$C_{2-6}$ alkenyl (group)" include styryl.

Unless otherwise specifically stated, in this specification, the "heterocyclic group" (and a heterocyclic moiety in a substituent) is a non-aromatic heterocyclic group, or a heteroaryl group (i.e., aromatic heterocyclic group), and examples thereof include 3- to 14-membered heterocyclic group having 1 to 5 hetero atoms selected from nitrogen, sulfur and oxygen. This "heterocyclic group" can be monocyclic, bicyclic or tricyclic.

Examples of the "3- to 14-membered heterocyclic group" include 3- to 14-membered aromatic heterocyclic group having 1 to 5 hetero atoms selected from nitrogen, sulfur and oxygen such as pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), pyrazolyl (e.g., 1-pyrazolyl, 3-pyrazolyl, 4-pyrazolyl), imidazolyl (e.g., 1-imidazolyl, 2-imidazolyl, 4-imidazolyl), isoxazolyl (e.g., 3-isoxazolyl, 4-isoxazolyl, 5-isoxazolyl), oxazolyl (e.g., 2-oxazolyl, 4-oxazolyl, 5-oxazolyl), isothiazolyl (e.g., 3-isothiazolyl, 4-isothiazolyl, 5-isothiazolyl), thiazolyl (e.g., 2-thiazolyl, 4-thiazolyl, 5-thiazolyl), triazolyl (e.g., 1,2,3-triazol-4-yl, 1,2,4-triazol-3-yl), oxadiazolyl (e.g., 1,2,4-oxadiazol-3-yl, 1,2,4-oxadiazol-5-yl), thiadiazolyl (e.g., 1,2,4-thiadiazol-3-yl, 1,2,4-thiadiazol-5-yl), tetrazolyl, pyridyl (e.g., 2-pyridyl, 3-pyridyl, 4-pyridyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl, indolyl, isoindolyl (e.g., 1-isoindolyl, 2-isoindolyl, 3-isoindolyl, 4-isoindolyl, 5-isoindolyl, 6-isoindolyl, 7-isoindolyl), indolyl (e.g., 1-indolyl, 2-indolyl, 3-indolyl, 4-indolyl, 5-indolyl, 6-indolyl, 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, 7-benzo[b]furanyl), benzo[c]furanyl (e.g., 1-benzo[c]furanyl, 4-benzo[c]furanyl, 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzo[c]thienyl (e.g., 1-benzo[c]thienyl, 4-benzo[c]thienyl, 5-benzo[c]thienyl), indazolyl (e.g., 1-indazolyl, 2-indazolyl, 3-indazolyl, 4-indazolyl, 5-indazolyl, 6-indazolyl, 7-indazolyl), benzimidazolyl (e.g., 1-benzimidazolyl, 2-benzimidazolyl, 4-benzimidazolyl, 5-benzimidazolyl), 1,2-benzoisoxazolyl (e.g., 1,2-benzisoxazol-3-yl, 1,2-benzisoxazol-4-yl, 1,2-benzisoxazol-5-yl, 1,2-benzisoxazol-6-yl, 1,2-benzisoxazol-7-yl), benzoxazolyl(e.g., 2-benzoxazolyl, 4-benzoxazolyl, 5-benzoxazolyl, 6-benzoxazolyl, 7-benzoxazolyl), 1,2-benzoisothiazolyl (e.g., 1,2-benzisothiazol-3-yl, 1,2-benzisothiazol-4-yl, 1,2-benzisothiazol-5-yl, 1,2-benzisothiazol-6-yl, 1,2-benzisothiazol-7-yl), benzothiazolyl (e.g., 2-benzothiazolyl, 4-benzothiazolyl, 5-benzothiazolyl, 6-benzothiazolyl, 7-benzothiazolyl), isoquinolyl (e.g., 1-isoquinolyl, 3-isoquinolyl, 4-isoquinolyl, 5-isoquinolyl), quinolyl (e.g., 2-quinolyl, 3-quinolyl, 4-quinolyl, 5-quinolyl, 8-quinolyl), cinnolinyl (e.g., 3-cinnolinyl, 4-cinnolinyl, 5-cinnolinyl, 6-cinnolinyl, 7-cinnolinyl, 8-cinnolinyl), phthalazinyl (e.g., 1-phthalazinyl, 4-phthalazinyl, 5-phthalazinyl, 6-phthalazinyl, 7-phthalazinyl, 8-phthalazinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 3-quinoxalinyl, 5-quinoxalinyl, 6-quinoxalinyl, 7-quinoxalinyl, 8-quinoxalinyl), pyrazolo[1,5-a]pyridyl (e.g., pyrazolo[1,5-1]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, imidazo[1,2-a]pyridin-8-yl); and saturated or unsaturated 3- to 14-membered non-aromatic heterocyclic group having 1 to 5 hetero atoms selected from nitrogen, sulfur and oxygen such as tetrahydrofuryl, oxazolidinyl, imidazolinyl (e.g., 1-imidazolinyl, 2-imidazolinyl, 4-imidazolinyl), aziridinyl (e.g., 1-aziridinyl, 2-aziridinyl), azetidinyl (e.g., 1-azetidinyl, 2-azetidinyl), pyrrolidinyl (e.g., 1-pyrrolidinyl, 2-pyrrolidinyl, 3-pyrrolidinyl), piperidinyl (e.g., 1-piperidinyl, 2-piperidinyl, 3-piperidinyl), azepanyl (e.g., 1-azepanyl, 2-azepanyl, 3-azepanyl, 4-azepanyl), azocanyl (e.g., 1-azocanyl, 2-azocanyl, 3-azocanyl, 4-azocanyl), piperazinyl (e.g., 1,4-piperazin-1-yl, 1,4-piperazin-2-yl), diazepinyl (e.g., 1,4-diazepin-1-yl, 1,4-diazepin-2-yl, 1,4-diazepin-5-yl, 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, and dihydroquinolyl.

Unless otherwise specifically stated, in this specification, examples of the "5- to 10-membered heterocyclic groups" include those having 5- to 10-members among the aforementioned "3- to 14-membered heterocyclic group".

Unless otherwise specifically stated, in this specification, examples of the "aromatic heterocyclic group" (and an aromatic heterocyclic moiety in a substituent) include the "3- to 14-membered aromatic heterocyclic group having 1 to 5 hetero atoms selected from nitrogen, sulfur and oxygen" as exemplified above as said "heterocyclic group".

Unless otherwise specifically stated, in this specification, examples of the "non-aromatic heterocyclic group" (and an aromatic heterocyclic moiety in a substituent) include the "saturated or unsaturated 3- to 14-membered non-aromatic heterocyclic group having 1 to 5 hetero atoms selected from nitrogen, sulfur and oxygen" as exemplified above as said "heterocyclic group".

Unless otherwise specifically stated, in this specification, examples of the "saturated heterocyclic group" (and a saturated heterocyclic moiety in a substituent) include those saturated among said "non-aromatic heterocyclic group". Specific examples thereof include tetrahydrofuryl, morpholinyl, thiomorpholinyl, piperidinyl, pyrrolidinyl, and piperazinyl group.

Unless otherwise specifically stated, in this specification, examples of the "5- to 6-membered saturated heterocyclic group" (and a saturated heterocyclic moiety in a substituent) include those having 5- to 6-members among said "saturated heterocyclic group".

Unless otherwise specifically stated, in this specification, examples of the "alkoxy (group)" include $C_{1-10}$ alkoxy (group).

Unless otherwise specifically stated, in this specification, examples of the "$C_{1-10}$ alkoxy (group)" include methoxy; ethoxy, propoxy, isopropoxy, butoxy, isobutoxy, sec-butoxy, pentyloxy and hexyloxy.

Unless otherwise specifically stated, in this specification, examples of the "$C_{3-7}$ cycloalkyloxy (group)" include cyclopropyloxy, cyclobutyloxy, cyclopentyloxy, cyclohexyloxy.

Unless otherwise specifically stated, in this specification, examples of the "$C_{6-14}$ aryloxy (group)" include phenyloxy, 1-naphthyloxy and 2-naphthyloxy.

Unless otherwise specifically stated, in this specification, examples of the "$C_{7-16}$ aralkyloxy (group)" include benzyloxy and phenethyloxy.

Unless otherwise specifically stated, in this specification, examples of the "alkyl-carbonyloxy (group)" include $C_{1-10}$ alkyl-carbonyloxy (group).

Unless otherwise specifically stated, in this specification, examples of the "$C_{1-10}$ alkyl-carbonyloxy (group)" include acetoxy and propionyloxy.

Unless otherwise specifically stated, in this specification, examples of the "alkoxy-carbonyloxy (group)" include $C_{1-10}$ alkoxy-carbonyloxy (group).

Unless otherwise specifically stated, in this specification, examples of the "$C_{1-10}$ alkoxy-carbonyloxy (group)" include methoxycarbonyloxy, ethoxycarbonyloxy, propoxycarbonyloxy and butoxycarbonyloxy.

Unless otherwise specifically stated, in this specification, examples of the "mono-alkyl-carbamoyloxy (group)" include mono-$C_{1-10}$ alkyl-carbamoyloxy (group).

Unless otherwise specifically stated, in this specification, examples of the "mono-$C_{1-10}$ alkyl-carbamoyloxy (group)" include methylcarbamoyloxy and ethylcarbamoyloxy.

Unless otherwise specifically stated, in this specification, examples of the "di-alkyl-carbamoyloxy (group)" include di-$C_{1-10}$ alkyl-carbamoyloxy (group).

Unless otherwise specifically stated, in this specification, examples of the "di-$C_{1-10}$ alkyl-carbamoyloxy (group)" include dimethylcarbamoyloxy and diethylcarbamoyloxy.

Unless otherwise specifically stated, in this specification, examples of the "$C_{6-14}$ aryl-carbonyloxy (group)" include benzoyloxy and naphthylcarbonyloxy.

Unless otherwise specifically stated, in this specification, examples of the "mono- or di-$C_{6-14}$ aryl-carbamoyloxy (group)" include phenylcarbamoyloxy and naphthylcarbamoyloxy.

Unless otherwise specifically stated, in this specification, examples of the heterocyclic moiety of the "heterocyclic-oxy (group)" include those similar to said "heterocyclic group" are included. Specifically, examples of the "heterocyclic-oxy (group)" include 5- to 14-membered heterocyclic-oxy (group) having 1 to 5 hetero atoms selected from nitrogen, sulfur and oxygen.

Unless otherwise specifically stated, in this specification, examples of the aromatic heterocyclic moiety of the "heterocyclic-oxy (group)" include those similar to the "aromatic heterocyclic group" as examples of said "heterocyclic group". Specifically, examples of the "aromatic heterocyclic-oxy (group)" include 3- to 14-membered aromatic heterocyclic-oxy (group) having 1 to 5 hetero atoms selected from nitrogen, sulfur and oxygen.

Unless otherwise specifically stated, in this specification, examples of the "$C_{1-10}$ alkylsulfonyloxy (group)" include methylsulfonyloxy and ethylsulfonyloxy.

Unless otherwise specifically stated, in this specification, examples of the "halogeno $C_{1-10}$ alkylsulfonyloxy (group)" include halogeno methylsulfonyloxy and halogeno ethylsulfonyloxy.

Unless otherwise specifically stated, in this specification, examples of the "alkylsulfanyl (group)" include $C_{1-10}$ alkylsulfanyl (group).

Unless otherwise specifically stated, in this specification, examples of the "$C_{1-10}$ alkylsulfanyl (group)" include methylsulfanyl, ethylsulfanyl, propylsulfanyl, isopropylsulfanyl, butylsulfanyl, sec-butylsulfanyl, and tert-butylsulfanyl.

Unless otherwise specifically stated, in this specification, examples of the "$C_{3-7}$ cycloalkylsulfanyl (group)" include cyclopropylsulfanyl, cyclobutylsulfanyl, cyclopentylsulfanyl and cyclohexylsulfanyl.

Unless otherwise specifically stated, in this specification, examples of the "$C_{6-14}$ arylsulfanyl (group)" include phenylsulfanyl, 1-naphthylsulfanyl and 2-naphthylsulfanyl.

Unless otherwise specifically stated, in this specification, examples of the "$C_{7-16}$ aralkylsulfanyl (group)" include benzylsulfanyl and phenethylsulfanyl.

Unless otherwise specifically stated, in this specification, examples of the heterocyclic moiety of the "heterocyclic-sulfanyl (group)" include those similar to said "heterocyclic group". Specifically, examples of the "heterocyclic-sulfanyl (group)" include 5- to 14-membered heterocyclic-sulfanyl (group) having 1 to 5 hetero atoms selected from nitrogen, sulfur and oxygen.

Unless otherwise specifically stated, in this specification, examples of the "alkyl-carbonyl (group)" include $C_{1-10}$ alkyl-carbonyl.

Unless otherwise specifically stated, in this specification, examples of the "$C_{1-10}$ alkyl-carbonyl (group)" include acetyl, propionyl and pivaloyl.

Unless otherwise specifically stated, in this specification, examples of the "$C_{3-7}$ cycloalkyl-carbonyl (group)" include cyclopropylcarbonyl, cyclopentylcarbonyl and cyclohexylcarbonyl group.

Unless otherwise specifically stated, in this specification, examples of the "$C_{6-14}$ aryl-carbonyl (group)" include benzoyl, 1-naphthoyl and 2-naphthoyl group.

Unless otherwise specifically stated, in this specification, examples of the "$C_{7-16}$ aralkyl-carbonyl (group)" include phenylacetyl and 3-phenylpropionyl group.

Unless otherwise specifically stated, in this specification, examples of the heterocyclic moiety of the "heterocyclic-carbonyl (group)" include those similar to said "heterocyclic group". Specifically, examples thereof include 3- to 14-membered heterocyclic-carbonyl (group) having 1 to 5 hetero atoms selected from nitrogen, sulfur and oxygen. Further, specific examples thereof include picolinoyl, nicotinoyl, isonicotinoyl, 2-thenoyl, 3-thenoyl, 2-furoyl, 3-furoyl, 1-morpholinylcarbonyl, 4-thiomorpholinylcarbonyl, aziridin-1-ylcarbonyl, aziridin-2-ylcarbonyl, azetidin-1-ylcarbonyl, azetidin-2-ylcarbonyl, pyrrolidine-1-ylcarbonyl, pyrrolidine-2-ylcarbonyl, pyrrolidine-3-ylcarbonyl, piperidine-1-ylcarbonyl, piperidine-2-ylcarbonyl, piperidine-3-ylcarbonyl, azepan-1-ylcarbonyl, azepan-2-ylcarbonyl, azepan-3-ylcarbonyl, azepan-4-ylcarbonyl, azocan-1-ylcarbonyl, azocan-2-ylcarbonyl, azocan-3-ylcarbonyl, azocan-4-ylcarbonyl, 1,4-piperazine-1-ylcarbonyl, 1,4-piperazine-2-ylcarbonyl, 1,4-diazepan-1-ylcarbonyl, 1,4-diazepan-2-ylcarbonyl, 1,4-diazepan-5-ylcarbonyl, 1,4-diazepan-6-ylcarbonyl, 1,4-diazocan-1-ylcarbonyl, 1,4-diazocan-2-ylcarbonyl, 1,4-diazocan-5-ylcarbonyl, 1,4-diazocan-6-ylcarbonyl, 1,5-diazocan-1-ylcarbonyl, 1,5-diazocan-2-ylcarbonyl and 1,5-diazocan-3-ylcarbonyl.

Unless otherwise specifically stated, in this specification, examples of the "carboxy (group) that can be esterified" include carboxy, alkoxy-carbonyl which can be substituted, $C_{6-14}$ aryloxy-carbonyl which can be substituted, $C_{7-16}$ aralkyloxy-carbonyl which can be substituted, silyloxy-carbonyl which can be substituted (e.g., TMS-O—CO—, TES-O—CO—, TBS-O—CO—, TIPS-O—CO—, TBDPS-O—CO—, etc.)

Unless otherwise specifically stated, in this specification, examples of the "alkoxy-carbonyl (group)" include methoxycarbonyl, ethoxycarbonyl, propoxycarbonyl, and tert-butoxycarbonyl.

Unless otherwise specifically stated, in this specification, examples of the "$C_{6-14}$ aryloxy-carbonyl (group)" include phenoxycarbonyl.

Unless otherwise specifically stated, in this specification, examples of the "$C_{7-16}$ aralkyl-carbonyl (group)" include benzyloxycarbonyl and phenethyloxycarbonyl.

Unless otherwise specifically stated, in this specification, examples of the "alkylsulfonyl (group)" include $C_{1-10}$ alkylsulfonyl (group).

Unless otherwise specifically stated, in this specification, examples of the "$C_{1-10}$ alkylsulfonyl (group)" include methylsulfonyl and ethylsulfonyl.

Unless otherwise specifically stated, in this specification, examples of the "$C_{3-7}$ cycloalkylsulfonyl (group)" include cyclopropylsulfonyl, cyclobutylsulfonyl, cyclopentylsulfonyl and cyclohexylsulfonyl.

Unless otherwise specifically stated, in this specification, examples of the "$C_{6-14}$ arylsulfonyl (group)" include phenylsulfonyl, 1-naphthylsulfonyl and 2-naphthylsulfonyl.

Unless otherwise specifically stated, in this specification, examples, of the heterocyclic moiety of the "heterocyclic-sulfonyl (group)" include those similar to said "heterocyclic group". Specifically, examples of the "heterocyclic-sulfonyl (group)" include 5- to 14-membered heterocyclic-sulfonyl (group) having 1 to 5 hetero atoms selected from nitrogen, sulfur and oxygen Unless otherwise specifically stated, in this specification, examples of the saturated heterocyclic moiety of the "saturated heterocyclic-sulfonyl (group)" include those similar to said "heterocyclic group". Specifically, examples of the "heterocyclic-sulfonyl (group)" include 5- to 14-membered heterocyclic-sulfonyl (group) having 1 to 5 hetero atoms selected from nitrogen, sulfur and oxygen.

Unless otherwise specifically stated, in this specification, examples of the "alkylsulfinyl (group)" include $C_{1-10}$ alkylsulfinyl (group).

Unless otherwise specifically stated, in this specification, examples of the "$C_{1-10}$ alkylsulfinyl (group)" include methylsulfinyl and ethylsulfinyl.

Unless otherwise specifically stated, in this specification, examples of the "$C_{3-7}$ cycloalkylsulfinyl (group)" include cyclopropylsulfinyl, cyclobutylsulfinyl, cyclopentylsulfinyl, and cyclohexylsulfinyl.

Unless otherwise specifically stated, in this specification, examples of the "$C_{6-14}$ arylsulfinyl (group)" include phenylsulfinyl, 1-naphthylsulfinyl and 2-naphthylsulfinyl.

Unless otherwise specifically stated, in this specification, examples of the heterocyclic moiety of the "heterocyclic-sulfinyl (group)" include those similar to said "heterocyclic group". Specifically, examples of the "heterocyclic-sulfinyl (group)" include 5- to 14-membered heterocyclic-sulfinyl (group) having 1 to 5 hetero atoms selected from nitrogen, sulfur and oxygen.

Unless otherwise specifically stated, in this specification, examples of the "alkyl-carbamoyl (group)" include $C_{1-10}$ alkyl-carbamoyl (group).

Unless otherwise specifically stated, in this specification, examples of the "$C_{1-10}$ alkyl-carbamoyl (group)" include methylcarbamoyl, ethylcarbamoyl and propylcarbamoyl.

Unless otherwise specifically stated, in this specification, examples of the "mono- or di-alkylamino (group)" include mono- or di-$C_{1-10}$ alkylamino (group).

Unless otherwise specifically stated, in this specification, examples of the "mono- or di-$C_{1-10}$ alkylamino (group)" include methylamino, ethylamino, propylamino, dimethylamino and diethylamino.

Unless otherwise specifically stated, in this specification, examples of the "alkyl-carbonylamino (group)" include $C_{1-10}$ alkyl-carbonylamino.

Unless otherwise specifically stated, in this specification, examples of the $C_{1-10}$ alkyl-carbonylamino (group)" include acetylamino, propionylamino and pivaloylamino.

Unless otherwise specifically stated, in this specification, examples of the heterocyclic moiety of the "heterocyclic-amino (group)" those similar to said "heterocyclic group". Examples of the "heterocyclic-amino (group)" include 2-pyridyl-amino.

Unless otherwise specifically stated, in this specification, examples of the "heterocyclic-carbonyl" of the "heterocyclic-carbonylamino (group)" those similar to said "heterocyclic-carbonyl". Examples of the "heterocyclic-carbonylamino (group)" include pyridyl-carbonylamino.

Unless otherwise specifically stated, in this specification, examples of the "heterocyclic (group)" of the "heterocyclic-oxycarbonylamino (group)" include those similar to said "heterocyclic group". Examples of the "heterocyclic-oxycarbonylamino (group)" include 2-pyridyl-oxycarbonylamino.

Unless otherwise specifically stated, in this specification, examples of the "heterocyclic (group)" of the "heterocyclic-sulfonylamino (group)" include those similar to said "heterocyclic group". Examples of the "heterocyclic-sulfonylamino (group)" include 2-pyridyl-sulfonylamino.

Unless otherwise specifically stated, in this specification, examples of the "alkoxy-carbonylamino (group)" include $C_{1-10}$ alkoxy-carbonylamino.

Unless otherwise specifically stated, in this specification, the $C_{1-10}$ alkoxy-carbonylamino (group)" include methoxycarbonylamino, ethoxycarbonylamino, propoxycarbonylamino and butoxycarbonylamino.

Unless otherwise specifically stated, in this specification, examples of the "alkyl-sulfonylamino (group)" include $C_{1-10}$ alkyl-sulfonylamino.

Unless otherwise specifically stated, in this specification, examples of the "$C_{1-10}$ alkyl-sulfonylamino (group)" include methylsulfonylamino and ethylsulfonylamino.

Unless otherwise specifically stated, in this specification, examples of the "mono- or di-$C_{3-7}$ cycloalkylamino (group)" include cyclopropylamino, cyclopentylamino and cyclohexylamino.

Unless otherwise specifically stated, in this specification, examples of the "$C_{3-7}$ cycloalkyl-carbonylamino (group)" include cyclopropylcarbonylamino, cyclopentylcarbonylamino and cyclohexylcarbonylamino.

Unless otherwise specifically stated, in this specification, examples of the "$C_{3-7}$ cycloalkyloxy-carbonylamino (group)" include cyclopropoxycarbonylamino, cyclopentyloxycarbonylamino and cyclohexyloxycarbonylamino.

Unless otherwise specifically stated, in this specification, examples of the "$C_{3-7}$ cycloalkyl-sulfonylamino (group)" include cyclopropylsulfonylamino, cyclopentylsulfonylamino and cyclohexylsulfonylamino.

Unless otherwise specifically stated, in this specification, examples of the "mono- or di-$C_{6-14}$ arylamino (group)" include phenylamino and diphenylamino.

Unless otherwise specifically stated, in this specification, examples of the "mono- or di-$C_{7-16}$ aralkylamino (group)" include benzylamino.

Unless otherwise specifically stated, in this specification, examples of the "$C_{6-14}$ aryl-carbonylamino (group)" include benzoylamino and naphthoylamino.

Unless otherwise specifically stated, in this specification, examples of the "$C_{6-14}$ aryl-sulfonylamino (group)" include phenylsulfonylamino, 2-naphthylsulfonylamino and 1-naphthylsulfonylamino.

Symbols in the aforementioned formulas (Formula $I_o$) and Formula (I)) will be explained below.

In the aforementioned formula, $R^1$ represents a substituent.

Examples of the substituent represented by $R^1$ include substituents selected from the below described substituent group A.

[Substituent Group A]
(1) a halogen atoms;
(2) a nitro group;
(3) a cyano group;
(4) a carboxy group that can be esterified;
(5) an alkyl group which can be substituted;
(6) an alkenyl group which can be substituted;
(7) an alkynyl group which can be substituted (e.g., an $C_{3-7}$ cycloalkyl-$C_{2-6}$ alkynyl group which can be substituted;
(8) a $C_{3-7}$ cycloalkyl group which can be substituted;
(9) a $C_{6-14}$ aryl group which can be substituted;
(10) a $C_{7-16}$ aralkyl group which can be substituted;
(11) a $C_{6-14}$ aryl-$C_{2-6}$ alkenyl group which can be substituted;
(12) a heterocyclic group which can be substituted;
(13) a hydroxy group;

(14) an alkoxy group which can be substituted;
(15) a $C_{3-7}$ cycloalkyloxy group which can be substituted;
(16) a $C_{6-14}$ aryloxy group which can be substituted;
(17) a $C_{7-16}$ aralkyloxy group which can be substituted;
(18) an alkyl-carbonyloxy group which can be substituted;
(19) an alkoxy-carbonyloxy group which can be substituted;
(20) a mono-alkyl-carbamoyloxy group which can be substituted;
(21) a di-alkyl-carbamoyloxy group which can be substituted;
(22) a $C_{6-14}$ aryl-carbonyloxy group which can be substituted;
(23) a mono- or di-$C_{6-14}$ aryl-carbamoyloxy group which can be substituted;
(24) a heterocyclic-oxy group which can be substituted (e.g., aromatic heterocyclic-oxy group which can be substituted)
(25) a $C_{1-10}$ alkylsulfonyloxy (group)" which can be substituted (e.g., halogeno $C_{1-10}$ alkylsulfonyloxy (group) which can be substituted);
(26) a mercapto group;
(27) an alkylsulfanyl group which can be substituted;
(28) a $C_{3-7}$ cycloalkylsulfanyl group which can be substituted;
(29) a $C_{6-14}$ arylsulfanyl group which can be substituted;
(30) a $C_{7-16}$ aralkylsulfanyl group which can be substituted;
(31) a heterocyclic-sulfanyl group which can be substituted;
(32) a formyl group;
(33) an alkyl-carbonyl group which can be substituted;
(34) a $C_{3-7}$ cycloalkylcarbonyl group which can be substituted;
(35) a $C_{6-14}$ arylcarbonyl group which can be substituted;
(36) a $C_{7-16}$ aralkylcarbonyl group which can be substituted;
(37) a heterocyclic-carbonyl group which can be substituted;
(38) an alkylsulfonyl group which can be substituted;
(39) a $C_{3-7}$ cycloalkylsulfonyl group which can be substituted;
(40) a $C_{6-14}$ arylsulfonyl group which can be substituted;
(41) a heterocyclic-sulfonyl group which can be substituted;
(42) an alkylsulfinyl group which can be substituted;
(43) a $C_{3-7}$ cycloalkylsulfinyl group which can be substituted;
(44) a $C_{6-14}$ arylsulfinyl group which can be substituted;
(45) a heterocyclic-sulfinyl group which can be substituted;
(46) a sulfo group;
(47) a sulfamoyl group;
(48) a sulfinamoyl group;
(49) a sulfenamoyl group;
(50) a thiocarbamoyl group:
(51) a carbamoyl group which can be substituted [e.g., alkyl-carbamoyl group which can be substituted]
(52) an amino group which can be substituted [e.g., amino,
mono- or di-alkylamino group which can be substituted,
mono- or di-$C_{3-7}$ cycloalkylamino group which can be substituted,
mono- or di-$C_{6-14}$ arylamino group which can be substituted,
mono- or di-$C_{7-16}$ aralkylamino group which can be substituted,
heterocyclic amino group which can be substituted,
$C_{6-14}$ aryl-carbonylamino group which can be substituted,
formylamino,
alkyl-carbonylamino group which can be substituted (e.g., mono-($C_{1-10}$ alkyl-carbonyl)-amino group which can be substituted),
$C_{3-7}$ cycloalkyl-carbonylamino group which can be substituted,
heterocyclic-carbonylamino group which can be substituted,
$C_{3-7}$ cycloalkyloxy-carbonylamino group which can be substituted,
heterocyclic-oxycarbonylamino group which can be substituted,
carbamoylamino group which can be substituted,
alkylsulfonylamino group which can be substituted,
$C_{3-7}$ cycloalkyl-sulfonylamino group which can be substituted,
heterocyclic sulfonylamino group which can be substituted,
$C_{6-14}$ arylsulfonylamino group which can be substituted]
Among the aforementioned substituent group A, i.e., particularly,
the "alkoxy-carbonyl group which can be substituted",
the "alkyl group which can be substituted",
the "alkenyl group which can be substituted",
the "alkynyl group which can be substituted",
the "alkoxy group which can be substituted",
the "alkyl-carbonyloxy group which can be substituted",
the "alkoxy-carbonyloxy group which can be substituted",
the "mono-alkyl-carbamoyloxy group which can be substituted",
the "dialkyl-carbamoyloxy group which can be substituted",
the "alkylsulfanyl group which can be substituted",
the "alkylcarbonyl group which can be substituted",
the "alkylsulfonyl group which can be substituted",
the "alkylsulfinyl group which can be substituted",
the "alkyl-carbamoyl group which can be substituted",
the "mono- or di-alkylamino group which can be substituted",
the "alkyl-carbonylamino group which can be substituted",
the "mono-($C_{1-10}$ alkyl-carbonyl)-amino group which can be substituted"
the "alkoxy-carbonylamino group which can be substituted", and
the "alkylsulfonylamino group which can be substituted",
substituents thereof may be selected from, for example, the following substituent group B. The number of the substituents ranges from 1 to the maximum number which can be substituted, more preferably from 1 to 3 and further preferably 1.

[Substituent Group B]

Substituent group B consists of
(a) a halogen atom;
(b) a hydroxy group;
(c) a nitro group;
(d) a cyano group;
(e) a $C_{6-14}$ aryl group which can be substituted (the "$C_{6-14}$ aryl group" can be substituted with one or more substituents selected from halogen, hydroxy, cyano, amino, $C_{1-10}$ alkyl that can be halogenated, mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl and so on);

(f) a $C_{6-14}$ aryloxy group which can be substituted (the "$C_{6-14}$ aryloxy group" can be substituted with one or more substituents selected from halogen, hydroxy, cyano, amino, $C_{1-10}$ alkyl that can be halogenated, mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl and so on);

(g) a $C_{7-16}$ aralkyloxy group which can be substituted (the "$C_{7-16}$ aralkyloxy group" can be substituted with one or more substituents selected from halogen atoms, hydroxy, cyano, amino, $C_{1-10}$ alkyl that can be halogenated, mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl and so on);

(h) a mono- or di-5- to 10-membered heterocyclic group having 1 to 4 hetero atoms selected from nitrogen, sulfur and oxygen (e.g., furyl, pyridyl, thienyl, pyrrolidino, 1-piperidinyl, 4-piperidyl, piperazinyl, 1-morpholinyl, 4-thiomorpholinyl, azepan-1-yl, azocan-1-yl, azonan-1-yl, 3,4-dihydroisoquinoline-2-yl and the like) which can be substituted (the "mono- or di-5- to 10-membered heterocyclic group having 1 to 4 hetero atoms selected from nitrogen, sulfur and oxygen" can be substituted with one or more substituents selected from halogen, hydroxy, cyano, amino, $C_{1-10}$ alkyl that can be halogenated, mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl group and so on);

(i) an amino group which can be substituted [e.g., Amino group which can be substituted by one or two substituents selected from the group consisting of $C_{1-10}$ alkyl, $C_{2-6}$ alkenyl, $C_{6-14}$ aryl, $C_{7-16}$ aralkyl, heterocyclic group and heterocyclic-alkyl group (The $C_{1-10}$ alkyl, $C_{2-6}$ alkenyl, $C_{6-14}$ aryl, $C_{7-16}$ aralkyl, heterocyclic group and heterocyclic-alkyl group can be substituted with halogen atoms, hydroxy, cyano, amino, $C_{1-10}$ alkyl that can be halogenated (not the alkyl and alkenyl substituents), mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{3-7}$ cycloalkyloxy-carbonyl, $C_{6-14}$ aryloxy-carbonyl, $C_{7-16}$ aralkyloxy-carbonyl, $C_{1-10}$ alkylsulfanyl, $C_{3-7}$ cycloalkylsulfanyl, $C_{1-10}$ alkylsulfinyl, $C_{3-7}$ cycloalkylsulfinyl, $C_{1-10}$ alkylsulfonyl, $C_{3-7}$ cycloalkylsulfonyl, carbamoyl, thiocarbamoyl, mono- or di-$C_{1-10}$ alkylcarbamoyl, mono- or di-$C_{6-14}$ aryl-carbamoyl group). "Heterocyclic" and "heterocyclic" in "heterocyclic-alkyl" are the same as the aforementioned "heterocyclic group"];

(j) a $C_{3-7}$ cycloalkyl;

(k) a $C_{1-10}$ alkoxy which can be substituted (the "$C_{1-10}$ alkoxy" can be substituted with one or more substituents selected from halogen, hydroxy, amino, mono- or di-$C_{1-10}$ alkylamino, mono- or di-$C_{6-14}$ arylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl, and so on);

(l) a formyl;

(m) a $C_{1-10}$ alkyl-carbonyl (e.g., acetyl);

(n) a $C_{3-7}$ cycloalkyl-carbonyl;

(o) a $C_{6-14}$ aryl-carbonyl;

(p) a $C_{7-16}$ aralkyl-carbonyl;

(q) a $C_{1-10}$ alkoxy-carbonyl;

(r) a $C_{6-14}$ aryloxy-carbonyl;

(s) a $C_{7-16}$ aralkyloxy-carbonyl;

(t) a $C_{1-10}$ alkylsulfanyl;

(u) a $C_{1-10}$ alkylsulfinyl;

(v) a $C_{1-10}$ alkylsulfonyl;

(w) a carbamoyl;

(x) a thiocarbamoyl;

(y) a mono-$C_{1-10}$ alkylcarbamoyl (e.g., methylcarbamoyl, ethylcarbamoyl, etc.);

(z) a di-$C_{1-10}$ alkylcarbamoyl (e.g., dimethylcarbamoyl, diethylcarbamoyl, ethylmethylcarbamoyl, etc.);

(aa) a mono- or di-$C_{6-14}$ aryl-carbamoyl (e.g., phenylcarbamoyl, 1-naphthylcarbamoyl, 2-naphthylcarbamoyl, etc.); and (bb) a mono- or di-5- to 7-membered heterocyclic-carbamoyl having 1 to 4 hetero atoms selected from nitrogen, sulfur and oxygen (e.g., 2-pyridylcarbamoyl, 3-pyridylcarbamoyl, 4-pyridylcarbamoyl, 2-thienylcarbamoyl, 3-thienylcarbamoyl, etc.).

Among the aforementioned substituent group A, i.e., particularly, the "$C_{6-14}$ aryloxy-carbonyl which can be substituted", the "$C_{7-16}$ aralkyloxy-carbonyl which can be substituted", the "$C_{3-7}$ cycloalkyl-$C_{2-6}$ alkynyl which can be substituted", the "$C_{3-7}$ cycloalkyl which can be substituted", the "$C_{6-14}$ aryl which can be substituted", the "$C_{7-16}$ aralkyl which can be substituted", the "$C_{6-14}$ aryl-$C_{2-6}$ alkenyl which can be substituted", the "heterocyclic group which can be substituted", the "$C_{3-7}$ cycloalkyloxy which can be substituted", the "$C_{6-14}$ aryloxy which can be substituted", the "$C_{7-16}$ aralkyloxy which can be substituted", the "$C_{6-14}$ aryl-carbonyloxy which can be substituted";

the "mono- or di-$C_{6-14}$ aryl-carbamoyloxy which can be substituted", the "heterocyclic-oxy which can be substituted", the "aromatic heterocyclic-oxy which can be substituted", the "$C_{3-7}$ cycloalkylsulfanyl which can be substituted", the "$C_{6-14}$ arylsulfanyl which can be substituted", the "$C_{7-16}$ aralkylsulfanyl which can be substituted", the "heterocyclic-sulfanyl which can be substituted", the "$C_{3-7}$ cycloalkyl-carbonyl which can be substituted", the "$C_{6-14}$ aryl-carbonyl which can be substituted", the "$C_{7-16}$ aralkyl-carbonyl which can be substituted", the "heterocyclic-carbonyl which can be substituted", the "$C_{3-7}$ cycloalkylsulfonyl which can be substituted", the "$C_{6-14}$ arylsulfonyl which can be substituted", the "heterocyclic-sulfonyl which can be substituted", the "$C_{3-7}$ cycloalkylsulfinyl which can be substituted", the "$C_{6-14}$ arylsulfinyl which can be substituted", the "heterocyclic-sulfinyl which can be substituted",
the "carbamoyl group which can be substituted",
the "amino group which can be substituted",
the "mono- or di-$C_{3-7}$ cycloalkylamino group which can be substituted,
the "mono- or di-$C_{6-14}$ arylamino group which can be substituted,
the "mono- or di-$C_{7-16}$ aralkylamino group which can be substituted,
the "heterocyclic amino group which can be substituted,
the "$C_{6-14}$ aryl-carbonylamino group which can be substituted,
the "$C_{3-7}$ cycloalkyl-carbonylamino group which can be substituted,
the "heterocyclic-carbonylamino group which can be substituted,
the "$C_{3-7}$ cycloalkyloxy-carbonylamino group which can be substituted,
the "heterocyclic-oxycarbonylamino group which can be substituted,
the "carbamoylamino group which can be substituted,
the "alkylsulfonylamino group which can be substituted,
the "$C_{3-7}$ cycloalkyl-sulfonylamino group which can be substituted,
the "heterocyclic sulfonylamino group which can be substituted, and
the "$C_{6-14}$ arylsulfonylamino group which can be substituted,
substituents thereof may be selected from, for example, the aforementioned substituent group B and the following substituent group B'. The number of substituents ranges from 1 to the maximum number which can be substituted, more preferably from 1 to 3 substituents and further preferably 1 substituent.

[Substituent Group B']
Substituent group B' consists of
(a) $C_{1-10}$ alkyl, which can be substituted by one or more substituents selected from halogen, hydroxy, cyano, amino, mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl, and so on;

(b) $C_{2-6}$ alkenyl, which can be substituted by one or more substituents selected from halogen, hydroxy, cyano, amino, mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl, and so on; and (c) $C_{2-6}$ alkynyl, which can be substituted by one or more substituents selected from halogen atoms, hydroxy, cyano, amino, mono- or di-$C_{1-10}$ alkylamino, mono- or di-$C_{6-14}$ arylamino, mono- or di-$C_{7-16}$ aralkylamino, $C_{3-7}$ cycloalkyl, $C_{1-10}$ alkoxy, formyl, $C_{1-10}$ alkyl-carbonyl, $C_{3-7}$ cycloalkyl-carbonyl, $C_{6-14}$ aryl-carbonyl, $C_{7-16}$ aralkyl-carbonyl, $C_{1-10}$ alkoxy-carbonyl, $C_{6-14}$ aryloxy-carbonyl, $C_{7-16}$ aralkyloxy-carbonyl, $C_{1-10}$ alkylsulfanyl, $C_{1-10}$ alkylsulfinyl, $C_{1-10}$ alkylsulfonyl, carbamoyl, thiocarbamoyl, mono- or di-$C_{1-10}$ alkylcarbamoyl, mono- or di-$C_{6-14}$ aryl-carbamoyl group, and so on.

Among them, $R^1$ is, for example, preferably
an alkyl group which can be substituted,
a $C_{3-7}$ cycloalkyl group which can be substituted,
a $C_{6-14}$ aryl group which can be substituted,
a non-aromatic heterocyclic group which can be substituted, or
a heterocyclic group which can be substituted.
Among them, specifically, $R^1$ is, for example,
preferably a phenyl group which can be substituted by 1 to 5 substituents selected from a halogen atom, a $C_{1-10}$ alkyl group which can be substituted, a $C_{1-10}$ alkoxy group which can be substituted,
more preferably a phenyl group which can be substituted by 1 to 5 substituents selected from a halogen atom, a $C_{1-10}$ alkyl group, and a $C_{1-10}$ alkoxy group, and
further preferably a phenyl group which can be substituted by 1 to 5 halogen atoms.

In another aspect of the present invention, as $R^1$, in particular, for example,
a 5- or 6-membered aromatic group (preferably phenyl group, pyridyl group) which can be substituted by one or more substituents selected from
a halogen atom (preferably, a chlorine atom, a fluorine atom),
a cyano group,
a hydroxy group,
an alkyl group (preferably, methyl group, isobutyl group) which can be substituted,
an alkoxy group (preferably methoxy group) which can be substituted,
an alkylsulfanyl group which can be substituted,
an alkylsulfinyl group which can be substituted,
an alkylsulfonyl group which can be substituted, and
an amino group which can be substituted
are preferable.
The number of substituents ranges from 1 to the maximum number which can be substituted, more preferably from 1 to 3 substituents and further preferably 1 substituent.

In particular, for example, aromatic group which can be substituted are desirable as $R^1$. The "aromatic group which can be substituted" include "$C_{6-14}$ aryl which can be substituted" and "heteroaryl which can be substituted" among the substituents listed above.

$R^1$ is, for example, preferably a phenyl group which is substituted by one or more
(preferably, 1 to 5) substituents selected from
(a) $C_{1-10}$ alkyl group (e.g., isopropyl, isobutyl), and
(b) halogen atoms (e.g., chlorine, fluorine), $C_{1-10}$ alkyl group (e.g., methyl), $C_{1-10}$ alkoxy group (e.g., methoxy).
In the aforementioned formula, $R^2$ represents a hydrogen atom or a substituent.
Examples of the substituent represented by $R^2$ include substituents selected from the aforementioned substituent group A.

Among them, $R^2$ is, for example, preferably
a halogen atom,
a hydroxy group,
an alkyl group which can be substituted, or
an alkoxy group which can be substituted.
Among them, specifically, $R^2$ is, for example,
preferably a halogen atom, a hydroxy group, a $C_{1-10}$ alkyl group which can be substituted, or a $C_{1-10}$ alkoxy group which can be substituted,
more preferably a $C_{1-10}$ alkoxy group which can be substituted by one or more substituents selected from a halogen atom, a $C_{1-10}$ alkoxy group, and a $C_{3-7}$ cycloalkyl group, and
further preferably a $C_{1-10}$ alkoxy group.

In another aspect of the present invention, as $R^2$, in particular, for example,
(i) a hydrogen atom,
(ii) a halogen atom,
(iii) a hydroxy group,
(iv) an alkyl group which can be substituted by one or more substituents selected from halogen atoms, hydroxy group, amino group, and alkoxy group,
(v) an amino group that can be mono- or di-substituted with alkyl group, or
(vi) an alkoxy group which can be substituted by one or more substituents selected from cyano group, amino group, alkoxy group, hydroxy group, halogen atoms and $C_{3-7}$ cycloalkyl group
is preferable, and, for example,
(i) a hydrogen atom,
(ii) a hydroxy group,
(iii) a $C_{1-10}$ alkyl group (e.g., methyl), or
(iv) a $C_{1-10}$ alkoxy group (e.g., methoxy, ethoxy, isopropoxy, cyclopropylmethoxy, difluoromethoxy) which can be substituted by one or more substituents selected from halogen atoms and $C_{3-7}$ cycloalkyl group
is more preferable.

In the aforementioned formula, $R^3$ represents a hydrogen atom or a substituent.

Examples of the substituents represented by $R^3$ include substituents selected from the aforementioned substituent group A.

Among them, $R^3$ is, for example, preferably
a halogen atom,
a hydroxy group,
an alkyl group which can be substituted, or
an alkoxy group which can be substituted.
Among them, specifically, $R^3$ is, for example,
preferably a hydrogen atom, or a $C_{1-10}$ alkoxy group which can be substituted,
more preferably a hydrogen atom, or a $C_{1-10}$ alkoxy group, and
further preferably a hydrogen atom.

In another aspect of the present invention, as $R^3$, in particular, for example,
(i) hydrogen atom,
(ii) halogen atoms,
(iii) alkyl group which can be substituted by one or more substituents selected from halogen atoms, hydroxy group, amino group, and alkoxy group,
(iv) amino group that can be mono- or di-substituted with alkyl group, or
(vi) alkoxy group, and for example,
is preferable, and, for example,
a hydrogen atom and a $C_{1-10}$ alkyl group (e.g., methyl)
is more preferable.

In the aforementioned formula, Ring A represents an aromatic ring which can be substituted.

The "aromatic ring" of the "aromatic ring which can be substituted" is preferably a 5 to 16-membered aromatic ring, more preferably a 5 to 6-membered aromatic ring, and further preferably a 6-membered aromatic ring.

The "aromatic ring" of the "aromatic ring which can be substituted" represented by the ring A, for example, includes (i) an aromatic cyclic hydrocarbon, (ii) an aromatic heterocyclic ring containing 1 to 4 heteroatoms selected from nitrogen, oxygen and sulfur.

Said "(i) aromatic cyclic hydrocarbon, for example, includes $C_{6-14}$ aromatic cyclic hydrocarbons such as benzene, naphthalene, anthracene, phenanthrene, acenaphthylene (preferably $C_{6-12}$ aromatic cyclic hydrocarbons, particularly benzene is preferable).

Said "(ii) aromatic heterocyclic ring containing 1 to 4 hetero atoms selected from nitrogen, oxygen, and sulfur, for example, includes 5- or 6-membered aromatic monocyclic type heterocyclic rings such as furan, thiophene, pyrrole, 1,3-oxazole, isoxazole, 1,3-thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, 1,2,3-triazine, 1,3,5-triazine, 1,2,4-triazine, 1,2,3,4-tetrazine, 1,2,3,5-tetrazine, 1,2,4,5-tetrazine and the like; and
8 to 16-membered (preferably 8 to 12-membered) aromatic condensed heterocyclic rings (preferably heterocyclic rings formed by condensation of 1 to 2 said 5- to 6-membered aromatic monocyclic heterocyclic rings (preferably 1 ring) with 1 to 2 benzene rings (preferably 1 ring), or heterocyclic rings formed by condensation of 2 to 3 said identical 5- to 6-membered aromatic monocyclic heterocyclic rings or different heterocyclic rings) such as benzofuran, isobenzofuran, benzothiophene, indole, isoindole, 1H-indazole, benzimidazole, benzoxazole, benzisoxazole, benzothiazole, benzisothiazole, 1H-benzotriazole, quinoline, isoquinoline, cinnoline, quinazoline, quinoxaline, phthalazine, naphthyridine, purine, pteridine, carbazole, α-carboline, β-carboline, γ-carboline, acridine, phenoxazine, phenothiazine, phenazine, phenoxathiin, thianthrene, phenanthridine, phenanthroline, indolizine, pyrrolopyridine, pyrrolo[1,2-b]pyridazine,
1H-pyrrolo[2,3-b]pyrazine, pyrazolo[1,5-a]pyridine, imidazo[1,2-a]pyridine, imidazo[1,2-b]pyridazine, imidazo[1,2-a]pyrimidine, 1,2,4-triazolo[4,3-a]pyridine, 1,2,4-triazolo[4,3-b]pyridazine and the like).

When the "(ii) aromatic heterocyclic ring containing 1 to 4 hetero atoms selected from nitrogen, oxygen, and sulfur contains nitrogen, the aromatic heterocyclic ring can form an N-oxide.

Among them, preferred is benzene, pyridine, pyridazine, pyrimidine, pyrazine, pyridine N-oxide, 1,2,3-triazine, 1,3,5-triazine, 1,2,4-triazine, 1,2,3,4-tetrazine, 1,2,3,5-tetrazine, 1,2,4,5-tetrazine, pyrrole, furan, thiophene, pyrazole, imidazole, isoxazole, isothiazole, 1,3-oxazole, 1,3-thiazole, 1,2,3-triazole, 1,2,4-triazole, tetrazole, 1,2,3-oxadiazole, 1,2,3-thiadiazole, naphthalene, quinoline, quinazoline, quinoxaline, benzofuran, benzothiophene, benzoxazole, benzothiazole, benzimidazole, indole, 1H-indazole, 1H-pyrrolo[2,3-b]pyrazine, 1H-pyrrolopyridine, 1H-imidazopyridine, 1H-imidazopyrazine, triazine, isoquinoline, benzothiadiazole, benzisoxazole, benzisothiazole, indazole, purine, isoquinoline, phthalazine, naphthyridine, cinnoline, pteridine or the like, especially preferred is, for example, benzene or pyridine, and most preferred is benzene.

The substituents of the "aromatic ring which can be substituted" as represented by the ring A, for example, include the substituents selected from the aforementioned substituent group A.

In particular, preferred examples of the substituents of the "aromatic ring which can be substituted" include
(1) a halogen atom,
(2) a $C_{1-10}$ alkyl group which can be substituted,
(3) a $C_{1-10}$ alkoxy group which can be substituted,
(4) a 4- to 6-membered heterocyclic group containing 0 or 1 oxygen atom, and 1 to 3 nitrogen atoms as heteroatoms which can be substituted,
(5) a $C_{1-10}$ alkylsulfonyl group which can be substituted,
(6) a $C_{3-7}$ cycloalkyl group which can be substituted, (7) a cyano group, (8) a carbamoyl group which can be substituted, (9) a $C_{1-10}$ alkylsulfonyloxy group which can be substituted,

(10) a $C_{3-7}$ cycloalkyl-$C_{2-6}$ alkynyl group which can be substituted,

(11) a tetrahydropyranyl group which can be substituted,

(12) a dihydropyranyl group which can be substituted,

(13) a mono-($C_{1-10}$ alkyl-carbonyl)-amino group which can be substituted,

(14) a $C_{1-10}$ alkoxy-carbonyl group which can be substituted,

(15) a $C_{1-10}$ alkylsulfinyl group which can be substituted,

(16) a $C_{1-10}$ alkylsulfanyl group which can be substituted, and so on.

As it is apparent for a person of ordinary skill in the art, the "4- to 6-membered heterocyclic group containing 0 or 1 oxygen atom, and 1 to 3 nitrogen atoms as heteroatoms" of the "4- to 6-membered heterocyclic group containing 0 or 1 oxygen atom, and 1 to 3 nitrogen atoms as heteroatoms which can be substituted" is included in the "heterocyclic group" of the "heterocyclic group which can be substituted".

The number of substituents preferably ranges from 1 to 5.

The number of the substituents of the "heterocyclic group which can be substituted" is one or more, preferably in the range of 1 to 5, more preferably in the range of 1 to 3, further preferably one or two.

When the number of the substituents is two or more, the substituents on the Ring A can be combined to form a ring which can be substituted. The "ring" of the "ring which can be substituted" include a 5- to 6-membered heterocyclic ring containing one nitrogen atom or two oxygen atoms as heteroatoms.

The "ring" can be substituted by one or more (preferably, 1 to 5) substituents selected from the Substituent group A.

In another aspect of the present invention, preferred examples of the substituents of the "aromatic ring which can be substituted" represented by Ring A include a halogen atoms (preferably halogen atom)

a cyano group, a hydroxy group, an alkyl group which can be substituted (preferably $C_{1-10}$ alkyl group which can be substituted by 1 to 3 halogen atoms [e.g., trifluoromethyl group]), a alkoxy group which can be substituted (preferably $C_{1-10}$ alkoxy group which can be substituted by 1 to 3 halogen atoms [e.g., methoxy group, difluoromethoxy group]), a carbamoyl group a heterocyclic-oxy group (preferably 5- to 10-membered heterocyclic-oxy group containing 1 to 3 hetero atoms selected from nitrogen, oxygen and sulfur [e.g., benzimidazolyloxy group]), an alkylsulfanyl group which can be substituted, an alkylsulfinyl group which can be substituted, an alkylsulfonyl group which can be substituted (preferably $C_{1-10}$ alkylsulfonyl group [e.g., methylsulfonyl group]), a heterocyclic-sulfonyl group (preferably 5- to 6-membered saturated heterocyclic-sulfonyl group containing 1 to 3 hetero atoms selected from nitrogen, oxygen and sulfur [e.g., morpholinylsulfonyl group]), an amino group which can be substituted, a cycloalkyl group (preferably $C_{3-7}$ cycloalkyl [e.g., cyclohexyl]) and saturated heterocyclic group (preferably 5- to 6-membered saturated heterocyclic group containing 1 to 3 hetero atoms selected from nitrogen, oxygen and sulfur [e.g., morpholinyl group and piperidyl group]).

Ring A is, for example, preferably a benzene ring which can be substituted by 1 to 5 substituents selected from (1) a halogen atom, (2) a $C_{1-10}$ alkyl group which can be substituted, (3) a $C_{1-10}$ alkoxy group which can be substituted, (4) a $C_{3-7}$ cycloalkyl group, (5) a halogeno $C_{1-10}$ alkylsulfonyloxy group, (6) a $C_{3-7}$ cycloalkyl-$C_{2-6}$ alkynyl group, and (7) a 4- to 6-membered heterocyclic group containing 0 or 1 oxygen atom, and 1 to 3 nitrogen atoms as heteroatoms which can be substituted by one or more substituents selected from a halogen atom, a hydroxy group, an oxo group, a $C_{1-10}$ alkoxy-carbonyl group, a $C_{1-10}$ alkoxy group which can be substituted, and a $C_{1-10}$ alkyl group which can be substituted.

Ring A is, for example, more preferably a benzene ring which can be substituted by 1 to 5 substituents selected from (1) a halogen atom, (2) a $C_{1-10}$ alkyl group which can be substituted by 1 to 3 halogen atoms, (3) a $C_{1-10}$ alkoxy group which can be substituted by 1 to 3 halogen atoms, (4) a $C_{3-7}$ cycloalkyl group, (5) a halogeno $C_{1-10}$ alkylsulfonyloxy group, (6) a $C_{3-7}$ cycloalkyl-$C_{2-6}$ alkynyl group, and (7) a 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen.

Ring A is, for example, further preferably a benzene ring which is substituted with (1) (i) 1 or 2 halogen atoms, or (ii) one $C_{1-10}$ alkoxy group, and (2) one 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen.

Here, as the "one 4- to 6-membered heterocyclic group containing 0 or 1 oxygen atom, and 1 to 3 nitrogen atoms as heteroatoms", for example, preferred is a morpholino group, a pyrrolyl group, a dihydropyrrolyl group, a pyrazolyl group, a dihydropyrazolyl group, a piperidyl group, an azetidinyl group, a pyrrolidinyl group, an oxazolidinyl group, an imidazolyl group or an imidazolidinyl group.

In another aspect of the present invention, as ring A, in particular, for example, preferred is a 5- to 6-membered aromatic group which can be substituted by one or more substituents selected from halogen atoms, cyano group, hydroxy group, alkyl group which can be substituted, alkoxy group which can be substituted, carbamoyl group, alkylsulfanyl group which can be substituted, alkylsulfinyl group which can be substituted, alkylsulfonyl group which can be substituted, heterocyclic-sulfonyl group, amino group which can be substituted, cycloalkyl group, and saturated heterocyclic group, and further specifically, preferred is a 5- to 6-membered aromatic group (e.g., phenyl, pyridyl) which can be substituted by one or more substituents selected from (a) a halogen atom (e.g., chlorine, fluorine), (b) a Cyano group, (c) a $C_{1-10}$ alkyl group which can be substituted by 1 to 3 halogen atoms (e.g., methyl, trifluoromethyl),
(d) a $C_{3-7}$ cycloalkyl group (e.g., methyl, trifluoromethyl),
(e) a $C_{1-10}$ alkoxy group which can be substituted by 1 to 3 halogen atoms (e.g., difluoromethoxy, methoxy),
(f) a 5- to 10-membered heterocyclic group containing 1 to 3 hetero atoms selected from nitrogen, oxygen and sulfur (e.g., morpholinyl, benzimidazolyl, piperidinyl),
(g) a $C_{1-10}$ alkyl-sulfonyl group (e.g., methylsulfonyl),
(h) a 5- to 10-membered heterocyclic-sulfonyl group containing 1 to 3 hetero atoms selected from nitrogen, oxygen and sulfur (e.g., morpholinylsulfonyl), and
(i) a carbamoyl group.

In the aforementioned formula, the ring B represents a "5-membered aromatic heterocyclic ring which can be substituted".

Examples of the "5-membered aromatic heterocyclic ring which can be substituted" represented by the ring B include 5-membered aromatic heterocyclic rings containing 1 to 4 hetero atoms (preferably 1 to 2 atoms) selected from nitrogen, oxygen and sulfur such as pyrrole, furan, thiophene, pyrazole, imidazole, isoxazole, isothiazole, 1,3-oxazole, 1,3-thiazole, triazole (e.g., 1,23-triazole, 1,2,4-triazole), tetrazole, oxadiazole (e.g., 1,2,3-oxadiazole), and thiadiazole (e.g., 1,2,3-thiadiazole). Among them, pyrazole, triazole, and tetrazole are preferable, and pyrazole is most preferable.

As the substituents of the "5-membered aromatic heterocyclic represented by the ring B, for example, the substituents selected from the aforementioned substituent group A can be included.

Preferable examples of the substituents include a halogen atom, an alkyl group which can be substituted and a $C_{6-14}$ aryl group which can be substituted, more preferable examples thereof include a halogen atom, an alkyl group, and a $C_{6-14}$ aryl group, further preferable examples thereof include an alkyl group (e.g., methyl).

Also preferably, the ring B does not have such a substituent. In other words, the ring B has only substituents shown in the general formula of $(I_0)$.

The ring B is preferably a 5-membered nitrogen-containing aromatic heterocyclic ring having 1 to 3 hetero atoms selected from nitrogen, oxygen and sulfur, which can be substituted by a $C_{1-10}$ alkyl group (e.g., methyl) (e.g., pyrazole, triazole, tetrazole).

As the Ring B, preferred is an imidazole ring, a pyrazole ring, a triazole ring or a tetrazole ring, each of which can be further substituted with 1 to 3 substituents selected from a halogen atom, and a $C_{1-10}$ alkyl group which can be substituted by halogen, more preferred is a pyrazole ring which can be further substituted with 1 to 3 substituents selected from a halogen atom, and a $C_{1-10}$ alkyl group which can be substituted by halogen, especially preferred is a pyrazole ring.

In another aspect of the present invention, the ring B is preferably a 5-membered nitrogen-containing aromatic heterocyclic ring having 1 to 3 nitrogen atoms (e.g., pyrazole, triazole, tetrazole), which can be substituted by a $C_{1-10}$ alkyl group (e.g., methyl)

Further preferably, examples of the substituents, moieties and rings as explained in the present specification are used in combination.

For example, the following compounds, i.e., compounds $(I_0\text{-A})$; $(I_0\text{-B})$, $(I_0\text{-C})$, $(I_0\text{-D})$, $(I_0\text{-E})$, $(I_0\text{-F})$, and $(I_0\text{-G})$ are preferable as a compound $(I_o)$.

[Compound $(I_0\text{-A})$]
The above described compound $(I_0)$, wherein
$R^1$ represents
a phenyl group which can be substituted by 1 to 5 substituents selected from a halogen atom, a $C_{1-10}$ alkyl group which can be substituted, and a $C_{1-10}$ alkoxy group which can be substituted,
$R^2$ represents
a halogen atom, a hydroxy group, a $C_{1-10}$ alkyl group which can be substituted, or a $C_{1-10}$ alkoxy group which can be substituted,
$R^3$ represents
a hydrogen atom, or a $C_{1-10}$ alkoxy group which can be substituted,
Ring A represents
a benzene ring which can be substituted by 1 to 5 substituents selected from
(1) a halogen atom,
(2) a $C_{1-10}$ alkyl group which can be substituted,
(3) a $C_{1-10}$ alkoxy group which can be substituted,
(4) a 4- to 6-membered heterocyclic group containing 0 or 1 oxygen atom, and 1 to 3 nitrogen atoms as heteroatoms which can be substituted,
(5) a $C_{1-10}$ alkylsulfonyl group which can be substituted,
(6) a $C_{3-7}$ cycloalkyl group which can be substituted,
(7) a cyano group,
(8) a carbamoyl group which can be substituted,
(9) a $C_{1-10}$ alkylsulfonyloxy group which can be substituted,
(10) a $C_{3-7}$ cycloalkyl-$C_{2-6}$ alkynyl group which can be substituted,
(11) a tetrahydropyranyl group which can be substituted,
(12) a dihydropyranyl group which can be substituted,
(13) a mono-($C_{1-10}$ alkyl-carbonyl)-amino group which can be substituted,
(14) a $C_{1-10}$ alkoxy-carbonyl group which can be substituted,
(15) a $C_{1-10}$ alkylsulfinyl group which can be substituted, and
(16) a $C_{1-10}$ alkylsulfanyl group which can be substituted, and
Ring B represents
an imidazole ring, pyrazole ring, a triazole ring or a tetrazole ring, each of which can be further substituted with 1 to 3 substituents selected from a halogen atom, and a $C_{1-10}$ alkyl group which can be substituted by halogen.

[Compound $(I_0\text{-B})$]
The above described compound $(I_0\text{-A})$, wherein
Ring A represents
a benzene ring which can be substituted by 1 to 5 substituents selected from
(1) a halogen atom,
(2) a $C_{1-10}$ alkyl group which can be substituted,
(3) a $C_{1-10}$ alkoxy group which can be substituted,
(4) a $C_{3-7}$ cycloalkyl group,
(5) a halogeno $C_{1-10}$ alkylsulfonyloxy group,
(6) a $C_{3-7}$ cycloalkyl-$C_{2-6}$ alkynyl group, and
(7) a 4- to 6-membered heterocyclic group containing 0 or 1 oxygen atom, and 1 to 3 nitrogen atoms as heteroatoms which can be substituted by one or more substituents selected from a halogen atom, a hydroxy group, an oxo group, a $C_{1-10}$ alkoxy-carbonyl group, a $C_{1-10}$ alkoxy group which can be substituted, and a $C_{1-10}$ alkyl group which can be substituted.

[Compound $(I_0\text{-C})$]
The above described compound $(I_0)$, wherein
$R^1$ represents
a phenyl group which can be substituted by 1 to 5 substituents selected from a halogen atom, a $C_{1-10}$ alkyl group, and a $C_{1-10}$ alkoxy group, R² represents a $C_{1-10}$ alkoxy group which can be substituted by one or more substituents selected from a halogen atom, a $C_{1-10}$ alkoxy group, and a $C_{3-7}$ cycloalkyl group, R³ represents a hydrogen atom, or a $C_{1-10}$ alkoxy group, Ring A represents a benzene ring which can be substituted by 1 to 5 substituents selected from (1) a halogen atom,
(2) a $C_{1-10}$ alkyl group which can be substituted by 1 to 3 halogen atoms,
(3) a $C_{1-10}$ alkoxy group which can be substituted by 1 to 3 halogen atoms,
(4) a $C_{3-7}$ cycloalkyl group,
(5) a halogeno $C_{1-10}$ alkylsulfonyloxy group,
(6) a $C_{3-7}$ cycloalkyl-$C_{2-6}$ alkynyl group, and
(7) a 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen, Ring B represents a pyrazole ring which can be further substituted with 1 to 3 substituents selected from a halogen atom, and a $C_{1-10}$ alkyl group which can be substituted by halogen.

[Compound ($I_0$-D)]

The above described compound ($I_0$), wherein

R¹ represents a phenyl group which can be substituted by 1 to 5 halogen atoms,

R² represents a $C_{1-10}$ alkoxy group,

R³ represents a hydrogen atom,

Ring A represents a benzene ring which is substituted with (1) (i) 1 or 2 halogen atoms, or (ii) one alkoxy group, and
(2) one 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, a $C_{1-10}$ alkoxy-carbonyl group, a $C_{1-10}$ alkoxy group which can be substituted by halogen, and a $C_{1-10}$ alkyl group which can be substituted by halogen, Ring B represents a pyrazole ring.

Here, as the "one 4- to 6-membered heterocyclic group containing 0 or 1 oxygen atom, and 1 to 3 nitrogen atoms as heteroatoms", for example, preferred is a morpholino group, a pyrrolyl group, a dihydropyrrolyl group, a pyrazolyl group, a dihydropyrazolyl group, a piperidyl group, an azetidinyl group, a pyrrolidinyl group, an oxazolidinyl group, an imidazolyl group or an imidazolidinyl group.

[Compound ($I_0$-E)]

The above described compound ($I_0$), wherein

R¹ represents an aromatic group which can be substituted,

Ring A represents an aromatic ring which is substituted with (a) one substituent selected from
(1) a $C_{3-7}$ cycloalkyl group which can be substituted, and
(2) a 4- to 6-membered heterocyclic group containing 1 to 5 heteroatoms selected from a nitrogen atom, a sulfur atom, and an oxygen atom which can be substituted, and
(b) one or more further substituents.

Here, especially preferably, the further substituents are 1 to 4 substituents selected from (1) a halogen atom,
(2) an oxo group,
(3) a hydroxy group,
(4) a $C_{1-10}$ alkyl group which can be substituted,
(5) a $C_{1-10}$ alkoxy group which can be substituted,
(6) a $C_{1-10}$ alkylsulfonyl group,
(7) a morpholin-4-yl sulfonyl group,
(8) a cyano group,
(9) a carbamoyl group,
(10) a halogeno $C_{1-10}$ alkylsulfonyloxy group,
(11) a $C_{3-7}$ cycloalkyl-$C_{2-6}$ alkynyl group,
(12) a di-$C_{1-10}$ alkyl-amino group,
(13) a mono-($C_{1-10}$ alkyl-carbonyl)-amino group,
(14) a $C_{1-10}$ alkoxy-carbonyl group,
(15) a phenoxy group,
(16) a $C_{1-10}$ alkylsulfinyl group,
17 a benzimidazole-2-yloxy group, and
(18) a benzimidazole-2-yl sulfonyl group.

[Compound ($I_0$-F)]

The above described compound ($I_0$-E), wherein

R¹ represents a phenyl group which can be substituted,

R² represents a hydrogen atom, a halogen atom, a hydroxy group, a $C_{1-10}$ alkyl group which can be substituted, or a $C_{1-10}$ alkoxy group which can be substituted, R³ represents a hydrogen atom, or a $C_{1-10}$ alkoxy group which can be substituted, Ring A represents a benzene ring which is substituted with one substituent selected from (1) a $C_{3-7}$ cycloalkyl group which can be substituted,
(2) a dihydropyranyl group which can be substituted,
(3) a tetrahydropyranyl group which can be substituted, and
(4) a 4- to 6-membered heterocyclic group containing 0 or 1 oxygen atom, and 1 to 3 nitrogen atoms as heteroatoms which can be substituted, and can be substituted by further substituents, and Ring B represents an imidazole ring, a pyrazole ring, a triazole ring, a tetrazole ring, an isoxazole ring, an 1,3-oxazole ring, a furan ring, or a thiophene ring, each of which can be substituted.

Here, as the "one 4- to 6-membered heterocyclic group containing 0 or 1 oxygen atom, and 1 to 3 nitrogen atoms as heteroatoms", for example, preferred is a morpholino group, a pyrrolyl group, a dihydropyrrolyl group, a pyrazolyl group, a dihydropyrazolyl group, a piperidyl group, an azetidinyl group, a pyrrolidinyl group, an oxazolidinyl group, an imidazolyl group, an imidazolidinyl group, an isoxazolyl group, a pyridyl group, a piperazinyl group, or a thiazolyl group.

[Compound ($I_0$-G)]

The Compound ($I_0$-E), or the Compound ($I_0$-F), wherein

R¹ represents a phenyl group which can be substituted by 1 to 5 halogen atoms,

R² represents a hydrogen atom or a $C_{1-10}$ alkoxy group,

R³ represents a hydrogen atom,

Ring A represents a benzene ring, which is substituted with one 4- to 6-membered heterocyclic group containing 0 or 1 oxygen atom, and 1 to 3 nitrogen atoms as heteroatoms which can be substituted by 1 to 4 substituents selected from a halogen atom, a hydroxy group, an oxo group, halogeno $C_{1-10}$ alkoxy group, a $C_{1-10}$ alkoxycarbonyl, and a $C_{1-10}$ alkyl group which can be substituted by halogen, and which can be further substituted with 1 or 2 substituents selected from a halogen atom and a $C_{1-10}$ alkoxy group, and Ring B represents
a pyrazole ring.

Here, as the "one 4- to 6-membered heterocyclic group containing 0 or 1 oxygen atom, and 1 to 3 nitrogen atoms as heteroatoms", for example, preferred is a morpholino group, a pyrrolyl group, a dihydropyrrolyl group, a pyrazolyl group, a dihydropyrazolyl group, a piperidyl group, an azetidinyl group, a pyrrolidinyl group, an oxazolidinyl group, an imidazolyl group or an imidazolidinyl group.

In another aspect of the present invention, the following compounds, i.e., compounds ($I_O$-H) and ($I_O$-I) are preferable as a compound ($I_O$).

[Compound ($I_O$-H)]
Compound ($I_O$), wherein
wherein
$R^1$ represents alkyl group which can be substituted, alkoxy group which can be substituted, cycloalkyl group which can be substituted, or aromatic group which can be substituted,
$R^2$ represents a hydrogen atom, a hydroxy group, alkyl group which can be substituted, or alkoxy group which can be substituted,
$R^3$ represents a hydrogen atom or alkyl group which can be substituted,
Ring A represents a 5- or 6-membered aromatic ring which can be substituted by one or more substituents selected from halogen atoms, cyano group, hydroxy group, alkyl group which can be substituted, alkoxy group which can be substituted, carbamoyl group, alkylsulfanyl group which can be substituted, alkylsulfinyl group which can be substituted, heterocyclic-sulfonyl group, amino group which can be substituted, cycloalkyl group, and saturated heterocyclic group, and
Ring B represents a 5-membered aromatic heterocyclic ring which can be substituted.

[Compound ($I_O$-I)]
Compound ($I_O$), wherein
Ring A is a 5- to 6-membered aromatic ring (e.g., phenyl pyridyl) which can be substituted by one or more substituents selected from
(a) halogen atoms (e.g., chlorine, fluorine, iodine)
(b) cyano group
(c) $C_{1-10}$ alkyl group which can be substituted by 1 to 3 halogen atoms (e.g., methyl, trifluoromethyl),
(d) $C_{3-7}$ cycloalkyl group (e.g., methyl, trifluoromethyl),
(e) $C_{1-10}$ alkoxy group which can be substituted by 1 to 3 halogen atoms (e.g., difluoromethoxy, methoxy),
(f) 5- to 10-membered heterocyclic group containing 1 to 3 hetero atoms selected from nitrogen, oxygen and sulfur (e.g., morpholinyl, benzimidazolyl, piperidinyl),
(g) $C_{1-10}$ alkyl-sulfonyl group (e.g., methylsulfonyl)
(h) 5- to 10-membered heterocyclic-sulfonyl group containing 1 to 3 hetero atoms selected from nitrogen, oxygen and sulfur (e.g., morpholinylsulfonyl),
(i) carbamoyl group,
$R^1$ represents
(a) $C_{1-10}$ alkyl group (e.g., isopropyl, isobutyl), or
(b) halogen atoms (e.g., chlorine, fluorine), $C_{1-10}$ alkyl group (e.g., methyl) $C_{1-10}$ alkoxy group (e.g., methoxy),
$R^2$ represents
(a) hydrogen
(b) hydroxy group (c) $C_{1-10}$ alkyl group (e.g., methyl), or
(d) $C_{1-10}$ alkoxy group which can be substituted by one or more substituents selected from halogen atoms and $C_{3-7}$ cycloalkyl group (e.g., methoxy, ethoxy, isopropoxy, cyclopropylmethoxy, difluoromethoxy),
$R^3$ represents
hydrogen, or $C_{1-10}$ alkyl group (e.g., methyl),
the ring B is preferably a 5-membered nitrogen-containing aromatic heterocyclic ring having 1 to 3 nitrogen atoms (e.g., pyrazole, triazole, tetrazole), which can be substituted by a $C_{1-10}$ alkyl group (e.g., methyl)

Preferably, the compound ($I_o$) does not include the following compounds or salts thereof:

1-(2-chlorophenyl)-6-methyl-3-{5-thioxo-4-[3-(trifluoromethyl)phenyl]-4,5-dihydro-1H-1,2,4-triazol-3-yl}pyridazin-4(1H)-one, 1-(4-chlorophenyl)-3-[4-(2-fluorophenyl)-5-thioxo-4,5-dihydro-1H-1,2,4-triazol-3-yl]-6-methylpyridazin-4(1H)-one, 1-(4-chlorophenyl)-6-methyl-3-{5-thioxo-4-[3-(trifluoromethyl)phenyl]-4,5-dihydro-1H-1,2,4-triazol-3-yl}pyridazin-4(1H)-one, 1-(4-chlorophenyl)-3-[4-(2-fluorophenyl)-5-(methylsulfanyl)-4H-1,2,4-triazol-3-yl]-6-methylpyridazin-4(1H)-one, 1-(4-chlorophenyl)-6-methyl-3-{5-(methylsulfanyl)-4-[3-(trifluoromethyl)phenyl]-4H-1,2,4-triazol-3-yl}pyridazin-4(1H)-one, 1-(2-chlorophenyl)-6-methyl-3-{5-(methylsulfanyl)-4-[3-(trifluoromethyl)phenyl]-4H-1,2,4-triazol-3-yl}pyridazin-4(1H)-one, 3-(3,5-dimethyl-1H-pyrazol-1-yl)-1-phenylpyridazin-4(1H)-one, 1-(4-chlorophenyl)-3-{1-[3-chloro-5-(trifluoromethyl)pyridin-2-yl]-1H-pyrazol-5-yl}pyridazin-4(1H)-one, 3-[1-(2-fluorophenyl)-1H-pyrazol-5-yl]-1-[3-(trifluoromethyl)phenyl]pyridazin-4(1H)-one, 3-[1-(3-chlorophenyl)-1H-pyrazol-5-yl]-1-[3-(trifluoromethyl)phenyl]pyridazin-4(1H)-one, 3-[1-(4-methoxyphenyl)-1H-pyrazol-5-yl]-1-[3-(trifluoromethyl)phenyl]pyridazin-4(1H)-one, 3-(1-phenyl-1H-pyrazol-5-yl)-1-[3-(trifluoromethyl)phenyl]pyridazin-4(1H)-one, 3-[1-(3-nitrophenyl)-1H-pyrazol-5-yl]-1-[3-(trifluoromethyl)phenyl]pyridazin-4(1H)-one, 3-[1-(1,1-dioxidotetrahydrothiophen-3-yl)-1H-pyrazol-5-yl]-1-[3-(trifluoromethyl)phenyl]pyridazin-4(1H)-one, 3-[1-(4-methylphenyl)-1H-pyrazol-5-yl]-1-phenylpyridazin-4(1H)-one, 3-[1-(4-chlorophenyl)-1H-pyrazol-5-yl]-1-phenylpyridazin-4(1H)-one, 3-(4-ethyl-5-thioxo-4,5-dihydro-1H-1,2,4-triazol-3-yl)-1-(4-methylphenyl)pyridazin-4(1H)-one, 1-(4-chlorophenyl)-3-{1-[3-chloro-5-(trifluoromethyl)pyridin-2-yl]-1H-pyrazol-3-yl}pyridazin-4(1H)-one, 3-[1-(2-fluorophenyl)-1H-pyrazol-3-yl]-1-[3-(trifluoromethyl)phenyl]pyridazin-4(1H)-one, 3-[1-(3-chlorophenyl)-1H-pyrazol-3-yl]-1-[3-(trifluoromethyl)phenyl]pyridazin-4(1H)-one, 3-[1-(3-methoxyphenyl)-1H-pyrazol-3-yl]-1-[3-(trifluoromethyl)phenyl]pyridazin-4(1H)-one, 3-(1-phenyl-1H-pyrazol-3-yl)-1-[3-(trifluoromethyl)phenyl]pyridazin-4(1H)-one, 3-[1-(3-nitrophenyl)-1H-pyrazol-3-yl]-1-[3-(trifluoromethyl)phenyl]pyridazin-4(1H)-one, 3-[1-(4-methylphenyl)-1H-pyrazol-3-yl]-1-phenylpyridazin-4(1H)-one,
3-[1-(4-chlorophenyl)-1H-pyrazol-3-yl]-1-phenylpyridazin-4(1H)-one,
a compound of formula:

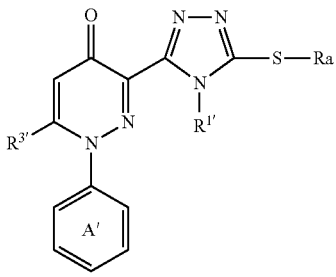

wherein
Ring A' is a benzene ring which can be substituted by one substituent selected from a halogen atom, and an alkyl group,
$R^{1'}$ is
(1) an ethyl group, or
(2) a phenyl group which can be substituted by one or more substituents selected from a fluorine atom, and a trifluoromethyl group,
$R^{3'}$ is a hydrogen atom, or a methyl group, and
Ra is a hydrogen atom, or a $C_{1-4}$ acyclic hydrocarbon group which can be substituted,
a compound of formula:

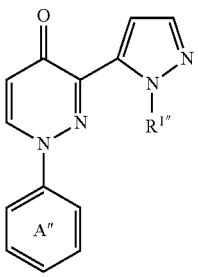

wherein
Ring A'' is a benzene ring which can be substituted by halogen, and
$R^{1''}$ is an acyl group.
Specifically, especially preferable examples of the Compound ($I_o$) include the following compounds.
1-[2-fluoro-4-(3,3,4,4-tetrafluoropyrrolidin-1-yl)phenyl]-5-methoxy-3-(1-phenyl-1H-pyrazol-5-yl)pyridazin-4(1H)-one, or a salt thereof.
1-[2-fluoro-4-(2-oxopyrrolidin-1-yl)phenyl]-5-methoxy-3-(1-phenyl-1H-pyrazol-5-yl)pyridazin-4(1H)-one, or a salt thereof.
1-[4-(3,4-difluoro-1H-pyrrol-1-yl)-2-fluorophenyl]-5-methoxy-3-(1-phenyl-1H-pyrazol-5-yl)pyridazin-4(1H)-one, or a salt thereof.
1-[2-fluoro-4-(1H-pyrazol-1-yl)phenyl]-5-methoxy-3-(1-phenyl-1H-pyrazol-5-yl)pyridazin-4(1H)-one, or a salt thereof.
1-[4-(4-chloro-1H-pyrazol-1-yl)-2-fluorophenyl]-5-methoxy-3-(1-phenyl-1H-pyrazol-5-yl)pyridazin-4(1H)-one, or a salt thereof.
1-[2-fluoro-4-(2-oxo-1,3-oxazolidin-3-yl)phenyl]-5-methoxy-3-(1-phenyl-1H-pyrazol-5-yl)pyridazin-4(1H)-one, or a salt thereof 3-[1-(2-fluorophenyl)-1H-pyrazol-5-yl]-1-[2-fluoro-4-(1H-pyrazol-1-yl)phenyl]-5-methoxypyridazin-4(1H)-one, or a salt thereof.
3-[1-(3-chlorophenyl)-1H-pyrazol-5-yl]-1-[2-fluoro-4-(1H-pyrazol-1-yl)phenyl]-5-methoxypyridazin-4(1H)-one, or a salt thereof.
1-[4-(4,4-dimethyl-2-oxopyrrolidin-1-yl)-2-fluorophenyl]-5-methoxy-3-(1-phenyl-1H-pyrazol-5-yl)pyridazin-4(1H)-one, or a salt thereof.
1-[4-(5,5-dimethyl-2-oxo-1,3-oxazolidin-3-yl)-2-fluorophenyl]-5-methoxy-3-(1-phenyl-1H-pyrazol-5-yl)pyridazin-4(1H)-one, or a salt thereof.
5-methoxy-1-[2-methoxy-4-(1H-pyrazol-1-yl)phenyl]-3-(1-phenyl-1H-pyrazol-5-yl)pyridazin-4(1H)-one, or a salt thereof.

When the compound ($I_o$) is a salt, for example, metal salts, ammonium salts, salts with organic bases, salts with inorganic acids, salts with organic acids, salts with basic or acidic amino acids can be included. Preferable examples of metal salts, for example, include alkali metal salts such as sodium salts, potassium salts and the like; alkali earth metal salts such as calcium salts, magnesium salts, barium salts and the like; and aluminum salts. Preferable examples of salts with organic bases include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine and the like. Preferable examples of salts with inorganic acids include salts with hydrochloric acid, hydrobromic acid, nitric acid, sulfuric acid, phosphoric acid and the like. Preferable examples of salts with organic acids include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid and the like. Preferable examples of salts with basic amino acids include salts with arginine, lysine, ornithine and the like. Preferable examples of salts with acidic amino acids include salts with aspartic acid, glutamic acid and the like. Among them, salts that are pharmacologically acceptable are preferable. For example, in the case when acidic functional group are present in the compound, for example, inorganic salts including alkali metal salts (e.g., sodium salts, etc.) and alkali earth metal salts (e.g., calcium salts, magnesium salts, barium salts, etc.) and ammonium salts are preferable. In contrast, in the case when basic functional group are present in the compound, for example, salts with inorganic acids such as hydrochloric acid, hydrobromic acid, nitric acid, sulfuric acid, phosphoric acid, etc. or salts with organic acid such as acetic acid, phthalic acid, fumaric acid, oxalic acid, tartaric acid, maleic acid, citric acid, succinic acid, methanesulfonic acid, p-toluenesulfonic acid, etc. are preferable.

If the compound ($I_o$) includes isomers such as tautomers, optical isomers, steric isomers, reverse isomers and rotational isomers, one of the other isomers or mixture are also included in the compound of the present invention. Further, if the compound ($I_o$) has an optical isomer, the optical isomer separated from the racemate is included in the compound ($I_o$).

The compound ($I_o$) can be obtained in the crystal form. Either single crystalline form or crystalline mixture can be included in the compound ($I_o$).

The compound of the formula ($I_o$) can be a pharmaceutically acceptable co-crystal or a co-crystal salt. The term "co-crystal" or "co-crystal salt" as used herein means a crystalline material composed of two or more unique solids at room temperature, each of which has distinctive physical characteristics such as structure, melting point, and heats of fusion, hygroscopicity, solubility, and stability. A co-crystal or a co-crystal salt can be obtained according to a per se known co-crystallization method.

The compound ($I_o$) can be provided as a solvate (for example, hydrate) or as a non-solvate and both are included in the compound ($I_o$).

The compounds labeled with isotopes (e.g., $^2H$, $^3H$, $^{11}C$, $^{14}C$, $^{18}F$, $^{35}S$, $^{125}I$, etc.) are also included in the compound ($I_o$).

[Manufacturing Methods]

The compound of the present invention and the compound as raw materials can be manufactured by the known means, for example, by the methods shown in the following schemes. Hereinafter, "room temperature" indicates a temperature generally ranging from 0 to 35° C. and "a low temperature" indicates a temperature generally from −78 to 0° C.

The compound ($I_o$) can be obtained, for example, by the method explained below or by a comparable method thereto. The methods of manufacturing the compound ($I_o$) is explained below by explaining the methods of manufacturing the compounds (I-a), (I-b), (I-c), (I-d), (I-e), (I-f), (I-g), (I-h), (I-i), and (I-j) included in the compound ($I_o$).

The symbols used for the compounds in the reaction schemes indicate the same meanings as mentioned above. In this specification, a methyl group ($CH_3$) is sometimes abbreviated as Me. The compounds in the schemes can include salts thereof in the cases when salts can be formed and such salts are similar to the salts of the compound ($I_o$). Further, the compound obtained in each process can be used directly in the form of a reaction mixture or as a crude product in the following reactions. However, it can be isolated from the reaction mixture according to the ordinary method. The product itself can be easily purified by the known means of isolation such as extraction, concentration, neutralization, filtration, distillation, recrystallization and chromatography. Alternatively, if the compound in the schemes is commercially available, a commercial product can be used directly and in addition, those which are manufactured by the known methods or by a comparable method can be used. If the compound as a raw material contains amino, carboxy, hydroxyl or heterocyclic group, the group can be protected by a protective group that is generally used in the peptide chemistry. In this case, if desirable, target compound can be obtained by removing the protective group. The protective group can be introduced or removed by the known methods, for example, based on the methods described in "Protective Groups in Organic Synthesis, 3$^{rd}$ Edition" (by Theodora W. Greene, Peter G. M. Wuts, published in 1999 by Wiley-Interscience Corporation).

Examples of "X$^-$" include halogen anions (e.g., chlorine anion, bromine anion, iodine anion, etc.), nitrate ion, and phosphate ion.

In these manufacturing methods, substituent conversions of each substituents of $R^1$ to $R^9$ and each substituents on the Rings A and B be carried out according to the a per se known method, for example, the method described in "Comprehensive Organic Transformations" (by Richard C. Larock, published in 1999 by Wiley-VCH).

The following respective processes can be carried out without a solvent or the raw materials can be dissolved or suspended in an appropriate solvent prior to the reaction. In this case, one kind of solvent can be used independently or two or more solvents can be combined at an appropriate ratio. Specific examples of the solvents to be used in the manufacturing methods of the present compound are given specifically as follows:

Alcohols: methanol, ethanol, 1-propanol, 2-propanol, tert-butyl alcohol, 2-methoxyethanol, etc.

Ethers: diethyl ether, diisopropyl ether, diphenyl ether, tetrahydrofuran, 1,4-dioxane, 1,2-dimethoxyethane, etc.

Aromatic hydrocarbons: benzene, chlorobenzene, toluene, xylene, etc.

Saturated hydrocarbons: cyclohexane, hexane, etc.

Amides: N,N-dimethylformamide, N,N-dimethylacetamide, hexamethylphosphoric triamide, etc.

Halogenated hydrocarbons: dichloromethane, chloroform, carbon tetrachloride, 1,2-dichloroethane, etc.

Nitriles: acetonitrile, propionitrile, etc.

Sulfoxides: dimethylsulfoxide, etc.

Aromatic organic bases: pyridine, lutidine, etc.

Acid anhydrides: acetic anhydride, etc.

Organic acids: formic acid, acetic acid, propionic acid, trifluoroacetic acid, methanesulfonic acid, etc.

Inorganic acids: hydrochloric acid, sulfuric acid, etc.

Esters: methyl acetate, ethyl acetate, butyl acetate, etc.

Ketones: acetone, methyl ethyl ketone, etc.

Specific examples of bases or deoxidizers that are used in the manufacturing methods for the compound of the present invention are given as follows:

Inorganic bases: sodium hydroxide, potassium hydroxide, magnesium hydroxide, etc.

Basic salts: sodium carbonate, potassium carbonate, cesium carbonate, calcium carbonate, sodium hydrogen carbonate, etc.

Organic bases: triethylamine, diisopropylethylamine, tributylamine, cyclohexyldimethylamine, pyridine, lutidine, 4-dimethylaminopyridine, N,N-dimethylaniline, N-methylpiperidine, N-methylpyrrolidine, N-methylmorpholine, 1,5-diazabicyclo[4.3.0]-5-nonene, 1,4-diazabicyclo[2.2.2]octane, 1,8-diazabicyclo[5.4.0]-7-undecene, imidazole, etc.

Metal alkoxides: sodium methoxide, sodium ethoxide, potassium tert-butoxide, etc.

Alkali metal hydrides: sodium hydride, potassium hydride, etc.

Metal amides: sodium amide, lithium diisopropylamide, lithium hexamethyldisilazide, etc.

Organic lithium reagents: methyl lithium, n-butyl lithium, sec-butyl lithium, tert-butyl lithium, etc.

Specific examples of acids or acid catalysts that are used in the manufacturing methods for the compound of the present invention are given as follows:

Inorganic acids: hydrochloric acid, sulfuric acid, nitric acid, hydrobromic acid, phosphoric acid, etc.

Organic acids: acetic acid, trifluoroacetic acid, oxalic acid, phthalic acid, fumaric acid, tartaric acid, maleic acid, citric acid, succinic acid, methanesulfonic acid, p-toluenesulfonic acid, 10-camphorsulfonic acid, etc.

Lewis acids: trifluoroboron ether complex, zinc iodide, anhydrous aluminum chloride, anhydrous zinc chloride, anhydrous iron chloride, etc.

When binding "heterocyclic compounds", "carbamate compounds", "acetylene derivatives", "boronic acid derivatives", or "organotin compounds" to Ring A having a leaving group, the product can be produced by a coupling reaction in the presence of a base using both palladium catalyst and copper catalyst or one of them. The "heterocyclic compounds" include an imidazole ring compound, pyrazole ring compound, pyrrolidine ring compound, azetidine ring compound, a pyrrolidone ring compound, piperidone ring compound, etc., the "carbamate compounds" include oxazolidone ring compound, etc., the "acetylene derivatives" include cyclopropylacetylene, etc. the "boronic acid derivatives" include (1-methyl-1H-pyrazol-4-yl)boronic acid pinacol esters, etc., the "organotin compounds" includes 2-(tributylstannyl)-1,3-oxazole, etc.

As the "palladium catalyst", for example, tris(dibenzylideneacetone)dipalladium(0), tetrakistriphenylphosphine-palladium(0) and the like can be used. The palladium catalyst can be used in an amount ranging from about 0.01 to 1 mol and preferably from 0.05 to 0.2 mol relative to 1 mol of the reaction substrate. The "palladium catalyst" can be used in combination with phosphine ligands. When the phosphine ligand is used, it is used in an amount ranging from about 0.01 to 4 mol and preferably from 0.05 to 1 mol relative to 1 mol of the reaction substrate. As the "phosphine ligand", for example, a phosphine ligand such as triphenylphosphine, and 4,5-bis(diphenylphosphino)-9,9-dimethylxanthene are exemplified. As the "copper catalysts", for example, cuprous iodide (CuI), and copper oxide ($Cu_2O$) can be used. The "copper catalyst" can be used in an amount ranging from about 0.1 to 1 mol and preferably from 0.1 to 0.5 mol relative to 1 mol of the reaction substrate. In addition, the "copper catalyst" can be used along with a ligand such as N,N'-dimethylethane-1,2-diamine, trans-1,2-diaminocyclohexane and salicylaldoxime. Such a ligand is used in an amount ranging from about 0.1 to 4 mol and preferably from 0.1 to 2 mol relative to 1 mol of the reaction substrate. As the "base", sodium tert-butoxide or potassium phosphate can be used and the amount ranges from about 1 to 10 mol and preferably from 1 to 3 mol relative to 1 mol of the reaction substrate. It is advantageous to carry out the present reaction in the absence of a solvent or in the presence of an inert solvent in the reaction. The solvent to be used is not particularly limited as long as the reaction proceeds, but for example, ethers, nitriles and the like are desirable. It is desirable to carry out the reaction generally at room temperature or under reflux conditions by heating and preferably under reflux conditions by heating. The reaction time generally ranges from 0.5 to 48 hours and preferably from 1 to 24 hours.

This coupling reaction can be carried out by the methods described in "Cross-Coupling Reactions: A Practical Guide (Topics in Current Chemistry)" (Springer) "Experimental Organic Metallic Chemistry for Synthesizing Chemists" (Kodansha) and "Organic Synthesis using Transition Metals" (Kagaku Dojin) or by a comparable method.

The compounds (I-a), (I-b), (I-c), (I-d), (I-e), (I-f), (I-g), (I-h), (I-i), and (I-j), each of which is included in the compound ($I_0$) can be prepared by the manufacturing method A, manufacturing method B, manufacturing method C, manufacturing method D, manufacturing method E, manufacturing method F, manufacturing method G, manufacturing method H, manufacturing method I or manufacturing method J as explained below.

The symbols in each general formula in the reaction schemes represent the same meanings as mentioned above unless otherwise specifically mentioned.

[Manufacturing Method A]

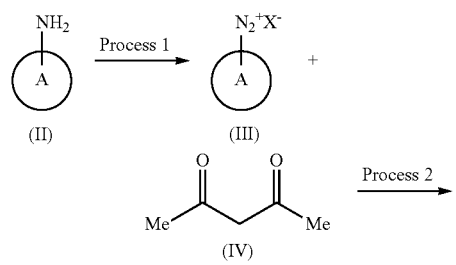

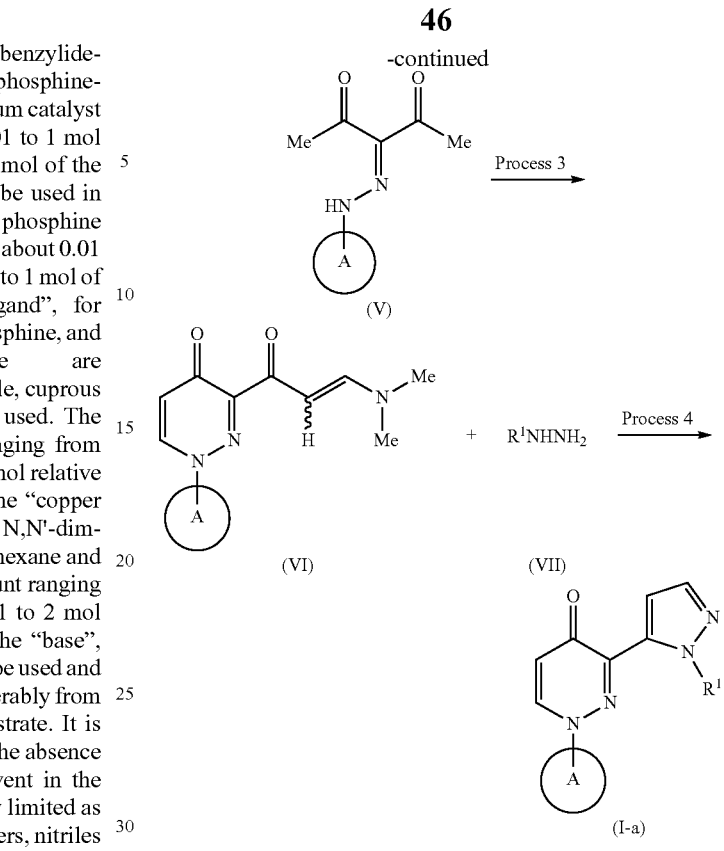

[Manufacturing Method C]
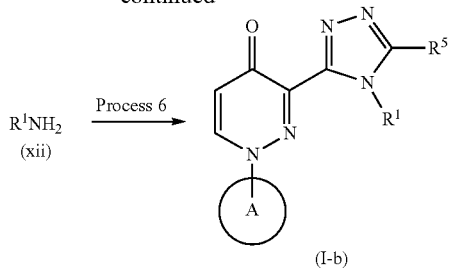
[Manufacturing Method D]
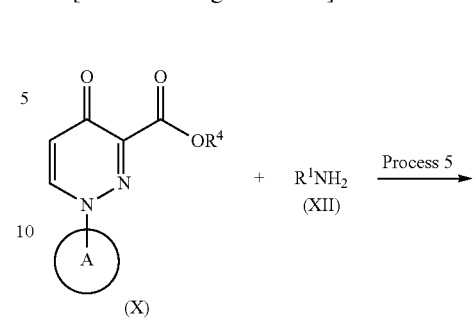
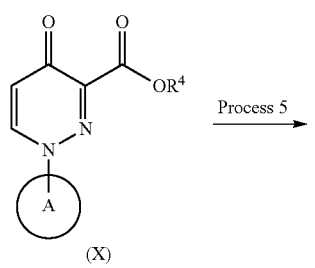
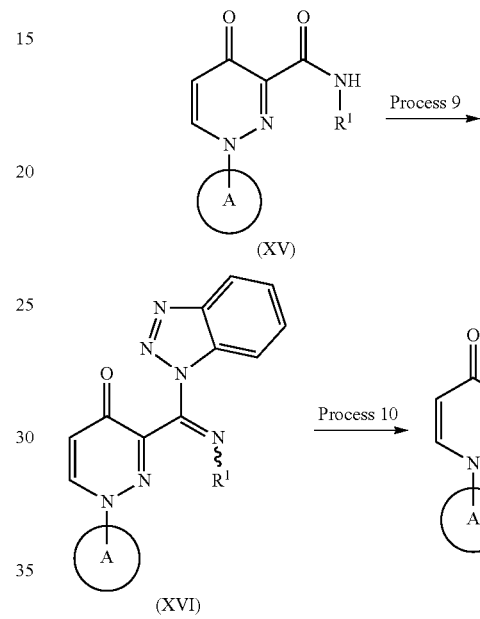
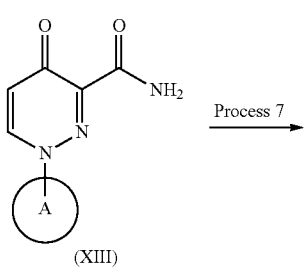
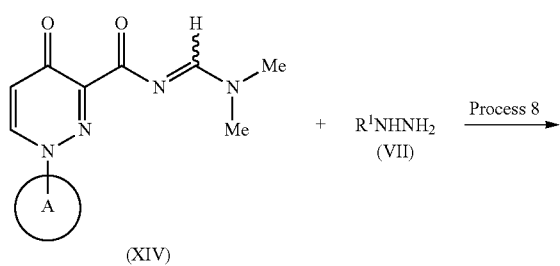
[Manufacturing Method E]
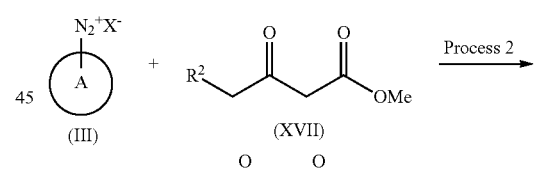
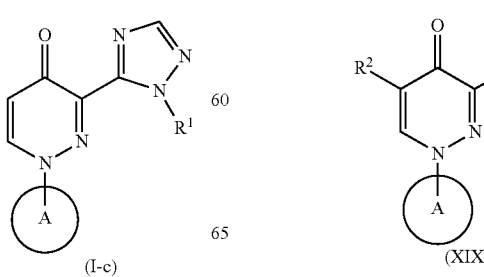

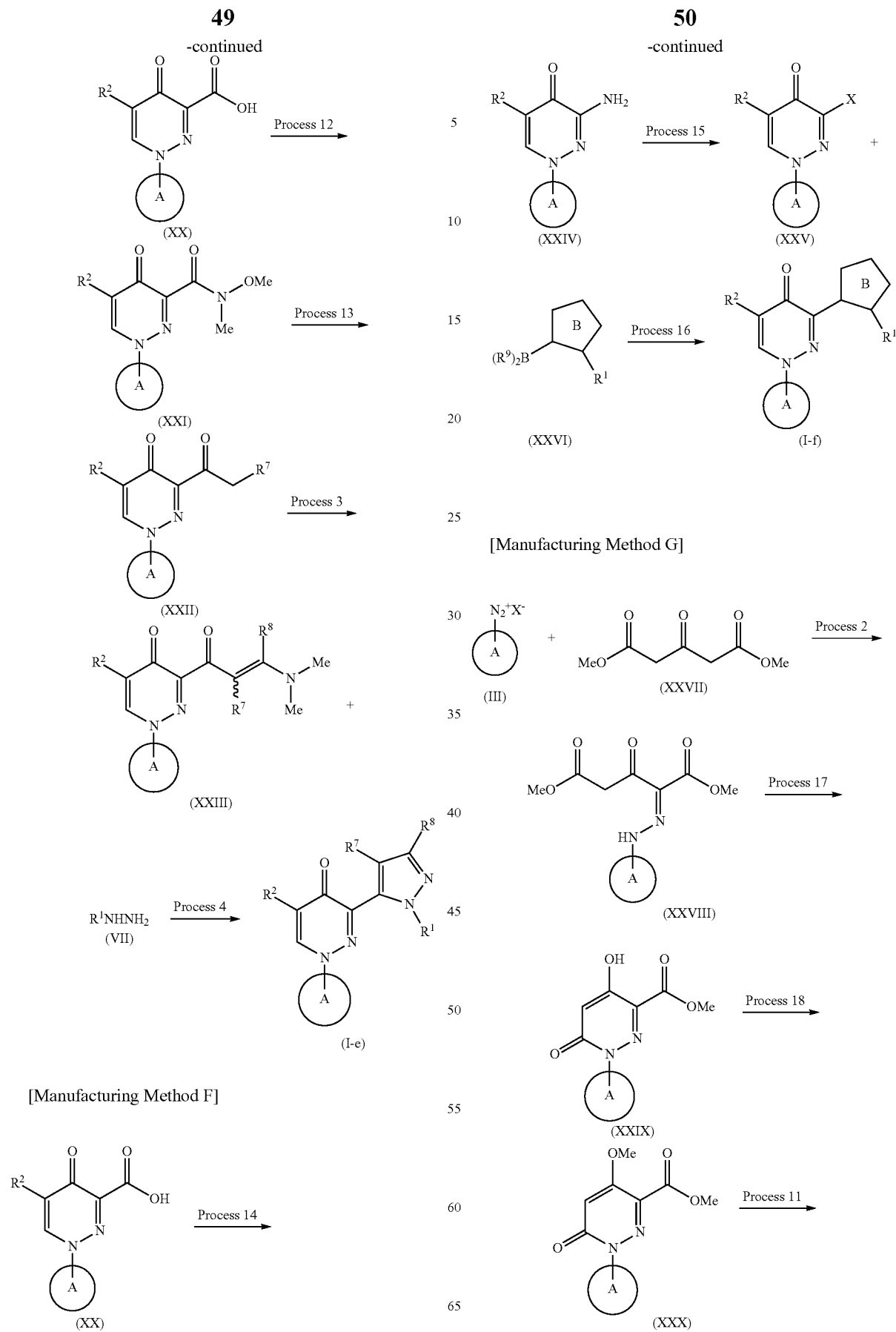

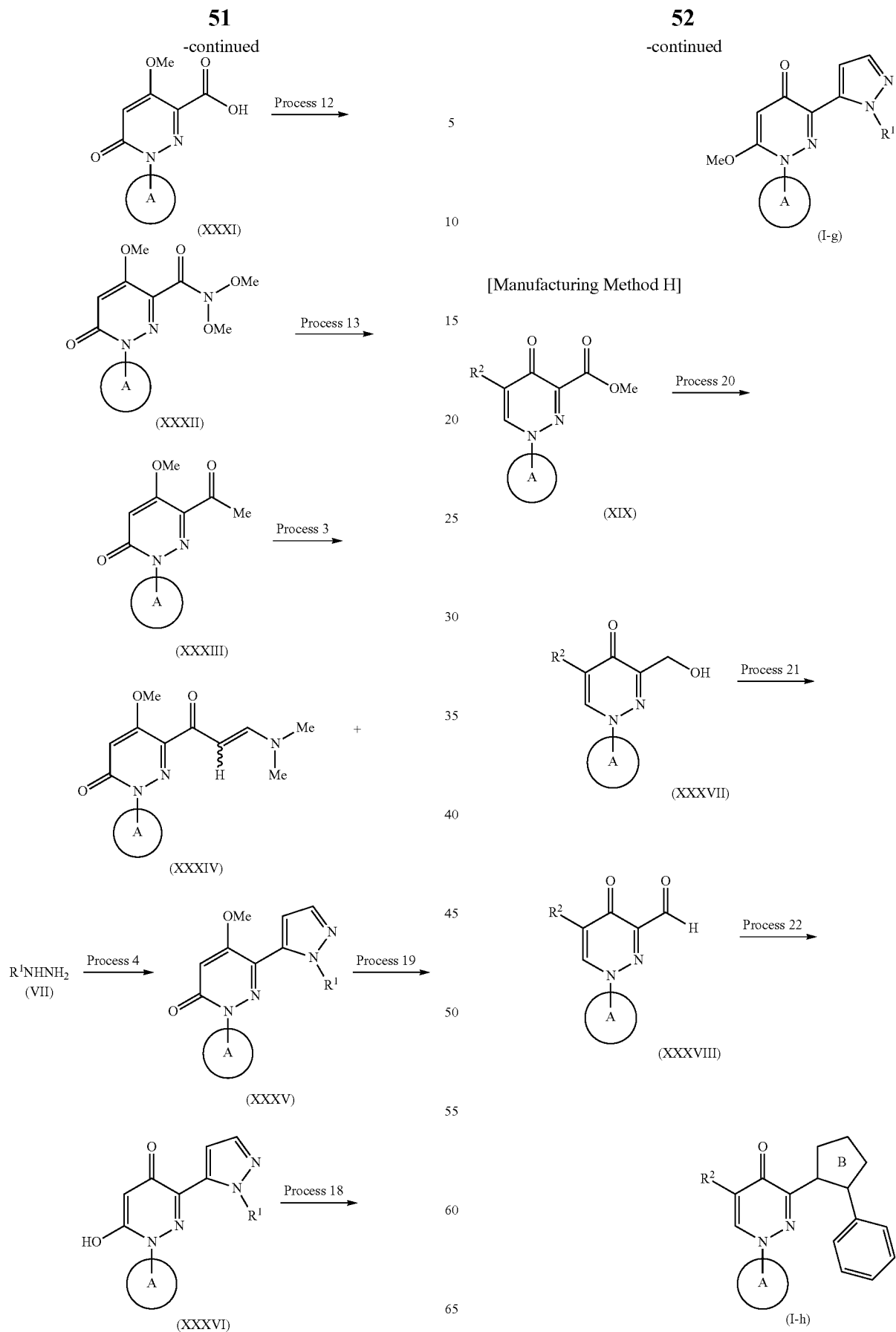

[Manufacturing Method I]

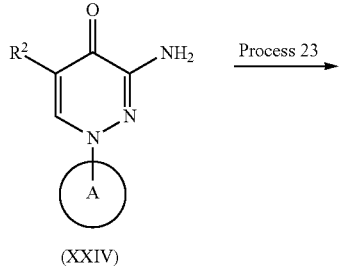

(XXIV)

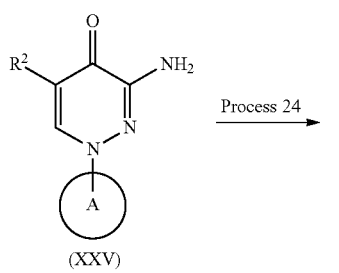

(I-i)

[Manufacturing Method J]

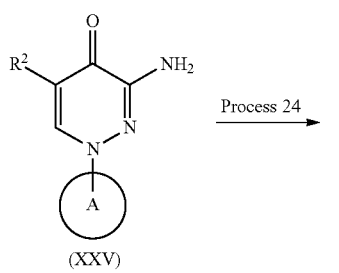

(XXV)

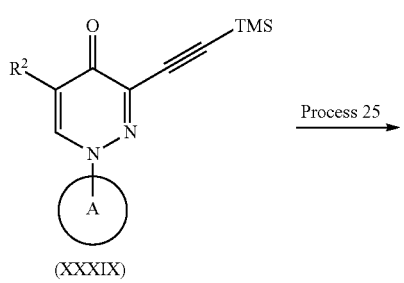

(XXXIX)

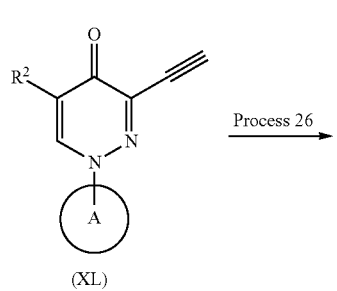

(XL)

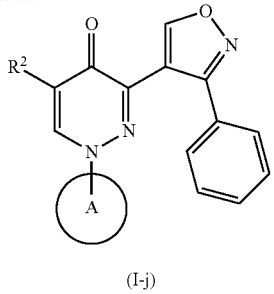

(I-j)

Process 1 is a method of producing a compound (III) by reacting a compound (II) with a diazotization agent. If desirable, the reaction can be carried out in the presence of an acid.

Examples of a diazotization agent are as follows: alkali metal nitrites such as sodium nitrite and potassium nitrite; $C_{2-6}$ nitrous acid alkyl esters such as t-butyl nitrite and isoamyl nitrite; nitrosyl chloride, nitrosyl sulfate, and nitrogen monoxide. Among them, sodium nitrite is desirable from the standpoint that it can be obtained easily at a low cost. Further, nitrous acid alkyl esters are desirable from the standpoint that the reactivity is enhanced. In this case, since an alkali metal nitrite is solid at room temperature, it is dissolved in advance in water prior to its use.

As the "acid", for example, hydrochloric acid, sulfuric acid and acetic acid are applicable and they can be also used as a mixture.

From the standpoint of increasing reactivity and economical efficiency, the amount of a diazotization agent ranges from 1 to 5 mol and preferably from 1 to 2 mol relative to 1 mol of the compound (II). It is desirable to carry out the reaction generally at room temperature or at a low temperature and preferably at a temperature ranging from −30° C. to 0° C.

The reaction time generally ranges from 1 minute to 3 hours and preferably from 1 minute to 1 hour.

It is advantageous to carry out the present reaction in the absence of a solvent or in the presence of an inert solvent in the reaction. These solvents are not limited as long as the reaction proceeds, but water is preferred.

Process 2 is a method of producing a compound (V), a compound (IX), a compound (XVIII) or a compound (XXVIII) by placing a compound (III) together with a compound (IV), a compound (VIII), a compound (XVII) or a compound (XXVII).

This process can be carried out by the method described in Tetrahedron Lett., 2008, 49(14), 2262-2264 or by a comparable method. If desirable, the reaction can be carried out in the presence of a base.

The amount of the compounds (IV), (VIII), (XVII) or (XXVII) to be used ranges from approximately 1 to 5 mol and preferably from 1 to 2 mol relative to 1 mol of the compound (III).

As the "base", for example, sodium acetate can be used.

The amount of the "base" to be used generally ranges from 1 to 10 equivalents and preferably from 2 to 6 equivalents relative to the compound (III).

It is advantageous to carry out the present reaction in the absence of a solvent or in the presence of an inert solvent in the reaction. These solvents are not limited as long as the reaction proceeds, but a mixed solvent of alcohols and water is desirable.

It is desirable to carry out the reaction generally at room temperature or at a low temperature while being cooled in an ice bath.

The reaction time generally ranges from 5 seconds to 24 hours and preferably ranges from 5 seconds to 1 hour.

$R^4$ is a $C_{1-10}$ alkyl group which can be substituted, and preferably a methyl group, or an ethyl group. In this process, $R^2$ represents a $C_{1-10}$ alkyl group which can be substituted or a $C_{1-10}$ alkoxy group which can be substituted.

Process 3 is a method of producing a compound (VI), a compound (X), a compound (XIX), a compound (XXIII) or a compound (XXXIV) from the compound (V), the compound (IX), the compound (XVIII), the compound (XXII) or the compound (XXXIII). The reaction can be carried out in the presence of N,N-dimethylformamide dimethylacetal and the like as a solvent.

This process can be carried out by the method described in the Journal of Heterocyclic Chemistry, 1981, 18, 333-334 or by a comparable method.

It is desirable to carry out the reaction generally under reflux conditions by heating and preferably at 100° C. to 150° C.

The reaction time generally ranges from 1 to 10 hours and preferably from 1 to 5 hours.

Process 4 is a method of producing a compound (I-a), a compound (I-e) or a compound (XXXV) by placing the compound (VII) together with the compound (VI), the compound (XXIII) or the compound (XXXIV).

The amount of the compound (VII) to be used ranges from approximately 1 to 10 mol and preferably from approximately 2 to 5 mol relative to 1 mol of the compound (VI), the compound (XXIII) or the compound (XXXIV).

It is advantageous to carry out the reaction in the absence of a solvent or in the presence of an inert solvent in the reaction. The solvent to be used is not limited as long as the reaction proceeds, but alcohols, organic acids or mixed solvents thereof are desirable.

It is desirable to carry out the reaction generally in an ice bath, at room temperature, or under reflux conditions by heating and preferably at 0° C. to 150° C.

The reaction time generally ranges from 0.1 to 10 hours and preferably from 0.5 to 5 hours.

This process can be carried out by the method described in the Journal of Heterocyclic Chemistry, 1981, 18, 333-334 or by a comparable method.

In this process, $R^1$ represents a $C_{1-10}$ alkyl group which can be substituted, a $C_{3-7}$ cycloalkyl group which can be substituted, or an aromatic group which can be substituted.

Process 5 is a method of producing a compound (XI) by reacting the compound (X) with hydrazine, a method of producing a compound (XIII) by reacting the compound (X) with ammonia, or a method of producing a compound (XV) by reacting the compound (X) with an amine compound (XII).

The amount of hydrazine, ammonia and the amine compound (XII) to be used ranges from approximately 1 to 10 mol and preferably from approximately 2 to 5 mol relative to 1 mol of the compound (X).

It is advantageous if the reaction is carried out in the absence of a solvent or in the presence of an inert solvent in the reaction. The solvent is not limited as long as the reaction proceeds, but for example, alcohols or ethers are desirable.

It is desirable to carry out the reaction generally under heated conditions and preferably at 50° C. to 100° C.

The reaction time generally ranges from 1 to 10 hours and preferably from 1 to 5 hours.

This process can be carried out by the method described in the Journal of Heterocyclic Chemistry, 1981, 18, 333-334 or by a comparable method.

Further, a method of heating under microwave conditions or a method of heating in the presence of trimethyl aluminum as an activator is applicable.

The reaction temperature in the case when heating under microwave conditions range generally from 50° C. to 150° C. and preferably from 100° C. to 130° C. The reaction time generally ranges from 10 to 60 min. and preferably from 10 to 20 min. It is advantageous to carry out the reaction in the absence of a solvent or using an inert solvent in the reaction. The solvent is not limited as long as the reaction proceeds, but for example, alcohols or ethers are desirable.

If the reaction is carried out in the presence of trimethyl aluminum as an activator, trimethyl aluminum is used in an amount ranging from approximately 1 to 5 mol and preferably from about 1 to 3 mol relative to 1 mol of the compound (X). It is advantageous to carry out the reaction in the absence of a solvent or using an inert solvent in the reaction. The solvent is not limited as long as the reaction proceeds, but methylene chloride is desirable. It is desirable to carry out the reaction generally under heated conditions and preferably at 50° C. to 100° C. The reaction time generally ranges from 1 to 15 hours and preferably from 1 to 10 hours.

Process 6 is a method of producing a compound (I-b) by placing the compound (XI) together with an amine compound (XII).

In the case when $R^5$ is a hydrogen, the compound (XI) is reacted with N,N-dimethylformamide dimethylacetal or the like, and subsequently reacted with an amine compound (XII) under an acidic condition without isolation to produce a compound (I-b). In contrast, if $R^5$ is a methyl group, the compound (XI) is reacted with N,N-dimethylacetamide dimethylacetal and the reaction is carried out with an amine compound (XII) under an acidic condition as mentioned above to produce a compound (I-b).

The amount of N,N-dimethylformamide dimethylacetal or N,N-dimethylacetamide dimethylacetal to be used ranges from about 1 to 5 mol and preferably from about 1 to 2 mol relative to 1 mol of the compound (XI).

It is desirable to carry out the reaction generally under heated conditions and preferably at 50° C. to 100° C.

The reaction time generally ranges from 0.5 to 3 hours and preferably from 0.5 to 1 hour.

It is advantageous to carry out the reaction in the absence of a solvent or using an inert solvent in the reaction. The solvent is not limited as long as the reaction proceeds, but for example, nitriles are desirable.

The amount of an amine compound (XII) to be used ranges from about 1 to 5 mol and preferably from 1 to 2 mol relative to 1 mol of the compound (XI).

As the "acid", for example, acetic acid can be used.

As for the amount of an acid to be used, it is desirable to use the same amount as acetonitrile used as a solvent in the aforementioned reaction.

It is desirable to carry out the reaction generally under heated conditions and preferably at 100° C. to 130° C.

The reaction time generally ranges from 0.5 to 3 hours and preferably from 0.5 to 1 hour.

This process can be carried out by the method described in Org. Lett., 2004, 6 (17), 2969-2971 or by a comparable method.

Process 7 is a method of producing a compound (XIV) from the compound (XIII). The product can be produced in the presence of N,N-dimethylformamide dimethylacetal as a solvent.

It is desirable to carry out the reaction generally under heated conditions and preferably at 100° C. to 150° C.

The reaction time generally ranges from 0.1 to 5 hours and preferably from 0.1 to 1 hour.

This process can be carried out by the method described in Arch. Pharm. Chem. Life Sci., 2007, 340, 17-25 or by a comparable method.

Process 8 is a method of producing a compound (I-c) by placing the compound (XIV) together with a hydrazine compound (VII). The reaction can be carried out in the presence of an organic acid.

The amount of the hydrazine compound (VII) to be used ranges from about 1 to 5 mol and preferably from 1 to 2 mol relative to 1 mol of the compound (XIV).

As the "organic acid", for example, acetic acid can be used.

The amount of the organic acid to be used is similar to the amount when it is generally used as a solvent.

It is desirable to carry out the reaction generally under heated conditions and preferably at 100° C. to 130° C.

The reaction time generally ranges from 0.5 to 3 hours and preferably from 0.5 to 1 hour.

This process can be carried out by the method described in Arch. Pharm. Chem. Life Sci., 2007, 340, 17-25 or by a comparable method.

Process 9 is a method of producing a compound (XVI) from the compound (XV). The reaction can be carried out in the presence of 1H-benzo[d][1,2,3]triazole and an acid halide.

It is advantageous to carry out the reaction in the absence of a solvent or using an inert solvent in the reaction. The solvent is not particularly limited as long as the reaction proceeds, but for example, halogenated hydrocarbons are desirable.

The amount of 1H-benzo[d][1,2,3]triazole to be used ranges from about 1 to 10 mol and preferably from 1 to 5 mol relative to 1 mol of the compound (XV).

As the "acid halide", for example, thionyl chloride can be used.

The amount of the "acid halide" to be used ranges from about 1 to 5 equivalents and preferably from 1 to 2 equivalents relative to the compound (XV).

It is desirable to carry out the reaction under reflux conditions by heating and it is also possible to carry out the reaction in a short time under microwave conditions. If the reaction is carried out under microwave conditions, the reaction time ranges from 0.1 to 1 hour at 80 watts and preferably from 0.1 to 0.3 hours.

This process can be carried out by the method described in Synthesis, 2007, 1204-1208 or by a comparable method.

Process 10 is a method of producing a compound (I-d) from the compound (XVI). The product can be produced by reacting an acid as well as sodium azide in the presence of a phase transfer catalyst.

It is advantageous to carry out the reaction using an inert solvent in the reaction. The solvent to be used is not particularly limited as long as the reaction proceeds, but for example, it is desirable to use a halogenated hydrocarbon, a solvent mixed with water and the like.

As the "phase transfer catalyst, for example, tetrabutyl ammonium bromide can be used.

The amount of the "phase transfer catalyst" to be used ranges from about 0.1 to 1 equivalent and preferably from 0.1 to 0.3 equivalent relative to the compound (XVI).

The amount of sodium azide to be used ranges from about 1 to 5 mol and preferably from 1 to 3 mol relative to 1 mol of the compound (XVI).

As the "acid", for example, organic acids can be used.

The amount of the "acid" to be used ranges from about 1 to 5 equivalents and preferably from 1 to 2 equivalents relative to the compound (XVI).

The reaction temperature can range from 0° C. to 100° C. and preferably at room temperature.

The reaction time generally ranges from 0.1 to 48 hours and preferably from 10 to 24 hours.

This process can be carried out by the method described in Synthesis, 2007, 1204-1208 or by a comparable method.

Process 11 is a method of producing a compound (XX) or a compound (XXXI) from the compound (XIX) or the compound (XXX). The reaction can be carried out under an acidic or basic condition. It is advantageous to carry out this reaction without using a solvent or using an inert solvent in the reaction. The solvent to be used is not particularly limited as long as the reaction proceeds, but for example, it is desirable to use alcohols, a solvent mixed with water and ethers.

As the "acid", for example, inorganic acids can be used.

As the "base", for example, inorganic bases such as sodium hydroxide or potassium hydroxide can be used. Further, lithium hydroxide can also be used.

The amount of the acid or the base to be used ranges from about 1 to 10 mol and preferably from 1 to 5 mol relative to 1 mol of the compound (XIX) or the compound (XXX).

It is desirable to carry out the reaction generally at room temperature or under heated conditions and preferably at room temperature.

The reaction time generally ranges from 1 to 48 hours and preferably from 3 to 10 hours.

Process 12 is a method of producing a compound (XXI) or a compound (XXXII) from the compound (XX) or the compound (XXXI). The product can be produced using N,O-dimethylhydroxylamine hydrochloride with a condensation agent in the presence of a base such as triethylamine or N,N-diisopropylethylamine. Alternatively, a carboxylic acid of the substrate is converted to a corresponding acid halide which is then reacted with N,O-dimethylhydroxylamine hydrochloride to produce the target products.

As the "condensation agent", for example, 1-ethyl-3-(3-dimethylaminopropyl)carbodiimide hydrochloride can be used in the presence of 1-hydroxybenzotriazole.

It is advantageous to carry out this reaction without using a solvent or using an inert solvent in the reaction. The solvent to be used is not particularly limited as long as the reaction proceeds, but for example, nitriles, ethers and amides are desirable.

The amount of the condensation agent to be used ranges from about 1 to 5 mol and preferably from 1 to 3 mol relative to 1 mol of the compound (XX) or the compound (XXXI).

A base such as triethylamine or N,N-diisopropylethylamine is preferably used in an amount ranging from about 1 to 10 mol and preferably from 2 to 3 mol relative to 1 mol of the compound (XX) or the compound (XXXI).

It is desirable to carry out the reaction generally at room temperature or under heated conditions and preferably at room temperature.

The reaction time generally ranges from 1 to 48 hours and preferably from 5 to 10 hours.

The reaction with an acid halide is carried out in the presence of a base such as triethylamine using N,O-dimethylhydroxylamine hydrochloride to synthesize a target product.

It is advantageous to carry out this reaction without using a solvent or using an inert solvent in the reaction. The solvent to be used is not particularly limited as long as the reaction proceeds, but for example, ethers, esters amides are desirable.

The amount of the base such as triethylamine ranges from about 1 to 10 mol and preferably from 2 to 3 mol relative to 1 mol of the compound (XX) or the compound (XXXI).

It is desirable to carry out the reaction generally while cooling in an ice bath or at room temperature and preferably by cooling in an ice bath.

The reaction time generally ranges from 0.5 to 5 hours and preferably from 1 to 3 hours.

Further, the compound (XXI) or the compound (XXXII) can be produced by reacting the compound (XIX) or the compound (XXX) with trimethyl aluminum and N,O-dimethylhydroxylamine hydrochloride in the presence of an organic base. The amount of an organic base, trimethyl aluminum and N,O-dimethylhydroxylamine hydrochloride ranges from about 1 to 10 mol and preferably from 2 to 5 mol relative to 1 mol of the compound (XIX) or the compound (XXX). It is advantageous to carry out this reaction without using a solvent or using an inert solvent in the reaction. The solvent to be used is not particularly limited as long as the reaction proceeds, but for example, halogenated hydrocarbons are desirable. It is desirable to carry out the reaction generally by cooling in an ice bath or at room temperature and preferably by cooling in an ice bath. The reaction time generally ranges from 1 to 24 hours and preferably from 1 to 5 hours.

Process 13 is a method of producing a compound (XXII) or a compound (XXXIII) from the compound (XXI) or the compound (XXXII). The product can be produced using an "alkylating agent" such as a Grignard reagent or an organic lithium reagent.

It is advantageous to carry out this reaction without using a solvent or using an inert solvent in the reaction. The solvent to be used is not particularly limited as long as the reaction proceeds, but for example, ethers are desirable.

The amount of the "alkylating agent" ranges from about 1 to 10 mol and preferably from 2 to 3 mol relative to 1 mol of the compound (XXI) or the compound (XXXII).

It is desirable to carry out the reaction generally at −78° C. or while cooling in an ice bath and preferably at −78° C.

$R^7$ is a hydrogen atom, or a $C_{1-10}$ alkyl group which can be substituted, and preferably a hydrogen atom, or a methyl group.

$R^8$ is a hydrogen atom, or a $C_{1-10}$ alkyl group which can be substituted, and preferably a hydrogen atom, or a methyl group.

The reaction time generally ranges from 1 to 10 hours and preferably from 1 to 3 hours.

Process 14 is a method of producing a compound (XXIV) from the compound (XX). The product can be produced using diphenylphosphoryl azide in the presence of a base such as triethylamine.

It is advantageous to carry out this reaction without using a solvent or using an inert solvent in the reaction. The solvent to be used is not particularly limited as long as the reaction proceeds. For example, in the case when using tert-butanol as a solvent, a tert-butyl carbamate derivative is temporarily obtained and its hydrolysis is carried out under an acidic condition to produce a compound (XXIV). Further, in the case when using toluene as a solvent, an isocyanate as an intermediate is hydrolyzed with an aqueous sodium hydroxide solution to produce a compound (XXIV).

The amount of diphenylphosphoryl azide ranges from about 1 to 10 mol and preferably from 1 to 3 mol relative to 1 mol of the compound (XX).

The amount of triethylamine ranges from about 1 to 10 mol and preferably from 1 to 3 mol relative to 1 mol of the compound (XX).

It is desirable to carry out the reaction generally at room temperature or under reflux conditions by heating and preferably under reflux conditions by heating.

The reaction time generally ranges from 1 to 20 hours and preferably from 1 to 10 hours.

This process can be carried out by the method described in Tetrahedron 1974, 30, 2151-2157 or by a comparable method.

Process 15 is a method of producing a compound (XXV) from the compound (XXIV). The product can be produced using a nitrite in the presence of a copper salt.

It is advantageous to carry out this reaction without using a solvent or using an inert solvent in the reaction. The solvent to be used is not particularly limited as long as the reaction proceeds, but for example, amides are desirable.

As the "copper salt", cupric bromide ($CuBr_2$) and the like can be used and its amount ranges from about 1 to 5 mol and preferably from 1 to 2 mol relative to 1 mol of the compound (XXIV).

As the "nitrite", isoamyl nitrite or pentyl nitrite and the like can be used and its amount ranges from about 1 to 10 mol and preferably from 1 to 3 mol relative to 1 mol of the compound (XXIV).

It is desirable to carry out the reaction generally in an ice bath, at room temperature or under heated conditions and preferably at a temperature ranging from 0 to 70° C.

The reaction time generally ranges from 1 to 10 hours and preferably from 1 to 5 hours.

This process can be carried out by the method described in U.S. Pat. No. 5,059,599 or by a comparable method.

Process 16 is a method of producing a compound (I-f) from the compound (XXV) and the compound (XXVI). The product can be produced using a palladium catalyst in the presence of a base.

The amount of the compound (XXVI) to be used ranges from approximately 1 to 10 mol and preferably from approximately 1 to 3 mol relative to 1 mol of the compound (XXV).

As the "base", potassium acetate or potassium carbonate and the like can be used and its amount ranges from about 1 to 10 mol and preferably from 1 to 3 mol relative to 1 mol of the compound (XXV).

As the "palladium catalyst", bis[di-tert-butyl(4-dimethylaminophenyl)phosphine]dichloropalladium(II) or tetrakis(triphenylphosphine)palladium and the like can be used and its amount ranges from about 0.01 to 0.5 mol and preferably from 0.03 to 0.1 mol relative to 1 mol of the compound (XXV).

It is advantageous to carry out this reaction without using a solvent or using an inert solvent in the reaction. The solvent to be used is not particularly limited as long as the reaction proceeds, but for example, alcohols, solvent mixture with water, aromatic hydrocarbons, ethers, amides and the like are desirable.

It is desirable to carry out the reaction generally at room temperature or under reflux conditions by heating and preferably under reflux conditions by heating.

The reaction time generally ranges from 5 to 48 hours and preferably from 10 to 20 hours.

This process can be carried out by the method described in Org. Lett., 2006, 8, 1787-1789 or by a comparable method.

$R^9$ represents an alkoxy group which can be substituted or a hydroxyl group and the like.

Process 17 is a method of producing a compound (XXIX) from the compound (XXVIII) and the reaction can be carried out in the presence of a base.

As the base, basic salts, organic bases, metal alkoxides or metal amides and the like can be used and potassium carbonate or sodium methoxide is desirable. The amount of the base ranges from about 1 to 10 mol and preferably from 1 to 3 mol relative to 1 mol of the compound (XXVIII). It is advantageous to carry out this reaction without using a solvent or using an inert solvent in the reaction. The solvent to be used is not particularly limited as long as the reaction proceeds, but for example, ethers or amides are desirable. It is desirable to carry out the reaction generally at room temperature or under reflux conditions by heating and preferably at room temperature.

The reaction time generally ranges from 1 to 24 hours and preferably from 2 to 4 hours.

Process 18 is a method of producing a compound (XXX) or a compound (I-g) from the compound (XXIX) or the compound (XXXVI).

Methylation can be carried out under the condition using trimethylsilyldiazomethane or methyl iodide in the presence of a base.

In the case when the reaction is carried out using trimethylsilyldiazomethane, trimethylsilyldiazomethane is used in an amount ranging from about 10 to 50 mol and preferably from 5 to 20 mol relative to 1 mol of the compound (XXIX) or the compound (XXXVI) using a solvent such as methanol and the like. It is desirable to carry out the reaction generally by cooling in an ice bath or under room temperature conditions and preferably by cooling in an ice bath.

The reaction time generally ranges from 1 to 5 hours and preferably from 1 to 2 hours.

In the case when using methyl iodide in the presence of a base, the reaction can be carried out using an ether solvent in the presence of sodium hydroxide and the like.

Methyl iodide is used in an amount ranging from about 1 to 10 mol and preferably from 1 to 3 mol relative to 1 mol of the compound (XXIX) or the compound (XXXVI). In addition, a base such as sodium hydroxide is also used in an amount ranging from about 1 to 10 mol and preferably from 1 to 3 mol relative to 1 mol of the compound (XXIX) or the compound (XXXVI). It is desirable to carry out the reaction generally by cooling in an ice bath or under room temperature conditions and preferably by cooling in an ice bath.

The reaction time generally ranges from 1 to 5 hours and preferably from 1 to 2 hours.

Process 19 is a method of producing a compound (XXXVI) from the compound (XXXV) and the product can be obtained using trimethylsilyl chloride in the presence of sodium iodide.

The amount of sodium iodide ranges from about 1 to 10 mol and preferably from 1 to 5 mol relative to 1 mol of the compound (XXXV). The amount of trimethylsilyl chloride ranges from about 1 to 10 mol and preferably from 1 to 5 mol relative to 1 mol of the compound (XXXV).

It is advantageous to carry out this reaction without using a solvent or using an inert solvent in the reaction. The solvent to be used is not particularly limited as long as the reaction proceeds, but for example, nitriles are desirable. It is desirable to carry out the reaction generally at room temperature or under reflux conditions by heating and preferably under reflux conditions by heating. The reaction time generally ranges from 1 to 20 hours and preferably from 3 to 10 hours.

Process 20 is a method of producing a compound (XXXVII) from the compound (XIX) and the product can be obtained using an appropriate reductant.

As the "reductant", lithium aluminum hydride, diisobutylaluminum hydride and the like can be used. It can be used in an amount ranging from about 1 to 10 mol and preferably from 1 to 3 mol relative to 1 mol of the compound (XIX). It is advantageous to carry out this reaction without using a solvent or using an inert solvent in the reaction. The solvent to be used is not particularly limited as long as the reaction proceeds, but for example, ethers are desirable. It is desirable to carry out the reaction generally at −78° C. or by cooling in an ice bath and preferably at −78° C.

The reaction time generally ranges from 0.5 to 5 hours and preferably from 1 to 3 hours.

This process can be carried out by the method described in Comprehensive Organic Transformations (WILEY-VCH) or by a comparable method.

Process 21 is a method of producing a compound (XXXVIII) from the compound (XXXVII) and the product can be produced using an appropriate oxidation.

As the "oxidation", for example, Swern oxidation, or oxidation using an oxidant such as a sulfur trioxide pyridine complex, pyridinium chlorochromate and the like can be used. When the oxidation using the oxidant is conducted, the oxidant is used in the amount ranging from about 1 to 10 mol and preferably from 1 to 3 mol relative to 1 mol of the compound (XXXVII). It is advantageous to carry out this reaction without using a solvent or using an inert solvent in the reaction. The solvent to be used is not particularly limited as long as the reaction proceeds, but for example, dimethylsulfoxide, halogenated hydrocarbons, ethers and esters are desirable. It is desirable to carry out the reaction generally under low temperature conditions or at room temperature. The reaction time generally ranges from 1 to 10 hours and preferably from 1 to 3 hours.

This process can be carried out by the method described in Comprehensive Organic Transformations (WILEY-VCH) or in Oxidation in Organic Chemistry (American Chemical Society) by a comparable method.

Process 22 is a method of producing a compound (I-h) from the compound (XXXVIII). Using α-tosyl benzyl isocyanide (Organic Syntheses, Coll. Vol. 10, p 692 (2004): Vol. 77, p 198 (2000)), an 1,3-oxazole compound or an 1,3-imidazole compound can be produced. In the case when producing "1,3-oxazole compound", the reaction is carried out in the presence of a base such as potassium carbonate. In contrast, in the case when producing "1,3-imidazole compound", the reaction is carried out in the presence of a base such as potassium carbonate along with the presence of aqueous ammonia or an amine such as methylamine.

A base such as potassium carbonate, aqueous ammonia or methylamine is used in an amount ranging from about 1 to 10 mol and preferably from 1 to 3 mol relative to the compound (XXXVIII). It is advantageous to carry out this reaction without using a solvent or using an inert solvent in the reaction. The solvent to be used is not particularly limited as long as the reaction proceeds, but for example, ethers, nitriles and amides are desirable. It is desirable to carry out the reaction generally under low temperature conditions or at room temperature and preferably under room temperature conditions.

The reaction time generally ranges from 5 to 30 hours and preferably from 5 to 15 hours.

This process can be carried out by the method described in New Edition: Heterocyclic Compounds (Kodansha) or by a comparable method.

Process 23 is a method of producing a compound (I-i) from the compound (XXIV). As long as the reaction proceeds, it is not particularly limited, but after reacting with an aqueous glyoxal solution in an alcoholic solvent, under an acidic condition, the compound (XXIV) can be reacted with ammonium chloride and benzaldehyde to give the compound (I-i).

An aqueous glyoxal solution is used in an amount ranging from about 1 to 5 mol and preferably from 1 to 3 mol relative to 1 mol of the compound (XXIV). It is desirable to carry out the reaction, generally under low temperature conditions or under room temperature conditions and preferably under room temperature conditions.

The reaction time generally ranges from 5 to 30 hours and preferably from 10 to 20 hours.

Benzaldehyde and ammonium chloride are used in an amount ranging from about 1 to 5 mol and preferably from 1 to 3 mol relative to 1 mol of the compound (XXIV). An acid to be used is not particularly limited as long as the reaction proceeds, but for example, phosphoric acid and the like are desirable. It is desirable to carry out the reaction generally under room temperature conditions or under reflux conditions by heating and preferably under reflux conditions by heating. The reaction time generally ranges from 5 to 40 hours and preferably from 20 to 30 hours.

This process can be carried out by the method described in New Edition: Heterocyclic Compounds (Kodansha) or by a comparable method.

Process 24 is a method of producing a compound (XXXIX) from the compound (XXV). As long as the reaction proceeds, it is not particularly limited, but the product can be produced by reacting the compound (XXV) with trimethylsilylacetylene in an ether solvent such as tetrahydrofuran in the presence of a palladium catalyst and a copper catalyst as well as a base. As the palladium catalyst, for example, bis(triphenylphosphine)palladium (II)dichloride and the like can be used. The palladium catalyst is used in an amount ranging from about 0.01 to 1 mol and preferably from 0.05 to 0.2 mol relative to 1 mol of the compound (XXV). In addition, the palladium catalyst is used along with a phosphine ligand such as triphenylphosphine. The phosphine ligand is used in an amount ranging from about 0.01 to 1 mol and preferably from 0.05 to 0.2 mol relative to 1 mol of the compound (XXV). As the copper catalyst, for example, cuprous iodide (CuI) and the like can be used. The copper catalyst is used in an amount ranging from about 0.1 to 1 mol and preferably from 0.1 to 0.5 mol relative to 1 mol of the compound (XXV). Trimethylsilylacetylene is used in an amount ranging from about 1 to 5 mol and preferably from 1 to 3 mol relative to 1 mol of the compound (XXV). The reaction is carried out in the presence of a base such as triethylamine and the amount of a base to be used ranges from about 1 to 5 mol and preferably from 1 to 3 mol relative to 1 mol of the compound (XXV). It is desirable to carry out the reaction generally by heating at a temperature ranging from 40 to 60° C.

The reaction time generally ranges from 1 to 10 days and preferably from 5 to 7 days.

This process can be carried out by the method described in Tetrahedron Lett., 1975, 16, 4467-4470 or by a comparable method.

Process 25 is a method of producing a compound (XL) from the compound (XXXIX). As long as the reaction proceeds, it is not particularly limited, but the product can be produced by reacting the compound (XXXIX) with sodium hydroxide aqueous solution or a fluoride ion such as tetrabutylammonium fluoride in an alcohol or an ether as a solvent. The amount of aqueous sodium hydroxide solution or fluoride ion ranges from about 1 to 100 mol or greater and preferably from 1 to 3 mol relative to 1 mol of the compound (XXXIX). It is desirable to carry out the reaction generally by cooling in an ice bath or under room temperature conditions and preferably under room temperature conditions. The reaction time generally ranges from 0.5 to 5 hours and preferably from 1 to 3 hours.

Process 26 is a method of producing a compound (I-j) from the compound (XL). As long as the reaction proceeds, it is not particularly limited, but the product can be produced by reacting the compound (XL) with N-hydroxybenzenecarboximidoyl chloride in an ether as a solvent. N-hydroxybenzenecarboximidoyl chloride is used in an amount ranging from about 1 to 5 mol and preferably from 1 to 3 mol relative to 1 mol of the compound (XL). The present reaction is carried out in the presence of a base such as triethylamine and the amount of a base to be used ranges from about 1 to 5 mol and preferably from 1 to 3 mol relative to 1 mol of the compound (XL). It is desirable to carry out the reaction generally by cooling in an ice bath or under room temperature conditions and preferably under room temperature conditions. The reaction time generally ranges from 1 to 48 hours and preferably from 5 to 20 hours.

This process can be carried out by the method described in "New Edition: Heterocyclic Compounds" (Kodansha) or by a comparable method.

The compound (I-e) wherein $R^2$ is a halogen atom (e.g., a bromine atom) can be produced by the following method. Initially, the compound (V) is reacted with a reagent such as N,N-dimethylformamide dimethyl acetal to obtain a compound (XXII) wherein $R^2$ and $R^7$ are hydrogen atoms. The amount of the reagent such as N,N-dimethylformamide dimethyl acetal is about 1 to 5 mol, preferably 1 to 2 mol relative to 1 mol of the compound (V). It is desirable that this reaction is carried out using an inert solvent in the reaction (e.g., amides). It is desirable that the reaction is carry out at room temperature or while heating and preferably at a temperature ranging from 40 to 100° C. The reaction time generally ranges from 1 to 20 hours, and preferably from 1 to 10 hours. Then, the obtained compound (XXII) is reacted with a halogen molecule (e.g., a bromine molecule) to introduce a halogen atom at $R^2$ position of the compound (XXII). The amount of the halogen molecule to be used ranges from about 1 to 5 mol and preferably about 1 to 2 mol relative to 1 mol of the compound (XXII). It is desirable that this reaction is carried out using an inert solvent in the reaction (e.g., organic acids). It is desirable that the reaction is carried out at room temperature or at a low temperature and preferably at room temperature. The reaction time generally ranges from 1 to 10 hours, and preferably from 1 to 3 hours.

The compound (I-e) wherein $R^8$ is an alkyl group (e.g., a methyl group) can be produced by the following method. Initially, the compound (XXII) is reacted with a reagent such as N,N-dimethylacetamide dimethyl acetal to obtain a compound (XXIII). The amount of N,N-dimethylacetamide dimethyl acetal to be used ranges from about 1 to 30 mol and preferably from 5 to 20 mol relative to 1 mol of the compound (XXII). This reaction is preferably carried out without using a solvent or using an inert solvent in the reaction. Further, it is desirable to carry out the reaction under reflux conditions by heating, or it is possible to be heated under microwave conditions. The reaction temperature when heating under microwave conditions generally ranges from 50° C. to 150° C. and preferably at a temperature ranging from 100° C. to 130° C. The reaction time generally ranges from 1 to 60 min. and preferably from 3 to 20 min.

The compound (I-e) wherein $R^8$ is an alkyl group which is substituted by a fluorine atom (e.g., a trifluoromethyl group) can be produced by the following method. Initially, the compound (XXII) is reacted with an ester having an alkyl group substituted with a fluorine atom (e.g., ethyl trifluoroacetate) under basic conditions. The amount of the ester to be used ranges from 1 to 20 mol and preferably from 1 to 10 mol relative to 1 mol of the compound (XXII). This reaction is carried out in the presence of a base such as sodium methoxide and the amount of the base to be used ranges from about 1 to 5 mol and preferably from 1 to 3 mol relative to 1 mol of the compound (XXII). It is desirable that this reaction is carried out using an inert solvent in the reaction (e.g., ethers). It is desirable to carry out the reaction under ice cold conditions or at room temperature and preferably at room temperature. The reaction time generally ranges from 0.5 to 7 days and preferably from 1 to 3 days. Furthermore, the compound (I-e) can be produced by placing the reaction product along with the compound (VII). The amount of the compound (VII) to be used ranges from about 1 to 10 mol and preferably from about 2 to 5 mol relative to 1 mol of the raw material. It is advantageous to carry out this reaction without using a solvent or using an inert solvent in the reaction. The solvent to be used is not particularly limited as long as the reaction proceeds, but for example, alcohols and organic acids or mixed solvents thereof are desirable. It is desirable to carry out the reaction under ice cold conditions or at room temperature or while heating and preferably at a temperature ranging from 0° C. to 150° C. The reaction time generally ranges from 0.1 to 10 hours and preferably from 0.5 to 5 hours. This process can be carried out by the method described in the Journal of Heterocyclic Chemistry, 1981, 18, 333-334 or by a comparable method.

The compound (I-e) wherein $R^7$ is a halogen atom (e.g., a fluorine atom) can be produced by reacting the compound (I-e) wherein $R^7$ is a hydrogen atom with a reagent such as a halogenating agent. For example, when introducing a fluorine atom, 1-(chloromethyl)-4-fluoro-1,4-diazoniabicyclo[2.2.2]octane bis(tetrafluoroborate) (hereinafter referred to as Selectfluor) can be used as a fluorinating agent. The amount of the Selectfluor to be used ranges from about 1 to 30 mol and preferably from 5 to 20 mol relative to 1 mol of the compound (I-e). This reaction is preferably carried out using an inert solvent in the reaction (e.g., nitriles, etc.). Further, it is desirable to carry out the reaction under ice cold conditions or at room temperature and preferably at room temperature. The reaction time generally ranges from 1 to 20 days and preferably from 5 to 15 days.

The compound (I-e) wherein $R^7$ is an alkyl group (e.g., a methyl group) can be produced by the following reaction. Initially, the compound (XXII) is reacted with an ester (e.g., methyl formate) under basic conditions. The ester is works also as a solvent. This reaction is carried out in the presence of a base such as sodium methoxide, and the amount of the base to be used ranges from about 1 to 5 mol and preferably from 1 to 3 mol relative to 1 mol of the compound (XXII). Generally, it is desirable to carry out the reaction under ice cold conditions or at room temperature and preferably at room temperature. The reaction time generally ranges from 1 to 20 hours and preferably from 2 to 10 hours.

The compound (I-e) can be produced by further placing the reaction product along with the compound (VII). The amount of the compound (VII) to be used ranges from about 1 to 10 mol and preferably from about 2 to 5 mol relative to 1 mol of the raw material. It is advantageous to carry out this reaction without using a solvent or using an inert solvent in the reaction. The solvent to be used is not particularly limited as long as the reaction proceeds, but for example, alcohols and organic acids or mixed solvents thereof are preferable. Generally, it is desirable to carry out the reaction under ice cold conditions or at room temperature or under reflux, conditions by heating and preferably at a temperature ranging from 0° C. to 150° C. The reaction time generally ranges from 0.1 to 10 hours and preferably from 0.5 to 5 hours. This process can be carried out by the method described in the Journal of Heterocyclic Chemistry, 1981, 18, 333-334 or by a comparable method.

If the raw material compounds contain an amino group, a carboxyl group, a hydroxyl group as a substituent, in each reaction in the manufacturing methods of said compounds (I-a), (I-b), (I-c), (I-d), (I-e), (I-f), (I-g), (I-h), (I-i), and (I-j), or salts thereof, and in each reaction in the synthesis of the raw material compounds, a protective group that is generally used in peptide chemistry can be introduced into these group. If preferable, the protective group is removed after the reaction to be able to obtain a target compound.

As a protective group for the amino group, for example, formyl and the following group that can be respectively substituted can be used: $C_{1-10}$ alkylcarbonyl (e.g., acetyl, ethylcarbonyl, etc.), phenylcarbonyl, $C_{1-10}$ alkyl-oxycarbonyl (e.g., methoxycarbonyl, ethoxycarbonyl, etc.), phenyloxycarbonyl, $C_{7-10}$ aralkyl-carbonyl (e.g., benzylcarbonyl, etc.), trityl, phthaloyl, or N,N-dimethylaminomethylene. The substituents to be used can include halogen (e.g., fluorine, chlorine, bromine, iodine, etc.), $C_{1-10}$ alkyl-carbonyl (e.g., methylcarbonyl, ethylcarbonyl, butylcarbonyl, etc.), nitro group and the like. The number of substituents ranges from 1 to 3.

As a protective group for the carboxyl group, for example, the following group that can be respectively substituted can be used: $C_{1-10}$ alkyl (e.g., methyl, ethyl, n-propyl, i-propyl, n-butyl, tert-butyl, etc.), phenyl, trityl, or silyl and the like. The substituents to be used can include halogen (e.g., fluorine, chlorine, bromine, iodine, etc.), formyl, $C_{1-10}$ alkyl-carbonyl (e.g., acetyl, ethylcarbonyl, butylcarbonyl, etc.), nitro groups and the like. The number of substituents ranges from 1 to 3.

As a protective group for the hydroxyl group, for example, the following group that can be respectively substituted can be used: $C_{1-10}$ alkyl (e.g., methyl, ethyl, n-propyl, i-propyl, n-butyl, tert-butyl, etc.), phenyl, $C_{7-10}$ aralkyl (e.g., benzyl, etc.), formyl, $C_{1-10}$ alkyl-carbonyl (e.g., acetyl, ethylcarbonyl, etc.), phenyloxycarbonyl, benzoyl, $C_{7-10}$ aralkyl-carbonyl (e.g., benzylcarbonyl, etc.), pyranyl, furanyl, or silyl and the like. The substituents to be used can include halogen (e.g., fluorine, chlorine, bromine, iodine, etc.), $C_{1-10}$ alkyl (e.g., methyl, ethyl, n-propyl, etc.), phenyl, $C_{7-10}$ aralkyl (e.g., benzyl, etc.), nitro group and the like. The number of substituents ranges from 1 to 4.

Further, as a method of removing the protective group, the known method or a comparable method can be used. For example, a method of treating with acids, bases, reduction, UV-light, hydrazine, phenylhydrazine, sodium N-methyldithiocarbamate, tetrabutylammonium fluoride, palladium acetate and the like can be used.

In each reaction in the manufacturing methods of said compounds (I-a), (I-b), (I-c), (I-d), (I-e), (I-f), (I-g), (I-h), (I-i), and (I-j), or their salts, and in each reaction in the synthesis of the raw material compounds, solvents that are generally known may be used during the reaction.

For example, the following generally known solvents can be used:

ethers such as tetrahydrofuran, diethylether, 1,2-dimethoxyethane, 1,4-dioxane and the like;

esters such as ethyl acetate, butyl acetate and the like;

aromatic hydrocarbons such as benzene, toluene and the like;

aromatic heterocyclic compounds such as pyridine, lutidine and the like;

amides such as N,N-dimethylformamide, N-methylpyrrolidone and the like;

halogenated compounds such as chloroform, methylene chloride and the like;

alcohols such as methanol, ethanol, 2-propanol, 2,2-dimethylethanol and the like;

aliphatic hydrocarbon compounds such as hexane, heptane, petroleum ether and the like;

carboxylic acids such as formic acid, acetic acid and the like; and water.

Further, the solvents used in the reaction can be used as a single solvent or as a solvent mixture of two kinds to 6 kinds.

Further, the reaction can be carried out in the presence of amines such as triethylamine, N,N-diisopropylamine, pyridine, N-methylmorpholine and the like or bases such as sodium hydroxide, potassium carbonate and the like. Alternatively, the reaction can be carried out in the presence of an acid such as hydrochloric acid, sulfuric acid, acetic acid and the like.

The compounds obtained by the aforementioned methods: (I-a), (I-b), (I-c), (I-d), (I-e), (I-f), (I-g), (I-h), (I-i), and (I-j) can be isolated or purified by the ordinary separation means such as recrystallization, distillation, chromatography and the like. If the compounds of the present invention: (I-a), (I-b), (I-c), (I-d), (I-e), (I-f), (I-g), (I-h), (I-i), and (I-j) are obtained in a free form, they can be converted to their salts by the known methods or by a comparable method (e.g., neutralization, etc.), or in reverse, if they are obtained in the salt form, they can be converted to a free form or other salts by the known methods or by a comparable method. If the compound obtained are racemates, they can be separated into a d-form and l-form by the ordinary optical separation means.

The raw material compounds of the compounds (I-a), (I-b), (I-c), (I-d), (I-e), (I-f), (I-g), (I-h), (I-i), and (I-j) or salts thereof are not particularly limited as long as there are no interference with the reaction. Examples of such salts are same as the salts of the compounds (I-a), (I-b), (I-c), (I-d), (I-e), (I-f), (I-g), (I-h), (I-i), and (I-j).

In any of the above mentioned manufacturing methods or processes, if desired, a compound ($I_o$) can be synthesized by further applying one or combination of known reactions such as protection/deprotection reactions, acylation reactions, alkylation reactions, hydrogenation reactions, oxidation reactions, reduction reactions, carbon chain extension reactions, substituent exchanging reactions, and so on.

If the target products are obtained in the free form by the aforementioned reactions, they can be converted to the corresponding salts by the ordinary methods, or if they are obtained in the salt form, they can be converted to the free form or other salts by the ordinary methods. The compound ($I_o$) obtained can be isolated from the reaction mixture and purified by the known means such as phase transfer, concentration, solvent extraction, fractional distillation, crystallization, recrystallization, chromatography and the like.

If the compound ($I_o$) is present as a configurational isomer, diastereomer, or conformer, if desired, they can be isolated respectively by the aforementioned isolation and purification means. If the compound ($I_o$) is present as a racemate, it can be separated to a d-form and l-form by the ordinary optical separation means.

As in the case of the compound ($I_o$), a prodrug of the compound ($I_o$) can be used. The prodrug of the compound ($I_o$) is a compound that is converted to a compound ($I_o$) by reactions using enzymes or gastric acid under physiological conditions in vivo. Namely, it includes a compound that is converted to a compound ($I_o$) by enzymatic oxidation, reduction and hydrolysis or a compound that is converted to a compound ($I_o$) by hydrolysis using gastric acid.

Prodrugs of the compound ($I_o$) include compounds wherein an amino group in the compound ($I_o$) is acylated, alkylated or phosphorylated (e.g., the amino group in the compound ($I_o$) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated or tert-butylated); the hydroxyl group in the compound ($I_o$) is acylated, alkylated, phosphorylated or borated (e.g., the hydroxyl group in the compound ($I_o$) is acetylated, palmitoylated, propanoylated, pivaloylated, succinylated, fumarylated, alanylated, dimethylaminomethylcarbonylated); the carboxyl group in the compound ($I_o$) is esterified or amidated (e.g., the carboxyl group in the compound ($I_o$) is ethyl-esterified, phenyl-esterified, carboxymethyl-esterified, dimethylaminomethyl-esterified, pivaloyloxymethyl-esterified, ethoxycarbonyloxyethyl-esterified, phthalidyl-esterified, (5-methyl-2-oxo-1,3-dioxolen-4-yl)methyl-esterified, cyclohexyloxycarbonylethyl-esterified, or methylamidated). These compounds, can be produced from the compound ($I_o$) by the known methods. Prodrugs of the compound ($I_o$) can be converted to the compound ($I_o$) under the physiological conditions as described in "Development of Drugs" Vol. 7 Molecular Design published in 1990 by Hirokawa Shoten, page 163 to 198.

The compound of the present invention has an excellent PDE10A inhibitory activity and is useful for the following diseases and symptoms in mammals (e.g., humans, cows, horses, dogs, cats, monkeys, mice, rats, etc. particularly in humans):

psychotic disorder (e.g., brief psychotic disorder, shared psychotic disorder);

psychosis induced by alcohol, amphetamine, cannabis, cocaine, hallucinogens, obesity, inhalants, opioids, or phencyclidine;

delusional disorder;

anxiety disorder;

movement disorder;

mood disorder;

major depressive disorder;

a major depressive disorder superimposed on a psychotic disorder comprising a delusional disorder or schizophrenia;

major depressive episode of the mild, moderate or severe type;

manic or mixed mood episode;

hypomanic mood episode;

depressive episode with atypical features;

depressive episode with melancholic features;

depressive episode with catatonic features;

mood episode with postpartum onset;

post-stroke depression;

dysthymic disorder;

minor depressive disorder;

autism drug addiction neurodegenerative disorder;

neurodegeneration associated with cerebral trauma;

neurodegeneration associated with stroke;

neurodegeneration associated with cerebral infarct;

hypoglycemia-induced neurodegeneration;

neurodegeneration associated with epileptic seizure;

neurodegeneration associated with neurotoxin poisoning;

multi-system atrophy;

Alzheimer's disease;

dementia;

multi-infarct dementia;

alcoholic dementia or other drug-related dementia;

dementia associated with intracranial tumors or cerebral trauma;

dementia associated with Huntington's disease or Parkinson's disease;

AIDS-related dementia;

Fronto temperal dementia;

delirium;

amnestic disorder;

post-traumatic stress disorder;

mental retardation;

learning disorder (e.g., reading disorder, mathematics disorder, or a disorder of written expression);

attention-deficit/hyperactivity disorder;

age-related cognitive decline;

premenstrual dysphoric disorder;

post-psychotic depressive disorder of schizophrenia;

bipolar disorder comprising bipolar I disorder, bipolar II disorder;

cyclothymic disorder;

Parkinson's disease;

Huntington's disease;

paranoid;

schizophrenia (e.g., paranoid schizophrenia, disorganized schizophrenia, catatonic schizophrenia, undifferentiated schizophrenia, residual schizophrenia);

schizophreniform disorder;

schizoaffective disorder of the delusional type or the depressive type;

personality disorder of the paranoid type;

personality disorder of the schizoid type;

obesity;

metabolic syndrome;

non-insulin dependent diabetes (NIDDM);

glucose intolerance;

In particular, the compound of the present invention is useful for preventing or treating schizophrenia.

Since the compound of the present invention demonstrates excellent metabolic stability, superior therapeutic effects on the aforementioned diseases are expected even at a low dosage.

The compound of the present invention can be administered safely, as it is, or in a dosage form which is manufactured according to a per se known method for manufacturing pharmaceutical formulations (e.g., methods described in Japanese Pharmacopoeia) such as tablets (inclusive of sugar coated tablet, film coated tablet, sublingual tablet, orally disintegrable tablet, and buccal), pills, powders, granules, capsules (inclusive of soft capsule, and microcapsule), troches, syrups, liquid dosage forms, emulsions, controlled-release preparations (e.g., quick-release preparation, sustained-release preparation, sustained-release microcapsule), aerosols, films (e.g., orally disintegrable film, adhesive film for application to oral-cavity mucosa), injections (e.g., subcutaneous injection, intravenous injection, intramuscular injection, intraperitoneal injection), drip infusion, percutaneous absorbent, ointment, lotion, patch, suppositories (e.g., rectal suppository, vaginal suppository), pellets, transnasal preparations, pulmonary preparations (inhalant), eye drops and the like, in an oral or parenteral route (e.g., intravenous, intramuscular, subcutaneous, intraorgan, intranasal, intradermal, ophthalmic instillation, intracerebral, intrarectal, intravaginal, intraperitoneal, directly to lesion).

Here, as a pharmaceutical acceptable carrier, common organic or inorganic carrier substances are used as formulation raw materials. Carriers are added as vehicles, lubricants, binders and disintegrants in the solid formulations; and as solubilizing agents, suspending agents, isotonization agents, buffers and soothing agents in the liquid formulations. If desired, formulation additives such as antiseptics, antioxidants, colorants, sweeteners, etc. can be used.

Favorable examples of the vehicles are as follows: lactose, sucrose, D-mannitol, D-sorbitol, starch, α-starch, dextrin, crystalline cellulose, low-substituted hydroxypropyl cellulose, sodium carboxymethylcellulose, gum Arabic, pullulan, light silicic anhydride, synthetic aluminum silicate and magnesium metasilicic aluminate.

Favorable examples of the lubricants include magnesium stearate, calcium stearate, talc and colloidal silica.

Favorable examples of the binders are as follows: α-starch, sucrose, gelatin, gum Arabic, methylcellulose, carboxymethylcellulose, sodium carboxymethylcellulose, crystalline cellulose, sucrose, D-mannitol, trehalose, dextrin, pullulan, hydroxypropylcellulose, hydroxypropyl methyl cellulose and polyvinylpyrrolidone.

Favorable examples of the disintegrants are as follows: lactose, sucrose, starch, carboxymethylcellulose, calcium carboxymethylcellulose, croscarmellose sodium, sodium carboxymethyl starch, light silicic anhydride and low-substituted hydroxypropylcellulose.

Favorable examples of the solvents are as follows: water for injection, physiological saline, Linger solution, alcohol, propylene glycol, polyethylene glycol, sesame oil, corn oil, olive oil and cottonseed oil.

Favorable examples of the solubilizing agents are as follows: polyethylene glycol, propylene glycol, D-mannitol, trehalose, benzylbenzoate, ethanol, tris-aminomethane, cholesterol, triethanolamine, sodium carbonate, sodium citrate, sodium salicylate and sodium acetate.

Favorable examples of the suspending agents are as follows: surfactants such as stearyl triethanolamine, sodium lauryl sulfate, laurylamino propionic acid, lecithin, benzalkonium chloride, benzethonium chloride, and glycerin monostearate; hydrophilic polymers such as polyvinyl alcohol, polyvinyl pyrrolidone, sodium carboxymethylcellulose, methylcellulose, hydroxymethyl cellulose, hydroxyethyl cellulose and hydroxypropyl cellulose; polysorbates, and polyoxyethylene-hardened castor oil.

Favorable examples of the isotonization agents include sodium chloride, glycerin, D-mannitol, D-sorbitol and glucose.

Favorable examples of the buffers include buffer solutions of phosphates, acetates, carbonates and citrates.

Favorable examples of the soothing agents include benzyl alcohol.

Favorable examples of antiseptics include para-oxybenzoic acid esters, chlorobutanol, benzyl alcohol, phenethyl alcohol, dehydroacetic acid and sorbic acid.

Favorable examples of antioxidants include sulfites and ascorbates.

Favorable examples of the colorants include water soluble edible tar dyes (e.g., edible dyes such as Food Red No. 2 and No. 3, Food Yellow No. 4 and No. 5, Food Blue No. 1 and 2); water insoluble lake dyes (e.g., aluminum salts of the aforementioned water soluble edible tar dyes), natural dyes (e.g., β-carotene, chlorophyll, red iron oxide).

Favorable examples of the sweeteners include sodium saccharin, dipotassium glycyrrhizate, aspartame and stevia.

The medical compositions of the present invention can be manufactured by the common methods in the field of formulation technology, for example, methods listed in the Japanese pharmacopoeia. Specific manufacturing methods for formulations are described in detail below.

The content of the compound of the present invention in the medical compositions of the present invention varies based on the dosage forms, dosages of the compound of the present invention, etc. For example, the content approximately ranges from 0.01 to 100 wt % and preferably from 0.1 to 95 wt % relative to the entire amount of the composition.

The dosage of the compound of the present invention depends upon injection targets, administration routes, target diseases, symptoms, etc. For example, in the case of oral administration in patients with schizophrenia (adults, body-weight of approximately 60 kg), generally a single dose ranges from approximately 0.1 to 20 mg/kg bodyweight, preferably from approximately 0.2 to 10 mg/kg bodyweight, further preferably from approximately 0.5 to 10 mg/kg bodyweight, and this dosage is preferably administered once daily or several times daily (e.g., 3 times).

The compounds can be administered as the sole active agent or in combination with other pharmaceutical agents such as other agents used in the treatment of psychosis, especially schizophrenia and bipolar disorder, obsessive-compulsive disorder, major depression, Parkinson's disease, Alzheimer's disease, cognitive impairment and/or memory loss, e.g., nicotinic α7 agonists, nicotinic α7 partial agonists, nicotinic α7 positive allosteric modulators, PDE2 inhibitors, PDE4 inhibitors, PDE5 inhibitors, other PDE inhibitors, calcium channel blockers, muscarinic m1 and m2 modulators, adenosine receptor modulators, ampakines, Glycine transporter 1 inhibitors, NMDA-R modulators, mGluR modulators, dopamine modulators, serotonin modulators, selective serotonin reuptake inhibitors, serotonin and norepinephrine reuptake inhibitors, norepinephrine and dopamine reuptake inhibitors, triple reuptake inhibitors, cannabinoid modulators, and cholinesterase inhibitors (e.g., donepezil, rivastigmine, and galantamine). In such combinations, each active ingredient can be administered either in accordance with their usual dosage range or a dose below their usual dosage range, and can be administered either simultaneously or sequentially.

Drugs suitable in combination with the compounds of the present invention include, but are not limited to, other suitable schizophrenia drugs such as Haldol, Clozaril, Zyprexa, Risperdal, Abilify, Geodon, Invega, and Seroquel; bipolar disorder drug, including, but not limited to, Lithium, Zyprexa, Abilify, and Depakote; Parkinson's disease drugs, including, but not limited to, Levodopa, Parlodel, Permax, Mirapex, Tasmar, Kemadrin, Artane, and Cogentin; agents used in the treatment of major depression, including, but not limited to, Elavil, Tofranil, Norpramin, Pamelor, Paxil, Prozac, Zoloft, Wellbutrin, Lexapro, Remeron, Effexor, Cymbalta; agents used in the treatment of Alzheimer's disease, including, but not limited to, Reminyl, Cognex, Aricept, Exelon, Akatinol, Neotropin, Eldepryl, Estrogen and Clioquinol; agents used in the treatment of dementia, including, but not limited to, Mellaril, Haldol, Risperdal, Cognex, Aricept, and Exelon; agents used in the treatment of epilepsy, including, but not limited to, Dilantin, Luminal, Tegretol, Depakote, Depakene, Zarontin, Neurontin, Barbita, Solfeton and Felbatol; agents used in the treatment of multiple sclerosis, including, but not limited to, Detrol, Ditropan XL, Oxy-Contin, Betaseron, Avonex, Azathioprine, Trexall and Copaxone; agents used in the treatment of Huntington's disease, including, but not limited to, Elavil, Tofranil, Norpramin, Pamelor, Paxil, Prozac, Zoloft, Nitoman, Haldol, Thorazine, Mellaril, Dogmatil, Seroquel, Clozaril, and Risperdal; agents useful in the treatment of diabetes, including, but not limited to, PPAR ligands (e.g. agonists, antagonists, such as Rosiglitazone, Troglitazone and Pioglitazone), insulin secretagogues (e.g., sulfonylurea drugs, such as Glyburide, Glimepiride, Chlorpropamide, Tolbutamide, and Glipizide, and non-sulfonyl secretagogues), α-glucosidase inhibitors (such as Acarbose, Miglitol, and Voglibose), insulin sensitizers (such as the PPAR-γ agonists, e.g., the glitazones; biguanides, PTP-1B inhibitors, DPP-IV inhibitors, and 11beta-HSD inhibitors), hepatic glucose output lowering compounds (such as glucagon antagonists and metformin, e.g., Glucophage and Glucophage XR), insulin and insulin derivatives (both long and short acting forms and formulations of insulin); and antiobesity drugs, including, but not limited to, β-3 agonists, CB-1 agonists, neuropeptide Y5 inhibitors, Ciliary Neurotrophic Factor and derivatives (e.g., Axokine), appetite suppressants (e.g., Sibutramine), and lipase inhibitors (e.g., Orlistat).

The form of administration of concomitant drugs with the compound of the present invention is not particularly limited and is acceptable as long as the compound of the present invention is combined with concomitant drugs at the time of administration. Examples of such forms of administration are as follows:

(1) Administration of a single formula obtained simultaneous formulation of the compound of the present invention with a concomitant drug, (2) Simultaneous administration via the same administration route for two kinds of formulas obtained by independent formulations of the compound of the present invention and a concomitant drug, (3) Administrations at different times via the same administration route for two kings of formulas obtained by independent formulations of the compound of the present invention and a concomitant drug, (4) Simultaneous administration via different administration routes for two kinds of formulas obtained by independent formulations of the compound of the present invention and a concomitant drug, (5) Administrations at different times via different administration routes for two kinds of formulas obtained by independent formulations of the compound of the present invention and a concomitant drug. (For example, administration in the order of the composition of the present invention a concomitant drug, or administration in the reversed order). These forms of administration are summarized below and abbreviated as a concomitant agent of the present invention.

When administering the concomitant agent of the present invention, a concomitant drug and the compound of the present invention can be administered at the same time, but the compound of the present invention can be administered after a concomitant drug is administered or after the compound of the present invention is administered, a concomitant drug can be administered. When administering at different times, the time difference depends upon the active ingredients to be administered, drug forms and methods of administration. For example, when a concomitant drug is administered first, the compound of the present invention can be administered within 1 min. to 3 days, preferably within 10 min. to 1 day and more preferably within 15 min. to 1 hour after the concomitant drug is administered. However, if the compound of the present invention is administered first, a concomitant drug can be administered within 1 min. to 1 day, preferably within 10 min. to 6 hours and more preferably within 15 min. to 1 hour after the compound of the present invention is administered.

If there are no problems with side effects of the concomitant drugs, any dosages can be set. A daily dosage as a concomitant drug depends upon dosages, administration subjects, administration routes, target diseases, symptoms, etc. For example, in the case of oral administration in patients with schizophrenia (adults, bodyweight of approximately 60 kg), a normal daily dosage ranges from about 0.1 to 20 mg/kg bodyweight, preferably from about 0.2 to 10 mg/kg bodyweight and more preferably from about 0.5 to 10 mg/kg bodyweight. It is preferable that this dosage is administered once daily to several times daily (e.g., 3 times).

If the compound of the present invention is used in combination with a concomitant drug, the respective dosages can be reduced within a safe range with consideration of the opposite effects of the respective drugs.

The concomitant agent of the present invention exhibits low toxicity. For example, the compound of the present invention or (and) the aforementioned concomitant drug can be combined with a pharmaceutically acceptable carrier according to the known method to prepare a medical composition such as tablets (including sugar-coated tablets and film-coated tablets), powder agents, granular agents, capsules (including soft capsules), liquids, injection solutions, suppositories, sustained-release agents, etc. These compositions can be administered safely orally or non-orally (e.g., including local, rectal and venous routes).

The pharmaceutically acceptable carriers that can be used for manufacturing the concomitant agent of the present invention can be the same as those used in the medical composition of the present invention as mentioned above.

A mixing ratio between the compound of the present invention and a concomitant drug in the concomitant agent of the present invention can be selected appropriately based on the administration subjects, administration routes and diseases.

The aforementioned concomitant drugs can be combined at an appropriate proportion if two or more drugs are combined.

A dosage of the concomitant drug can be selected appropriately based on the dosages used clinically. In addition, a mixing ratio between the compound of the present invention and a concomitant drug can be selected appropriately based on the administration subjects, administration routes, target diseases, symptoms, combinations, etc. For example, if the administration subject is humans, a concomitant drug can be used in an amount ranging from 0.01 to 100 parts by weight relative to 1 part by weight of the compound of the present invention.

For example, the content of the compound of the present invention in the concomitant agent of the present invention varies with the drug form of formulations. Generally, it is present in a range from about 0.01 to 99.9 wt %, preferably from about 0.1 to 50 wt % and more preferably from about 0.5 to 20 wt % relative to the entire formula.

The content of a concomitant drug in the concomitant agent of the present invention varies with the drug form of formulations. Generally it is present in a range from about 0.01 to 99.9 wt %, preferably from about 0.1 to 50 wt % and more preferably from about 0.5 to 20 wt % relative to the entire formula.

The content of an additive such as carriers in the concomitant agent of the present invention varies with the drug form of formulations. Generally it is present in a range from about 1 to 99.99 wt % and preferably from about 10 to 90 wt % relative to the entire formula.

When the compound of the present invention and a concomitant drug are formulated independently, the same contents can be applied.

Since the dosages may fluctuate under various conditions as mentioned above, a dosage less than the aforementioned dosages may be sufficient or it may be necessary to administer at a dosage exceeding the range.

EXAMPLES

The present invention will be explained in detail below with reference to the reference examples, embodiments, formulation examples and experimental examples. Since these are simply examples, the present invention will not be limited to these examples and the present invention can be modified in the range not deviating from the scope of the present invention.

In the following reference examples and embodiments, "room temperature" indicates generally approximately 10° C. to 35° C. As for %, % in terms of yields indicates mol/mol %, % in terms of the solvent used for chromatography indicates vol %, and % in other cases indicates wt %. In the proton NMR spectrum, OH and NH protons that cannot be identified due to broad bands are not recorded in the data. Kieselgel 60 by Merck & Co., Inc. was used in silica gel chromatography and Chromatorex NH by Fuji Silysia Chemical Ltd. was used in basic silica gel chromatography.

| Abbreviations used in other sections of the text imply the following meanings. | |
|---|---|
| s: | singlet |
| d: | doublet |
| dd: | doublet of doublets |
| dt: | doublet of triplets |
| t: | triplet |
| tt: | triplet of triplets |
| td: | triplet of doublets |
| q: | quartet |
| septet: | septet |
| m: | multiplet |
| br: | broad |
| J: | coupling constant |
| Hz: | hertz |
| $CDCl_3$: | deuterochloroform |
| $DMSO\text{-}d_6$: | deutero-dimethyl sulfoxide |
| $^1H\text{-}NMR$: | proton nuclear magnetic resonance |
| HPLC: | high performance liquid chromatography |
| THF: | tetrahydrofuran |
| DMF: | N,N-dimethylformamide |
| DMSO: | dimethylsulfoxide |
| NMP: | N-methylpyrrolidone |
| HOBt: | 1-hydroxybenzotriazole |
| WSC: | 1-ethyl-3-(3-dimethylaminopropyl)-carbodiimide hydrochloride |
| HATU: | hexafluorophosphate 2-(7-aza-1H-benzotriazole-1-yl)-1,1,3,3-tetramethyluronium |
| DMTMM: | 4-(4,6-dimethoxy-1,3,5-triazin-2-yl)-4-methylmorpholinium chloride n-hydrate |
| DBU: | 1,8-diazabicyclo[5.4.0]-7-undecene |
| LC-MS: | liquid chromatography/mass spectroscopy |
| ESI: | electrospray ionization |
| CDI: | 1,1'-carbonyldiimidazole |
| dba: | dibenzylideneacetone |
| DIBAL: | diisobutylaluminium hydride |
| DME: | 1,2-dimethoxyethane |
| DPPA: | diphenylphosphoryl azide |
| HMPA: | hexamethylphosphoric triamide |
| selectfluor: | 1-chloromethyl-4-fluoro-1,4-diazoniabicyclo[2.2.2]octane bis(tetrafluoroborate) |
| TEA: | triethylamine |
| TFA: | trifluoroacetic acid |
| TMSCl: | trimethylsilyl chloride |
| Xantphos: | 4,5-bis(diphenylphosphino)-9,9-dimethylxanthene |
| Rt: | retention time |

All reagents and solvents were of commercial quality and used without further purification. Column chromatography was performed using Merck silica gel 60 (230-400 mesh). The compounds and/or intermediates were purified by preparative high performance liquid chromatography (prep. HPLC) using a Gilson High through Put purification system.

The columns were reversed phase YMC CombiPrep Pro C18, S-5 μm, 19×50 mm. A gradient elution was used (flow rate 20 mL/min), typically starting with 5% acetonitrile/95% water and progressing to 100% acetonitrile over a Period of 7 min. All solvents contained 0.1% trifluoroacetic acid (TFA).

Mass spectrometric analysis was performed according to liquid chromatography/mass spectroscopy (LCMS) methods.

The method employed a Waters LC-MS System (Agilent HP1100 HPLC and a Micromass ZMD mass spectrometer for the LCMS instrument, a CAPCELL PAK C18, UG120, S-3 μm, 1.5×35 mm for the chromatography column, and a solvent system that was a 5-95% gradient of acetonitrile in water with 0.04% TFA over a 3.60 min period (flow rate 0.5 mL/min molecular weight range 200-800; cone Voltage 20 V; column temperature 40° C.). All masses were reported as those of the protonated parent ions.

Reference Example 1

3-{[3-(Trifluoromethyl)phenyl]hydrazono}pentane-2,4-dione

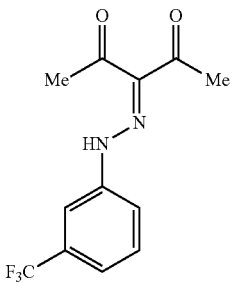 [SMILES: CC(=O)C(=NNc1cccc(C(F)(F)F)c1)C(C)=O]

3-(Trifluoromethyl)aniline (34.6 g, 215 mmol) was dissolved in a mixture of concentrated hydrochloric acid (64 mL) and water (64 mL). To the resulting mixture was added dropwise at 0° C. a solution of sodium nitrite (16.6 g, 240 mmol) in water (100 mL). The mixture was stirred for 1 h at 0° C. To the resulting diazonium salt solution was added dropwise a solution of pentane-2,4-dione (22.0 g, 220 mmol) and sodium acetate (52.5 g, 640 mmol) in ethanol (225 mL) and water (80 mL) at room temperature. The mixture was stirred for 18 h at room temperature with a mechanical stirrer. The orange precipitate was filtered off and washed with water (150 mL×3), 50 percent aqueous ethanol (100 mL×2), and n-hexane (100 mL), and then dried in vacuo at 50° C. for 5 h affording 52.7 g (90%) of 3-{[3-(trifluoromethyl)phenyl]hydrazono}pentane-2,4-dione as an orange solid.

$^1$H NMR (400 MHz, CDCl$_3$): δ ppm 2.52 (s, 3H), 2.63 (s, 3H), 7.45-7.44 (m, 1H), 7.58-7.51 (m, 2H), 7.66 (s, 1H), 14.68 (s, 1H). LC-MS (MH$^+$) 273.10.

Reference Example 2

3-[3-(Dimethylamino)prop-2-enoyl]-1-[3-(trifluoromethyl)phenyl]pyridazin-4(1H)-one

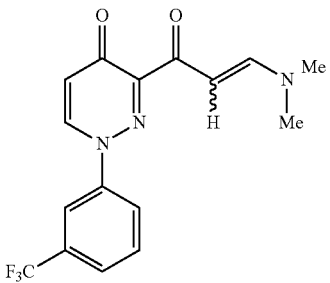 [SMILES: CNC=CC(=O)c1nn(-c2cccc(C(F)(F)F)c2)ccc1=O]

A mixture of 3-{[3-(trifluoromethyl)phenyl]hydrazono}pentane-2,4-dione (4.3 g, 15.8 mmol) and N,N-dimethylformamide dimethylacetal (40 mL) was heated in an oil bath at 120° C. for 5 h. The solvent was removed under reduced pressure to give quantitative yield of 3-[3-(dimethylamino)prop-2-enoyl]-1-[3-(trifluoromethyl)phenyl]pyridazin-4(1H)-one as a black oil, which was used as is in the next step without further purification.

LC-MS (MH$^+$) 338.16.

Reference Example 3

3-{[4-(Trifluoromethyl)phenyl]hydrazono}pentane-2,4-dione

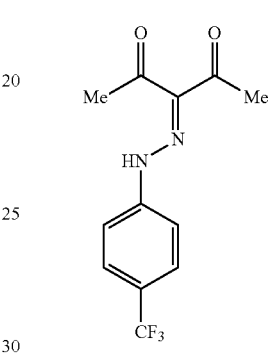

To a solution of 4-(trifluoromethyl)aniline (1090 mg, 6.80 mmol) in 5 mL of water and 5 mL of concentrated hydrochloride solution, sodium nitrite (563 mg, 8.16 mmol) in 4 mL of water was added dropwise at 0° C., and the mixture was stirred at 0° C. for 1 h. Then to the reaction mixture was added dropwise a solution of sodium acetate (1670 mg, 20.40 mmol) and acetylacetone (748 mg, 7.48 mmol) in 10 mL of ethanol and 6 mL of water. The mixture was stirred at room temperature overnight, filtered, washed with water, EtOH/H$_2$O (1:1) and hexane, and dried to give 3-{[4-(trifluoromethyl)phenyl]hydrazono}pentane-2,4-dione (580 mg, 31%).

$^1$H NMR (300 MHz, CDCl$_3$): δ ppm 2.51 (s, 3H), 2.62 (s, 3H), 7.44 (d, J=8.7 Hz, 2H), 7.69 (d, J=8.7 Hz, 2H), 14.59 (s, 1H).

Reference Example 4

3-[3-(Dimethylamino)prop-2-enoyl]-1-[4-(trifluoromethyl)phenyl]pyridazin-4(1H)-one

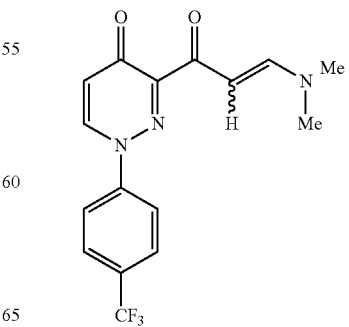

3-{[4-(Trifluoromethyl)phenyl]hydrazono}pentane-2,4-dione (580 mg, 2.13 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-[4-(trifluoromethyl)phenyl]pyridazin-4(1H)-one which was used to the next step without further purification.

Reference Example 5

3-[(3-Chlorophenyl)hydrazono]pentane-2,4-dione

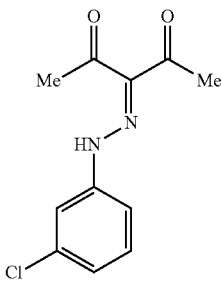 [SMILES: CC(=O)C(=NNc1cccc(Cl)c1)C(C)=O]

To a solution of 3-chloroaniline (1000 mg, 7.87 mmol) in 5 mL of water and 5 mL of concentrated hydrochloride solution, sodium nitrite (652 mg, 9.45 mmol) in 4 mL of water was added dropwise at 0° C., and the mixture was stirred at 0° C. for 1 h. Then to the reaction mixture was added dropwise a solution of sodium acetate (1936 mg, 23.61 mmol) and acetylacetone (866 mg, 8.66 mmol) in 10 mL of ethanol and 6 mL of water. The mixture was stirred at room temperature overnight, filtered, washed with water, EtOH/H$_2$O (1:1) and hexane, and dried to give 3-[(3-chlorophenyl)hydrazono]pentane-2,4-dione (450 mg, 24%).

LCMS: m/z=239 [35Cl, M$^+$+H].

Reference Example 6

1-(3-Chlorophenyl)-3-[3-(dimethylamino)prop-2-enoyl]pyridazin-4(1H)-one

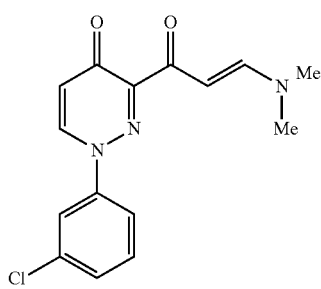 [SMILES: CN/C=C/C(=O)c1nn(-c2cccc(Cl)c2)ccc1=O]

3-[(3-Chlorophenyl)hydrazono]pentane-2,4-dione (450 mg, 1.89 mmol) was dissolved in 10 mL of N,N-dimethylformamide dimethyl acetal (DMF-DMA), and the mixture was refluxed for 4 h, then concentrated under reduced pressure to give crude 1-(3-chlorophenyl)-3-[3-(dimethylamino)prop-2-enoyl]pyridazin-4(1H)-one which was used to the next step without further purification.

Reference Example 7

3-[(2-Methoxyphenyl)hydrazono]pentane-2,4-dione

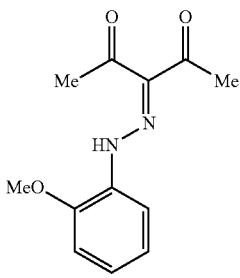 [SMILES: COc1ccccc1NN=C(C(C)=O)C(C)=O]

To a solution of 2-methoxyaniline (1000 mg, 8.13 mmol) in 10 mL of acetic acid and 2 mL of concentrated hydrochloride solution, sodium nitrite (673 mg, 9.76 mmol) in 4 mL of water was added dropwise at 0° C., and the mixture was stirred at 0° C. for 1 h. Then to the reaction mixture was added dropwise a solution of sodium acetate (2000 mg, 24.39 mmol) and acetylacetone (1057 mg, 10.57 mmol) in 10 mL of ethanol and 6 mL of water. The mixture was stirred at room temperature overnight, filtered, washed with water, EtOH/H$_2$O (1:1) and hexane, and dried to give 3-[(2-methoxyphenyl)hydrazono]pentane-2,4-dione (1500 mg, 79%).

LCMS: m/z=235 [M$^+$+H].

Reference Example 8

3-[3-(Dimethylamino)prop-2-enoyl]-1-(2-methoxyphenyl)pyridazin-4(1H)-one

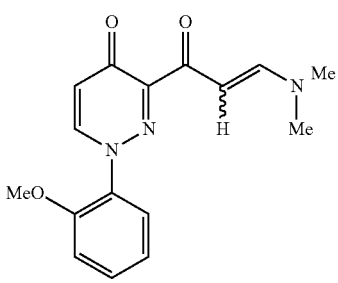 [SMILES: CNC=CC(=O)c1nn(-c2ccccc2OC)ccc1=O]

3-[(2-Methoxyphenyl)hydrazono]pentane-2,4-dione (500 mg, 2.14 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(2-methoxyphenyl)pyridazin-4(1H)-one which was used to the next step without further purification.

Reference Example 9

3-[(4-Methoxyphenyl)hydrazono]pentane-2,4-dione

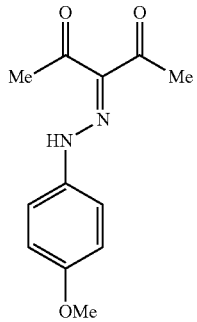

To a solution of 4-methoxyaniline (1000 mg, 8.13 mmol) in 10 mL of acetic acid and 2 mL of concentrated hydrochloride solution, sodium nitrite (673 mg, 9.76 mmol) in 4 mL of water was added dropwise at 0° C., and the mixture was stirred at 0° C. for 1 h. Then to the reaction mixture was added dropwise a solution of sodium acetate (2000 mg, 24.39 mmol) and acetylacetone (1057 mg, 10.57 mmol) in 10 mL of ethanol and 6 mL of water. The mixture was stirred at room temperature overnight, filtered, washed with water, EtOH/H$_2$O (1:1) and hexane, and dried to give 3-[(4-methoxyphenyl)hydrazono]pentane-2,4-dione (950 mg, 50%).

$^1$H NMR (400 MHz, CDCl$_3$): δ ppm 2.50 (s, 3H), 2.62 (s, 3H), 3.86 (s, 3H), 6.96-6.98 (m, 2H), 7.38-7.41 (m, 2H), 14.99 (s, 1H).

Reference Example 10

3-[3-(Dimethylamino)prop-2-enoyl]-1-(4-methoxyphenyl)pyridazin-4(1H)-one

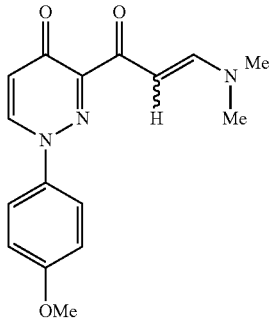 [SMILES: CNC=CC(=O)c1nn(-c2ccc(OC)cc2)ccc1=O]

3-[(4-Methoxyphenyl)hydrazono]pentane-2,4-dione (500 mg, 2.14 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(4-methoxyphenyl)pyridazin-4(1H)-one which was used to the next step without further purification.

Reference Example 11

3-[(3-Fluorophenyl)hydrazono]pentane-2,4-dione

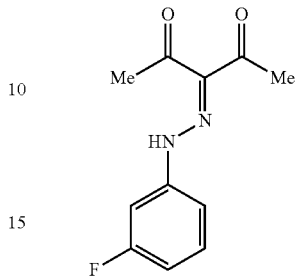

To a solution of 3-fluoroaniline (1000 mg, 9.00 mmol) in 5 mL of water and 5 mL of concentrated hydrochloride solution, sodium nitrite (746 mg, 10.80 mmol) in 4 mL of water was added dropwise at 0° C., and the mixture was stirred at 0° C. for 1 h. Then to the reaction mixture was added dropwise a solution of sodium acetate (2220 mg, 27.00 mmol) and acetylacetone (990 mg, 9.90 mmol) in 10 mL of ethanol and 6 mL of water. The mixture was stirred at room temperature overnight, filtered, washed with water, EtOH/H$_2$O (1:1) and hexane, and dried to give 3-[(3-fluorophenyl)hydrazono]pentane-2,4-dione (650 mg, 33%).

$^1$H NMR (400 MHz, CDCl$_3$): δ ppm 2.50 (s, 3H), 2.62 (s, 3H), 6.90 (dt, J=2.4, 8.0 Hz, 1H), 7.11 (dd, J=1.6, 8.0 Hz, 1H), 7.21 (td, J=2.4, 10.0 Hz, 1H), 7.34-7.39 (m, 1H), 14.61 (s, 1H).

Reference Example 12

3-[3-(Dimethylamino)prop-2-enoyl]-1-(3-fluorophenyl)pyridazin-4(1H)-one

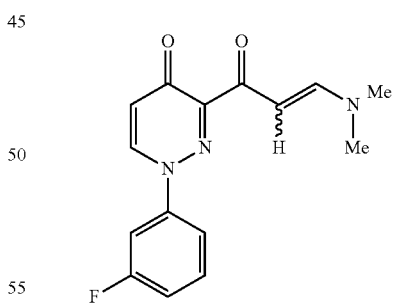

3-[(3-Fluorophenyl)hydrazono]pentane-2,4-dione (650 mg, 2.93 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(3-fluorophenyl)pyridazin-4(1H)-one which was used to the next step without further purification.

Reference Example 13

3-[(2-Fluorophenyl)hydrazono]pentane-2,4-dione

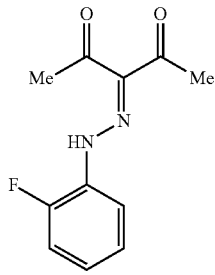 [SMILES: CC(=O)C(=NNc1ccccc1F)C(C)=O]

To a solution of 2-fluoroaniline (1000 mg, 9.00 mmol) in 10 mL of acetic acid and 2 mL of concentrated hydrochloride solution, sodium nitrite (746 mg, 10.80 mmol) in 4 mL of water was added dropwise at 0° C., and the mixture was stirred at 0° C. for 1 h. Then to the reaction mixture was added dropwise a solution of sodium acetate (2220 mg, 27.00 mmol) and acetylacetone (990 mg, 9.90 mmol) in 10 mL of ethanol and 6 mL of water. The mixture was stirred at room temperature overnight, filtered, washed with water, EtOH/$H_2O$ (1:1) and hexane, and dried to give 3-[(2-fluorophenyl)hydrazono]pentane-2,4-dione (1280 mg, 64%).

$^1$H NMR (400 MHz, $CDCl_3$): δ ppm 2.51 (s, 3H), 2.62 (s, 3H), 7.14-7.24 (m, 3H), 7.77 (d, J=8.0 Hz, 1H), 14.71 (s, 1H).

Reference Example 15

3-[(4-Fluorophenyl)hydrazono]pentane-2,4-dione

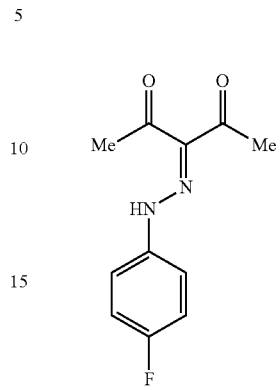

To a solution of 4-fluoroaniline (1000 mg, 9.00 mmol) in 10 mL of acetic acid and 2 mL of concentrated hydrochloride solution, sodium nitrite (746 mg, 10.80 mmol) in 4 mL of water was added dropwise at 0° C., and the mixture was stirred at 0° C. for 1 h. Then to the reaction mixture was added dropwise a solution of sodium acetate (2220 mg, 27.00 mmol) and acetylacetone (990 mg, 9.90 mmol) in 10 mL of ethanol and 6 mL of water. The mixture was stirred at room temperature overnight, filtered, washed with water, EtOH/$H_2O$ (1:1) and hexane, and dried to give 3-[(4-fluorophenyl)hydrazono]pentane-2,4-dione (1200 mg, 60%).

$^1$H NMR (300 MHz, $CDCl_3$): δ ppm 2.49 (s, 3H), 2.61 (s, 3H), 7.09-7.15 (m, 2H), 7.37-7.41 (m, 2H), 14.85 (s, 1H).

Reference Example 14

3-[3-(Dimethylamino)prop-2-enoyl]-1-(2-fluorophenyl)pyridazin-4(1H)-one

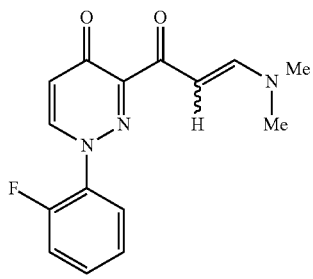 [SMILES: CNC=CC(=O)c1nn(-c2ccccc2F)ccc1=O]

3-[(2-Fluorophenyl)hydrazono]pentane-2,4-dione (600 mg, 2.70 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(2-fluorophenyl)pyridazin-4(1H)-one which was used to the next step without further purification.

Reference Example 16

3-[3-(Dimethylamino)prop-2-enoyl]-1-(4-fluorophenyl)pyridazin-4(1H)-one

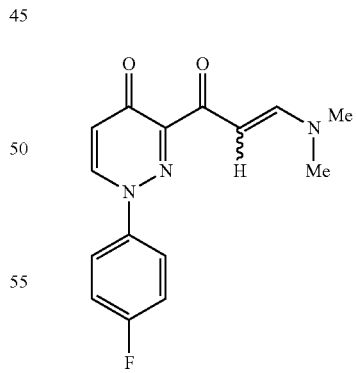

3-[(4-Fluorophenyl)hydrazono]pentane-2,4-dione (650 mg, 2.93 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(4-fluorophenyl)pyridazin-4(1H)-one which was used to the next step without further purification.

Reference Example 17

3-[(4-Chlorophenyl)hydrazono]pentane-2,4-dione

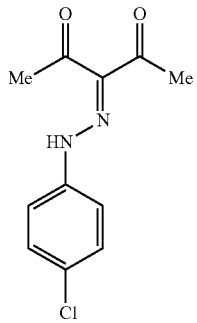

To a solution of 4-chloroaniline (1000 mg, 7.87 mmol) in 10 mL of acetic acid and 2 mL of concentrated hydrochloride solution, sodium nitrite (652 mg, 9.45 mmol) in 4 mL of water was added dropwise at 0° C., and the mixture was stirred at 0° C. for 1 h. Then to the reaction mixture was added dropwise a solution of sodium acetate (1936 mg, 23.61 mmol) and acetylacetone (1023 mg, 10.23 mmol) in 10 mL of ethanol and 6 mL of water. The mixture was stirred at room temperature overnight, filtered, washed with water, EtOH/H$_2$O (1:1) and hexane, and dried to give 3-[(4-chlorophenyl)hydrazono]pentane-2,4-dione (1680 mg, 90%).

$^1$H NMR (400 MHz, CDCl$_3$): δ ppm 2.49 (s, 3H), 2.61 (s, 3H), 7.33-7.39 (m, 4H), 14.70 (s, 1H).

Reference Example 18

1-(4-Chlorophenyl)-3-[3-(dimethylamino)prop-2-enoyl]pyridazin-4(1H)-one

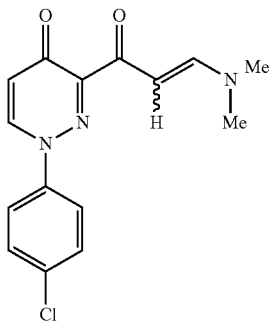 [SMILES: CNC=CC(=O)c1nn(-c2ccc(Cl)cc2)ccc1=O]

3-[(4-Chlorophenyl)hydrazono]pentane-2,4-dione (600 mg, 2.52 mmol) was dissolved in 10 mL of N,N-dimethylformamide dimethyl acetal (DMF-DMA), and the mixture was refluxed for 4 hours, then concentrated under reduced pressure to give crude 1-(4-chlorophenyl)-3-[3-(dimethylamino)prop-2-enoyl]pyridazin-4(1H)-one which was used to the next step without further purification.

Reference Example 19

3-[(2-Methylphenyl)hydrazono]pentane-2,4-dione

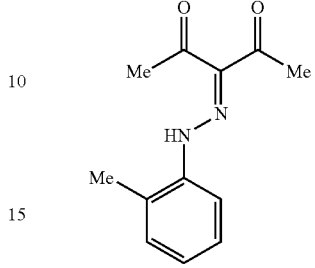

To a solution of 2-methylaniline (1000 mg, 9.34 mmol) in 10 mL of acetic acid and 2 mL of concentrated hydrochloride solution, sodium nitrite (774 mg, 11.21 mmol) in 4 mL of water was added dropwise at 0° C., and the mixture was stirred at 0° C. for 1 h. Then to the reaction mixture was added dropwise a solution of sodium acetate (2299 mg, 28.04 mmol) and acetylacetone (1215 mg, 12.15 mmol) in 10 mL of ethanol and 6 mL of water. The mixture was stirred at room temperature overnight, filtered, washed with water, EtOH/H$_2$O (1:1) and hexane, and dried to give 3-[(2-methylphenyl)hydrazono]pentane-2,4-dione (1000 mg, 49%). LCMS: m/z=219 [M$^+$+H].

Reference Example 20

3-[3-(Dimethylamino)prop-2-enoyl]-1-(2-methylphenyl)pyridazin-4(1H)-one

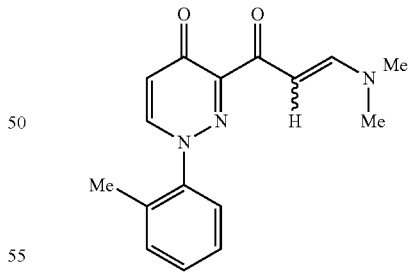

3-[(2-Methylphenyl)hydrazono]pentane-2,4-dione (1000 mg, 4.59 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(2-methylphenyl)pyridazin-4(1H)-one which was used to the next step without further purification.

Reference Example 21

3-[(3-Methylphenyl)hydrazono]pentane-2,4-dione

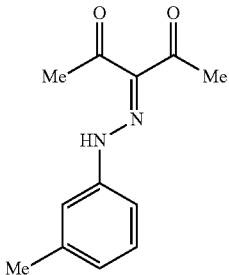

To a solution of 3-methylaniline (1000 mg, 9.34 mmol) in 10 mL of acetic acid and 2 mL of concentrated hydrochloride solution, sodium nitrite (774 mg, 11.21 mmol) in 4 mL of water was added dropwise at 0° C., and the mixture was stirred at 0° C. for 1 h. Then to the reaction mixture was added dropwise a solution of sodium acetate (2299 mg, 28.04 mmol) and acetylacetone (1215 mg, 12.15 mmol) in 10 mL of ethanol and 6 mL of water. The mixture was stirred at room temperature overnight, filtered, washed with water, EtOH/$H_2O$ (1:1) and hexane, and dried to give 3-[(3-methylphenyl)hydrazono]pentane-2,4-dione (500 mg, yield 24%). LCMS: m/z=219 [$M^+$+H].

Reference Example 22

3-[3-(Dimethylamino)prop-2-enoyl]-1-(3-methylphenyl)pyridazin-4(1H)-one

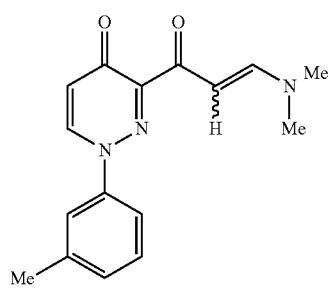

3-[(3-Methylphenyl)hydrazono]pentane-2,4-dione (500 mg, 2.29 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(3-methylphenyl)pyridazin-4(1H)-one which was used to the next step without further purification.

Reference Example 23

3-[(3-Methoxyphenyl)hydrazono]pentane-2,4-dione

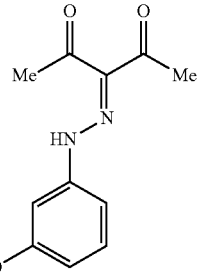

To a solution of 3-methoxyaniline (1000 mg, 8.13 mmol) in 10 mL of acetic acid and 2 mL of concentrated hydrochloride solution, sodium nitrite (673 mg, 9.76 mmol) in 4 mL of water was added dropwise at 0° C., and the mixture was stirred at 0° C. for 1 h. Then to the reaction mixture was added dropwise a solution of sodium acetate (2000 mg, 24.39 mmol) and acetylacetone (1057 mg, 10.57 mmol) in 10 mL of ethanol and 6 mL of water. The mixture was stirred at room temperature overnight, filtered, washed with water, EtOH/$H_2O$ (1:1) and hexane, and dried to give 3-[(3-methoxyphenyl)hydrazono]pentane-2,4-dione (840 mg, 44%). LCMS: m/z=235 [$M^+$+H].

Reference Example 24

3-[3-(Dimethylamino)prop-2-enoyl]-1-(3-methoxyphenyl)pyridazin-4(1H)-one

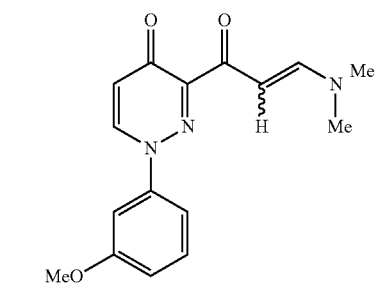

3-[(3-Methoxyphenyl)hydrazono]pentane-2,4-dione (500 mg, 2.14 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(3-methoxyphenyl)pyridazin-4(1H)-one which was used to the next step without further purification.

Reference Example 25

3-{[2-(Trifluoromethyl)phenyl]hydrazono}pentane-2,4-dione

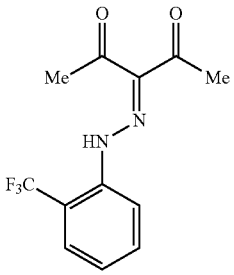 [SMILES: CC(=O)C(=NNc1ccccc1C)C(C)=O]

To a solution of 2-(trifluoromethyl)aniline (1.09 g, 6.80 mmol) in 5 mL of water and 5 mL of concentrated hydrochloride solution, sodium nitrite (563 mg, 8.16 mmol) in 4 mL of water was added dropwise at 0° C., and the mixture was stirred at 0° C. for 1 h. Then to the reaction mixture was added dropwise a solution of sodium acetate (1.67 g, 20.40 mmol) and acetylacetone (748 mg, 7.48 mmol) in 10 mL of ethanol and 6 mL of water. The mixture was stirred at room temperature overnight, filtered, washed with water, EtOH/H$_2$O (1:1) and hexane, and dried to give 3-{[2-(trifluoromethyl)phenyl]hydrazono}pentane-2,4-dione (634 mg, 33%).

$^1$H NMR (300 MHz, CDCl$_3$): δ ppm 2.52 (s, 3H), 2.63 (s, 3H), 7.24-7.29 (m, 1H), 7.60-7.66 (m, 2H), 7.96 (8.4 Hz, 1H), 15.06 (s, 1H).

Reference Example 26

3-[3-(Dimethylamino)prop-2-enoyl]-1-[2-(trifluoromethyl)phenyl]pyridazin-4(1H)-one

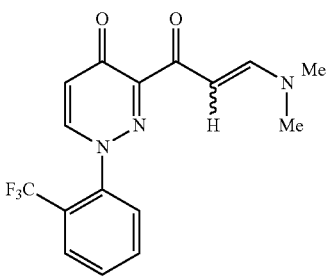 [SMILES: CNC=CC(=O)c1nn(-c2ccccc2C)ccc1=O]

3-{[2-(Trifluoromethyl)phenyl]hydrazono}pentane-2,4-dione (634 mg, 2.33 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-[2-(trifluoromethyl)phenyl]pyridazin-4(1H)-one which was used to the next step without further purification.

Reference Example 27

3-[(4-Morpholin-4-ylphenyl)hydrazono]pentane-2,4-dione

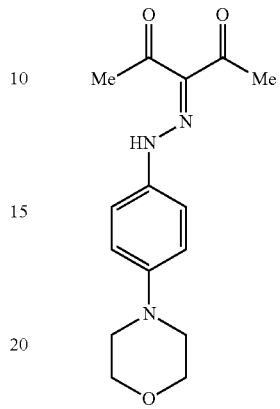

To a solution of 4-morpholin-4-ylaniline (1000 mg, 5.62 mmol) in 10 mL of acetic acid and 2 mL of concentrated hydrochloride solution, sodium nitrite (465 mg, 6.74 mmol) in 4 mL of water was added dropwise at 0° C., and the mixture was stirred at 0° C. for 1 h. Then to the reaction mixture was added dropwise a solution of sodium acetate (2764 mg, 33.71 mmol) and acetylacetone (730 mg, 7.30 mmol) in 10 mL of ethanol and 6 mL of water. The mixture was stirred at room temperature overnight, filtered, washed with water, EtOH/H$_2$O (1:1) and hexane, and dried to give 3-[(4-morpholin-4-ylphenyl)hydrazono]pentane-2,4-dione (900 mg, 55%).

LCMS: m/z=290 [M$^+$+H].

Reference Example 28

3-[3-(Dimethylamino)prop-2-enoyl]-1-(4-morpholin-4-ylphenyl)pyridazin-4(1H)-one

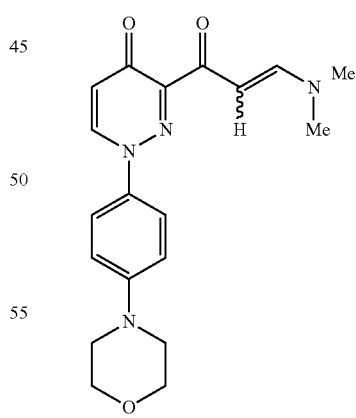

3-[(4-Morpholin-4-ylphenyl)hydrazono]pentane-2,4-dione (900 mg, 3.11 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(4-morpholin-4-ylphenyl)pyridazin-4(1H)-one which was used to the next step without further purification.

Reference Example 29

3-(Phenylhydrazono)pentane-2,4-dione

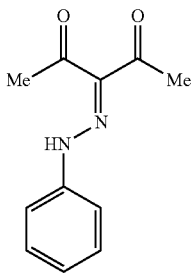

To a solution of aniline (2000 mg, 21.50 mmol) in 30 mL of acetic acid and 5 mL of concentrated hydrochloride solution, sodium nitrite (1780 mg, 25.80 mmol) in 8 mL of water was added dropwise at 0° C., and the mixture was stirred at 0° C. for 1 h. Then to the reaction mixture was added dropwise a solution of sodium acetate (5290 mg, 64.50 mmol) and acetylacetone (2795 mg, 27.95 mmol) in 20 mL of ethanol and 12 mL of water. The mixture was stirred at room temperature overnight, filtered, washed with water, EtOH/H$_2$O (1:1) and hexane, and dried to give 3-(phenylhydrazono)pentane-2,4-dione (2955 mg, 67%).

$^1$H NMR (400 MHz, CDCl$_3$): δ ppm 2.50 (s, 3H), 2.61 (s, 3H), 7.21 (dd, J=8.0, 4.4 Hz, 1H), 7.41 (d, J=4.4 Hz, 4H), 14.74 (s, 1H).

Reference Example 30

3-[3-(Dimethylamino)prop-2-enoyl]-1-phenylpyridazin-4(1H)-one

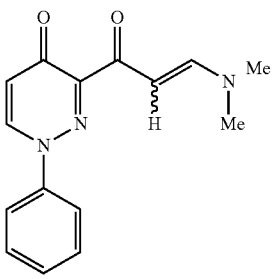 [SMILES: CNC=CC(=O)c1nn(-c2ccccc2)ccc1=O]

3-(Phenylhydrazono)pentane-2,4-dione (470 mg, 2.30 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-phenylpyridazin-4(1H)-one which was used to the next step without further purification.

$^1$H NMR of the crude product (400 MHz, DMSO-d$_6$): δ ppm 2.84 (s, 3H), 3.11 (s, 3H), 5.50 (br, 1H), 6.55 (d, J=8.0 Hz, 1H), 7.43-7.46 (m, 1H), 7.57 (t, J=7.6 Hz, 2H), 7.70 (d, J=8.0 Hz, 2H), 8.81 (d, J=8.0 Hz, 1H).

Reference Example 31

3-[(4-Methylphenyl)hydrazono]pentane-2,4-dione

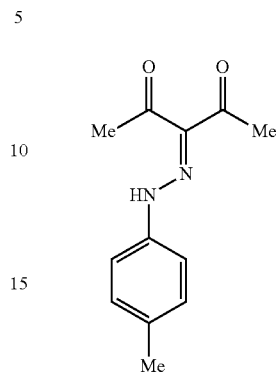

To a solution of 4-methylaniline (1000 mg, 9.34 mmol) in 10 mL of acetic acid and 2 mL of concentrated hydrochloride solution, sodium nitrite (774 mg, 11.21 mmol) in 4 mL of water was added dropwise at 0° C., and the mixture was stirred at 0° C. for 1 h. Then to the reaction mixture was added dropwise a solution of sodium acetate (2299 mg, 28.04 mmol) and acetylacetone (1215 mg, 12.15 mmol) in 10 mL of ethanol and 6 mL of water. The mixture was stirred at room temperature overnight, filtered, washed with water, EtOH/H$_2$O (1:1) and hexane, and dried to give 3-[(4-methylphenyl)hydrazono]pentane-2,4-dione (480 mg, 24%).

$^1$H NMR (400 MHz, CDCl$_3$): δ ppm 2.36 (s, 3H), 2.49 (s, 3H), 2.60 (s, 3H), 7.21 (d, J=8.0 Hz, 2H), 7.32 (d, J=8.0 Hz, 2H), 14.82 (s, 1H).

Reference Example 32

3-[3-(Dimethylamino)prop-2-enoyl]-1-(4-methylphenyl)pyridazin-4(1H)-one

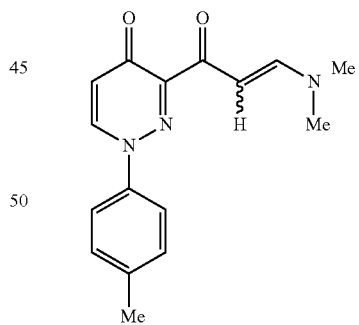

3-[(4-Methylphenyl)hydrazono]pentane-2,4-dione (462 mg, 2.12 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(4-methylphenyl)pyridazin-4(1H)-one which was used to the next step without further purification.

$^1$H NMR of the crude product (400 MHz, DMSO-d$_6$): δ ppm 2.38 (s, 3H), 2.84 (s, 3H), 3.10 (s, 3H), 6.53 (d, J=8.0 Hz, 1H), 7.37 (d, J=8.0 Hz, 2H), 7.58 (d, J=8.0 Hz, 2H), 8.76 (d, J=8.0 Hz, 1H).

Reference Example 33

3-{[2-(Difluoromethoxy)phenyl]hydrazono}pentane-2,4-dione

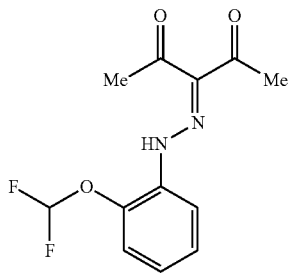 [SMILES: CC(=O)C(=NNc1ccccc1OC(F)F)C(C)=O]

To a solution of 2-(difluoromethoxy)aniline (1000 mg, 6.25 mmol) in 15 mL of acetic acid and 2.5 mL of concentrated hydrochloride solution, sodium nitrite (518 mg, 7.50 mmol) in 4 mL of water was added dropwise at 0° C., and the mixture was stirred at 0° C. for 1 h. Then to the reaction mixture was added dropwise a solution of sodium acetate (1538 mg, 18.75 mmol) and acetylacetone (812 mg, 8.12 mmol) in 10 mL of ethanol and 6 mL of water. The mixture was stirred at room temperature overnight, filtered, washed with water, EtOH/H$_2$O (1:1) and hexane, and dried give 3-{[2-(difluoromethoxy)phenyl]hydrazono}pentane-2,4-dione (1590 mg, 94%).

LCMS: m/z=271 [M$^+$+H].

Reference Example 34

1-[2-(Difluoromethoxy)phenyl]-3-[3-(dimethylamino)prop-2-enoyl]pyridazin-4(1H)-one

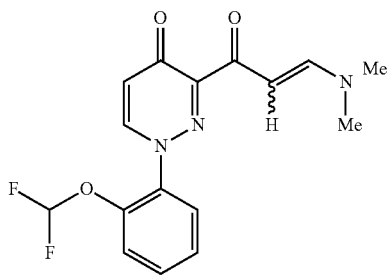 [SMILES: CNC=CC(=O)c1nn(-c2ccccc2OC(F)F)ccc1=O]

3-{[2-(Difluoromethoxy)phenyl]hydrazono}pentane-2,4-dione (500 mg, 1.85 mmol) was dissolved in 10 mL of N,N-dimethylformamide dimethyl acetal (DMF-DMA), and the mixture was refluxed for 4 hours, then concentrated under reduced pressure to give crude 1-[2-(difluoromethoxy)phenyl]-3-[3-(dimethylamino)prop-2-enoyl]pyridazin-4(1H)-one which was used to the next step without further purification.

Reference Example 35

3-{[3-(Difluoromethoxy)phenyl]hydrazono}pentane-2,4-dione

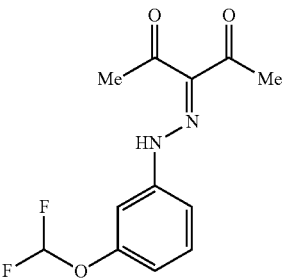 [SMILES: CC(=O)C(=NNc1cccc(OC(F)F)c1)C(C)=O]

To a solution of 3-(difluoromethoxy)aniline (1000 mg, 6.25 mmol) in 10 mL of acetic acid and 2 mL of concentrated hydrochloride solution, sodium nitrite (518 mg, 7.50 mmol) in 4 mL of water was added dropwise at 0° C., and the mixture was stirred at 0° C. for 1 h. Then to the reaction mixture was added dropwise a solution of sodium acetate (1538 mg, 18.75 mmol) and acetylacetone (812 mg, 8.12 mmol) in 10 mL of ethanol and 6 mL of water. The mixture was stirred at room temperature overnight, filtered, washed with water, EtOH/H$_2$O (1:1) and hexane, and dried to give 3-{[3-(difluoromethoxy)phenyl]hydrazono}pentane-2,4-dione (1500 mg, 89%).

LCMS: m/z=271 [M$^+$+H].

Reference Example 36

1-[3-(Difluoromethoxy)phenyl]-3-[3-(dimethylamino)prop-2-enoyl]pyridazin-4(1H)-one

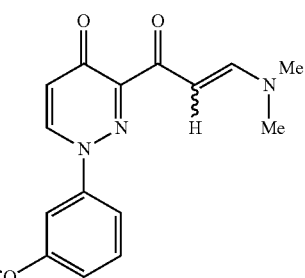

3-{[3-(Difluoromethoxy)phenyl]hydrazono}pentane-2,4-dione (800 mg, 2.96 mmol) was dissolved in 10 mL of N,N-dimethylformamide dimethyl acetal (DMF-DMA), and the mixture was refluxed for 4 h, then concentrated under reduced pressure to give crude 1-[3-(difluoromethoxy)phenyl]-3-[3-(dimethylamino)prop-2-enoyl]pyridazin-4(1H)-one which was used to the next step without further purification.

Reference Example 37

3-{[4-(Difluoromethoxy)phenyl]hydrazono}pentane-2,4-dione

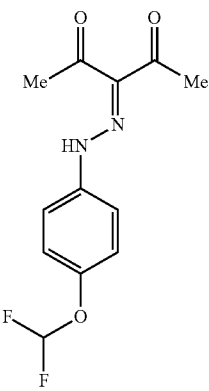 [SMILES: CC(=O)C(=NNc1ccc(OC(F)F)cc1)C(C)=O]

To a solution of 4-(difluoromethoxy)aniline (1000 mg, 6.25 mmol) in 10 mL of acetic acid and 2 mL of concentrated hydrochloride solution, sodium nitrite (518 mg, 7.50 mmol) in 4 mL of water was added dropwise at 0° C., and the mixture was stirred at 0° C. for 1 h. Then to the reaction mixture was added dropwise a solution of sodium acetate (1538 mg, 18.75 mmol) and acetylacetone (812 mg, 8.12 mmol) in 10 mL of ethanol and 6 mL of water. The mixture was stirred at room temperature overnight, filtered, washed with water, EtOH/H$_2$O (1:1) and hexane, and dried to give 3-{[4-(difluoromethoxy)phenyl]hydrazono}pentane-2,4-dione (1400 mg, yield 82%).

LCMS: m/z=271 [M$^+$+H].

Reference Example 38

1-[4-(Difluoromethoxy)phenyl]-3-[3-(dimethylamino)prop-2-enoyl]pyridazin-4(1H)-one

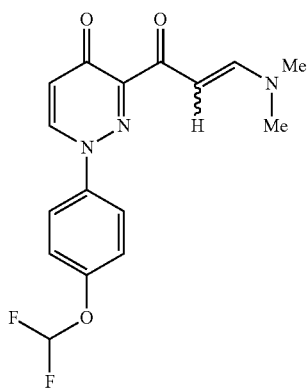 [SMILES: CNC=CC(=O)c1nn(-c2ccc(OC(F)F)cc2)ccc1=O]

3-{[4-(Difluoromethoxy)phenyl]hydrazono}pentane-2,4-dione (600 mg, 2.22 mmol) was dissolved in 10 mL of N,N-dimethylformamide dimethyl acetal (DMF-DMA), and the mixture was refluxed for 4 h, then concentrated under reduced pressure to give crude 1-[4-(difluoromethoxy)phenyl]-3-[3-(dimethylamino)prop-2-enoyl]pyridazin-4(1H)-one which was used to the next step without further purification.

Reference Example 39

3-[(2-Morpholin-4-ylphenyl)hydrazono]pentane-2,4-dione

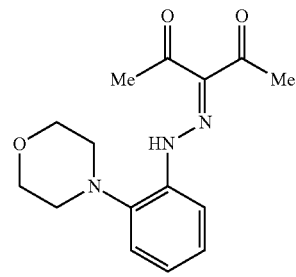 [SMILES: CC(=O)C(=NNc1ccccc1N1CCOCC1)C(C)=O]

To a solution of 2-morpholin-4-ylaniline (1000 mg, 5.62 mmol) in 10 mL of acetic acid and 2 mL of concentrated hydrochloride solution, sodium nitrite (465 mg, 6.74 mmol) in 4 mL of water was added dropwise at 0° C., and the mixture was stirred at 0° C. for 1 h. Then to the reaction mixture was added dropwise a solution of sodium acetate (2764 mg, 33.71 mmol) and acetylacetone (730 mg, 7.30 mmol) in 10 mL of ethanol and 6 mL of water. The mixture was stirred at room temperature overnight, filtered, washed with water, EtOH/H$_2$O (1:1) and hexane, and dried to give 3-[(2-morpholin-4-ylphenyl)hydrazono]pentane-2,4-dione (1000 mg, 62%).

LCMS: m/z=290 [M$^+$+H].

Reference Example 40

3-[3-(Dimethylamino)prop-2-enoyl]-1-(2-morpholin-4-ylphenyl)pyridazin-4(1H)-one

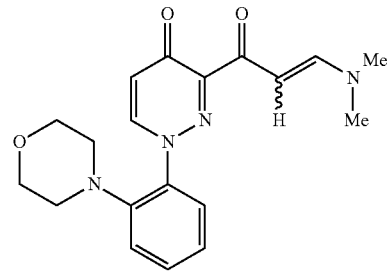 [SMILES: CNC=CC(=O)c1nn(-c2ccccc2N2CCOCC2)ccc1=O]

3-[(2-Morpholin-4-ylphenyl)hydrazono]pentane-2,4-dione (1000 mg, 2.46 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(2-morpholin-4-ylphenyl)pyridazin-4(1H)-one which was used to the next step without further purification.

Reference Example 41

3-(Pyridin-3-ylhydrazono)pentane-2,4-dione

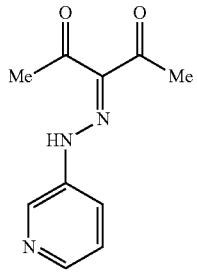

To 3-aminopyridine (564 mg, 6.00 mmol) were added 4 mL of concentrated sulfuric acid and 1.2 mL of water at 0° C., and the mixture was stirred at room temperature until it was clear. To the reaction mixture was added a solution of sodium nitrite (414 mg, 6.00 mmol) in water (1.2 mL) at 0° C. The mixture was stirred for several min (>15 min). The solution of diazonium salt was poured into the solution of 2,4-pentanedione (600 mg, 6.00 mmol) and potassium acetate (18.0 g, 180 mmol) in ethanol (120 mL) at 0° C. The mixture was stirred at 0° C. for 30 min and at room temperature for 30 min. The reaction mixture was added to 120 mL of saturated $Na_2CO_3$ aqueous solution. The mixture was extracted with dichloromethane, washed with water and brine, dried over $Na_2SO_4$, and concentrated under reduced pressure to give 3-(pyridin-3-ylhydrazono)pentane-2,4-dione (242 mg, yield 20%).

LCMS: m/z=206 [M$^+$+H].

Reference Example 42

3-[3-(Dimethylamino)prop-2-enoyl]-1-pyridin-3-ylpyridazin-4(1H)-one

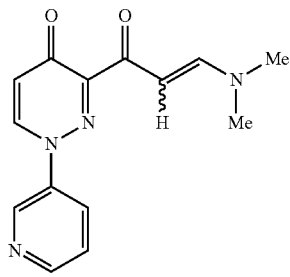 [SMILES: CN(C)C=CC(=O)c1nn(-c2cccnc2)ccc1=O]

3-(Pyridin-3-ylhydrazono)pentane-2,4-dione (200 mg, 0.98 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-pyridin-3-ylpyridazin-4(1H)-one which was used to the next step without further purification.

$^1$H NMR of the crude product (400 MHz, CDCl$_3$): δ ppm 2.90 (s, 3H), 3.15 (s, 3H), 5.64 (d, J=11.6 Hz, 1H), 6.74 (d, J=8.4 Hz, 1H), 7.45-7.48 (m, 1H), 8.00-8.03 (m, 1H), 8.20 (d, J=8.0 Hz, 1H), 8.65-8.66 (m, 1H), 8.88 (d, J=2.8 Hz, 1H).

Reference Example 43

3-(Pyridin-4-ylhydrazono)pentane-2,4-dione

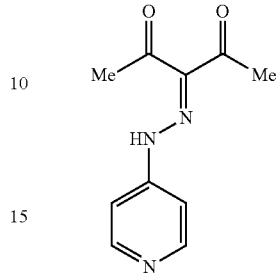

4-Aminopyridine (470 mg, 5.00 mmol) was added to a solution of 3 mL of phosphoric acid (85%) and 2 mL of nitric acid (65%) at −6° C. When the mixture reached to room temperature it was cooled to −6° C. and solid sodium nitrite (350 mg, 5.00 mmol) was added during 10 min. Small pieces of ice (50 g) were added into the solution. The mixture was added at 0° C. to a suspension of corresponding 2,4-pentanedione (500 mg, 5.00 mmol) and potassium acetate (20 g) in ethanol (250 mL). The solution was stirred for 15 min, added to 250 mL of saturated $Na_2CO_3$ aqueous solution, extracted with dichloromethane, washed with water and brine, dried over $Na_2SO_4$, and concentrated under reduced pressure to give 3-(pyridin-4-ylhydrazono)pentane-2,4-dione (149 mg, yield 14%).

$^1$H NMR (400 MHz, CDCl$_3$): δ ppm 2.52 (s, 3H), 2.62 (s, 3H), 7.27-7.29 (m, 2H), 8.59-8.61 (m, 2H), 14.23 (s, 1H).

Reference Example 44

3-[3-(Dimethylamino)prop-2-enoyl]-1-pyridin-4-ylpyridazin-4(1H)-one

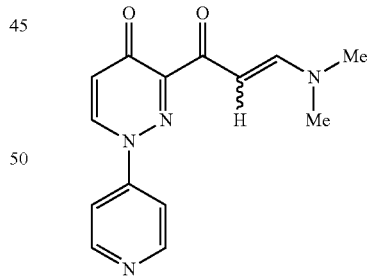

3-(Pyridin-4-ylhydrazono)pentane-2,4-dione (120 mg, 0.58 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-pyridin-4-ylpyridazin-4(1H)-one which was used to the next step without further purification.

$^1$H NMR of the crude product (400 MHz, CDCl$_3$): δ ppm 2.92 (s, 3H), 3.16 (s, 3H), 5.56-5.58 (m, 1H), 6.73 (d, J=8.0 Hz, 1H), 7.59 (dd, J=4.8, 1.6 Hz, 2H), 8.30 (d, J=8.0 Hz, 1H), 8.74 (dd, J=4.8, 1.6 Hz, 2H).

Reference Example 45

3-[(2-Chlorophenyl)hydrazono]pentane-2,4-dione

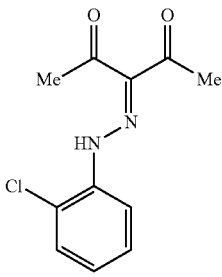 [SMILES: CC(=O)C(=NNc1ccccc1Cl)C(C)=O]

To a solution of 2-chloroaniline (1000 mg, 7.87 mmol) in 10 mL of acetic acid and 2 mL of concentrated hydrochloride solution, sodium nitrite (652 mg, 9.45 mmol) in 4 mL of water was added dropwise at 0° C., and the mixture was stirred at 0° C. for 1 h. Then to the reaction mixture was added dropwise a solution of sodium acetate (1940 mg, 23.62 mmol) and acetylacetone (1024 mg, 10.24 mmol) in 10 mL of ethanol and 6 mL of water. The mixture was stirred at room temperature overnight, filtered, washed with water, EtOH/H$_2$O (1:1) and hexane, and dried to give 3-[(2-chlorophenyl)hydrazono]pentane-2,4-dione (860 mg, 46%).

$^1$H NMR (400 MHz, CDCl$_3$): δ ppm 2.52 (s, 3H), 2.64 (s, 3H), 7.11-7.15 (m, 1H), 7.34-7.37 (m, 1H), 7.42 (dd, J=8.0, 1.2 Hz, 1H), 7.81 (dd, J=8.0, 1.2 Hz, 1H), 14.88 (s, 1H).

Reference Example 46

1-(2-Chlorophenyl)-3-[3-(dimethylamino)prop-2-enoyl]pyridazin-4(1H)-one

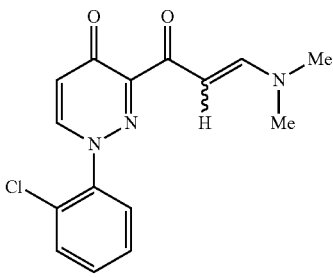 [SMILES: CN(C)C=CC(=O)c1nn(-c2ccccc2Cl)ccc1=O]

3-[(2-Chlorophenyl)hydrazono]pentane-2,4-dione (500 mg, 2.10 mmol) was dissolved in 10 mL of N,N-dimethylformamide dimethyl acetal (DMF-DMA), and the mixture was refluxed for 4 h, then concentrated under reduced pressure to give crude 1-(2-chlorophenyl)-3-[3-(dimethylamino)prop-2-enoyl]pyridazin-4(1H)-one which was used to the next step without further purification.

$^1$H NMR of the crude product (400 MHz, CDCl$_3$): δ ppm 2.90 (s, 3H), 3.12 (s, 3H), 5.56-5.59 (m, 1H), 6.67 (d, J=8.0 Hz, 1H), 7.42-7.45 (m, 2H), 7.52-7.57 (m, 2H), 7.91 (d, J=8.0 Hz, 1H).

Reference Example 47

3-{[3-(Methylsulfanyl)phenyl]hydrazono}pentane-2,4-dione

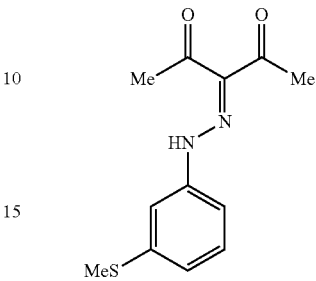

A solution of 3-(methylsulfanyl)aniline (13.9 g, 100 mmol) in hydrochloric acid (6 N, 100 mL) was cooled with an ice brine bath and treated with a solution of sodium nitrite (8.38 g, 121 mmol) in water (25 mL) dropwise to keep the temperature between −5° C. and 5° C. The in situ formed diazonium solution was quickly added to a mixture of 2,4-pentanedione (10.2 g, 102 mmol) and sodium acetate (150 g, 183 mmol) in ethanol (170 mL) and water (60 mL) cooled to below 0° C. After stirring at 0° C. for 30 min, the suspension was filtered, washed with water (40 mL) and evaporated with toluene to afford 3-{[3-(methylsulfanyl)phenyl]hydrazono}pentane-2,4-dione (23.10 g, 92%) as a yellow-red solid.

$^1$H NMR (500 MHz, DMSO-d$_6$) δ ppm 2.43 (s, 6H), 2.47 (s, 3H), 7.04-7.06 (m, 1H), 7.31-7.36 (m, 2H), 7.46 (s, 1H), 13.80 (br s, 1H); APCI MS m/z 251 [M+H]$^+$.

Reference Example 48

3-[3-(Dimethylamino)prop-2-enoyl]-1-[3-(methylsulfanyl)phenyl]pyridazin-4(1H)-one

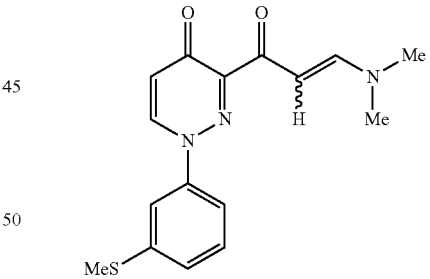

A mixture of 3-{[3-(methylsulfanyl)phenyl]hydrazono}pentane-2,4-dione (14.9 g, 59.6 mmol) in N,N-dimethylformamide dimethylacetal (70 mL) was stirred at 125° C. for 2.5 h. After this time, the reaction was directly concentrated and then dissolved in methanol (80.0 mL). After concentration, the crude product was purified by flash chromatography (silica gel, methylene chloride to 95:5 methylene chloride/methanol) to afford 3-[3-(dimethylamino)prop-2-enoyl]-1-[3-(methylsulfanyl)phenyl]pyridazin-4(1H)-one (16.3 g, 87%) as a yellow-brown solid.

$^1$H NMR (500 MHz, DMSO-d$_6$) δ 2.54 (s, 3H), 2.83 (s, 3H), 3.09 (s, 3H), 5.23 (br s, 1H), 6.53 (d, J=8.0 Hz, 1H), 7.29-7.32 (m, 1H), 7.43-7.53 (m, 4H), 8.81 (d, J=8.0 Hz, 1H); APCI MS m/z 316 [M+H]$^+$.

Reference Example 49

1-[3-(Methylsulfanyl)phenyl]-3-(1-phenyl-1H-pyrazol-5-yl)pyridazin-4(1H)-one and 1-[3-(methylsulfanyl)phenyl]-3-(1-phenyl-1H-pyrazol-3-yl)pyridazin-4(1H)-one

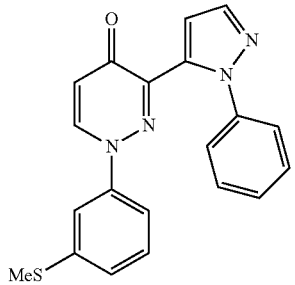

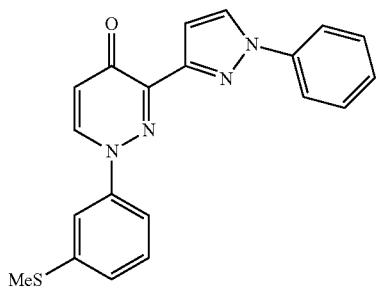

A mixture of 3-[3-(dimethylamino)prop-2-enoyl]-1-[3-(methylsulfanyl)phenyl]pyridazin-4(1H)-one (3.69 g, 11.7 mmol) in methanol (80 mL) was treated with phenylhydrazine (2.66 g, 24.6 mmol) and the resulting mixture was stirred at reflux for 8 h. After this time, the reaction was directly concentrated to remove methanol and then dissolved in methylene chloride (100 mL). The solution was washed with 2 N hydrochloride (60 mL), water (60 mL), and brine (60 mL). After concentration, the crude product was purified by flash chromatography (silica gel, methylene chloride to 95:5 methylene chloride/methanol) afforded 1-[3-(methylsulfanyl)phenyl]-3-(1-phenyl-1H-pyrazol-5-yl)pyridazin-4(1H)-one and 1-[3-(methylsulfanyl)phenyl]-3-(1-phenyl-1H-pyrazol-3-yl)pyridazin-4(1H)-one (2.72 g, 65%) in a regiomeric ratio of about 1:1 as a white solid.

$^1$H NMR for 2 isomers (500 MHz, DMSO-$d_6$) δ ppm 6.63 (d, J=8.0 Hz, 1H), 6.66 (d, J=7.9 Hz, 1H), 6.82-6.85 (m, 1H), 7.05 (s, 1H), 7.19-7.22 (m, 2H), 7.29 (t, J=8.0 Hz, 1H), 7.34-7.39 (m, 5H), 7.42 (d, J=7.1 Hz, 1H), 7.45-7.49 (m, 2H), 7.50-7.56 (m, 3H), 7.59 (d, J=9.3 Hz, 1H), 7.68 (s, 1H), 7.82 (d, J=1.7 Hz, 1H), 7.92 (d, J=7.8 Hz, 2H), 8.59 (d, J=2.4 Hz, 1H), 8.84 (d, J=8.0 Hz, 1H), 8.89 (d, J=7.9 Hz, 1H); APCI MS m/z 361 [M+H]$^+$.

Reference Example 50

3-[(3-Hydroxyphenyl)hydrazono]pentane-2,4-dione

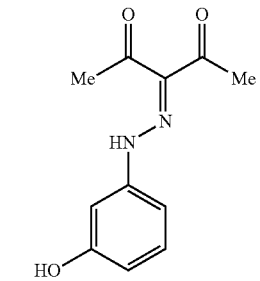 [SMILES: CC(=O)C(=NNc1cccc(O)c1)C(C)=O]

A solution of 3-aminophenol (5.16 g, 47.3 mmol) in tetrafluoroboric acid (30 mL, 50% in water) was cooled with ice brine bath and treated with sodium nitrite (3.92 g, 56.8 mmol) in water (18 mL) dropwise to keep the bath temperature between −5° C. and 5° C. The in situ formed diazonium solution was quickly added to a mixture of 2,4-pentanedione (4.73 g, 47.3 mmol) and sodium acetate (100 g, 73.5 mmol) in ethanol (80 mL) and water (30 mL) below 0° C. After stirring at 0° C. for 30 min, the suspension was filtered, washed with water (70 mL) and evaporated with toluene to afford 3-[(3-hydroxyphenyl)hydrazono]pentane-2,4-dione (5.85 g, 56%) as a brick-red solid.

$^1$H NMR (500 MHz, DMSO-$d_6$) δ ppm 2.42 (s, 6H), 3.44 (br s, 1H), 6.58-6.60 (m, 1H), 6.90-6.93 (m, 1H), 6.99 (d, J=2.1 Hz, 1H), 7.15-7.18 (m, 1H); ESI MS m/z 221 [M+H]$^+$.

Reference Example 51

3-[3-(Dimethylamino)prop-2-enoyl]-1-(3-hydroxyphenyl)pyridazin-4(1H)-one

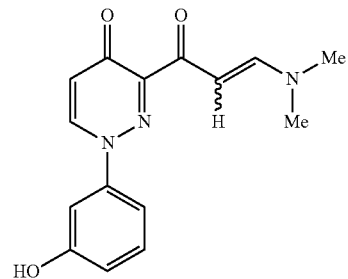 [SMILES: CN(C)C=CC(=O)c1nn(-c2cccc(O)c2)ccc1=O]

A mixture of 3-[(3-hydroxyphenyl)hydrazono]pentane-2,4-dione (2.02 g, 9.18 mmol) in N,N-dimethylformamide dimethylacetal (20 mL) was stirred at 100° C. for 1 h. After this time, the reaction was directly concentrated and then dissolved in methanol (60 mL). After evaporation with silica gel, the crude product was purified by flash chromatography (silica gel, methylene chloride to 92:8 methylene chloride/methanol) to afford 3-[3-(dimethylamino)prop-2-enoyl]-1-(3-hydroxyphenyl)pyridazin-4(1H)-one (1.72 g, 66%) as a brown-red solid.

$^1$H NMR (500 MHz, DMSO-$d_6$) δ ppm 2.83 (s, 3H), 3.09 (s, 3H), 5.21-5.23 (m, 1H), 6.50 (d, J=8.0 Hz, 1H), 6.79-6.82 (m, 1H), 7.08-7.11 (m, 2H), 7.33 (t, J=8.1 Hz, 1H), 8.74 (d, J=8.0 Hz, 1H), 9.93 (s, 1H); ESI MS m/z 286 [M+H]$^+$.

Reference Example 52

1-(3-Hydroxyphenyl)-3-(1-phenyl-1H-pyrazol-5-yl)pyridazin-4(1H)-one

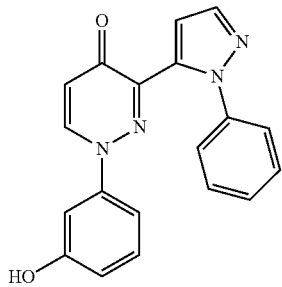 [SMILES: O=c1ccn(-c2cccc(O)c2)nc1-c1ccnn1-c1ccccc1]

A mixture of 3-[3-(dimethylamino)prop-2-enoyl]-1-(3-hydroxyphenyl)pyridazin-4(1H)-one (0.481 g, 1.69 mmol) in methanol (10 mL) was treated with phenylhydrazine (0.462 g, 4.28 mmol) and the resulting mixture was stirred at reflux for 14 h. After this time, the reaction was directly concentrated to remove methanol and then dissolved in methylene chloride (60 mL). The solution was washed with water (60 mL), and brine (20 mL). After concentrated with silica gel, chromatography (silica, methylene chloride to 1:19 methanol/methylene chloride) afforded 1-(3-hydroxyphenyl)-3-(1-phenyl-1H-pyrazol-5-yl)pyridazin-4(1H)-one (0.360 g, 65%) as a brown-yellow solid.

$^1$H NMR (500 MHz, DMSO-$d_6$) δ ppm 6.63 (d, J=7.8 Hz, 1H), 6.85 (d, J=9.0 Hz, 1H), 7.21-7.23 (m, 2H), 7.35-7.39 (m, 3H), 7.52-7.56 (m, 2H), 7.92 (d, J=7.9 Hz, 2H), 8.59 (d, J=2.3 Hz, 1H), 8.81 (d, J=7.8 Hz, 1H), 10.0 (s, 1H); ESI MS m/z 331 [M+H]$^+$.

Reference Example 53

3-(1-Phenyl-1H-pyrazol-5-yl)-1-(3-sulfanylphenyl)pyridazin-4(1H)-one and 3-(1-phenyl-1H-pyrazol-3-yl)-1-(3-sulfanylphenyl)pyridazin-4(1H)-one

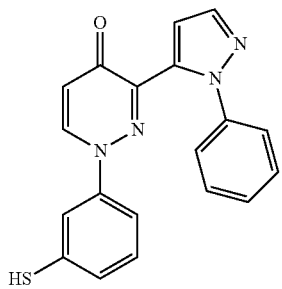

-continued

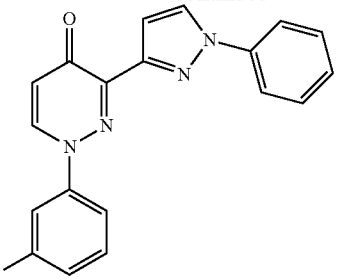

A solution of 1-[3-(methylsulfanyl)phenyl]-3-(1-phenyl-1H-pyrazol-5-yl)pyridazin-4(1H)-one and 1-[3-(methylsulfanyl)phenyl]-3-(1-phenyl-1H-pyrazol-3-yl)pyridazin-4(1H)-one (0.300 g, 0.83 mmol) and sodium t-butylthiolate (0.295 g, 2.63 mmol) in DMF (6 mL) was heated at 170° C. in a sealed tube for 2.5 days. After that time, the reaction was cooled to room temperature and diluted with water (60 mL). Aqueous HCl (1 N, 2 mL, 2 mmol) was added and the reaction extracted with ethyl acetate (2×80 mL). The combined organic phases were washed with aqueous 5% LiCl solution (100 mL) and saturated NaCl aqueous solution (80 mL). The organics were dried (MgSO$_4$) and concentrated to yield the mixture of the title compounds as a brown gum (0.325 g). LCMS analysis of the reaction product indicated that 2 isomers of the thiol product were produced in ≈1.5:1 ratio. The crude product was used in the following reaction without further purification or characterization.

Reference Example 54

1-[3-(1H-Benzimidazol-2-ylsulfanyl)phenyl]-3-(1-phenyl-1H-pyrazol-5-yl)pyridazin-4(1H)-one and 1-[3-(1H-benzimidazol-2-ylsulfanyl)phenyl]-3-(1-phenyl-1H-pyrazol-3-yl)pyridazin-4(1H)-one

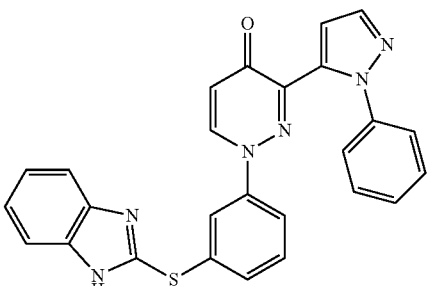

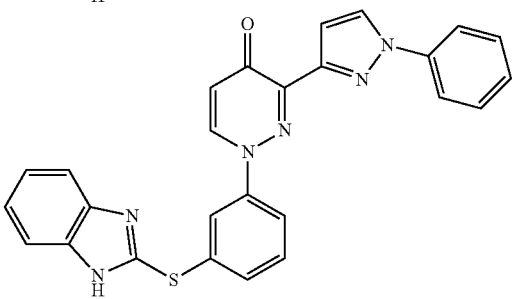

A solution of the crude mixture of 3-(1-phenyl-1H-pyrazol-5-yl)-1-(3-sulfanylphenyl)pyridazin-4(1H)-one and 3-(1-phenyl-1H-pyrazol-3-yl)-1-(3-sulfanylphenyl)pyridazin-4(1H)-one (0.325 g, 0.94 mmol), 2-chlorobenzimidazole (0.195 g, 1.27 mmol), and potassium carbonate (0.234 g, 1.70 mmol) in N-methylpyrrolidone (8.0 mL) was heated at 170° C. in a sealed tube for 24 hours. After that time, the reaction was cooled to room temperature and diluted with water (50 mL). Aqueous HCl (2 N, 0.800 mL, 1.60 mmol) was added and the reaction extracted with ethyl acetate (3×60 mL). The combined organic phases were washed with aqueous 5% LiCl solution (100 mL) and saturated NaCl aqueous solution (100 mL). The organics were dried (MgSO$_4$) and concentrated to a brown solid (0.312 g). The crude product was used in the following reaction without further purification or characterization.

Reference Example 55

Methyl 3-oxo-2-{[3-(trifluoromethyl)phenyl]hydrazono}butanoate

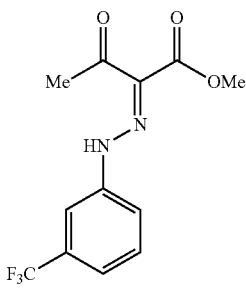 [SMILES: COC(=O)/C(=N/Nc1cccc(C(F)(F)F)c1)C(C)=O]

A slurry of 3-(trifluoromethyl)aniline (16.12 g, 100 mmol) in 6 N HCl (100 mL) was cooled to 0° C. and treated dropwise with a solution of sodium nitrite (8.33 g, 121 mmol) in water (20 mL). The resulting pale yellow solution was poured into a slurry of methyl acetoacetate (11.62 g, 100 mmol) and sodium acetate (150 g) in ethanol (170 mL), pre-cooled to 0° C. The resulting orange slurry was stirred for 10 min. After that time, the product was collected by filtration and washed with water (500 mL). The crude material was dissolved in ethyl acetate (250 mL) and dried (MgSO$_4$). The product crystallized upon concentration of the ethyl acetate to give 19.997 g (69%) of methyl 3-oxo-2-{[3-(trifluoromethyl)phenyl]hydrazono}butanoate as light yellow crystals.

$^1$H NMR (300 MHz, CDCl$_3$) shows a mixture of isomers. Major isomer δ ppm 2.62 (s, 3H), 3.90 (s, 3H), 7.37-7.45 (m, 1H), 7.46-7.54 (m, 1H), 7.58 (s, 1H), 7.67 (s, 1H), 14.76 (br s, 1H); Minor isomer δ ppm 2.52 (s, 3H), 3.93 (s, 3H), 7.37-7.45 (m, 1H), 7.46-7.54 (m, 2H), 7.56 (s, 1H), 12.81 (br s, 1H); APCI MS m/z 289 [C$_{12}$H$_{11}$F$_3$N$_2$O$_3$+H]$^+$.

Reference Example 56

Methyl 4-oxo-1-[3-(trifluoromethyl)phenyl]-1,4-dihydropyridazine-3-carboxylate

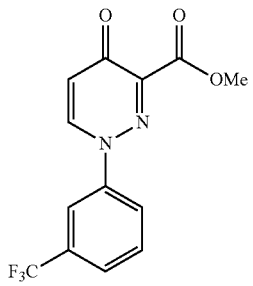 [SMILES: COC(=O)c1nn(-c2cccc(C(F)(F)F)c2)ccc1=O]

A solution of methyl 3-oxo-2-{[3-(trifluoromethyl)phenyl]hydrazono}butanoate (15.20 g, 52.7 mmol) in N,N-dimethylformamide dimethylacetal (150 mL) was heated at reflux for 2 h. After that time, the reaction was cooled to room temperature and then on an ice water bath. The product was collected by filtration to give methyl 4-oxo-1-[3-(trifluoromethyl)phenyl]-1,4-dihydropyridazine-3-carboxylate (13.7 g, 87%) as pale yellow crystals.

$^1$H NMR (300 MHz, CDCl$_3$) δ ppm 4.00 (s, 3H), 6.80 (d, J=8.1 Hz, 1H), 7.61-7.76 (m, 2H), 7.76-7.91 (m, 2H), 8.28 (d, J=8.1 Hz, 1H); APCI MS m/z 299 [C$_{13}$H$_9$F$_3$N$_2$O$_3$+H]$^+$.

Reference Example 57

4-Oxo-1-[3-(trifluoromethyl)phenyl]-1,4-dihydropyridazine-3-carbohydrazide

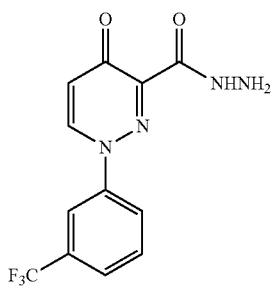 [SMILES: NNC(=O)c1nn(-c2cccc(C(F)(F)F)c2)ccc1=O]

A solution of methyl 4-oxo-1-[3-(trifluoromethyl)phenyl]-1,4-dihydropyridazine-3-carboxylate (1.019 g, 3.42 mmol) and hydrazine monohydrate (0.3 mL, 6.19 mmol) in ethanol (10 mL) was heated under microwave conditions for 10 min at 120° C. After that time, the reaction was cooled to room temperature and the product was collected by filtration and washed with cold ethanol to give 4-oxo-1-[3-(trifluoromethyl)phenyl]-1,4-dihydropyridazine-3-carbohydrazide (0.607 g, 60%) as bright orange crystals.

$^1$H NMR (300 MHz, CDCl$_3$) δ ppm 4.34 (d, J=4.6 Hz, 2H), 6.93 (d, J=7.8 Hz, 1H), 7.66-7.79 (m, 2H), 7.86-8.00 (m, 2H), 8.36 (d, J=7.8 Hz, 1H), 10.98 (br s, 1H); APCI MS m/z 299 [C$_{12}$H$_9$F$_3$N$_4$O$_2$+H]$^+$.

Reference Example 58

4-Oxo-1-[3-(trifluoromethyl)phenyl]-1,4-dihydropyridazine-3-carboxamide

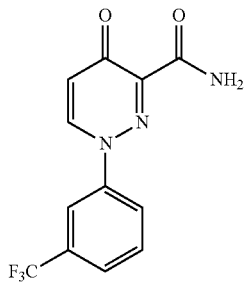 [SMILES: NC(=O)c1nn(-c2cccc(C(F)(F)F)c2)ccc1=O]

A solution of methyl 4-oxo-1-[3-(trifluoromethyl)phenyl]-1,4-dihydropyridazine-3-carboxylate (1.007 g, 3.38 mmol) in ammonia (7 N in MeOH, 12 mL, 84 mmol) was heated under microwave heating conditions at 100° C. for 5 min. After that time the reaction was cooled to room temperature and concentrated to give a yellow solid. This was recrystallized from EtOAc to give 0.613 g (64%) of 4-oxo-1-[3-(trifluoromethyl)phenyl]-1,4-dihydropyridazine-3-carboxamide as colorless crystals.

$^1$H NMR (300 MHz, CDCl$_3$) δ ppm 6.46 (br s, 1H), 6.94 (d, J=7.8 Hz, 1H), 7.59-7.80 (m, 2H), 7.84-8.01 (m, 2H), 8.38 (d, J=7.8 Hz, 1H), 9.68 (br s, 1H); APCI MS m/z 284 [M+H]$^+$.

Reference Example 59

N-[(Dimethylamino)methylidene]-4-oxo-1-[3-(trifluoromethyl)phenyl]-1,4-dihydropyridazine-3-carboxamide

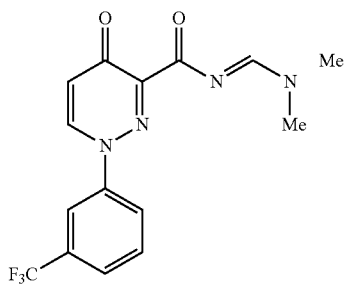 [SMILES: CN/C=N/C(=O)c1nn(-c2cccc(C(F)(F)F)c2)ccc1=O ; "Me"]

A slurry of 4-oxo-1-[3-(trifluoromethyl)phenyl]-1,4-dihydropyridazine-3-carboxamide (0.54 g, 1.91 mmol) in N,N-dimethylformamide dimethylacetal (10 mL) was heated under microwave heating conditions at 130° C. for 15 min. After that time the reaction was cooled on an ice water bath and the resulting crystals collected by filtration and washed with hexanes to give 0.491 g (76%) of N-[(dimethylamino)methylidene]-4-oxo-1-[3-(trifluoromethyl)phenyl]-1,4-dihydropyridazine-3-carboxamide as off white crystals. $^1$H NMR (300 MHz, CDCl$_3$) δ ppm 3.16 (s, 3H), 3.22 (s, 3H), 6.72 (d, J=8.1 Hz, 1H), 7.57-7.71 (m, 2H), 7.74-7.85 (m, 1H), 7.89 (s, 1H), 8.25 (d, J=8.1 Hz, 1H), 8.70 (s, 1H).

Reference Example 60

4-Oxo-N-phenyl-1-[3-(trifluoromethyl)phenyl]-1,4-dihydropyridazine-3-carboxamide

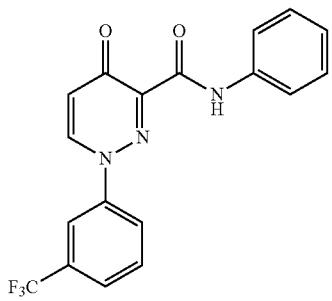 [SMILES: O=C(Nc1ccccc1)c1nn(-c2cccc(C(F)(F)F)c2)ccc1=O]

A solution of aniline (0.360 mL, 3.95 mmol) in methylene chloride (10 mL) was cooled on an ice water bath then treated with a solution of trimethyl aluminum (2 M in toluene, 2.0 mL, 4.0 mmol). After the addition was complete, the reaction was allowed to warm to room temperature and stirred for 30 min. At that point, methyl 4-oxo-1-[3-(trifluoromethyl)phenyl]-1,4-dihydropyridazine-3-carboxylate (0.595 g, 2.00 mmol) was added and the reaction was heated at reflux for 18 h. After that time, the reaction was cooled to room temperature and carefully quenched with HCl aqueous solution (1 N, 5 mL). The organic layer was separated and the aqueous layer was extracted with methylene chloride (3×10 mL). The combined organic extracts were washed with saturated NaHCO$_3$ aqueous solution (50 mL) and brine (50 mL), dried (MgSO$_4$), and concentrated. The residue was recrystallized from ethyl acetate/hexanes to give 0.214 g (30%) of 4-oxo-N-phenyl-1-[3-(trifluoromethyl)phenyl]-1,4-dihydropyridazine-3-carboxamide as yellow crystals.

$^1$H NMR (300 MHz, CDCl$_3$) δ ppm 6.96 (d, J=7.7 Hz, 1H), 7.16 (t, J=7.4 Hz, 1H), 7.37 (t, J=7.9 Hz, 2H), 7.61-7.85 (m, 4H), 7.88-8.01 (m, 2H), 8.42 (d, J=7.8 Hz, 1H), 12.19 (br s, 1H); APCI MS m/z 360 [M+H]$^+$; mp 181-182° C.

Reference Example 61

3-[1H-Benzotriazol-1-yl(phenylimino)methyl]-1-[3-(trifluoromethyl)phenyl]pyridazin-4(1H)-one

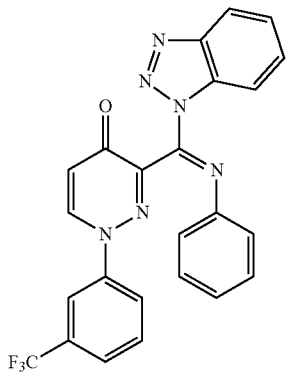 [SMILES: O=c1ccn(-c2cccc(C(F)(F)F)c2)nc1/C(=N\c1ccccc1)n1nnc2ccccc21]

A solution of 4-oxo-N-phenyl-1-[3-(trifluoromethyl)phenyl]-1,4-dihydropyridazine-3-carboxamide (0.153 g, 0.426 mmol), 1H-benzo[d][1,2,3]triazole (0.201 g, 1.69 mmol) and thionyl chloride (0.06 mL, 0.82 mmol) in methylene chloride (2 mL) was heated under microwave heating conditions at 80 watts of power for 10 min. After that time, the reaction was concentrated and the crude product purified by flash column chromatography (silica gel, hexanes to ethyl acetate) to give 0.114 g (58%) of 3-[1H-benzotriazol-1-yl(phenylimino)methyl]-1-[3-(trifluoromethyl)phenyl]pyridazin-4(1H)-one as a pale red solid that was used without further characterization.

Reference Example 62

3-[(4-Piperidin-1-ylphenyl)hydrazono]pentane-2,4-dione

4-Piperidin-1-ylaniline (510 mg, 2.90 mmol) was added to a solution of 3 mL of phosphoric acid (85%) and 2 mL of nitric acid (65%) at −6° C. When the mixture reached to room temperature it was cooled to −6° C. and solid sodium nitrite (200 mg, 2.90 mmol) was added during 10 min. Small pieces of ice (50 g) were added into the solution. The mixture was added at 0° C. to a suspension of corresponding 2,4-pentanedione (290 mg, 2.90 mmol) and potassium acetate (20 g) in ethanol (250 mL). The solution was stirred for 15 min, added to 250 mL of saturated $Na_2CO_3$ aqueous solution, extracted with dichloromethane, washed with water and brine, dried over $Na_2SO_4$, and concentrated under reduced pressure to give 3-[(4-piperidin-1-ylphenyl)hydrazono]pentane-2,4-dione (570 mg, yield 68%).

LCMS: m/z=288 [M$^+$+H].

Reference Example 63

3-[3-(Dimethylamino)prop-2-enoyl]-1-(4-piperidin-1-ylphenyl)pyridazin-4(1H)-one

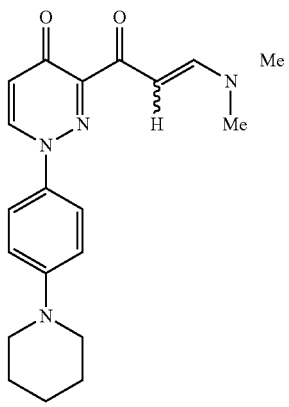 [SMILES: CNC=CC(=O)c1nn(-c2ccc(N3CCCCC3)cc2)ccc1=O ; "Me"]

3-[(4-Piperidin-1-ylphenyl)hydrazono]pentane-2,4-dione (570 mg, 1.99 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-(4-piperidin-1-ylphenyl)pyridazin-4(1H)-one which was used to the next step without further purification.

Reference Example 64

3-[(4-Cyclohexylphenyl)hydrazono]pentane-2,4-dione

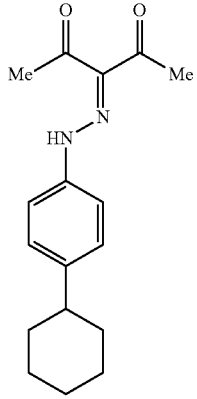 [SMILES: CC(=O)C(=NNc1ccc(C2CCCCC2)cc1)C(C)=O]

To a solution of 4-cyclohexylaniline (500 mg, 2.86 mmol) in 10 mL of acetic acid and 2 mL of concentrated hydrochloride solution, sodium nitrite (237 mg, 3.43 mmol) in 4 mL of water was added dropwise at 0° C., and the mixture was stirred at 0° C. for 1 h. Then to the reaction mixture was added dropwise a solution of sodium acetate (703 mg, 8.58 mmol) and acetylacetone (372 mg, 3.72 mmol) in 10 mL of ethanol and 6 mL of water. The mixture was stirred at room temperature overnight, filtered, washed with water, EtOH/H$_2$O (1:1) and hexane, and dried to give 3-[(4-cyclohexylphenyl)hydrazono]pentane-2,4-dione (420 mg, 51%).

¹H NMR (400 MHz, CDCl₃): δ ppm 1.24-1.27 (m, 2H), 1.38-1.43 (m, 4H), 1.85-1.87 (m, 4H), 2.49-2.52 (m, 4H), 2.60 (s, 3H), 7.25 (d, J=8.4 Hz, 2H), 7.35 (d, J=8.8 Hz, 2H), 14.81 (s, 1H).

Reference Example 65

1-(4-Cyclohexylphenyl)-3-[3-(dimethylamino)prop-2-enoyl]pyridazin-4(1H)-one

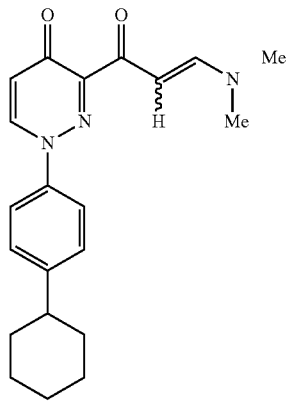 [SMILES: CNC=CC(=O)c1nn(-c2ccc(C3CCCCC3)cc2)ccc1=O ; "Me"]

3-[(4-Cyclohexylphenyl)hydrazono]pentane-2,4-dione (406 mg, 1.42 mmol) was dissolved in 10 mL of N,N-dimethylformamide dimethyl acetal (DMF-DMA), and the mixture was refluxed for 4 h, then concentrated under reduced pressure to give crude 1-(4-cyclohexylphenyl)-3-[3-(dimethylamino)prop-2-enoyl]pyridazin-4(1H)-one which was used to the next step without further purification.

¹H NMR of the crude product (400 MHz, CDCl₃): δ ppm 1.25-1.28 (m, 2H), 1.39-1.44 (m, 4H), 1.86-1.88 (m, 4H), 2.52-2.54 (m, 1H), 2.90 (s, 3H), 3.13 (s, 3H), 5.62-5.64 (m, 1H), 6.71 (d, J=7.6 Hz, 1H), 7.32 (d, J=8.8 Hz, 2H), 7.49 (d, J=8.8 Hz, 2H), 8.17 (d, J=8.0 Hz, 1H).

Reference Example 66

4-[2-(1-Acetyl-2-oxopropylidene)hydrazino]benzonitrile

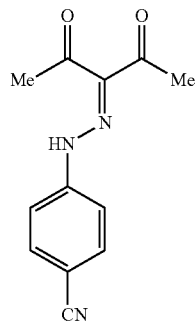

4-Aminobenzonitrile (500 mg, 4.24 mmol) was added to a solution of 3 mL of phosphoric acid (85%) and 2 mL of nitric acid (65%) at −6° C. When the mixture reached to room temperature it was cooled to −6° C. and solid sodium nitrite (292 mg, 4.24 mmol) was added during 10 min. Small pieces of ice (50 g) were added into the solution. The mixture was added at 0° C. to a suspension of corresponding 2,4-pentanedione (424 mg, 4.24 mmol) and potassium acetate (20 g) in ethanol (250 mL). The solution was stirred for 15 min, added to 250 mL of saturated Na₂CO₃ aqueous solution, extracted with dichloromethane, washed with water and brine, dried over Na₂SO₄, and concentrated under reduced pressure to give 4-[2-(1-acetyl-2-oxopropylidene)hydrazino]benzonitrile (280 mg, 29%).

¹H NMR (400 MHz, CDCl₃): δ ppm 2.51 (s, 3H), 2.63 (s, 3H), 7.47 (dd, J=7.2, 1.6 Hz, 2H), 7.70 (dd, J=7.2, 1.6 Hz, 2H), 14.51 (s, 1H).

Reference Example 67

4-{3-[3-(Dimethylamino)prop-2-enoyl]-4-oxopyridazin-1(4H)-yl}benzonitrile

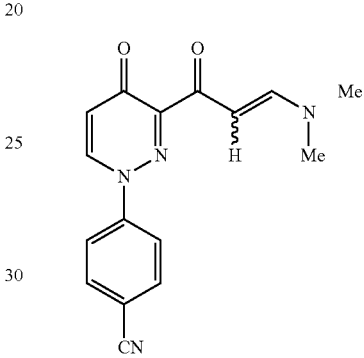

4-[2-(1-Acetyl-2-oxopropylidene)hydrazino]benzonitrile (266 mg, 1.16 mmol) was dissolved in 10 mL of N,N-dimethylformamide dimethyl acetal (DMF-DMA), and the mixture was refluxed for 4 h, then concentrated under reduced pressure to give crude 4-{3-[3-(dimethylamino)prop-2-enoyl]-4-oxopyridazin-1(4H)-yl}benzonitrile which was used to the next step without further purification.

¹H NMR of the crude product (400 MHz, CDCl₃): δ ppm 2.96 (s, 3H), 3.20 (s, 3H), 6.13 (d, J=12.4 Hz, 1H), 7.35 (d, J=8.8 Hz, 2H), 7.62 (d, J=8.8 Hz, 2H), 7.83 (d, J=12.0 Hz, 1H).

Reference Example 68

3-{[4-(Methylsulfonyl)phenyl]hydrazono}pentane-2,4-dione

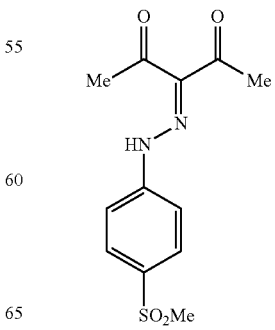

4-(Methylsulfonyl)aniline (500 mg, 2.92 mmol) was added to a solution of 3 mL of phosphoric acid (85%) and 2 mL of nitric acid (65%) at −6° C. When the mixture reached to room temperature it was cooled to −6° C. and solid sodium nitrite (201 mg, 2.92 mmol) was added during 10 min. Small pieces of ice (50 g) were added into the solution. The mixture was added at 0° C. to a suspension of corresponding 2,4-pentanedione (292 mg, 2.92 mmol) and potassium acetate (20 g) in ethanol (250 mL). The solution was stirred for 15 min, added to 250 mL of saturated Na$_2$CO$_3$ aqueous solution, extracted with dichloromethane, washed with water and brine, dried over Na$_2$SO$_4$, and concentrated under reduced pressure to give 3-{[4-(methylsulfonyl)phenyl]hydrazono}pentane-2,4-dione (780 mg, 95%).

$^1$H NMR (400 MHz, CDCl$_3$): δ ppm 2.52 (s, 3H), 2.63 (s, 3H), 3.08 (s, 3H), 7.54 (dd, J=7.2, 2.0 Hz, 2H), 7.98 (dd, J=7.2, 2.0 Hz, 2H), 14.78 (s, 1H).

Reference Example 69

3-[3-(Dimethylamino)prop-2-enoyl]-1-[4-(methylsulfonyl)phenyl]pyridazin-4(1H)-one

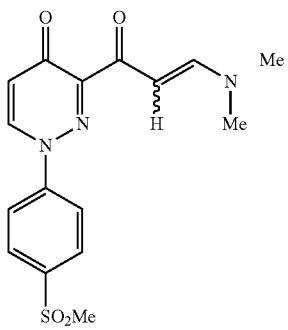 [SMILES: CNC=CC(=O)c1nn(-c2ccc(S(C)(=O)=O)cc2)ccc1=O ; "Me"]

3-{[4-(Methylsulfonyl)phenyl]hydrazono}pentane-2,4-dione (500 mg, 1.77 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-[4-(methylsulfonyl)phenyl]pyridazin-4(1H)-one which was used to the next step without further purification.

Reference Example 70

3-{[4-(Morpholin-4-ylsulfonyl)phenyl]hydrazono}pentane-2,4-dione

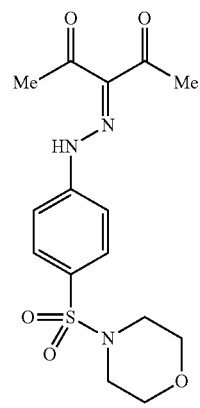 [SMILES: CC(=O)C(=NNc1ccc(S(=O)(=O)N2CCOCC2)cc1)C(C)=O]

4-(Morpholin-4-ylsulfonyl)aniline (300 mg, 1.24 mmol) was added to a solution of 3 mL of phosphoric acid (85%) and 2 mL of nitric acid (65%) at −6° C. When the mixture reached to room temperature it was cooled to −6° C. and solid sodium nitrite (85 mg, 1.24 mmol) was added during 10 min. Small pieces of ice (50 g) were added into the solution. The mixture was added at 0° C. to a suspension of corresponding 2,4-pentanedione (124 mg, 1.24 mmol) and potassium acetate (20 g) in ethanol (250 mL). The solution was stirred for 15 min, added to 250 mL of a saturated solution of Na$_2$CO$_3$, extracted with dichloromethane, washed with water and brine, dried over Na$_2$SO$_4$, and concentrated under reduced pressure to give 3-{[4-(morpholin-4-ylsulfonyl)phenyl]hydrazono}pentane-2,4-dione (375 mg, 86%).

$^1$H NMR (400 MHz, CDCl$_3$): δ ppm 2.53 (s, 3H), 2.64 (s, 3H), 3.03 (t, J=4.8 Hz, 4H), 3.76 (t, J=4.8 Hz, 4H), 7.54 (dd, J=7.2, 2.0 Hz, 2H), 7.80 (d, J=8.8 Hz, 2H), 14.56 (s, 1H).

Reference Example 71

3-[3-(Dimethylamino)prop-2-enoyl]-1-[4-(morpholin-4-ylsulfonyl)phenyl]pyridazin-4(1H)-one

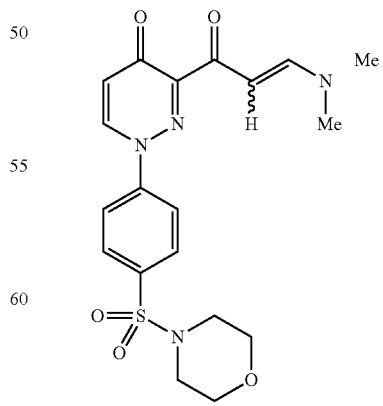

3-{[4-(Morpholin-4-ylsulfonyl)phenyl]hydrazono}pentane-2,4-dione (300 mg, 0.85 mmol) was dissolved in 10 mL of N,N-dimethylformamide dimethyl acetal (DMF-DMA), and the mixture was refluxed for 4 h, then concentrated under reduced pressure to give crude 3-[3-(dimethylamino)prop-2-enoyl]-1-[4-(morpholin-4-ylsulfonyl)phenyl]pyridazin-4(1H)-one which was used to the next step without further purification.

Reference Example 72

4-[2-(1-Acetyl-2-oxopropylidene)hydrazino]benzamide

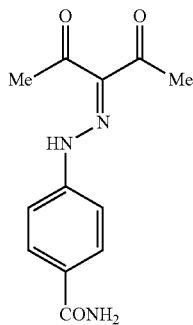

4-Aminobenzamide (1000 mg, 7.36 mmol) was added to a solution of 6 mL of phosphoric acid (85%) and 4 mL of nitric acid (65%) at −6° C. When the mixture reached to room temperature it was cooled to −6° C. and solid sodium nitrite (508 mg, 7.36 mmol) was added during 10 min. Small pieces of ice (100 g) were added into the solution. The mixture was added at 0° C. to a suspension of corresponding 2,4-pentanedione (736 mg, 7.36 mmol) and potassium acetate (40 g) in ethanol (400 mL). The solution was stirred for 15 min, added to 250 mL of saturated $Na_2CO_3$ aqueous solution, extracted with dichloromethane, washed with water and brine, dried over $Na_2SO_4$, and concentrated under reduced pressure to give 4-[2-(1-acetyl-2-oxopropylidene)hydrazino]benzamide (460 mg, 25%).

$^1$H NMR (400 MHz, $CDCl_3$): δ ppm 2.52 (s, 3H), 2.62 (s, 3H), 7.46 (d, J=8.4 Hz, 2H), 7.88 (d, J=8.4 Hz, 2H), 14.62 (s, 1H).

Reference Example 73

4-{3-[3-(Dimethylamino)prop-2-enoyl]-4-oxopyridazin-1(4H)-yl}benzamide

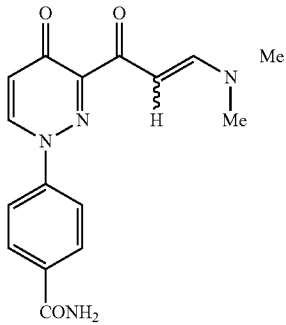 [SMILES: CNC=CC(=O)c1nn(-c2ccc(C(N)=O)cc2)ccc1=O ; "Me"]

4-[2-(1-Acetyl-2-oxopropylidene)hydrazino]benzamide (540 mg, 2.19 mmol) was dissolved in 10 mL of N,N-dimethylformamide dimethyl acetal (DMF-DMA), and the mixture was refluxed for 4 h, then concentrated under reduced pressure to give crude 4-{3-[3-(dimethylamino)prop-2-enoyl]-4-oxopyridazin-1(4H)-yl}benzamide which was used to the next step without further purification.

$^1$H NMR of the crude product (400 MHz, $CDCl_3$): δ ppm 2.91 (s, 3H), 3.14 (s, 3H), 5.60-5.62 (m, 1H), 6.73 (d, J=8.0 Hz, 1H), 7.65 (d, J=8.8 Hz, 2H), 8.31 (d, J=8.0 Hz, 1H), 8.40 (d, J=9.2 Hz, 2H), 8.67 (s, 1H).

Reference Example 74

Methyl 3-oxo-2-{[3-(trifluoromethyl)phenyl]hydrazono}pentanoate

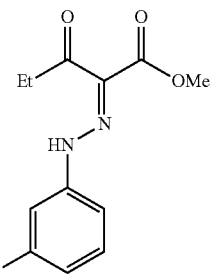

A slurry of 3-(trifluoromethyl)aniline (8.03 g, 50 mmol) in 6 N HCl (50 mL) was cooled to 0° C. and treated dropwise with a solution of sodium nitrite (4.10 g, 60 mmol) in water (10 mL). The resulting pale yellow solution was poured into a suspension of methyl propionylacetate (6.50 g, 50 mmol) and sodium acetate (24.00 g, 292 mmol) in ethanol (80 mL), pre-cooled to 0° C. The resulting yellow/orange slurry was stirred for 30 min. The product was collected by filtration and washed with water (100 mL). The crude material was dissolved in ethyl acetate (100 mL) and dried ($Na_2SO_4$). The product crystallized upon concentration of the ethyl acetate to give (14.00 g, 93%) of methyl 3-oxo-2-{[3-(trifluoromethyl)phenyl]hydrazono}pentanoate as a yellow/orange solid.

$^1$H NMR (500 MHz, $CDCl_3$) shows a mixture of isomers. Major isomer δ ppm 1.18 (t, J=7.5 Hz, 3H), 2.96 (q, J=7.5 Hz, 2H), 3.92 (s, 3H), 7.39-7.42 (m, 1H), 7.48-7.55 (m, 2H), 7.56 (s, 1H), 12.75 (br s, 1H); Minor isomer δ ppm 1.15 (t, J=7.5 Hz, 3H), 3.04 (q, J=7.5, 2H), 3.90 (s, 3H), 7.39-7.42 (m, 1H), 7.48-7.55 (m, 2H), 7.67 (s, 1H), 14.76 (br s, 1H); ESI MS m/z 303 [M+H]$^+$.

Reference Example 75

Methyl 5-methyl-4-oxo-1-[3-(trifluoromethyl)phenyl]-1,4-dihydropyridazine-3-carboxylate

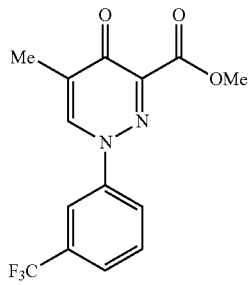 [SMILES: COC(=O)c1nn(-c2cccc(C(F)(F)F)c2)cc(C)c1=O]

A solution of methyl 3-oxo-2-{[3-(trifluoromethyl)phenyl]hydrazono}pentanoate (4.00 g, 13.2 mmol) in N,N-dimethylformamide dimethylacetal (33 mL) was heated at reflux for 2.5 hours. After that time, the reaction was cooled to room temperature and the resulting solid was collected by filtration and washed with a small amount of hexanes to give methyl 5-methyl-4-oxo-1-[3-(trifluoromethyl)phenyl]-1,4-dihydropyridazine-3-carboxylate (3.55 g, 87%) as a pale yellow solid.

$^1$H NMR (500 MHz, CDCl$_3$) δ ppm 2.19 (s, 3H), 4.00 (s, 3H), 7.65-7.71 (m, 2H), 7.81-7.85 (m, 2H), 8.20 (s, 1H); APCI MS m/z 313 [M+H]$^+$.

Reference Example 76

N-Methoxy-N,5-dimethyl-4-oxo-1-[3-(trifluoromethyl)phenyl]-1,4-dihydropyridazine-3-carboxamide

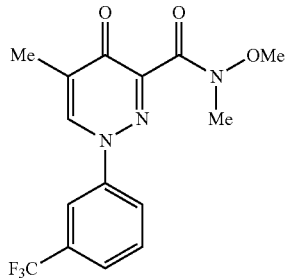 [SMILES: CON(C)C(=O)c1nn(-c2cccc(C(F)(F)F)c2)cc(C)c1=O]

To a stirred suspension of N,O-dimethylhydroxylamine hydrochloride (0.468 g, 4.8 mmol) in dichloromethane (5 mL) was added trimethylaluminum (2.4 mL, 4.8 mmol, 2 M solution in toluene) dropwise at 0° C. Following addition, the suspension was stirred at 0° C. for 10 min then at room temperature for 30 min to provide a homogenous solution. The flask was then re-cooled in an ice bath. In a separate flask, methyl 5-methyl-4-oxo-1-[3-(trifluoromethyl)phenyl]-1,4-dihydropyridazine-3-carboxylate (0.500 g, 1.6 mmol) was dissolved in dichloromethane (5 mL) and added dropwise and allowed to stir for 2 h. The reaction was quenched with water (5 mL) and 2 N HCl aqueous solution (2 mL). The layers were separated and the aqueous layer was extracted with dichloromethane (2×10 mL). The combined organic extracts were washed with brine (20 mL), dried (Na$_2$SO$_4$), filtered and concentrated to provide N-methoxy-N,5-dimethyl-4-oxo-1-[3-(trifluoromethyl)phenyl]-1,4-dihydropyridazine-3-carboxamide (0.535 g, 98%) as a yellow solid.

$^1$H NMR (500 MHz, CDCl$_3$) δ ppm 2.18 (s, 3H), 3.41 (s, 3H), 3.68 (s, 3H), 7.63-7.70 (m, 2H), 7.80-7.90 (m, 2H), 8.21 (s, 1H); APCI MS m/z 342 [M+H]$^+$.

Reference Example 77

3-Acetyl-5-methyl-1-[3-(trifluoromethyl)phenyl]pyridazin-4(1H)-one

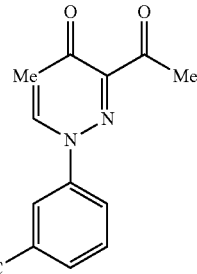

To a solution of N-methoxy-N,5-dimethyl-4-oxo-1-[3-(trifluoromethyl)phenyl]-1,4-dihydropyridazine-3-carboxamide (0.535 g, 1.6 mmol) in THF (10 mL) at −78° C. was added methylmagnesium bromide (1.1 mL, 3.2 mmol, 3 M in diethyl ether). The reaction was stirred at that temperature for 1 h then quenched with saturated ammonium chloride aqueous solution (5 mL) then water (2 mL) with slow warming to room temperature. The reaction mixture was diluted with ethyl acetate (20 mL) and the layers were separated. The aqueous layer was extracted with ethyl acetate (2×10 mL) and the combined organic extracts are washed with 1 N HCl aqueous solution (15 mL), brine (15 mL), dried (Na$_2$SO$_4$), filtered and concentrated to provide 3-acetyl-5-methyl-1-[3-(trifluoromethyl)phenyl]pyridazin-4(1H)-one (0.463 g, 98%) as a light yellow solid.

$^1$H NMR (500 MHz, CDCl$_3$) δ ppm 2.19 (s, 3H), 2.69 (s, 3H), 7.67-7.72 (m, 2H), 7.82-7.85 (m, 2H), 8.21 (s, 1H); APCI MS m/z 297 [M+H]$^+$.

Reference Example 78

3-[3-(Dimethylamino)prop-2-enoyl]-5-methyl-1-[3-(trifluoromethyl)phenyl]pyridazin-4(1H)-one

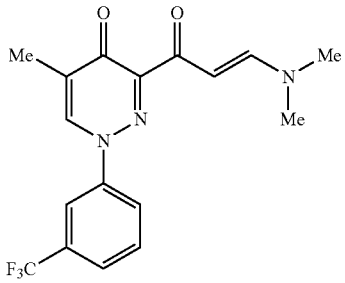 [SMILES: Cc1cn(-c2cccc(C(F)(F)F)c2)nc(C(=O)/C=C/N(C)C)c1=O]

A microwave vial containing 3-acetyl-5-methyl-1-[3-(trifluoromethyl)phenyl]pyridazin-4(1H)-one (0.363 g, 1.2 mmol) and N,N-dimethylformamide dimethylacetal (2.5 mL) was heated at 120° C. for 20 min. The crude material was concentrated and purified by flash column chromatography (silica gel; methylene chloride to 1:9 methanol/methylene chloride) to provide 3-[3-(dimethylamino)prop-2-enoyl]-5-methyl-1-[3-(trifluoromethyl)phenyl]pyridazin-4(1H)-one (0.365 g, 87%) as an orange solid.

$^1$H NMR (300 MHz, CDCl$_3$) δ ppm 2.18 (s, 3H), 2.92 (s, 3H), 3.14 (s, 3H), 5.69-5.82 (m, 1H), 7.63-7.65 (m, 2H), 7.83-7.87 (m, 3H), 8.20 (s, 1H); APCI MS m/z 352 [M+H]$^+$.

Reference Example 79

3-[3-(Dimethylamino)but-2-enoyl]-1-[3-(trifluoromethyl)phenyl]pyridazin-4(1H)-one

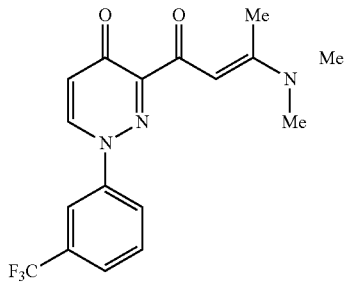 [SMILES: CN/C(C)=C/C(=O)c1nn(-c2cccc(C(F)(F)F)c2)ccc1=O ; "Me"]

A slurry of 3-acetyl-1-[3-(trifluoromethyl)phenyl]pyridazin-4(1H)-one (0.369 g, 1.30 mmol) in N,N-dimethylacetamide dimethylacetal (3.5 mL, 18.3 mmol) was heated under microwave conditions at 120° C. for 5 min. After this time, the reaction was cooled to room temperature and concentrated onto silica gel. The crude product was purified by column chromatography (silica gel, dichloromethane to 90:10 dichloromethane/methanol) to give 3-[3-(dimethylamino)but-2-enoyl]-1-[3-(trifluoromethyl)phenyl]pyridazin-4(1H)-one (0.314 g, 68%) as a yellow foam.

$^1$H NMR (500 MHz, CDCl$_3$) δ ppm 2.71 (s, 3H), 3.07 (br s, 6H), 5.52 (s, 1H), 6.71 (d, J=8.0 Hz, 1H), 7.59-7.69 (m, 2H), 7.76-7.85 (m, 1H), 7.87 (s, 1H), 8.21 (d, J=7.9 Hz, 1H); APCI MS m/z 352 [M+H]$^+$.

Reference Example 80

Methyl 2-[(2-fluorophenyl)hydrazono]-4-methoxy-3-oxobutanoate

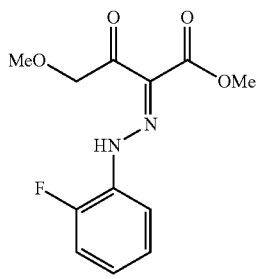 [SMILES: COCC(=O)/C(=N\Nc1ccccc1F)C(=O)OC]

A solution of NaNO$_2$ (1.66 g, 24 mmol) in H$_2$O (5 mL) was added dropwise at 0° C. to a mixture of 2-fluoroaniline (1.93 mL, 20 mmol) and 6 M HCl aqueous solution (20 mL, 120 mmol). After stirring for 15 min, the resulting aqueous solution was added to a suspension of methyl 4-methoxyacetoacetate (2.59 mL, 20 mmol) and NaOAc (9.84 g, 120 mmol) in MeOH (40 mL) pre-cooled at 0° C. The reaction mixture was poured into water and extracted with AcOEt. The extract was washed with saturated NaHCO$_3$ aqueous solution and brine, dried over MgSO$_4$, and concentrated under reduced pressure. The residue was recrystallized from hexane/AcOEt to give the title compound (5.03 g, 94% yield) as pale yellow crystals: mp 121-126° C.; $^1$H NMR (300 MHz, CDCl$_3$): δ ppm 151 (3H, s), 3.94 (3H, s), 4.68 (2H, s), 7.08-7.25 (3H, m), 7.63 (1H, dt, J=1.5, 7.9 Hz), 13.06 (1H, br s). Anal. Calcd for C$_{12}$H$_{13}$FN$_2$O$_4$: C, 53.73; H, 4.88; N, 10.44. Found: C, 53.69; H, 4.96; N, 10.47.

Reference Example 81

Methyl 1-(2-fluorophenyl)-5-methoxy-4-oxo-1,4-dihydropyridazine-3-carboxylate

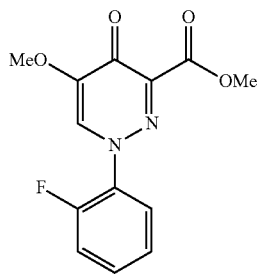 [SMILES: COC(=O)c1nn(-c2ccccc2F)cc(OC)c1=O]

A solution of methyl 2-[(2-fluorophenyl)hydrazono]-4-methoxy-3-oxobutanoate (5.02 g, 18.7 mmol) in N,N-dimethylformamide dimethyl acetal (35 mL) was refluxed for 1 h. After cooling to room temperature, the precipitate was collected by filtration and washed with hexane/AcOEt (2/1) to give the title compound (4.70 g, 90% yield) as off-white crystals: mp 155-157° C.; $^1$H NMR (300 MHz, CDCl$_3$): δ ppm 3.91 (3H, s), 3.97 (3H, s), 7.29-7.36 (2H, m), 7.44-7.51 (1H, m), 7.65 (1H, dt, J=1.9, 7.9 Hz), 7.77 (1H, d, J=2.3 Hz). Anal. Calcd for C$_{13}$H$_{11}$FN$_2$O$_4$: C, 56.12; H, 3.98; N, 10.07. Found: C, 56.17; H, 3.97; N, 10.25.

Reference Example 82

1-(2-Fluorophenyl)-N,5-dimethoxy-N-methyl-4-oxo-1,4-dihydropyridazine-3-carboxamide

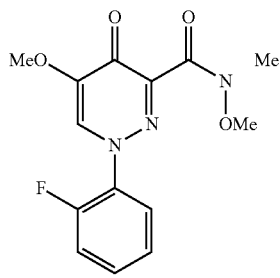 [SMILES: CONC(=O)c1nn(-c2ccccc2F)cc(OC)c1=O ; "Me"]

To a solution of N,O-dimethylhydroxylamine hydrochloride (4.74 g, 48.6 mmol) and iPr$_2$NEt (8.47 mL, 48.6 mmol)

in CH$_2$Cl$_2$ (50 mL) was added AlMe$_3$ (1.8 M solution in toluene, 27 mL, 48.6 mmol) dropwise at 0° C. under Ar atmosphere. After stirring for 1 h, a solution of methyl 1-(2-fluorophenyl)-5-methoxy-4-oxo-1,4-dihydropyridazine-3-carboxylate (4.51 g, 16.2 mmol) in CH$_2$Cl$_2$ (50 mL) was added dropwise, and the mixture was stirred for 1 h at 0° C. The reaction mixture was poured into ice-water, acidified with 1 M HCl aqueous solution, saturated with NaCl, and extracted with AcOEt five times. The combined extracts were dried over MgSO$_4$, and concentrated under reduced pressure. The residue was recrystallized from AcOEt to give the title compound (3.23 g, 65% yield) as colorless crystals: mp 152-154° C.; $^1$H NMR (300 MHz, CDCl$_3$): δ ppm 3.39 (3H, s), 3.71 (3H, s), 3.91 (3H, s), 7.25-7.33 (2H, m), 7.41-7.48 (1H, m), 7.65 (1H, dt, J=1.9, 7.9 Hz), 7.81 (1H, d, J=2.3 Hz). Anal. Calcd for C$_{14}$H$_{14}$FN$_3$O$_4$: C, 54.72; H, 4.59; N, 13.67. Found: C, 54.85; H, 4.54; N, 13.86.

Reference Example 83

3-Acetyl-1-(2-fluorophenyl)-5-methoxypyridazin-4(1H)-one

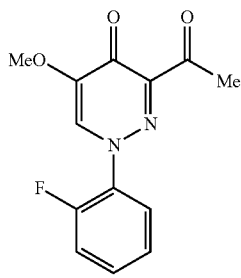 [SMILES: COc1cn(-c2ccccc2F)nc(C(C)=O)c1=O]

MeMgBr (1 M solution in THF, 30 mL, 30 mmol) was added dropwise at −78° C. to a solution of 1-(2-fluorophenyl)-N,5-dimethoxy-N-methyl-4-oxo-1,4-dihydropyridazine-3-carboxamide (3.20 g, 10.4 mmol) in THF (30 mL). After stirring for 1 h, the reaction mixture was quenched with 1 M HCl aqueous solution, saturated with NaCl, and extracted with AcOEt rive times. The combined extracts were dried over MgSO$_4$, and concentrated under reduced pressure. The residue was recrystallized from AcOEt to give the title compound (2.32 g, 85% yield) as pale yellow crystals: mp 154-156° C.; $^1$H NMR (300 MHz, CDCl$_3$): δ ppm 2.69 (3H, s), 3.91 (3H, s), 7.27-7.38 (2H, m), 7.45-7.53 (1H, m), 7.65 (1H, dt, J=1.5, 7.9 Hz), 7.77 (1H, d, J=2.3 Hz). Anal. Calcd for C$_{13}$H$_{11}$FN$_2$O$_3$: C, 59.54; H, 4.23; N, 10.68. Found: C, 59.62; H, 4.22; N, 10.79.

Reference Example 84

Methyl 2-{[2-(difluoromethoxy)phenyl]hydrazono}-4-methoxy-3-oxobutanoate

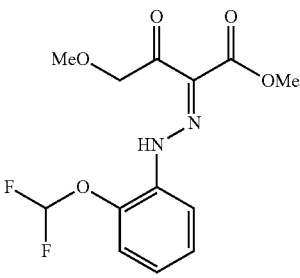 [SMILES: COCC(=O)/C(=N\Nc1ccccc1OC(F)F)C(=O)OC]

A solution of NaNO$_2$ (2.378 g, 34.5 mmol) in H$_2$O (10 mL) was added dropwise at 0° C. to a solution of 2-(difluoromethoxy)aniline (3.59 mL, 28.7 mmol) in 6 M HCl aqueous solution (28.7 mL, 172 mmol). After stirring for 15 min, the resulting aqueous solution was added to a suspension of methyl 4-methoxyacetoacetate (3.72 mL, 28.7 mmol) and NaOAc (14.14 g, 172 mmol) in MeOH (50 mL) pre-cooled at 0° C. The precipitate was collected by filtration, washed with water, and dissolved in AcOEt. The organic solution was washed with water, saturated NaHCO$_3$ aqueous solution and brine, dried over MgSO$_4$, and concentrated under reduced pressure. The residue was washed with hexane/AcOEt (3/1) to give the title compound (8.70 g, 96% yield) as yellow crystals: $^1$H NMR (300 MHz, CDCl$_3$): δ ppm 3.51 (3H, s), 3.89 (3H×0.5, s), 3.94 (3H×0.5, s), 4.68 (1H×0.5, s), 4.70 (1H×0.5, s), 6.63 (1H×0.5, t, J=72.7 Hz), 6.66 (1H×0.5, t, J=72.3 Hz), 7.10-7.34 (4H, m), 7.67 (1H×0.5, dd, J=8.3, 1.5 Hz), 7.90 (1H×0.5, dd, J=8.3, 1.5 Hz), 13.14 (1H×0.5, s), 14.96 (1H×0.5, br s).

Reference Example 85

Methyl 1-[2-(difluoromethoxy)phenyl]-5-methoxy-4-oxo-1,4-dihydropyridazine-3-carboxylate

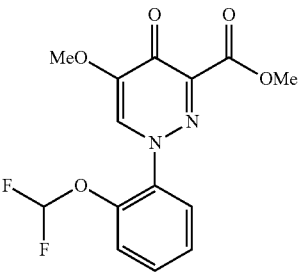 [SMILES: COC(=O)c1nn(-c2ccccc2OC(F)F)cc(OC)c1=O]

A solution of methyl 2-{[2-(difluoromethoxy)phenyl]hydrazono}-4-methoxy-3-oxobutanoate (8.70 g, 27.5 mmol) in N,N-dimethylformamide dimethyl acetal (60 mL) was refluxed for 3 h and stirred at room temperature for 3 days. The precipitate was collected by filtration and washed with hexane/AcOEt (3/1) to give the title compound (7.92 g, 88% yield) as yellow crystals: $^1$H NMR (300 MHz, CDCl$_3$): δ ppm 3.89 (3H, s), 3.96 (3H, s), 6.55 (1H, d, J=72.7 Hz), 7.35-7.45 (2H, m), 7.49-7.56 (1H, m), 7.61 (1H, dd, J=7.9, 1.5 Hz), 7.73 (1H, s).

Reference Example 86

1-[2-(Difluoromethoxy)phenyl]-N,5-dimethoxy-N-methyl-4-oxo-1,4-dihydropyridazine-3-carboxamide

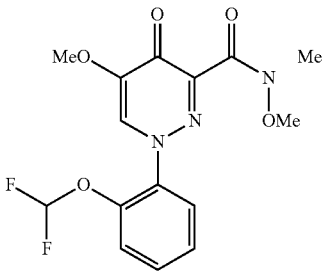 [SMILES: CONC(=O)c1nn(-c2ccccc2OC(F)F)cc(OC)c1=O ; "Me"]

To a solution of N,O-dimethylhydroxylamine hydrochloride (5.27 g, 54.0 mmol) and iPr₂NEt (9.40 mL, 54.0 mmol) in CH₂Cl₂ (60 mL) was added AlMe₃ (1.8 M solution in toluene, 30.0 mL, 54.0 mmol) dropwise at 0° C. After stirring at 0° C. for 1 h, a solution of methyl 1-[2-(difluoromethoxy)phenyl]-5-methoxy-4-oxo-1,4-dihydropyridazine-3-carboxylate (5.87 g, 17.99 mmol) in CH₂Cl₂ (60 mL) was added dropwise, and the mixture was stirred at 0° C. for 1 h. The reaction mixture was poured into ice-water and extracted with AcOEt. The extract was washed with brine, dried over MgSO₄, and concentrated under reduced pressure. The residue was washed with hexane/AcOEt (3/1) to give the title compound (4.79 g, 75% yield) as pale yellow crystals: $^1$H NMR (300 MHz, CDCl₃): δ ppm 3.38 (3H, s), 3.68 (3H, s), 3.89 (3H, s), 6.52 (1H, t, J=72.6 Hz), 7.37 (2H, m), 7.46-7.53 (1H, m), 7.62 (1H, dd, J=7.8, 1.5 Hz), 7.76 (1H, s).

Reference Example 87

3-Acetyl-1-[2-(difluoromethoxy)phenyl]-5-methoxy-pyridazin-4(1H)-one

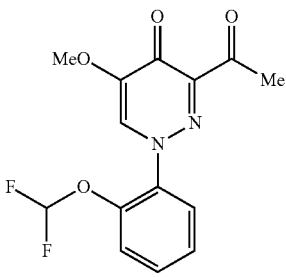 [SMILES: COc1cn(-c2ccccc2OC(F)F)nc(C(C)=O)c1=O]

MeMgBr (1 M solution in THF, 40.4 ml, 40.4 mmol) was added dropwise at −78° C. to a solution of 1-[2-(difluoromethoxy)phenyl]-N,5-dimethoxy-N-methyl-4-oxo-1,4-dihydropyridazine-3-carboxamide (4.79 g, 13.48 mmol) in THF (500 mL). After stirring for 1 h, the reaction mixture was quenched with 1 M HCl aqueous solution and warm to room temperature. The reaction mixture was concentrated under reduced pressure and extracted with AcOEt. The extract was washed with brine, dried over MgSO₄, and concentrated under reduced pressure. The residue was purified by silica gel column chromatography eluting with hexane/AcOEt (1/1-0/1) and recrystallized from diisopropyl ether/AcOEt to give the title compound (3.33 g, 80% yield) as colorless crystals: $^1$H NMR (300 MHz, CDCl₃): δ ppm 2.68 (3H, s), 3.89 (3H, s), 6.55 (1H, t, J=72.7 Hz), 7.36-7.45 (2H, m), 7.50-7.57 (1H, m), 7.61 (1H, dd, J=7.8, 1.7 Hz), 7.72 (1H, s).

Reference Example 88

1-[2-(Difluoromethoxy)phenyl]-3-[3-(dimethylamino)prop-2-enoyl]-5-methoxypyridazin-4(1H)-one

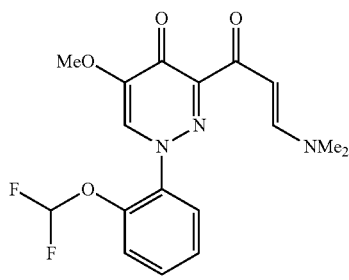 [SMILES: COc1cn(-c2ccccc2OC(F)F)nc(C(=O)/C=C/N(C)C)c1=O]

A mixture of 3-acetyl-1-[2-(difluoromethoxy)phenyl]-5-methoxypyridazin-4(1H)-one (3.70 g, 11.93 mmol) and N,N-dimethylformamide dimethyl acetal (50 mL) was refluxed for 5 h and stirred overnight at room temperature. The precipitate was collected by filtration and washed with AcOEt to give the title compound (4.07 g, 93% yield) as yellow crystals: $^1$H NMR (300 MHz, CDCl₃): δ ppm 2.90 (3H, s), 3.12 (3H, br s), 3.87 (3H, s), 5.87 (1H, br s), 6.31-6.82 (2H, m), 7.30-7.41 (2H, m), 7.43-7.50 (1H, m), 7.63 (1H, dd, J=7.8, 1.8 Hz), 7.74 (1H, s).

Reference Example 89

Methyl 4-methoxy-3-oxo-2-{[3-(trifluoromethyl)phenyl]hydrazono}butanoate

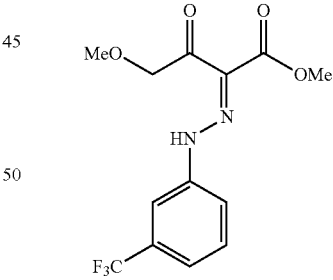

A solution of NaNO₂ (4.14 g, 60 mmol) in H₂O (15 mL) was added dropwise at 0° C. to a mixture of 3-(trifluoromethyl)aniline (6.24 mL, 50 mmol) and 6 M HCl aqueous solution (50 mL, 300 mmol). After stirring for 15 min, the resulting aqueous solution was added to a suspension of methyl 4-methoxyacetoacetate (7.31 mL, 50 mmol) and NaOAc (24.6 g, 300 mmol) in EtOH (80 mL) pre-cooled at 0° C. The precipitate was collected by filtration, washed with water, and dissolved in AcOEt. The organic solution was washed with water and brine, dried over Na₂SO₄, and concentrated under reduced pressure. The residue was crystallized from hexane/AcOEt to give the title compound (14.0 g, 88% yield) as pale yellow crystals: ¹H NMR (300 MHz, CDCl₃): δ ppm 3.51 (3H×0.36, s), 3.52 (3H×0.64, s), 3.90 (3H×0.36, s), 3.94 (3H×0.64, s), 4.68 (2H×0.64, s), 4.70 (2H×0.36, s), 7.41-7.59 (3H+1H×0.64, m), 7.71 (1H×0.36, s), 13.00 (1H×0.64, s), 14.87 (1H×0.36, s).

Reference Example 90

Methyl 5-methoxy-4-oxo-1-[3-(trifluoromethyl)phenyl]-1,4-dihydropyridazine-3-carboxylate

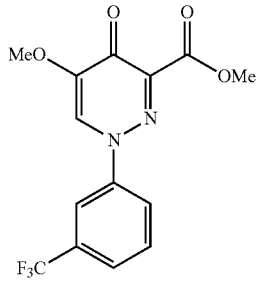 [SMILES: COC(=O)c1nn(-c2cccc(C(F)(F)F)c2)cc(OC)c1=O]

A solution of methyl 4-methoxy-3-oxo-2-{[3-(trifluoromethyl)phenyl]hydrazono}butanoate (14.0 g, 44 mmol) in N,N-dimethylformamide dimethyl acetal (100 mL) was refluxed for 4 h. After cooling to room temperature, the precipitate was collected by filtration and washed with hexane/AcOEt (3/1) to give the title compound (12.9 g, 89% yield) as off-white crystals: mp 169-170° C.; ¹H NMR (300 MHz, CDCl₃): δ ppm 3.98 (3H, s), 3.99 (3H, s), 7.66-7.74 (2H, m), 7.83-7.89 (2H, m), 7.95 (1H, s). Anal. Calcd for C₁₄H₁₁F₃N₂O₄: C, 51.23; H, 3.38; N, 8.53. Found: C, 51.15; H, 3.47; N, 8.60.

Reference Example 91

N,5-Dimethoxy-N-methyl-4-oxo-1-[3-(trifluoromethyl)phenyl]-1,4-dihydropyridazine-3-carboxamide

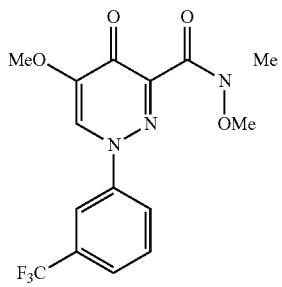 [SMILES: CONC(=O)c1nn(-c2cccc(C(F)(F)F)c2)cc(OC)c1=O ; "Me"]

To a solution of N,O-dimethylhydroxylamine hydrochloride (2.63 g, 27 mmol) and iPr₂NEt (4.70 mL, 27 mmol) in CH₂Cl₂ (30 mL) was added AlMe₃ (1.8 M solution in toluene, 15 mL, 27 mmol) dropwise at 0° C. under Ar atmosphere. After stirring for 1 h, a solution of methyl 5-methoxy-4-oxo-1-[3-(trifluoromethyl)phenyl]-1,4-dihydropyridazine-3-carboxylate (2.95 g, 9 mmol) in CH₂Cl₂ (30 mL) was added dropwise, and the mixture was stirred for 1 h at 0° C. The reaction mixture was poured into ice-water and extracted with AcOEt. The extract was washed with brine, dried over MgSO₄, and concentrated under reduced pressure. The residue was purified by basic silica gel column chromatography eluting with AcOEt and recrystallized from hexane/AcOEt to give the title compound (2.15 g, 67% yield) as off-white crystals: mp 170-171° C.; ¹H NMR (300 MHz, CDCl₃): δ ppm 3.41 (3H, s), 3.71 (3H, s), 3.98 (3H, s), 7.63-7.71 (2H, m), 7.80-7.86 (1H, m), 7.88 (1H, s), 7.98 (1H, s). Anal. Calcd for C₁₅H₁₄F₃N₃O₄: C, 50.42; H, 3.95; N, 11.76. Found: C, 50.48; H, 4.07; N, 11.66.

Reference Example 92

3-Acetyl-5-methoxy-1-[3-(trifluoromethyl)phenyl]pyridazin-4(1H)-one

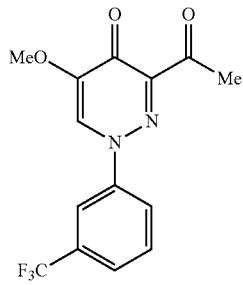 [SMILES: COc1cn(-c2cccc(C(F)(F)F)c2)nc(C(C)=O)c1=O]

MeMgBr (3 M solution in diethyl ether, 4 mL, 12 mmol) was added dropwise at −78° C. to a solution of N,5-dimethoxy-N-methyl-4-oxo-1-[3-(trifluoromethyl)phenyl]-1,4-dihydropyridazine-3-carboxamide (2.09 g, 5.85 mmol) in THF (50 mL). After stirring for 1 h, the reaction mixture was quenched with saturated NH₄Cl aqueous solution and extracted with AcOEt three times. The combined extracts were washed with brine, dried over MgSO₄, and concentrated under reduced pressure. The residue was purified by silica gel column chromatography eluting with AcOEt/MeOH (1/0-10/1) and recrystallized from hexane/AcOEt to give the title compound (1.44 g, 79% yield) as off-white crystals: mp 155-156° C.; ¹H NMR (300 MHz, CDCl₃): δ ppm 2.71 (3H, s), 3.98 (3H, s), 7.68-7.76 (2H, m), 7.83-7.88 (2H, m), 7.94 (1H, s). Anal. Calcd for C₁₄H₁₁F₃N₂O₃: C, 53.85; H, 3.55; N, 8.97. Found: C, 53.79; H, 3.59; N, 9.02.

Reference Example 93

3-[3-(Dimethylamino)prop-2-enoyl]-5-methoxy-1-[3-(trifluoromethyl)phenyl]pyridazin-4(1H)-one

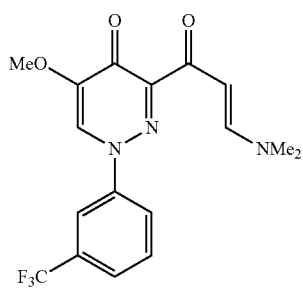 [SMILES: COc1cn(-c2cccc(C(F)(F)F)c2)nc(C(=O)/C=C/N(C)C)c1=O]

A solution of 3-acetyl-5-methoxy-1-[3-(trifluoromethyl)phenyl]pyridazin-4(1H)-one (1.39 g, 4.45 mmol) in N,N-dimethylformamide dimethyl acetal (15 mL) was refluxed for 3 h. After cooling to room temperature, the reaction mixture was concentrated under reduced pressure, and the residue was dissolved in AcOEt. The organic solution was washed with half-saturated brine, and the aqueous solution was extracted with AcOEt four times. The combined organic layers were dried over MgSO$_4$, and concentrated under reduced pressure. The residue was recrystallized from AcOEt to give the title compound (1.46 g, 89% yield) as orange crystals: mp 176-178° C.; $^1$H NMR (300 MHz, CDCl$_3$): δ ppm 2.91 (3H, s), 3.14 (3H, s), 3.96 (3H, s), 5.80 (1H, d, J=13.2 Hz), 7.61-7.68 (2H, m), 7.80 (1H, br s), 7.84-7.90 (2H, m), 7.96 (1H, s). Anal. Calcd for C$_{17}$H$_{16}$F$_3$N$_3$O$_3$: C, 55.59; H, 4.39; N, 11.44. Found: C, 55.32; H, 4.51; N, 11.30.

Reference Example 94

Methyl 2-[(2-fluoro-4-iodophenyl)hydrazono]-4-methoxy-3-oxobutanoate

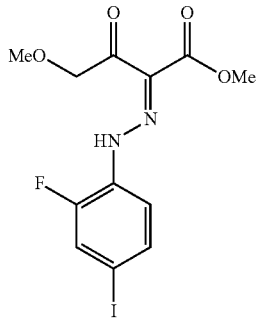 [SMILES: COCC(=O)/C(=N\Nc1ccc(I)cc1F)C(=O)OC]

A solution of NaNO$_2$ (1.66 g, 24 mmol) in H$_2$O (5 mL) was added dropwise at 0° C. to a mixture of 2-fluoro-4-iodoaniline (4.74 g, 20 mmol) and 6 M HCl aqueous solution (20 mL, 120 mmol). After stirring for 15 min, the resulting aqueous solution was added to a suspension of methyl 4-methoxyacetoacetate (2.59 mL, 20 mmol) and NaOAc (9.84 g, 120 mmol) in MeOH (40 mL) pre-cooled at 0° C. The reaction mixture was poured into water and extracted with AcOEt. The extract was washed with saturated NaHCO$_3$ aqueous solution and brine, dried over MgSO$_4$, and concentrated under reduced pressure. The residue was recrystallized from hexane/AcOEt to give the title compound (6.29 g, 80% yield) as yellow crystals: mp 141-146° C.; $^1$H NMR (300 MHz, CDCl$_3$): δ ppm 3.50 (3H, s), 3.93 (3H, s), 4.64 (2H, s), 7.35 (1H, t, J=8.5 Hz), 7.49-7.55 (2H, m), 12.97 (1H, br s). Anal. Calcd for C$_{12}$H$_{12}$FIN$_2$O$_4$: C, 36.57; H, 3.07; N, 7.11. Found: C, 36.74; H, 3.10; N, 7.32.

Reference Example 95

Methyl 1-(2-fluoro-4-iodophenyl)-5-methoxy-4-oxo-1,4-dihydropyridazine-3-carboxylate

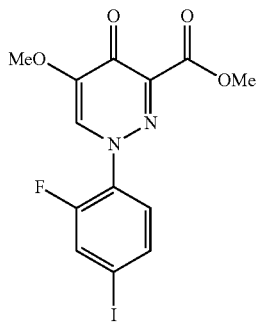 [SMILES: COC(=O)c1nn(-c2ccc(I)cc2F)cc(OC)c1=O]

A solution of methyl 2-[(2-fluoro-4-iodophenyl)hydrazono]-4-methoxy-3-oxobutanoate (6.27 g, 15.9 mmol) in N,N-dimethylformamide dimethyl acetal (60 mL) was refluxed for 3 h. After cooling to room temperature, the reaction mixture was poured into water and extracted with AcOEt. The extract was washed with water and brine, dried over MgSO$_4$, and concentrated under reduced pressure. The residue was purified by silica gel column chromatography eluting with AcOEt and recrystallized from MeOH to give the title compound (3.77 g, 59% yield) as off-white crystals: mp 160-162° C.; $^1$H NMR (300 MHz, CDCl$_3$): δ ppm 3.90 (3H, s), 3.97 (3H, s), 7.36-7.41 (1H, m), 7.64-7.70 (2H, m), 7.73 (1H, d, J=2.6 Hz). Anal. Calcd for C$_{13}$H$_{10}$FIN$_2$O$_4$: C, 38.64; H, 2.49; N, 6.93. Found: C, 38.68; H, 2.59; N, 6.98.

Reference Example 96

1-(2-Fluoro-4-iodophenyl)-N,5-dimethoxy-N-methyl-4-oxo-1,4-dihydropyridazine-3-carboxamide

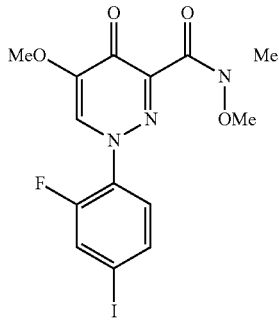 [SMILES: COc1cn(-c2ccc(I)cc2F)nc(C(N)=O)c1=O ; "OMe" ; "Me"]

To a solution of N,O-dimethylhydroxylamine hydrochloride (8.78 g, 90 mmol) and iPr$_2$NEt (15.7 mL, 90 mmol) in CH$_2$Cl$_2$ (100 mL) was added AlMe$_3$ (1.8 M solution in toluene, 50 mL, 90 mmol) slowly at 0° C. under Ar atmosphere. After stirring for 1 h, a solution of methyl 1-(2-fluoro-4-iodophenyl)-5-methoxy-4-oxo-1,4-dihydropyridazine-3-carboxylate (12.1 g, 30 mmol) in CH$_2$Cl$_2$ (100 mL) was added slowly, and the mixture was stirred for 1 h at 0° C. The reaction mixture was poured into ice-water and the organic layer was separated. The aqueous layer was extracted with AcOEt. The combined organic layers were washed with brine, dried over MgSO$_4$, and concentrated under reduced pressure. The residue was purified by basic silica gel column chromatography eluting with AcOEt to give the title compound (9.96 g, 77% yield) as a white amorphous solid: $^1$H NMR (300 MHz, CDCl$_3$): δ ppm 3.39 (3H, s), 3.70 (3H, s), 3.90 (3H, s), 7.39 (1H, t, J=8.1 Hz), 7.63-7.67 (2H, m), 7.77 (1H, d, J=2.3 Hz).

Reference Example 97

3-Acetyl-1-(2-fluoro-4-iodophenyl)-5-methoxypyridazin-4(1H)-one

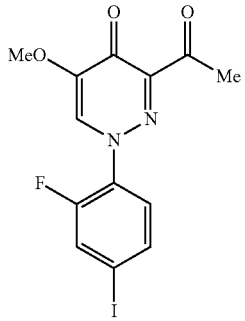 [SMILES: COc1cn(-c2ccc(I)cc2F)nc(C(C)=O)c1=O]

MeMgBr (1 M solution in THF, 70 mL, 70 mmol) was added dropwise at −78° C. to a solution of 1-(2-fluoro-4- iodophenyl)-N,5-dimethoxy-N-methyl-4-oxo-1,4-dihydropyridazine-3-carboxamide (9.96 g, 23 mmol) in THF (250 mL). After stirring for 1 h, the reaction mixture was quenched with 1 M HCl aqueous solution and extracted with AcOEt. The extract was washed with brine, dried over MgSO$_4$, and concentrated under reduced pressure. The residue was purified by silica gel column chromatography eluting with AcOEt and recrystallized from MeOH to give the title compound (2.05 g, 23% yield) as pale yellow crystals: mp 196-198° C.; $^1$H NMR (300 MHz, CDCl$_3$): δ ppm 2.67 (3H, s), 3.90 (3H, s), 7.36-7.41 (1H, m), 7.66-7.71 (2H, m), 7.73 (1H, d, J=2.6 Hz). Anal. Calcd for C$_{13}$H$_{10}$FIN$_2$O$_3$: C, 40.23; H, 2.60; N, 7.22. Found: C, 40.25; H, 2.87; N, 7.28.

Reference Example 98

Methyl 5-(methoxymethyl)-4-oxo-1-[3-(trifluoromethyl)phenyl]-1,4-dihydropyridazine-3-carboxylate

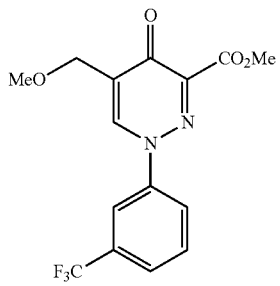 [SMILES: COCc1cn(-c2cccc(C(F)(F)F)c2)nc(C(=O)OC)c1=O]

A solution of NaNO$_2$ (2.48 g, 36 mmol) in H$_2$O (10 mL) was added dropwise at 0° C. to a mixture of 3-(trifluoromethyl)aniline (3.75 mL, 30 mmol) and 6 M HCl aqueous solution (30 mL, 180 mmol). After stirring for 15 min, the resulting aqueous solution was added to a suspension of methyl 5-methoxy-3-oxovalerate (4.37 mL, 30 mmol) and NaOAc (14.8 g, 180 mmol) in EtOH (50 mL) pre-cooled at 0° C. After stirring for 5 min, the reaction mixture was poured into water and extracted with AcOEt. The extract was washed with saturated NaHCO$_3$ aqueous solution and brine, dried over MgSO$_4$, and concentrated under reduced pressure.

A solution of the residue in N,N-dimethylformamide dimethyl acetal (50 mL) was refluxed for 4 h. After cooling to room temperature, the precipitate was collected by filtration and recrystallized from AcOEt to give the title compound (7.13 g, 69% yield) as a yellow solid: mp 138-140° C.; $^1$H NMR (300 MHz, CDCl$_3$): δ ppm 3.53 (3H, s), 4.00 (3H, s), 4.49 (2H, d, J=1.5 Hz), 7.65-7.73 (2H, m), 7.82-7.85 (1H, m), 7.89 (1H, s), 8.38 (1H, t, J=1.5 Hz). Anal. Calcd for C$_{15}$H$_{13}$F$_3$N$_2$O$_4$: C, 52.64; H, 3.83; N, 8.18. Found: C, 52.50; H, 3.89; N, 8.17.

Reference Example 99

N-Methoxy-5-(methoxymethyl)-N-methyl-4-oxo-1-[3-(trifluoromethyl)phenyl]-1,4-dihydropyridazine-3-carboxamide

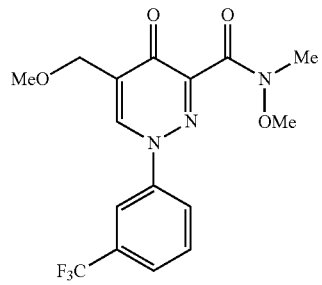

To a solution of N,O-dimethylhydroxylamine hydrochloride (2.63 g, 27 mmol) and iPr$_2$NEt (4.70 mL, 27 mmol) in CH$_2$Cl$_2$ (30 mL) was added AlMe$_3$ (1.8 M solution in toluene, 15 mL, 27 mmol) dropwise at 0° C. under Ar atmosphere. After stirring for 1 h, a solution of methyl 5-(methoxymethyl)-4-oxo-1-[3-(trifluoromethyl)phenyl]-1,4-dihydropyridazine-3-carboxylate (3.08 g, 9 mmol) in CH$_2$Cl$_2$ (30 mL) was added dropwise, and the mixture was stirred for 1 h at 0° C. The reaction mixture was poured into ice-water and extracted with AcOEt. The extract was washed with brine, dried over MgSO$_4$, and concentrated under reduced pressure. The residue was purified by silica gel column chromatography eluting with AcOEt and recrystallized from hexane/AcOEt to give the title compound (1.99 g, 60% yield) as an off-white solid: mp 157-159° C.; $^1$H NMR (300 MHz, CDCl$_3$): δ ppm 3.41 (3H, s), 3.53 (3H, s), 3.67 (3H, s), 4.50 (2H, d, J=1.1 Hz), 7.62-7.71 (2H, m), 7.79-7.85 (1H, m), 7.90 (1H, s), 8.39 (1H, t, J=1.1 Hz). Anal. Calcd for C$_{16}$H$_{16}$F$_3$N$_3$O$_4$: C, 51.75; H, 4.34; N, 11.32. Found: C, 51.77; H, 4.25; N, 11.24.

Reference Example 100

3-Acetyl-5-(methoxymethyl)-1-[3-(trifluoromethyl)phenyl]pyridazin-4(1H)-one

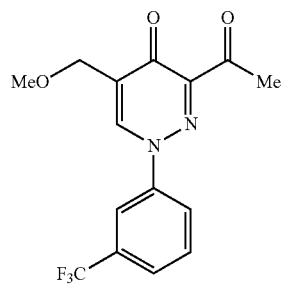 [SMILES: COCc1cn(-c2cccc(C(F)(F)F)c2)nc(C(C)=O)c1=O]

MeMgBr (1 M solution in THF, 16 mL, 16 mmol) was added dropwise at −78° C. to a solution of N-methoxy-5-(methoxymethyl)-N-methyl-4-oxo-1-[3-(trifluoromethyl)phenyl]-1,4-dihydropyridazine-3-carboxamide (1.95 g, 5.25 mmol) in THF (50 mL). After stirring for 1 h, the reaction mixture was quenched with saturated NH$_4$Cl aqueous solution and extracted with AcOEt. The extract was washed with brine, dried over MgSO$_4$, and concentrated under reduced pressure. The residue was purified by silica gel column chromatography eluting with AcOEt and recrystallized from hexane/AcOEt to give the title compound (1.42 g, 83% yield) as a pale yellow solid: mp 141-143° C.; $^1$H NMR (300 MHz, CDCl$_3$): δ ppm 2.68 (3H, s), 3.54 (3H, s), 4.50 (2H, d, J=1.5 Hz), 7.66-7.74 (2H, m), 7.81-7.87 (1H, m), 7.89 (1H, s), 8.38 (1H, t, J=1.5 Hz). Anal. Calcd for C$_{15}$H$_{13}$F$_3$N$_2$O$_3$: C, 55.22; H, 4.02; N, 8.59. Found: C, 55.26; H, 3.95; N, 8.58.

Reference Example 101

3-Acetyl-1-[3-(trifluoromethyl)phenyl]pyridazin-4(1H)-one

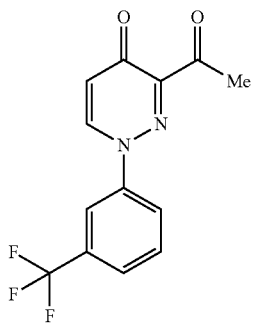 [SMILES: CC(=O)c1nn(-c2cccc(C(F)(F)F)c2)ccc1=O]

A mixture of 3-{[3-(trifluoromethyl)phenyl]hydrazono}pentane-2,4-dione (5.00 g, 18.4 mmol) and N,N-dimethylformamide dimethyl acetal (2.44 mL, 18.4 mmol) in DMF (100 mL) was heated to 80° C. for 4 h. The mixture was diluted with 1 M HCl aqueous solution, extracted with EtOAc, washed with brine, dried over Na$_2$SO$_4$, filtered, concentrated in vacuo, purified by column chromatography on silica gel (hexane/EtOAc=50/50 to 0/100 and EtOAc/MeOH=100/0 to 80/20) and triturated with EtOAc/hexane to yield the title compound (3.38 g, 65% yield) as a pale yellow solid: $^1$H NMR (DMSO-d$_6$, 300 MHz): δ ppm 2.55 (3H, s), 6.75 (1H, d, J=8.0 Hz), 7.78-7.88 (2H, m), 8.06-8.16 (2H, m), 8.96 (1H, d, J=8.2 Hz).

Reference Example 102

3-Acetyl-5-bromo-1-[3-(trifluoromethyl)phenyl]pyridazin-4(1H)-one

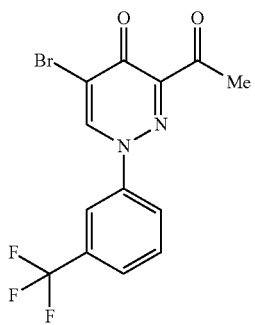 [SMILES: CC(=O)c1nn(-c2cccc(C(F)(F)F)c2)cc(Br)c1=O]

To a solution of 3-acetyl-1-[3-(trifluoromethyl)phenyl]pyridazin-4(1H)-one (1.00 g, 3.54 mmol) in AcOH (3.5 mL) was added Br$_2$ (0.181 mL, 3.54 mmol) at room temperature. The mixture was stirred at room temperature for 2 h. The mixture was diluted with water and NaHCO$_3$ aqueous solution, extracted with EtOAc, dried over MgSO$_4$, filtered, concentrated in vacuo and purified by column chromatography on silica gel (hexane/EtOAc=50/50 to 0/100) to yield the title compound (332 mg, 26% yield) as a pale yellow solid: $^1$H NMR (DMSO-d$_6$, 300 MHz): δ ppm 2.57 (3H, s), 7.79-7.91 (2H, m), 8.09-8:17 (1H, m), 8.22 (1H, s), 9.58 (1H, s).

Reference Example 103

Methyl 4-methoxy-6-oxo-1-[3-(trifluoromethyl)phenyl]-1,6-dihydropyridazine-3-carboxylate

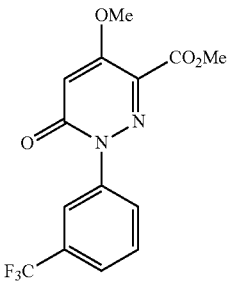 [SMILES: COC(=O)c1nn(-c2cccc(C(F)(F)F)c2)c(=O)cc1OC]

A solution of NaNO$_2$ (2.07 g, 30 mmol) in H$_2$O (10 mL) was added dropwise at 0° C. to a mixture of 3-(trifluoromethyl)aniline (3.12 mL, 25 mmol) and 6 M HCl aqueous solution (25 mL, 150 mmol). After stirring for 15 min, the resulting aqueous solution was added to a suspension of dimethyl 1,3-acetonedicarboxylate (3.61 mL, 25 mmol) and NaOAc (12.3 g, 150 mmol) in EtOH (40 mL) pre-cooled at 0° C. After stirring for 10 min, the reaction mixture was poured into water and extracted with AcOEt. The extract was washed with saturated NaHCO$_3$ aqueous solution and brine, dried over MgSO$_4$, and concentrated under reduced pressure.

A solution of the residue and NaOMe (2.70 g, 50 mmol) in MeOH (50 mL) was stirred for 30 min at room temperature. The reaction mixture was poured into 1 M HCl aqueous solution and extracted with AcOEt. The extract was washed with brine, dried over MgSO$_4$, and concentrated under reduced pressure.

A suspension of the residue, MeI (3.11 mL, 50 mmol), and K$_2$CO$_3$ (10.4 g, 75 mmol) in DMF (50 mL) was stirred for 1 h at room temperature. The reaction mixture was poured into water and extracted with AcOEt. The extract was washed with water and brine, dried over MgSO$_4$, and concentrated under reduced pressure. The residue was purified by basic silica gel column chromatography eluting with hexane/AcOEt (1/1) and recrystallized from hexane/AcOEt to give the title compound (1.83 g, 22% yield) as a pale yellow solid: mp 124-125° C.; $^1$H NMR (300 MHz, CDCl$_3$): δ ppm 3.94 (3H, s), 3.95 (3H, s), 6.32 (1H, s), 7.57-7.62 (1H, m), 7.65-7.68 (1H, m), 7.80-7.84 (1H, m), 7.88 (1H, s). Anal. Calcd for C$_{14}$H$_{11}$F$_3$N$_2$O$_4$: C, 51.23; H, 3.38; N, 8.53. Found: C, 51.29; H, 3.40; N, 8.52.

Reference Example 104

N,4-Dimethoxy-N-methyl-6-oxo-1-[3-(trifluoromethyl)phenyl]-1,6-dihydropyridazine-3-carboxamide

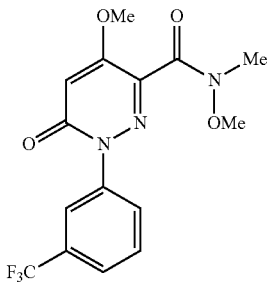 [SMILES: COc1cc(=O)n(-c2cccc(C(F)(F)F)c2)nc1C(=O)N(C)OC]

To a solution of N,O-dimethylhydroxylamine hydrochloride (1.58 g, 16.2 mmol) and iPr$_2$NEt (2.82 mL, 16.2 mmol) in CH$_2$Cl$_2$ (13 mL) was added AlMe$_3$ (1.8 M solution in toluene, 9.0 mL, 16.2 mmol) dropwise at 0° C. under Ar atmosphere. After stirring for 1 h, a solution of methyl 4-methoxy-6-oxo-1-[3-(trifluoromethyl)phenyl]-1,6-dihydropyridazine-3-carboxylate (1.77 g, 5.4 mmol) in CH$_2$Cl$_2$ (15 mL) was added dropwise, and the mixture was stirred for 1 h at 0° C. The reaction mixture was poured into ice-water and extracted with AcOEt. The extract was washed with brine, dried over MgSO$_4$, and concentrated under reduced pressure. The residue was purified by silica gel column chromatography eluting with AcOEt and crystallized from hexane/AcOEt to give the title compound (1.48 g, 83% yield) as a white solid: mp 127-129° C.; $^1$H NMR (300 MHz, CDCl$_3$): δ ppm 3.37 (3H, s), 3.64 (3H, s), 3.91 (3H, s), 6.30 (1H, s), 7.55-7.60 (1H, m), 7.62-7.65 (1H, m), 7.82-7.86 (1H, m), 7.88 (1H, s). Anal. Calcd for C$_{15}$H$_{14}$F$_3$N$_3$O$_4$: C, 50.42; H, 3.95; N, 11.76. Found: C, 50.47; H, 3.99; N, 11.83.

Reference Example 105

6-Acetyl-5-methoxy-2-[3-(trifluoromethyl)phenyl]pyridazin-3(2H)-one

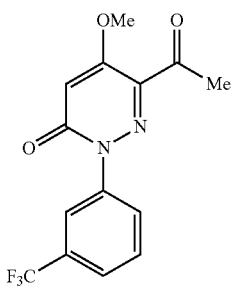 [SMILES: COc1cc(=O)n(-c2cccc(C(F)(F)F)c2)nc1C(C)=O]

MeMgBr (1 M solution in THF, 4 mL, 12 mmol) was added dropwise at −78° C. to a solution of N,4-dimethoxy-N-methyl-6-oxo-[3-(trifluoromethyl)phenyl]-1,6-dihydropyridazine-3-carboxamide (1.43 g, 4 mmol) in THF (15 mL). After stirring for 1 h, the reaction mixture was quenched with saturated NH$_4$Cl aqueous solution and extracted with AcOEt. The extract was washed with brine, dried over MgSO$_4$, and concentrated under reduced pressure. The residue was purified by silica gel column chromatography eluting with hexane/AcOEt (1/1) and recrystallized from hexane/AcOEt to give the title compound (566 mg, 45% yield) as a white solid: mp 136-138° C.; $^1$H NMR (300 MHz, CDCl$_3$): δ ppm 2.57 (3H, s), 3.93 (3H, s), 6.31 (1H, s), 7.63 (1H, t, J=7.9 Hz), 7.69 (1H, d, J=7.9 Hz), 7.84-7.88 (1H, m), 7.91 (1H, s). Anal. Calcd for C$_{14}$H$_{11}$F$_3$N$_2$O$_3$: C, 53.85; H, 3.55; N, 8.97. Found: C, 53.96; H, 3.57; N, 8.96.

Reference Example 106

5-Methoxy-6-(1-phenyl-1H-pyrazol-5-yl)-2-[3-(trifluoromethyl)phenyl]pyridazin-3 (2H)-one A solution of 6-acetyl-5-methoxy-2-[3-(trifluoromethyl)phenyl]pyridazin-3(2H)-one (540 mg, 1.73 mmol) in N,N-dimethylformamide dimethyl acetal (5 mL) was refluxed for 3 h. After cooling to room temperature, the reaction mixture was concentrated under reduced pressure. The residue was diluted with AcOEt, washed with water and brine, dried over MgSO$_4$, and concentrated under reduced pressure.

A solution of the residue and phenylhydrazine (0.551 mL, 5.19 mmol) in MeOH (5 mL) was refluxed for 2 h. After cooling to room temperature, the reaction mixture was poured into 1 M HCl aqueous solution and extracted with AcOEt. The extract was washed with brine, dried over MgSO$_4$, and concentrated under reduced pressure. The residue was purified by silica gel column chromatography eluting with hexane/AcOEt (1/1) and recrystallized from hexane/AcOEt to give the title compound (323 mg, 45% yield) as a white solid: mp 165-167° C.; $^1$H NMR (300 MHz, CDCl$_3$): δ ppm 3.73 (3H, s), 6.27 (1H, s), 6.78 (1H, d, J=1.9 Hz), 7.31-7.50 (8H, m), 7.52-7.58 (1H, m), 7.77 (1H, d, J=1.9 Hz). LC-MS (ESI) m/z 413 [M+H]$^+$. Anal. Calcd for C$_{21}$H$_{15}$F$_3$N$_4$O$_2$: C, 61.17; H, 3.67; N, 13.59. Found: C, 61.12; H, 3.72; N, 13.54.

Reference Example 107

4-oxo-1-[3-(trifluoromethyl)phenyl]-1,4-dihydropyridazine-3-carboxylic acid

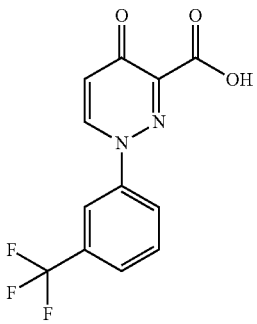 [SMILES: O=C(O)c1nn(-c2cccc(C(F)(F)F)c2)ccc1=O]

To a suspension of methyl 4-oxo-1-[3-(trifluoromethyl)phenyl]-1,4-dihydropyridazine-3-carboxylate (10.0 g, 33.5 mmol) in MeOH (150 mL) was added 1 M NaOH aqueous solution (50 mL) at 0° C. The mixture was stirred at room temperature for 30 min. To the suspension was added 1 M HCl aqueous solution (50 mL) at 0° C. The mixture was concentrated in vacuo. The precipitates were collected by filtration, washed with water and dried in vacuo at 50° C. to yield the title compound (9.25 g, 97% yield) as a pale yellow solid: $^1$H NMR (DMSO-$d_6$, 300 MHz): δ ppm 7.02 (1H, d, J=7.7 Hz), 7.81-7.96 (2H, m), 8.06-8.21 (2H, m), 9.16 (1H, d, J=7.7 Hz).

Reference Example 108

N-Methoxy-N-methyl-4-oxo-1-[3-(trifluoromethyl)phenyl]-1,4-dihydropyridazine-3-carboxamide

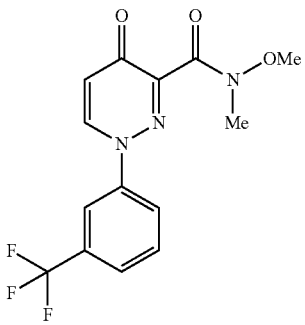 [SMILES: CON(C)C(=O)c1nn(-c2cccc(C(F)(F)F)c2)ccc1=O]

A mixture of 4-oxo-1-[3-(trifluoromethyl)phenyl]-1,4-dihydropyridazine-3-carboxylic acid (2.00 g, 7.04 mmol) and CDI (1.26 g, 7.74 mmol) in THF (20 mL) was heated to 40° C. for 2 h. To the solution were added N-methoxymethanamine hydrochloride (1.03 g, 10.6 mmol) and i-Pr$_2$NEt (1.84 mL, 10.6 mmol) at room temperature. The solution was stirred at room temperature for 20 h. The mixture was diluted with water, extracted with EtOAc, washed with brine, dried over Na$_2$SO$_4$, filtered, concentrated in vacuo and purified by column chromatography on silica gel (hexane/EtOAc=50/50 to 0/100 and EtOAc/MeOH=100/0 to 80/20) to yield the crude title compound (2.40 g) as a pale yellow solid: $^1$H NMR (DMSO-$d_6$, 300 MHz): δ ppm 3.28 (3H, s), 3.61 (3H, s), 6.67 (1H, d, J=7.9 Hz), 7.77-7.90 (2H, m), 8.00-8.14 (2H, m), 8.99 (1H, d, J=7.9 Hz).

Reference Example 109

3-Propanoyl-1-[3-(trifluoromethyl)phenyl]pyridazin-4(1H)-one

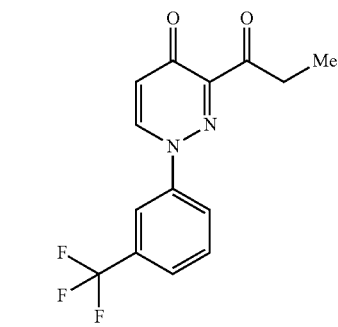 [SMILES: CCC(=O)c1nn(-c2cccc(C(F)(F)F)c2)ccc1=O]

To a solution of N-methoxy-N-methyl-4-oxo-[3-(trifluoromethyl)phenyl]-1,4-dihydropyridazine-3-carboxamide (1.20 g, 3.52 mmol) in THF (20 mL) was added EtMgBr (1.0 M in THF, 7.04 mL, 7.04 mmol) at −78° C. under N$_2$. The mixture was stirred at −78° C. for 1 h. The reaction was quenched with saturated NH$_4$Cl aqueous solution at −78° C. The mixture was warmed to room temperature, extracted with EtOAc, dried over Na$_2$SO$_4$, filtered, concentrated in vacuo and purified by column chromatography on silica gel (hexane/EtOAc=50/50 to 0/100) to yield the title compound (767 mg, 74% yield) as a pale yellow solid: $^1$H NMR (DMSO-$d_6$, 300 MHz): δ ppm 1.06 (3H, t, J=7.2 Hz), 2.99 (2H, q, J=7.2 Hz), 6.73 (1H, d, J=8.3 Hz), 7.79-7.88 (2H, m), 8.06-8.17 (2H, m), 8.97 (1H, d, J=8.3 Hz).

Reference Example 110

4-Bromo-3-phenyl-1H-pyrazole

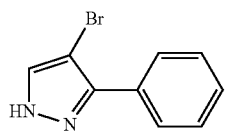

A solution of 3-phenyl-1H-pyrazole (4.08 g, 28.3 mmol) and NBS (5.04 g, 28.3 mmol) in DMF (40 mL) was stirred for 1 h at room temperature. The reaction mixture was poured into water and extracted with AcOEt. The extract was washed with water and brine, dried over MgSO$_4$, and concentrated under reduced pressure. The residue was recrystallized from hexane/AcOEt to give the title compound (5.84 g, 93% yield) as a white solid: mp 114-116° C.; $^1$H NMR (300 MHz, CDCl$_3$): δ ppm 7.39-7.50 (3H, m), 7.64 (1H, s), 7.77 (2H, d, J=6.8 Hz), 10.73 (1H, brs).

Reference Example 111

4-Bromo-3-phenyl-1-trityl-1H-pyrazole

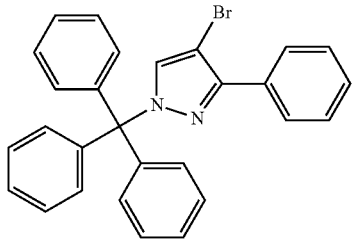 [SMILES: Brc1cn(C(c2ccccc2)(c2ccccc2)c2ccccc2)nc1-c1ccccc1]

A suspension of 4-bromo-3-phenyl-1H-pyrazole (6.13 g, 27.5 mmol), trityl chloride (15.3 g, 55.0 mmol), and $K_2CO_3$ (11.4 g, 82.5 mmol) in DMF (100 mL) was stirred for 60 h at 90° C. After cooling to room temperature, the reaction mixture was poured into water and extracted with AcOEt. The extract was washed with water and brine, dried over $MgSO_4$, concentrated under reduced pressure. The residue was recrystallized from hexane/THF to give the title compound (8.00 g, 63% yield) as a white solid: mp 181-183° C.; $^1$H NMR (300 MHz, $CDCl_3$): δ ppm 7.16-7.22 (6H, m), 7.28-7.41 (13H, m), 7.87-7.91 (2H, m). Anal. Calcd for $C_{28}H_{21}BrN_2$: C, 72.26; H, 4.55; N, 6.02. Found: C, 72.43; H, 4.66; N, 5.91.

Reference Example 112

3-Amino-1-[3-(trifluoromethyl)phenyl]pyridazin-4(1H)-one

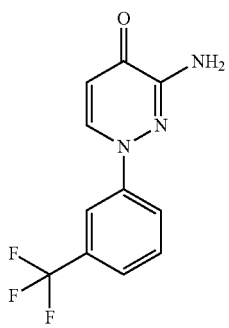 [SMILES: Nc1nn(-c2cccc(C(F)(F)F)c2)ccc1=O]

A mixture of 4-oxo-1-[3-(trifluoromethyl)phenyl]-1,4-dihydropyridazine-3-carboxylic acid (5.00 g, 17.6 mmol), DPPA (5.67 mL, 26.4 mmol) and $Et_3N$ (3.65 mL, 26.4 mmol) in toluene (35 mL) was heated to 100° C. for 2 h. To the mixture was added 8 M NaOH aqueous solution (22 mL) at 0° C. The mixture was stirred at room temperature for 2 h, diluted with brine, extracted with EtOAc, dried over $Na_2SO_4$, filtered, and concentrated in vacuo. The residue was washed with EtOAc/i-$Pr_2O$ and filtered. The filtrate was concentrated in vacuo, purified by column chromatography on basic silica gel (hexane/EtOAc=50/50 to 0/100) and washed with EtOAc/hexane to yield the title compound (2.50 g, 56% yield) as a pale yellow solid: $^1$H NMR (DMSO-$d_6$, 300 MHz): δ ppm 6.17 (1H, d, J=7.5 Hz), 6.52 (2H, brs), 7.67-7.81 (2H, m), 8.04 (1H, d, J=7.5 Hz), 8.10 (1H, s), 8.75 (1H, d, J=7.5 Hz).

Reference Example 113

3-Bromo-1-[3-(trifluoromethyl)phenyl]pyridazin-4(1H)-one

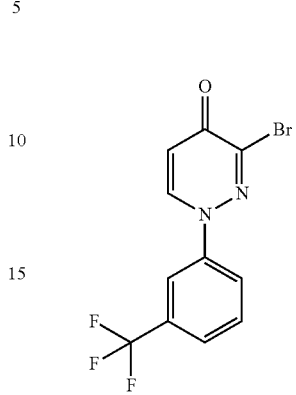

To DMF (18 mL) were added isoamyl nitrite (2.44 mL, 18.3 mmol) and $CuBr_2$ (1.89 g, 8.46 mmol) at 0° C. To the mixture was dropwise added a solution of 3-amino-1-[3-(trifluoromethyl)phenyl]pyridazin-4(1H)-one (1.80 g, 7.05 mmol) in DMF (7.2 mL) at 0° C. The mixture was stirred at 0° C. for 1 h and at 60° C. for 3 h. The mixture was diluted with brine, extracted with EtOAc, washed with brine, dried over $MgSO_4$, filtered, concentrated in vacuo, purified by column chromatography on silica gel (hexane/EtOAc=50/50 to 0/100) and triturated with hexane to yield the title compound (1.85 g, 82% yield) as a white solid: $^1$H NMR (DMSO-$d_6$, 300 MHz): δ ppm 6.64 (1H, d, J=7.7 Hz), 7.78-7.87 (2H, m), 8.01-8.07 (1H, m), 8.08 (1H, s), 9.00 (1H, d, J=7.7 Hz).

Reference Example 114

1-[3-(Trifluoromethyl)phenyl]-3-[(trimethylsilyl)ethynyl]pyridazin-4(1H)-one

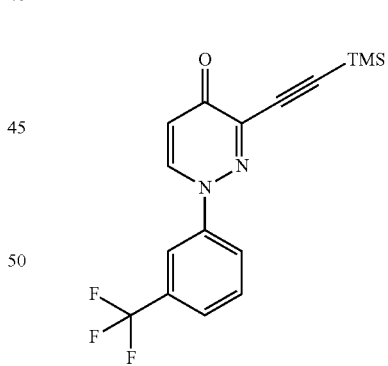

A mixture of 3-bromo-1-[3-(trifluoromethyl)phenyl]pyridazin-4(1H)-one (500 mg, 1.57 mmol), (trimethylsilyl)acetylene (0.222 mL, 1.57 mmol), $Et_3N$ (0.329 mL, 2.36 mmol), CuI (4.5 mg, 0.0236 mmol), $Pd(PPh_3)_2Cl_2$ (55.1 mg, 0.0785 mmol) and $PPh_3$ (10.3 mg, 0.0393 mmol) in THF (7.5 mL) was heated to 40° C. for 8 h under Ar. To the suspension was added (trimethylsilyl)acetylene (0.111 mL, 0.785 mmol). The suspension was heated to 40° C. for 14 h under Ar. To the suspension was added (trimethylsilyl)acetylene (0.0888 mL, 0.628 mmol). The suspension was heated to 40° C. for 96 h under Ar. The mixture was diluted with brine, extracted with EtOAc, dried over $MgSO_4$, filtered, concentrated in vacuo and purified by column chromatography on silica gel (hexane/EtOAc=50/50 to 0/100) to yield the title compound (148 mg, 28% yield) as a brown solid: $^1$H NMR (DMSO-$d_6$, 300 MHz): δ ppm 0.26 (9H, s), 6.64 (1H, d, J=7.9 Hz), 7.75-7.92 (2H, m), 8.00-8.15 (2H, m), 8.90 (1H, d, J=8.3 Hz).

Reference Example 115

3-Ethynyl-1-[3-(trifluoromethyl)phenyl]pyridazin-4(1H)-one

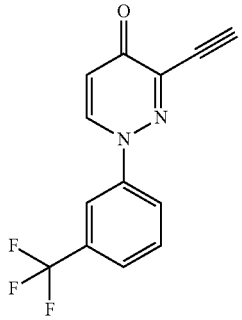 [SMILES: C#Cc1nn(-c2cccc(C(F)(F)F)c2)ccc1=O]

A mixture of 1-[3-(trifluoromethyl)phenyl]-3-[(trimethylsilyl)ethynyl]pyridazin-4(1H)-one (148 mg, 0.439 mmol) in MeOH (3 mL) and 1 M NaOH aqueous solution (5 mL) was stirred at 0° C. for 5 min and at room temperature for 2 h. The mixture was neutralized with 1 M HCl aqueous solution at 0° C. The mixture was extracted with EtOAc, washed with brine, dried over Na$_2$SO$_4$, filtered, concentrated in vacuo and purified by column chromatography on silica gel (hexane/EtOAc=50/50 to 0/100) to yield the title compound (69 mg, 59% yield) as a pale red solid: $^1$H NMR (DMSO-$d_6$, 300 MHz): δ ppm 4.70 (1H, s), 6.65 (1H, d, J=7.9 Hz), 7.76-7.92 (2H, m), 7.99-8.17 (2H, m), 8.93 (1H, d, J=7.9 Hz).

Reference Example 116

3-(Hydroxymethyl)-1-[3-(trifluoromethyl)phenyl]pyridazin-4(1H)-one

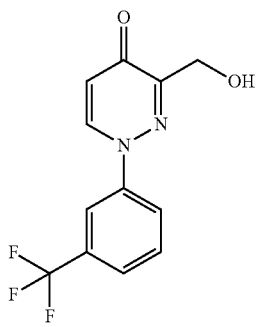 [SMILES: O=c1ccn(-c2cccc(C(F)(F)F)c2)nc1CO]

To a solution of methyl 4-oxo-1-[3-(trifluoromethyl)phenyl]-1,4-dihydropyridazine-3-carboxylate (2.00 g, 6.70 mmol) in THF (134 mL) was added DIBAL (1.5 M in toluene, 13.4 mL, 20.1 mmol) at −78° C. The solution was stirred at −78° C. for 1 h, gradually warmed to room temperature, stirred at room temperature for 18 h, diluted with 1 M HCl aqueous solution at 0° C., extracted with EtOAc, washed with brine, dried over MgSO$_4$, filtered, concentrated in vacuo and purified by column chromatography on silica gel (hexane/EtOAc=50/50 to 0/100 and EtOAc/MeOH=100/0 to 70/30) to yield the title compound (509 mg, 28% yield) as a pale yellow solid: $^1$H NMR (DMSO-$d_6$, 300 MHz): δ ppm 4.53 (2H, d, J=6.0 Hz), 5.11-5.16 (1H, m), 6.48 (1H, d, J=8.0 Hz), 7.76-7.84 (2H, m), 8.08-8.16 (1H, m), 8.19 (1H, s), 8.94 (1H, d, J=8.0 Hz).

Reference Example 117

4-Oxo-1-[3-(trifluoromethyl)phenyl]-1,4-dihydropyridazine-3-carbaldehyde

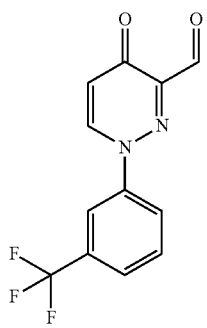 [SMILES: O=Cc1nn(-c2cccc(C(F)(F)F)c2)ccc1=O]

To a solution of oxalyl chloride (0.175 mL, 2.07 mmol) in THF (7.5 mL) was added DMSO (0.294 mL, 4.14 mmol) at −78° C. To the suspension was added a solution of 3-(hydroxymethyl)-1-[3-(trifluoromethyl)phenyl]pyridazin-4(1H)-one (509 mg, 1.88 mmol) in THF (7.5 mL) at −78° C. The suspension was stirred at −78° C. for 1 h. To the mixture was added Et$_3$N (1.05 mL, 7.52 mmol) at −78° C. The mixture was gradually warmed to room temperature, stirred at room temperature for 18 h, diluted with 1 M HCl aqueous solution, extracted with EtOAc, washed with saturated NaHCO$_3$ aqueous solution and brine, dried over Na$_2$SO$_4$, filtered, concentrated in vacuo and purified by column chromatography on silica gel (hexane/EtOAc=50/50 to 0/100 and EtOAc/MeOH=100/0 to 70/30). To a solution of oxalyl chloride (0.477 mL, 5.64 mmol) in THF (19 mL) was added DMSO (0.801 mL, 11.3 mmol) at −78° C. To the suspension was added a mixture of the above residue in THF (9.5 mL) at −78° C. The suspension was stirred at −78° C. for 2 h. To the mixture was added Et$_3$N (3.14 mL, 22.6 mmol) at −78° C. The mixture was gradually warmed to room temperature, stirred at room temperature for 17 h, diluted with 1 M HCl aqueous solution, extracted with EtOAc, washed with saturated NaHCO$_3$ aqueous solution and brine, dried over Na$_2$SO$_4$, filtered, concentrated in vacuo and purified by column chromatography on silica gel (hexane/EtOAc=50/50 to 0/100) to yield the title compound (257 mg, 51% yield) as a yellow solid: $^1$H NMR (DMSO-$d_6$, 300 MHz): δ ppm 6.87 (1H, d, J=8.2 Hz), 7.81-7.91 (2H, m), 8.08-8.15 (1H, m), 8.16 (1H, s), 8.98 (1H, d, J=8.0 Hz), 10.07 (1H, s).

Reference Example 118

5-Methoxy-4-oxo-1-[3-(trifluoromethyl)phenyl]-1,4-dihydropyridazine-3-carboxylic acid

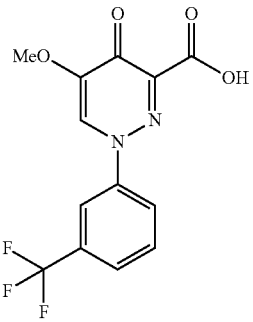 [SMILES: COc1cn(-c2cccc(C(F)(F)F)c2)nc(C(=O)O)c1=O]

To a suspension of methyl 5-methoxy-4-oxo-1-[3-(trifluoromethyl)phenyl]-1,4-dihydropyridazine-3-carboxylate (10.0 g, 30.5 mmol) in MeOH (100 mL) was added 1 M NaOH aqueous solution (61 mL) at 0° C. The mixture was stirred at room temperature for 30 min. To the solution was added 1 M HCl aqueous solution (61 mL) at 0° C. The mixture was concentrated in vacuo. The precipitates were collected by filtration, washed with water and dried in vacuo at 60° C. to yield the title compound (8.78 g, 92% yield) as a pale yellow solid: $^1$H NMR (DMSO-$d_6$, 300 MHz): δ ppm 3.98 (3H, s), 7.82-8.01 (2H, m), 8.11-8.34 (2H, m), 8.97 (1H, s), 15.00 (1H, brs).

Reference Example 119

3-Amino-5-methoxy-1-[3-(trifluoromethyl)phenyl]pyridazin-4(1H)-one

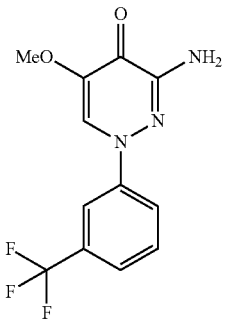 [SMILES: COc1cn(-c2cccc(C(F)(F)F)c2)nc(N)c1=O]

A mixture of 5-methoxy-4-oxo-1-[3-(trifluoromethyl)phenyl]-1,4-dihydropyridazine-3-carboxylic acid (6.00 g, 19.1 mmol), DPPA (6.16 mL, 28.6 mmol) and Et$_3$N (3.99 mL, 28.6 mmol) in toluene (60 mL) was heated to 100° C. for 2 h. To the mixture was added 8 M NaOH aqueous solution (23.8 mL) at 0° C. The mixture was stirred at room temperature for 3 h, extracted with EtOAc, dried over Na$_2$SO$_4$, filtered and concentrated in vacuo. The residue was washed with EtOAc/i-Pr$_2$O and filtered. The filtrate was concentrated in vacuo, purified by column chromatography on basic silica gel (hexane/EtOAc=50/50 to 0/100) and recrystallized with EtOAc/hexane to yield the title compound (3.57 g, 66% yield) as a pale yellow solid: $^1$H NMR (DMSO-$d_6$, 300 MHz): δ ppm 3.83 (3H, s), 6.31 (2H, s), 7.64-7.79 (2H, m), 8.13 (2H, s), 8.64 (1H, s).

Reference Example 120

(2-Phenylfuran-3-yl)boronic acid

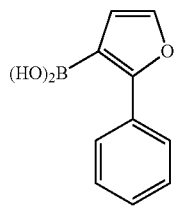

To a mixture of 3-bromo-2-phenylfuran (6.70 g, 30.0 mmol) and B(Oi-Pr)$_3$ (10.4 mL, 45.0 mmol) in THF (67 mL) was added n-BuLi (1.65 M in hexane, 36.4 mL, 60 mmol) at −78° C. The mixture was stirred at −78° C. for 30 min and at 0° C. for 30 min. The mixture was diluted with 1 M HCl aqueous solution at 0° C., extracted with EtOAc, washed with brine, dried over Na$_2$SO$_4$, filtered, concentrated in vacuo and triturated with EtOAc/hexane to yield the title compound (2.23 g, 40% yield) as a green solid: $^1$H NMR (DMSO-$d_6$, 300 MHz): δ ppm 6.64 (1H, d, J=1.4 Hz), 7.21-7.45 (3H, m), 7.69 (1H, d, J=1.6 Hz), 8.00-8.08 (2H, m).

Reference Example 121

(2-Phenylthiophen-3-yl)boronic acid

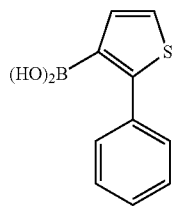 [SMILES: OB(O)c1ccoc1-c1ccccc1]

To a mixture of 3-bromo-2-phenylthiophene (1.99 g, 8.32 mmol) and B(Oi-Pr)$_3$ (1.81 mL, 12.5 mmol) in TI-IF (20 mL) was added n-BuLi (1.65 M in hexane, 10.1 mL, 16.6 mmol) at −78° C. The mixture was stirred at −78° C. for 30 min and at 0° C. for 30 min. The mixture was diluted with 1 M HCl aqueous solution at 0° C., extracted with EtOAc, washed with brine, dried over Na$_2$SO$_4$, filtered, concentrated in vacuo and purified by column chromatography on silica gel (hexane/EtOAc=90/10 to 0/100) to yield the title compound (87.4 mg, 5% yield) as a white solid: $^1$H NMR (DMSO-$d_6$, 300 MHz): δ ppm 7.19 (1H, d, J=4.9 Hz), 7.27-7.44 (3H, m), 7.46-7.58 (3H, m), 8.06 (2H, s).

Reference Example 122

Methyl 4-methoxy-3-oxo-2-(pyridin-4-ylhydrazono)butanoate

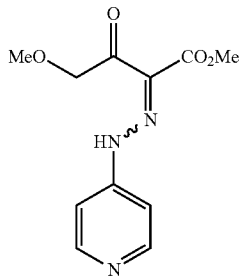 [SMILES: COCC(=O)C(=NNc1ccncc1)C(=O)OC]

4-Aminopyridine (3.6 g, 38 mmol) was added to a mixture of phosphoric acid (10 mL, 150 mmol) and nitric acid (5 mL, 78 mmol) at −6° C. Sodium nitrite (3.2 g, 46 mmol) was added portionwise to the mixture at −6° C., and then crushed ice (ca. 25 g) was added into the solution. After stirring at −6° C. for 10 min, the mixture was poured into a suspension of methyl 4-methoxyacetoacetate (5.0 mL, 38 mmol) and sodium acetate (44 g, 540 mmol) in MeOH (100 mL) at 0° C. The mixture was partitioned between AcOEt and water. The aqueous layer was extracted with AcOEt. The combined organic extract was washed with brine, dried over MgSO$_4$, filtered and concentrated under reduced pressure. The residual solid was washed with AcOEt/hexane (1/3) to give the title compound (1.8 g, 19% yield) as a yellow solid: $^1$H NMR (300 MHz, CDCl$_3$): δ ppm 3.48-3.53 (3H, m), 3.89-3.95 (3H, m), 4.64-4.69 (2H, m), 7.17-7.34 (2H, m), 8.54-8.60 (2H, m), 12.65 (1H, brs).

Reference Example 123

Methyl 5-methoxy-4-oxo-1-pyridin-4-yl-1,4-dihydropyridazine-3-carboxylate

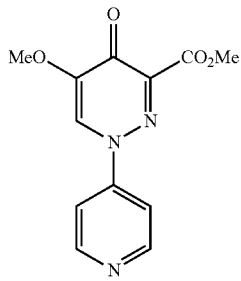 [SMILES: COC(=O)c1nn(-c2ccncc2)cc(OC)c1=O]

A mixture of methyl 4-methoxy-3-oxo-2-(pyridin-4-ylhydrazono)butanoate (18 g, 70 mmol) and N,N-dimethylformamide dimethyl acetal (28 mL, 210 mmol) in toluene (210 mL) was refluxed for 4 h. The mixture was concentrated under reduced pressure to give black crystals. The crystals were washed with 2-propanol/AcOEt (1:4) to give the title compound (8.2 g, 45% yield) as pale yellow crystals: $^1$H NMR (300 MHz, CDCl$_3$): δ ppm 3.99 (3H, s), 4.00 (3H, s), 7.62 (2H, dd, J=4.5, 1.5 Hz), 8.01 (1H, s), 8.79 (2H, dd, J=4.5, 1.5 Hz).

Reference Example 124

5-Methoxy-4-oxo-1-pyridin-4-yl-1,4-dihydropyridazine-3-carboxylic acid

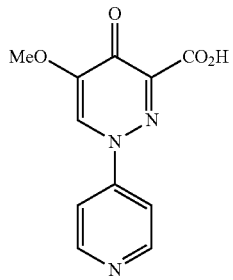 [SMILES: COc1cn(-c2ccncc2)nc(C(=O)O)c1=O]

To a solution of methyl 5-methoxy-4-oxo-1-pyridin-4-yl-1,4-dihydropyridazine-3-carboxylate (0.50 g, 1.9 mmol) in MeOH (10 mL) and THF (10 mL) was added 1 M NaOH aqueous solution (3.0 mL, 3.0 mmol), and the mixture was stirred at room temperature overnight. The mixture was concentrated under reduced pressure. To the residue was added 1 M HCl aqueous solution (3.1 mL). The formed precipitate was collected by filtration, washed with water and dried to give the title compound (0.47 g, 99% yield) as an off-white solid: $^1$H NMR (300 MHz, DMSO-d$_6$): δ ppm 3.98 (3H, s), 7.97 (2H, dd, J=4.7, 1.7 Hz), 8.83 (2H, dd, J=4.7, 1.7 Hz), 8.92 (1H, s), 14.63 (1H, brs).

Reference Example 125

N,5-Dimethoxy-N-methyl-4-oxo-1-pyridin-4-yl-1,4-dihydropyridazine-3-carboxamide

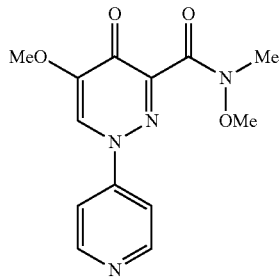 [SMILES: COc1cn(-c2ccncc2)nc(C(=O)N(C)OC)c1=O]

To a mixture of 5-methoxy-4-oxo-1-pyridin-4-yl-1,4-dihydropyridazine-3-carboxylic acid (8.2 g, 33 mmol), HOBt (7.6 g, 50 mmol) and WSC (9.5 g, 50 mmol) in DMF (160 mL) was added N,O-dimethylhydroxylamine hydrochloride (6.5 g, 66 mmol) and TEA (14 mL, 100 mmol), and the mixture was stirred at room temperature overweekend. The mixture was concentrated under reduced pressure. The residue was diluted with water, saturated with K$_2$CO$_3$, and extracted with AcOEt. (There were three layers.) The highest organic layer was dried over MgSO$_4$, filtered and concentrated under reduced pressure. The middle layer was extracted with CH$_2$Cl$_2$ (50 mL×4), and the combined extracts were dried over MgSO$_4$, filtered and concentrated under reduced pressure. Two of the residues were combined and chromatographed on basic silica gel (0/100-10/90 MeOH/AcOEt) to give the title compound (9.6 g, 100% yield) as a pale yellow oil: ¹H NMR (300 MHz, CDCl₃): δ ppm 3.40 (3H, s), 3.68 (3H, s), 3.98 (3H, s), 7.61 (2H, dd, J=4.8, 1.5 Hz), 8.08 (1H, s), 8.73 (2H, dd, J=4.8, 1.5 Hz).

Reference Example 126

3-Acetyl-5-methoxy-1-pyridin-4-ylpyridazin-4(1H)-one

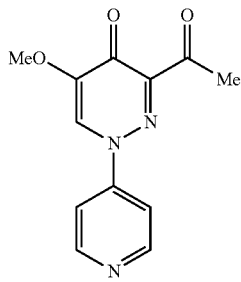 [SMILES: COc1cn(-c2ccncc2)nc(C(C)=O)c1=O]

To a solution of N,5-dimethoxy-N-methyl-4-oxo-1-pyridin-4-yl-1,4-dihydropyridazine-3-carboxamide (9.6 g, 33 mmol) in THF (100 mL) was added dropwise 1 M MeMgBr in THF (66 mL, 66 mmol) at −78° C. for 15 min. After stirring at −78° C. for 1 h, the mixture was quenched with 1 M HCl aqueous solution (70 mL). The mixture was warmed to room temperature, basified with 1 M NaOH aqueous solution, washed with AcOEt. The aqueous layer was extracted with CH₂Cl₂ (50 mL×4). The combined extract was dried over MgSO₄, filtered and concentrated under reduced pressure to give the title compound (2.1 g, 26% yield) as yellow crystals: ¹H NMR (300 MHz, CDCl₃): δ ppm 2.70 (3H, s), 3.98 (3H, s), 7.64 (2H, dd, J=4.7, 1.6 Hz), 8.04 (1H, s), 8.79 (2H, dd, J=4.7, 1.6 Hz).

Reference Example 127

Methyl 5-methoxy-4-oxo-1-quinolin-8-yl-1,4-dihydropyridazine-3-carboxylate

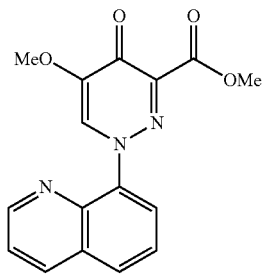 [SMILES: COC(=O)c1nn(-c2cccc3cccnc23)cc(OC)c1=O]

To a suspension of quinolin-8-amine (10.0 g, 69.4 mmol) in 6 M HCl aqueous solution (69.4 mL) was added a solution of NaNO₂ (5.74 g, 83.2 mmol) in water (13.9 mL) at 0° C. To a suspension of methyl 4-methoxy-3-oxobutanoate (8.98 mL, 69.4 mmol) and NaOAc (104 g) in EtOH (118 mL) was added the above solution at 0° C. The mixture was stirred at 0° C. for 10 min. The precipitates were collected by filtration, washed with water and EtOAc, and dried. To the solid was added N,N-dimethylformamide dimethyl acetal (255 mL) at room temperature. The mixture was heated to reflux for 2.5 h and cooled to room temperature. The precipitates were collected by filtration, washed with hexane and dried to yield the title compound (16.6 g, 77% yield) as a gray solid: ¹H NMR (DMSO-d₆, 300 MHz): δ ppm 3.77 (3H, s), 3.80 (3H, s), 7.72 (1H, dd, J=8.5, 4.0 Hz), 7.81 (1H, t, J=7.9 Hz), 8.09 (1H, d, J=7.2 Hz), 8.25 (1H, d, J=8.3 Hz), 8.58 (1H, s), 8.65 (1H, s), 8.97-9.04 (1H, m).

Reference Example 128

5-Methoxy-4-oxo-1-quinolin-8-yl-1,4-dihydropyridazine-3-carboxylic acid

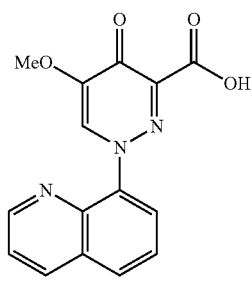 [SMILES: COc1cn(-c2cccc3cccnc23)nc(C(=O)O)c1=O]

To a suspension of methyl 5-methoxy-4-oxo-1-quinolin-8-yl-1,4-dihydropyridazine-3-carboxylate (5.00 g, 16.1 mmol) in MeOH (64 mL) were added 1 M NaOH aqueous solution (64 mL) and THF (64 mL) at 0° C. The mixture was heated to 80° C. The homogeneous mixture was cooled to 0° C. To the mixture was added 1 M HCl aqueous solution (64 mL) at 0° C. The mixture was stirred at room temperature for 1 h and concentrated in vacuo. The precipitates were collected by filtration, washed with water and dried in vacuo at 60° C. to yield the title compound (3.59 g, 75% yield) as a fresh-colored solid: ¹H NMR (DMSO-d₆, 300 MHz): δ ppm 3.86 (3H, s), 7.73 (1H, dd, J=8.4, 4.3 Hz), 7.81-7.89 (1H, m), 8.12 (1H, dd, J=7.4, 1.4 Hz), 8.30 (1H, dd, J=8.4, 1.2 Hz), 8.61 (1H, dd, J=8.5, 1.6 Hz), 8.96-9.05 (2H, m).

Reference Example 129

3-Amino-5-methoxy-1-quinolin-8-ylpyridazin-4(1H)-one

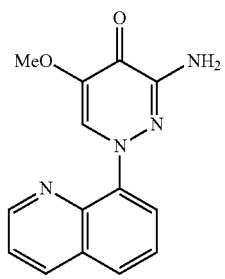 [SMILES: COc1cn(-c2cccc3cccnc23)nc(N)c1=O]

A mixture of 5-methoxy-4-oxo-1-quinolin-8-yl-1,4-dihydropyridazine-3-carboxylic acid (2.59 g, 8.71 mmol), DPPA (2.81 mL, 13.1 mmol) and Et₃N (1.82 mL, 13.1 mmol) in toluene (26 mL) was heated to reflux for 1 h. To the suspension were added DMF (52 mL), DPPA (2.81 mL, 13.1 mmol) and Et₃N (1.82 mL, 13.1 mmol) at room temperature. The mixture was heated to 100° C. for 1.5 h. To the mixture was added 8 M NaOH aqueous solution (10.9 mL) at 0° C. The mixture was stirred at room temperature for 1.5 h, extracted with EtOAc, dried over Na$_2$SO$_4$, filtered, concentrated in vacuo, purified by column chromatography on basic silica gel (hexane/EtOAc=50/50 to 0/100 and EtOAc/MeOH=100/0 to 80/20) and on silica gel (EtOAc/MeOH=100/0 to 50/50) and triturated with EtOAc/hexane to yield the title compound (479 mg, 20% yield) as a pale yellow solid: $^1$H NMR (DMSO-d$_6$, 300 MHz): δ ppm 3.75 (3H, s), 6.11 (2H, s), 7.67 (1H, dd, J=8.5, 4.4 Hz), 7.72-7.80 (1H, m), 7.99 (1H, dd, J=7.6, 1.5 Hz), 8.12 (1H, dd, J=8.3, 1.1 Hz), 8.48-8.61 (2H, m), 8.99 (1H, dd, J=4.4, 1.7 Hz).

Reference Example 130

3-Bromo-5-methoxy-1-quinolin-8-ylpyridazin-4 (1H)-one

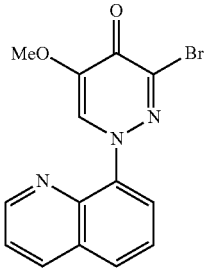 [SMILES: COc1cn(-c2cccc3cccnc23)nc(Br)c1=O]

To DMF (3 mL) were added isoamyl nitrite (0.387 mL, 2.91 mmol) and CuBr$_2$ (299 mg, 1.34 mmol) at 0° C. To the mixture was added a solution of 3-amino-5-methoxy-1-quinolin-8-ylpyridazin-4(1H)-one (300 mg, 1.12 mmol) in DMF (3 mL) at 0° C. The mixture was stirred at 0° C. for 1 h and at 60° C. for 2.5 h. The mixture was diluted with water, extracted with EtOAc, washed with brine, dried over MgSO$_4$, filtered, concentrated in vacuo, purified by column chromatography on basic silica gel (hexane/EtOAc=50/50 to 0/100 and EtOAc/MeOH=100/0 to 70/30) and triturated with EtOAc/hexane to yield the title compound (148 mg, 41% yield) as a pale yellow solid: $^1$H NMR (DMSO-d$_6$, 300 MHz): δ ppm 3.78 (3H, s), 7.72 (1H, dd, J=8.3, 4.2 Hz), 7.82 (1H, t, J=8.0 Hz), 8.10 (1H, d, J=7.2 Hz), 8.25 (1H, d, J=8.3 Hz), 8.59 (1H, dd, J=8.3, 1.5 Hz), 8.73 (1H, s), 9.01 (1H, dd, J=4.2, 1.5 Hz).

Reference Example 131

(1-Phenyl-1H-pyrazol-5-yl)boronic acid

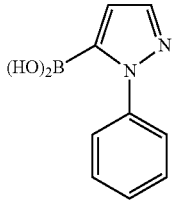

To a solution of 1-phenyl-1H-pyrazole (12.8 g, 88.9 mmol) in THF (355 mL) was dropwise added n-BuLi (1.63 M solution in hexane, 57.2 mL, 93.3 mmol) at −78° C. under N$_2$. The mixture was stirred at −78° C. for 1 h. To the mixture was added B(Oi-Pr)$_3$ (82.0 mL, 355 mmol) at −78° C. The mixture was stirred at −78° C. for 1 h, gradually warmed to room temperature and stirred at room temperature overnight. The pH of the mixture was adjusted to 5 with 1 M HCl aqueous solution. The mixture was concentrated in vacuo, extracted with EtOAc, washed with brine, dried over Na$_2$SO$_4$, filtered, concentrated in vacuo and crystallized with MeOH/EtOAc/hexane to yield the title compound (12.6 g, 76% yield) as a pale yellow solid: $^1$H NMR (DMSO-d$_6$, 300 MHz): δ ppm 6.73 (1H, brs), 7.28-7.39 (1H, m), 7.39-7.54 (4H, m), 7.66 (1H, s).

Reference Example 132

1-Phenyl-5-(4,4,5,5-tetramethyl-1,3,2-dioxaborolan-2-yl)-1H-pyrazole

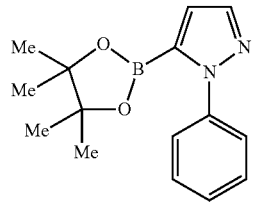 [SMILES: CC1(C)OB(c2ccnn2-c2ccccc2)OC1(C)C]

To a mixture of (1-phenyl-1H-pyrazol-5-yl)boronic acid (8.57 g, 45.6 mmol) in toluene (86 mL) was added pinacol (5.39 g, 45.6 mmol) at room temperature. The mixture was heated to 40° C. for 2 days. The mixture was concentrated in vacuo and triturated with hexane to yield the title compound (7.93 g, 64% yield) as a pale yellow solid: $^1$H NMR (DMSO-d$_6$, 300 MHz): δ ppm 1.23 (12H, s), 6.84 (1H, s), 7.34-7.59 (5H, m), 7.75 (1H, d, J=1.9 Hz)

Reference Example 133

Methyl 1-(2,2-difluoro-1,3-benzodioxol-4-yl)-5-methoxy-4-oxo-1,4-dihydropyridazine-3-carboxylate

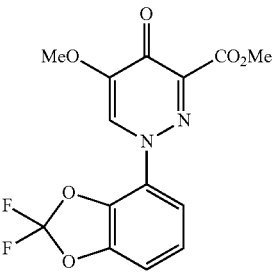 [SMILES: COC(=O)c1nn(-c2cccc3c2OC(F)(F)O3)cc(OC)c1=O]

A solution of sodium nitrite (1.4 g, 21 mmol) in H$_2$O (10 mL) was added dropwise to a solution of 2,2-difluoro-1,3-benzodioxol-4-amine (3.0 g, 17 mmol) in 6 M HCl aqueous solution (18 mL, 108 mmol) at 0° C. After stirring for 15 min at 0° C., the mixture was added to a suspension of methyl 4-methoxyacetoacetate (2.2 mL, 17 mmol) and sodium acetate (9.0 g, 110 mmol) in MeOH (40 mL) pre-cooled at 0° C. The mixture was partitioned between AcOEt and water. The organic layer was washed with brine, dried over MgSO$_4$, filtered and concentrated under reduced pressure.

A solution of the residue in N,N-dimethylformamide dimethyl acetal (20 mL, 150 mmol) was refluxed for 3 h. The mixture was concentrated under reduced pressure. The residual solid was washed with AcOEt/hexane (1/3) to give the title compound (4.1 g, 71% yield) as an orange solid: ¹H NMR (300 MHz, CDCl₃): δ ppm 3.96 (3H, s), 3.99 (3H, s), 7.15 (1H, dd, J=8.0, 1.1 Hz), 7.23-7.30 (1H, m), 7.56 (1H, dd, J=8.5, 1.1 Hz), 8.01 (1H, s).

Reference Example 134

1-(2,2-Difluoro-1,3-benzodioxol-4-yl)-5-methoxy-4-oxo-1,4-dihydropyridazine-3-carboxylic acid

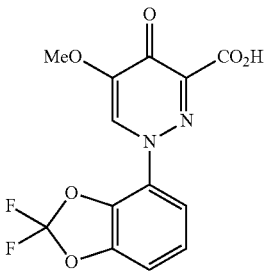 [SMILES: COc1cn(-c2cccc3c2OC(F)(F)O3)nc(C(=O)O)c1=O]

To a solution of methyl 1-(2,2-difluoro-1,3-benzodioxol-4-yl)-5-methoxy-4-oxo-1,4-dihydropyridazine-3-carboxylate (4.1 g, 12 mmol) in THF (100 mL) and MeOH (50 mL) was added 1 M NaOH aqueous solution (18 mL, 18 mmol), and the mixture was stirred at room temperature for 1 h. The mixture was concentrated under reduced pressure, and acidified with 1 M HCl aqueous solution. The mixture was diluted with AcOEt, washed with water and brine, dried over MgSO₄, filtered and concentrated under reduced pressure to give the title compound (3.8 g, 97% yield) as a yellow amorphous solid: ¹H NMR (300 MHz, CDCl₃): δ ppm 4.06 (3H, s), 7.22-7.26 (1H, m), 7.34 (1H, t, J=8.3 Hz), 7.72 (1H, dd, J=8.3, 1.1 Hz), 8.29 (1H, s).

Reference Example 135

1-(2,2-Difluoro-1,3-benzodioxol-4-yl)-N,5-dimethoxy-N-methyl-4-oxo-1,4-dihydropyridazine-3-carboxamide

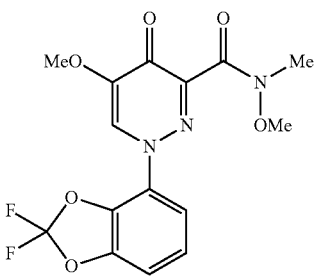 [SMILES: COc1cn(-c2cccc3c2OC(F)(F)O3)nc(C(=O)N(C)OC)c1=O]

To a mixture of 1-(2,2-difluoro-1,3-benzodioxol-4-yl)-5-methoxy-4-oxo-1,4-dihydropyridazine-3-carboxylic acid (3.8 g, 12 mmol), HOBt (2.7 g, 17 mmol) and WSC (3.4 g, 17 mmol) in DMF (50 mL) was added N,O-dimethylhydroxylamine hydrochloride (2.3 g, 23 mmol) and Et₃N (4.9 mL, 35 mmol), and the mixture was stirred at room temperature overnight. The mixture was diluted with water (200 mL) and extracted with AcOEt (250 mL×2). The combined organic layer was washed with saturated NaHCO₃ aqueous solution and brine, dried over MgSO₄, filtered and concentrated under reduced pressure to give orange crystals. The crystals were washed with AcOEt/hexane (1/4) to give the title compound (2.7 g, 62% yield) as pale yellow crystals: ¹H NMR (300 MHz, CDCl₃): δ ppm 3.41 (3H, s), 3.71 (3H, s), 3.96 (3H, s), 7.12 (1H, dd, J=7.9, 1.1 Hz), 7.23 (1H, d, J=8.7 Hz), 7.57 (1H, dd, J=8.7, 1.1 Hz), 8.06 (1H, s).

Reference Example 136

3-Acetyl-1-(2,2-difluoro-1,3-benzodioxol-4-yl)-5-methoxypyridazin-4(1H)-one

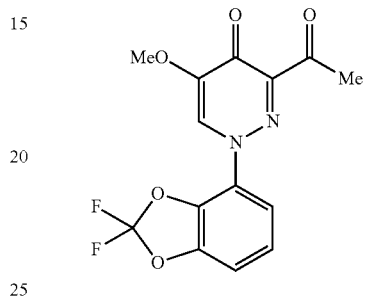

To a solution of 1-(2,2-difluoro-1,3-benzodioxol-4-yl)-N,5-dimethoxy-N-methyl-4-oxo-1,4-dihydropyridazine-3-carboxamide (2.7 g, 7.2 mmol) in THF (70 mL) was added dropwise 1 M MeMgBr in THF (14 mL, 14 mmol) at −78° C. for 15 min. After stirring at −78° C. for 1 h, the mixture was quenched with 1 M HCl aqueous solution (30 mL). The mixture was warmed to room temperature and extracted with AcOEt. The organic layer was washed with brine, dried over MgSO₄, filtered and concentrated under reduced pressure to give the title compound (2.3 g, 99% yield) as yellow crystals: ¹H NMR (300 MHz, CDCl₃): δ ppm 2.69 (3H, s), 3.95 (3H, s), 7.17 (1H, dd, J=7.9, 1.1 Hz), 7.26-7.32 (1H, m), 7.55 (1H, dd, J=8.7, 1.1 Hz), 8.00 (1H, s).

Reference Example 137

1-(2,2-Difluoro-1,3-benzodioxol-4-yl)-3-[3-(dimethylamino)prop-2-enoyl]-5-methoxypyridazin-4(1H)-one

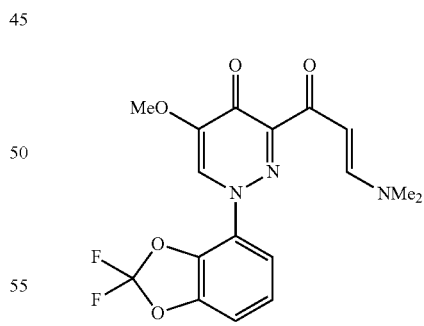

A solution of 3-acetyl-1-(2,2-difluoro-1,3-benzodioxol-4-yl)-5-methoxypyridazin-4(1H)-one (2.3 g, 7.1 mmol) in N,N-dimethylformamide dimethyl acetal (75 mL) was refluxed for 3 h. The mixture was concentrated under reduced pressure. The brown crystals were washed with AcOEt/hexane (1/1) to give the title compound (2.0 g, 74% yield) as yellow crystals: ¹H NMR (300 MHz, CDCl₃): δ ppm 2.91 (3H, s), 3.14 (3H, s), 3.94 (3H, s), 5.78 (1H, d, J=11.7 Hz), 7.10 (1H, dd, J=8.3, 1.1 Hz), 7.23 (1H, t, J=8.3 Hz), 7.63 (1H, d, J=8.7 Hz), 7.79 (1H, brs), 8.03 (1H, s).

Reference Example 138

4-(Benzyloxy)-2-fluoroaniline

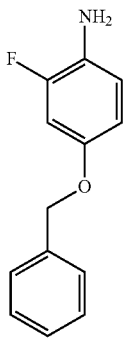

A suspension of 3-fluoro-4-nitrophenol (6.28 g, 40 mmol), benzyl bromide (5.00 mL, 42 mmol), and $K_2CO_3$ (6.63 g, 48 mmol) in acetone (80 mL) was refluxed for 2 h. After cooling to room temperature, the reaction mixture was poured into water and extracted with AcOEt. The extract was washed with brine, dried over $MgSO_4$, and concentrated under reduced pressure. The residue was recrystallized from hexane/AcOEt to give 4-(benzyloxy)-2-fluoro-1-nitrobenzene (16.0 g, 92% yield) as a pale yellow solid.

A solution of $Na_2S_2O_4$ (34.8 g, 200 mmol) in $H_2O$ (200 mL) was added to a mixture of 4-(benzyloxy)-2-fluoro-1-nitrobenzene (16.0 g, 64.7 mmol), THF (150 mL), and EtOH (150 mL), and the mixture was stirred for 30 min at room temperature. The reaction mixture was poured into water and extracted with AcOEt. The extract was washed with water and brine, dried over $MgSO_4$, and concentrated under reduced pressure. The residue was purified by basic silica gel column chromatography eluting with hexane/AcOEt (1/1) to give the title compound (5.84 g, 42% yield) as a light brown oil: $^1$H NMR (300 MHz, $CDCl_3$): δ ppm 3.42 (2H, brs), 4.97 (2H, s), 6.60 (1H, ddd, J=1.1, 2.6, 8.7 Hz), 6.67-6.74 (2H, m), 7.28-7.43 (5H, m).

Reference Example 139

Methyl 2-{[4-(benzyloxy)-2-fluorophenyl]hydrazono}-4-methoxy-3-oxobutanoate

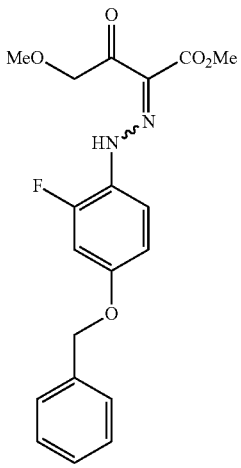 [SMILES: COCC(=O)C(=NNc1ccc(OCc2ccccc2)cc1F)C(=O)OC]

A solution of $NaNO_2$ (2.07 g, 30 mmol) in $H_2O$ (5 mL) was added dropwise at 0° C. to a mixture of 4-(benzyloxy)-2-fluoroaniline (5.43 g, 25 mmol) and 6 M HCl aqueous solution (25 mL, 150 mmol). After stirring for 15 min, the resulting aqueous solution was added to a suspension of methyl 4-methoxyacetoacetate (3.24 mL, 24 mmol) and NaOAc (12.3 g, 150 mmol) in MeOH (50 mL) pre-cooled at 0° C. The reaction mixture was poured into water and extracted with AcOEt. The extract was washed with brine, dried over $MgSO_4$, and concentrated under reduced pressure. The residue was recrystallized from hexane/AcOEt to give the title compound (8.48 g, 91% yield) as a yellow solid: $^1$H NMR (300 MHz, $CDCl_3$): δ ppm 3.500 (3H×0.46, s), 3.502 (3H×0.54, s), 3.88 (3H×0.54, s), 3.92 (3H×0.46, s), 4.65 (2H×0.46, s), 4.68 (2H×0.54, s), 5.06 (2H×0.54, s), 5.07 (2H×0.46, s), 6.75-6.86 (2H, m), 7.32-7.44 (5H, m), 7.53 (1H×0.46, t, J=9.0 Hz), 7.76 (1H×0.54, t, J=9.0 Hz), 13.12 (1H×0.46, brs), 15.13 (1H×0.54, brs).

Reference Example 140

Methyl 1-[4-(benzyloxy)-2-fluorophenyl]-5-methoxy-4-oxo-1,4-dihydropyridazine-3-carboxylate

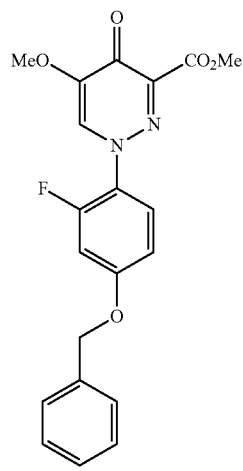 [SMILES: COC(=O)c1nn(-c2ccc(OCc3ccccc3)cc2F)cc(OC)c1=O]

A solution of methyl 2-{[4-(benzyloxy)-2-fluorophenyl]hydrazono}-4-methoxy-3-oxobutanoate (8.46 g, 22.6 mmol) in N,N-dimethylformamide dimethyl acetal (80 mL) was refluxed for 3 h. After cooling to room temperature, the reaction mixture was concentrated under reduced pressure. The residue was diluted with AcOEt, washed with water and brine, dried over $MgSO_4$, and concentrated under reduced pressure. The residue was purified by silica gel column chromatography eluting with THF and recrystallized from hexane/THF to give the title compound (8.12 g, 93% yield) as a white solid: mp 143-144° C.; $^1$H NMR (300 MHz, $CDCl_3$): δ ppm 3.89 (3H, s), 3.96 (3H, s), 5.12 (2H, s), 6.83-6.91 (2H, m), 7.33-7.44 (5H, m), 7.48-7.54 (1H, m), 7.69 (1H, d, J=2.3 Hz). Anal. Calcd for $C_{20}H_{17}FN_2O_5$: C, 62.50; H, 4.46; N, 7.29. Found: C, 62.40; H, 4.59; N, 7.26.

Reference Example 141

1-[4-(Benzyloxy)-2-fluorophenyl]-N,5-dimethoxy-N-methyl-4-oxo-1,4-dihydropyridazine-3-carboxamide

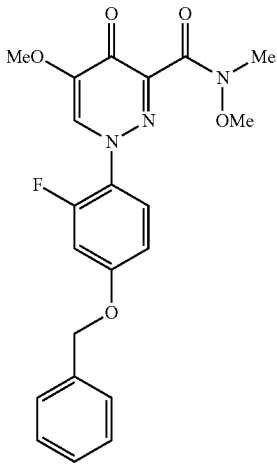 [SMILES: COc1cn(-c2ccc(OCc3ccccc3)cc2F)nc(C(=O)N(C)OC)c1=O]

To a solution of N,O-dimethylhydroxylamine hydrochloride (5.27 g, 54 mmol) and iPr$_2$NEt (9.41 mL, 54 mmol) in CH$_2$Cl$_2$ (50 mL) was added AlMe$_3$ (1.8 M solution in toluene, 30 mL, 54 mmol) slowly at 0° C. under Ar atmosphere. After stirring for 1 h, a solution of methyl 1-[4-(benzyloxy)-2-fluorophenyl]-5-methoxy-4-oxo-1,4-dihydropyridazine-3-carboxylate (8.07 g, 21 mmol) in CH$_2$Cl$_2$ (50 mL) was added slowly, and the mixture was stirred for 1 h at 0° C. The reaction mixture was poured into ice-water and extracted with AcOEt. The extract was washed with brine, dried over MgSO$_4$, and concentrated under reduced pressure. The residue was purified by basic silica gel column chromatography eluting with AcOEt to give the title compound (7.79 g, 90% yield) as a pale yellow amorphous solid: $^1$H NMR (300 MHz, CDCl$_3$): δ ppm 3.38 (3H, s), 3.70 (3H, s), 3.89 (3H, s), 5.11 (2H, s), 6.82-6.91 (2H, m), 7.33-7.45 (5H, m), 7.48-7.55 (1H, m), 7.73 (1H, d, J=1.9 Hz).

Reference Example 142

3-Acetyl-1-[4-(benzyloxy)-2-fluorophenyl]-5-methoxypyridazin-4(1H)-one

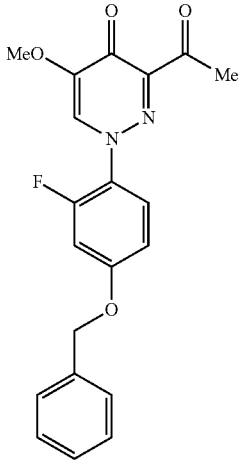 [SMILES: COc1cn(-c2ccc(OCc3ccccc3)cc2F)nc(C(C)=O)c1=O]

MeMgBr (1 M solution in THF, 56.4 mL, 56.4 mmol) was added dropwise at −78° C. to a solution of 1-[4-(benzyloxy)-2-fluorophenyl]-N,5-dimethoxy-N-methyl-4-oxo-1,4-dihydropyridazine-3-carboxamide (7.77 g, 18.8 mmol) in THF (120 mL). After stirring for 1 h, the reaction mixture was quenched with 1 M HCl aqueous solution and extracted with AcOEt. The extract was washed with brine, dried over MgSO$_4$, and concentrated under reduced pressure. The residue was purified by silica gel column chromatography eluting with AcOEt and crystallized from hexane/AcOEt to give the title compound (5.86 g, 85% yield) as a pale yellow solid: mp 101-103° C.; $^1$H NMR (300 MHz, CDCl$_3$): δ ppm 2.67 (3H, s), 3.89 (3H, s), 5.13 (2H, s), 6.84-6.93 (2H, m), 7.34-7.44 (5H, m), 7.48-7.55 (1H, m), 7.69 (1H, d, J=2.3 Hz). Anal. Calcd for C$_{20}$H$_{17}$FN$_2$O$_4$: C, 65.21; H, 4.65; N, 7.60. Found: C, 65.37; H, 4.68; N, 7.47.

Reference Example 143

2-Fluoro-4-(trifluoromethoxy)aniline

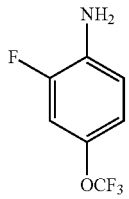

A mixture of 4-bromo-3-fluoro(trifluoromethoxy)benzene (6.6 g, 26 mmol), benzophenone imine (6.4 mL, 38 mmol), Pd$_2$(dba)$_3$ (0.58 g, 0.64 mmol), Xantphos (1.5 g, 2.6 mmol) and sodium tert-butoxide (3.7 g, 38 mmol) in 1,4-dioxane (120 mL) was stirred at 100° C. under N$_2$ atmosphere for 5 h. After stirring at room temperature overnight, the mixture was concentrated under reduced pressure. The residue was partitioned between AcOEt and water. The organic layer was washed with brine, dried over MgSO$_4$, filtered and concentrated under reduced pressure. The residue was chromatographed on silica gel (0/100-5/95 AcOEt/hexane) to give a yellow oil. The residual oil was dissolved in THF (150 mL), and 1 M HCl aqueous solution (50 mL) was added to the mixture. After stirring at room temperature for 1 h, the mixture was basified with 8 M NaOH aqueous solution and extracted with diethyl ether. The organic layer was washed with brine, dried over MgSO$_4$, filtered and concentrated under reduced pressure. The residue was chromatographed on silica gel (0/100-5/95 AcOEt/hexane) to give the title compound (4.2 g, 85% yield) as a pale yellow oil: $^1$H NMR (300 MHz, DMSO-d$_6$): δ ppm 5.36 (2H, s), 6.75-6.85 (1H, m), 6.89-6.94 (1H, m), 7.12 (1H, dd, J=11.7, 2.3 Hz).

Reference Example 144

Methyl 2-{[2-fluoro-4-(trifluoromethoxy)phenyl]hydrazono}-4-methoxy-3-oxobutanoate

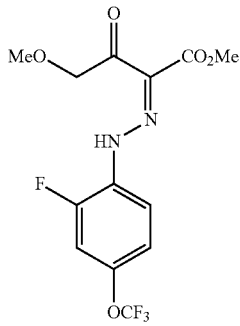 [SMILES: COCC(=O)/C(=N\Nc1ccc(OC(F)(F)F)cc1F)C(=O)OC]

A solution of sodium nitrite (1.9 g, 28 mmol) in H$_2$O (10 mL) was added dropwise to a solution of 2-fluoro-4-(trifluoromethoxy)aniline (4.6 g, 24 mmol) in 6 M HCl (24 mL, 144 mmol) at 0° C. After stirring for 15 min at 0° C.; the mixture was added to a suspension of methyl 4-methoxyacetoacetate (3.1 mL, 24 mmol) and sodium acetate (12 g, 144 mmol) in MeOH (50 mL) pre-cooled at 0° C. The formed precipitate was collected by filtration, washed with water and dried under reduced pressure to give the title compound (4.8 g, 58% yield) as yellow crystals: $^1$H NMR (300 MHz, CDCl$_3$): δ ppm 3.51 (3H, s), 3.94 (3H, s), 4.65 (2H, s), 7.06-7.14 (2H, m), 7.59-7.68 (1H, m), 12.98 (1H, brs).

Reference Example 145

Methyl 1-[2-fluoro-4-(trifluoromethoxy)phenyl]-5-methoxy-4-oxo-1,4-dihydropyridazine-3-carboxylate

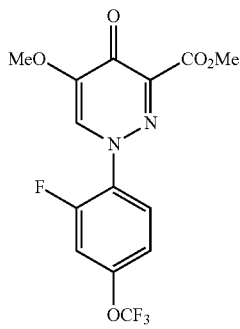 [SMILES: COC(=O)c1nn(-c2ccc(OC(F)(F)F)cc2F)cc(OC)c1=O]

A solution of methyl 2-{[2-fluoro-4-(trifluoromethoxy)phenyl]hydrazono}-4-methoxy-3-oxobutanoate (3.8 g, 11 mmol) and N,N-dimethylformamide diisopropyl acetal (9.5 mL, 54 mmol) in toluene (60 mL) was refluxed for 5 h. The mixture was concentrated under reduced pressure. The residue was diluted with AcOEt, washed with water and brine. The organic layer was dried over MgSO$_4$, filtered and concentrated under reduced pressure. The residue was chromatographed on silica gel (10/90-100/0 AcOEt/hexane) to give the title compound (3.4 g, 86% yield) as pale yellow crystals: $^1$H NMR (300 MHz, CDCl$_3$): δ ppm 3.91 (3H, s), 3.97 (3H, s), 7.17-7.25 (2H, m), 7.68-7.76 (2H, m).

Reference Example 146

1-[2-Fluoro-4-(trifluoromethoxy)phenyl]-5-methoxy-4-oxo-1,4-dihydropyridazine-3-carboxylic acid

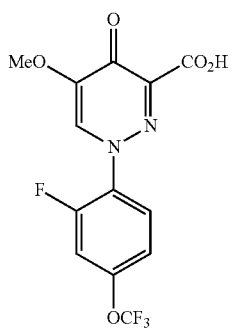

To a solution of methyl 1-[2-fluoro-4-(trifluoromethoxy)phenyl]-5-methoxy-4-oxo-1,4-dihydropyridazine-3-carboxylate (3.4 g, 9.3 mmol) in THF (150 mL) was added 1 M NaOH aqueous solution (14 mL, 14 mmol), and the mixture was stirred at room temperature for 30 min. The mixture was acidified with 1 M HCl aqueous solution and concentrated under reduced pressure. The residue was diluted with AcOEt, washed with water and brine, dried over MgSO$_4$, filtered and concentrated under reduced pressure to give the title compound (3.2 g, 97% yield) as a pale yellow amorphous solid: $^1$H NMR (300 MHz, DMSO-d$_6$): δ ppm 3.88 (3H, s), 7.52-7.59 (1H, m), 7.86 (1H, dd, J=10.8, 2.5 Hz), 7.97 (1H, t, J=8.7 Hz), 8.91 (1H, d, J=1.1 Hz), 14.83 (1H, brs).

Reference Example 147

3-Acetyl-1-[2-fluoro-4-(trifluoromethoxy)phenyl]-5-methoxypyridazin-4(1H)-one

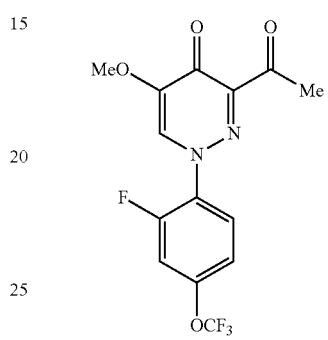

To a mixture of 1-[2-fluoro-4-(trifluoromethoxy)phenyl]-5-methoxy-4-oxo-1,4-dihydropyridazine-3-carboxylic acid (3.8 g, 11 mmol), HOBt (2.5 g, 16 mmol) and WSC (3.1 g, 16 mmol) in DMF (50 mL) was added N,O-dimethylhydroxylamine hydrochloride (2.1 g, 22 mmol) and Et$_3$N (4.5 mL, 32 mmol), and the mixture was stirred at room temperature overnight. The mixture was diluted with water (200 mL) and extracted with AcOEt (250 mL×2). The combined organic layer was washed with saturated NaHCO$_3$ aqueous solution and brine, dried over MgSO$_4$, filtered and concentrated under reduced pressure.

To a solution of the residue in THF (100 mL) was added dropwise 1 M MeMgBr in THF (18 mL, 18 mmol) at −78° C. for 15 min. After stirring at −78° C. for 1 h, the mixture was quenched with 1 M HCl aqueous solution (50 mL). The mixture was warmed to room temperature and extracted with AcOEt. The organic layer was washed with brine, dried over MgSO$_4$, filtered and concentrated under reduced pressure to give the title compound (2.8 g, 75% yield) as a yellow oil: $^1$H NMR (300 MHz, CDCl$_3$): δ ppm 2.68 (3H, s), 3.91 (3H, s), 7.18-7.25 (2H, m), 7.69-7.77 (2H, m).

Reference Example 148

Methyl 2-[(3-bromo-2-fluorophenyl)hydrazono]-4-methoxy-3-oxobutanoate

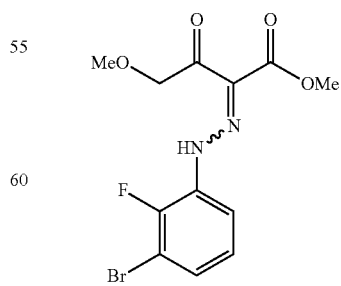

To a solution of tert-butyl (3-bromo-2-fluorophenyl)carbamate (7.23 g, 24.9 mmol) in EtOAc (125 mL) was added 4

M HCl/EtOAc (62 mL) at 0° C. The mixture was stirred at room temperature for 12 h and concentrated in vacuo. The residue was diluted with 6 M HCl aqueous solution (62 mL). To the suspension was added a solution of NaNO₂ (2.06 g, 29.9 mmol) in water (5 mL) at 0° C. To a suspension of methyl 4-methoxy-3-oxobutanoate (3.22 mL, 24.9 mmol) and NaOAc (92.9 g) in EtOH (84 mL) was added the above mixture at 0° C. The mixture was stirred at 0° C. for 20 min. The precipitates were collected by filtration, diluted with EtOAc, washed with NaHCO₃ aqueous solution, dried over MgSO₄, filtered and concentrated in vacuo to yield the title compound (5.36 g, 62% yield) as a brown solid: $^1$H NMR (DMSO-d₆, 300 MHz): δ ppm 3.30 (3H, s), 3.75-3.94 (3H, m), 4.56-4.71 (2H, m), 7.15-7.34 (1H, m), 7.37-7.59 (1H, m), 7.63-7.80 (1H, m), 12.26 (1H, s).

Reference Example 149

Methyl 1-(3-bromo-2-fluorophenyl)-5-methoxy-4-oxo-1,4-dihydropyridazine-3-carboxylate

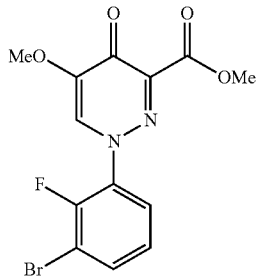 [SMILES: COC(=O)c1nn(-c2cccc(Br)c2F)cc(OC)c1=O]

A mixture of methyl 2-[(3-bromo-2-fluorophenyl)hydrazono]-4-methoxy-3-oxobutanoate (5.36 g, 15.4 mmol) in N,N-dimethylformamide dimethyl acetal (54 mL) was heated to reflux for 2 h and cooled to 0° C. The precipitates were collected by filtration, washed with hexane and dried to yield the title compound (4.16 g, 75% yield) as a brown solid: $^1$H NMR (DMSO-d₆, 300 MHz): δ ppm 3.80 (3H, s), 3.83 (3H, s), 7.40 (1H, td, J=8.1, 1.1 Hz), 7.75-7.84 (1H, m), 7.94 (1H, ddd, J=8.1, 6.4, 1.7 Hz), 8.60 (1H, d, J=1.9 Hz).

Reference Example 150

1-(3-Bromo-2-fluorophenyl)-5-methoxy-4-oxo-1,4-dihydropyridazine-3-carboxylic acid

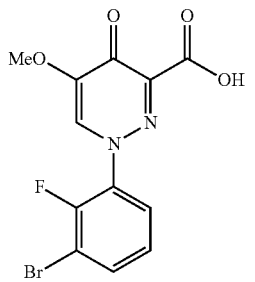 [SMILES: COc1cn(-c2cccc(Br)c2F)nc(C(=O)O)c1=O]

To a suspension of methyl 1-(3-bromo-2-fluorophenyl)-5-methoxy-4-oxo-1,4-dihydropyridazine-3-carboxylate (4.16 g, 11.7 mmol) in MeOH (46 mL) was added 1 M NaOH aqueous solution (23 mL) at 0° C. The mixture was stirred at room temperature for 1 h. To the solution was added 1 M HCl aqueous solution (23 mL) at 0° C. The mixture was concentrated in vacuo. The precipitates were collected by filtration, washed with water and dried in vacuo at 50° C. to yield the title compound (3.76 g, 94% yield) as a pale yellow solid: $^1$H NMR (DMSO-d₆, 300 MHz): δ ppm 3.87 (3H, s), 7.43 (1H, td, J=8.1, 1.5 Hz), 7.76-7.85 (1H, m), 7.98 (1H, ddd, J=8.0, 6.5, 1.3 Hz), 8.86 (1H, s), 14.84 (1H, brs).

Reference Example 151

1-(3-Bromo-2-fluorophenyl)-N,5-dimethoxy-N-methyl-4-oxo-1,4-dihydropyridazine-3-carboxamide

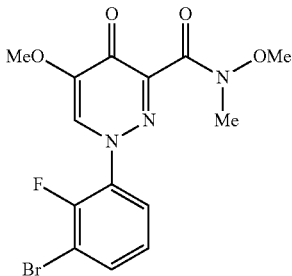 [SMILES: COc1cn(-c2cccc(Br)c2F)nc(C(=O)N(C)OC)c1=O]

A mixture of 1-(3-bromo-2-fluorophenyl)-5-methoxy-4-oxo-1,4-dihydropyridazine-3-carboxylic acid (3.76 g, 11.0 mmol) and CDI (1.95 g, 12.1 mmol) in THF (38 mL) was heated to 40° C. for 2 h. To the solution were added N,O-dimethylhydroxylamine hydrochloride (1.60 g, 16.4 mmol) and i-Pr₂NEt (2.86 mL, 16.4 mmol) at room temperature. The mixture was stirred at room temperature for 18 h. The mixture was diluted with water and 1 M HCl aqueous solution, extracted with EtOAc, dried over Na₂SO₄, filtered, concentrated in vacuo and purified by column chromatography on basic silica gel (EtOAc/MeOH=100/0 to 80/20) to yield the title compound (4.22 g, >99% yield) as a white solid: $^1$H NMR (DMSO-d₆, 300 MHz): δ ppm 3.25 (3H, s), 3.58 (3H, s), 3.80 (3H, s), 7.39 (1H, td, J=8.1, 1.5 Hz), 7.78 (1H, ddd, J=8.2, 6.9, 1.5 Hz), 7.92 (1H, ddd, J=8.0, 6.3, 1.5 Hz), 8.58 (1H, s).

Reference Example 152

3-Acetyl-1-(3-bromo-2-fluorophenyl)-5-methoxypyridazin-4(1H)-one

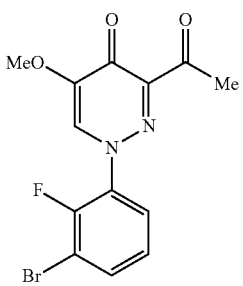 [SMILES: COc1cn(-c2cccc(Br)c2F)nc(C(C)=O)c1=O]

To a solution of 1-(3-bromo-2-fluorophenyl)-N,5-dimethoxy-N-methyl-4-oxo-1,4-dihydropyridazine-3-carboxamide (4.22 g, 10.9 mmol) in THF (218 mL) was added MeMgBr (1.0 M in THF, 16.4 mL, 16.4 mmol) at −78° C. under N₂. The mixture was stirred at −78° C. for 2 h. The reaction was quenched with saturated NH₄Cl aqueous solution at −78° C. The mixture was diluted with NaHCO₃ aqueous solution, extracted with EtOAc, dried over Na₂SO₄, filtered, concentrated in vacuo and purified by column chromatography on silica gel (EtOAc/MeOH=100/0 to 50/50) to yield the title compound (3.48 g, 93% yield) as a yellow solid: ¹H-NMR (DMSO-d₆, 300 MHz): δ ppm 2.50 (3H, s), 3.80 (3H, s), 7.36-7.46 (1H, m), 7.77-7.85 (1H, m), 7.89-7.99 (1H, m), 8.57 (1H, d, J=1.9 Hz).

Reference Example 153

Methyl 4-methoxy-3-oxo-2-[(2,2,6-trifluoro-1,3-benzodioxol-5-yl)hydrazono]butanoate

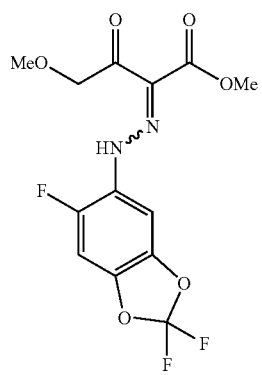 [SMILES: COCC(=O)C(=NNc1cc2c(cc1F)OC(F)(F)O2)C(=O)OC]

To a suspension of 2,2,6-trifluoro-1,3-benzodioxol-5-amine (4.95 g, 25.9 mmol) in 6 M HCl aqueous solution (25.9 mL) was added a solution of NaNO₂ (2.15 g, 31.1 mmol) in water (5.2 mL) at 0° C. To a suspension of methyl 4-methoxy-3-oxobutanoate (3.35 mL, 25.9 mmol) and NaOAc (38.9 g) in EtOH (44 mL) was added the above solution at 0° C. The mixture was stirred at 0° C. for 10 min. The precipitates were collected by filtration, washed with water, dissolved in EtOAc, washed with brine and NaHCO₃ aqueous solution, dried over MgSO₄, filtered and concentrated in vacuo to yield the title compound (6.31 g, 70% yield) as a red solid: ¹H NMR (DMSO-d₆, 300 MHz): δ ppm 3.33 (3H, s), 3.82 (3H, s), 4.66 (2H, s), 7.57-7.92 (2H, m), 12.32 (1H, brs).

Reference Example 154

Methyl 5-methoxy-4-oxo-1-(2,2,6-trifluoro-1,3-benzodioxol-5-yl)-1,4-dihydropyridazine-3-carboxylate

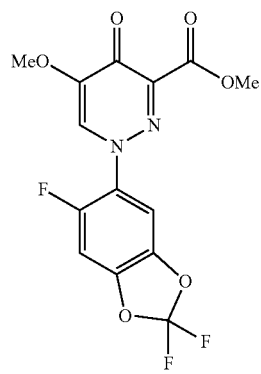

A mixture of methyl 4-methoxy-3-oxo-2-[(2,2,6-trifluoro-1,3-benzodioxol-5-yl)hydrazono]butanoate (6.31 g, 18.1 mmol) in N,N-dimethylformamide dimethyl acetal (63 mL) was heated to reflux for 2.5 h. The mixture was concentrated in vacuo and purified by column chromatography on silica gel (hexane/EtOAc=50/50 to 0/100 and EtOAc/MeOH=100/0 to 70/30) and on basic silica gel (hexane/EtOAc=50/50 to 0/100) to yield the title compound (1.53 g, 24% yield) as a pale yellow solid: ¹H NMR (DMSO-d₆, 300 MHz): δ ppm 3.79 (3H, s), 3.82 (3H, s), 7.94 (1H, d, J=9.4 Hz), 8.04 (1H, d, J=6.4 Hz), 8.54 (1H, s).

Reference Example 155

5-Methoxy-4-oxo-1-(2,2,6-trifluoro-1,3-benzodioxol-5-yl)-1,4-dihydropyridazine-3-carboxylic acid

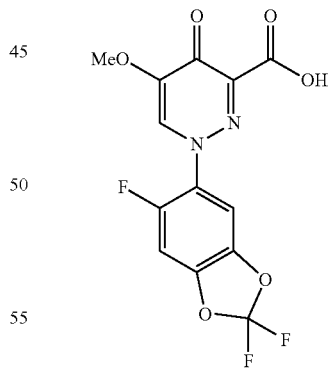

To a suspension of methyl 5-methoxy-4-oxo-1-(2,2,6-trifluoro-1,3-benzodioxol-5-yl)-1,4-dihydropyridazine-3-carboxylate (1.53 g, 4.27 mmol) in MeOH (17 mL) was added 1 M NaOH aqueous solution (8.5 mL) at 0° C. The mixture was stirred at room temperature for 30 min. To the mixture was added 1 M HCl aqueous solution (8.5 mL) at 0° C. The mixture was concentrated in vacuo. The precipitates were collected by filtration, washed with water and dried in vacuo at 60° C. to yield the title compound (1.18 g, 80% yield) as a pale yellow solid: $^1$H NMR (DMSO-d$_6$, 300 MHz): δ ppm 3.86 (3H, s), 7.98 (1H, d, J=9.4 Hz), 8.03 (1H, d, J=6.4 Hz), 8.79 (1H, s), 14.77 (1H, brs).

Reference Example 156

3-Amino-5-methoxy-1-(2,2,6-trifluoro-1,3-benzodioxol-5-yl)pyridazin-4(1H)-one

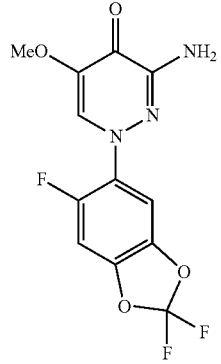 [SMILES: COc1cn(-c2cc3c(cc2F)OC(F)(F)O3)nc(N)c1=O]

A mixture of 5-methoxy-4-oxo-1-(2,2,6-trifluoro-1,3-benzodioxol-5-yl)-1,4-dihydropyridazine-3-carboxylic acid (1.18 g, 3.42 mmol), DPPA (1.10 mL, 5.13 mmol) and Et$_3$N (0.715 mL, 5.13 mmol) in toluene (12 mL) was heated to 100° C. for 1 h. To the mixture was added 8 M NaOH aqueous solution (4.3 mL) at 0° C. The mixture was stirred at room temperature for 1 h, extracted with EtOAc, dried over Na$_2$SO$_4$, filtered, concentrated in vacuo and purified by column chromatography on basic silica gel (hexane/EtOAc=50/50 to 0/100) and recrystallized with EtOAc/hexane to yield the title compound (704 mg, 65% yield) as a white solid: $^1$H NMR (DMSO-d$_6$, 300 MHz): δ ppm 173 (3H, s), 6.21 (2H, s), 7.85 (1H, d, J=9.4 Hz), 7.90 (1H, d, J=6.4 Hz), 8.33 (1H, s).

Reference Example 157

3-Bromo-5-methoxy-1-(2,2,6-trifluoro-1,3-benzodioxol-5-yl)pyridazin-4(1H)-one

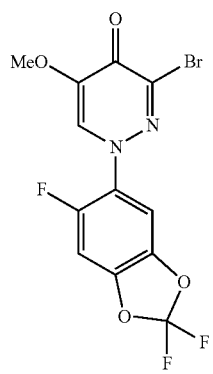 [SMILES: COc1cn(-c2cc3c(cc2F)OC(F)(F)O3)nc(Br)c1=O]

To a mixture of isoamyl nitrite (0.22 mL, 1.65 mmol) and CuBr$_2$ (0.17 g, 0.762 mmol) in DMF (2 mL) was added a mixture of 3-amino-5-methoxy-1-(2,2,6-trifluoro-1,3-benzodioxol-5-yl)pyridazin-4(1H)-one (200 mg, 0.635 mmol) in DMF (4 mL) at 0° C. The mixture was stirred at 0° C. for 1 h and at 60° C. for 2 h. The mixture was diluted with water and brine, extracted with EtOAc, dried over Na$_2$SO$_4$, filtered, concentrated in vacuo and purified by column chromatography on silica gel (hexane/EtOAc=50/50 to 0/100) to yield the title compound (145 mg, 60% yield) as a pale yellow solid: $^1$H NMR (DMSO-d$_6$, 300 MHz): δ ppm 3.79 (3H, s), 7.93 (1H, d, J=9.5 Hz), 8.02 (1H, d, J=6.4 Hz), 8.59 (1H, d, J=1.5 Hz).

Reference Example 158

Methyl 4-methoxy-3-oxo-2-[(2,2,3,3,7-pentafluoro-2,3-dihydro-1,4-benzodioxin-6-yl)hydrazono]butanoate

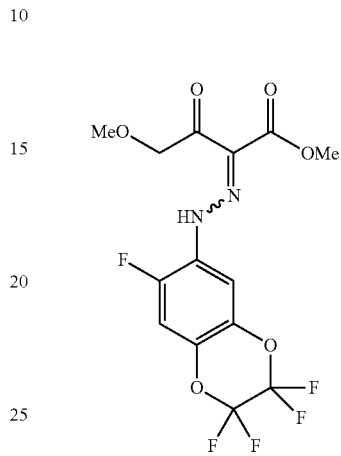

To a suspension of 2,2,3,3,7-pentafluoro-2,3-dihydro-1,4-benzodioxin-6-amine (4.87 g, 20.2 mmol) in 6 M HCl aqueous solution (20.2 mL) was added a solution of NaNO$_2$ (1.67 g, 24.2 mmol) in water (4 mL) at 0° C. The mixture was stirred at 0° C. for 15 min. To a suspension of methyl 4-methoxy-3-oxobutanoate (2.61 mL, 20.2 mmol) and NaOAc (303 g) in EtOH (34 mL) was added the above solution at 0° C. The mixture was stirred at 0° C. for 15 min. The precipitates were collected by filtration, washed with water, dissolved in EtOAc, washed with brine, dried over MgSO$_4$, filtered and concentrated in vacuo to yield the title compound (6.84 g, 85% yield) as a red solid: $^1$H NMR (DMSO-d$_6$, 300 MHz): δ ppm 3.33 (3H, s), 3.82 (3H, s), 4.68 (2H, s), 7.66-7.93 (2H, m), 12.16 (1H, brs).

Reference Example 159

Methyl 5-methoxy-4-oxo-1-(2,2,3,3,7-pentafluoro-2,3-dihydro-1,4-benzodioxin-6-yl)-1,4-dihydropyridazine-3-carboxylate

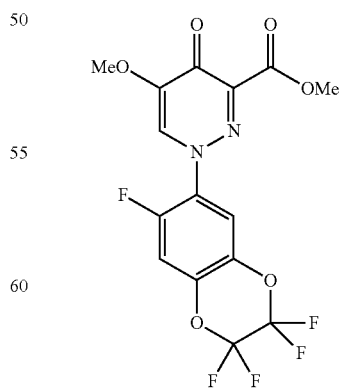

A mixture of methyl 4-methoxy-3-oxo-2-[(2,2,3,3,7-pentafluoro-2,3-dihydro-1,4-benzodioxin-6-yl)hydrazono]butanoate (6.84 g, 17.2 mmol) in N,N-dimethylformamide dimethyl acetal (68 mL) was heated to reflux for 2.5 h. The mixture was concentrated in vacuo, diluted with brine, extracted with EtOAc, dried over MgSO₄, filtered, concentrated in vacuo and purified by column chromatography on silica gel (hexane/EtOAc=50/50 to 0/100 and EtOAc/MeOH=100/0 to 70/30) and on basic silica gel (hexane/EtOAc=80/20 to 0/100 and EtOAc/MeOH=100/0 to 70/30) to yield the title compound (2.58 g, 37% yield) as a pale yellow solid: ¹H NMR (DMSO-d₆, 300 MHz): δ ppm 3.79 (3H, s), 3.83 (3H, s), 8.01 (1H, d, J=10.2 Hz), 8.16 (1H, d, J=7.2 Hz), 8.58 (1H, s).

Reference Example 160

5-Methoxy-4-oxo-1-(2,2,3,3,7-pentafluoro-2,3-dihydro-1,4-benzodioxin-6-yl)-1,4-dihydropyridazine-3-carboxylic acid

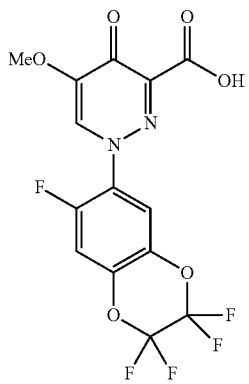 [SMILES: COc1cn(-c2cc3c(cc2F)OC(F)(F)C(F)(F)O3)nc(C(=O)O)c1=O]

To a solution of methyl 5-methoxy-4-oxo-1-(2,2,3,3,7-pentafluoro-2,3-dihydro-1,4-benzodioxin-6-yl)-1,4-dihydropyridazine-3-carboxylate (2.58 g, 6.31 mmol) in MeOH (26 mL) was added 1 M NaOH aqueous solution (13 mL) at 0° C. The mixture was stirred at room temperature for 90 min. To the mixture was added 1 M HCl aqueous solution (13 mL) at 0° C. The mixture was concentrated in vacuo. The precipitates were collected by filtration, washed with water and dried in vacuo at 60° C. to yield the title compound (2.33 g, 94% yield) as a white solid: ¹H NMR (DMSO-d₆, 300 MHz): δ ppm 3.86 (3H, s), 8.06 (1H, d, J=10.2 Hz), 8.17 (1H, d, J=6.8 Hz), 8.82 (1H, s), 14.66 (1H, brs).

Reference Example 161

3-Amino-5-methoxy-1-(2,2,3,3,7-pentafluoro-2,3-dihydro-1,4-benzodioxin-6-yl)pyridazin-4(1H)-one

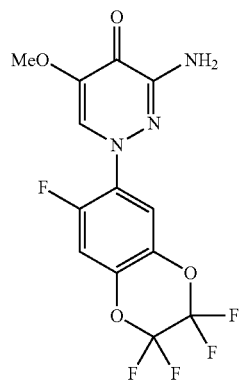 [SMILES: COc1cn(-c2cc3c(cc2F)OC(F)(F)C(F)(F)O3)nc(N)c1=O]

A mixture of 5-methoxy-4-oxo-1-(2,2,3,3,7-pentafluoro-2,3-dihydro-1,4-benzodioxin-6-yl)-1,4-dihydropyridazine-3-carboxylic acid (2.33 g, 5.91 mmol), DPPA (1.90 mL, 8.86 mmol) and Et₃N (1.23 mL, 8.86 mmol) in toluene (23 mL) was heated to 100° C. for 90 min. To the mixture was added 8 M NaOH aqueous solution (7.4 mL) at 0° C. The mixture was stirred at room temperature for 2 h, extracted with EtOAc, dried over Na₂SO₄, filtered, concentrated in vacuo, purified by column chromatography on basic silica gel (hexane/EtOAc=50/50 to 0/100) and on silica gel (hexane/EtOAc=80/20 to 0/100) and triturated with EtOAc/hexane to yield the title compound (1.12 g, 53% yield) as a white solid: ¹H NMR (DMSO-d₆, 300 MHz): δ ppm 3.73 (3H, s), 6.24 (2H, s), 7.92 (1H, d, J=10.5 Hz), 7.99 (1H, d, J=6.8 Hz), 8.37 (1H, d, J=1.5 Hz).

Reference Example 162

3-Bromo-5-methoxy-1-(2,2,3,3,7-pentafluoro-2,3-dihydro-1,4-benzodioxin-6-yl)pyridazin-4(1H)-one

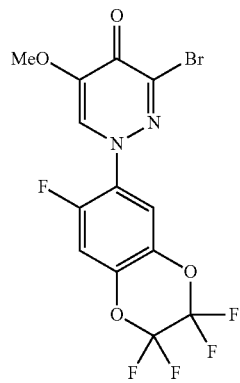 [SMILES: COc1cn(-c2cc3c(cc2F)OC(F)(F)C(F)(F)O3)nc(Br)c1=O]

To a mixture of isoamyl nitrite (0.473 mL, 3.56 mmol) and CuBr₂ (367 mg, 1.64 mmol) in DMF (5 mL) was added a mixture of 3-amino-5-methoxy-1-(2,2,3,3,7-pentafluoro-2,3-dihydro-1,4-benzodioxin-6-yl)pyridazin-4(1H)-one (500 mg, 1.37 mmol) in DMF (2.5 mL) at 0° C. The mixture was stirred at 0° C. for 1 h and at 60° C. for 2.5 h. The mixture was diluted with water and brine, extracted with EtOAc, dried over MgSO$_4$, filtered, concentrated in vacuo, purified by column chromatography on silica gel (hexane/EtOAc=50/50 to 0/100) and crystallized with EtOH/hexane to yield the title compound (381 mg, 65% yield) as a white solid: $^1$H NMR (DMSO-d$_6$, 300 MHz): δ ppm 3.79 (3H, s), 8.02 (1H, d, J=10.5 Hz), 8.14 (1H, d, J=6.8 Hz), 8.63 (1H, s).

Reference Example 163

1-[2-Fluoro-3-(1-methyl-1H-pyrazol-4-yl)phenyl]-N,5-dimethoxy-N-methyl-4-oxo-1,4-dihydropyridazine-3-carboxamide

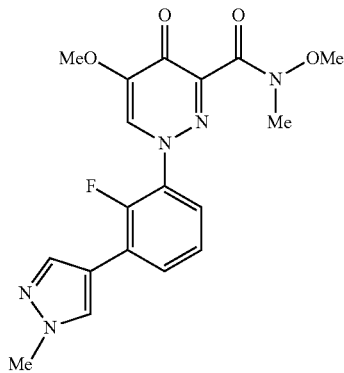 [SMILES: COc1cn(-c2cccc(-c3cnn(C)c3)c2F)nc(C(=O)N(C)OC)c1=O]

A mixture of 1-(3-bromo-2-fluorophenyl)-N,5-dimethoxy-N-methyl-4-oxo-1,4-dihydropyridazine-3-carboxamide (500 mg, 1.29 mmol), 1-methyl-4-(4,4,5,5-tetramethyl-1,3,2-dioxaborolan-2-yl)-1H-pyrazole (295 mg, 1.42 mmol), Na$_2$CO$_3$ (302 mg, 2.85 mmol) and Pd(PPh$_3$)$_4$ (74.5 mg, 0.0645 mmol) in DME (11.4 mL) and water (2.9 mL) was heated to reflux for 15 h under Ar. The mixture was diluted with water, extracted with EtOAc, washed with brine, dried over Na$_2$SO$_4$, filtered, concentrated in vacuo, and purified by column chromatography on basic silica gel (EtOAc/MeOH=100/0 to 70/30) to yield the title compound (345 mg, 69% yield) as a white solid: $^1$H NMR (DMSO-d$_6$, 300 MHz): δ ppm 3.25 (3H, s), 3.59 (3H, s), 3.80 (3H, s), 3.90 (3H, s), 7.35-7.44 (1H, m), 7.50-7.59 (1H, m), 7.84-7.94 (1H, m), 7.97 (1H, s), 8.23 (1H, d, J=2.5 Hz), 8.58 (1H, s).

Reference Example 164

3-Acetyl-1-[2-fluoro-3-(1-methyl-1H-pyrazol-4-yl)phenyl]-5-methoxypyridazin-4(1H)-one

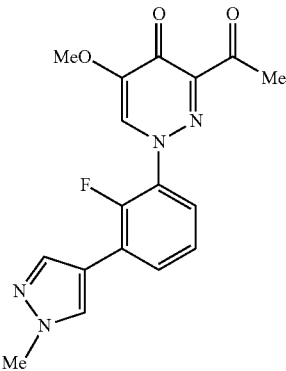 [SMILES: COc1cn(-c2cccc(-c3cnn(C)c3)c2F)nc(C(C)=O)c1=O]

To a solution of 1-[2-fluoro-3-(1-methyl-1H-pyrazol-4-yl)phenyl]-N,5-dimethoxy-N-methyl-4-oxo-1,4-dihydropyridazine-3-carboxamide (345 mg, 0.890 mmol) in THF (100 mL) was added MeMgBr (1.0 M in THF, 2.67 mL, 2.67 mmol) at −78° C. under N$_2$. The mixture was stirred at −78° C. for 100 min. The reaction was quenched with saturated NH$_4$Cl aqueous solution at −78° C. The mixture was extracted with EtOAc, dried over Na$_2$SO$_4$, filtered, concentrated in vacuo and purified by column chromatography on silica gel (EtOAc/MeOH=100/0 to 70/30) to yield the title compound (243 mg, 80% yield) as a white solid: $^1$H NMR (DMSO-d$_6$, 300 MHz): δ ppm 2.51 (3H, brs), 3.81 (3H, s), 3.91 (3H, s), 7.38-7.46 (1H, m), 7.54-7.64 (1H, m), 7.86-7.95 (1H, m, J=15.0, 1.7 Hz), 7.98 (1H, s), 8.25 (1H, d, J=2.3 Hz), 8.58 (1H, d, J=1.9 Hz).

Reference Example 165

Methyl 2-[(2-fluoro-5-iodophenyl)hydrazono]-4-methoxy-3-oxobutanoate

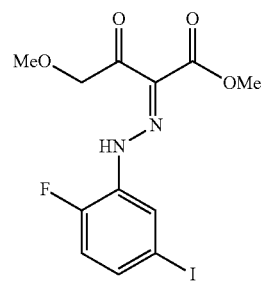 [SMILES: COCC(=O)/C(=N\Nc1cc(I)ccc1F)C(=O)OC]

To a suspension of 2-fluoro-5-iodoaniline (9.83 g, 41.5 mmol) in 6 M HCl aqueous solution (83.0 mL) was added a solution of NaNO$_2$ (3.43 g, 49.8 mmol) in water (8.3 mL) at 0° C. To a suspension of methyl 4-methoxy-3-oxobutanoate (5.37 mL, 41.5 mmol) and NaOAc (124 g) in EtOH (70 mL) was added the above solution at 0° C. The mixture was stirred at 0° C. for 10 min. The precipitates were collected by filtration, washed with water, dissolved in EtOAc, washed with brine, dried over MgSO$_4$, filtered and concentrated in vacuo to yield the title compound (14.2 g, 87% yield) as a red solid:

¹H NMR (DMSO-d₆, 300 MHz): δ ppm 3.31 (3H, s), 3.83 (3H, s), 4.64 (2H, s), 7.03-7.41 (1H, m), 7.43-7.66 (1H, m), 7.85-8.07 (1H, m), 12.20 (1H, brs).

Reference Example 166

Methyl 1-(2-fluoro-5-iodophenyl)-5-methoxy-4-oxo-1,4-dihydropyridazine-3-carboxylate

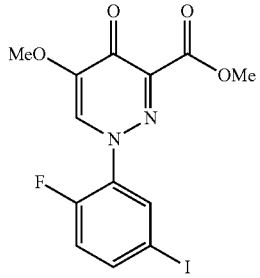 [SMILES: COC(=O)c1nn(-c2cc(I)ccc2F)cc(OC)c1=O]

A mixture of methyl 2-[(2-fluoro-5-iodophenyl)hydrazono]-4-methoxy-3-oxobutanoate (14.2 g, 35.9 mmol) in N,N-dimethylformamide dimethyl acetal (142 mL) was heated to reflux for 1.5 h and cooled to 0° C. The precipitates were collected by filtration, washed with hexane and dried to yield the title compound (11.3 g, 78% yield) as a pale yellow solid: ¹H NMR (DMSO-d₆, 300 MHz): δ ppm 3.80 (3H, s), 3.82 (3H, s), 7.37 (1H, dd, J=10.6, 8.7 Hz), 7.90-8.01 (1H, m), 8.14 (1H, dd, J=7.2, 2.3 Hz), 8.55 (1H, s).

Reference Example 167

1-(2-Fluoro-5-iodophenyl)-5-methoxy-4-oxo-1,4-dihydropyridazine-3-carboxylic acid

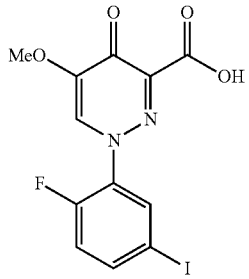 [SMILES: COc1cn(-c2cc(I)ccc2F)nc(C(=O)O)c1=O]

To a suspension of methyl 1-(2-fluoro-5-iodophenyl)-5-methoxy-4-oxo-1,4-dihydropyridazine-3-carboxylate (11.3 g, 28.1 mmol) in MeOH (112 mL) was added 1 M NaOH aqueous solution (56 mL) at 0° C. The mixture was stirred at room temperature for 90 min. To the mixture was added 1 M HCl aqueous solution (56 mL) at 0° C. The mixture was concentrated in vacuo. The precipitates were collected by filtration, washed with water and dried in vacuo at 60° C. to yield the title compound (9.96 g, 91% yield) as a yellow solid: ¹H NMR (DMSO-d₆, 300 MHz): δ ppm 3.88 (3H, s), 7.42 (1H, dd, J=10.6, 8.7 Hz), 8.00 (1H, ddd, J=8.7, 4.5, 2.3 Hz), 8.16 (1H, dd, J=7.2, 2.3 Hz), 8.85 (1H, s), 14.86 (1H, brs).

Reference Example 168

1-(2-Fluoro-5-iodophenyl)-N,5-dimethoxy-N-methyl-4-oxo-1,4-dihydropyridazine-3-carboxamide

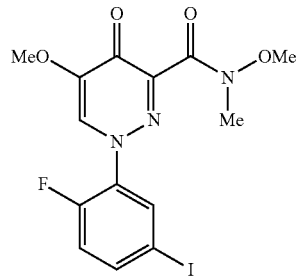 [SMILES: COc1cn(-c2cc(I)ccc2F)nc(C(=O)N(C)OC)c1=O]

A mixture of 1-(2-fluoro-5-iodophenyl)-5-methoxy-4-oxo-1,4-dihydropyridazine-3-carboxylic acid (9.96 g, 25.5 mmol) and CDI (4.55 g, 28.1 mmol) in THF (200 mL) was heated to 40° C. for 30 min and 50° C. for 90 min. To the mixture was added DMF (20 mL). The mixture was stirred at 50° C. for 70 min. To the solution were added N,O-dimethylhydroxylamine hydrochloride (3.74 g, 38.3 mmol) and i-Pr₂NEt (6.67 mL, 38.3 mmol) at room temperature. The solution was stirred at room temperature for 16 h. The mixture was concentrated in vacuo, diluted with water and 1 M HCl aqueous solution, extracted with EtOAc, washed with saturated NaHCO₃ aqueous solution, dried over Na₂SO₄, filtered, concentrated in vacuo and purified by column chromatography on silica gel (hexane/EtOAc=20/80 to 0/100 and EtOAc/MeOH=100/0 to 0/100) and triturated with MeOH/EtOH/hexane to yield the title compound (9.11 g, 82% yield) as a pale yellow solid: ¹H NMR (DMSO-d₆, 300 MHz): δ ppm 3.24 (3H, s), 3.56 (3H, s), 3.80 (3H, s), 7.36 (1H, dd, J=10.6, 8.7 Hz), 7.93 (1H, ddd, J=8.7, 4.5, 2.3 Hz), 8.12 (1H, dd, J=7.4, 2.1 Hz), 8.53 (1H, s).

Reference Example 169

1-[2-Fluoro-5-(1-methyl-1H-pyrazol-4-yl)phenyl]-N,5-dimethoxy-N-methyl-4-oxo-1,4-dihydropyridazine-3-carboxamide

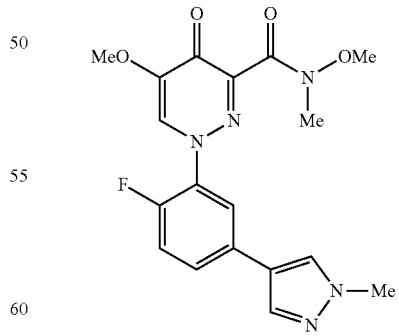

A mixture of 1-(2-fluoro-5-iodophenyl)-N,5-dimethoxy-N-methyl-4-oxo-1,4-dihydropyridazine-3-carboxamide (500 mg, 1.15 mmol), 1-methyl-4-(4,4,5,5-tetramethyl-1,3,2-dioxaborolan-2-yl)-1H-pyrazole (264 mg, 1.27 mmol), Na₂CO₃ (268 mg, 2.53 mmol) and Pd(PPh₃)₄ (66.4 mg, 0.0575 mmol) in DME (10.1 mL) and water (2.5 mL) was heated to reflux for 14 h under Ar. The mixture was diluted with water, brine and saturated NaHCO$_3$ aqueous solution, extracted with EtOAc, dried over Na$_2$SO$_4$, filtered, concentrated in vacuo, and purified by column chromatography on basic silica gel (hexane/EtOAc=50/50 to 0/100 and EtOAc/MeOH=100/0 to 60/40) to yield the title compound (267 mg, 60% yield) as a pale yellow solid: $^1$H NMR (DMSO-d$_6$, 300 MHz): δ ppm 3.25 (3H, s), 3.59 (3H, s), 3.82 (3H, s), 3.87 (3H, s), 7.51 (1H, dd, J=10.4, 8.9 Hz), 7.73-7.80 (1H, m), 7.89-7.97 (2H, m), 8.23 (1H, s), 8.58 (1H, s).

Reference Example 170

3-Acetyl-1-[2-fluoro-5-(1-methyl-1H-pyrazol-4-yl)phenyl]-5-methoxypyridazin-4(1H)-one

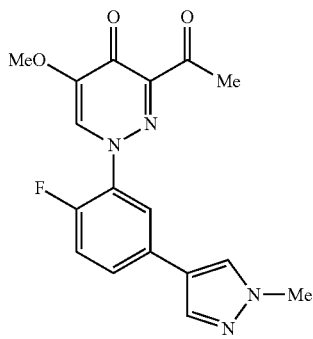 [SMILES: COc1cn(-c2cc(-c3cnn(C)c3)ccc2F)nc(C(C)=O)c1=O]

To a mixture of 1-[2-fluoro-5-(1-methyl-1H-pyrazol-4-yl)phenyl]-N,5-dimethoxy-N-methyl-4-oxo-1,4-dihydropyridazine-3-carboxamide (267 mg, 0.687 mmol) in THF (80 mL) was added MeMgBr (1.0 M in THF, 2.06 mL, 2.06 mmol) at −78° C. under N$_2$. The mixture was stirred at −78° C. for 2 h. To the mixture was added MeMgBr (1.0 M in THF, 0.687 mL, 0.687 mmol) at −78° C. The mixture was stirred at −78° C. for 1 h. To the mixture was added MeMgBr (1.0 M in TI-IF, 1.37 mL, 1.37 mmol) at −78° C. The mixture was stirred at −78° C. for 3 h. The reaction was quenched with saturated NH$_4$Cl aqueous solution at −78° C. The mixture was diluted with saturated NaHCO$_3$ aqueous solution, extracted with EtOAc, dried over Na$_2$SO$_4$, filtered, concentrated in vacuo and purified by column chromatography on silica gel (EtOAc/MeOH=100/0 to 70/30) to yield the title compound (201 mg, 85% yield) as a yellow solid: $^1$H NMR (DMSO-d$_6$, 300 MHz): δ ppm 2.52 (3H, s), 3.82 (3H, s), 3.87 (3H, s), 7.53 (1H, dd, J=10.6, 8.7 Hz), 7.78 (1H, ddd, J=8.7, 4.5, 2.3 Hz), 7.92-8.00 (2H, m), 8.23 (1H, s), 8.56 (1H, d, J=1.5 Hz).

Reference Example 171

1-(Difluoromethyl)-1H-pyrazole-4-boronic acid pinacol ester

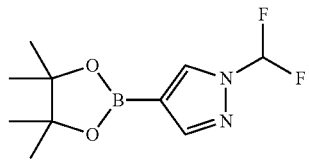 [SMILES: CC1(C)OB(c2cnn(C(F)F)c2)OC1(C)C]

A suspension of 1H-pyrazole-4-boronic acid pinacol ester (5.16 g, 26.6 mmol), CF$_2$ClCO$_2$Na (4.86 g, 31.9 mmol), and 18-crown-6 (1.41 g, 5.32 mmol) in CH$_3$CN (100 mL) was refluxed for 20 h. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with AcOEt to give the title compound (3.03 g, 47% yield) as a yellow oil: $^1$H NMR (300 MHz, CDCl$_3$): δ ppm 1.33 (12H, s), 7.22 (1H, t, J=60.7 Hz), 7.89 (1H, s), 8.13 (1H, s).

Reference Example 172 tert-Butyl 1-{3-fluoro-4-[5-methoxy-4-oxo-3-(1-phenyl-1H-pyrazol-5-yl)pyridazin-1(4H)-yl]phenyl}hydrazinecarboxylate

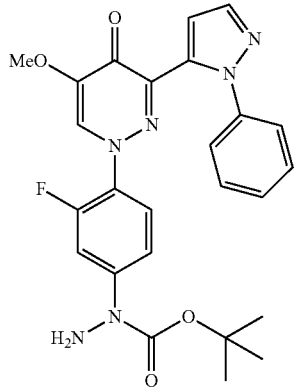 [SMILES: COc1cn(-c2ccc(N(N)C(=O)OC(C)(C)C)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (2.44 g, 5.0 mmol), tert-butyl carbazate (0.727 g, 5.5 mmol), CuI (0.0095 g, 0.05 mmol), 1,10-phenanthroline (0.072 g, 0.4 mmol), and Cs$_2$CO$_3$ (2.28 g, 7.0 mmol) in DMF (25 mL) was stirred for 5 h at 100° C. under Ar atmosphere. After cooling to room temperature, the reaction mixture was poured into water and extracted with AcOEt three times. The combined extracts were washed with water and brine, dried over MgSO$_4$, and concentrated under reduced pressure. The residue was purified by basic silica gel column chromatography eluting with AcOEt and crystallized from hexane/AcOEt to give the title compound (2.04 g, 83% yield) as a pale yellow solid: mp 163-165° C.; $^1$H NMR (300 MHz, CDCl$_3$): δ ppm 1.58 (9H, s), 3.90 (3H, s), 4.36 (2H, s), 6.31 (1H, t, J=9.0 Hz), 7.28-7.45

(7H, m), 7.55 (1H, dd, J=2.3, 14.3 Hz), 7.78 (2H, d, J=1.9 Hz). Anal. Calcd for $C_{25}H_{25}FN_6O_4$: C, 60.97; H, 5.12; N, 17.06. Found: C, 61.20; H, 5.13; N, 16.81.

Reference Example 173

3-{[2-(1-Methylethyl)phenyl]hydrazono}pentane-2,4-dione

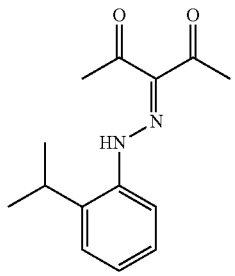 [SMILES: CC(=O)C(=NNc1ccccc1C(C)C)C(C)=O]

2-(1-Methylethyl)aniline (2.00 g, 14.81 mmol) was added to a solution of 12 mL of phosphoric acid (85%) and 8 mL of nitric acid (65%) at −6° C., followed by sodium nitrite (1.23 g, 17.78 mmol) in 4 mL of water dropwise at 0° C., and the mixture was stirred at 0° C. for 30 min. Then, to the reaction mixture was added dropwise a solution of potassium acetate (4.35 g, 44.43 mmol) and acetylacetone (1.92 g, 19.25 mmol) in 80 mL of ethanol and 20 mL of water. The mixture was stirred at room temperature overnight, filtered, washed with water, EtOH/$H_2O$ (1/1) and hexane, and dried to give the title compound (0.98 g, 27% yield): $^1$H NMR (400 MHz, CDCl$_3$): δ ppm 1.34 (6H, d, J=6.8 Hz), 2.52 (3H, s), 2.63 (3H, s), 3.12-3.21 (1H, m), 7.19-7.23 (1H, m), 7.28-7.34 (2H, m), 7.77-8.00 (1H, m), 15.23 (1H, brs).

Reference Example 174

2-[2-(1-Acetyl-2-oxopropylidene)hydrazino]benzonitrile

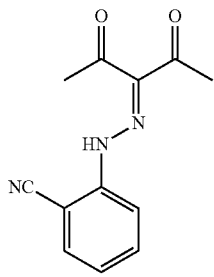 [SMILES: CC(=O)C(=NNc1ccccc1C#N)C(C)=O]

2-Aminobenzonitrile (5.00 g, 42.37 mmol) was added to a solution of 30 mL of phosphoric acid (85%) and 20 mL of nitric acid (65%) at −6° C., followed by sodium nitrite (3.50 g, 50.78 mmol) in 10 mL of water dropwise at 0° C., and the mixture was stirred at 0° C. for 30 min. Then, to the reaction mixture was added dropwise a solution of potassium acetate (12.45 g, 127.11 mmol) and acetylacetone (5.51 g, 55.08 mmol) in 80 mL of ethanol and 48 mL of water. The mixture was stirred at room temperature overnight, filtered, washed with water, EtOH/$H_2O$ (1/1) and hexane, and dried to give the title compound (4.00 g, 41% yield): $^1$H NMR (400 MHz, CDCl$_3$): δ ppm 2.50 (3H, s), 2.63 (3H, s), 7.21-7.25 (1H, m), 7.62-7.66 (2H, m), 7.77-7.79 (1H, m), 15.01 (1H, s).

Reference Example 175

3-(Biphenyl-2-ylhydrazono)pentane-2,4-dione

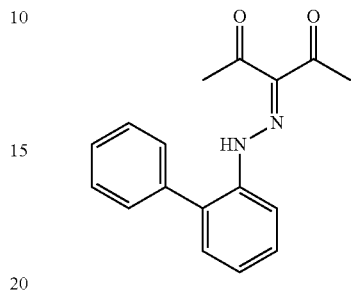

Biphenyl-2-amine (500 mg, 2.96 mmol) was added to a solution of 3 mL of phosphoric acid (85%) and 2 mL of nitric acid (65%) at −6° C., followed by sodium nitrite (254 mg, 3.55 mmol) in 1 mL of water dropwise at 0° C., and the mixture was stirred at 0° C. for 30 min. Then, to the reaction mixture was added dropwise a solution of potassium acetate (870 mg, 8.88 mmol) and acetylacetone (385 mg, 3.85 mmol) in 60 mL of ethanol and 32 mL of water. The mixture was stirred at room temperature overnight, filtered, washed with water, EtOH/$H_2O$ (1/1) and hexane, and dried to give the title compound (420 mg, 51% yield): $^1$H NMR (400 MHz, CDCl$_3$): δ ppm 2.51 (3H, s), 2.52 (3H, s), 7.29-7.60 (9H, m), 14.63 (1H, s).

Reference Example 176

3-[(2-Ethoxyphenyl)hydrazono]pentane-2,4-dione

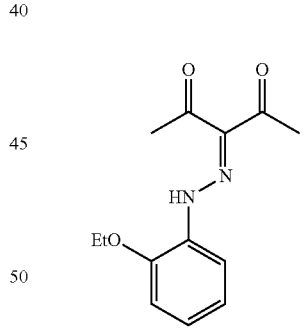

2-Ethoxyaniline (2.00 g, 14.60 mmol) was added to a solution of 12 mL of phosphoric acid (85%) and 8 mL of nitric acid (65%) at −6° C., followed by sodium nitrite (1.21 g, 17.52 mmol) in 10 mL of water dropwise at 0° C., and the mixture was stirred at 0° C. for 30 min. Then, to the reaction mixture was added dropwise a solution of potassium acetate (4.29 g, 43.80 mmol) and acetylacetone (1.90 g, 18.98 mmol) in 60 mL of ethanol and 25 mL of water. The mixture was stirred at room temperature overnight; filtered, washed with water, EtOH/$H_2O$ (1/1) and hexane, and dried to give the title compound (2.00 g, 55% yield): $^1$H NMR (400 MHz, CDCl$_3$): δ ppm 1.57 (3H, t, J=7.2 Hz), 2.53 (3H, s), 2.63 (3H, s), 4.20 (2H, t, J=7.2 Hz), 7.03-7.07 (1H, m), 7.14-7.18 (1H, m), 7.74-7.84 (2H, m), 14.86 (1H, s).

Reference Example 177

3-{[2-(1-Methylethoxy)phenyl]hydrazono}pentane-2,4-dione

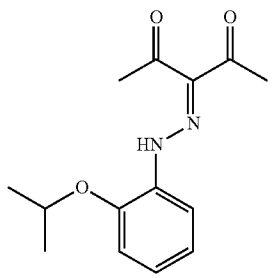 [SMILES: CC(=O)C(=NNc1ccccc1OC(C)C)C(C)=O]

2-(1-Methylethoxy)aniline (1.00 g, 6.62 mmol) was added to a solution of 6 mL of phosphoric acid (85%) and 4 mL of nitric acid (65%) at −6° C., followed by sodium nitrite (0.55 g, 7.95 mmol) in 2 mL of water dropwise at 0° C., and the mixture was stirred at 0° C. for 30 min. Then, to the reaction mixture was added dropwise a solution of potassium acetate (1.95 g, 19.86 mmol) and acetylacetone (0.86 g, 8.61 mmol) in 40 mL of ethanol and 10 mL of water. The mixture was stirred at room temperature overnight, filtered, washed with water, EtOH/H$_2$O (1/1) and hexane, and dried to give the title compound (0.53 g, 30% yield): $^1$H NMR (400 MHz, CDCl$_3$): δ ppm 1.28-1.41 (6H, m), 2.50 (3H, s), 2.63 (3H, s), 4.53-4.59 (1H, m), 7.21-7.25 (1H, m), 7.62-7.66 (2H, m), 7.77-7.79 (1H, m), 15.01 (1H, s).

Reference Example 178

3-{[2-(Trifluoromethoxy)phenyl]hydrazono}pentane-2,4-dione

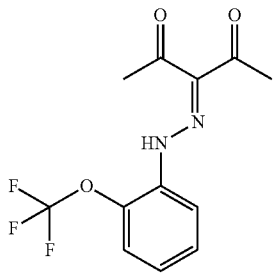 [SMILES: CC(=O)C(=NNc1ccccc1OC(F)(F)F)C(C)=O]

2-(Trifluoromethoxy)aniline (1.00 g, 5.64 mmol) was added to a solution of 6 mL of phosphoric acid (85%) and 4 mL of nitric acid (65%) at −6° C., followed by sodium nitrite (389 mg, 5.64 mmol, 1.0 equiv.) in 2 mL of water dropwise at 0° C., and the mixture was stirred at 0° C. for 30 min. Then to the reaction mixture was added dropwise a mixture of potassium acetate (1.66 g, 16.92 mmol) and acetylacetone (564 mg, 5.64 mmol) in 80 mL of ethanol and 48 mL of water. The mixture was stirred at room temperature overnight, filtered, washed with water, EtOH/H$_2$O (1/1) and hexane, and dried to give the title compound (1.3 g, 80% yield): $^1$H NMR (400 MHz, CDCl$_3$): δ ppm 2.54 (s, 3H), 2.65 (s, 3H), 7.20-7.24 (m, 1H), 7.33-7.42 (m, 2H), 7.87 (dd, J=8.4, 1.6 Hz, 1H), 14.86 (s, 1H).

Reference Example 179

3-[(2-Phenoxyphenyl)hydrazono]pentane-2,4-dione

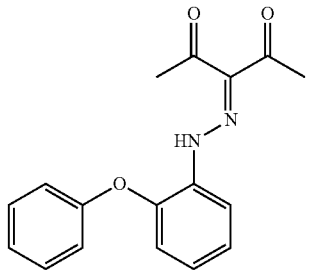 [SMILES: CC(=O)C(=NNc1ccccc1Oc1ccccc1)C(C)=O]

2-Phenoxyaniline (2.00 g, 10.81 mmol) was added to a solution of 12 mL of phosphoric acid (85%) and 8 mL of nitric acid (65%) at −6° C., followed by sodium nitrite (0.90 g, 12.97 mmol) in 2 mL of water dropwise at 0° C., and the mixture was stirred at 0° C. for 30 min. Then, to the reaction mixture was added dropwise a mixture of potassium acetate (3.18 g, 32.43 mmol) and acetylacetone (1.40 g, 14.05 mmol) in 80 mL of ethanol and 48 mL of water. The mixture was stirred at room temperature overnight, filtered, washed with water, EtOH/H$_2$O (1/1) and hexane, and dried to give the title compound (1.00 g, 31% yield): $^1$H NMR (400 MHz, CDCl$_3$): δ ppm 2.50 (3H, s), 2.63 (3H, s), 7.26-7.88 (9H, m), 14.91 (1H, s).

Reference Example 180

3-{[2-(Methylsulfinyl)phenyl]hydrazono}pentane-2,4-dione

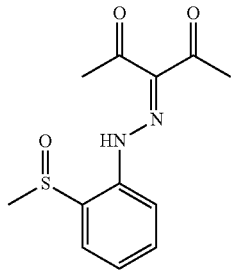 [SMILES: CC(=O)C(=NNc1ccccc1S(C)=O)C(C)=O]

2-(Methylsulfinyl)aniline (0.50 g, 3.22 mmol) was added to a solution of 3 mL of phosphoric acid (85%) and 2 mL of nitric acid (65%) at −6° C., followed by sodium nitrite (0.27 g, 3.87 mmol) in 2 mL of water dropwise at 0° C., and the mixture was stirred at 0° C. for 30 min. Then, to the reaction mixture was added dropwise a mixture of potassium acetate (0.95 g, 9.66 mmol) and acetylacetone (0.42 g, 4.19 mmol) in 80 mL of ethanol and 48 mL of water. The mixture was stirred at room temperature overnight, filtered, washed with water, EtOH/H$_2$O (1/1) and hexane, and dried to give the title compound (0.66 g, 77% yield): $^1$H NMR (400 MHz, CDCl$_3$): δ ppm 2.07 (3H, s), 2.55 (3H, s), 2.64 (3H, s), 7.29-7.87 (4H, m), 15.06 (1H, s).

Reference Example 181

3-{[3-(Trifluoromethoxy)phenyl]hydrazono}pentane-2,4-dione

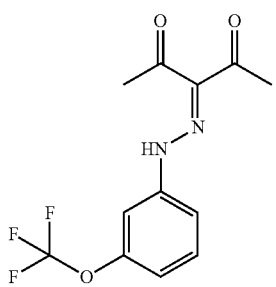 [SMILES: CC(=O)C(=NNc1cccc(OC(F)(F)F)c1)C(C)=O]

3-(Trifluoromethoxy)aniline (1.00 g, 5.64 mmol) was added to a solution of 0.6 mL of phosphoric acid (85%) and 4 mL of nitric acid (65%) at −6° C., followed by sodium nitrite (389 mg, 5.64 mmol) in 2 mL of water dropwise at 0° C., and the mixture was stirred at 0° C. for 30 min. Then to the reaction mixture was added dropwise a mixture of potassium acetate (1.66 g, 16.92 mmol) and acetylacetone (564 mg, 5.64 mmol) in 80 mL of ethanol and 48 mL of water. The mixture was stirred at room temperature overnight, filtered, washed with water, EtOH/H$_2$O (1/1) and hexane, and dried to give the title compound (1.2 g, 74% yield): $^1$H NMR (400 MHz, CDCl$_3$): δ ppm 2.49 (s, 3H), 2.61 (s, 3H), 7.05-7.08 (m, 1H), 7.25-7.27 (m, 1H), 7.32 (s, 1H), 7.42 (t, J=8.0 Hz, 1H), 14.59 (s, 1H).

Reference Example 182

N-{4-[2-(1-Acetyl-2-oxopropylidene)hydrazino]phenyl}acetamide

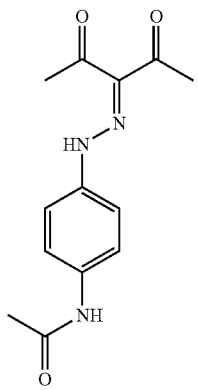 [SMILES: CC(=O)Nc1ccc(NN=C(C(C)=O)C(C)=O)cc1]

N-(4-Aminophenyl)acetamide (1000 mg, 6.66 mmol) was added to a solution of 6 mL of phosphoric acid (85%) and 4 mL of nitric acid (65%) at −6° C. When the mixture reached to room temperature, it was cooled to −6° C. and solid sodium nitrite (460 mg, 6.66 mmol) was added during 10 min. Small piece of ice (50 g) was added into the solution. The mixture was added at 0° C. to a suspension of 2,4-pentanedione (666 mg, 6.66 mmol) and potassium acetate (40 g) in ethanol (400 mL). The solution was stirred for 15 min, and then was added to 250 mL of saturated Na$_2$CO$_3$ aqueous solution, extracted with dichloromethane, washed with water and brine, dried over Na$_2$SO$_4$, and concentrated under reduced pressure to give the title compound (1400 mg, 80% yield): $^1$H NMR (400 MHz, CDCl$_3$): δ ppm 2.22 (3H, s), 2.48 (3H, s), 2.60 (3H, s), 7.22 (1H, brs), 7.38 (2H, d, J=8.8 Hz), 7.57 (2H, d, J=8.8 Hz), 14.84 (1H, s).

Reference Example 183

3-{[4-(Dimethylamino)phenyl]hydrazono}pentane-2,4-dione

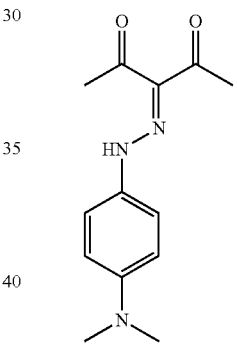

N,N-Dimethylbenzene-1,4-diamine (500 mg, 3.67 mmol) was added to a solution of 3 mL of phosphoric acid (85%) and 2 mL of nitric acid (65%) at −6° C. When the mixture reached to room temperature, it was cooled to −6° C. and sodium nitrite (253 mg, 3.67 mmol) was added during 10 min. Small piece of ice (50 g) was added into the solution. The mixture was added at 0° C. to a suspension of 2,4-pentanedione (367 mg, 3.67 mmol) and potassium acetate (20 g) in ethanol (250 mL). The solution was stirred for 15 min, and then was added to 250 mL of saturated Na$_2$CO$_3$ aqueous solution, extracted with dichloromethane, washed with water and brine, dried over Na$_2$SO$_4$, and concentrated under reduced pressure to give the title compound (870 mg, 96% yield) as a brown solid: $^1$H NMR (400 MHz, CDCl$_3$): δ ppm 2.89 (3H, s), 2.93 (3H, s), 2.96 (3H, s), 3.16 (3H, s), 7.77-7.83 (4H, m), 14.80 (1H, brs).

Reference Example 184

3-{[4-(4-Methylpiperazin-1-yl)phenyl]hydrazono}pentane-2,4-dione

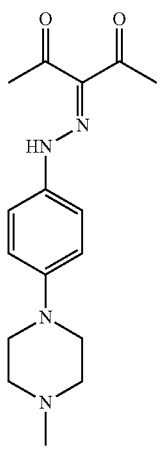 [SMILES: CC(=O)C(=NNc1ccc(N2CCN(C)CC2)cc1)C(C)=O]

4-(4-Methylpiperazin-1-yl)aniline (1000 mg, 5.24 mmol) was added to a solution of 6 mL of phosphoric acid (85%) and 4 mL of nitric acid (65%) at −6° C. When the mixture reached to room temperature, it was cooled to −6° C. and sodium nitrite (361 mg, 5.24 mmol) was added during 10 min. Small piece of ice (50 g) was added into the solution. The mixture was added at 0° C. to a suspension of 2,4-pentanedione (524 mg, 5.24 mmol) and potassium acetate (30 g) in ethanol (400 mL). The solution was stirred for 15 min, and then was added to 250 mL of saturated $Na_2CO_3$ aqueous solution, extracted with dichloromethane, washed with water and brine, dried over $Na_2SO_4$, and concentrated under reduced pressure to give the title compound (610 mg, 39% yield): $^1$H NMR (400 MHz, $CDCl_3$): δ ppm 2.40 (3H, s), 2.50 (3H, s), 2.62 (3H, s), 3.10 (4H, t, J=5.2 Hz), 3.25 (4H, t, J=4.8 Hz), 7.30 (2H, d, J=8.8 Hz), 7.37 (2H, d, J=7.6 Hz), 15.08 (1H, brs).

Reference Example 185

3-{[4-(1H-1,2,4-Triazol-1-yl)phenyl]hydrazono}pentane-2,4-dione

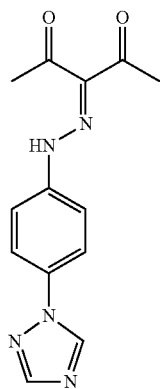

4-(1H-1,2,4-Triazol-1-yl)aniline (500 mg, 3.12 mmol) was added to a solution of 3 mL of phosphoric acid (85%) and 2 mL of nitric acid (65%) at −6° C. When the mixture reached to room temperature, it was cooled to −6° C. and sodium nitrite (216 mg, 3.12 mmol) was added during 10 min. Small piece of ice (50 g) was added into the solution. The mixture was added at 0° C. to a suspension of 2,4-pentanedione (312 mg, 3.12 mmol) and potassium acetate (20 g) in ethanol (250 mL). The solution was stirred for 15 min, and then was added to 250 mL of saturated $Na_2CO_3$ aqueous solution, extracted with dichloromethane, washed with water and brine, dried over $Na_2SO_4$, and concentrated under reduced pressure to give the title compound (600 mg, 71% yield) as a brown solid: $^1$H NMR (400 MHz, $CDCl_3$): δ ppm 2.54 (3H, s), 2.63 (3H, s), 7.55 (2H, d, J=8.8 Hz), 7.74 (2H, d, J=8.8 Hz), 8.12 (1H, s), 8.54 (1H, s), 14.76 (1H, s).

Reference Example 186

3-{[4-(Trifluoromethoxy)phenyl]hydrazono}pentane-2,4-dione

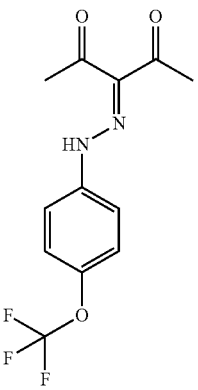 [SMILES: CC(=O)C(=NNc1ccc(OC(F)(F)F)cc1)C(C)=O]

4-(Trifluoromethoxy)aniline (1.00 g, 6.9 mmol) was added to a solution of 6 mL of phosphoric acid (85%) and 4 mL of nitric acid (65%) at −6° C., followed by sodium nitrite (0.601 g, 8.7 mmol, 1.2 equiv.) in 10 mL of water dropwise at 0° C., and the mixture was stirred at 0° C. for 30 min. Then to the reaction mixture was added dropwise a mixture of potassium acetate (2.028 g, 20.7 mmol, 3.0 equiv.) and acetylacetone (0.8 mL, 7.0 mmol, 1.0 equiv.) in 20 mL of ethanol. The mixture was stirred at room temperature for 15 min, filtered, extract with AcOEt, washed with brine and dried to give crude product (1.58 g, 88% yield), which was used directly to the next step. $^1$H NMR (400 MHz, $CDCl_3$): δ ppm 2.50 (s, 3H), 2.61 (s, 3H), 7.26-7.28 (m, 2H), 7.40-7.43 (m, 2H), 14.69 (s, 1H).

Reference Example 187

3-{[2-Fluoro-3-(trifluoromethyl)phenyl]hydrazono}pentane-2,4-dione

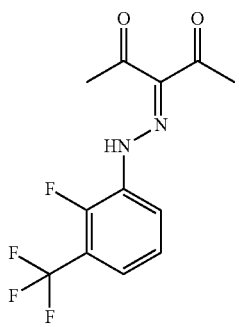 [SMILES: CC(=O)C(=NNc1cccc(C(F)(F)F)c1F)C(C)=O]

To a solution of 2-fluoro-3-(trifluoromethyl)aniline (1.0 g, 5.58 mmol) in 8 mL of acetic acid and 1.3 mL of concentrated hydrochloride solution, sodium nitrite (462 mg, 6.69 mmol) in 2.1 mL of water was added dropwise at 0° C., and the mixture was stirred at 0° C. for 1 h. Then to the reaction mixture were added sodium acetate (1.37 g, 16.8 mmol) and acetylacetone (726 mg, 7.26 mmol). The mixture was stirred at room temperature for 2 h, filtered, washed with water, EtOH/$H_2O$ (1/1) and hexane, and dried to give the title compound (900 mg, 55% yield). $^1$H NMR (400 MHz, $CDCl_3$): δ ppm 2.51 (s, 3H), 2.63 (s, 3H), 7.30-7.34 (m, 1H), 7.38-7.41 (m, 1H), 7.94-7.96 (m, 1H), 14.66 (s, 1H).

Reference Example 188

3-[(2,3-Difluorophenyl)hydrazono]pentane-2,4-dione

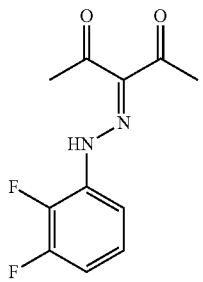 [SMILES: CC(=O)C(=NNc1cccc(F)c1F)C(C)=O]

To a solution of 2,3-difluoroaniline (1.0 g, 7.75 mmol) in 11.1 mL of acetic acid and 1.69 mL of concentrated hydrochloride solution, sodium nitrite (600 mg, 9.3 mmol) in 2.7 mL of water was added dropwise at 0° C., and the mixture was stirred at 0° C. for 1 h. Then to the reaction mixture was added dropwise a mixture of sodium acetate (1.78 g, 21.7 mmol, 3.0 equiv.) and acetylacetone (1 g, 10 mmol, 1.3 equiv.). The mixture was stirred at room temperature for 2 h, filtered, washed with water, EtOH/$H_2O$ (1/1) and hexane, and dried to give the title compound (900 mg, 48% yield): $^1$H NMR (400 MHz, $CDCl_3$): δ ppm 2.49 (s, 3H), 2.61 (s, 3H), 6.93-7.00 (m, 1H), 7.11-7.17 (m, 1H), 7.50-7.56 (m, 1H), 14.64 (s, 1H).

Reference Example 189

3-[(2,2-Difluoro-1,3-benzodioxol-4-yl)hydrazono]pentane-2,4-dione

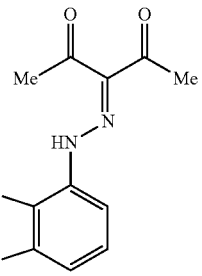

A solution of sodium nitrite (0.96 g, 14 mmol) in $H_2O$ (5 mL) was added dropwise to a solution of 2,2-difluoro-1,3-benzodioxol-4-amine (2.0 g, 12 mmol) in 6 M HCl aqueous solution (12 mL, 72 mmol) at 0° C. After stirring for 15 min at 0° C., the mixture was added to a suspension of 2,4-pentanedione (1.2 mL, 12 mmol) and sodium acetate (5.9 g, 72 mmol) in MeOH (20 mL) pre-cooled at 0° C. The formed precipitate was collected by filtration, washed with water and dissolved in AcOEt. The organic solution was washed with saturated $NaHCO_3$ aqueous solution and brine, dried over $MgSO_4$, filtered and concentrated under reduced pressure to give the title compound (3.0 g, 90% yield) as orange crystals: $^1$H NMR (300 MHz, $CDCl_3$): δ ppm 2.49 (3H, s), 2.63 (3H, s), 6.88 (1H, dd, J=8.0, 1.1 Hz), 7.13 (1H, t, J=8.1 Hz), 7.30 (1H, dd, J=8.5, 1.1 Hz), 14.56 (1H, brs).

Reference Example 190

3-{[2-Fluoro-4-(trifluoromethyl)phenyl]hydrazono}pentane-2,4-dione

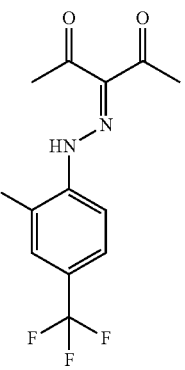

To a solution of 2-fluoro-4-(trifluoromethyl)aniline (1.0 g, 5.58 mmol) in 8 mL of acetic acid and 1.3 mL of concentrated hydrochloride solution, sodium nitrite (462 mg, 6.69 mmol) in 2.1 mL of water was added dropwise at 0° C., and the mixture was stirred at 0° C. for 1 h. Then to the reaction mixture were added sodium acetate (1.37 g, 16.8 mmol, 3.0 equiv.) and acetylacetone (726 mg, 7.26 mmol, 1.3 equiv.) The mixture was stirred at room temperature for 2 h, filtered, washed with water, EtOH/$H_2O$ (1/1) and hexane, and dried to give the title compound (720 mg, yield 44%): $^1$H NMR (400

MHz, CDCl$_3$): δ ppm 2.51 (s, 3H), 2.63 (s, 3H), 7.42-7.50 (m, 2H), 7.86 (t, J=8.0 Hz, 1H), 14.56 (s, 1H).

Reference Example 191 tert-Butyl [4-(difluoromethoxy)-2-fluorophenyl]carbamate

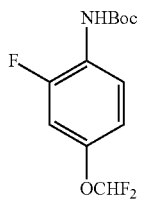

A solution of 4-(difluoromethoxy)-2-fluorobenzoic acid (1 g, 4.85 mmol), DPPA (1.6 g, 5.83 mmol) and Et$_3$N (0.59 g, 5.83 mmol) in 16 mL of t-BuOH was refluxed for 4 h, and then concentrated. The residue was dissolved in dichloromethane (40 mL), washed with 1M HCl aqueous solution, dried over Na$_2$SO$_4$, and concentrated under reduced pressure. The crude product was purified by flash column chromatography on silica gel (petroether/AcOEt=4/1) to get the title compound (850 mg, yield 63%) as a yellow solid: $^1$H NMR (400 MHz, CDCl$_3$): δ ppm 1.53 (s, 9H), 6.44 (t, J=73.6 Hz, 1H), 6.89-6.92 (m, 1H), 7.24-7.27 (m, 1H), 7.37-7.41 (m, 1H).

Reference Example 192

3-{[4-(Difluoromethoxy)-2-fluorophenyl]hydrazono}pentane-2,4-dione

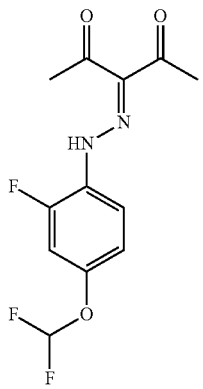 [SMILES: CC(=O)C(=NNc1ccc(OC(F)F)cc1F)C(C)=O]

A solution of tert-butyl [4-(difluoromethoxy)-2-fluorophenyl]carbamate (850 mg, 3.07 mmol) in 300 mL of HCl in AcOEt was stirred overnight and concentrated under reduced pressure.

To a solution of the residue in 5.5 mL of acetic acid and 0.9 mL of concentrated hydrochloride solution, sodium nitrite (239 mg, 3.39 mmol) in 1.4 mL of water was added dropwise at 0° C., and the mixture was stirred at 0° C. for 1 h. Then to the reaction mixture were added sodium acetate (703 mg, 8.47 mmol, 3.0 equiv.) and acetylacetone (367 mg, 3.67 mmol, 1.3 equiv.). The mixture was stirred at room temperature for 2 h, filtered, washed with water, EtOH/H$_2$O (1/1) and hexane, and dried to give the title compound (300 mg, 37% yield): $^1$H NMR (400 MHz, CDCl$_3$): δ ppm 2.49 (s, 3H), 2.62 (s, 3H), 6.51 (t, J=72.8 Hz, 1H), 6.95-7.04 (m, 2H), 7.73-7.77 (m, 1H), 14.70 (s, 1H).

Reference Example 193

2-Fluoro-4-(trifluoromethoxy)benzoic acid

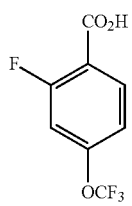

A solution of 1-bromo-2-fluoro-4-(trifluoromethoxy)benzene (8 g, 30.8 mmol) in 170 mL of THF was cooled to −40° C., and then i-PrMgBr (0.4 mol/L in THF, 91 mL) was injected. After being stirred for 3 h, CO$_2$ was injected for 2 h at 0° C. The mixture was washed with 1M HCl aqueous solution, separated. The aqueous layer was extracted with CH$_2$Cl$_2$. The combined organic layers were dried over Na$_2$SO$_4$, and concentrated under reduced pressure. The residue was washed with petroether to give the title compound (6 g, 87% yield): $^1$H NMR (400 MHz, CDCl$_3$): δ ppm 7.05-7.12 (m, 2H), 8.10 (t, J=8.4 Hz, 1H).

Reference Example 194 tert-Butyl [2-fluoro-4-(trifluoromethoxy)phenyl]carbamate

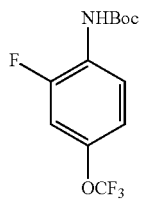

A solution of 2-fluoro-4-(trifluoromethoxy)benzoic acid (3 g, 13.4 mmol), DPPA (4.4 g, 16.1 mmol) and Et$_3$N (1.63 g, 16.1 mmol) in 130 mL of t-BuOH was refluxed for 4 h, and then concentrated. The residue was dissolved in dichloromethane (200 mL), washed with 1M HCl aqueous solution, dried over Na$_2$SO$_4$, and concentrated under reduced pressure. The crude product was purified by flash column chromatography on silica gel (petroether/AcOEt=4/1) to get the title compound (2 g, 50% yield) as a yellow solid: $^1$H NMR (400 MHz, CDCl$_3$): δ ppm 1.27 (s, 9H), 6.97-7.03 (m, 1H), 7.21-7.27 (m, 1H), 7.37-7.41 (m, 1H).

Reference Example 195

3-{[2-Fluoro-4-(trifluoromethoxy)phenyl]hydrazono}pentane-2,4-dione

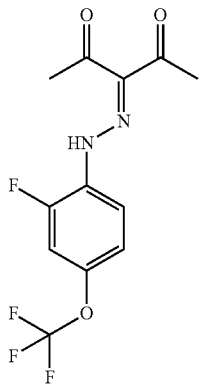 [SMILES: CC(=O)C(=NNc1ccc(OC(F)(F)F)cc1F)C(C)=O]

A solution of tert-butyl [2-fluoro4-(trifluoromethoxy)phenyl]carbamate (2 g, 6.8 mmol) in 300 mL of HCl in AcOEt was stirred for 3 h at 0° C. and concentrated under reduced pressure.

To a solution of the residue in 20 mL of acetic acid and 3.5 mL of concentrated hydrochloride solution, sodium nitrite (507 mg, 7.34 mmol) in 5 mL of water was added dropwise at 0° C., and the mixture was stirred at 0° C. for 1 h. Then to the reaction mixture were added sodium acetate (1.5 g, 18.3 mmol, 3.0 equiv.) and acetylacetone (793 mg, 7.93 mmol, 1.3 equiv.). The mixture was stirred at room temperature for 2 h, filtered, washed with water, EtOH/H$_2$O (1/1) and hexane, and dried to give the title compound (920 mg, 50% yield): $^1$H NMR (400 MHz, CDCl$_3$): δ ppm 2.50 (s, 3H), 2.63 (s, 3H), 7.08-7.13 (m, 2H), 7.78 (t, J=8.8 Hz, 1H), 14.65 (s, 1H).

Reference Example 196

3-[(2,4-Difluorophenyl)hydrazono]pentane-2,4-dione

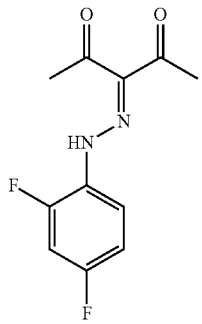 [SMILES: CC(=O)C(=NNc1ccc(F)cc1F)C(C)=O]

To a solution of 2,4-difluoroaniline (1.0 g, 7.75 mmol) in 11.1 mL of acetic acid and 1.69 mL of concentrated hydrochloride solution, sodium nitrite (600 mg, 9.3 mmol) in 2.7 mL of water was added dropwise at 0° C., and the mixture was stirred at 0° C. for 1 h. Then to the reaction mixture was added dropwise a mixture of sodium acetate (1.78 g, 21.7 mmol) and acetylacetone (1 g, 10 mmol). The mixture was stirred at room temperature for 2 h, filtered, washed with water, EtOH/H$_2$O (1/1) and hexane, and dried to give the title compound (550 mg, 30% yield): $^1$H NMR (400 MHz, CDCl$_3$): δ ppm 2.48 (s, 3H), 2.61 (s, 3H), 6.91-7.00 (m, 2H), 7.70-7.76 (m, 1H), 14.72 (s, 1H).

Reference Example 197

3-[(4-Chloro-2-fluorophenyl)hydrazono]pentane-2,4-dione

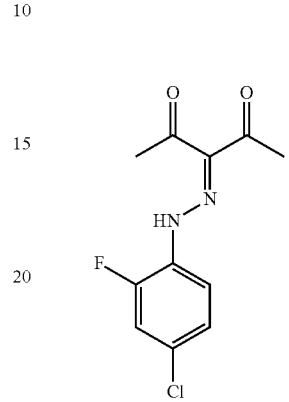

To a solution of 4-chloro-2-fluoroaniline (1 g, 6.87 mmol) in 9.8 mL of acetic acid and 1.6 mL of concentrated hydrochloride solution, sodium nitrite (568 mg, 8.24 mmol) in 2.6 mL of water was added dropwise at 0° C., and the mixture was stirred at 0° C. for 1 h. Then to the reaction mixture were added sodium acetate (1.69 g, 20.6 mmol) and acetylacetone (893 mg, 8.93 mmol). The mixture was stirred at room temperature for 2 h, filtered, washed with water, EtOH/H$_2$O (1/1) and hexane, and dried to give the title compound (1 g, 57% yield): $^1$H NMR (400 MHz, CDCl$_3$): δ ppm 2.49 (s, 3H), 2.60 (s, 3H), 7.15-7.25 (m, 2H), 7.69 (t, J=8.4 Hz, 1H), 14.64 (s, 1H).

Reference Example 198

3-{[2-Fluoro-5-(trifluoromethyl)phenyl]hydrazono}pentane-2,4-dione

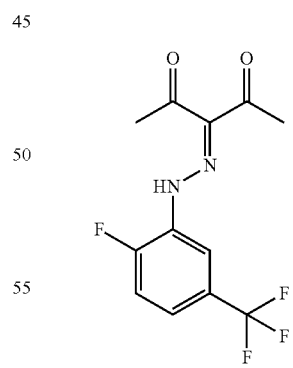

2-Fluoro-5-(trifluoromethyl)aniline (2.00 g, 15.6 mmol) was added to a solution of 15.6 mL of HOAc and 2.6 mL of concentrated HCl, stirred, followed by sodium nitrite (0.925 g, 13.4 mmol) in 4 mL of water dropwise at 0° C., and the mixture was stirred at 0° C. for 60 min. Then potassium acetate (3.28 g, 3.5 mmol) and acetylacetone (1.83 mL, 14.5 mmol) were added dropwise. The mixture was stirred at room temperature overnight, filtered. The precipitate was dissolved in CH$_2$Cl$_2$, washed with water, dried over Na$_2$SO$_4$ and concentrated under reduced pressure to give the title compound (2.06 g, 64% yield): $^1$H NMR (400 MHz, CDCl$_3$): δ ppm 2.53 (s, 3H), 2.64 (s, 3H), 7.26-6.30 (m, 1H), 7.39-7.42 (m, 1H), 7.99-8.01 (m, 1H), 14.62 (s, 1H).

Reference Example 199

3-[(2,5-Difluorophenyl)hydrazono]pentane-2,4-dione

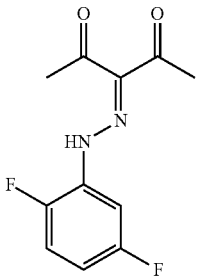 [SMILES: CC(=O)C(=NNc1cc(F)ccc1F)C(C)=O]

2,5-Difluoroaniline (2.10 g, 15.5 mmol) was added to a solution of 21.6 mL of HOAc and 3.6 mL of concentrated HCl, stirred, followed by sodium nitrite (1.28 g, 18.6 mmol) in 6 mL of water dropwise at 0° C., and the mixture was stirred at 0° C. for 60 min. Then potassium acetate (4.56 g, 46.5 mmol) and acetylacetone (2.07 mL, 20.15 mmol) were added dropwise. The mixture was stirred at room temperature overnight, filtered. The precipitate was dissolved in CH$_2$Cl$_2$, washed with water, dried over Na$_2$SO$_4$ and concentrated under reduced pressure to give a crude product (4.00 g, 67% yield), which was used directly to the next step: $^1$H NMR (400 MHz, CDCl$_3$): δ ppm 2.51 (s, 3H), 2.62 (s, 3H), 6.79-6.83 (m, 1H), 7.09-7.15 (m, 1H), 7.43-7.47 (m, 1H), 14.57 (s, 1H)

Reference Example 200

3-[(2,6-Difluorophenyl)hydrazono]pentane-2,4-dione

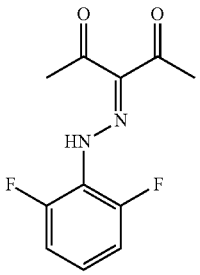 [SMILES: CC(=O)C(=NNc1c(F)cccc1F)C(C)=O]

To a solution of 2,6-difluoroaniline (1.0 g, 7.75 mmol) in 11.1 mL of acetic acid and 1.69 mL of concentrated hydrochloride solution, sodium nitrite (600 mg, 9.3 mmol) in 2.7 mL of water was added dropwise at 0° C., and the mixture was stirred at 0° C. for 1 h. Then to the reaction mixture were added sodium acetate (1.78 g, 21.7 mmol) and acetylacetone (1 g, 10 mmol). The mixture was stirred at room temperature for 2 h, filtered, washed with water, EtOH/H$_2$O (1:1) and hexane, and dried to give the title compound (400 mg, 21% yield): $^1$H NMR (400 MHz, CDCl$_3$): δ ppm 2.43 (s, 3H), 2.61 (s, 3H), 6.97-7.03 (m, 2H), 7.05-7.15 (m, 1H), 14.42 (s, 1H).

Reference Example 201

3-(1H-Pyrazol-5-yl)-1-[3-(trifluoromethyl)phenyl]pyridazin-4(1H)-one

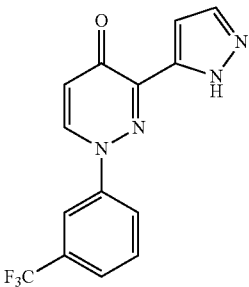 [SMILES: O=c1ccn(-c2cccc(C(F)(F)F)c2)nc1-c1ccn[nH]1]

A solution of 3-[3-(dimethylamino)prop-2-enoyl]-1-[3-(trifluoromethyl)phenyl]pyridazin-4(1H)-one (2.70 g, 8 mmol) and NH$_2$NH$_2$.H$_2$O (1.94 mL, 40 mmol) in MeOH (25 mL) was refluxed overnight. After cooling to room temperature, the reaction mixture was poured into 1 M HCl aqueous solution and extracted with AcOEt. The extract was washed with brine, dried over MgSO$_4$, and concentrated under reduced pressure. The residue was purified by basic silica gel column chromatography eluting with AcOEt and recrystallized from AcOEt to give the title compound (0.969 g, 40% yield) as an off-white solid: mp 192-194° C.; $^1$H NMR (300 MHz, CDCl$_3$): δ ppm 6.82 (1H, d, J=7.9 Hz), 7.03 (1H, d, J=1.9 Hz), 7.69 (1H, d, J=1.9 Hz), 7.72-7.76 (2H, m), 7.83-7.89 (1H, m), 7.91-7.93 (1H, m), 8.33 (1H, d, J=7.9 Hz), 12.85 (1H, brs). LC-MS (ESI) m/z 307 [M+H]$^+$. Anal. Calcd for C$_{14}$H$_9$F$_3$N$_4$O: C, 54.91; H, 2.96; N, 18.29. Found: C, 54.92; H, 2.99; N, 18.33.

Reference Example 202

3-[(4-Morpholin-4-ylphenyl)hydrazono]pentane-2,4-dione

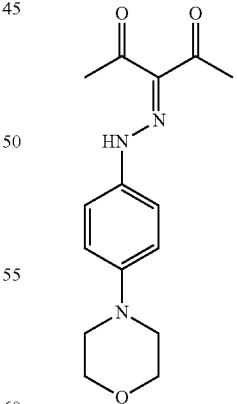

4-Morpholin-4-ylaniline (653 mg, 3.67 mmol) was added to a mixture of 3 mL of phosphoric acid (85%) and 2 mL of nitric acid (65%) at −6° C. When the resulting mixture reached to room temperature, it was cooled to −6° C. and sodium nitrite (253 mg, 3.67 mmol) was added during 10 min. Small piece of ice (50 g) was added into the solution. The mixture was added at 0° C. to a suspension of 2,4-pentanedione (367 mg, 3.67 mmol) and potassium acetate (20 g) in ethanol (250 mL). The solution was stirred for 15 min, and then added to 250 mL of saturated Na$_2$CO$_3$ aqueous solution, extracted with dichloromethane, washed with water and brine, dried over anhydrous Na$_2$SO$_4$, and concentrated under reduced pressure to give the title compound (870 mg, 82% yield) as a brown solid: $^1$H NMR (400 MHz, CDCl$_3$): δ 2.50 (3H, s), 2.61 (3H, s), 3.15-3.18 (4H, m), 3.80-3.83 (4H, m), 6.98-7.03 (2H, m), 7.45-7.50 (2H, m), 14.37 (1H, s).

Reference Example 203

3-[3-(Dimethylamino)prop-2-enoyl]-1-(4-morpholin-4-ylphenyl)pyridazin-4(1H)-one

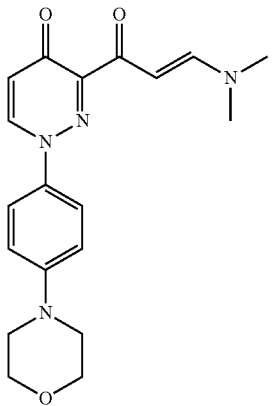 [SMILES: CN(C)/C=C/C(=O)c1nn(-c2ccc(N3CCOCC3)cc2)ccc1=O]

3-[(4-Morpholin-4-ylphenyl)hydrazono]pentane-2,4-dione (500 mg, 1.73 mmol) was dissolved in 10 mL of N,N-Dimethylformamide dimethyl acetal. The mixture was refluxed for 4 h and concentrated under reduced pressure to give the title compound as a brown oil which was used to the next step without further purification: $^1$H NMR (400 MHz, CDCl$_3$): δ 2.85-2.90 (3H, m), 3.10-3.14 (3H, m), 3.18-3.21 (4H, m), 3.85-3.88 (4H, m), 5.63-5.66 (1H, m), 6.68 (1H, d, J=8.0 Hz), 6.94-6.96 (2H, m), 7.45-7.48 (2H, m), 7.72 (1H, brs), 8.12 (1H, d, J=8.0 Hz).

Reference Example 204

3-Acetyl-1-(2-fluoro-5-iodophenyl)-5-methoxypyridazin-4(1H)-one

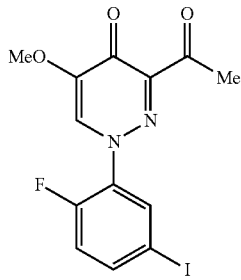 [SMILES: COc1cn(-c2cc(I)ccc2F)nc(C(C)=O)c1=O]

To a mixture of 1-(2-fluoro-5-iodophenyl)-N,5-dimethoxy-N-methyl-4-oxo-1,4-dihydropyridazine-3-carboxamide (4.33 g, 10.0 mmol) in THF (1.0 L) was added MeMgBr (1.0 M in THF, 20.0 mL, 20.0 mmol) at −78° C. under N$_2$. The mixture was stirred at −78° C. for 2 h. The reaction was quenched with saturated NH$_4$Cl aqueous solution at −78° C. The mixture was diluted with saturated NaHCO$_3$ aqueous solution, extracted with EtOAc, dried over Na$_2$SO$_4$, filtered, concentrated in vacuo, purified by column chromatography on silica gel (hexane/EtOAc=50/50 to 0/100 and EtOAc/MeOH=100/0 to 0/100) and triturated with EtOAc/hexane to yield the title compound (3.58 g, 92% yield) as a pale yellow solid: $^1$H NMR (DMSO-d$_6$, 300 MHz): δ ppm 2.50 (3H, s), 3.80 (3H, s), 7.38 (1H, dd, J=11.0, 8.7 Hz), 7.95 (1H, ddd, J=8.7, 4.5, 2.3 Hz), 8.15 (1H, dd, J=7.2, 2.3 Hz), 8.52 (1H, d, J=1.5 Hz).

Reference Example 205

1-[2-Fluoro-4-(1H-pyrazol-1-yl)phenyl]-N,5-dimethoxy-N-methyl-4-oxo-1,4-dihydropyridazine-3-carboxamide

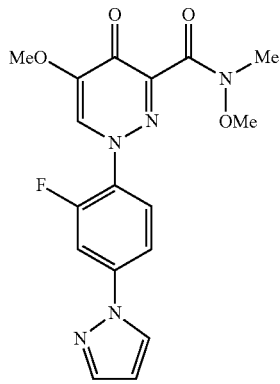 [SMILES: COc1cn(-c2ccc(-n3cccn3)cc2F)nc(C(=O)N(C)OC)c1=O]

A suspension of 1-(2-fluoro-4-iodophenyl)-N,5-dimethoxy-N-methyl-4-oxo-1,4-dihydropyridazine-3-carboxamide (1.73 g, 4 mmol), pyrazole (0.408 g, 6 mmol), Cu$_2$O (0.057 g, 0.4 mmol), salicylaldoxime (0.219 g, 1.6 mmol), and Cs$_2$CO$_3$ (2.60 g, 8 mmol) in CH$_3$CN (8 mL) was refluxed for 6 h under Ar atmosphere. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with AcOEt and recrystallized from MeOH/H$_2$O to give the title, compound (0.370 g, 25% yield) as a white solid: mp 187-189° C.; $^1$H NMR (300 MHz, CDCl$_3$): δ ppm 3.40 (3H, s), 3.72 (3H, s), 3.93 (3H, s), 6.55 (1H, dd, J=1.5, 2.3 Hz), 7.60 (1H, ddd, J=1.1, 2.3, 9.0 Hz), 7.71-7.77 (3H, m), 7.84 (1H, d, J=2.3 Hz), 7.98 (1H, d, J=2.6 Hz). Anal. Calcd for C$_{17}$H$_{16}$FN$_5$O$_4$: C, 54.69; H, 4.32; N, 18.76. Found: C, 54.58; H, 4.40; N, 18.67.

Reference Example 206

3-Acetyl-1-[2-fluoro-4-(1H-pyrazol-1-yl)phenyl]-5-methoxypyridazin-4(1H)-one

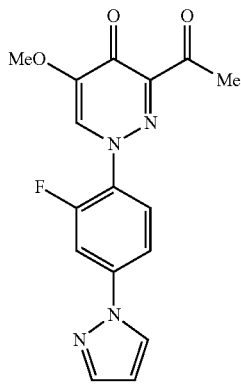 [SMILES: COc1cn(-c2ccc(-n3cccn3)cc2F)nc(C(C)=O)c1=O]

MeMgBr (1 M solution in THF, 2.8 mL, 2.8 mmol) was added dropwise at −78° C. to a solution of 1-[2-fluoro-4-(1H-pyrazol-1-yl)phenyl]-N,5-dimethoxy-N-methyl-4-oxo-1,4-dihydropyridazine-3-carboxamide (351 mg, 0.94 mmol) in THF (100 mL). After stirring for 1 h, the reaction mixture was quenched with 1 M HCl aqueous solution and extracted with AcOEt. The extract was washed with brine, dried over MgSO$_4$, and concentrated under reduced pressure. The residue was purified by silica gel column chromatography eluting with AcOEt and recrystallized from MeOH/H$_2$O to give the title compound (223 mg, 72% yield) as a pale yellow solid: mp 159-161° C.; $^1$H NMR (300 MHz, CDCl$_3$): δ ppm 2.69 (3H, s), 3.93 (3H, s), 6.56 (1H, dd, J=1.5, 2.3 Hz), 7.64 (1H, ddd, J=1.1, 2.3, 9.0 Hz), 7.71-7.79 (4H, m), 7.99 (1H, d, J=2.6 Hz). Anal. Calcd for C$_{16}$H$_{13}$FN$_4$O$_3$: C, 58.54; H, 3.99; N, 17.07. Found: C, 58.42; H, 4.01; N, 16.98.

Reference Example 207

Methyl 4-methoxy-3-oxo-2-(pyridin-3-ylhydrazono)butanoate

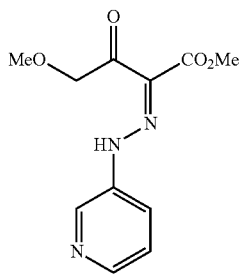 [SMILES: COCC(=O)/C(=N\Nc1cccnc1)C(=O)OC]

A solution of 3-aminopyridine (20 g, 210 mmol) in 6 M HCl aqueous solution (200 ml, 1200 mmol) was cooled with ice bath. To the solution was added dropwise a solution of sodium nitrite (18 g, 260 mmol) in water (40 mL). After stirring at 0° C. for 5 min, the mixture was added to a mixture of sodium acetate (130 g, 1300 mmol) and methyl 4-methoxyacetoacetate (28 ml, 210 mmol) in EtOH (300 ml) and water (150 ml) at 0° C., and the mixture was stirred at 0° C. for 1 h. The mixture was diluted with water (150 ml), extracted with AcOEt (500 ml×3). The combined organic layer was washed with saturated NaHCO$_3$ aqueous solution (300 ml×3) and brine (300 ml), dried over Na$_2$SO$_4$, filtered and concentrated under reduced pressure to give the title compound (52 g, 97% yield) as a brown oil: $^1$H NMR (300 MHz, CDCl$_3$): δ ppm 3.50 (3H×½, s), 3.51 (3H×½, s), 3.89 (3H×½, s), 3.93 (3H×½, s), 4.67 (2H×½, s), 4.70 (2H×½, s), 7.35-7.43 (1H, m), 7.67-7.74 (1H×½, m), 7.84-7.91 (1H×½, m), 8.41-8.49 (1H, m), 8.64-8.71 (1H, m), 12.90 (1H×½, s), 14.76 (1H×½, brs).

Reference Example 208

Methyl 5-methoxy-4-oxo-1-pyridin-3-yl-1,4-dihydropyridazine-3-carboxylate

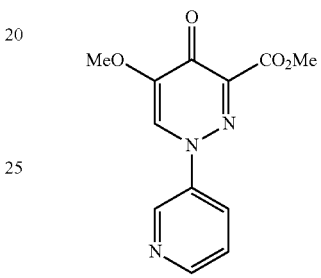

A mixture of methyl 4-methoxy-3-oxo-2-(pyridin-3-ylhydrazono)butanoate (52 g, 210 mmol) in N,N-dimethylformamide dimethyl acetal (80 mL, 600 mmol) was refluxed for 30 min. The mixture was allowed to cool to room temperature and stayed at room temperature overnight. The formed crystals were collected by filtration and washed with AcOEt to give the title compound (35 g, 64% yield) as pale yellow crystals: $^1$H NMR (300 MHz, CDCl$_3$): δ ppm 3.98 (3H, s), 3.98 (3H, s), 7.48-7.54 (1H, m), 7.96 (1H, s), 8.04 (1H, ddd, J=8.4, 2.6, 1.5 Hz), 8.71 (1H, dd, J=4.9, 1.5 Hz), 8.93 (1H, d, J=2.6 Hz).

Reference Example 209

5-Methoxy-4-oxo-1-pyridin-3-yl-1,4-dihydropyridazine-3-carboxylic acid hydrochloride

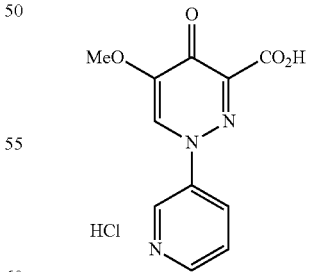

A solution of methyl 5-methoxy-4-oxo-1-pyridin-3-yl-1,4-dihydropyridazine-3-carboxylate (2.0 g, 7.7 mmol) in 6 M HCl aqueous solution (20 ml) was refluxed for 4 h. The mixture was concentrated under reduced pressure to give the title compound (2.1 g, 95% yield) as off-white crystals: $^1$H NMR (300 MHz, DMSO-d$_6$): δ ppm 3.98 (3H, s), 7.78 (1H, dd, J=8.7, 4.5 Hz), 8.36-8.42 (1H, m), 8.79 (1H, dd, J=4.5, 1.1 Hz), 9.02 (1H, s), 9.15 (1H, d, J=2.6 Hz).

Reference Example 210

N,5-Dimethoxy-N-methyl-4-oxo-1-pyridin-3-yl-1,4-dihydropyridazine-3-carboxamide

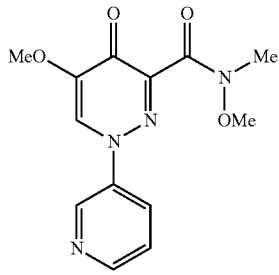 [SMILES: COc1cn(-c2cccnc2)nc(C(=O)N(C)OC)c1=O]

A mixture of 5-methoxy-4-oxo-1-pyridin-3-yl-1,4-dihydropyridazine-3-carboxylic acid hydrochloride (1.0 g, 3.5 mmol), N,O-dimethylhydroxylamine hydrochloride (0.52 g, 5.3 mmol), TEA (1.5 ml, 11 mmol) and O-benzotriazol-1-yl-N,N,N',N'-tetramethyluronium tetrafluoroborate (1.2 g, 3.9 mmol) in DMF (15 ml) was stirred at room temperature overnight. The mixture was diluted with AcOEt. The precipitate was filtered off and the filtrate was concentrated under reduced pressure. The residue was chromatographed on basic silica gel (0/100-20/80 MeOH/AcOEt) to give the title compound (0.81 g, 79% yield) as white crystals: $^1$H NMR (300 MHz, CDCl$_3$): δ ppm 3.41 (3H, s), 3.71 (3H, s), 3.98 (3H, s), 7.48 (1H, dd, J=8.3, 4.5 Hz), 7.97 (1H, s), 8.00-8.05 (1H, m), 8.67 (1H, dd, J=4.5, 1.3 Hz), 8.91 (1H, d, J=2.6 Hz).

Reference Example 211

3-Acetyl-5-methoxy-1-pyridin-3-ylpyridazin-4(1H)-one

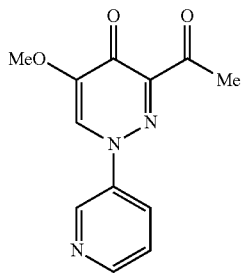 [SMILES: COc1cn(-c2cccnc2)nc(C(C)=O)c1=O]

To a solution of N,5-dimethoxy-N-methyl-4-oxo-1-pyridin-3-yl-1,4-dihydropyridazine-3-carboxamide (0.40 g, 1.4 mmol) in THF (10 ml) was added dropwise 1 M MeMgBr in THF (3.0 ml, 3.0 mmol) at −78° C. After stirring at −78° C. for 2 h, the mixture was quenched with water (0.5 ml) and stirred at room temperature for 0.1 h. The mixture was concentrated under reduced pressure. The residue was partitioned between CHCl$_3$ (25 ml) and brine. The aqueous layer was extracted with CHCl$_3$ (25 ml×3). The combined organic layer was dried over Na$_2$SO$_4$, filtered and concentrated under reduced pressure to give the title compound (0.21 g, 62% yield) as yellow crystals: $^1$H NMR (300 MHz, CDCl$_3$): δ ppm 2.70 (3H, s), 3.97 (3H, s), 7.49-7.56 (1H, m), 7.95 (1H, s), 8.01-8.08 (1H, m), 8.72 (1H, dd, J=4.7, 1.3 Hz), 8.95 (1H, d, J=2.6 Hz).

Reference Example 212

Methyl 2-[(4-bromo-2,5-difluorophenyl)hydrazono]-4-methoxy-3-oxobutanoate

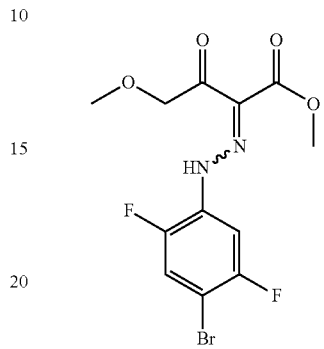

A solution of NaNO$_2$ (7.9 g, 115 mmol) in H$_2$O (20 mL) was added dropwise at 0° C. to a mixture of 4-bromo-2,5-difluoroaniline (20 g, 96 mmol) and 6 M HCl aqueous solution (96 mL, 576 mmol). After stirring for 15 min, the resulting aqueous solution was added to a suspension of methyl 4-methoxyacetoacetate (12.4 mL, 96 mmol) and NaOAc (34 g, 576 mmol) in MeOH (165 mL) pre-cooled at 0° C. The precipitate was collected by filtration, washed with water and dried at room temperature to give the title compound (37 g, 100% yield) as a red solid: $^1$H NMR (300 MHz, DMSO-d$_6$): δ ppm 3.34 (3H, s), 3.83 (3H, s), 4.68 (2H, s), 7.70 (1H, dd, J=9.7, 7.0 Hz), 7.89 (1H, dd, J=10.6, 6.1 Hz), 12.16 (1H, s).

Reference Example 213

Methyl 1-(4-bromo-2,5-difluorophenyl)-5-methoxy-4-oxo-1,4-dihydropyridazine-3-carboxylate

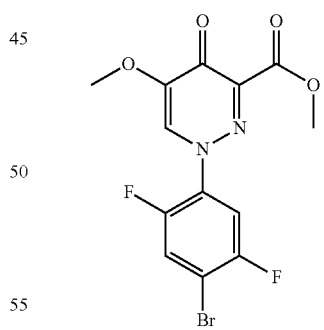

A solution of methyl 2-[(4-bromo-2,5-difluorophenyl)hydrazono]-4-methoxy-3-oxobutanoate (33 g, 90 mmol) in N,N-dimethylformamide dimethyl acetal (72 mL) was stirred at 110° C. for 3 h. After cooling to room temperature, the mixture was concentrated under reduce pressure. To the residue were added MeOH and silica gel The mixture was evaporated and purified by silica gel column chromatography eluting with hexane/AcOEt (1/0 to 0/1) and then AcOEt/MeOH (4/1) to give the title compound (27.9 g, 83% yield) as a brown gum: $^1$H NMR (300 MHz, DMSO-d$_5$): δ ppm 3.80

(3H, s), 3.83 (3H, s), 8.01 (1H, dd, J=8.7, 6.8 Hz), 8.15 (1H, dd, J=9.8, 6.0 Hz), 8.55 (1H, d, J=1.5 Hz). LC-MS (ESI) m/z 376 [M+H]$^+$.

Reference Example 214

1-(4-Bromo-2,5-difluorophenyl)-5-methoxy-4-oxo-1,4-dihydropyridazine-3-carboxylic acid

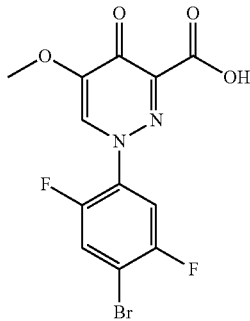 [SMILES: COc1cn(-c2cc(F)c(Br)cc2F)nc(C(=O)O)c1=O]

A solution of methyl 1-(4-bromo-2,5-difluorophenyl)-5-methoxy-4-oxo-1,4-dihydropyridazine-3-carboxylate (25 g, 68 mmol) and 2 M NaOH aqueous solution (68 mL) in EtOH (68 mL) was stirred at room temperature overnight. The solvent was removed by evaporation and resulting aqueous solution was acidified by 6 M HCl aqueous solution (12 mL). The precipitate was collected by filtration and azeotroped with toluene to give the title compound (25 g, 100% yield) as a brown solid: LC-MS (ESI) m/z 376 [M+H]$^+$.

Reference Example 215

1-(4-Bromo-2,5-difluorophenyl)-N,5-dimethoxy-N-methyl-4-oxo-1,4-dihydropyridazine-3-carboxamide

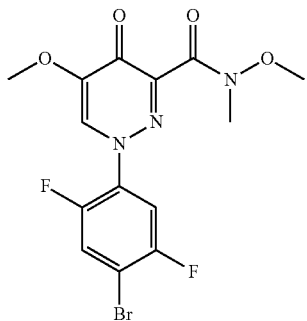

A mixture of 1-(4-bromo-2,5-difluorophenyl)-5-methoxy-4-oxo-1,4-dihydropyridazine-3-carboxylic acid (25 g, 83 mmol), N,O-dimethylhydroxylamine hydrochloride (8.9 g, 91 mmol), HOBt (12 g, 91 mmol), triethylamine (24 mL, 174 mmol) and WSC (17 g, 91 mmol) in DMF (160 mL) was stirred at room temperature for 18 h. The mixture was diluted with AcOEt, washed with water and brine, dried over MgSO$_4$ and concentrated under reduced pressure. The residue was purified by silica gel column chromatography eluting with Hexane/AcOEt (1/0 to 0/1) and then AcOEt/MeOH (10/1) to give the title compound (11 g, 31% yield) as a yellow solid: LC-MS (ESI) m/z 405 [M+H]$^+$.

Reference Example 216

3-Acetyl-1-(4-bromo-2,5-difluorophenyl)-5-methoxypyridazin-4(1H)-one

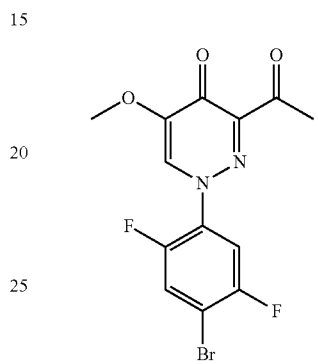

A solution of 1-(4-bromo-2,5-difluorophenyl)-N,5-dimethoxy-N-methyl-4-oxo-1,4-dihydropyridazine-3-carboxamide (5.0 g, 12 mmol) in THF (100 mL) was added dropwise to MeMgBr (1.0 M in THF, 50 mL, 50 mmol) at −78° C. under N$_2$. The mixture was stirred at −78° C. for 1 h. The reaction was quenched with 1 M HCl aqueous solution (70 mL) at −78° C. The mixture warmed up to room temperature and extracted with AcOEt. The organic layer was dried over MgSO$_4$ and concentrated under reduced pressure to give the title compound (3.6 g, 80% yield) as a yellow solid: $^1$H NMR (300 MHz, DMSO-d$_6$): δ ppm 2.50 (3H, s), 3.80 (3H, s), 8.03 (1H, dd, J=8.9, 6.6 Hz), 8.17 (1H, dd, J=10.0, 6.2 Hz), 8.52 (1H, d, J=1.5 Hz). LC-MS (ESI) m/z 360 [M+H]$^+$.

Reference Example 217

5,5-Dimethyl-1,3-oxazolidin-2-one

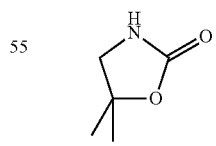

The mixture of 1-amino-2-methylpropan-2-ol (1.03 g, 11.6 mmol) and CDI (1.87 g, 11.6 mmol) in THF (40 ml) was stirred at room temperature for 15 h. After solvent evaporated, the residue was purified by silica gel column chromatography (AcOEt/hexane=25%-100%) to give the title compound (1.13 g, 85% yield) as a colorless solid: $^1$H NMR (300 MHz, CDCl$_3$): ε ppm 1.48 (6H, s), 3.35 (2H, s), 5.86 (1H, brs)

Reference Example 218

4-Oxa-6-azaspiro[2.4]heptan-5-one

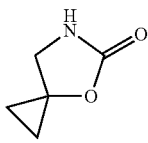

A solution of 1-(aminomethyl)cyclopropanol (0.58 g, 6.7 mmol) and CDI (1.1 g, 6.7 mmol) in THF (20 ml) was stirred at room temperature overnight. The mixture was concentrated under reduced pressure. The residue was chromatographed on silica gel (25/75-70/30 AcOEt/hexane) to give the title compound (0.42 g, 56% yield) as white crystals: $^1$H NMR (300 MHz, CDCl$_3$): δ ppm 0.68-0.75 (2H, m), 1.20-1.27 (2H, m), 3.68 (2H, s), 5.48 (1H, brs).

Reference Example 219

1-(4-Iodo-2-methoxyphenyl)-N,5-dimethoxy-N-methyl-4-oxo-1,4-dihydropyridazine-3-carboxamide

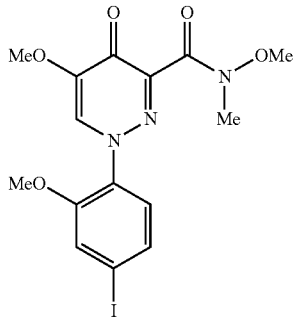 [SMILES: COc1cc(I)ccc1-n1cc(OC)c(=O)c(C(=O)N(C)OC)n1]

A solution of NaNO$_2$ (24.8 g, 360 mmol) in H$_2$O (75 mL) was added dropwise at 0° C. to a mixture of 2-fluoro-4-iodoaniline (71.1 g, 300 mmol) and 6 M HCl aqueous solution (300 mL). After stirring for 15 min, the resulting aqueous solution was added to a suspension of methyl 4-methoxyacetoacetate (43.8 g, 300 mmol) and NaOAc (147.6 g, 1.8 mol) in MeOH (600 mL) pre-cooled at 0° C. The precipitate was collected by filtration, washed with water, dried in air overnight. A solution of the product in N,N-dimethylformamide dimethyl acetal (450 mL) was refluxed for 4 h. After cooling to room temperature, the precipitate was collected by filtration and rinsed with hexane/AcOEt (1/1). The resulting products (54 g) were used the next reaction without further purification.

To a suspension of the products (54 g) in THF/MeOH (1/1, 400 mL) was added 10% NaOH aqueous solution (200 mL) at 0° C. The mixture was stirred at room temperature for 45 min. To the suspension was added 10% HCl aqueous solution (200 mL) at 0° C. The mixture was stirred at room temperature for 1 h. The precipitates were collected by filtration and rinsed with $^i$Pr$_2$O. The resulting products (45 g) were used the next reaction without further purification.

A mixture of the products (45 g), N-methoxymethanamine hydrochloride (12.4 g, 127 mmol), HOBt (18.7 g, 138 mmol), WSC (26.5 g, 138 mmol) and Et$_3$N (48.2 mL, 346 mmol) in DMF (500 mL) was stirred at room temperature overnight. The mixture was partitioned between AcOEt and H$_2$O; and the organic layer was washed with NaCl aqueous solution, dried over Na$_2$SO$_4$ and evaporated. The residue was purified by column chromatography on silica gel (AcOEt/MeOH=100/0 to 95/5) to yield the title compound (32.7 g, 20% yield) as a white solid and 1-(2-fluoro-4-iodophenyl)-N,5-dimethoxy-N-methyl-4-oxo-1,4-dihydropyridazine-3-carboxamide (10 g, 6% yield) as a white solid. $^1$H NMR (300 MHz, CDCl$_3$): δ ppm 3.38 (3H, s), 3.70 (3H, s), 3.88 (3H, s), 3.89 (3H, s), 7.23 (1H, d, J=8.3 Hz), 7.37 (1H, d, J=1.9 Hz), 7.43 (1H, dd, J=8.3, 1.9 Hz), 7.77 (1H, s). LC-MS (ESI) m/z 446 [M+H]$^+$.

Reference Example 220

N,5-Dimethoxy-1-[2-methoxy-4-(1H-pyrazol-1-yl)phenyl]-N-methyl-4-oxo-1,4-dihydropyridazine-3-carboxamide

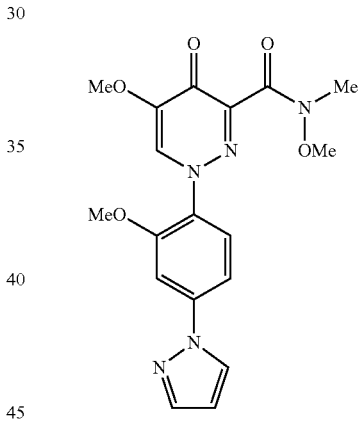

A suspension of 1-(4-iodo-2-methoxyphenyl)-N,5-dimethoxy-N-methyl-4-oxo-1,4-dihydropyridazine-3-carboxamide (10.7 g, 24 mmol), pyrazole (1.63 g, 24 mmol), Cu$_2$O (0.343 g, 2.4 mmol), salicylaldoxime (1.32 g, 9.6 mmol), and Cs$_2$CO$_3$ (15.6 g, 48 mmol) in CH$_3$CN (100 mL) was refluxed for 4 h under Ar atmosphere. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with AcOEt/THF (1/0-0/1) to give the title compound (6.32 g, 68% yield) as a pale yellow amorphous solid: $^1$H NMR (300 MHz, CDCl$_3$): δ ppm 3.39 (3H, s), 3.73 (3H, s), 3.91 (3H, s), 3.99 (3H, s), 6.53 (1H, dd, J=1.9, 2.3 Hz), 7.27 (1H, dd, J=2.3, 8.7 Hz), 7.58 (1H, d, J=8.7 Hz), 7.61 (1H, d, J=1.9 Hz), 7.77 (1H, d, J=1.5 Hz), 7.84 (1H, s), 7.98 (1H, d, J=2.3 Hz).

Reference Example 221

3-Acetyl-5-methoxy-1-[2-methoxy-4-(1H-pyrazol-1-yl)phenyl]pyridazin-4(1H)-one

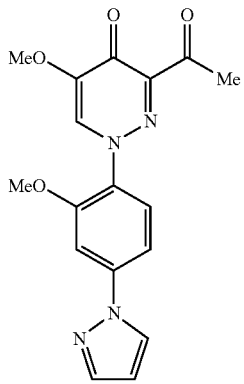 [SMILES: COc1cc(-n2cccn2)ccc1-n1cc(OC)c(=O)c(C(C)=O)n1]

MeMgBr (1 M solution in THF, 50 mL, 50 mmol) was added dropwise at −78° C. to a solution of N,5-dimethoxy-1-[2-methoxy-4-(1H-pyrazol-1-yl)phenyl]-N-methyl-4-oxo-1,4-dihydropyridazine-3-carboxamide (6.32 g, 16.4 mmol) in THF (100 mL). After stirring for 1 h, the reaction mixture was quenched with 1 M HCl aqueous solution and extracted with AcOEt. The extract was washed with brine, dried over MgSO$_4$, and concentrated under reduced pressure. The residue was washed with AcOEt and recrystallized from MeOH to give the title compound (1.53 g, 27% yield) as pale yellow prisms: mp 193-196° C.; $^1$H NMR (300 MHz, CDCl$_3$): δ ppm 2.69 (3H, s), 3.90 (3H, s), 4.00 (3H, s), 6.54 (1H, dd, J=1.9, 2.3 Hz), 7.30 (1H, dd, J=2.3, 8.7 Hz), 7.57 (1H, d, J=8.7 Hz), 7.63 (1H, d, J=2.3 Hz), 7.77-7.78 (2H, m), 8.00 (1H, d, J=2.3 Hz). Anal. Calcd for C$_{17}$H$_{16}$N$_4$O$_4$: C, 59.99; H, 4.74; N, 16.46. Found: C, 59.68; H, 5.00; N, 16.26.

Reference Example 222

4-(2,3-Difluoro-4-nitrophenyl)morpholine

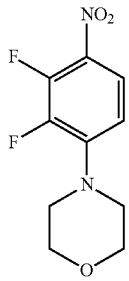

A mixture of 1,2,3-trifluoro-4-nitrobenzene (4.0 mL, 35 mmol), morpholine (3.1 mL, 35 mmol), and K$_2$CO$_3$ (4.8 g, 35 mmol) in DMSO (35 mL) was stirred at room temperature overnight. The mixture was diluted with AcOEt and washed with water and brine. The organic layer was dried over MgSO$_4$, and concentrated under reduced pressure. The residue was recrystallized from AcOEt to give the title compound (11.5 g, 67% yield) as a pale yellow solid: $^1$H NMR (300 MHz, DMSO-d$_6$): δ ppm 3.09-3.51 (4H, m), 3.58-4.08 (4H, m), 6.98 (1H, ddd, J=9.8, 8.1, 2.1 Hz), 7.94 (1H, ddd, J=9.9, 8.0, 2.1 Hz). LC-MS (ESI) m/z 245 [M+H]$^+$.

Reference Example 223

2,3-Difluoro-4-morpholin-4-ylaniline

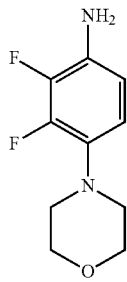

A mixture of 4-(2,3-difluoro-4-nitrophenyl)morpholine (11.5 g, 47 mmol) and 10% Pd—C (50% wet, 1.2 g) in EtOH (150 mL) was hydrogenated for 5 h at room temperature. The reaction mixture was filtered by celite and the filtrate was concentrated under reduced pressure. The residue was recrystallized from $^i$Pr$_2$O/AcOEt to give the title compound (8.7 g, 86% yield) as a pale red powder: $^1$H NMR (300 MHz, DMSO-d$_6$): δ ppm 2.77-2.95 (4H, m), 3.60-3.79 (4H, m), 5.07 (2H, s), 6.49 (1H, td, J=9.0, 1.9 Hz), 6.62 (1H, td, J=8.9, 2.3 Hz). LC-MS (ESI) ink 215 [M+H]$^+$.

Reference Example 224

Methyl 2-[(2,3-difluoro-4-morpholin-4-ylphenyl)hydrazono]-4-methoxy-3-oxobutanoate

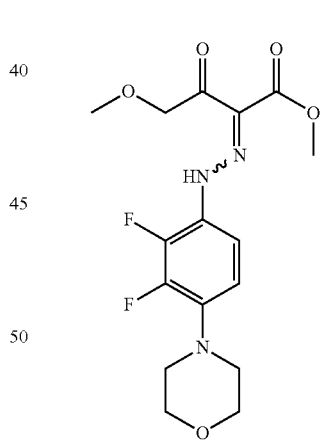

A solution of NaNO$_2$ (3.4 g, 49 mmol) in H$_2$O (10 mL) was added dropwise at 0° C. to a mixture of 2,3-difluoro-4-morpholin-4-ylaniline (8.7 g, 41 mmol) and 6 M HCl aqueous solution (41 mL, 244 mmol). After stirring for 15 min, the resulting aqueous solution was added to a suspension of methyl 4-methoxyacetoacetate (5.2 mL, 41 mmol) and NaOAc (14.3 g, 244 mmol) in MeOH (40 mL) pre-cooled at 0° C. The mixture was adjusted to pH 7 with 1 M NaOH aqueous solution (200 mL). The precipitate was collected by filtration, washed with water and dried at room temperature to give the title compound (4.7 g, 31% yield) as a red solid: LC-MS (ESI) m/z 372 [M+H]$^+$.

Reference Example 225

Methyl 1-(2,3-difluoro-4-morpholin-4-ylphenyl)-5-methoxy-4-oxo-1,4-dihydropyridazine-3-carboxylate

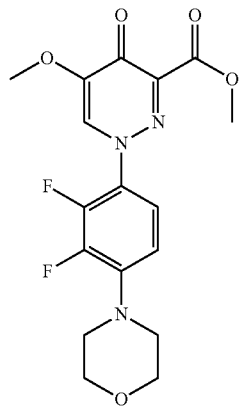

A solution of methyl 2-[(2,3-difluoro-4-morpholin-4-ylphenyl)hydrazono]-4-methoxy-3-oxobutanoate (4.7 g, 13 mmol) in N,N-dimethylformamide dimethyl acetal (20 mL) was stirred at 100° C. for 80 min. After cooling to room temperature, the precipitate was collected by filtration and washed with $^i$Pr$_2$O to give the title compound (4.1 g, 84% yield) as a brown powder: $^1$H NMR (300 MHz, DMSO-d$_6$): δ ppm 3.13 (4H, dt, J=4.4, 2.5 Hz), 3.49-4.05 (10H, m), 7.03 (1H, td, J=8.8, 2.5 Hz), 7.51 (1H, td, J=8.5, 2.3 Hz), 8.53 (1H, d, J=1.5 Hz). LC-MS (ESI) m/z 382 [M+H]$^+$.

Reference Example 226

1-(2,3-Difluoro-4-morpholin-4-ylphenyl)-5-methoxy-4-oxo-1,4-dihydropyridazine-3-carboxylic acid

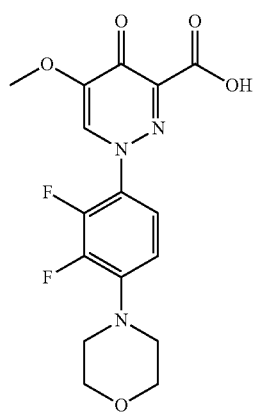 [SMILES: COc1cn(-c2ccc(N3CCOCC3)c(F)c2F)nc(C(=O)O)c1=O]

A solution of methyl 1-(2,3-difluoro-4-morpholin-4-ylphenyl)-5-methoxy-4-oxo-1,4-dihydropyridazine-3-carboxylate (4.1 g, 11 mmol) and 2 M NaOH aqueous solution (11 mL, 22 mmol) in EtOH (20 mL) was stirred at room temperature for 16 h. To the mixture was added 1 M HCl aqueous solution (21 mL). The precipitate was collected by filtration and dried over under reduced pressure to give the title compound (3.8 g, 98% yield) as a white solid: $^1$H NMR (300 MHz, DMSO-d$_6$): δ ppm 3.06-3.23 (4H, m), 3.66-3.82 (4H, m), 3.88 (3H, s), 6.84-7.27 (1H, m), 7.36-7.74 (1H, m), 8.86 (1H, d, J=1.1 Hz), 14.95 (1H, brs). LC-MS (ESI) m/z 368 [M+H]$^+$.

Reference Example 227

1-(2,3-Difluoro-4-morpholin-4-ylphenyl)-N,5-dimethoxy-N-methyl-4-oxo-1,4-dihydropyridazine-3-carboxamide

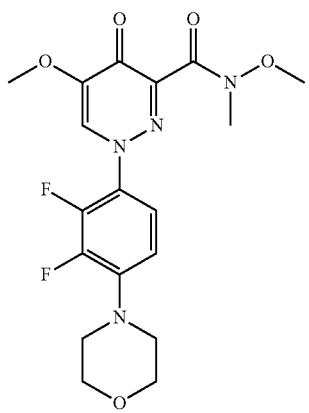

A mixture of 1-(2,3-difluoro-4-morpholin-4-ylphenyl)-5-methoxy-4-oxo-1,4-dihydropyridazine-3-carboxylic acid (3.8 g, 10 mmol), N,O-dimethylhydroxylamine hydrochloride (1.1 g, 11 mmol), HOBt (1.5 g, 11 mmol), triethylamine (2.9 mL, 21 mmol) and WSC (2.2 g, 11 mmol) in DMF (20 mL) was stirred at room temperature overnight. The mixture was diluted with AcOEt, washed with water and brine, dried over MgSO$_4$ and concentrated under reduced pressure to give the title compound (3.3 g, 77% yield) as a brown solid: $^1$H NMR (300 MHz, DMSO-d$_6$): δ ppm 3.05-3.18 (4H, m), 3.24 (3H, s), 3.57 (3H, s), 3.68-4.02 (7H, m), 7.03 (1H, td, J=8.8, 2.1 Hz), 7.27-7.81 (1H, m), 8.50 (1H, s). LC-MS (ESI) m/z 411 [M+H]$^+$.

Reference Example 228

3-Acetyl-1-(2,3-difluoro-4-morpholin-4-ylphenyl)-5-methoxypyridazin-4(1H)-one

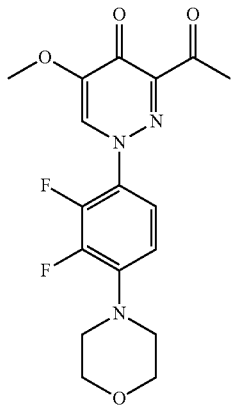 [SMILES: COc1cn(-c2ccc(N3CCOCC3)c(F)c2F)nc(C(C)=O)c1=O]

A solution of 1-(2,3-difluoro-4-morpholin-4-ylphenyl)-N,5-dimethoxy-N-methyl-4-oxo-1,4-dihydropyridazine-3-carboxamide (1.1 g, 2.6 mmol) in THF (25 mL) was added dropwise to MeMgBr (1.0 M in THF, 11 mL, 11 mmol) at −78° C. under $N_2$. The mixture was stirred at −78° C. for 1 h. The reaction was quenched with 1 M HCl aqueous solution (11 mL) at −78° C. The mixture warmed up to room temperature, diluted with AcOEt, and washed with brine. The organic layer was dried over $MgSO_4$, and concentrated under reduced pressure. The residue was recrystallized from $^iPr_2O$/AcOEt to give the title compound (870 mg, 92% yield) as a pale yellow solid: $^1$H NMR (300 MHz, DMSO-$d_6$): δ ppm 2.49 (3H, s), 2.90-3.28 (4H, m), 3.64-4.01 (7H, m), 7.05 (1H, td, J=8.9, 2.3 Hz), 7.53 (1H, td, J=8.6, 2.5 Hz), 8.50 (1H, d, J=1.9 Hz). LC-MS (ESI) m/z 366 [M+H]$^+$.

Reference Example 229

4-(2,5-Difluoro-4-nitrophenyl)morpholine

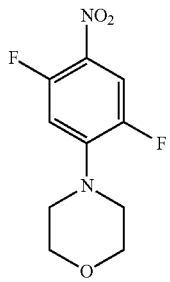 [SMILES: O=[N+]([O-])c1cc(F)c(N2CCOCC2)cc1F]

A mixture of 1,2,4-trifluoro-5-nitrobenzene (4.0 mL, 35 mmol), morpholine (3.1 mL, 35 mmol), and $K_2CO_3$ (4.8 g, 35 mmol) in DMSO (35 mL) was stirred at room temperature overnight. The mixture was diluted with AcOEt and washed with water and brine. The organic layer was dried over $MgSO_4$, and concentrated under reduced pressure. The residue was recrystallized from AcOEt to give the title compound (10 g, 63% yield) as a pale yellow solid: $^1$H NMR (300 MHz, DMSO-$d_6$): δ ppm 3.15-3.49 (4H, m), 3.50-3.90 (4H, m), 7.13 (1H, dd, J=14.3, 7.5 Hz), 8.01 (1H, dd, J=13.6, 7.5 Hz). LC-MS (ESI) m/z 245 [M+H]$^+$.

Reference Example 230

2,5-Difluoro-4-morpholin-4-ylaniline

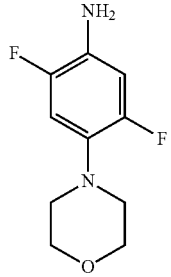

A mixture of 4-(2,5-difluoro-4-nitrophenyl)morpholine (11 g, 44 mmol) and 10% Pd—C (50% wet, 1.1 g) in EtOH (150 mL) was hydrogenated for 5 h at room temperature. The reaction mixture was filtered by celite, and the filtrate was concentrated under reduced pressure. The residue was recrystallized from $^iPr_2O$/AcOEt to give the title compound (8.6 g, 91% yield) as a pale red powder: $^1$H NMR (300 MHz, DMSO-$d_6$): δ ppm 2.66-2.95 (4H, m), 3.56-3.83 (4H, m), 5.00 (2H, s), 6.55 (1H, dd, J=13.8, 8.5 Hz), 6.77 (1H, dd, J=12.8, 8.3 Hz). LC-MS (ESI) m/z 215 [M+H]$^+$.

Reference Example 231

Methyl 2-[(2,5-difluoro-4-morpholin-4-ylphenyl)hydrazono]-4-methoxy-3-oxobutanoate

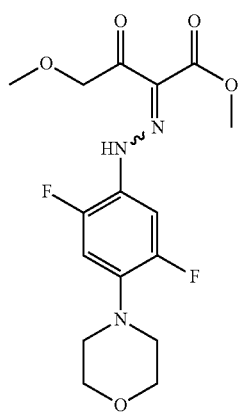

A solution of $NaNO_2$ (3.3 g, 48 mmol) in $H_2O$ (10 mL) was added dropwise at 0° C. to a mixture of 2,5-difluoro-4-morpholin-4-ylaniline (8.6 g, 40 mmol) and 6 M HCl aqueous solution (40 mL, 240 mmol). After stirring for 15 min, the resulting aqueous solution was added to a suspension of methyl 4-methoxyacetoacetate (5.2 mL, 40 mmol) and NaOAc (14 g, 240 mmol) in MeOH (40 mL) pre-cooled at 0° C. The mixture was adjusted to pH 7 with 1 M NaOH aqueous solution (200 mL). The precipitate was collected by filtration, washed with water and dried at room temperature to give the title compound (9.51 g, 64% yield) as a red solid: LC-MS (ESI) m/z 372 [M+H]$^+$.

Reference Example 232

Methyl 1-(2,5-difluoro-4-morpholin-4-ylphenyl)-5-methoxy-4-oxo-1,4-dihydropyridazine-3-carboxylate

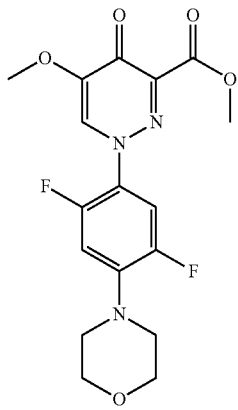

A solution of methyl 2-[(2,5-difluoro-4-morpholin-4-ylphenyl)hydrazono]-4-methoxy-3-oxobutanoate (2.8 g, 7.5 mmol) in N,N-dimethylformamide dimethyl acetal (18 mL) was stirred at 100° C. for 80 min. After cooling to room temperature, the precipitate was collected by filtration and washed with $^i$Pr$_2$O to give the title compound (2.7 g, 95% yield) as a brown powder: $^1$H NMR (300 MHz, DMSO-d$_6$): δ ppm 3.12 (4H, dt, J=4.4, 2.5 Hz), 3.48-4.31 (10H, m), 7.18 (1H, dd, J=12.5, 7.6 Hz), 7.72 (1H, dd, J=12.5, 7.2 Hz), 8.50 (1H, s). LC-MS (ESI) m/z 382 [M+H]$^+$.

Reference Example 233

1-(2,5-Difluoro-4-morpholin-4-ylphenyl)-5-methoxy-4-oxo-1,4-dihydropyridazine-3-carboxylic acid

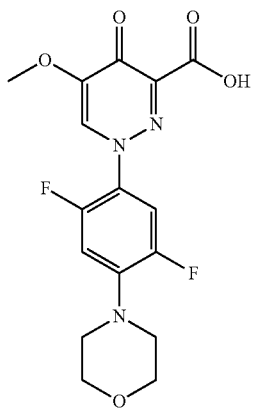 [SMILES: COc1cn(-c2cc(F)c(N3CCOCC3)cc2F)nc(C(=O)O)c1=O]

A solution of methyl 1-(2,5-difluoro-4-morpholin-4-ylphenyl)-5-methoxy-4-oxo-1,4-dihydropyridazine-3-carboxylate (2.7 g, 7.1 mmol) and 2 M NaOH aqueous solution (7.2 mL, 14.4 mmol) in EtOH (14 mL) was stirred at room temperature for 16 h. To the mixture was added 1 M HCl aqueous solution (14 mL). The precipitate was collected by filtration and dried over under reduced pressure to give the title compound (2.5 g, 96% yield) as a white solid: $^1$H NMR (300 MHz, DMSO-d$_6$): δ ppm 3.00-3.24 (4H, m), 3.67-3.82 (4H, m), 3.88 (3H, s), 7.23 (1H, dd, J=12.7, 7.7 Hz), 7.74 (1H, dd, J=12.8, 7.2 Hz), 8.83 (1H, d, J=1.1 Hz), 14.95 (1H, brs). LC-MS (ESI) m/z 368 [M+H]$^+$.

Reference Example 234

1-(2,5-Difluoro-4-morpholin-4-ylphenyl)-N,5-dimethoxy-N-methyl-4-oxo-1,4-dihydropyridazine-3-carboxamide

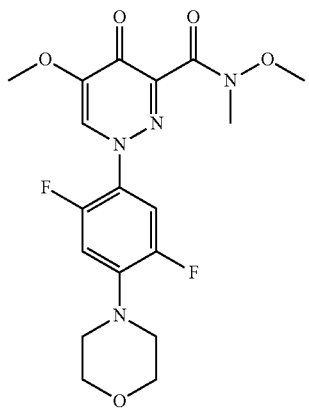

A mixture of 1-(2,5-difluoro-4-morpholin-4-ylphenyl)-5-methoxy-4-oxo-1,4-dihydropyridazine-3-carboxylic acid (2.5 g, 6.8 mmol), N,O-dimethylhydroxylamine hydrochloride (0.73 g, 7.5 mmol), HOBt (1.0 g, 7.5 mmol), triethylamine (2.0 mL, 14 mmol) and WSC (1.4 g, 7.5 mmol) in DMF (28 mL) was stirred at room temperature overnight. The mixture was diluted with AcOEt, washed with water and brine, dried over MgSO$_4$ and concentrated under reduced pressure to give the title compound (1.6 g, 58% yield) as a brown solid: $^1$H NMR (300 MHz, DMSO-d$_6$): δ ppm 3.01-3.19 (4H, m), 3.24 (3H, s), 3.56 (3H, s), 3.62-3.91 (7H, m), 7.17 (1H, dd, J=12.7, 7.7 Hz), 7.62-7.82 (1H, m), 8.48 (1H, s). LC-MS (ESI) m/z 411 [M+H]$^+$.

Reference Example 235

3-Acetyl-1-(2,5-difluoro-4-morpholin-4-ylphenyl)-5-methoxypyridazin-4(1H)-one

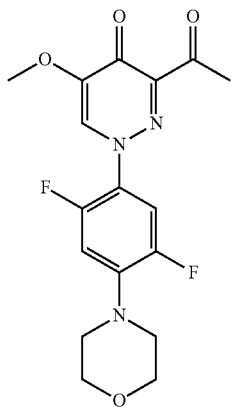 [SMILES: COc1cn(-c2cc(F)c(N3CCOCC3)cc2F)nc(C(C)=O)c1=O]

A solution of 1-(2,5-difluoro-4-morpholin-4-ylphenyl)-N,5-dimethoxy-N-methyl-4-oxo-1,4-dihydropyridazine-3-carboxamide (0.51 g, 1.2 mmol) in THF (40 mL) was added dropwise to MeMgBr (1.0 M in THF, 5.0 mL, 5.0 mmol) at −78° C. under $N_2$. The mixture was stirred at −78° C. for 2 h. The reaction was quenched with 1 M HCl aqueous solution (5.0 mL) at −78° C. The mixture warmed up to room temperature, diluted with AcOEt, and washed with brine. The organic layer was dried over $MgSO_4$, and concentrated under reduced pressure. The residue was purified by silica gel column chromatography eluting with AcOEt/MeOH (10/0 to 10/1) to give the title compound (340 mg, 75% yield) as a pale yellow solid: $^1$H NMR (300 MHz, DMSO-$d_6$): δ ppm 2.49 (3H, s), 2.91-3.21 (4H, m), 3.54-3.89 (7H, m), 7.19 (1H, dd, J=12.7, 7.7 Hz), 7.74 (1H, dd, J=12.8, 7.2 Hz), 8.46 (1H, d, J=1.5 Hz). LC-MS (ESI) m/z 366 [M+H]$^+$.

Example 1

3-[1-(4-Methylphenyl)-1H-pyrazol-5-yl]-1-[3-(trifluoromethyl)phenyl]pyridazin-4(1H)-one

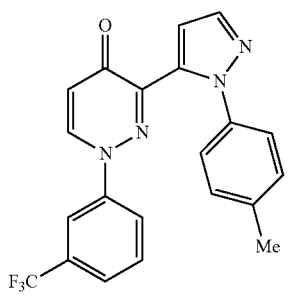 [SMILES: Cc1ccc(-n2nccc2-c2nn(-c3cccc(C(F)(F)F)c3)ccc2=O)cc1]

To a solution of 3-[3-(dimethylamino)prop-2-enoyl]-1-[3-(trifluoromethyl)phenyl]pyridazin-4(1H)-one (337 mg, 1.0 mmol) in ethanol (100 mL) were added 4-methylphenylhydrazine hydrochloride (237 mg, 1.5 mmol) and $Et_3N$ (0.28 mL, 2.0 mmol). The mixture was stirred at 100° C. for 3 h and the solvent was removed under reduced pressure. Preparative HPLC chromatography provided 3-[1-(4-methylphenyl)-1H-pyrazol-5-yl]-1-[3-(trifluoromethyl)phenyl]pyridazin-4 (1H)-one as a pale yellow solid (108 mg, 27%).

$^1$H NMR (400 MHz, DMSO-$d_6$): δ ppm 2.33 (s, 3H), 6.68 (d, J=8 Hz, 1H), 7.20 (d, J=1.6 Hz, 1H), 7.29-7.23 (m, 4H), 7.46 (d, J=8 Hz, 1H), 7.50 (s, 1H), 7.62 (t, J=8 Hz, 1H), 7.72 (d, J=8 Hz, 1H), 7.81 (d, J=1.6 Hz, 1H), 8.95 (d, J=8 Hz, 1H). LC-MS (MH$^+$) 397.15; mp 164-165° C.

Example 2

3-[1-(4-Fluorophenyl)-1H-pyrazol-5-yl]-1-[3-(trifluoromethyl)phenyl]pyridazin-4(1H)-one

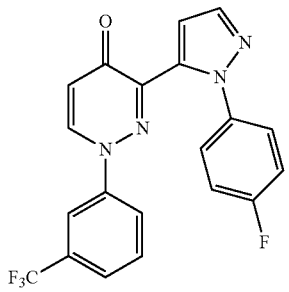 [SMILES: O=c1ccn(-c2cccc(C(F)(F)F)c2)nc1-c1ccnn1-c1ccc(F)cc1]

To a solution of 3-[3-(dimethylamino)prop-2-enoyl]-1-[3-(trifluoromethyl)phenyl]pyridazin-4(1H)-one (337 mg, 1.0 mmol) in ethanol (100 mL) were added 4-fluorophenylhydrazine hydrochloride (244 mg, 1.5 mmol) and $Et_3N$ (0.28 mL, 2.0 mmol). The mixture was stirred at 100° C. for 3 h and the solvent was removed under reduced pressure. Preparative HPLC chromatography provided 3-[1-(4-fluorophenyl)-1H-pyrazol-5-yl]-1-[3-(trifluoromethyl)phenyl]pyridazin-4 (1H)-one as a pale brown solid (119 mg, 30%).

$^1$H NMR (400 MHz, DMSO-$d_6$): δ ppm 6.68 (d, J=8 Hz, 1H), 7.29-7.24 (m, 3H), 7.50-7.45 (m, 3H), 7.62 (d, J=8 Hz, 1H), 7.68 (d, J=8 Hz, 1H), 7.74 (d, J=8 Hz, 1H), 7.84 (d, J=1.6 Hz, 1H), 8.95 (d, J=8 Hz, 1H). LC-MS (MH$^+$) 401.14; mp 130-131° C.

Example 3

3-[1-(4-Chlorophenyl)-1H-pyrazol-5-yl]-1-[3-(trifluoromethyl)phenyl]pyridazin-4(1H)-one

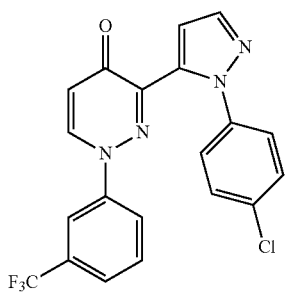

To a solution of 3-[3-(dimethylamino)prop-2-enoyl]-1-[3-(trifluoromethyl)phenyl]pyridazin-4(1H)-one (337 mg, 1.0 mmol) in ethanol (100 mL) were added 4-chlorophenylhydrazine hydrochloride (269 mg, 1.5 mmol) and Et₃N (0.28 mL, 2.0 mmol). The mixture was stirred at 100° C. for 3 h and the solvent was removed under reduced pressure. Preparative HPLC chromatography provided 3-[1-(4-chlorophenyl)-1H-pyrazol-5-yl]-1-[3-(trifluoromethyl)phenyl]pyridazin-4(1H)-one as a pale brown solid (126 mg, 30%).

¹H NMR (400 MHz, DMSO-d₆): δ ppm 6.69 (d, J=8 Hz, 1H), 7.25 (d, J=1.2 Hz, 1H), 7.51-7.47 (m, 4H), 7.57 (m, 2H), 7.68 (t, J=8 Hz, 1H), 7.75 (d, J=8 Hz, 1H), 7.86 (d, J=1.2 Hz, 1H), 8.98 (d, J=8 Hz, 1H). LC-MS (MH⁺) δ17.08; mp 166-167° C.

Example 4

3-[1-(4-Methoxyphenyl)-1H-pyrazol-5-yl]-1-[3-(trifluoromethyl)phenyl]pyridazin-4(1H)-one

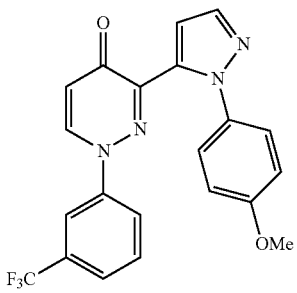 [SMILES: COc1ccc(-n2nccc2-c2nn(-c3cccc(C(F)(F)F)c3)ccc2=O)cc1]

To a solution of 3-[3-(dimethylamino)prop-2-enoyl]-1-[3-(trifluoromethyl)phenyl]pyridazin-4(1H)-one (337 mg, 1.0 mmol) in ethanol (100 mL) were added 4-methoxyphenylhydrazine hydrochloride (262 mg, 1.5 mmol) and Et₃N (0.28 mL, 2.0 mmol). The mixture was stirred at 100° C. for 3 h and the solvent was removed under reduced pressure. Preparative HPLC chromatography provided 3-[1-(4-methoxyphenyl)-1H-pyrazol-5-yl]-1-[3-(trifluoromethyl)phenyl]pyridazin-4(1H)-one as a pale yellow solid (154 mg, 37%).

¹H NMR (400 MHz, DMSO-d₆): δ ppm 3.76 (s, 3H), 6.67 (d, J=8 Hz, 1H), 6.98 (d, J=8 Hz, 2H), 7.20 (d, J=1.6 Hz, 1H), 7.32 (d, J=8 Hz, 2H), 7.50 (d, J=8 Hz, 1H), 7.55 (s, 1H), 7.62 (t, J=8 Hz, 1H), 7.73 (d, J=8 Hz, 1H), 7.79 (d, J=1.6 Hz, 1H), 8.95 (d, J=8 Hz, 1H). LC-MS (MH⁺) 413.16; mp 173-174° C.

Example 5

3-[1-(3-Methylphenyl)-1H-pyrazol-5-yl]-1-[3-(trifluoromethyl)phenyl]pyridazin-4(1H)-one

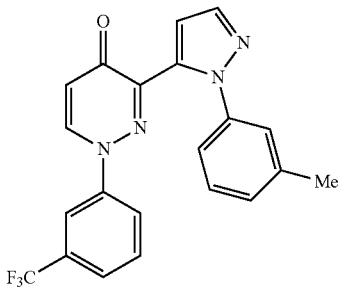 [SMILES: Cc1cccc(-n2nccc2-c2nn(-c3cccc(C(F)(F)F)c3)ccc2=O)c1]

To a solution of 3-[3-(dimethylamino)prop-2-enoyl]-1-[3-(trifluoromethyl)phenyl]pyridazin-4(1H)-one (337 mg, 1.0 mmol) in ethanol (100 mL) were added 3-methylphenylhydrazine hydrochloride (237 mg, 1.5 mmol) and Et₃N (0.28 mL, 2.0 mmol). The mixture was stirred at 100° C. for 3 h and the solvent was removed under reduced pressure. Preparative HPLC chromatography provided 3-[1-(3-methylphenyl)-1H-pyrazol-5-yl]-1-[3-(trifluoromethyl)phenyl]pyridazin-4(1H)-one as a pale yellow solid (84 mg, 21%).

¹H NMR (400 MHz, DMSO-d₆): δ ppm 2.31 (s, 3H), 6.68 (d, J=8 Hz, 1H), 7.12 (d, J=8 Hz, 1H), 7.21 (d, J=8 Hz, 1H), 7.23 (d, J=1.6 Hz, 1H), 7.32-7.28 (m, 2H), 7.43 (d, J=8 Hz, 1H), 7.49 (s, 1H), 7.62 (t, J=8 Hz, 1H), 7.72 (d, J=8 Hz, 1H), 7.82 (d, J=1.6 Hz, 1H), 8.94 (d, J=8 Hz, 1H). LC-MS (MH⁺) 397.18; mp 142-143° C.

Example 6

3-[1-(3-Fluorophenyl)-1H-pyrazol-5-yl]-1-[3-(trifluoromethyl)phenyl]pyridazin-4(1H)-one

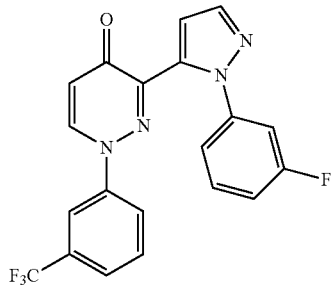 [SMILES: O=c1ccn(-c2cccc(C(F)(F)F)c2)nc1-c1ccnn1-c1cccc(F)c1]

To a solution of 3-[3-(dimethylamino)prop-2-enoyl]-1-[3-(trifluoromethyl)phenyl]pyridazin-4(1H)-one (674 mg, 2.0 mmol) in ethanol (200 mL) were added 3-fluorophenylhydrazine hydrochloride (488 mg, 3.0 mmol) and Et₃N (0.56 mL, 4.0 mmol). The mixture was stirred at 100° C. for 3 h and the solvent was removed under reduced pressure. Preparative HPLC chromatography provided 3-[1-(3-fluorophenyl)-1H-pyrazol-5-yl]-1-[3-(trifluoromethyl)phenyl]pyridazin-4(1H)-one as a pale yellow solid (201 mg, 25%).

¹H NMR (400 MHz, DMSO-d₆): δ ppm 6.69 (d, J=8 Hz, 1H), 7.24-7.20 (m, 2H), 7.26 (d, J=2.0 Hz, 1H), 7.40 (d, J=2.0 Hz, 1H), 7.46 (q, J=2.0 Hz, 1H), 7.54 (s, 1H), 7.61 (d, J=8 Hz, 1H), 7.67 (d, J=8 Hz, 1H), 7.74 (d, J=8 Hz, 1H), 7.87 (d, J=2.0 Hz, 1H), 8.97 (d, J=8 Hz, 1H). LC-MS (MH⁺) 401.14; mp 104-105° C.

Example 7

3-[1-(2-Methylphenyl)-1H-pyrazol-5-yl]-1-[3-(trifluoromethyl)phenyl]pyridazin-4(1H)-one

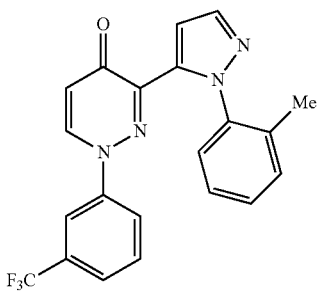 [SMILES: Cc1ccccc1-n1nccc1-c1nn(-c2cccc(C(F)(F)F)c2)ccc1=O]

To a solution of 3-[3-(dimethylamino)prop-2-enoyl]-1-[3-(trifluoromethyl)phenyl]pyridazin-4(1H)-one (337 mg, 1.0 mmol) in ethanol (100 mL) were added 2-methylphenylhydrazine hydrochloride (237 mg, 1.5 mmol) and $Et_3N$ (0.28 mL, 2.0 mmol). The mixture was stirred at 100° C. for 3 h and the solvent was removed under reduced pressure. Preparative HPLC chromatography provided 3-[1-(2-methylphenyl)-1H-pyrazol-5-yl]-1-[3-(trifluoromethyl)phenyl]pyridazin-4(1H)-one as a pale pink solid (85 mg, 21%).

$^1$H NMR (400 MHz, DMSO-$d_6$): δ ppm 1.92 (s, 3H), 6.68 (d, J=8 Hz, 1H), 7.05 (d, J=8 Hz, 1H), 7.23 (d, J=8 Hz, 1H), 7.31-7.28 (m, 1H), 7.38-7.35 (m, 2H), 7.42 (d, J=2.0 Hz, 1H), 7.56 (t, J=8 Hz, 2H), 7.70 (d, J=8 Hz, 1H), 7.84 (d, J=2.0 Hz, 1H), 8.88 (d, J=8 Hz, 1H). LC-MS (MH$^+$) 397.11; mp 126-127° C.

Example 8

3-[1-(2-Chlorophenyl)-1H-pyrazol-5-yl]-1-[3-(trifluoromethyl)phenyl]pyridazin-4(1H)-one

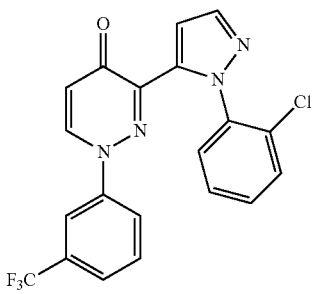 [SMILES: O=c1ccn(-c2cccc(C(F)(F)F)c2)nc1-c1ccnn1-c1ccccc1Cl]

To a solution of 3-[3-(dimethylamino)prop-2-enoyl]-1-[3-(trifluoromethyl)phenyl]pyridazin-4(1H)-one (674 mg, 2.0 mmol) in ethanol (200 mL) were added 2-chlorophenylhydrazine hydrochloride (538 mg, 3.0 mmol) and $Et_3N$ (0.56 mL, 4.0 mmol). The mixture was stirred at 100° C. for 3 h and the solvent was removed under reduced pressure. Preparative HPLC chromatography provided 3-[1-(2-chlorophenyl)-1H-pyrazol-5-yl]-1-[3-(trifluoromethyl)phenyl]pyridazin-4(1H)-one as a pale yellow solid (280 mg, 34%).

$^1$H NMR (400 MHz, DMSO-$d_6$): δ ppm 6.70 (d, J=8 Hz, 1H), 7.12 (d, J=8 Hz, 1H), 7.61-7.48 (m, 7H), 7.71 (d, J=8 Hz, 1H), 7.88 (d, J=1.6 Hz, 1H), 8.90 (d, J=8 Hz, 1H). LC-MS (MH$^+$) 417.08; mp 139-140° C.

Example 9

3-[1-(2-Methoxyphenyl)-1H-pyrazol-5-yl]-1-[3-(trifluoromethyl)phenyl]pyridazin-4(1H)-one

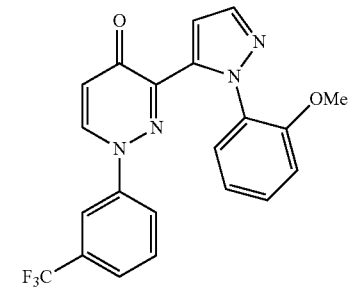 [SMILES: COc1ccccc1-n1nccc1-c1nn(-c2cccc(C(F)(F)F)c2)ccc1=O]

To a solution of 3-[3-(dimethylamino)prop-2-enoyl]-1-[3-(trifluoromethyl)phenyl]pyridazin-4(1H)-one (337 mg, 1.0 mmol) in ethanol (100 mL) were added 2-methoxyphenylhydrazine hydrochloride (262 mg, 1.5 mmol) and $Et_3N$ (0.28 mL, 2.0 mmol). The mixture was stirred at 100° C. for 3 h and the solvent was removed under reduced pressure. Preparative HPLC chromatography provided 3-[1-(2-methoxyphenyl)-1H-pyrazol-5-yl]-1-[3-(trifluoromethyl)phenyl]pyridazin-4(1H)-one as a pale yellow solid (78 mg, 19%).

$^1$H NMR (400 MHz, DMSO-$d_6$): δ ppm 3.46 (s, 3H), 6.69 (d, J=8 Hz, 1H), 7.03 (d, J=8 Hz, 1H), 7.14 (t, J=8 Hz, 2H), 7.25 (d, J=2.0 Hz, 1H), 7.41 (t, J=8 Hz, 2H), 7.50 (d, J=8 Hz, 1H), 7.58 (t, J=8 Hz, 1H), 7.68 (d, J=8 Hz, 1H), 7.79 (d, J=1.6 Hz, 1H), 8.90 (d, J=8 Hz, 1H). LC-MS (MH$^+$) 413.16; mp 146-147° C.

Example 10

3-(1-Phenyl-1H-pyrazol-5-yl)-1-[3-(trifluoromethyl)phenyl]pyridazin-4(1H)-one

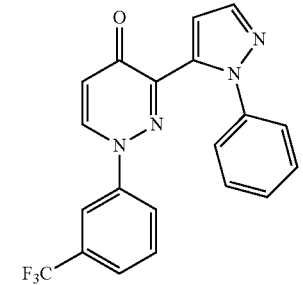 [SMILES: O=c1ccn(-c2cccc(C(F)(F)F)c2)nc1-c1ccnn1-c1ccccc1]

To a solution of 3-[3-(dimethylamino)prop-2-enoyl]-1-[3-(trifluoromethyl)phenyl]pyridazin-4(1H)-one (337 mg, 1.0 mmol) in ethanol (100 mL) was added phenylhydrazine (163 mg, 1.5 mmol). The mixture was stirred at 100° C. for 3 h, and the solvent was removed under reduced pressure. Preparative HPLC chromatography provided 3-(1-phenyl-1H-pyrazol-5-yl)-1-[3-(trifluoromethyl)phenyl]pyridazin-4(1H)-one as a gray solid (55 mg, 15%).

$^1$H NMR (400 MHz, DMSO-$d_6$): δ ppm 6.68 (d, J=8 Hz, 1H), 7.23 (d, J=1.6 Hz, 1H), 7.48-7.39 (m, 6H), 7.51 (s, 1H), 7.61 (t, J=8 Hz, 1H), 7.71 (d, J=8 Hz, 1H), 7.84 (d, J=1.6 Hz, 1H), 8.95 (d, J=8 Hz, 1H). LC-MS (MH$^+$) 383.15; mp 156-157° C.

Example 11

3-(1-Phenyl-1H-pyrazol-5-yl)-1-[4-(trifluoromethyl)phenyl]pyridazin-4(1H)-one

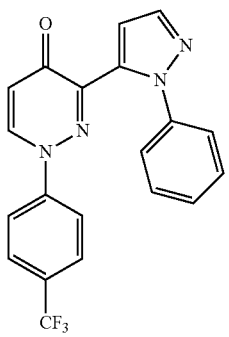

To a solution of 3-[3-(dimethylamino)prop-2-enoyl]-1-[4-(trifluoromethyl)phenyl]pyridazin-4(1H)-one (crude 718 mg, 2.13 mmol) in 20 mL of methanol was added phenylhydrazine (345 mg, 3.20 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 3-(1-phenyl-1H-pyrazol-5-yl)-1-[4-(trifluoromethyl)phenyl]pyridazin-4(1H)-one (100 mg, 12% for two steps) as a yellow solid.

$^1$H NMR (300 MHz, CDCl$_3$): δ ppm 6.74 (d, J=7.6 Hz, 1H), 6.90 (d, J=8.4 Hz, 2H), 7.39-7.41 (m, 1H), 7.42 (d, J=2.0 Hz, 1H), 7.44-7.50 (m, 4H), 7.53 (d, J=8.4 Hz, 2H), 7.81 (d, J=1.6 Hz, 1H), 8.21 (d, J=8.0 Hz, 1H); LCMS (mobile phase: from 70% water and 30% CH$_3$CN to 5% water and 95% CH$_3$CN in 6 min, finally under these conditions for 0.5 min.) purity is >95%, Rt=3.422 min; MS Calcd.: 382, MS Found: 383 (M$^+$+H); mp 237-238° C.

Example 12

1-(3-Chlorophenyl)-3-(1-phenyl-1H-pyrazol-5-yl)pyridazin-4(1H)-one

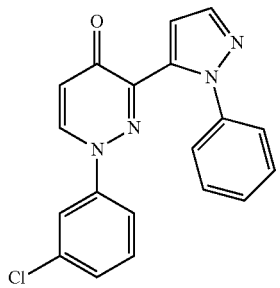 [SMILES: O=c1ccn(-c2cccc(Cl)c2)nc1-c1ccnn1-c1ccccc1]

To a solution of 1-(3-chlorophenyl)-3-[3-(dimethylamino)prop-2-enoyl]pyridazin-4(1H)-one (crude 573 mg, 1.89 mmol) in 20 mL of methanol was added phenylhydrazine (306 mg, 2.84 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 1-(3-chlorophenyl)-3-(1-phenyl-1H-pyrazol-5-yl)pyridazin-4(1H)-one (125 mg, 19% for two steps) as a yellow solid.

$^1$H NMR (300 MHz, DMSO-d$_6$): δ ppm 6.71-6.74 (m, 2H), 6.80-6.83 (m, 1H), 7.22-7.25 (m, 2H), 7.39-7.49 (m, 6H), 7.81 (d, J=1.6 Hz, 1H), 8.15 (d, J=8.0 Hz, 1H); LCMS (mobile phase: from 70% water and 30% CH$_3$CN to 5% water and 95% CH$_3$CN in 6 min, finally under these conditions for 0.5 min.) purity is >95%, Rt=3.150 min; MS Calcd.: 348, MS Found: 349 (M$^+$+H); mp 146-147° C.

Example 13

1-(2-Methoxyphenyl)-3-(1-phenyl-1H-pyrazol-5-yl)pyridazin-4(1H)-one

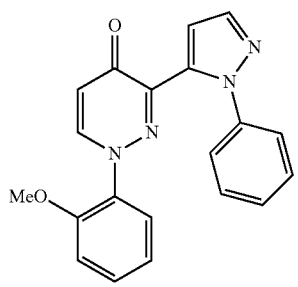 [SMILES: COc1ccccc1-n1ccc(=O)c(-c2ccnn2-c2ccccc2)n1]

To a solution of 3-[3-(dimethylamino)prop-2-enoyl]-1-(2-methoxyphenyl)pyridazin-4(1H)-one (crude 639 mg, 2.14 mmol) in 20 mL of methanol was added phenylhydrazine (347 mg, 3.21 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 1-(2-methoxyphenyl)-3-(1-phenyl-1H-pyrazol-5-yl)pyridazin-4(1H)-one (35 mg, 5% for two steps) as a yellow solid.

$^1$H NMR (400 MHz, CDCl$_3$): δ ppm 3.82 (s, 3H), 6.37 (dd, J=10.4, 2.4 Hz, 1H), 6.60 (d, J=10.0 Hz, 1H), 6.78-6.83 (m, 1H), 6.96 (dd, J=11.2, 1.6 Hz, 1H), 7.25 (d, J=2.4 Hz, 1H), 7.21-7.41 (m, 6H), 7.76 (d, J=2.8 Hz, 1H), 8.01 (d, J=10.4 Hz, 1H); LCMS (mobile phase: from 70% water and 30% CH$_3$CN to 5% water and 95% CH$_3$CN in 6 min, finally under these conditions for 0.5 min.) purity is >95%, Rt=2.589 min; MS Calcd.: 344, MS Found: 345 (M$^+$+H); mp 153-154° C.

Example 14

1-(4-Methoxyphenyl)-3-(1-phenyl-1H-pyrazol-5-yl)pyridazin-4(1H)-one

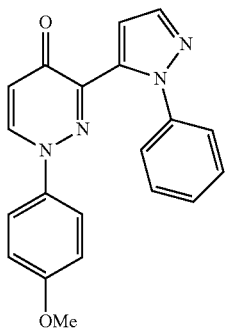

To a solution of 3-[3-(dimethylamino)prop-2-enoyl]-1-(4-methoxyphenyl)pyridazin-4(1H)-one (crude 640 mg, 2.14 mmol) in 20 mL of methanol was added phenylhydrazine (347 mg, 3.21 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-(4-methoxyphenyl)-3-(1-phenyl-1H-pyrazol-5-yl)pyridazin-4(1H)-one (127 mg, 17% for two steps) as a yellow solid.

$^1$H NMR (400 MHz, CDCl$_3$): δ ppm 3.81 (s, 3H), 6.67-6.76 (m, 5H), 7.38-7.44 (m, 6H), 7.78 (d, J=2.8 Hz, 1H), 8.08 (d, J=10.4 Hz, 1H); LCMS (mobile phase: from 70% water and 30% CH$_3$CN to 5% water and 95% CH$_3$CN in 6 min, finally under these conditions for 0.5 min.) purity is >95%, Rt=2.639 min; MS Calcd.: 344, MS Found: 345 (M$^+$+H); mp 179-180° C.

Example 15

1-(3-Fluorophenyl)-3-(1-phenyl-1H-pyrazol-5-yl)pyridazin-4(1H)-one

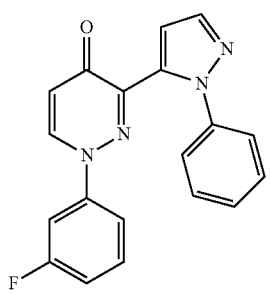 [SMILES: O=c1ccn(-c2cccc(F)c2)nc1-c1ccnn1-c1ccccc1]

To a solution of 3-[3-(dimethylamino)prop-2-enoyl]-1-(3-fluorophenyl)pyridazin-4(1H)-one (crude, 840 mg, 2.93 mmol) in 20 mL of methanol was added phenylhydrazine (474 mg, 4.39 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-(3-fluorophenyl)-3-(1-phenyl-1H-pyrazol-5-yl)pyridazin-4(1H)-one (169 mg, 17% for two steps) as a yellow solid.

$^1$H NMR (400 MHz, CDCl$_3$): δ ppm 6.36-6.41 (m, 1H), 6.68-6.75 (m, 2H), 6.95-7.01 (m, 1H), 7.24-7.32 (m, 1H), 7.38-7.49 (m, 6H), 7.79 (d, J=2.4 Hz, 1H), 8.15 (d, J=10.4 Hz, 1H); LCMS (mobile phase: from 70% water and 30% CH$_3$CN to 5% water and 95% CH$_3$CN in 6 min, finally under these conditions for 0.5 min.) purity is >95%, Rt=2.834 min; MS Calcd.: 332, MS Found: 333 (M$^+$+H); mp 170-171° C.

Example 16

1-(2-Fluorophenyl)-3-(1-phenyl-1H-pyrazol-5-yl)pyridazin-4(1H)-one

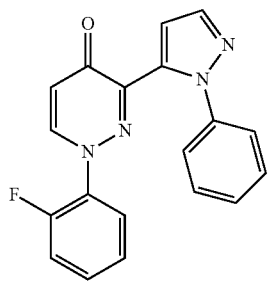 [SMILES: O=c1ccn(-c2ccccc2F)nc1-c1ccnn1-c1ccccc1]

To a solution of 3-[3-(dimethylamino)prop-2-enoyl]-1-(2-fluorophenyl)pyridazin-4(1H)-one (crude 776 mg, 2.70 mmol) in 20 mL of methanol was added phenylhydrazine (438 mg, 4.10 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-(2-fluorophenyl)-3-(1-phenyl-1H-pyrazol-5-yl)pyridazin-4(1H)-one (278 mg, 31% for two steps) as a yellow solid.

$^1$H NMR (300 MHz, CDCl$_3$): δ ppm 6.39-6.46 (m, 1H), 6.65 (d, J=7.8 Hz, 1H), 6.97-7.03 (m, 1H), 7.13-7.20 (m, 1H), 7.27-7.46 (m, 7H), 7.78 (d, J=1.8 Hz, 1H), 8.02 (dd, J=7.8, 2.4 Hz, 1H); LCMS (mobile phase: from 70% water and 30% CH$_3$CN to 5% water and 95% CH$_3$CN in 6 min, finally under these conditions for 0.5 min.) purity is >95%, Rt=2.634 min; MS Calcd.: 332, MS Found: 333 (M$^+$+H); mp 124-125° C.

Example 17

1-(4-Fluorophenyl)-3-(1-phenyl-1H-pyrazol-5-yl)pyridazin-4(1H)-one

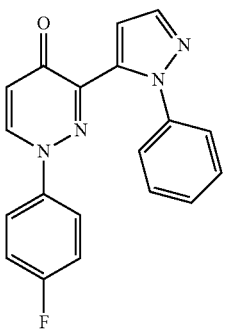

To a solution of 3-[3-(dimethylamino)prop-2-enoyl]-1-(4-fluorophenyl)pyridazin-4(1H)-one (crude 840 mg, 2.93 mmol) in 20 mL of methanol was added phenylhydrazine (474 mg, 4.39 mmol) The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-(4-fluorophenyl)-3-(1-phenyl-1H-pyrazol-5-yl)pyridazin-4(1H)-one (260 mg, 27% for two steps) as a brown solid.

$^1$H NMR (300 MHz, DMSO-d$_6$): δ ppm 6.62 (d, J=7.8 Hz, 1H), 7.11-7.15 (m, 2H), 7.20-7.26 (m, 3H), 7.37-7.40 (m, 2H), 7.44-7.49 (m, 3H), 7.81 (d, J=1.8 Hz, 1H), 8.78 (d, J=8.1 Hz, 1H); LCMS (mobile phase: from 70% water and 30% CH$_3$CN to 5% water and 95% CH$_3$CN in 6 min, finally under these conditions for 0.5 min.) purity is >95%, Rt=2.779 min; MS Calcd.: 332, MS Found: 333 (M$^+$+H); mp 252-253° C.

Example 18

1-(4-Chlorophenyl)-3-(1-phenyl-1H-pyrazol-5-yl)pyridazin-4(1H)-one

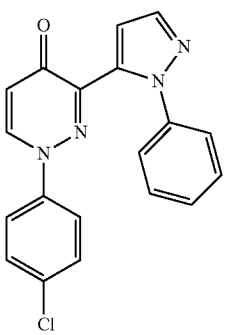

To a solution of 1-(4-chlorophenyl)-3-[3-(dimethylamino)prop-2-enoyl]pyridazin-4(1H)-one (crude, 764 mg, 2.52 mmol) in 20 mL of methanol was added phenylhydrazine (408 mg, 3.78 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-(4-chlorophenyl)-3-(1-phenyl-1H-pyrazol-5-yl)pyridazin-4(1H)-one (70 mg, 8% for two steps) as a brown solid.

$^1$H NMR (300 MHz, CDCl$_3$): δ ppm 6.68-6.73 (m, 3H), 7.24 (dd, J=6.9, 2.4 Hz, 2H), 7.38-7.46 (m, 6H), 7.78 (d, J=1.8 Hz, 1H), 8.12 (d, J=7.8 Hz, 1H); LCMS (mobile phase: from 70% water and 30% CH$_3$CN to 5% water and 95% CH$_3$CN in 6 min, finally under these conditions for 0.5 min.) purity is >95%, Rt=3.180 min; MS Calcd.: 348, MS Found: 349 (M$^+$+H); mp 219-220° C.

Example 19

1-(2-Methylphenyl)-3-(1-phenyl-1H-pyrazol-5-yl)pyridazin-4(1H)-one

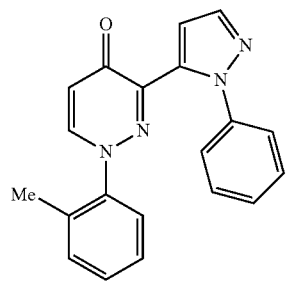 [SMILES: Cc1ccccc1-n1ccc(=O)c(-c2ccnn2-c2ccccc2)n1]

To a solution of 3-[3-(dimethylamino)prop-2-enoyl]-1-(2-methylphenyl)pyridazin-4(1H)-one (crude, 1298 mg, 4.59 mmol) in 20 mL of methanol was added phenylhydrazine (744 mg, 6.89 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-(2-methylphenyl)-3-(1-phenyl-1H-pyrazol-5-yl)pyridazin-4(1H)-one (180 mg, 12% for two steps) as a yellow solid.

$^1$H NMR (400 MHz, CDCl$_3$): δ ppm 2.01 (s, 3H), 6.67 (d, J=8.0 Hz, 1H), 6.84 (d, J=7.6 Hz, 1H), 7.15-7.25 (m, 2H), 7.29-7.38 (m, 7H), 7.79-7.83 (m, 2H); LCMS (mobile phase: from 70% water and 30% CH$_3$CN to 5% water and 95% CH$_3$CN in 6 min, finally under these conditions for 0.5 min.) purity is >95%, Rt=2.679 min; MS Calcd.: 328, MS Found: 329 (M$^+$+H); mp 120-121° C.

Example 20

1-(3-Methylphenyl)-3-(1-phenyl-1H-pyrazol-5-yl)pyridazin-4(1H)-one

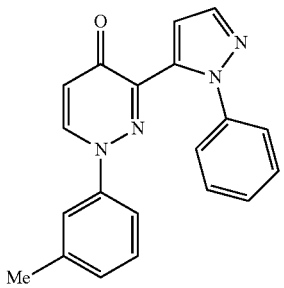 [SMILES: Cc1cccc(-n2ccc(=O)c(-c3ccnn3-c3ccccc3)n2)c1]

To a solution of 3-[3-(dimethylamino)prop-2-enoyl]-1-(3-methylphenyl)pyridazin-4(1H)-one (crude, 650 mg, 2.29 mmol) in 20 mL of methanol was added phenylhydrazine (370 mg, 3.44 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-(3-methylphenyl)-3-(1-phenyl-1H-pyrazol-5-yl)pyridazin-4(1H)-one (55 mg, 7% for two steps) as a brown solid.

$^1$H NMR (400 MHz, $CDCl_3$): δ ppm 2.32 (s, 3H), 6.60 (s, 1H), 6.72-6.74 (m, 2H), 7.12 (d, J=7.6 Hz, 1H), 7.21 (t, J=8.0 Hz, 1H), 7.41-7.50 (m, 6H), 7.81 (s, 1H), 8.19 (d, J=8.0 Hz, 1H); LCMS (mobile phase: from 70% water and 30% $CH_3CN$ to 5% water and 95% $CH_3CN$ in 6 min, finally under these conditions for 0.5 min.) purity is >95%, Rt=2.972 min; MS Calcd.: 328, MS Found: 329 ($M^+$+H); mp 115-116° C.

Example 21

1-(3-Methoxyphenyl)-3-(1-phenyl-1H-pyrazol-5-yl)pyridazin-4(1H)-one

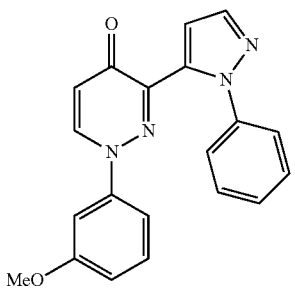 [SMILES: COc1cccc(-n2ccc(=O)c(-c3ccnn3-c3ccccc3)n2)c1]

To a solution of 3-[3-(dimethylamino)prop-2-enoyl]-1-(3-methoxyphenyl)pyridazin-4(1H)-one (crude 640 mg, 2.14 mmol) in 20 mL of methanol was added phenylhydrazine (347 mg, 3.21 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-(3-methoxyphenyl)-3-(1-phenyl-1H-pyrazol-5-yl)pyridazin-4(1H)-one (106 mg, 14% for two steps) as a yellow solid.

$^1$H NMR (400 MHz, $CDCl_3$): δ ppm 3.76 (s, 3H), 6.46 (dd, J=8.0, 1.6 Hz, 1H), 6.51 (t, J=2.0 Hz, 1H), 6.71 (d, J=8.0 Hz, 1H), 6.84 (dd, J=8.4, 2.0 Hz, 1H), 7.21 (t, J=8.4 Hz, 1H), 7.35-7.43 (m, 6H), 7.81 (d, J=2.0 Hz, 1H), 8.17 (d, J=8.4 Hz, 1H); LCMS (mobile phase: from 70% water and 30% $CH_3CN$ to 5% water and 95% $CH_3CN$ in 6 min, finally under these conditions for 0.5 min.) purity is >95%, Rt=2.753 min; MS Calcd.: 344, MS Found: 345 ($M^+$+H); mp 110-111° C.

Example 22

3-(1-Phenyl-1H-pyrazol-5-yl)-1-[2-(trifluoromethyl)phenyl]pyridazin-4(1H)-one

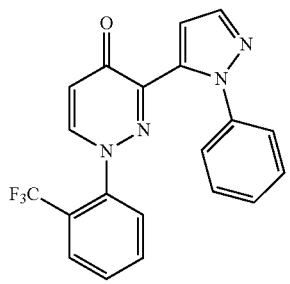

To a solution of 3-[3-(dimethylamino)prop-2-enoyl]-1-[2-(trifluoromethyl)phenyl]pyridazin-4(1H)-one (crude 785 mg, 2.33 mmol) in 20 mL of methanol was added phenylhydrazine (377 mg, 3.50 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 3-(1-phenyl-1H-pyrazol-5-yl)-1-[2-(trifluoromethyl)phenyl]pyridazin-4(1H)-one (105 mg, 12% for two steps) as a yellow solid.

$^1$H NMR (400 MHz, $CDCl_3$): δ ppm 6.59 (d, J=7.6 Hz, 1H), 6.97-7.00 (m, 1H), 7.14 (d, J=2.0 Hz, 1H), 7.27-7.35 (m, 5H), 7.57-7.60 (m, 2H), 7.75-7.81 (m, 3H); LCMS (mobile phase: from 70% water and 30% $CH_3CN$ to 5% water and 95% $CH_3CN$ in 6 min, finally under these conditions for 0.5 min.) purity is >95%, Rt=2.896 min; MS Calcd.: 382, MS Found: 383 ($M^+$+H); mp 145-146° C.

Example 23

1-(4-Morpholin-4-ylphenyl)-3-(1-phenyl-1H-pyrazol-5-yl)pyridazin-4(1H)-one

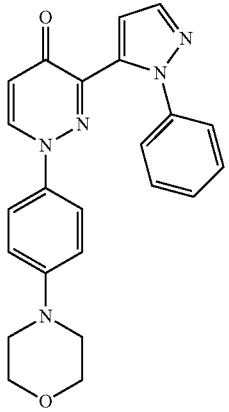 [SMILES: O=c1ccn(-c2ccc(N3CCOCC3)cc2)nc1-c1ccnn1-c1ccccc1]

To a solution of 3-[3-(dimethylamino)prop-2-enoyl]-1-(4-morpholin-4-ylphenyl)pyridazin-4(1H)-one (crude, 1100 mg, 3.11 mmol) in 20 mL of methanol was added phenylhydrazine (504 mg, 4.67 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 1-(4-morpholin-4-ylphenyl)-3-(1-phenyl-1H-pyrazol-5-yl)pyridazin-4(1H)-one (95 mg, 8% for two steps) as a yellow solid.

$^1$H NMR (400 MHz, CDCl$_3$): δ ppm 3.19 (t, J=4.8 Hz, 4H), 3.89 (t, J=4.8 Hz, 4H), 6.71-6.79 (m, 5H), 7.40-7.48 (m, 6H), 7.82 (s, 1H), 8.11 (d, J=7.6 Hz, 1H); LCMS (mobile phase: from 70% water and 30% CH$_3$CN to 5% water and 95% CH$_3$CN in 6 min, finally under these conditions for 0.5 min.) purity is >95%, Rt=2.391 min; MS Calcd.: 399, MS Found: 400 (M$^+$+H); mp 205-206° C.

Example 24

1-Phenyl-3-(1-phenyl-1H-pyrazol-5-yl)pyridazin-4(1H)-one

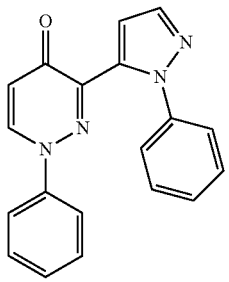 [SMILES: O=c1ccn(-c2ccccc2)nc1-c1ccnn1-c1ccccc1]

To a solution of 3-[3-(dimethylamino)prop-2-enoyl]-1-phenylpyridazin-4(1H)-one (crude 620 mg, 2.30 mmol) in 20 mL of methanol was added phenylhydrazine (996 mg, 9.22 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 1-phenyl-3-(1-phenyl-1H-pyrazol-5-yl)pyridazin-4(1H)-one (50 mg, yield 7% for two steps) as a yellow solid.

$^1$H NMR (400 MHz, CDCl$_3$): δ ppm 6.71 (d, J=8.0 Hz, 1H), 6.81-6.84 (m, 2H), 7.29-7.30 (m, 3H), 7.40-7.47 (m, 6H), 7.79 (d, J=2.0 Hz, 1H), 8.17 (d, J=8.0 Hz, 1H); LCMS (mobile phase: from 90% water and 10% CH$_3$CN to 5% water and 95% CH$_3$CN in 6 min, finally under these conditions for 0.5 min.) purity is >95%, Rt=3.548 min; MS Calcd.: 314, MS Found: 315 (M$^+$+H); mp 179-180° C.

Example 25

1-(4-Methylphenyl)-3-(1-phenyl-1H-pyrazol-5-yl)pyridazin-4(1H)-one

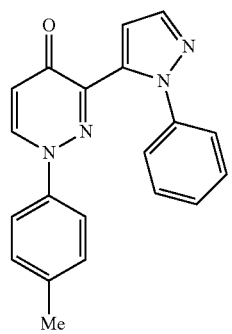 [SMILES: Cc1ccc(-n2ccc(=O)c(-c3ccnn3-c3ccccc3)n2)cc1]

To a solution of 3-[3-(dimethylamino)prop-2-enoyl]-1-(4-methylphenyl)pyridazin-4(1H)-one (crude, 600 mg, 2.12 mmol) in 20 mL of methanol was added phenylhydrazine (916 mg, 8.48 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 1-(4-methylphenyl)-3-(1-phenyl-1H-pyrazol-5-yl)pyridazin-4(1H)-one (50 mg, 7% for two steps) as a yellow solid.

$^1$H NMR (400 MHz, CDCl$_3$): δ ppm 2.34 (s, 3H), 6.69 (d, J=7.6 Hz, 3H), 7.08 (d, J=8.4 Hz, 2H), 7.40-7.47 (m, 6H), 7.79 (d, J=2.0 Hz, 1H), 8.13 (d, J=8.0 Hz, 1H); LCMS (mobile phase: from 90% water and 10% CH$_3$CN to 5% water and 95% CH$_3$CN in 6 min, finally under these conditions for 0.5 min.) purity is >95%, Rt=3.789 min; MS Calcd.: 328, MS Found: 329 (M$^+$+H); mp 182-183° C.

Example 26

1-[2-(Difluoromethoxy)phenyl]-3-(1-phenyl-1H-pyrazol-5-yl)pyridazin-4(1H)-one

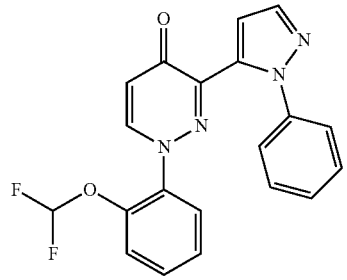 [SMILES: O=c1ccn(-c2ccccc2OC(F)F)nc1-c1ccnn1-c1ccccc1]

To a solution of 1-[2-(difluoromethoxy)phenyl]-3-[3-(dimethylamino)prop-2-enoyl]pyridazin-4(1H)-one (crude 622 mg, 1.85 mmol) in 20 mL of methanol was added phenylhydrazine (800 mg, 7.40 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-[2-(difluoromethoxy)phenyl]-3-(1-phenyl-1H-pyrazol-5-yl)pyridazin-4(1H)-one (30 mg, 4% for two steps) as a yellow solid.

$^1$H NMR (400 MHz, $CDCl_3$): δ ppm 6.38 (t, J=72.0 Hz, 1H), 6.57-6.60 (m, 1H), 6.63 (d, J=8.0 Hz, 1H), 7.13 (dd, J=8.0, 0.8 Hz, 1H), 7.23-7.26 (m, 2H), 7.36-7.40 (m, 6H), 7.78 (d, J=1.6 Hz, 1H), 7.96 (d, J=8.0 Hz, 1H); LCMS (mobile phase: from 80% water and 20% $CH_3CN$ to 5% water and 95% $CH_3CN$ in 6 min, finally under these conditions for 0.5 min.) purity is >95%, Rt=3.317 min; MS Calcd.: 380, MS Found: 381 ($M^+$+H); mp 123-124° C.

Example 27

1-[3-(Difluoromethoxy)phenyl]-3-(1-phenyl-1H-pyrazol-5-yl)pyridazin-4(1H)-one

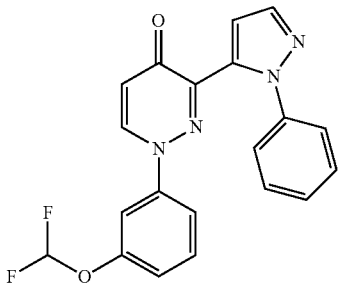 [SMILES: O=c1ccn(-c2cccc(OC(F)F)c2)nc1-c1ccnn1-c1ccccc1]

To a solution of 1-[3-(difluoromethoxy)phenyl]-3-[3-(dimethylamino)prop-2-enoyl]pyridazin-4(1H)-one (crude, 993 mg, 2.96 mmol) in 20 mL of methanol was added phenylhydrazine (480 mg, 4.44 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-[3-(difluoromethoxy)phenyl]-3-(1-phenyl-1H-pyrazol-5-yl)pyridazin-4(1H)-one (160 mg, 14% for two steps) as a yellow solid.

$^1$H NMR (400 MHz, $CDCl_3$): δ ppm 6.31 (s, 0.25*1H), 6.49 (s, 0.5*1H), 6.62 (t, J=2.4 Hz, 1H), 6.68 (s, 0.25*1H), 6.74 (d, J=7.6 Hz, 1H), 6.79 (dq, J=8.0, 0.8 Hz, 1H), 7.09 (dd, J=8.4, 1.2 Hz, 1H), 7.33 (t, J=8.0 Hz, 1H), 7.72-7.48 (m, 6H), 7.83 (d, J=2.0 Hz, 1H), 8.19 (d, J=8.0 Hz, 1H); LCMS (mobile phase: from 70% water and 30% $CH_3CN$ to 5% water and 95% $CH_3CN$ in 6 min, finally under these conditions for 0.5 min.) purity is >95%, Rt=3.027 min; MS Calcd.: 380, MS Found: 381 ($M^+$+H); mp 159-160° C.

Example 28

1-[4-(Difluoromethoxy)phenyl]-3-(1-phenyl-1H-pyrazol-5-yl)pyridazin-4(1H)-one

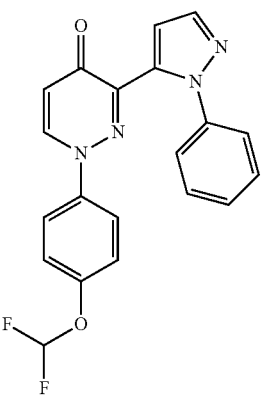 [SMILES: O=c1ccn(-c2ccc(OC(F)F)cc2)nc1-c1ccnn1-c1ccccc1]

To a solution of 1-[4-(difluoromethoxy)phenyl]-3-[3-(dimethylamino)prop-2-enoyl]pyridazin-4(1H)-one (crude 747 mg, 2.22 mmol) in 20 mL of methanol was added phenylhydrazine (360 mg, 3.33 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-[4-(difluoromethoxy)phenyl]-3-(1-phenyl-1H-pyrazol-5-yl)pyridazin-4(1H)-one (190 mg, 22% for two steps) as a yellow solid.

$^1$H NMR (400 MHz, $CDCl_3$): δ ppm 6.35 (s, 0.25*1H), 6.54 (s, 0.5*1H), 6.72 (s, 0.25*1H), 6.73 (d, J=8.0 Hz, 1H), 6.82 (dd, J=6.8, 2.0 Hz, 2H), 7.07 (d, J=9.2 Hz, 2H), 7.42-7.51 (m, 6H), 7.82 (d, J=2.0 Hz, 1H), 8.14 (d, J=8.0 Hz, 1H); LCMS (mobile phase: from 70% water and 30% $CH_3CN$ to 5% water and 95% $CH_3CN$ in 6 min, finally under these conditions for 0.5 min.) purity is >95%, Rt=3.007 min; MS Calcd.: 380, MS Found: 381 ($M^+$+H); mp 175-176° C.

Example 29

1-(2-Morpholin-4-ylphenyl)-3-(1-phenyl-1H-pyrazol-5-yl)pyridazin-4(1H)-one

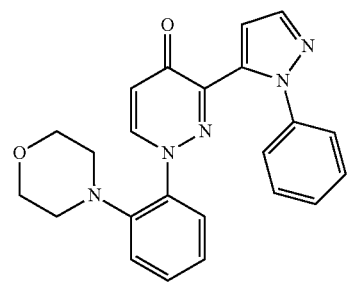 [SMILES: O=c1ccn(-c2ccccc2N2CCOCC2)nc1-c1ccnn1-c1ccccc1]

To a solution of 3-[3-(dimethylamino)prop-2-enoyl]-1-(2-morpholin-4-ylphenyl)pyridazin-4(1H)-one (crude, 870 mg, 2.46 mmol) 20 mL of methanol was added phenylhydrazine (400 mg, 3.69 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 1-(2-morpholin-4-ylphenyl)-3-(1-phenyl-1H-pyrazol-5-yl)pyridazin-4(1H)-one (50 mg, 5% for two steps) as a yellow solid.

$^1$H NMR (400 MHz, CDCl$_3$): δ ppm 2.73 (t, J=4.4 Hz, 4H), 3.70 (t, J=4.4 Hz, 4H), 6.45 (dd, J=8.0, 1.6 Hz, 1H), 6.68 (d, J=8.0 Hz, 1H), 6.95-6.99 (m, 1H), 7.07 (dd, J=8.0, 1.2 Hz, 1H), 7.28-7.29 (m, 1H), 7.32-7.41 (m, 6H), 7.81 (d, J=2.4 Hz, 1H), 8.27 (d, J=7.6 Hz, 1H); LCMS (mobile phase: from 70% water and 30% CH$_3$CN to 5% water and 95% CH$_3$CN in 6 min, finally under these conditions for 0.5 min.) purity is >95%, Rt=2.641 min; MS Calcd.: 399, MS Found: 400 (M$^+$+H); mp 200-201° C.

Example 30

3-(1-Phenyl-1H-pyrazol-5-yl)-1-pyridin-3-ylpyridazin-4(1H)-one

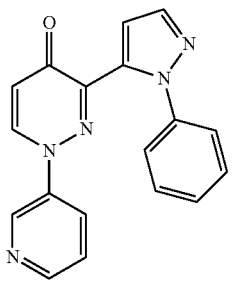 [SMILES: O=c1ccn(-c2cccnc2)nc1-c1ccnn1-c1ccccc1]

To a solution of 3-[3-(dimethylamino)prop-2-enoyl]-1-pyridin-3-ylpyridazin-4(1H)-one (crude 260 mg, 0.98 mmol) in 20 mL of methanol was added phenylhydrazine (423 mg, 3.92 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 3-(1-phenyl-1H-pyrazol-5-yl)-1-pyridin-3-ylpyridazin-4(1H)-one (60 mg, 19% for two steps) as a yellow solid.

$^1$H NMR (400 MHz, CDCl$_3$): δ ppm 6.75 (d, J=7.2 Hz, 1H), 7.00-7.03 (m, 1H), 7.22-7.26 (m, 1H), 7.39-7.50 (m, 6H), 7.82 (d, J=2.0 Hz, 1H), 8.18 (d, J=7.6 Hz, 1H), 8.26 (d, J=2.4 Hz, 1H), 8.55 (dd, J=4.8, 1.2 Hz, 1H); LCMS (mobile phase: from 90% water and 10% CH$_3$CN to 5% water and 95% CH$_3$CN in 6 min, finally under these conditions for 0.5 min.) purity is >95%, Rt=2.872 min; MS Calcd.: 315, MS Found: 316 (M$^+$+H); mp 176-177° C.

Example 31

3-(1-Phenyl-1H-pyrazol-5-yl)-1-pyridin-4-ylpyridazin-4(1H)-one

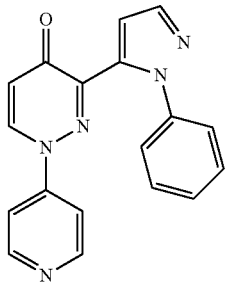 [SMILES: N=C/C=C(\Nc1ccccc1)c1nn(-c2ccncc2)ccc1=O]

To a solution of 3-[3-(dimethylamino)prop-2-enoyl]-1-pyridin-4-ylpyridazin-4(1H)-one (crude 158 mg, 0.58 mmol) in 20 mL of methanol was added phenylhydrazine (253 mg, 2.34 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 3-(1-phenyl-1H-pyrazol-5-yl)-1-pyridin-4-ylpyridazin-4(1H)-one (30 mg, 16% for two steps) as a yellow solid.

$^1$H NMR (400 MHz, CDCl$_3$): δ ppm 6.72-6.75 (m, 3H), 7.31-7.52 (m, 6H), 7.82 (d, J=1.6 Hz, 1H), 8.27 (d, J=8.0 Hz, 1H), 8.50-8.52 (m, 2H); LCMS (mobile phase: from 90% water and 10% CH$_3$CN to 5% water and 95% CH$_3$CN in 6 min, finally under these conditions for 0.5 min.) purity is >95%, Rt=2.850 min; MS Calcd.: 315, MS Found: 316 (M$^+$+H); mp 202-203° C.

Example 32

1-(2-Chlorophenyl)-3-(1-phenyl-1H-pyrazol-5-yl)pyridazin-4(1H)-one

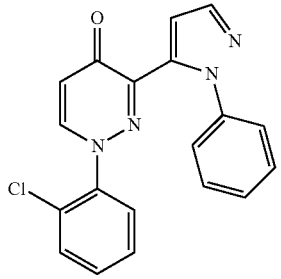 [SMILES: N=C/C=C(\Nc1ccccc1)c1nn(-c2ccccc2Cl)ccc1=O]

To a solution of 1-(2-chlorophenyl)-3-[3-(dimethylamino)prop-2-enoyl]pyridazin-4(1H)-one (crude, 636 mg, 2.10 mmol) in 20 mL of methanol was added phenylhydrazine (907 mg, 8.40 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 1-(2-chlorophenyl)-3-(1-phenyl-1H-pyrazol-5-yl)pyridazin-4(1H)-one (60 mg, 8% for two steps) as a red gel.

¹H NMR (400 MHz, CDCl₃): δ ppm 6.63 (d, J=8.0 Hz, 1H), 6.67 (dd, J=8.0, 1.6 Hz, 1H), 7.18-7.22 (m, 2H), 7.27-7.40 (m, 6H), 7.44-7.46 (m, 1H), 7.76 (d, J=1.6 Hz, 1H), 7.91 (d, J=8.0 Hz, 1H); LCMS (mobile phase: from 70% water and 30% CH₃CN to 5% water and 95% CH₃CN in 6 min, finally under these conditions for 0.5 min.) purity is >95%, Rt=2.662 min; MS Calcd.: 348, MS Found: 349 (M⁺+H); mp 138-139° C.

Example 33

3-[1-(1-Methylethyl)-1H-pyrazol-5-yl]-1-[3-(trifluoromethyl)phenyl]pyridazin-4(1H)-one

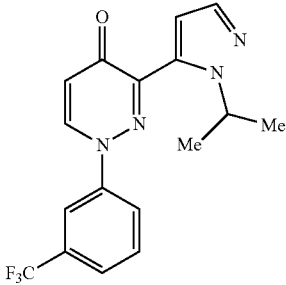 [SMILES: CC(C)N/C(=C\C=N)c1nn(-c2cccc(C(F)(F)F)c2)ccc1=O]

To a solution of 3-[3-(dimethylamino)prop-2-enoyl]-1-[3-(trifluoromethyl)phenyl]pyridazin-4(1H)-one (500 mg, 1.5 mmol) in ethanol (10 mL) were added isopropylhydrazine hydrochloride (246 mg, 2.2 mmol) and Et₃N (0.41 mL, 3.0 mmol). The mixture was stirred at 100° C. for 5 h. The mixture was diluted with 1N HCl aqueous solution, extracted with AcOEt, washed with brine, dried over Na₂SO₄, concentrated in vacuo, purified by column chromatography on silica gel (hexane/AcOEt=10/90 to 0/100) and recrystallized with AcOEt/i-Pr₂O to yield the title compound as a pale yellow solid (323 mg, 63%).
¹H NMR (300 MHz, DMSO-d₆) δ ppm 1.43 (d, J=6.4 Hz, 6H), 4.84-5.07 (m, 1H), 6.70 (d, J=8.0 Hz, 1H), 6.92 (d, J=1.9 Hz, 1H), 7.58 (d, J=1.5 Hz, 1H), 7.83 (d, J=5.3 Hz, 2H), 8.04-8.13 (m, 1H), 8.14 (s, 1H), 9.00 (d; J=8.0 Hz, 1H). LC-MS (M⁺) 348.55.; mp 183-184° C.

Example 34

3-[1-(2-Methylpropyl)-1H-pyrazol-5-yl]-1-[3-(trifluoromethyl)phenyl]pyridazin-4(1H)-one

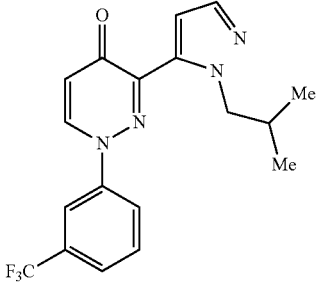 [SMILES: CC(C)CN/C(=C\C=N)c1nn(-c2cccc(C(F)(F)F)c2)ccc1=O]

To a solution of 3-[3-(dimethylamino)prop-2-enoyl]-1-[3-(trifluoromethyl)phenyl]pyridazin-4(1H)-one (500 mg, 1.5 mmol) in ethanol (10 mL) were added 2-methylpropylhydrazine hydrochloride (274 mg, 2.2 mmol) and Et₃N (0.41 mL, 3.0 mmol). The mixture was stirred at 100° C. for 5 h. The mixture was diluted with 1N HCl aqueous solution, extracted with AcOEt, washed with brine, dried over Na₂SO₄, concentrated in vacuo, purified by column chromatography on silica gel (hexane/AcOEt=10/90 to 0/100) and recrystallized with AcOEt/i-Pr₂O to yield the title compound as a pale yellow solid (289 mg, 54%).
¹H NMR (300 MHz, DMSO-d₆) δ ppm 0.73 (d, J=6.8 Hz, 6H), 2.12 (dt, J=13.6, 6.8 Hz, 1H), 4.22 (d, J=7.6 Hz, 2H), 6.70 (d, J=8.0 Hz, 1H), 7.14 (d, J=1.9 Hz, 1H), 7.55 (d, J=1.9 Hz, 1H), 7.74-7.93 (m, 2H), 7.98-8.26 (m, 2H), 8.95 (d, J=7.6 Hz, 1H). LC-MS (M⁺) 362.77; mp 120-121° C.

Example 35

3-(1-Pyridin-2-yl-1H-pyrazol-5-yl)-1-[3-(trifluoromethyl)phenyl]pyridazin-4(1H)-one

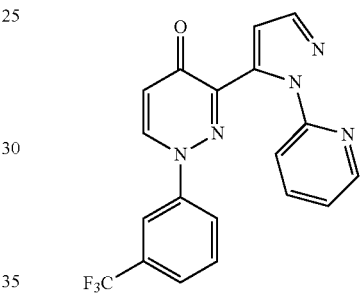

To a solution of 3-[3-(dimethylamino)prop-2-enoyl]-1-[3-(trifluoromethyl)phenyl]pyridazin-4(1H)-one (800 mg, 2.4 mmol) in ethanol (20 mL) were added 2-hydrazinepyridine (388 mg, 3.6 mmol) and Et₃N (0.66 mL, 4.7 mmol). The mixture was stirred at 100° C. for 5 h. The mixture was diluted with water, extracted with AcOEt, washed with brine, dried over Na₂SO₄, concentrated in vacuo, purified by HPLC and recrystallized with AcOEt/hexane to yield the title compound as a pale yellow solid (460 mg, 51%).
¹H NMR (300 MHz, DMSO-d₆) δ ppm 6.57 (d, J=7.9 Hz, 1H), 6.97 (s, 1H), 7.18-7.42 (m, 1H), 7.60-8.10 (m, 7H), 8.21 (d, J=4.5 Hz, 1H), 8.99 (d, J=8.3 Hz, 1H). LC-MS (M⁺) 383.82; mp 189-190° C.

Preparative HPLC was performed at the conditions described below.

Column: Sepax HP-C18 (30×50 mm S-10 μm)

Column temp: 25° C.

Mobile phase: (A) 0.1% TFA in distilled water, (B) 0.1% TFA in acetonitrile

Gradient: 0 min (A/B=90/10)→1.20 min (A/B=90/10)→4.75 min (A/B=0/100)→7.80 min (A/B=0/100)→7.90 min (A/B=90/10)→9.00 min (A/B=90/10)

Flow rate: 70 mL/min

Detector: UV 220 nm

Concentration: 80 mg/mL

Inject volume: 1250 μL

Example 36

1-[3-(Methylsulfonyl)phenyl]-3-(1-phenyl-1H-pyrazol-5-yl)pyridazin-4(1H)-one

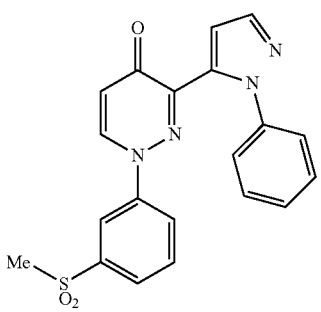 [SMILES: CS(=O)(=O)c1cccc(-n2ccc(=O)c(/C(=C/C=N)Nc3ccccc3)n2)c1]

A mixture of 1-[3-(methylsulfanyl)phenyl]-3-(1-phenyl-1H-pyrazol-5-yl)pyridazin-4(1H)-one and 1-[3-(methylsulfanyl)phenyl]-3-(1-phenyl-1H-pyrazol-3-yl)pyridazin-4(1H)-one (0.727 g, 2.02 mmol) in acetic acid (25 mL, 80% in water) was treated with potassium permanganate (0.500 g, 3.16 mmol) and the resulting mixture was stirred at ambient temperature for 2 h. After this time, the reaction was directly concentrated to remove acetic acid and neutralized with saturated sodium bicarbonate to pH=7. After extraction with ethyl acetate (3×100 mL), the combined organic layers were dried over magnesium sulfate, filtered and concentrated. Flash chromatography (silica, methylene chloride to 94:6 methylene chloride:methanol), followed by crystallization from methanol and two subsequent preparative HPLC purifications gave 1-[3-(methylsulfonyl)phenyl]-3-(1-phenyl-1H-pyrazol-5-yl)pyridazin-4(1H)-one (0.062 g, 8%) as a white solid.

$^1$H NMR (500 MHz, DMSO-$d_6$) δ ppm 3.26 (s, 3H), 6.67 (d, J=7.9 Hz, 1H), 7.18 (d, J=1.9 Hz, 1H), 7.26-7.29 (m, 1H), 7.39-7.42 (m, 3H), 7.44-7.48 (m, 2H), 7.63 (t, J=8.0 Hz, 1H), 7.83 (d, J=1.9 Hz, 1H), 7.87-7.90 (m, 1H), 8.01 (t, J=2.0 Hz, 1H), 8.96 (d, J=7.9 Hz, 1H); APCI MS m/z 393 [M+H]$^+$; mp 199-200° C.

Example 37

1-[3-(1H-Benzimidazol-2-yloxy)phenyl]-3-(1-phenyl-1H-pyrazol-5-yl)pyridazin-4(1H)-one

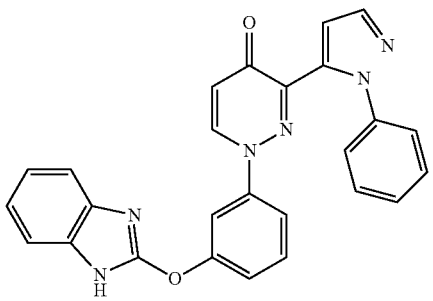 [SMILES: N=C/C=C(\Nc1ccccc1)c1nn(-c2cccc(Oc3nc4ccccc4[nH]3)c2)ccc1=O]

A mixture of 1-(3-hydroxyphenyl)-3-(1-phenyl-1H-pyrazol-5-yl)pyridazin-4(1H)-one (0.113 g, 0.342 mmol) and 2-chlorobenzimidazole (0.075 g, 0.49 mmol) in Et$_3$N (1 mL) was sealed and stirred at 120° C. for 14 h and then at 160° C. for 64 h. After this time, the reaction was diluted with ethyl acetate (50 mL), washed with saturated sodium bicarbonate aqueous solution (40 mL), and then with 2 N sodium hydroxide (3×20 mL). The organic layer was washed with brine, dried over magnesium sulfate, filtered and concentrated. Flash chromatography (silica, methylene chloride to 1:19 methanol/methylene chloride) afforded 1-[3-(1H-benzimidazol-2-yloxy)phenyl]-3-(1-phenyl-1H-pyrazol-5-yl)pyridazin-4(1H)-one (33 mg, 18%) as a light-yellow solid.

$^1$H NMR (500 MHz, DMSO-$d_6$) δ 6.65 (d, J=7.9 Hz, 1H), 6.90 (s, 1H), 7.12-7.19 (m, 4H), 7.25-7.34 (m, 5H), 7.37-7.46 (m, 3H), 7.47 (t, J=8.2 Hz, 1H), 7.81 (d, J=1.8 Hz, 1H), 8.87 (d, J=8.0 Hz, 1H), 12.43 (s, 1H); APCI MS m/z 447 [M+H]$^+$; mp 149-150° C.

Example 38

1-[3-(Methylsulfinyl)phenyl]-3-(1-phenyl-1H-pyrazol-5-yl)pyridazin-4(1H)-one

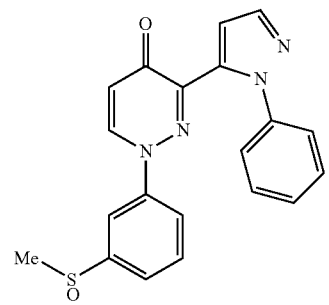

A mixture of 1-[3-(methylsulfanyl)phenyl]-3-(1-phenyl-1H-pyrazol-5-yl)pyridazin-4(1H)-one and 1-[3-(methylsulfanyl)phenyl]-3-(1-phenyl-1H-pyrazol-3-yl)pyridazin-4(1H)-one (0.180 g, 0.50 mmol), sodium bicarbonate (0.168 g, 2.0 mmol) in methylene chloride (8 mL) was treated with 3-chloroperoxybenzoic acid (0.140 g, 77%, 0.62 mmol) and the resulting mixture was stirred at ambient temperature for 2 h. After this time, the reaction was diluted with methylene chloride (20 mL), quenched with sodium thiosulfate (10%, 30 mL) and extracted with methylene chloride (2×20 mL). The combined organic layers were dried over magnesium sulfate, filtered and concentrated. Flash chromatography (silica, methylene chloride to 1:10 methanol/methylene chloride), followed by preparative HPLC gave 1-[3-(methylsulfinyl)phenyl]-3-(1-phenyl-1H-pyrazol-5-yl)pyridazin-4(1H)-one (84 mg, 45%) as a white solid.

$^1$H NMR (500 MHz, DMSO-$d_6$) δ ppm 2.85 (s, 3H), 6.70 (d, J=7.9 Hz, 1H), 7.35-7.38 (m, 2H), 7.52-7.56 (m, 2H), 7.76 (d, J=7.7 Hz, 1H), 7.81 (t, J=7.8 Hz, 1H), 7.91-7.93 (m, 2H), 8.00 (dt, J=8.9, 1.1 Hz, 1H), 8.11-8.12 (m, 1H), 8.60 (d, J=2.6 Hz, 1H), 8.96 (d, J=7.9 Hz, 1H); APCI MS m/z 377 [M+H]$^+$.

Example 39

1-[3-(1H-Benzimidazol-2-ylsulfonyl)phenyl]-3-(1-phenyl-1H-pyrazol-5-yl)pyridazin-4(1H)-one

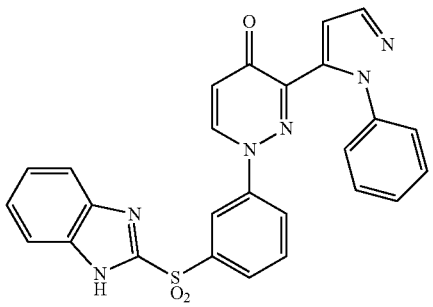 [SMILES: N=C/C=C(\Nc1ccccc1)c1nn(-c2cccc(S(=O)(=O)c3nc4ccccc4[nH]3)c2)ccc1=O]

A solution of a mixture of 1-[3-(1H-benzimidazol-2-ylsulfanyl)phenyl]-3-(1-phenyl-1H-pyrazol-5-yl)pyridazin-4(1H)-one and 1-[3-(1H-benzimidazol-2-ylsulfanyl)phenyl]-3-(1-phenyl-1H-pyrazol-3-yl)pyridazin-4(1H)-one (0.312 g, 0.68 mmol), 3-chloroperbenzoic acid (0.327 g of a 77% pure solid, 1.46 mmol) and sodium bicarbonate (0.227 g, 2.70 mmol) in dichloromethane (20 mL) was stirred for 2 h at room temperature. After that time, the reaction was diluted with dichloromethane (40 mL) and quenched with saturated sodium bisulfite solution (50 mL). The organic layer was separated and the aqueous layer extracted with dichloromethane (2×60 mL) and ethyl acetate (2×50 mL). The combined organic extracts were dried (MgSO$_4$) and concentrated. The crude product was purified by flash chromatography (silica gel, methylene chloride to 95:5 dichloromethane/methanol), followed by crystallization from methanol and preparative reverse phase HPLC to give 1-[3-(1H-benzimidazol-2-ylsulfonyl)phenyl]-3-(1-phenyl-1H-pyrazol-5-yl)pyridazin-4(1H)-one (0.005 g, 2%) as a white solid.
$^1$H NMR (500 MHz, DMSO-d$_6$) δ ppm 6.64 (d, J=7.9 Hz, 1H), 7.14 (d, J=1.9 Hz, 1H), 7.25-7.31 (m, 1H), 7.33-7.42 (m, 6H), 7.44 (dd, J=2.4, 8.2 Hz, 1H), 7.64-735 (m, 3H), 7.83 (d, J=1.9 Hz, 1H), 8.04 (d, J=7.9 Hz, 1H), 8.14 (t, J=1.9 Hz, 1H), 8.91 (d, J=7.9 Hz, 1H), 14.17 (br s, 1H); ESI MS m/z 495 [M+H]$^+$; mp 160-161° C.

Example 40

3-(4-Phenyl-4H-1,2,4-triazol-3-yl)-1-[3-(trifluoromethyl)phenyl]pyridazin-4(1H)-one

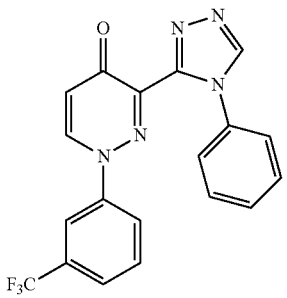 [SMILES: O=c1ccn(-c2cccc(C(F)(F)F)c2)nc1-c1nncn1-c1ccccc1]

A solution of 4-oxo-1-[3-(trifluoromethyl)phenyl]-1,4-dihydropyridazine-3-carbohydrazide (0.2 g, 0.67 mmol) and N,N-dimethylformamide dimethylacetal (0.09 mL, 0.67 mmol) in acetonitrile (2 mL) was heated at 55° C. for 45 min. After that time, acetic acid (2 mL) and aniline (0.06 mL, 0.66 mmol) were added and the temperature was increased to 125° C. for an additional 2 h. During this time, the acetonitrile was allowed to distill-off. The reaction was then concentrated to a dark residue and the crude product purified by column chromatography (silica gel, ethyl acetate to 4:1 ethyl acetate/methanol) to give 3-(4-phenyl-4H-1,2,4-triazol-3-yl)-1-[3-(trifluoromethyl)phenyl]pyridazin-4(1H)-one (0.137 g, 53%) as a light yellow oil that crystallized upon standing.
$^1$H NMR (300 MHz, CDCl$_3$) δ ppm 6.67 (1H, d, J=8.0 Hz), 730-7.41 (2H, m), 7.41-7.52 (3H, m), 7.57-7.72 (4H, m), 8.28 (1H, d, J=8.0 Hz), 8.43 (1H, s); APCI MS m/z 384 [C$_{19}$H$_{12}$F$_3$N$_5$O+H]$^+$; mp 103-104° C.

Example 41

3-(5-Methyl-4-phenyl-4H-1,2,4-triazol-3-yl)-1-[3-(trifluoromethyl)phenyl]pyridazin-4(1H)-one

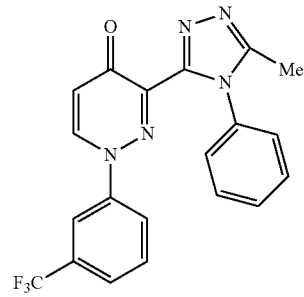 [SMILES: Cc1nnc(-c2nn(-c3cccc(C(F)(F)F)c3)ccc2=O)n1-c1ccccc1]

A solution of 4-oxo-1-[3-(trifluoromethyl)phenyl]-1,4-dihydropyridazine-3-carbohydrazide (0.207 g, 0.69 mmol) and N,N-dimethylacetamide dimethylacetal (0.1 mL, 0.68 mmol) in acetonitrile (2 mL) was heated at 60° C. for 2.5 h. After that time, acetic acid (2 mL) and aniline (0.06 mL, 0.66 mmol) were added and the temperature was increased to 125° C. for an additional 2 hours. During this time, the acetonitrile was allowed to distill-off. The reaction was then concentrated to a dark residue and the crude product purified by column chromatography (silica gel, ethyl acetate to 4:1 ethyl acetate/methanol) to give a yellow solid that was recrystallized from ethyl acetate/hexanes to give 3-(5-methyl-4-phenyl-4H-1,2,4-triazol-3-yl)-1-[3-(trifluoromethyl)phenyl]pyridazin-4(1H)-one (0.126 g, 46%) as light yellow crystals.
$^1$H NMR (300 MHz, CDCl$_3$) δ ppm 2.40 (s, 3H), 6.63 (d, J=8.0 Hz, 1H), 7.28-7.36 (m, 2H), 7.41-7.52 (m, 3H), 7.56-7.71 (m, 4H), 8.20 (d, J=8.1 Hz, 1H); APCI MS m/z 398 [M+H]$^+$; mp 191-192° C.

Example 42

3-(1-Phenyl-1H-1,2,4-triazol-5-yl)-1-[3-(trifluoromethyl)phenyl]pyridazin-4(1H)-one

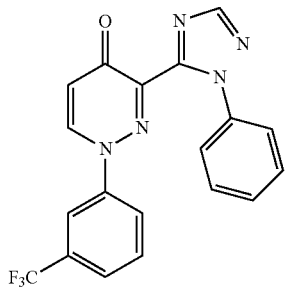

A solution of N-[(dimethylamino)methylidene]-4-oxo-1-[3-(trifluoromethyl)phenyl]-1,4-dihydropyridazine-3-carboxamide (0.119 g, 0.35 mmol) in acetic acid (5.0 mL) was treated with phenyl hydrazine (0.070 mL, 0.71 mmol). The resulting solution was heated under microwave heating conditions at 120° C. for 10 min. After that time the reaction was cooled to room temperature and the crude product purified by flash column chromatography (silica gel, ethyl acetate to 85:15 ethyl acetate/methanol) to give a colorless solid that was recrystallized from ethyl acetate/hexanes to give 0.126 g (46%) of 3-(1-phenyl-1H-1,2,4-triazol-5-yl)-1-[3-(trifluoromethyl)phenyl]pyridazin-4(1H)-one as colorless crystals.

$^1$H NMR (300 MHz, CDCl$_3$) δ ppm 6.75 (d, J=8.1 Hz, 1H), 7.38-7.49 (m, 5H), 7.49-7.56 (m, 2H), 7.56-7.70 (m, 2H), 8.17-8.31 (m, 2H); APCI MS m/z 384 [M+H]$^+$; mp 167-168° C.

Example 43

3-(1-Phenyl-1H-tetrazol-5-yl)-1-[3-(trifluoromethyl)phenyl]pyridazin-4(1H)-one

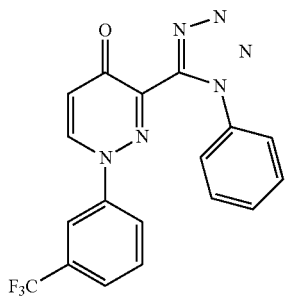

A solution of 3-[1H-benzotriazol-1-yl(phenylimino)methyl]-1-[3-(trifluoromethyl)phenyl]pyridazin-4(1H)-one (0.094 g, 0.20 mmol), sodium azide (0.030 g, 0.46 mmol), and tetrabutylammonium bromide (0.015 g, 0.047 mmol) in methylene chloride (5 mL) and water (5 mL) was treated with trifluoroacetic acid (0.040 mL, 0.52 mmol) and stirred 24 h at room temperature. After that time, the organic layer was separated and the aqueous layer was extracted with methylene chloride (3×25 mL). The combined organic extracts were washed with saturated NaCl aqueous solution (50 mL), dried (MgSO$_4$), and concentrated. The crude product purified by flash column chromatography (silica gel, 80:20 hexanes/ethyl acetate to ethyl acetate) to give an off-white solid that was recrystallized from ethyl acetate/hexanes to give 0.034 g (56%) of 3-(1-phenyl-1H-tetrazol-5-yl)-1-[3-(trifluoromethyl)phenyl]pyridazin-4(1H)-one as colorless crystals.

$^1$H NMR (300 MHz, CDCl$_3$) δ ppm 6.76 (d, J=8.0 Hz, 1H), 7.43-7.59 (m, 5H), 7.59-7.75 (m, 4H), 8.42 (d, J=8.0 Hz, 1H); APCI MS m/z 385 [M+H]$^+$; mp 172-173° C.

Example 44

3-(1-Phenyl-1H-pyrazol-5-yl)-1-(4-piperidin-1-ylphenyl)pyridazin-4(1H)-one

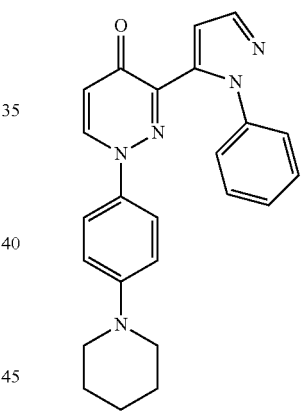

To a solution of 3-[3-(dimethylamino)prop-2-enoyl]-1-(4-piperidin-1-ylphenyl)pyridazin-4(1H)-one (crude 700 mg, 1.99 mmol) in 20 mL of methanol was added phenylhydrazine (858 mg, 7.94 mmol). The mixture was refluxed for 4 h and concentrated. The residue was dissolved in dichloromethane (20 mL), washed with 1N HCl aqueous solution and brine, dried over Na$_2$SO$_4$, and concentrated under reduced pressure. The residue was purified by prep-HPLC to give 3-(1-phenyl-1H-pyrazol-5-yl)-1-(4-piperidin-1-ylphenyl)pyridazin-4(1H)-one (30 mg, 4% for two steps) as a yellow solid.

$^1$H NMR (400 MHz, CDCl$_3$): δ ppm 1.51-1.60 (m, 2H), 1.67-1.70 (m, 4H), 3.18 (t, J=5.6 Hz, 4H), 6.65-6.70 (m, 3H), 6.74-6.77 (m, 2H), 7.37 (d, J=1.6 Hz, 1H), 7.42-7.45 (m, 5H), 7.79 (d, J=2.0 Hz, 1H), 8.08 (d, J=8.0 Hz, 1H); LCMS (mobile phase: from 70% water and 30% CH$_3$CN to 5% water and 95% CH$_3$CN in 6 min, finally under these conditions for 0.5 min.) purity is >95%, Rt=3.532 min; MS Calcd.: 397, MS Found: 398 (M$^+$+H).

Example 45

1-(4-Cyclohexylphenyl)-3-(1-phenyl-1H-pyrazol-5-yl)pyridazin-4(1H)-one

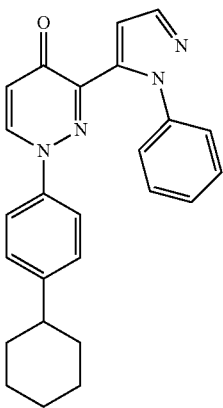 [SMILES: N=C/C=C(\Nc1ccccc1)c1nn(-c2ccc(C3CCCCC3)cc2)ccc1=O]

To a solution of 1-(4-cyclohexylphenyl)-3-[3-(dimethylamino)prop-2-enoyl]pyridazin-4(1H)-one (crude, 500 mg, 1.42 mmol) in 20 mL of methanol was added phenylhydrazine (615 mg, 5.70 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-(4-cyclohexylphenyl)-3-(1-phenyl-1H-pyrazol-5-yl)pyridazin-4(1H)-one (170 mg, 30% for two steps) as a yellow solid.

$^1$H NMR (400 MHz, $CDCl_3$): δ ppm 1.23-1.44 (m, 5H), 1.75-1.84 (m, 5H), 2.47-2.53 (m, 1H), 6.69-6.73 (m, 3H), 7.11 (d, J=8.4 Hz, 2H), 7.38-7.49 (m, 6H), 7.79 (d, J=2.0 Hz, 1H), 8.14 (d, J=8.0 Hz, 1H); LCMS (mobile phase: from 40% water and 60% $CH_3CN$ to 5% water and 95% $CH_3CN$ in 6 min, finally under these conditions for 0.5 min.) purity is >95%, Rt=2.358 min; MS Calcd.: 396, MS Found: 397 ($M^+$+H).

Example 46

4-[4-Oxo-3-(1-phenyl-1H-pyrazol-5-yl)pyridazin-1(4H)-yl]benzonitrile

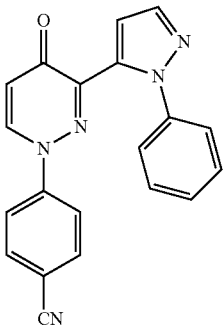

To a solution of 4-{3-[3-(dimethylamino)prop-2-enoyl]-4-oxopyridazin-1(4H)-yl}benzonitrile (crude, 340 mg, 1.16 mmol) in 20 mL of methanol was added phenylhydrazine (500 mg, 4.62 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 4-[4-oxo-3-(1-phenyl-1H-pyrazol-5-yl)pyridazin-1(4H)-yl]benzonitrile (18 mg, 4% for two steps) as a yellow solid.

$^1$H NMR (400 MHz, $CDCl_3$): δ ppm 6.74 (d, J=8.0 Hz, 2H), 6.88 (d, J=8.8 Hz, 2H), 7.40-7.52 (m, 5H), 7.57 (dd, J=8.8, 2.0 Hz, 2H), 7.81 (d, J=2.0 Hz, 1H), 8.20 (d, J=8.0 Hz, 1H); LCMS (mobile phase: from 80% water and 20% $CH_3CN$ to 5% water and 95% $CH_3CN$ in 6 min, finally under these conditions for 0.5 min.) purity is >95%, Rt=3.077 min; MS Calcd.: 339, MS Found: 340 ($M^+$+H).

Example 47

1-[4-(Methylsulfonyl)phenyl]-3-(1-phenyl-1H-pyrazol-5-yl)pyridazin-4(1H)-one

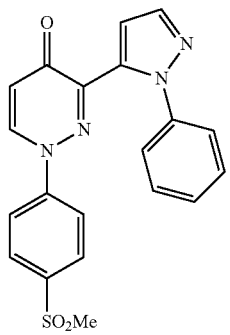 [SMILES: CS(=O)(=O)c1ccc(-n2ccc(=O)c(-c3ccnn3-c3ccccc3)n2)cc1]

To a solution of 3-[3-(dimethylamino)prop-2-enoyl]-1-[4-(methylsulfonyl)phenyl]pyridazin-4(1H)-one (crude 615 mg, 1.77 mmol) in 20 mL of methanol was added phenylhydrazine (765 mg, 7.08 mmol). The mixture was, refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-[4-(methylsulfonyl)phenyl]-3-(1-phenyl-1H-pyrazol-5-yl)pyridazin-4(1H)-one (42 mg, 6% for two steps) as a yellow solid.

$^1$H NMR (400 MHz, DMSO-$d_6$): δ ppm 3.26 (s, 3H), 6.69 (d, J=8.0 Hz, 1H), 7.27-7.30 (m, 3H), 7.41-7.43 (m, 2H), 7.48-7.52 (m, 3H), 7.84-7.89 (m, 3H), 8.94 (d, J=8.0 Hz, 1H); LCMS (mobile phase: from 90% water and 10% $CH_3CN$ to 5% water and 95% $CH_3CN$ in 6 min, finally under these conditions for 0.5 min.) purity is >90%, Rt=3.102 min; MS Calcd.: 392, MS Found: 393 ($M^+$+H).

Example 48

1-[4-(Morpholin-4-ylsulfonyl)phenyl]-3-(1-phenyl-1H-pyrazol-5-yl)pyridazin-4(1H)-one

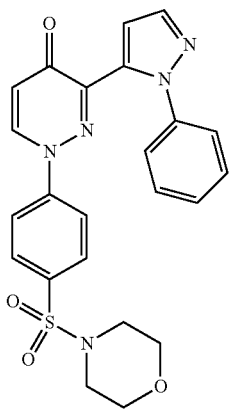 [SMILES: O=c1ccn(-c2ccc(S(=O)(=O)N3CCOCC3)cc2)nc1-c1ccnn1-c1ccccc1]

To a solution of 3-[3-(dimethylamino)prop-2-enoyl]-1-[4-(morpholin-4-ylsulfonyl)phenyl]pyridazin-4(1H)-one (crude 355 mg, 0.85 mmol) in 20 mL of methanol was added phenylhydrazine (367 mg, 3.40 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 1-[4-(morpholin-4-ylsulfonyl)phenyl]-3-(1-phenyl-1H-pyrazol-5-yl)pyridazin-4(1H)-one (60 mg, 15% for two steps) as a yellow solid.

$^1$H NMR (400 MHz, CDCl$_3$): δ ppm 2.97 (t, J=4.8 Hz, 4H), 3.74 (t, J=4.8 Hz, 4H), 6.73 (d, J=8.0 Hz, 1H), 6.91 (dd, J=7.2, 1.6 Hz, 2H), 7.39-7.48 (m, 6H), 7.61-7.64 (m, 2H), 7.80 (d, J=1.6 Hz, 1H), 8.22 (d, J=8.0 Hz, 1H); LCMS (mobile phase: from 80% water and 20% CH$_3$CN to 5% water and 95% CH$_3$CN in 6 min, finally under these conditions for 0.5 min.) purity is >95%, Rt=3.035 min; MS Calcd.: 463, MS Found: 464 (M$^+$+H).

Example 49

4-[4-Oxo-3-(1-phenyl-1H-pyrazol-5-yl)pyridazin-1(4H)-yl]benzamide

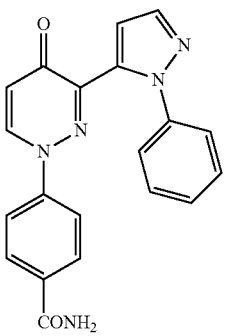

To a solution of 4-{3-[3-(dimethylamino)prop-2-enoyl]-4-oxopyridazin-1(4H)-yl}benzamide (crude 682 mg, 2.19 mmol) in 20 mL of methanol was added phenylhydrazine (946 mg, 8.76 mmol). The mixture was refluxed for 4 h and concentrated. The residue was dissolved in dichloromethane (20 mL), washed with 1N HCl aqueous solution and brine, dried over $Na_2SO_4$, and concentrated under reduced pressure. The residue was purified by prep-HPLC to give 4-[4-oxo-3-(1-phenyl-1H-pyrazol-5-yl)pyridazin-1(4H)-yl]benzamide (50 mg, 6% for two steps) as a yellow solid.

$^1$H NMR (400 MHz, CDCl$_3$): δ ppm 6.75 (d, J=8.0 Hz, 1H), 6.87 (d, J=8.4 Hz, 2H), 7.25-7.26 (m, 1H), 7.41-7.49 (m, 5H), 7.74 (d, J=8.8 Hz, 2H), 7.82 (d, J=2.0 Hz, 1H), 8.23 (d, J=8.0 Hz, 1H); LCMS (mobile phase: from 90% water and 10% CH$_3$CN to 5% water and 95% CH$_3$CN in 6 min, finally under these conditions for 0.5 min.) purity is >95%, Rt=2.663 min; MS Calcd.: 357, MS Found: 358 (M$^+$+H).

Example 50

5-Methyl-3-(1-phenyl-1H-pyrazol-5-yl)-1-[3-(trifluoromethyl)phenyl]pyridazin-4(1H)-one

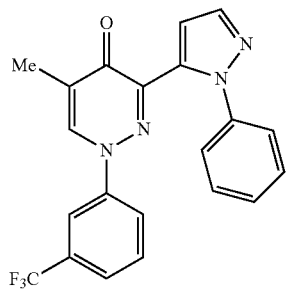

A microwave vial containing 3-[3-(dimethylamino)prop-2-enoyl]-5-methyl-1-[3-(trifluoromethyl)phenyl]pyridazin-4(1H)-one (0.215 g, 0.61 mmol) and phenylhydrazine (0.24 mL, 2.44 mmol) in acetic acid (3 mL) was heated at 120° C. for 10 min. The crude material was concentrated and dissolved in ethyl acetate (20 mL). The organic layer was washed with saturated sodium bicarbonate aqueous solution (3×10 mL), dried (Na$_2$SO$_4$), filtered and concentrated to provide a crude residue. The residue was purified by flash column chromatography (silica gel; 35:65 ethyl acetate/hexanes to ethyl acetate) to provide 5-methyl-3-(1-phenyl-1H-pyrazol-5-yl)-1-[3-(trifluoromethyl)phenyl]pyridazin-4(1H)-one (0.0545 g, 23%) as an off-white solid.

$^1$H NMR (300 MHz, DMSO-d$_6$) δ ppm 2.06 (s, 3H), 7.22 (d, J=2.1 Hz, 1H), 7.37-7.48 (m, 6H), 7.52 (s, 1H), 7.59 (t, J=8.1 Hz, 1H), 7.68-7.71 (m, 1H), 7.83 (d, J=1.8 Hz, 1H) 9.00 (s, 1H); APCI MS m/z 397 [M+H]$^+$; mp 147-150° C.

Example 51

3-(3-Methyl-1-phenyl-1H-pyrazol-5-yl)-1-[3-(trifluoromethyl)phenyl]pyridazin-4(1H)-one

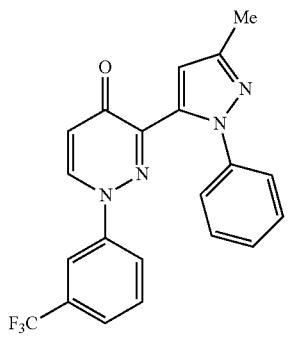 [SMILES: Cc1cc(-c2nn(-c3cccc(C(F)(F)F)c3)ccc2=O)n(-c2ccccc2)n1]

A solution of 3-[3-(dimethylamino)but-2-enoyl]-1-[3-(trifluoromethyl)phenyl]pyridazin-4(1H)-one (0.270 g, 0.77 mmol) and phenyl hydrazine (0.200 mL, 2.0 mmol) in acetic acid (5.0 mL) was heated under microwave conditions at 120° C. for 10 min. After this time, the reaction was cooled to room temperature and concentrated onto silica gel. The crude product purified by column chromatography (silica gel, 50:50 ethyl acetate/hexanes to ethyl acetate) to separate the two isomers, followed by preparative reverse phase HPLC and crystallization from diethyl ether to give 3-(3-methyl-1-phenyl-1H-pyrazol-5-yl)-1-[3-(trifluoromethyl)phenyl]pyridazin-4(1H)-one (0.048 g, 16%) as a white solid. $^1$H NMR (300 MHz, CDCl$_3$) δ ppm 2.42 (s, 3H), 6.73 (d, J=7.9 Hz, 1H), 6.99 (dd, J=1.7, 8.1 Hz, 1H), 7.18 (br s, 1H), 7.21 (s, 1H), 7.30-7.49 (m, 6H), 7.55 (d, J=7.8 Hz, 1H), 8.19 (d, J=7.9 Hz, 1H); APCI MS m/z 397 [M+H]$^+$; mp 167-168° C.

Example 52

1-(2-Fluorophenyl)-5-methoxy-3-(1-phenyl-1H-pyrazol-5-yl)pyridazin-4(1H)-one

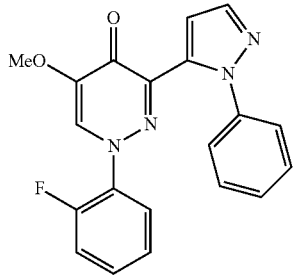 [SMILES: COc1cn(-c2ccccc2F)nc(-c2ccnn2-c2ccccc2)c1=O]

A solution of 3-acetyl-1-(2-fluorophenyl)-5-methoxypyridazin-4(1H)-one (1.89 g, 7.2 mmol) in N,N-dimethylformamide dimethyl acetal (20 mL) was refluxed for 6 h. After cooling to room temperature, the reaction mixture was concentrated under reduced pressure.

A solution of the residue and phenylhydrazine (2.34 mL, 21.6 mmol) in AcOH (20 mL) was refluxed for 2 h. After cooling to room temperature, the reaction mixture was concentrated under reduced pressure. The residue was diluted with AcOEt, washed successively with 1 M HCl aqueous solution, 1 M NaOH aqueous solution, and brine, dried over MgSO$_4$, and concentrated under reduced pressure. The residue was purified by basic silica gel column chromatography eluting with hexane/AcOEt (1/2) and recrystallized from MeOH/H$_2$O to give the title compound (1.53 g, 59% yield) as off-white crystals: mp 163-165° C.; $^1$H NMR (300 MHz, CDCl$_3$): δ ppm 3.90 (3H, s), 6.43 (1H, dt, J=1.5, 7.9 Hz), 6.98-7.04 (1H, m), 7.18 (1H, ddd, J=1.1, 8.3, 11.3 Hz), 7.28-7.46 (7H, m), 7.78 (1H, d, J=1.9 Hz), 7.81 (1H, d, J'=2.3 Hz). LC-MS (ESI) m/z 363 [M+H]$^+$. Anal. Calcd for C$_{20}$H$_{15}$FN$_4$O$_2$: C, 66.29; H, 4.17; N, 15.46. Found: C, 66.09; H, 4.22; N, 15.42.

Example 53

1-[2-(Difluoromethoxy)phenyl]-5-methoxy-3-(1-phenyl-1H-pyrazol-5-yl)pyridazin-4(1H)-one

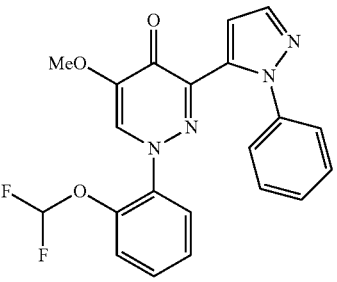 [SMILES: COc1cn(-c2ccccc2OC(F)F)nc(-c2ccnn2-c2ccccc2)c1=O]

A solution of 1-[2-(difluoromethoxy)phenyl]-3-[3-(dimethylamino)prop-2-enoyl]-5-methoxypyridazin-4(1H)-one (0.50 g, 1.369 mmol) and phenylhydrazine (0.269 mL, 2.74 mmol) in AcOH (5 mL) was refluxed for 2 h. After cooling to room temperature, the mixture was concentrated under reduced pressure. The residue was diluted with AcOEt, washed successively with 1 M HCl aqueous solution, saturated NaHCO$_3$ aqueous solution, and brine, dried over MgSO$_4$, and concentrated under reduced pressure. The residue was purified by silica gel column chromatography eluting with hexane/AcOEt (7/3-0/10) to give the title compound (0.38 g, 68% yield) as an off-white amorphous solid: $^1$H NMR (300 MHz, CDCl$_3$): δ ppm 3.88 (3H, s), 6.37 (1H, t, J=72.3 Hz), 6.57 (1H, dd, J=8.1, 1.7 Hz), 7.09-7.16 (1H, m), 7.22-7.25 (2H, m), 7.34-7.42 (6H, m), 7.76-7.78 (2H, m). LC-MS (ESI) m/z 411 [M+H]$^+$. Anal. Calcd. for C$_{21}$H$_{16}$F$_2$N$_4$O$_3$: C, 61.15; H, 4.07; N, 13.79. Found: C, 61.23; H, 4.11; N, 13.71.

Example 54

5-Methoxy-3-(1-phenyl-1H-pyrazol-5-yl)-1-[3-(trifluoromethyl)phenyl]pyridazin-4(1H)-one

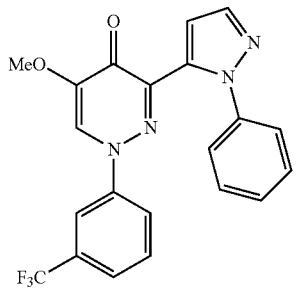 [SMILES: COc1cn(-c2cccc(C(F)(F)F)c2)nc(-c2ccnn2-c2ccccc2)c1=O]

A solution of 3-[3-(dimethylamino)prop-2-enoyl]-5-methoxy-1-[3-(trifluoromethyl)phenyl]pyridazin-4(1H)-one (3.41 g, 9.29 mmol) and phenylhydrazine (1.83 mL, 18.6 mmol) in AcOH (25 mL) was refluxed for 2 h. After cooling to room temperature, the reaction mixture was concentrated under reduced pressure. The residue was diluted with AcOEt, washed successively with 1 M HCl aqueous solution, 1 M NaOH aqueous solution, and brine, dried over $MgSO_4$, and concentrated under reduced pressure. The residue was purified by silica gel column chromatography eluting with AcOEt and crystallized from hexane/AcOEt to give the title compound (2.70 g, 71% yield) as colorless crystals: mp 139-141° C.; $^1$H NMR (300 MHz, $CDCl_3$): δ ppm 3.98 (3H, s), 7.05 (1H, dd, J=1.9, 7.9 Hz), 7.19 (1H, s), 7.34-7.47 (7H, m), 7.56 (1H, d, J=7.9 Hz), 7.80 (1H, d, J=1.9 Hz), 7.92 (1H, s). LC-MS (ESI) m/z 413 [M+H]$^+$. Anal. Calcd for $C_{21}H_{15}F_3N_4O_2$: C, 61.17; H, 3.67; N, 13.59. Found: C, 61.15; H, 3.65; N, 13.57.

Example 55

1-(2-Fluoro-4-iodophenyl)-5-methoxy-3-(1-phenyl-1H-pyrazol-5-yl)pyridazin-4(1H)-one

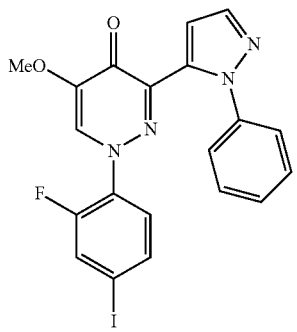 [SMILES: COc1cn(-c2ccc(I)cc2F)nc(-c2ccnn2-c2ccccc2)c1=O]

A mixture of 3-acetyl-1-(2-fluoro-4-iodophenyl)-5-methoxypyridazin-4(1H)-one (2.02 g, 5.2 mmol) and N,N-dimethylformamide dimethyl acetal (30 mL) was refluxed for 6 h. After cooling to room temperature, the reaction mixture was concentrated under reduced pressure.

A solution of the residue and phenylhydrazine (1.54 mL, 15.6 mmol) in AcOH (20 mL) was refluxed for 2 h. After cooling to room temperature, the reaction mixture was concentrated under reduced pressure. The residue was diluted with AcOEt, washed successively with 1 M HCl aqueous solution, 1 M NaOH aqueous solution, and brine, dried over $MgSO_4$, and concentrated under reduced pressure. The residue was purified by silica gel column chromatography eluting with AcOEt and recrystallized from MeOH to give the title compound (1.14 g, 45% yield) as pale yellow crystals: mp 194-196° C.; $^1$H NMR (300 MHz, $CDCl_3$): δ ppm 3.90 (3H, s), 6.04 (1H, t, J=8.5 Hz), 7.30-7.47 (7H, m), 7.54 (1H, dd, J=1.9, 10.6 Hz), 7.76 (1H, d, J=2.3 Hz), 7.78 (1H, d, J=2.3 Hz). LC-MS (ESI) m/z 489 [M+H]$^+$. Anal. Calcd for $C_{20}H_{14}FIN_4O_2$: C, 49.20; H, 2.89; N, 11.47. Found: C, 48.94; H, 3.01; N, 11.54.

Example 56

1-[2-Fluoro-4-(trifluoromethyl)phenyl]-5-methoxy-3-(1-phenyl-1H-pyrazol-5-yl)pyridazin-4(1H)-one

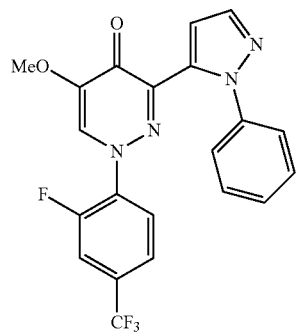 [SMILES: COc1cn(-c2ccc(C(F)(F)F)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.50 mmol), $FSO_2CF_2CO_2Me$ (0.318 mL, 2.5 mmol), HMPA (0.435 mL, 2.5 mmol), and CuI (114 mg, 0.6 mmol) in DMF (2.5 mL) was stirred for 24 h at 90° C. under Ar atmosphere. After cooling to room temperature, the reaction mixture was poured into water and extracted with AcOEt. The extract was washed with brine, dried over $MgSO_4$, and concentrated under reduced pressure. The residue was purified by basic silica gel column chromatography eluting with hexane/AcOEt (1/1) and recrystallized from hexane/AcOEt to give the title compound (71.7 mg, 33% yield) as off-white crystals: mp 169-171° C.; $^1$H NMR (300 MHz, $CDCl_3$): δ ppm 3.92 (3H, s), 6.42-6.47 (1H, m), 7.22-7.26 (1H, m), 7.37-7.49 (7H, m), 7.80 (1H, d, J=1.9 Hz), 7.84 (1H, d, J=2.3 Hz). LC-MS (ESI) m/z 431 [M+H]$^+$. Anal. Calcd for $C_{21}H_{14}F_4N_4O_2$: C, 58.61; H, 3.28; N, 13.02. Found: C, 58.50; H, 3.36; N, 12.93.

Example 57

1-(2-Fluoro-4-morpholin-4-ylphenyl)-5-methoxy-3-(1-phenyl-1H-pyrazol-5-yl)pyridazin-4(1H)-one

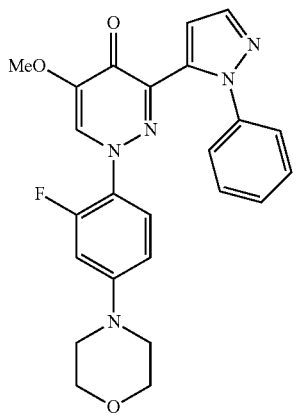 [SMILES: COc1cn(-c2ccc(N3CCOCC3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), morpholine (0.053 mL, 0.6 mmol), Pd$_2$(dba)$_3$ (18.3 mg, 0.02 mmol), Xantphos (46.3 mg, 0.08 mmol), and NaOtBu (67.3 mg, 0.7 mmol) in 1,4-dioxane (2.5 mL) was stirred for 2 h at 90° C. under Ar atmosphere. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with AcOEt and recrystallized from MeOH/H$_2$O to give the title compound (148 mg, 66% yield) as off-white crystals: mp 226-228° C.; $^1$H NMR (300 MHz, CDCl$_3$): δ ppm 3.16-3.19 (4H, m), 3.83-3.87 (4H, m), 3.89 (3H, s), 6.31 (1H, t, J=9.0 Hz), 6.45 (1H, dd, J=2.6, 9.0 Hz), 6.58 (1H, dd, J=2.6, 14.7 Hz), 7.26 (1H, d, J=1.9 Hz), 7.33-7.45 (5H, m), 7.74 (1H, d, J=2.3 Hz), 7.77 (1H, d, J=1.9 Hz). LC-MS (ESI) m/z 448 [M+H]$^+$. Anal. Calcd for C$_{24}$H$_{22}$FN$_5$O$_3$: C, 64.42; H, 4.96; N, 15.65. Found: C, 64.33; H, 4.98; N, 15.59.

Example 58

5-Hydroxy-3-(1-phenyl-1H-pyrazol-5-yl)-1-[3-(trifluoromethyl)phenyl]pyridazin-4(1H)-one

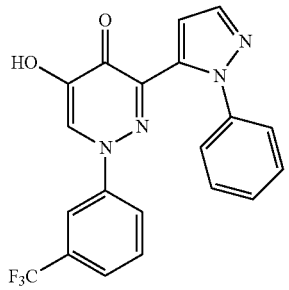

TMSCl (3.17 mL, 25 mmol) was added at room temperature to a solution of NaI (3.75 g, 25 mmol) in CH$_3$CN (150 mL). After stirring for 30 min, 5-methoxy-3-(1-phenyl-1H-pyrazol-5-yl)-1-[3-(trifluoromethyl)phenyl]pyridazin-4(1H)-one (2.06 g, 5 mmol) was added to the resulting suspension. The mixture was stirred for 30 min at room temperature and then refluxed for 1 h. After cooling to room temperature, the reaction mixture was poured into water and extracted with AcOEt. The extract was washed with brine, dried over MgSO$_4$, and concentrated under reduced pressure. The residue was washed with hexane/AcOEt (1/1) and recrystallized from MeOH/H$_2$O to give the title compound (1.68 g, 84% yield) as a colorless powder: mp 246-248° C.; $^1$H NMR (300 MHz, DMSO-d$_6$): δ ppm 7.17 (1H, d, J=1.9 Hz), 7.33-7.46 (5H, m), 7.53-7.64 (3H, m), 7.71 (1H, d, J=7.5 Hz), 7.83 (1H, d, J=1.9 Hz), 8.83 (1H, s). Anal. Calcd for C$_{20}$H$_{13}$F$_3$N$_4$O$_2$: C, 60.30; H, 3.29; N, 14.07. Found: C, 60.09; H, 3.33; N, 14.02.

Example 59

5-Ethoxy-3-(1-phenyl-1H-pyrazol-5-yl)-1-[3-(trifluoromethyl)phenyl]pyridazin-4(1H)-one

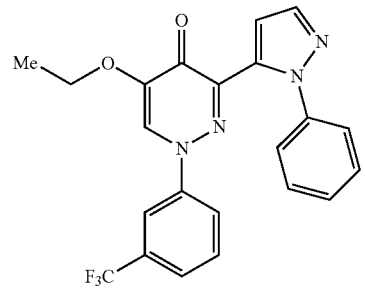 [SMILES: CCOc1cn(-c2cccc(C(F)(F)F)c2)nc(-c2ccnn2-c2ccccc2)c1=O]

A suspension of 5-hydroxy-3-(1-phenyl-1H-pyrazol-5-yl)-1-[3-(trifluoromethyl)phenyl]pyridazin-4(1H)-one (100 mg, 0.25 mmol), iodoethane (0.040 mL, 0.50 mmol), and K$_2$CO$_3$ (104 mg, 0.75 mmol) in DMF (1 mL) was stirred for 24 h at room temperature. The reaction mixture was poured into water and extracted with AcOEt. The extract was washed with brine, dried over MgSO$_4$, and concentrated under reduced pressure. The residue was purified by basic silica gel column chromatography eluting with hexane/AcOEt (1/1) to give the title compound (94.1 mg, 88% yield) as an off-white amorphous solid: $^1$H NMR (300 MHz, CDCl$_3$): δ ppm 1.52 (3H, t, J=6.8 Hz), 4.21 (2H, q, J=6.8 Hz), 7.03 (1H, dd, J=1.9, 7.9 Hz), 7.18 (1H, s), 7.33-7.46 (7H, m), 7.55 (1H, d, J=7.9 Hz), 7.80 (1H, d, J=1.9 Hz), 7.94 (1H, s). LC-MS (ESI) m/z 427 [M+H]$^+$. Anal. Calcd for C$_{22}$H$_{17}$F$_3$N$_4$O$_2$: C, 61.97; H, 4.02; N, 13.14. Found: C, 61.82; H, 4.15; N, 13.17.

Example 60

5-(1-Methylethoxy)-3-(1-phenyl-1H-pyrazol-5-yl)-1-[3-(trifluoromethyl)phenyl]pyridazin-4(1H)-one

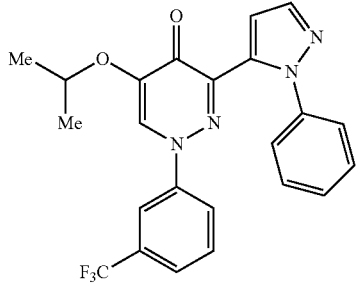 [SMILES: CC(C)Oc1cn(-c2cccc(C(F)(F)F)c2)nc(-c2ccnn2-c2ccccc2)c1=O]

A suspension of 5-hydroxy-3-(1-phenyl-1H-pyrazol-5-yl)-1-[3-(trifluoromethyl)phenyl]pyridazin-4(1H)-one (100 mg, 0.25 mmol), 2-iodopropane (0.050 mL, 0.50 mmol), and K$_2$CO$_3$ (104 mg, 0.75 mmol) in DMF (1 mL) was stirred for 20 h at 60° C. The reaction mixture was poured into water and extracted with AcOEt. The extract was washed with brine, dried over MgSO$_4$, and concentrated under reduced pressure. The residue was purified by basic silica gel column chromatography eluting with hexane/AcOEt (1/1) and crystallized from hexane/AcOEt to give the title compound (79.5 mg, 72% yield) as colorless prisms: mp 137-139° C.; $^1$H NMR (300 MHz, CDCl$_3$): δ ppm 1.38 (6H, d, J=6.4 Hz), 4.96-5.09 (1H, m), 7.05 (1H, dd, J=1.9, 7.9 Hz), 7.18 (1H, s), 7.33-7.46 (7H, m), 7.55 (1H, d, J=7.9 Hz), 7.80 (1H, d, J=1.9 Hz), 8.01 (1H, s). LC-MS (ESI) m/z 441 [M+H]$^+$. Anal. Calcd for C$_{23}$H$_{19}$F$_3$N$_4$O$_2$: C, 62.72; H, 4.35; N, 12.72. Found: C, 62.74; H, 4.40; N, 12.81.

Example 61

5-(Cyclopropylmethoxy)-3-(1-phenyl-1H-pyrazol-5-yl)-1-[3-(trifluoromethyl)phenyl]pyridazin-4(1H)-one

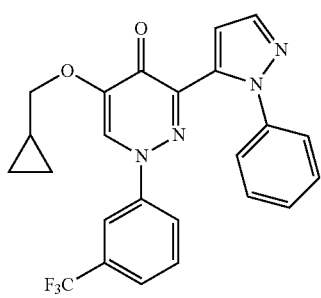 [SMILES: O=c1c(OCC2CC2)cn(-c2cccc(C(F)(F)F)c2)nc1-c1ccnn1-c1ccccc1]

A suspension of 5-hydroxy-3-(1-phenyl-1H-pyrazol-5-yl)-1-[3-(trifluoromethyl)phenyl]pyridazin-4(1H)-one (100 mg, 0.25 mmol), (bromomethyl)cyclopropane (0.048 mL, 0.50 mmol), and K$_2$CO$_3$ (104 mg, 0.75 mmol) in DMF (1 mL) was stirred for 20 h at room temperature. The reaction mixture was poured into water and extracted with AcOEt. The extract was washed with brine, dried over MgSO$_4$, and concentrated under reduced pressure. The residue was purified by basic silica gel column chromatography eluting with hexane/ AcOEt (1/1) and crystallized from MeOH to give the title compound (103 mg, 91% yield) as colorless prisms: mp 72-78° C.; $^1$H NMR (300 MHz, CDCl$_3$): δ ppm 0.32-0.47 (2H, m), 0.60-0.76 (2H, m), 1.26-1.39 (1H, m), 4.06 (2H, d, J=7.2 Hz), 7.04 (1H, dd, J=2.3, 8.3 Hz), 7.18 (1H, s), 7.33-7.46 (7H, m), 7.55 (1H, d, J=7.9 Hz), 7.80 (1H, d, J=1.9 Hz), 7.99 (1H, s). LC-MS (ESI) m/z 453 [M+H]$^+$. Anal. Calcd for C$_{24}$H$_{19}$F$_3$N$_4$O$_2$·0.5H$_2$O: C, 62.47; H, 4.37; N, 12.14. Found: C, 62.19; H, 4.41; N, 12.15.

Example 62

5-(Difluoromethoxy)-3-(1-phenyl-1H-pyrazol-5-yl)-1-[3-(trifluoromethyl)phenyl]pyridazin-4(1H)-one

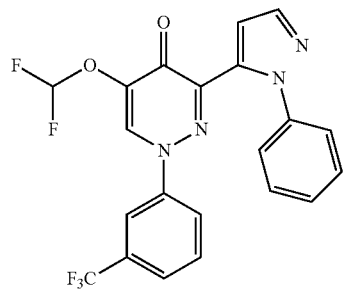 [SMILES: N=C/C=C(\Nc1ccccc1)c1nn(-c2cccc(C(F)(F)F)c2)cc(OC(F)F)c1=O]

A mixture of 5-hydroxy-3-(1-phenyl-1H-pyrazol-5-yl)-1-[3-(trifluoromethyl)phenyl]pyridazin-4(1H)-one (398 mg, 1.0 mmol), CF$_2$ClCO$_2$Na (305 mg, 2.0 mmol), K$_2$CO$_3$ (207 mg, 1.5 mmol), DMF (2 mL), and H$_2$O (0.4 mL) was stirred for 6 h at 100° C. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with hexane/AcOEt (3/1) and crystallized from hexane/AcOEt to give the title compound (267 mg, 59% yield) as colorless prisms: mp 132-134° C.; $^1$H NMR (300 MHz, CDCl$_3$): δ ppm 7.06 (1H, dd, J=23, 8.3 Hz), 7.16-7.66 (10H, m), 7.82 (1H, d, J=1.9 Hz), 8.33 (1H, s). LC-MS (ESI) m/z 449 [M+H]$^+$. Anal. Calcd for C$_{21}$H$_{13}$F$_5$N$_4$O$_2$: C, 56.26; H, 2.92; N, 12.50. Found: C, 55.98; H, 2.82; N, 12.43.

Example 63

1-(2-Fluorophenyl)-5-hydroxy-3-(1-phenyl-1H-pyrazol-5-yl)pyridazin-4(1H)-one

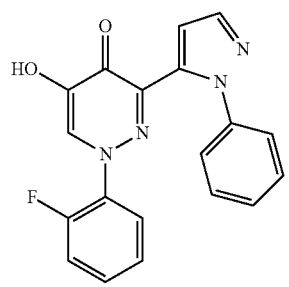 [SMILES: N=C/C=C(\Nc1ccccc1)c1nn(-c2ccccc2F)cc(O)c1=O]

TMSCl (1.27 mL, 10 mmol) was added at room temperature to a solution of NaI (1.50 g, 10 mmol) in CH$_3$CN (60 mL). After stirring for 30 min, 1-(2-fluorophenyl)-5-methoxy-3-(1-phenyl-1H-pyrazol-5-yl)pyridazin-4(1H)-one (0.725 g, 2 mmol) was added to the resulting suspension. The mixture was stirred for 30 min at room temperature and then refluxed for 1 h. After cooling to room temperature, the reaction mixture was poured into water and extracted with AcOEt. The extract was washed with brine, dried over MgSO$_4$, and concentrated under reduced pressure. The residue was washed with hexane/AcOEt (1/1) and recrystallized from MeOH/H$_2$O to give the title compound (0.648 g, 93% yield) as off-white prisms: mp 218-220° C.; $^1$H NMR (300 MHz, DMSO-d$_6$): δ ppm 6.99 (1H, d, J=1.9 Hz), 7.10 (1H, dt, J=1.5, 7.9 Hz), 7.21-7.26 (1H, m), 7.32-7.54 (7H, m), 7.80 (1H, d, J=1.9 Hz), 8.44 (1H, d, J=2.6 Hz). Anal. Calcd for C$_{19}$H$_{13}$FN$_4$O$_2$: C, 65.51; H, 3.76; N, 16.08. Found: C, 65.73; H, 3.88; N, 16.24.

Example 64

5-(Difluoromethoxy)-1-(2-fluorophenyl)-3-(1-phenyl-1H-pyrazol-5-yl)pyridazin-4(1H)-one

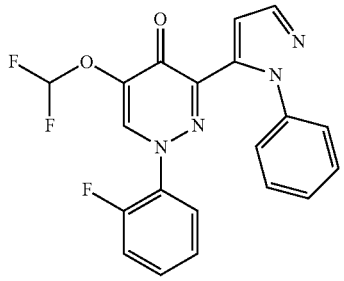 [SMILES: N=C/C=C(\Nc1ccccc1)c1nn(-c2ccccc2F)cc(OC(F)F)c1=O]

A mixture of 1-(2-fluorophenyl)-5-hydroxy-3-(1-phenyl-1H-pyrazol-5-yl)pyridazin-4(1H)-one (557 mg, 1.6 mmol), CF$_2$ClCO$_2$Na (488 mg, 3.2 mmol), K$_2$CO$_3$ (332 mg, 2.4 mmol), DMF (3 mL), and H$_2$O (0.6 mL) was stirred overnight at 100° C. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with hexane/AcOEt (2/1) and crystallized from hexane/AcOEt to give the title compound (485 mg, 76% yield) as colorless prisms: mp 109-114° C.; $^1$H NMR (300 MHz, CDCl$_3$): δ ppm 6.46 (1H, dd, J=1.5, 7.9 Hz), 7.00-7.06 (1H, m), 7.08-7.59 (9H, m), 7.80 (1H, d, J=1.9 Hz), 8.20 (1H, s). LC-MS (ESI) m/z 399 [M+H]$^+$. Anal. Calcd for C$_{20}$H$_{13}$F$_3$N$_4$O$_2$: C, 60.30; H, 3.29; N, 14.07. Found: C, 60.50; H, 3.41; N, 14.20.

Example 65

5-(2-Methoxyethoxy)-3-(1-phenyl-1H-pyrazol-5-yl)-1-[3-(trifluoromethyl)phenyl]pyridazin-4(1H)-one

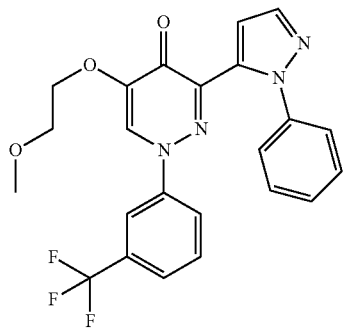 [SMILES: COCCOc1cn(-c2cccc(C(F)(F)F)c2)nc(-c2ccnn2-c2ccccc2)c1=O]

A suspension of 5-hydroxy-3-(1-phenyl-1H-pyrazol-5-yl)-1-[3-(trifluoromethyl)phenyl]pyridazin-4(1H)-one (100 mg, 0.25 mmol), 2-bromoethyl methyl ether (0.070 mL, 0.75 mmol), and K$_2$CO$_3$ (104 mg, 0.75 mmol) in DMF (1 mL) was stirred for 24 h at room temperature. The reaction mixture was poured into water and extracted with AcOEt. The extract was washed with brine, dried over MgSO$_4$, and concentrated under reduced pressure. The residue was purified by basic silica gel column-chromatography eluting with hexane/AcOEt (1/2) to give the title compound (89.9 mg, 79% yield) as a pale yellow amorphous solid: $^1$H NMR (300 MHz, CDCl$_3$): δ ppm 3.45 (3H, s), 3.78-3.81 (2H, m), 4.42-4.44 (2H, m), 7.02 (1H, dd, J=1.9, 7.9 Hz), 7.20 (1H, s), 7.34-7.45 (7H, m), 7.55 (1H, d, J=7.9 Hz), 7.80 (1H, d, J=1.9 Hz), 8.29 (1H, s). LC-MS (ESI) m/z 457 [M+H]$^+$. Anal. Calcd for C$_{23}$H$_{19}$F$_3$N$_4$O$_3$.0.25H$_2$O: C, 59.93; H, 4.26; N, 12.16. Found: C, 59.87; H, 4.09; N, 12.15.

Example 66

5-(Methoxymethyl)-3-(1-phenyl-1H-Pyrazol-5-yl)-1-[3-(trifluoromethyl)phenyl]pyridazin-4(1H)-one

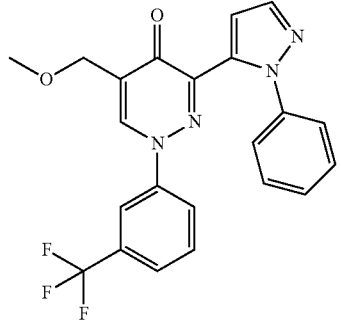 [SMILES: COCc1cn(-c2cccc(C(F)(F)F)c2)nc(-c2ccnn2-c2ccccc2)c1=O]

A solution of 3-acetyl-5-(methoxymethyl)-1-[3-(trifluoromethyl)phenyl]pyridazin-(1.39 g, 4.26 mmol) in N,N-dimethylformamide dimethyl acetal (15 mL) was refluxed for 4 h. After cooling to room temperature, the reaction mixture was poured into water and extracted with AcOEt three times. The combined extracts were washed with brine, dried over MgSO$_4$, and concentrated under reduced pressure.

A solution of the residue and phenylhydrazine (1.18 mL, 12 mmol) in MeOH (15 mL) was refluxed for 1 h. After cooling to room temperature, the reaction mixture was poured into 1 M HCl aqueous solution and extracted with AcOEt. The extract was washed with brine, dried over MgSO$_4$, and concentrated under reduced pressure. The residue was purified by basic silica gel column chromatography eluting with hexane/AcOEt (2/1) and recrystallized from hexane/AcOEt to give the title compound (759 mg, 42% yield) as a pale yellow solid: mp 137-139° C.; $^1$H NMR (300 MHz, CDCl$_3$): δ ppm 3.55 (3H, s), 4.53 (2H, d, J=1.1 Hz), 7.06 (1H, dd, J=1.9, 7.9 Hz), 7.19 (1H, s), 7.35-7.45 (7H, m), 7.55 (1H, d, J=7.9 Hz), 7.81 (1H, d, J=1.9 Hz), 8.34 (1H, t, J=1.1 Hz). LC-MS (ESI) m/z 427 [M+H]$^+$. Anal. Calcd for C$_{22}$H$_{17}$F$_3$N$_4$O$_2$: C, 61.97; H, 4.02; N, 13.14. Found: C, 61.60; H, 4.05; N, 13.07.

Example 67

5-Bromo-3-(1-phenyl-1H-pyrazol-5-yl)-1-[3-(trifluoromethyl)phenyl]pyridazin-4(1H)-one

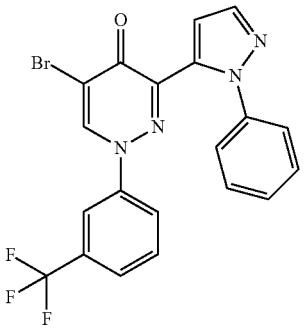 [SMILES: O=c1c(Br)cn(-c2cccc(C(F)(F)F)c2)nc1-c1ccnn1-c1ccccc1]

A mixture of 3-acetyl-5-bromo-1-[3-(trifluoromethyl)phenyl]pyridazin-4(1H)-one (332 mg, 0.92 mmol) and N,N-dimethylformamide dimethyl acetal (3.3 mL) was heated to reflux for 1 h. The mixture was concentrated in vacuo. To the residue were added AcOH (3.3 mL) and phenylhydrazine (0.181 mL, 1.84 mmol). The mixture was heated to reflux for 90 min. To the mixture was added phenylhydrazine (0.091 mL, 0.92 mmol). The mixture was heated to reflux for 90 min. The mixture was diluted with 1 M HCl aqueous solution, extracted with AcOEt, washed with saturated NaHCO$_3$ aqueous solution, dried over MgSO$_4$, filtered, concentrated in vacuo and purified by column chromatography on basic silica gel (hexane/AcOEt=50/50 to 0/100) and by HPLC to yield the title compound (151 mg, 35% yield) as a white solid: mp 145-146° C. $^1$H NMR (DMSO-d$_6$, 300 MHz): δ ppm 7.27 (1H, d, J=1.9 Hz), 7.35-7.52 (6H, m), 7.54-7.64 (2H, m), 7.73 (1H, d, J=8.0 Hz), 7.85 (1H, d, J=1.9 Hz), 9.52 (1H, s). Anal. Calcd for C$_{20}$H$_{12}$BrF$_3$N$_4$O: C, 52.08; H, 2.62; N, 12.15. Found: C, 52.07; H, 2.75; N, 12.28.

Preparative HPLC was performed at the conditions described below.

Column: Waters SunFire Column C18 (30×50 mm S-5 μm)

Column temp: 25° C.

Mobile phase: (A) 0.1% TFA in distilled water, (B) 0.1% TFA in acetonitrile

Gradient: 0 min (A/B=60/40)→1.20 min (A/B=60/40)→4.75 min (A/B=0/100)→7.75 min (A/B=0/100)→7.85 min (A/B=60/40)→8.50 min (A/B=60/40)

Flow rate: 70 mL/min

Detector: UV 220 nm

Concentration: 98 mg/mL

Inject volume: 825 μL

Example 68

1-[4-(Benzyloxy)-2-fluorophenyl]-5-methoxy-3-(1-phenyl-1H-pyrazol-5-yl)pyridazin-4(1H)-one

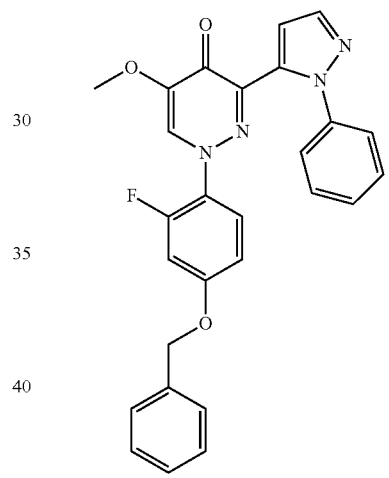

A solution of 3-acetyl-1-[4-(benzyloxy)-2-fluorophenyl]-5-methoxypyridazin-4(1H)-one (5.82 g, 15.8 mmol) in N,N-dimethylformamide dimethyl acetal (50 mL) was refluxed for 2 h. After cooling to room temperature, the reaction mixture was concentrated under reduced pressure.

A solution of the residue and phenylhydrazine (3.11 mL, 31.6 mmol) in AcOH (50 mL) was refluxed for 2 h. After cooling to room temperature, the reaction mixture was concentrated under reduced pressure. The residue was diluted with AcOEt, washed successively with 1 M HCl aqueous solution, 1 M NaOH aqueous solution, and brine, dried over MgSO$_4$, and concentrated under reduced pressure. The residue was washed with AcOEt and then purified by basic silica gel column chromatography eluting with THF. Recrystallization from MeOH/H$_2$O gave the title compound (5.57 g, 75% yield) as a pale yellow solid: mp 181-183° C.; $^1$H NMR (300 MHz, CDCl$_3$): δ ppm 3.89 (3H, s), 5.06 (2H, s), 6.35 (1H, t, J=9.0 Hz), 6.60 (1H, ddd, J=1.1, 2.6, 9.0 Hz), 6.74 (1H, dd, J=2.6, 12.8 Hz), 7.28 (1H, d, J=1.9 Hz), 7.31-7.45 (10H, m), 7.72 (1H, d, J=2.6 Hz), 7.78 (1H, d, J=1.9 Hz). LC-MS (ESI) m/z 469 [M+H]$^+$. Anal. Calcd for C$_{27}$H$_{21}$FN$_4$O$_3$: C, 69.22; H, 4.52; N, 11.96. Found: C, 69.04; H, 4.60; N, 11.98.

Example 69

6-Hydroxy-3-(1-phenyl-1H-pyrazol-5-yl)-1-[3-(trifluoromethyl)phenyl]pyridazin-4(1H)-one

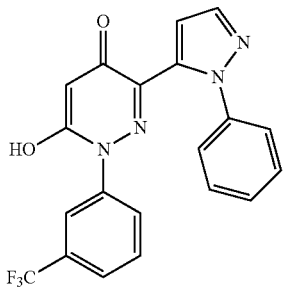 [SMILES: O=c1cc(O)n(-c2cccc(C(F)(F)F)c2)nc1-c1ccnn1-c1ccccc1]

Chlorotrimethylsilane (0.46 mL, 3.6 mmol) was added to a solution of sodium iodide (0.55 g, 0.73 mmol) in MeCN (20 mL) at room temperature. After stirring for 30 min, 5-methoxy-6-(1-phenyl-1H-pyrazol-5-yl)-2-[3-(trifluoromethyl)phenyl]pyridazin-3(2H)-one (0.30 g, 0.73 mmol) was added to the resulting suspension. The mixture was stirred at room temperature for 1 h, and then refluxed for 3 h. After cooling to room temperature, the mixture was poured into water and extracted with AcOEt. The extract was washed with brine, dried over MgSO$_4$, and concentrated under reduced pressure. The residue was washed with diisopropyl ether/hexane and recrystallized from AcOEt/hexane to give the title compound (0.21 g, 73% yield) as white crystals: mp 241-243° C.; $^1$H NMR (300 MHz, DMSO-d$_6$): δ ppm 6.16 (1H, s), 6.88 (1H, d, J=1.9. Hz), 7.36-7.42 (3H, m), 7.45-7.54 (4H, m), 7.59 (1H, t, J=7.9 Hz), 7.70 (1H, d, J=7.9 Hz), 7.82 (1H, d, J=1.9 Hz), 12.23 (1H, brs). LC-MS (ESI) m/z 399 [M+H]$^+$. Anal. Calcd for C$_{20}$H$_{13}$F$_3$N$_4$O$_2$: C, 60.30; H, 3.29; N, 14.07. Found: C, 60.35; H, 3.37; N, 14.10.

Example 70

3-[1-Phenyl-3-(trifluoromethyl)-1H-pyrazol-5-yl]-1-[3-(trifluoromethyl)phenyl]pyridazin-4(1H)-one

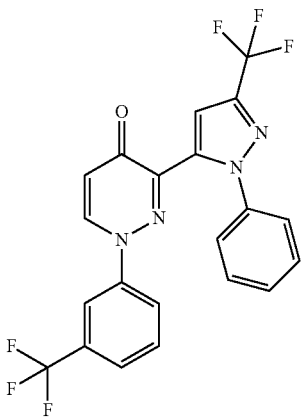 [SMILES: O=c1ccn(-c2cccc(C(F)(F)F)c2)nc1-c1cc(C(F)(F)F)nn1-c1ccccc1]

To a solution of ethyl trifluoroacetate (0.139 mL, 1.17 mmol) in methyl tert-butyl ether (1 mL) was added NaOMe (28% in MeOH, 245 mg, 1.27 mmol) at room temperature. To the mixture was added a solution of 3-acetyl-1-[3-(trifluoromethyl)phenyl]pyridazin-4(1H)-one (300 mg, 1.06 mmol) in THF (1.5 mL) and methyl tert-butyl ether (1.5 mL) at room temperature. The mixture was stirred at room temperature for 2 days. The mixture was diluted with 1 M HCl aqueous solution, extracted with AcOEt, washed with brine, dried over Na$_2$SO$_4$, filtered and concentrated in vacuo. To the residue were added phenylhydrazine (0.209 mL, 2.12 mmol) and AcOH (3.5 mL). The mixture was heated to reflux for 90 min. The mixture was diluted with 1 M HCl aqueous solution, extracted with AcOEt, washed with NaHCO$_3$ aqueous solution, dried over MgSO$_4$, filtered, concentrated in vacuo, purified by column chromatography on silica gel (hexane/AcOEt=50/50 to 0/100), crystallized with AcOEt/hexane and purified by HPLC to yield the title compound (9.6 mg, 2% yield) as a white solid: mp 190-191° C. $^1$H NMR (DMSO-d$_6$, 300 MHz): δ ppm 6.73 (1H, d, J=7.9 Hz), 7.37-7.81 (10H, m), 8.97 (1H, d, J=8.3 Hz). Anal. Calcd for C$_{21}$H$_{12}$F$_6$N$_4$O: C, 56.01; H, 2.69; N, 12.44. Found: C, 55.70; H, 2.81; N, 12.23.

Preparative HPLC was performed at the conditions described below.

Column: Waters SunFire Column C18 (30×50 mm S-5 µm)

Column temp: 25° C.

Mobile phase: (A) 0.1% TFA in distilled water, (B) 0.1% TFA in acetonitrile

Gradient: 0 min (A/B=52/48)→10.00 min (A/B=52/48)→10.50 min (A/B=0/100)→12.50 min (A/B=0/100)→12.60 min (A/B=52/48)→13.00 min (A/B=52/48)

Flow rate: 20 mL/min

Detector: UV 220 nm

Concentration: 100 mg/mL

Inject volume: 100 µL

Example 71

3-(4-Methyl-1-phenyl-1H-pyrazol-5-yl)-1-[3-(trifluoromethyl)phenyl]pyridazin-4(1H)-one

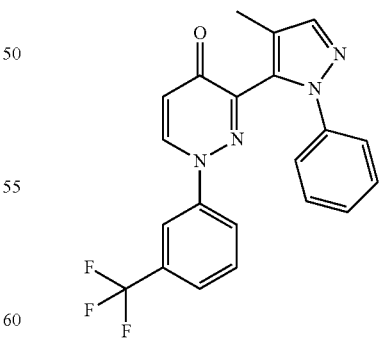

To a suspension of 3-propanoyl-1-[3-(trifluoromethyl)phenyl]pyridazin-4(1H)-one (384 mg, 1.30 mmol) in methyl formate (3.8 mL) was added NaOMe (28% in MeOH, 326 mg, 1.69 mmol) at room temperature. The mixture was stirred at room temperature for 3.5 h. The mixture was diluted with

Example 72

3-(4-Fluoro-1-phenyl-1H-pyrazol-5-yl)-1-[3-(trifluoromethyl)phenyl]pyridazin-4(1H)-one

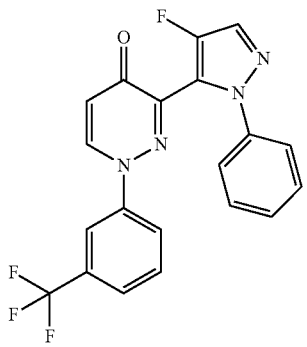 [SMILES: O=c1ccn(-c2cccc(C(F)(F)F)c2)nc1-c1c(F)cnn1-c1ccccc1]

A mixture of 3-(1-phenyl-1H-pyrazol-5-yl)-1-[3-(trifluoromethyl)phenyl]pyridazin-4(1H)-one (49.0 mg, 0.128 mmol) and selectfluor (45.4 mg, 0.128 mmol) in MeCN (1 mL) was stirred at room temperature for 6 days. To the mixture was added selectfluor (45.4 mg, 0.128 mmol) at room temperature. The mixture was stirred at room temperature for 1 day. To the mixture was added selectfluor (45.4 mg, 0.128 mmol) at room temperature. The mixture was stirred at room temperature for 1 day. To the mixture was added selectfluor (45.4 mg, 0.128 mmol) at room temperature. The mixture was stirred at room temperature for 1 day. To the mixture was added selectfluor (272 mg, 0.768 mmol) at room temperature. The mixture was stirred at room temperature for 3 days. The mixture was diluted with brine, extracted with AcOEt, dried over MgSO$_4$, filtered, concentrated in vacuo, purified by column chromatography on silica gel (hexane/AcOEt=50/50 to 0/100) and crystallized with AcOEt/hexane to yield the title compound (11.7 mg, 23% yield) as a pale yellow solid: mp 156-158° C. $^1$H NMR (DMSO-d$_6$, 300 MHz): δ ppm 6.67 (1H, d, J=8.2 Hz), 7.33-7.50 (5H, m), 7.63-7.83 (4H, m), 7.97 (1H, d, J=4.1 Hz), 8.96 (1H, d, J=8.0 Hz).

water and 1 M HCl aqueous solution, extracted with AcOEt, washed with brine, dried over Na$_2$SO$_4$, filtered, concentrated in vacuo and crystallized with AcOEt/hexane. To the solid were added phenylhydrazine (0.405 mL, 4.12 mmol) and MeOH (6.7 mL). The mixture was heated to reflux for 15 h. The mixture was diluted with 1 M HCl aqueous solution, extracted with AcOEt, washed with saturated NaHCO$_3$ aqueous solution, dried over Na$_2$SO$_4$, filtered, concentrated in vacuo, purified by column chromatography on silica gel (hexane/AcOEt=50/50 to 0/100) and crystallized with AcOEt/heptane to yield the title compound (161 mg, 39% yield) as a pale yellow solid: mp 208-211° C. $^1$H NMR (DMSO-d$_6$, 300 MHz): δ ppm 2.09 (3H, s), 6.62 (1H, d, J=8.0 Hz), 7.26-7.35 (3H, m), 7.35-7.44 (2H, m), 7.64-7.85 (5H, m), 8.95 (1H, d, J=8.2 Hz). Anal. Calcd for C$_{21}$H$_{15}$F$_3$N$_4$O: C, 63.63; H, 3.81; N, 14.14. Found: C, 63.46; H, 3.92; N, 13.98.

Example 73

3-(3-Phenyl-1-trityl-1H-pyrazol-4-yl)-1-[3-(trifluoromethyl)phenyl]pyridazin-4(1H)-one

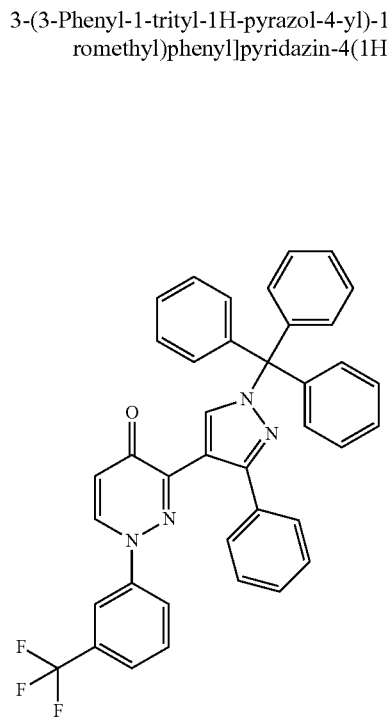

nBuLi (1.6 M solution in hexane, 25 mL, 40 mmol) was added dropwise at −78° C. to a solution of 4-bromo-3-phenyl-1-trityl-1H-pyrazole (7.96 g, 20.6 mmol) and B(OiPr)$_3$ (6.92 mL, 30 mmol) in THF (75 mL). After stirring for 1 h, the reaction mixture was allowed to warm to 0° C., quenched with saturated NH$_4$Cl aqueous solution, and extracted with AcOEt. The extract was washed with brine, dried over MgSO$_4$, and concentrated under reduced pressure. The residue was purified by silica gel column chromatography eluting with hexane/AcOEt (2/1-0/1) and crystallized from MeOH to give crude (3-phenyl-1-trityl-1H-pyrazol-4-yl)boronic acid (5.73 g) as a white solid.

A mixture of 3-bromo-1-[3-(trifluoromethyl)phenyl]pyridazin-4(1H)-one (319 mg, 1.0 mmol), (3-phenyl-1-trityl-1H-pyrazol-4-yl)boronic acid (645 mg, 1.5 mmol), Pd(PPh$_3$)$_4$ (58 mg, 0.05 mmol), Na$_2$CO$_3$ (318 mg, 3.0 mmol), DME (7.5 mL), and H$_2$O (1.5 mL) was refluxed overnight under Ar atmosphere. After cooling to room temperature, the reaction mixture was poured into water and extracted with AcOEt. The extract was washed with brine, dried over MgSO$_4$, and concentrated under reduced pressure. The residue was purified by silica gel column chromatography eluting with hexane/AcOEt (1/1) and crystallized from MeOH to give the title compound (418 mg, 67% yield) as a white solid: mp 216-218° C.; $^1$H NMR (300 MHz, CDCl$_3$): δ ppm 6.58 (1H, d, J=7.9 Hz), 7.08 (1H, dd, J=2.3, 7.9 Hz), 7.23-7.39 (20H, m), 7.47-7.54 (3H, m), 8.17 (1H, d, J=7.9 Hz), 8.67 (1H, s). LC-MS (ESI) m/z 625 [M+H]$^+$. Anal. Calcd for C$_{39}$H$_{27}$F$_3$N$_4$O: C, 74.99; H, 4.36; N, 8.97. Found: C, 74.84; H, 4.39; N, 9.01.

Example 74

3-(3-Phenyl-1H-pyrazol-4-yl)-1-[3-(trifluoromethyl)phenyl]pyridazin-4(1H)-one

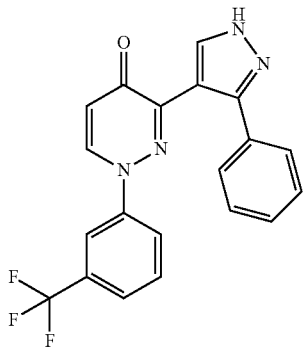 [SMILES: O=c1ccn(-c2cccc(C(F)(F)F)c2)nc1-c1c[nH]nc1-c1ccccc1]

A mixture of 3-(3-phenyl-1-trityl-1H-pyrazol-4-yl)-1-[3-(trifluoromethyl)phenyl]pyridazin-4(1H)-one (1.50 g, 2.4 mmol), TFA (5 mL), and $CH_2Cl_2$ (15 mL) was stirred overnight at room temperature. The reaction mixture was alkalinized with 1 M NaOH aqueous solution and extracted with AcOEt. The extract was washed with brine, dried over $MgSO_4$, and concentrated under reduced pressure. The residue was recrystallized from MeOH to give the title compound (751 mg, 82% yield) as a white solid: mp 206-208° C.; $^1$H NMR (300 MHz, DMSO-$d_6$): δ ppm 6.58 (1H, d, J=7.9 Hz), 7.37-7.67 (9H, m), 8.33 (0.35H, brs), 8.65 (0.65H, brs), 8.91 (1H, d, J=7.9 Hz), 13.17-13.46 (1H, m). LC-MS (ESI) m/z 383 [M+H]$^+$. Anal. Calcd for $C_{20}H_{13}F_3N_4O\cdot0.35H_2O$: C, 61.81; H, 3.55; N, 14.42. Found: C, 61.83; H, 3.61; N, 14.49.

Example 75

3-(1-Methyl-5-phenyl-1H-pyrazol-4-yl)-1-[3-(trifluoromethyl)phenyl]pyridazin-4(1H)-one

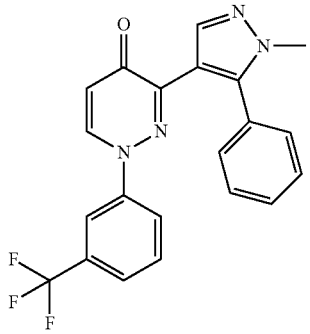 [SMILES: Cn1ncc(-c2nn(-c3cccc(C(F)(F)F)c3)ccc2=O)c1-c1ccccc1]

Example 76

3-(1-Methyl-3-phenyl-1H-pyrazol-4-yl)-1-[3-(trifluoromethyl)phenyl]pyridazin-4(1H)-one

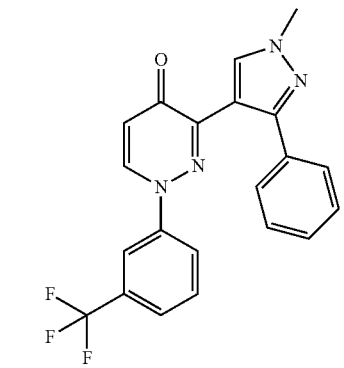 [SMILES: Cn1cc(-c2nn(-c3cccc(C(F)(F)F)c3)ccc2=O)c(-c2ccccc2)n1]

A suspension of 3-(3-phenyl-1H-pyrazol-4-yl)-1-[3-(trifluoromethyl)phenyl]pyridazin-4(1H)-one (325 mg, 0.85 mmol), iodomethane (0.081 mL, 1.3 mmol), and $K_2CO_3$ (235 mg, 1.7 mmol) in DMF (3 mL) was stirred overnight at room temperature. The reaction mixture was poured into water and extracted with AcOEt. The extract was washed with water and brine, dried over $MgSO_4$, and concentrated under reduced pressure. The residue was purified by silica gel column chromatography eluting with AcOEt and recrystallized from hexane/AcOEt to give 3-(1-methyl-5-phenyl-1H-pyrazol-4-yl)-1-[3-(trifluoromethyl)phenyl]pyridazin-4(1H)-one (100 mg, 30% yield) as a white solid: mp 193-195° C.; $^1$H NMR (300 MHz, CDCl$_3$): δ ppm 3.74 (3H, s), 6.61 (1H, d, J=7.9 Hz), 6.91 (1H, dd, J=2.3, 8.3 Hz), 7.25 (1H, s), 7.33-7.40 (3H, m), 7.45-7.52 (4H, m), 8.12 (1H, d, J=7.9 Hz), 8.67 (1H, s). LC-MS (ESI) m/z 397 [M+H]$^+$. Anal. Calcd for $C_{21}H_{15}F_3N_4O$: C, 63.63; H, 3.81; N, 14.14. Found: C, 63.56; H, 3.88; N, 14.09.

Further elution followed by recrystallization from hexane/AcOEt afforded 3-(1-methyl-3-phenyl-1H-pyrazol-4-yl)-1-[3-(trifluoromethyl)phenyl]pyridazin-4(1H)-one (66 mg, 20% yield) as a white solid: mp 181-183° C.; $^1$H NMR (300 MHz, CDCl$_3$): δ ppm 4.00 (3H, s), 6.67 (1H, d, J=7.9 Hz), 7.06 (1H, dd, J=2.3, 8.3 Hz), 7.35-7.40 (5H, m), 7.49-7.55 (3H, m), 8.21 (1H, d, J=7.9 Hz), 8.70 (1H, s). LC-MS (ESI) m/z 397 [M+H]$^+$. Anal. Found: C, 63.56; H, 3.85; N, 14.14.

Example 77

3-[1-(1-Methylethyl)-3-phenyl-1H-pyrazol-4-yl]-1-[3-(trifluoromethyl)phenyl]pyridazin-4(1H)-one

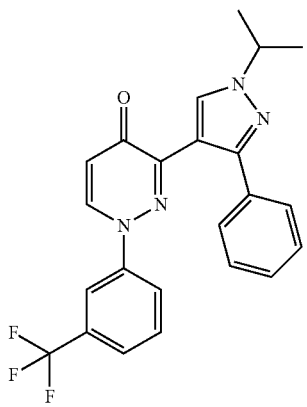 [SMILES: CC(C)n1cc(-c2nn(-c3cccc(C(F)(F)F)c3)ccc2=O)c(-c2ccccc2)n1]

Example 78

3-[1-(1-Methylethyl)-5-phenyl-1H-pyrazol-4-yl]-1-[3-(trifluoromethyl)phenyl]pyridazin-4(1H)-one

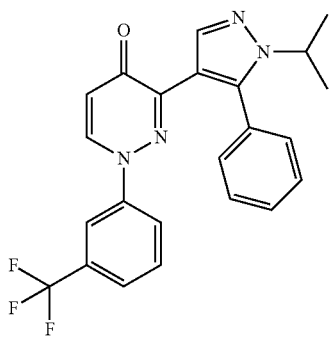 [SMILES: CC(C)n1ncc(-c2nn(-c3cccc(C(F)(F)F)c3)ccc2=O)c1-c1ccccc1]

A suspension of 3-(3-phenyl-1H-pyrazol-4-yl)-1-[3-(trifluoromethyl)phenyl]pyridazin-4(1H)-one (325 mg, 0.85 mmol), 2-iodopropane (0.130 mL, 1.3 mmol), and $K_2CO_3$ (235 mg, 1.7 mmol) in DMF (3 mL) was stirred overnight at 50° C. The reaction mixture was poured into water and extracted with AcOEt. The extract was washed with water and brine, dried over $MgSO_4$, and concentrated under reduced pressure. The residue was purified by basic silica gel column chromatography eluting with AcOEt followed by separation by preparative HPLC to give the title compounds.

3-[1-(1-Methylethyl)-3-phenyl-1H-pyrazol-4-yl]-1-[3-(trifluoromethyl)phenyl]pyridazin-4(1H)-one: a white solid (27.8 mg, 8% yield, crystallized from hexane/AcOEt); mp 13.8-140° C.; $^1$H NMR (300 MHz, $CDCl_3$): δ ppm 1.60 (6H, d, J=6.8 Hz), 4.53-4.67 (1H, m), 6.66 (1H, d, J=7.9 Hz), 7.04 (1H, dd, J=2.1, 8.1 Hz), 7.34-7.41 (5H, m), 7.49-7.57 (3H, m), 8.21 (1H, d, J=7.9 Hz), 8.74 (1H, s). LC-MS (ESI) m/z 425 [M+H]$^+$. Anal. Calcd for $C_{23}H_{19}F_3N_4O$: C, 65.09; H, 4.51; N, 13.20. Found: C, 64.68; H, 4.50; N, 12.98.

3-[1-(1-Methylethyl)-5-phenyl-1H-pyrazol-4-yl]-1-[3-(trifluoromethyl)phenyl]pyridazin-4(1H)-one: a white solid (17.0 mg, 5% yield, recrystallized from hexane/AcOEt); mp 183-186° C.; $^1$H NMR (300 MHz, $CDCl_3$): δ ppm 1.45 (6H, d, J=6.4 Hz), 4.25-4.38 (1H, m), 6.60 (1H, d, J=7.9 Hz), 6.87 (1H, dd, J=2.1, 8.1 Hz), 7.25 (1H, s), 7.32-7.38 (3H, m), 7.45-7.52 (4H, m), 8.11 (1H, d, J=7.9 Hz), 8.69 (1H, s). LC-MS (ESI) m/z 425 [M+H]$^+$. Anal. Found: C, 64.95; H, 4.59; N, 13.14.

Preparative HPLC was performed at the conditions described below.

Column: YMC CombiPrep Pro C18 RS (50×20 mm I.D. S-5 μm, 8 nm)

Column temp: 25° C.

Mobile phase: (A) 0.1% TFA in distilled water, (B) 0.1% TFA in acetonitrile

Gradient: 0 min (A/B=64/36)→1 min (A/B=64/36)→30 min (A/B=64/36)→30.30 min (A/B=0/100)→033.30 min (A/B=0/100)→30.60 min (A/B=64/36)→35 min (A/B=64/36)

Flow rate: 25 mL/min

Detector: UV 220 nm

Concentration: 100 mg/mL

Inject volume: 0.150 mL

Retention time: 20.9 min (example 77) and 24.5 min (example 78)

Example 79

3-(3-Phenylisoxazol-4-yl)-1-[3-(trifluoromethyl)phenyl]pyridazin-4(1H)-one

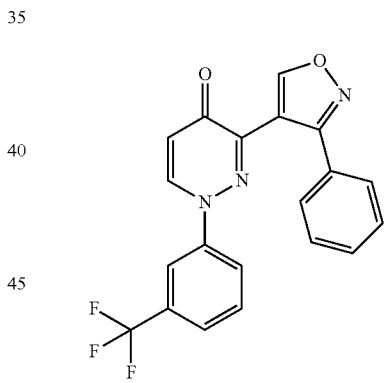

To a solution of 3-ethynyl-1-[3-(trifluoromethyl)phenyl]pyridazin-4(1H)-one (104 mg, 0.391 mmol) and N-hydroxybenzenecarboximidoyl chloride (122 mg, 0.782 mmol) in THF (5 mL) was added $Et_3N$ (0.108 mL, 0.782 mmol) at 0° C. The suspension was stirred at room temperature for 14 h. The reaction was quenched with water. The mixture was extracted with AcOEt, washed with brine, dried over $Na_2SO_4$, filtered, concentrated in vacuo, purified by column chromatography on silica gel (hexane/AcOEt=50/50 to 0/100) and on basic silica gel (hexane/AcOEt=50/50 to 43/57) and crystallized with AcOEt/heptane to yield the title compound (82.4 mg, 55% yield) as a white solid: mp 217-219° C. $^1$H NMR (DMSO-$d_6$, 300 MHz): δ ppm 6.87 (1H, d, J=8.0 Hz), 7.50-7.59 (3H, m), 7.86-7.92 (2H, m), 7.94-8.02 (3H, m), 8.15-8.26 (2H, m), 9.09 (1H, d, J=8.2 Hz). Anal. Calcd for $C_{20}H_{12}F_3N_3O_2$: C, 62.67; H, 3.16; N, 10.96. Found: C, 62.60; H, 3.19; N, 10.95.

Example 80

3-(4-Phenyl-1,3-oxazol-5-yl)-1-[3-(trifluoromethyl)phenyl]pyridazin-4(1H)-one

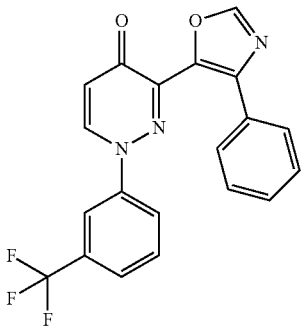 [SMILES: O=c1ccn(-c2cccc(C(F)(F)F)c2)nc1-c1ocnc1-c1ccccc1]

To a solution of 4-oxo-1-[3-(trifluoromethyl)phenyl]-1,4-dihydropyridazine-3-carbaldehyde (52.8 mg, 0.197 mmol) in MeCN (0.4 mL) were added N-methylidene-1-[(4-methylphenyl)sulfonyl]-1-phenylmethanamine (53.8 mg, 0.197 mmol) and $K_2CO_3$ (35.4 mg, 0.256 mmol) at room temperature. The suspension was stirred at room temperature for 1 day. The suspension was diluted with water, extracted with AcOEt, washed with brine, dried over $MgSO_4$, filtered, concentrated in vacuo, purified by column chromatography on silica gel (hexane/AcOEt=90/10 to 0/100) and crystallized with AcOEt/hexane to yield the title compound (18.6 mg, 25% yield) as a solid: $^1$H NMR (DMSO-$d_6$, 300 MHz): δ ppm 6.75 (1H, d, J=8.5 Hz), 7.33-7.43 (3H, m), 7.64-7.70 (2H, m), 7.72-7.83 (2H, m), 7.92-8.01 (2H, m), 8.65 (1H, s), 9.02 (1H, d, J=7.7 Hz). Anal. Calcd for $C_{20}H_{12}F_3N_3O_2 \cdot 0.2H_2O$: C, 62.08; H, 3.23; N, 10.86. Found: C, 62.08; H, 3.38; N, 10.67.

Example 81

3-(2-Phenyl-1H-imidazol-1-yl)-1-[3-(trifluoromethyl)phenyl]pyridazin-4(1H)-one

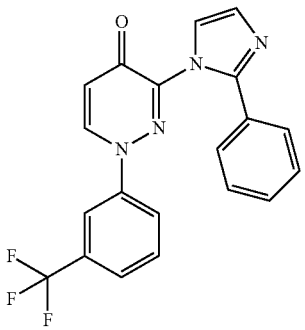 [SMILES: O=c1ccn(-c2cccc(C(F)(F)F)c2)nc1-n1ccnc1-c1ccccc1]

A solution of 3-amino-1-[3-(trifluoromethyl)phenyl]pyridazin-4(1H)-one (200 mg, 0.783 mmol) and glyoxal (40% solution, 0.0895 mL, 0.783 mmol) in MeOH (2 mL) was stirred at room temperature for 20 h. To the solution were added benzaldehyde (0.159 mL, 1.57 mmol) and $NH_4Cl$ (84 mg, 1.57 mmol). The mixture was heated to reflux for 90 min. To the mixture was added $H_3PO_4$ (0.106 mL). The mixture was heated to reflux for 24 h. The mixture was diluted with water, extracted with AcOEt, washed with $NaHCO_3$ aqueous solution, dried over $Na_2SO_4$, filtered, concentrated in vacuo, purified by column chromatography on silica gel (hexane/AcOEt=50/50 to 0/100) and on basic silica gel (hexane/AcOEt=50/50 to 0/100) and recrystallized with AcOEt/heptane to yield the title compound (9.3 mg, 3% yield) as a white solid: mp 204-205° C. $^1$H NMR (DMSO-$d_6$, 300 MHz): δ ppm 6.82 (1H, d, J=8.0 Hz), 7.20 (1H, d, J=1.6 Hz), 7.33-7.41 (3H, m), 7.44-7.50 (2H, m), 7.62 (1H, s), 7.64-7.81 (4H, m), 9.06 (1H, d, J=8.0 Hz). Anal. Calcd for $C_{20}H_{13}F_3N_4O$: C, 62.83; H, 3.43; N, 14.65. Found: C, 62.50; H, 3.64; N, 14.56.

Example 82

5-Methoxy-3-(2-phenyl-1H-imidazol-1-yl)-1-[3-(trifluoromethyl)phenyl]pyridazin-4(1H)-one

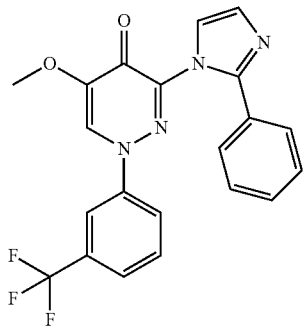 [SMILES: COc1cn(-c2cccc(C(F)(F)F)c2)nc(-n2ccnc2-c2ccccc2)c1=O]

A solution of 3-amino-5-methoxy-1-[3-(trifluoromethyl)phenyl]pyridazin-4(1H)-one (300 mg, 1.05 mmol) and glyoxal (40% solution, 0.240 mL, 2.10 mmol) in MeOH (3 mL) was stirred at room temperature for 24 h. To the solution were added benzaldehyde (0.428 mL, 4.21 mmol) and $NH_4Cl$ (225 mg, 4.21 mmol). The mixture was heated to reflux for 2 h. To the mixture was added $H_3PO_4$ (0.142 mL). The mixture was heated to reflux for 20 h. The mixture was diluted with water and saturated $NaHCO_3$ aqueous solution, extracted with AcOEt, dried over $Na_2SO_4$, filtered, concentrated in vacuo, purified by column chromatography on basic silica gel (hexane/AcOEt=50/50 to 0/100) and by HPLC and recrystallized with AcOEt/hexane to yield the title compound (126 mg, 29% yield) as a white solid: mp 167-170° C. $^1$H NMR (DMSO-$d_6$, 300 MHz): δ ppm 3.94 (3H, s), 7.19 (1H, d, J=1.5 Hz), 7.31-7.49 (5H, m), 7.61 (1H, d, J=1.5 Hz), 7.68-7.91 (4H, m), 8.80 (1H, s). Anal. Calcd for $C_{21}H_{15}F_3N_4O_2 \cdot 0.7H_2O$: C, 59.35; H, 3.89; N, 13.18. Found: C, 59.28; H, 3.69; N, 13.12.

Preparative HPLC was performed at the conditions described below.

Column: Waters SunFire Column C18 (30×50 mm S-5 µm)

Column temp: 25° C.

Mobile phase: (A) 0.1% TFA in distilled water, (B) 0.1% TFA in acetonitrile

Gradient: 0 min (A/B=90/10)→1.20 min (A/B=90/10)→4.75 min (A/B=0/100)→7.75 min (A/B=0/100)→7.85 min (A/B=90/10)→8.50 min (A/B=90/10)

Flow rate: 70 mL/min

Detector: UV 220 nm

Concentration: 94 mg/mL

Inject volume: 600 µL

Example 83

3-(4-Phenyl-1H-imidazol-5-yl)-1-[3-(trifluoromethyl)phenyl]pyridazin-4(1H)-one

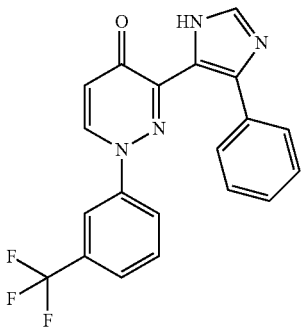 [SMILES: O=c1ccn(-c2cccc(C(F)(F)F)c2)nc1-c1[nH]cnc1-c1ccccc1]

A mixture of 4-oxo-1-[3-(trifluoromethyl)phenyl]-1,4-dihydropyridazine-3-carbaldehyde (129 mg, 0.479 mmol) and NH₃ (30% aqueous solution, 0.168 mL, 129 mmol) in THF (1.5 mL) was stirred at room temperature for 4 h. To the mixture were added N-methylidene-1-[(4-methylphenyl)sulfonyl]-1-phenylmethanamine (131 mg, 0.479 mmol) and piperazine (41.3 mg, 0.479 mmol) at room temperature. The mixture was stirred at room temperature for 2 days. The mixture was diluted with water and saturated NaHCO₃ aqueous solution, extracted with AcOEt, dried over Na₂SO₄, filtered, concentrated in vacuo, purified by column chromatography on basic silica gel (hexane/AcOEt=40/60 to 0/100 and AcOEt/MeOH=100/0 to 70/30) and recrystallized with AcOEt/hexane to yield the title compound (85.6 mg, 47% yield) as a pale yellow solid: ¹H NMR (DMSO-d₆, 300 MHz): δ ppm 6.70 (1H, d, J=7.7 Hz), 7.22-7.44 (3H, m), 7.57-7.85 (7H, m), 8.97 (1H, d, J=8.0 Hz), 12.75 (1H, s). Anal. Calcd for C₂₀H₁₃F₃N₄O.0.7H₂O: C, 60.82; H, 3.67; N, 14.19. Found: C, 60.79; H, 3.76; N, 13.84.

Example 84

3-(1-Methyl-4-phenyl-1H-imidazol-5-yl)-1-[3-(trifluoromethyl)phenyl]pyridazin-4(1H)-one

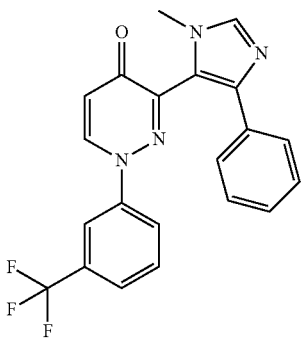 [SMILES: Cn1cnc(-c2ccccc2)c1-c1nn(-c2cccc(C(F)(F)F)c2)ccc1=O]

A mixture of 4-oxo-1-[3-(trifluoromethyl)phenyl]-1,4-dihydropyridazine-3-carbaldehyde (129 mg, 0.479 mmol) and MeNH₂ (40% aqueous solution, 0.050 mL, 0.575 mmol) in DMF (3.5 mL) was stirred at room temperature for 90 min. To the mixture were added N-methylidene-1-[(4-methylphenyl)sulfonyl]-1-phenylmethanamine (131 mg, 0.479 mmol) and K₂CO₃ (66.2 mg, 0.479 mmol) at room temperature. The mixture was stirred at room temperature for 27 h. The mixture was diluted with water, extracted with AcOEt, washed with NaHCO₃ aqueous solution, dried over Na₂SO₄, filtered, concentrated in vacuo, purified by column chromatography on basic silica gel (hexane/AcOEt=40/60 to 0/100 and AcOEt/MeOH=100/0 to 70/30) and recrystallized with AcOEt/hexane to yield the title compound (145 mg, 76% yield) as a pale yellow solid: mp 214-216° C. ¹H NMR (DMSO-d₆, 300 MHz): δ ppm 3.60 (3H, s), 6.74 (1H, d, J=8.0 Hz), 7.15-7.32 (3H, m), 7.45-7.53 (2H, m), 7.71-7.89 (4H, m), 7.91-7.98 (1H, m), 9.04 (1H, d, J=8.0 Hz). Anal. Calcd for C₂₁H₁₅F₃N₄O: C, 63.63; H, 3.81; N, 14.14. Found: C, 63.50; H, 3.89; N, 14.04.

Example 85

3-(2-Phenylfuran-3-yl)-1-[3-(trifluoromethyl)phenyl]pyridazin-4(1H)-one

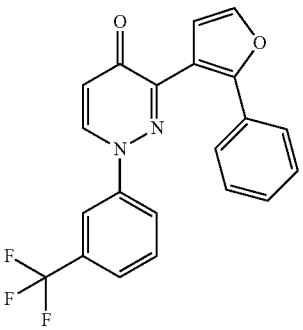 [SMILES: O=c1ccn(-c2cccc(C(F)(F)F)c2)nc1-c1ccoc1-c1ccccc1]

A mixture of 3-bromo-1-[3-(trifluoromethyl)phenyl]pyridazin-4(1H)-one (300 mg, 0.940 mmol), (2-phenylfuran-3-yl)boronic acid (265 mg, 1.41 mmol), Na₂CO₃ (299 mg, 2.82 mmol) and Pd(PPh₃)₄ (54.3 mg, 0.047 mmol) in DME (3.6 mL) and water (1.1 mL) was heated to 80° C. for 4 h under Ar atmosphere. The mixture was diluted with water, extracted with AcOEt, washed with NaHCO₃ aqueous solution, dried over Na₂SO₄, filtered, concentrated in vacuo, purified by column chromatography on basic silica gel (hexane/AcOEt=80/20 to 0/100) and recrystallized with AcOEt/heptane to yield the title compound (23.9 mg, 7% yield) as a pale yellow solid: mp 159-163° C. ¹H NMR (DMSO-d₆, 300 MHz): δ ppm 6.63 (1H, d, J=8.0 Hz), 6.99 (1H, d, J=1.9 Hz), 7.32-7.43 (3H, m), 7.54-7.60 (2H, m), 7.69-7.76 (2H, m), 7.78-7.82 (1H, m), 7.85 (1H, d, J=1.9 Hz), 7.85-7.92 (1H, m), 8.96 (1H, d, J=8.0 Hz). Anal. Calcd for C₂₁H₁₃F₃N₂O₂.0.3H₂O: C, 65.05; H, 3.54; N, 7.22. Found: C, 65.20; H, 3.63; N, 7.29.

Example 86

3-(2-Phenylthiophen-3-yl)-1-[3-(trifluoromethyl)phenyl]pyridazin-4(1H)-one

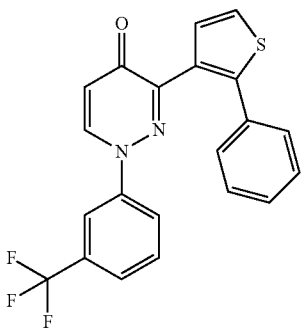 [SMILES: O=c1ccn(-c2cccc(C(F)(F)F)c2)nc1-c1ccsc1-c1ccccc1]

A mixture of 3-bromo-1-[3-(trifluoromethyl)phenyl]pyridazin-4(1H)-one (137 mg, 0.428 mmol), (2-phenylthiophen-3-yl)boronic acid (87.4 mg, 0.428 mmol), $Na_2CO_3$ (136 mg, 1.28 mmol) and $Pd(PPh_3)_4$ (24.7 mg, 0.021 mmol) in DME (1.6 mL) and water (0.49 mL) was heated to 80° C. for 18 h under Ar atmosphere. The mixture was diluted with water, extracted with AcOEt, washed with $NaHCO_3$ aqueous solution, dried over $Na_2SO_4$, filtered, concentrated in vacuo, purified by column chromatography on basic silica gel (hexane/AcOEt=80/20 to 0/100) and recrystallized with AcOEt/heptane to yield the title compound (38.6 mg, 23% yield) as a white solid: mp 167-168° C. $^1$H NMR (DMSO-$d_6$, 300 MHz): δ ppm 6.62 (1H, d, J=8.0 Hz), 7.30-7.41 (5H, m), 7.47 (1H, brs), 7.51 (1H, d, J=5.2 Hz), 7.55-7.72 (4H, m), 8.91 (1H, d, J=8.0 Hz). Anal. Calcd for $C_{21}H_{13}F_3N_2OS$: C, 63.31; H, 3.29; N, 7.03. Found: C, 63.08; H, 3.37; N, 7.01.

Example 87

5-Methoxy-3-(1-phenyl-1H-pyrazol-5-yl)-1-pyridin-4-ylpyridazin-4(1H)-one

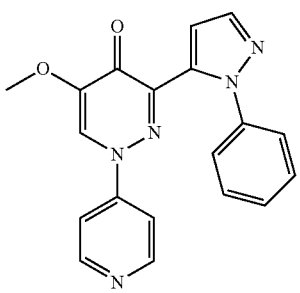 [SMILES: COc1cn(-c2ccncc2)nc(-c2ccnn2-c2ccccc2)c1=O]

A mixture of 3-acetyl-5-methoxy-1-pyridin-4-ylpyridazin-4(1H)-one (2.9 g, 12 mmol) and N,N-dimethylformamide dimethyl acetal (20 mL) was refluxed for 3 h. The mixture was concentrated under reduced pressure.

A solution of the residue and phenylhydrazine (2.3 mL, 23 mmol) in AcOH (30 mL) was refluxed for 3 h. After stirring at room temperature overnight, the mixture was concentrated under reduced pressure. The residue was diluted with AcOEt. The mixture was washed with saturated $NaHCO_3$ aqueous solution and brine. The organic layer was dried over $MgSO_4$, filtered and concentrated under reduced pressure. The residue was purified by basic silica gel column chromatography eluting with AcOEt/hexane (30/70-100/0) to give pale yellow crystals. The crystals were washed with AcOEt and recrystallized from MeOH/AcOEt/hexane to give the title compound (0.76 g, 19% yield) as white crystals: mp 195-197° C.; $^1$H NMR (300 MHz, DMSO-$d_6$): δ ppm 3.90 (3H, s), 7.17-7.23 (3H, m), 7.35-7.50 (5H, m), 7.82 (1H, d, J=1.9 Hz), 8.52 (2H, dd, J=4.8, 1.5 Hz), 8.64 (1H, s). LC-MS (ESI) m/z 346 [M+H]$^+$. Anal. Calcd for $C_{19}H_{15}N_5O_2$: C, 66.08; H, 4.38; N, 20.28. Found: C, 65.85; H, 4.30; N, 20.25.

Example 88

5-Methoxy-3-(1-phenyl-1H-pyrazol-5-yl)-1-quinolin-8-ylpyridazin-4(1H)-one

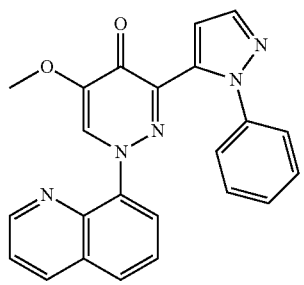 [SMILES: COc1cn(-c2cccc3cccnc23)nc(-c2ccnn2-c2ccccc2)c1=O]

A mixture of 3-bromo-5-methoxy-1-quinolin-8-ylpyridazin-4(1H)-one (70 mg, 0.217 mmol), 1-phenyl-5-(4,4,5,5-tetramethyl-1,3,2-dioxaborolan-2-yl)-1H-pyrazole (88.1 mg, 0.326 mmol), KOAc (42.6 mg, 0.434 mmol) and $PdCl_2\{P(t-Bu)_2(Ph-p-NMe_2)\}_2$ (7.7 mg, 0.0109 mmol) in BuOH (1.1 mL) and water (0.1 mL) was heated to reflux for 16 h under Ar atmosphere. The mixture was diluted with water, extracted with AcOEt, washed with saturated $NaHCO_3$ aqueous solution, dried over $Na_2SO_4$, filtered, concentrated in vacuo, purified by column chromatography on basic silica gel (hexane/AcOEt=50/50 to 0/100 and AcOEt/MeOH=100/0 to 70/30) and recrystallized with AcOEt/hexane to yield the title compound (69.9 mg, 81% yield) as a white solid: mp 189-192° C. $^1$H NMR (DMSO-$d_6$, 300 MHz): δ ppm 3.76 (3H, s), 6.98 (1H, s), 7.31-7.49 (6H, m), 7.58-7.73 (2H, m), 7.78 (1H, d, J=1.9 Hz), 8.14 (1H, d, J=8.3 Hz), 8.54 (1H, d, J=7.9 Hz), 8.67 (1H, s), 8.99 (1H, d, J=4.1 Hz). Anal. Calcd for $C_{23}H_{17}N_5O_2$: C, 69.86; H, 4.33; N, 17.71. Found: C, 69.61; H, 4.37; N, 17.57.

Example 89

5-Methoxy-3-(1-phenyl-1H-pyrazol-5-yl)-1-(1,2,3,4-tetrahydroquinolin-8-yl)pyridazin-4(1H)-one hydrochloride

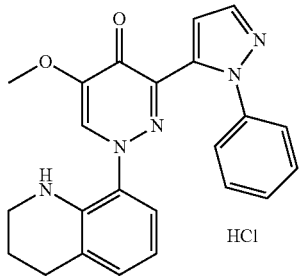 [SMILES: COc1cn(-c2cccc3c2NCCC3)nc(-c2ccnn2-c2ccccc2)c1=O ; Cl]

A mixture of 5-methoxy-3-(1-phenyl-1H-pyrazol-5-yl)-1-quinolin-8-ylpyridazin-4(1H)-one (42.6 mg, 0.108 mmol) and PtO$_2$ (4.0 mg, 0.018 mmol) in TFA (1 mL) was stirred at room temperature for 2 days under H$_2$ atmosphere. The mixture was diluted with MeOH, filtered through a pad of celite, diluted with saturated NaHCO$_3$ aqueous solution, concentrated in vacuo and purified by column chromatography on basic silica gel (hexane/AcOEt=50/50 to 0/100). To the residue was added 4 N HCl in AcOEt and triturated with toluene/hexane to yield the title compound (20 mg, 43% yield) as a yellow solid: $^1$H NMR (DMSO-d$_6$, 300 MHz): δ ppm 1.69-1.82 (2H, m), 2.70 (2H, t, J=6.6 Hz), 3.12 (2H, t, J=5.3 Hz), 3.75 (3H, s), 6.41 (1H, t, J=7.6 Hz), 6.64 (1H, d, J=6.4 Hz), 6.88 (1H, d, J=1.9 Hz), 6.94 (1H, d, J=6.0 Hz), 7.12-7.44 (5H, m), 7.76 (1H, d, J=1.9 Hz), 8.14 (1H, s).

Example 90

1-(2,2-Difluoro-1,3-benzodioxol-4-yl)-5-methoxy-3-(1-phenyl-1H-pyrazol-5-yl)pyridazin-4(1H)-one

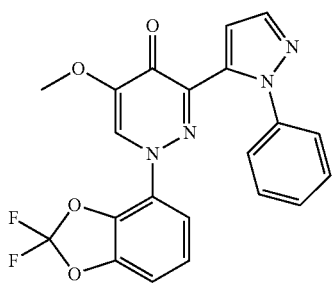 [SMILES: COc1cn(-c2cccc3c2OC(F)(F)O3)nc(-c2ccnn2-c2ccccc2)c1=O]

A solution of 1-(2,2-difluoro-1,3-benzodioxol-4-yl)-3-[3-(dimethylamino)prop-2-enoyl]-5-methoxypyridazin-4(1H)-one (2.0 g, 5.3 mmol) and phenylhydrazine (1.0 mL, 11 mmol) in AcOH (20 mL) was refluxed for 3 h. The mixture was concentrated under reduced pressure. The residue was diluted with AcOEt, and washed with saturated NaHCO$_3$ aqueous solution and brine. The organic layer was dried over MgSO$_4$, filtered and concentrated under reduced pressure. The residue was chromatographed on silica gel (30/70-100/0 AcOEt/Hexane) to give yellow crystals. The residual crystals were recrystallized from AcOEt/hexane to give the title compound (1.1 g, 51% yield) as white crystals: mp 181-183° C.; $^1$H NMR (300 MHz, CDCl$_3$): δ ppm 3.95 (3H, s), 6.19 (1H, dd, J=8.3, 1.1 Hz), 6.89 (1H, t, J=8.3 Hz), 6.99 (1H, dd, J=8.3, 1.1 Hz), 7.36-7.47 (6H, m), 7.80 (1H, d, J=2.3 Hz), 8.07 (1H, s). LC-MS (ESI) m/z 425 [M+H]$^+$. Anal. Calcd for C$_{21}$H$_{14}$F$_2$N$_4$O$_4$: C, 59.44; H, 3.33; N, 13.22. Found: C, 59.43; H, 3.44; N, 13.22.

Example 91

1-(2-Fluoro-4-hydroxyphenyl)-5-methoxy-3-(1-phenyl-1H-pyrazol-5-yl)pyridazin-4(1H)-one

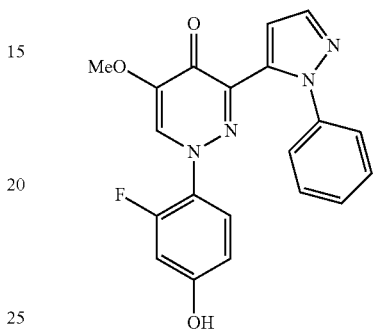

A mixture of 1-[4-(benzyloxy)-2-fluorophenyl]-5-methoxy-3-(1-phenyl-1H-pyrazol-5-yl)pyridazin-4(1H)-one (5.53 g, 11.8 mmol), 10% Pd—C (50% wet, 3.0 g), THF (150 mL), and MeOH (150 mL) was hydrogenated for 1.5 h at room temperature. The reaction mixture was filtered, and the filtrate was concentrated under reduced pressure. The residue was recrystallized from MeOH/H$_2$O to give the title compound (4.07 g, 91% yield) as a pale yellow solid: mp 223-224° C.; $^1$H NMR (300 MHz, DMSO-d$_6$): δ ppm 3.75 (3H, s), 6.60 (1H, ddd, J=1.1, 2.6, 8.7 Hz), 6.73 (1H, dd, J=2.6, 12.8 Hz), 6.90-6.96 (2H, m), 7.28-7.44 (5H, m), 7.78 (1H, d, J=1.9 Hz), 8.39 (1H, d, J=1.9 Hz), 10.44 (1H, brs). LC-MS (ESI) m/z 379 [M+H]$^+$. Anal. Calcd for C$_{20}$H$_{15}$FN$_4$O$_3$.0.5H$_2$O: C, 62.01; H, 4.16; N, 14.46. Found: C, 62.18; H, 4.16; N, 14.49.

Example 92

1-[2-Fluoro-4-(trifluoromethoxy)phenyl]-5-methoxy-3-(1-phenyl-1H-pyrazol-5-yl)pyridazin-4(1H)-one

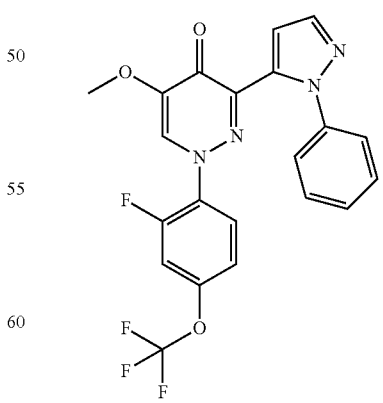

A solution of 3-acetyl-1-[2-fluoro-4-(trifluoromethoxy)phenyl]-5-methoxypyridazin-4(1H)-one (2.8 g, 8.1 mmol) and N,N-dimethylformamide diisopropyl acetal (8.5 mL, 40 mmol) in toluene (50 mL) was refluxed for 5 h. After stirring at room temperature overnight, the mixture was concentrated under reduced pressure.

A solution of the residue and phenylhydrazine (2.0 mL, 20 mmol) in AcOH (30 mL) was refluxed for 3 h. After stirring at room temperature overnight, the mixture was concentrated under reduced pressure. The residue was diluted with AcOEt, and washed with saturated NaHCO$_3$ aqueous solution and brine. The organic layer was dried over MgSO$_4$, filtered and concentrated under reduced pressure. The residue was chromatographed on silica gel (10/90-100/0 AcOEt/hexane) to give 2.4 g of the crude product.

One gram of the crude product was purified by preparative HPLC, and the combined fraction was concentrated under reduced pressure. The residual solution was basified with saturated NaHCO$_3$ aqueous solution and extracted with AcOEt. The organic layer was washed with brine, dried over MgSO$_4$, filtered and concentrated under reduced pressure. The residual crystals were recrystallized from AcOEt/hexane to give the title compound (0.66 g) as white crystals: mp 117-118° C.; $^1$H NMR (300 MHz, CDCl$_3$): δ ppm 3.90 (3H, s), 6.43 (1H, t, J=8.7 Hz), 6.85-6.90 (1H, m), 7.09 (1H, dd, J=11.5, 1.7 Hz), 7.34 (1H, d, J=1.9 Hz), 7.35-7.47 (5H, m), 7.77 (1H, d, J=2.3 Hz), 7.78 (1H, d, J=1.9 Hz). LC-MS (ESI) m/z 447 [M+H]$^+$. Anal. Calcd. for C$_{21}$H$_{14}$F$_4$N$_4$O$_3$: C, 56.51; H, 3.16; N, 12.55. Found: C, 56.51; H, 3.14; N, 12.61.

Preparative HPLC was performed at the conditions described below.
  Column: Waters SunFire Column C18 (30×50 mm S-5 μm)
  Column temp: 25° C.
  Mobile phase: (A) 0.1% TFA in distilled water, (B) 0.1% TFA in acetonitrile
  Gradient: 0 min (A/B=90/10)→1 min (A/B=90/10)→4.75 min (A/B=0/100)→7.40 min (A/B=0/100)→7.41 min (A/B=90/10)→8.50 min (A/B=90/10)
  Flow rate: 70 mL/min
  Detector: UV 220 nm
  Concentration: 100 mg/mL
  Inject volume: 10 mL Example 93

3-Fluoro-4-[5-methoxy-4-oxo-3-(1-phenyl-1H-pyrazol-5-yl)pyridazin-1(4H)-yl]phenyl trifluoromethanesulfonate

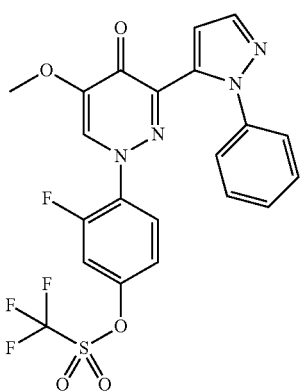 [SMILES: COc1cn(-c2ccc(OS(=O)(=O)C(F)(F)F)cc2F)nc(-c2ccnn2-c2ccccc2)c1=O]

NaH (60% in oil, 0.552 g, 13.8 mol) was added portionwise at room temperature to a solution of 1-(2-fluoro-4-hydroxyphenyl)-5-methoxy-3-(1-phenyl-1H-pyrazol-5-yl)pyridazin-4(1H)-one (4.01 g, 10.6 mmol) and N-phenylbis(trifluoromethanesulfonimide) (4.18 g, 11.7 mmol) in THF (600 mL). After stirring for 1 h, the reaction mixture was concentrated under reduced pressure. The residue was diluted with AcOEt, washed with water and brine; dried over MgSO$_4$, and concentrated under reduced pressure. The residue was purified by silica gel column chromatography eluting with hexane/AcOEt (1/2) and crystallized from hexane/AcOEt to give the title compound (4.73 g, 87% yield) as a white solid: mp 108-110° C.; $^1$H NMR (300 MHz, CDCl$_3$): δ ppm 3.91 (3H, s), 6.46 (1H, t, J=9.0 Hz), 6.94 (1H, ddd, J=1.5, 2.6, 9.0 Hz), 7.18 (1H, dd, J=2.6, 10.9 Hz), 7.34-7.47 (6H, m), 7.78 (1H, d, J=2.6 Hz), 7.79 (1H, d, J=1.9 Hz). LC-MS (ESI) m/z 511 [M+H]$^+$. Anal. Calcd for C$_{21}$H$_{14}$F$_4$N$_4$O$_5$S: C, 49.42; H, 2.76; N, 10.98. Found: C, 49.30; H, 2.79; N, 10.96.

Example 94

1-(3-Bromo-2-fluorophenyl)-5-methoxy-3-(1-phenyl-1H-pyrazol-5-yl)pyridazin-4(1H)-one

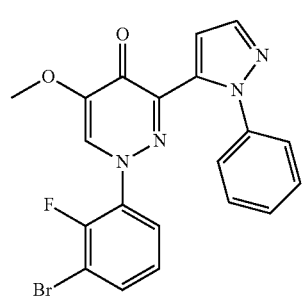 [SMILES: COc1cn(-c2cccc(Br)c2F)nc(-c2ccnn2-c2ccccc2)c1=O]

A mixture of 3-acetyl-1-(3-bromo-2-fluorophenyl)-5-methoxypyridazin-4(1H)-one (2.98 g, 8.74 mmol) in N,N-dimethylformamide dimethyl acetal (30 mL) was heated to reflux for 3.5 h. The mixture was concentrated in vacuo. To the residue were added AcOH (30 mL) and phenylhydrazine (1.72 mL, 17.5 mmol). The mixture was heated to reflux for 4 h. The mixture was diluted with 1 M HCl aqueous solution, extracted with AcOEt, washed with saturated NaHCO$_3$ aqueous solution, dried over Na$_2$SO$_4$, filtered, concentrated in vacuo, purified by column chromatography on basic silica gel (hexane/AcOEt=50/50 to 0/100) and recrystallized with EtOH to yield the title compound (2.29 g, 59% yield) as a yellow solid: mp 186-191° C. $^1$H NMR (DMSO-d$_6$, 300 MHz): δ ppm 3.77 (3H, s), 6.99 (1H, d, J=1.9 Hz), 7.08-7.15 (1H, m), 7.17-7.26 (1H, m), 7.28-7.47 (5H, m), 7.74-7.86 (2H, m), 8.55 (1H, d, J=2.3 Hz). Anal. Calcd for C$_{20}$H$_{14}$BrFN$_4$O$_2$: C, 54.44; H, 3.20; N, 12.70. Found: C, 54.70; H, 3.30; N, 12.82.

Example 95

5-Methoxy-3-(1-phenyl-1H-pyrazol-5-yl)-1-(2,2,6-trifluoro-1,3-benzodioxol-5-yl)pyridazin-4(1H)-one

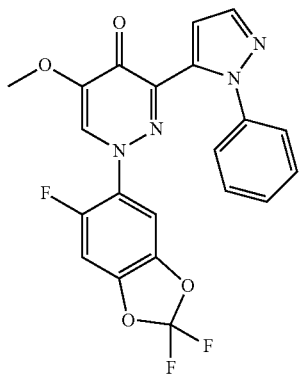 [SMILES: COc1cn(-c2cc3c(cc2F)OC(F)(F)O3)nc(-c2ccnn2-c2ccccc2)c1=O]

A mixture of 3-bromo-5-methoxy-1-(2,2,6-trifluoro-1,3-benzodioxol-5-yl)pyridazin-4(1H)-one (145 mg, 0.383 mmol), 1-phenyl-5-(4,4,5,5-tetramethyl-1,3,2-dioxaborolan-2-yl)-1H-pyrazole (155 mg, 0.575 mmol), $K_2CO_3$ (106 mg, 0.766 mmol) and $PdCl_2\{P(t-Bu)_2(Ph-p-NMe_2)\}_2$ (13.6 mg, 0.0192 mmol) in toluene (1.9 mL) and water (0.19 mL) was heated to reflux for 18 h under Ar. The mixture was diluted with $NaHCO_3$ aqueous solution, extracted with AcOEt, dried over $Na_2SO_4$, filtered, concentrated in vacuo and purified by column chromatography on basic silica gel (hexane/AcOEt=50/50 to 0/100) and recrystallized with AcOEt/hexane to yield the title compound (102 mg, 60% yield) as a pale yellow solid: mp 200-202° C. $^1$H NMR (DMSO-$d_6$, 300 MHz): δ ppm 3.76 (3H, s), 6.97 (1H, d, J=1.9 Hz), 7.27-7.47 (6H, m), 7.79 (1H, d, J=1.9 Hz), 7.86 (1H, d, J=9.4 Hz), 8.48 (1H, d, J=1.9 Hz). Anal. Calcd for $C_{21}H_{13}F_3N_4O_4$: C, 57.02; H, 2.96; N, 12.67. Found: C, 56.94; H, 3.01; N, 12.59.

Example 96

5-Methoxy-1-(2,2,3,3,7-pentafluoro-2,3-dihydro-1,4-benzodioxin-6-yl)-3-(1-phenyl-1H-pyrazol-5-yl)pyridazin-4(1H)-one

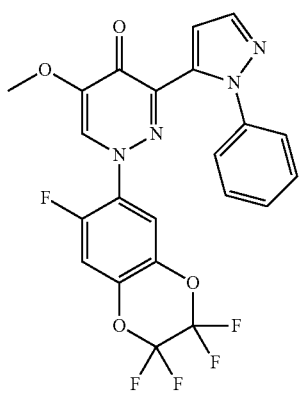 [SMILES: COc1cn(-c2cc3c(cc2F)OC(F)(F)C(F)(F)O3)nc(-c2ccnn2-c2ccccc2)c1=O]

A mixture of 3-bromo-5-methoxy-1-(2,2,3,3,7-pentafluoro-2,3-dihydro-1,4-benzodioxin-6-yl)pyridazin-4(1H)-one (200 mg, 0.466 mmol), 1-phenyl-5-(4,4,5,5-tetramethyl-1,3,2-dioxaborolan-2-yl)-1H-pyrazole (189 mg, 0.699 mmol), $K_2CO_3$ (129 mg, 0.932 mmol) and $PdCl_2\{P(t-Bu)_2(Ph-p-NMe_2)\}_2$ (16.5 mg, 0.0233 mmol) in toluene (2.3 mL) and water (0.23 mL) was heated to reflux for 20 h under Ar. The mixture was diluted with water, brine and saturated $NaHCO_3$ aqueous solution, extracted with AcOEt, dried over $Na_2SO_4$, filtered, concentrated in vacuo, purified by column chromatography on basic silica gel (hexane/AcOEt=50/50 to 0/100) and recrystallized with AcOEt/hexane to yield the title compound (150 mg, 66% yield) as a white solid: mp 192-194° C. $^1$H NMR (DMSO-$d_6$, 300 MHz): δ ppm 3.76 (3H, s), 7.00 (1H, d, J=1.9 Hz), 7.28-7.48 (6H, m), 7.79 (1H, d, J=1.9 Hz), 7.93 (1H, d, J=10.5 Hz), 8.51 (1H, d, J=1.9 Hz). Anal. Calcd for $C_{22}H_{13}F_5N_4O_4$: C, 53.67; H, 2.66; N, 11.38. Found: C, 53.73; H, 2.72; N, 11.33.

Example 97

1-[4-(Cyclopropylethynyl)-2-fluorophenyl]-5-methoxy-3-(1-phenyl-1H-pyrazol-5-yl)pyridazin-4(1H)-one

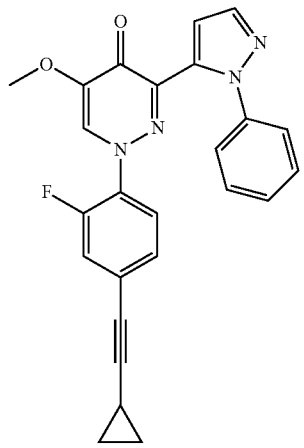 [SMILES: COc1cn(-c2ccc(C#CC3CC3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (255 mg, 0.5 mmol), cyclopropylethylene (0.0846 mL, 1.0 mmol), i-$Pr_2NEt$ (0.348 mL, 2.0 mmol), CuI (9.5 mg, 0.05 mmol), $Pd(PPh_3)_2Cl_2$ (17.5 mg, 0.025 mmol) and $PPh_3$ (6.6 mg, 0.025 mmol) in DMF (1 mL) was heated to 40° C. for 90 min under Ar. The mixture was diluted with $NaHCO_3$ aqueous solution, extracted with AcOEt, dried over $Na_2SO_4$, filtered, concentrated in vacuo, purified by column chromatography on basic silica gel (hexane/AcOEt=50/50 to 0/100) and recrystallized with AcOEt/hexane to yield the title compound (181 mg, 85% yield) as a yellow solid: mp 145-146° C. $^1$H NMR (DMSO-$d_6$, 300 MHz): δ ppm 0.74-0.82 (2H, m), 0.88-0.98 (2H, m), 1.58 (1H, tt, J=8.2, 5.1 Hz), 3.77 (3H, s), 6.91-7.01 (2H, m), 7.20 (1H, dd, J=8.3, 1.1 Hz), 7.28-7.51 (6H, m), 7.78 (1H, d, J=1.9 Hz), 8.47 (1H, d, J=1.9 Hz). Anal. Calcd for $C_{25}H_{19}FN_4O_2$: C, 70.41; H, 4.49; N, 13.14. Found: C, 70.33; H, 4.60; N, 13.08.

Example 98

1-(4-Cyclopropyl-2-fluorophenyl)-5-methoxy-3-(1-phenyl-1H-pyrazol-5-yl)pyridazin-4(1H)-one

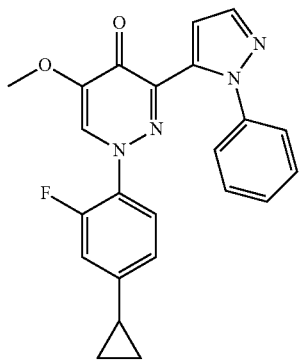 [SMILES: COc1cn(-c2ccc(C3CC3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (255 mg, 0.5 mmol), cyclopropylboronic acid (55.8 mg, 0.65 mmol), $K_3PO_4$ (372 mg, 1.75 mmol), Pd(OAc)$_2$ (5.6 mg, 0.025 mmol) and tricyclohexylphosphine (14 mg, 0.05 mmol) in toluene (2.25 mL) and water (0.11 mL) was heated to 100° C. for 4 h under Ar. The mixture was diluted with NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and recrystallized with AcOEt/hexane to yield the title compound (128 mg, 64% yield) as a white solid: mp 140-142° C. $^1$H NMR (DMSO-d$_6$, 300 MHz): δ ppm 0.70-0.82 (2H, m), 0.96-1.10 (2H, m), 1.94-2.09 (1H, m), 3.76 (3H, s), 6.87-7.01 (3H, m), 7.09-7.18 (1H, m), 7.28-7.50 (5H, m), 7.78 (1H, d, J=1.9 Hz), 8.44 (1H, d, J=1.9 Hz). Anal. Calcd for $C_{23}H_{19}FN_4O_2$: C, 68.65; H, 4.76; N, 13.92. Found: C, 68.47; H, 4.82; N, 13.84.

Example 99

1-[4-(3,6-Dihydro-2H-pyran-4-yl)-2-fluorophenyl]-5-methoxy-3-(1-phenyl-1H-pyrazol-5-yl)pyridazin-4(1H)-one

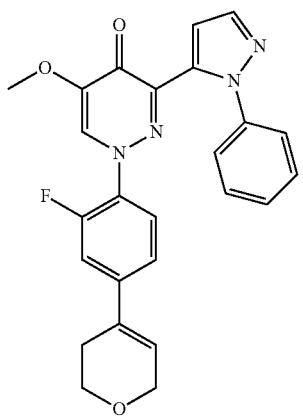 [SMILES: COc1cn(-c2ccc(C3=CCOCC3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (459 mg, 0.9 mmol), 3,6-dihydro-2H-pyran-4-boronic acid pinacol ester (210 mg, 1.0 mmol), Pd(PPh$_3$)$_4$ (52 mg, 0.045 mmol), Na$_2$CO$_3$ (212 mg, 2.0 mmol), DME (4 mL), and H$_2$O (1 mL) was refluxed overnight under Ar atmosphere. After cooling to room temperature, the precipitate was collected by filtration and recrystallized from THF/MeOH to give the title compound (364 mg, 91% yield) as a white solid: mp 229-231° C.; $^1$H NMR (300 MHz, DMSO-d$_6$): δ ppm 2.40-2.50 (2H, m), 3.77 (3H, s), 3.82 (2H, t, J=5.5 Hz), 4.22-4.27 (2H, m), 6.43-6.48 (1H, m), 6.97 (1H, d, J=1.9 Hz), 7.02 (1H, t, J=8.7 Hz), 7.29-7.46 (6H, m), 7.52 (1H, dd, J=1.9, 12.8 Hz), 7.79 (1H, d, J=1.9 Hz), 8.48 (1H, d, J=1.9 Hz). LC-MS (ESI) m/z 445 [M+H]$^+$. Anal. Calcd for $C_{25}H_{21}FN_4O_3$: C, 67.56; H, 4.76; N, 12.61. Found: C, 67.31; H, 4.58; N, 12.52.

Example 100

1-[2-Fluoro-4-(tetrahydro-2H-pyran-4-yl)phenyl]-5-methoxy-3-(1-phenyl-1H-pyrazol-5-yl)pyridazin-4(1H)-one

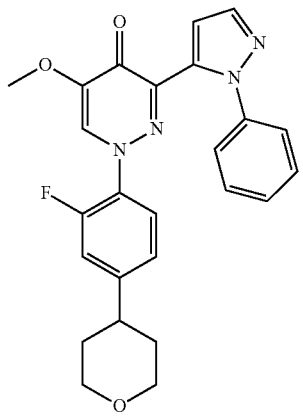 [SMILES: COc1cn(-c2ccc(C3CCOCC3)cc2F)nc(-c2ccnn2-c2ccccc2)c1=O]

A mixture of 1-[4-(3,6-dihydro-2H-pyran-4-yl)-2-fluorophenyl]-5-methoxy-3-(1-phenyl-1H-pyrazol-5-yl)pyridazin-4(1H)-one (300 mg, 0.675 mmol), 10% Pd—C (50% wet, 300 mg), THF (30 mL), and MeOH (30 mL) was hydrogenated for 2 h at room temperature. The reaction mixture was filtered, and the filtrate was concentrated under reduced pressure. The residue was recrystallized from MeOH/H$_2$O to give the title compound (255 mg, 85% yield) as a white solid: mp 187-189° C.; $^1$H NMR (300 MHz, CDCl$_3$): δ ppm 1.57-1.83 (4H, m), 2.72-2.82 (1H, m), 3.45-3.58 (2H, m), 3.90 (3H, s), 4.09 (2H, td, J=3.0, 11.3 Hz), 6.35 (1H, t, J=8.3 Hz), 6.86 (1H, dd, J=1.5, 8.3 Hz), 7.03 (1H, dd, J=1.9, 12.8 Hz), 7.28 (1H, d, J=1.9 Hz), 7.35-7.46 (5H, m), 7.78 (1H, d, J=1.9 Hz), 7.79 (1H, d, J=2.6 Hz). LC-MS (ESI) m/z 447 [M+H]$^+$. Anal. Calcd for $C_{25}H_{23}FN_4O_3$: C, 67.25; H, 5.19; N, 12.55. Found: C, 67.13; H, 5.13; N, 12.57.

Example 101

1-[2-Fluoro-4-(3-fluoroazetidin-1-yl)phenyl]-5-methoxy-3-(1-phenyl-1H-pyrazol-5-yl)pyridazin-4(1H)-one

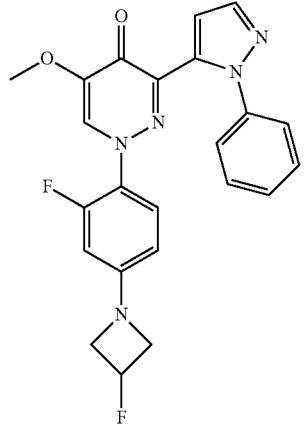 [SMILES: COc1cn(-c2ccc(N3CC(F)C3)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.5 mmol), 3-fluoroazetidine hydrochloride (66.9 mg, 0.6 mmol), NaO-t-Bu (125 mg, 1.3 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 13 h under N$_2$. The mixture was diluted with NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and recrystallized with AcOEt/hexane to yield the title compound (88 mg, 40% yield) as a pale yellow solid: mp 162-163° C. $^1$H NMR (DMSO-d$_6$, 300 MHz): δ ppm 3.76 (3H, s), 3.86-4.04 (2H, m), 4.12-4.29 (2H, m), 5.36-5.64 (1H, m), 6.25 (1H, dd, J=8.5, 2.1 Hz), 6.48 (1H, dd, J=12.8, 2.3 Hz), 6.81-6.95 (2H, m), 7.25-7.48 (5H, m), 7.77 (1H, d, J=1.9 Hz), 8.36 (1H, d, J=1.9 Hz). Anal. Calcd for C$_{23}$H$_{19}$F$_2$N$_5$O$_2$: C, 63.44; H, 4.40; N, 16.08. Found: C, 63.62; H, 4.44: N, 15.92.

Example 102

1-[4-(3,3-Difluoroazetidin-1-yl)-2-fluorophenyl]-5-methoxy-3-(1-phenyl-1H-pyrazol-5-yl)pyridazin-4(1H)-one

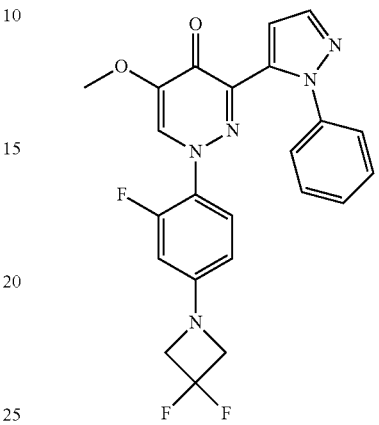

A mixture of 1-(2-fluoro-4-iodophenyl)-5-methoxy-3-(1-phenyl-1H-pyrazol-5-yl)pyridazin-4(1H)-one (244 mg, 0.5 mmol), 3,3-difluoroazetidine hydrochloride (77.7 mg, 0.6 mmol), NaO-t-Bu (125 mg, 1.3 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 16 h under Ar. The mixture was diluted with NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and recrystallized with AcOEt/hexane to yield the title compound (123 mg, 54% yield) as a pale yellow solid: mp 204-206° C. $^1$H NMR (DMSO-d$_6$, 300 MHz): δ ppm 3.76 (3H, s), 4.35 (4H, t, J=12.4 Hz), 6.36 (1H, dd, J=8.9, 2.4 Hz), 6.61 (1H, dd, J=12.8, 2.3 Hz), 6.87-6.99 (2H, m), 7.25-7.49 (5H, m), 7.78 (1H, d, J=1.9 Hz), 8.38 (1H, d, J=1.5 Hz). Anal. Calcd for C$_{23}$H$_{18}$F$_3$N$_5$O$_2$: C, 60.93; H, 4.00; N, 15.45. Found: C, 61.00; H, 3.99; N, 15.50.

Example 103

1-[4-(3,3-Difluoropyrrolidin-1-yl)-2-fluorophenyl]-5-methoxy-3-(1-phenyl-1H-pyrazol-5-yl)pyridazin-4(1H)-one

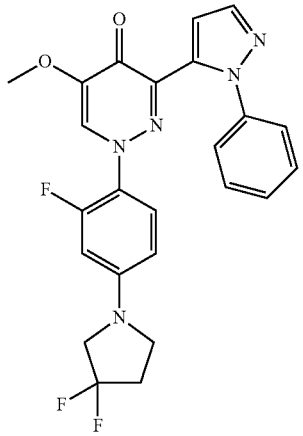 [SMILES: COc1cn(-c2ccc(N3CCC(F)(F)C3)cc2F)nc(-c2ccnn2-c2ccccc2)c1=O]

A suspension of 3-fluoro-4-[5-methoxy-4-oxo-3-(1-phenyl-1H-pyrazol-5-yl)pyridazin-1(4H)-yl]phenyl trifluoromethanesulfonate (204 mg, 0.4 mmol), 3,3-difluoropyrrolidine hydrochloride (71.8 mg, 0.5 mmol), Pd$_2$(dba)$_3$ (9.2 mg, 0.01 mmol), Xantphos (23.1 mg, 0.04 mmol), and NaOtBu (96.1 mg, 1.0 mmol) in 1,4-dioxane (2 mL) was stirred for 3 h at 90° C. under Ar atmosphere. The reaction mixture was poured into water and extracted with AcOEt. The extract was washed with brine, dried over MgSO$_4$, and concentrated under reduced pressure. The residue was subjected to basic silica gel column chromatography followed by purification by preparative HPLC. Recrystallization from MeOH/H$_2$O gave the title compound (21.0 mg, 11% yield) as a yellow solid: mp 195-197° C.; $^1$H NMR (300 MHz, CDCl$_3$): δ ppm 2.46-2.60 (2H, m), 3.52 (2H, t, J=7.2 Hz), 3.66 (2H, t, J=12.8 Hz), 3.89 (3H, s), 6.09 (1H, dd, J=2.6, 9.0 Hz), 6.23 (1H, dd, J=2.6, 13.9 Hz), 6.33 (1H, t, J=9.0 Hz), 7.25 (1H, J=1.9 Hz), 7.33-7.44 (5H, m), 7.71 (1H, d, J=2.3 Hz), 7.77 (1H, d, J=2.3 Hz). LC-MS (ESI) m/z 468 [M+H]$^+$. Anal. Calcd for C$_{24}$H$_{20}$F$_3$N$_5$O$_2$: C, 61.67; H, 4.31; N, 14.98. Found: C, 61.51; H, 4.38; N, 14.89.

Preparative HPLC was performed at the conditions described below.

Column: Waters SunFire Column C18 (30×50 mm S-5 μm)

Column temp: 25° C.

Mobile phase: (A) 0.1% TFA in distilled water, (B) 0.1% TFA in acetonitrile

Gradient: 0 min (A/B=60/40)→1 min (A/B=60/40)→4.75 min (A/B=0/100)→7.40 min (A/B=0/100)→7.41 min (A/B=60/40)→8.50 min (A/B=60/40)

Flow rate: 70 mL/min

Detector: UV 220 nm

Concentration: 50 mg/mL

Inject volume: 0.150 mL

Retention time: 2.44 min

Example 104

1-[2-Fluoro-4-(3,3,4,4-tetrafluoropyrrolidin-1-yl)phenyl]-5-methoxy-3-(1-phenyl-1H-pyrazol-5-yl)pyridazin-4(1H)-one

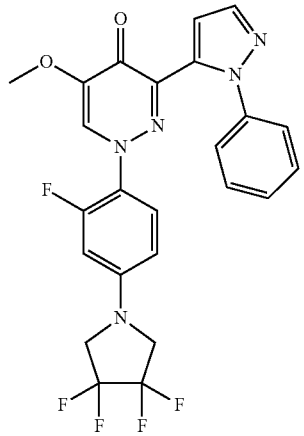 [SMILES: COc1cn(-c2ccc(N3CC(F)(F)C(F)(F)C3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (488 mg, 1.0 mmol), 3,3,4,4-tetrafluoropyrrolidine hydrochloride (215 mg, 1.2 mmol), Pd$_2$(dba)$_3$ (18.3 mg, 0.02 mmol), Xantphos (46.3 mg, 0.08 mmol), and NaOtBu (250 mg, 2.6 mmol) in 1,4-dioxane (5 mL) was stirred for 6 h at 90° C. under Ar atmosphere. The reaction mixture was poured into water and extracted with AcOEt. The extract was washed with brine, dried over MgSO$_4$, and concentrated under reduced pressure. The residue was subjected to basic silica gel column chromatography eluting with hexane/AcOEt (1/1-0/1) and crystallized from hexane/AcOEt to give the title compound (366 mg, 73% yield) as a white solid: mp 175-177° C.; $^1$H NMR (300 MHz, CDCl$_3$): δ ppm 3.75-3.89 (7H, m), 6.10 (1H, ddd, J=0.8, 2.6, 9.0 Hz), 6.26 (1H, dd, J=2.6, 13.6 Hz), 6.35 (1H, t, J=9.0 Hz), 7.27 (1H, d, J=1.9 Hz), 7.34-7.46 (5H, m), 7.71 (1H, d, J=2.6 Hz), 7.78 (1H, d, J=1.9. Hz). LC-MS (ESI) m/z 504 [M+H]$^+$. Anal. Calcd for C$_{24}$H$_{18}$F$_5$N$_5$O$_2$: C, 57.26; H, 3.60; N, 13.91. Found: C, 57.17; H, 3.61; N, 13.79.

Example 105

1-[4-(3,3-Difluoropiperidin-1-yl)-2-fluorophenyl]-5-methoxy-3-(1-phenyl-1H-pyrazol-5-yl)pyridazin-4(1H)-one

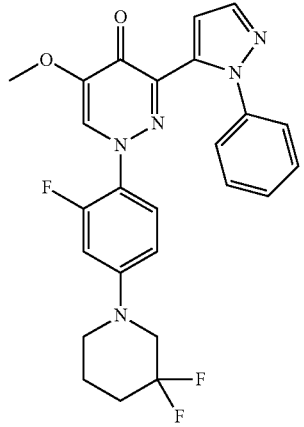 [SMILES: COc1cn(-c2ccc(N3CCCC(F)(F)C3)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.5 mmol), 3,3-difluoropiperidine hydrochloride (94.6 mg, 0.6 mmol), NaO-t-Bu (125 mg, 1.3 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 14 h under Ar. The mixture was diluted with NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and recrystallized with AcOEt/hexane to yield the title compound (132 mg, 55% yield) as a yellow solid: mp 182-187° C. $^1$H NMR (DMSO-d$_6$, 300 MHz): δ ppm 1.68-1.81 (2H, m), 1.97-2.16 (2H, m), 3.34-3.43 (2H, m), 3.67 (2H, t, J=11.9 Hz), 3.76 (3H, s), 6.73-7.10 (4H, m), 7.24-7.50 (5H, m), 7.78 (1H, d, J=1.9 Hz), 8.39 (1H, d, J=1.9 Hz). Anal. Calcd for C$_{25}$H$_{22}$F$_3$N$_5$O$_2$: C, 62.36; H, 4.61; N, 14.55. Found: C, 62.60; H, 4.60; N, 14.31.

Example 106

1-[4-(4,4-Difluoropiperidin-1-yl)-2-fluorophenyl]-5-methoxy-3-(1-phenyl-1H-pyrazol-5-yl)pyridazin-4(1H)-one

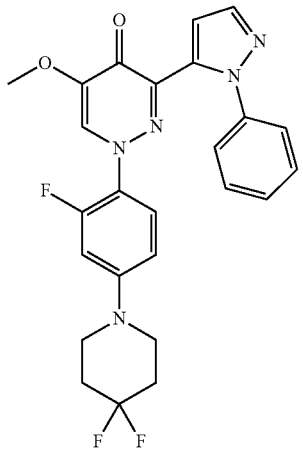 [SMILES: COc1cn(-c2ccc(N3CCC(F)(F)CC3)cc2F)nc(-c2ccnn2-c2ccccc2)c1=O]

A suspension of 3-fluoro-4-[5-methoxy-4-oxo-3-(1-phenyl-1H-pyrazol-5-yl)pyridazin-1(4H)-yl]phenyl trifluoromethanesulfonate (408 mg, 0.8 mmol), 4,4-difluoropiperidine hydrochloride (158 mg, 1.0 mmol), Pd$_2$(dba)$_3$ (36.6 mg, 0.04 mmol), Xantphos (92.6 mg, 0.16 mmol), and NaOtBu (192 mg, 2.0 mmol) in 1,4-dioxane (4 mL) was stirred for 3 h at 90° C. under Ar atmosphere. The reaction mixture was poured into water and extracted with AcOEt. The extract was washed with brine, dried over MgSO$_4$, and concentrated under reduced pressure. The residue was purified by basic silica gel column chromatography eluting with hexane/AcOEt (1/2-0/1) and crystallized from hexane/AcOEt to give the title compound (96.0 mg, 25% yield) as a yellow-green solid: mp 192-194° C.; $^1$H NMR (300 MHz, CDCl$_3$): δ ppm 2.01-2.14 (4H, m), 3.38-3.42 (4H, m), 3.89 (3H, s), 6.31 (1H, t, J=9.0 Hz), 6.47 (1H, dd, J=2.3, 9.0 Hz), 6.61 (1H, dd, J=2.6, 14.3 Hz), 7.25 (1H, d, J=1.9 Hz), 7.34-7.45 (5H, m), 7.73 (1H, d, J=2.3 Hz), 7.77 (1H, d, J=2.3 Hz). LC-MS (ESI) m/z 482 [M+H]$^+$. Anal. Calcd for C$_{25}$H$_{22}$F$_3$N$_5$O$_2$: C, 62.36; H, 4.61; N, 14.55. Found: C, 62.13; H, 4.62; N, 14.43.

Example 107

1-[2-Fluoro-4-(2-oxoazetidin-1-yl)phenyl]-5-methoxy-3-(1-phenyl-1H-pyrazol-5-yl)pyridazin-4(1H)-one

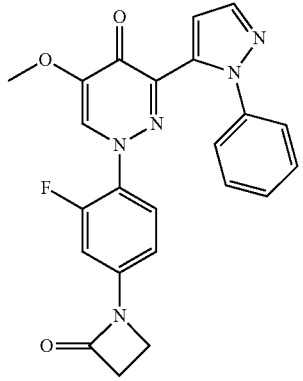 [SMILES: COc1cn(-c2ccc(N3CCC3=O)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.5 mmol), azetidin-2-one (42.6 mg, 0.6 mmol), K$_3$PO$_4$ (212 mg, 1.0 mmol), trans-1,2-diaminocyclohexane (0.012 mL, 0.1 mmol) and CuI (9.5 mg, 0.05 mmol) in 1,4-dioxane (2 mL) was heated to 110° C. for 18 h under Ar. To the mixture was added azetidin-2-one (42.6 mg, 0.6 mmol). The mixture was heated to 110° C. for 24 h under Ar. The mixture was diluted with NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and recrystallized with EtOH/hexane to yield the title compound (95 mg, 44% yield) as a pale yellow solid: mp 189-194° C. $^1$H NMR (DMSO-d$_6$, 300 MHz): δ ppm 3.15 (2H, t, J=4.5 Hz), 3.68 (2H, t, J=4.5 Hz), 3.77 (3H, s), 6.96 (1H, d, J=1.9 Hz), 7.06 (1H, t, J=8.7 Hz), 7.18 (1H, dd, J=8.7, 1.5 Hz), 7.29-7.48 (6H, m), 7.78 (1H, d, J=1.9 Hz), 8.45 (1H, d, J=1.9 Hz). Anal. Calcd for C$_{23}$H$_{18}$FN$_5$O$_3$: C, 64.03; H, 4.21; N, 16.23. Found: C, 63.75; H, 4.16; N, 16.22.

Example 108

1-[2-Fluoro-4-(2-oxopyrrolidin-1-yl)phenyl]-5-methoxy-3-(1-phenyl-1H-pyrazol-5-yl)pyridazin-4(1H)-one

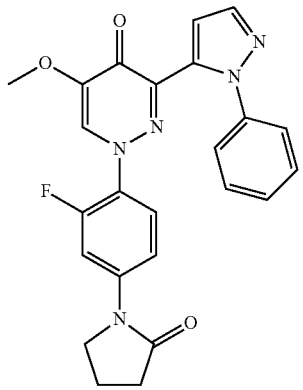 [SMILES: COc1cn(-c2ccc(N3CCCC3=O)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), 2-pyrrolidinone (0.046 mL, 0.6 mmol), CuI (9.5 mg, 0.05 mmol), trans-1,2-diaminocyclohexane (0.012 mL, 0.1 mmol), and K$_3$PO$_4$ (212 mg, 1.0 mmol) in 1,4-dioxane (2 mL) was refluxed for 6 h under Ar atmosphere. The reaction mixture was poured into water and extracted with AcOEt. The extract was washed with brine, dried over MgSO$_4$, and concentrated under reduced pressure. The residue was purified by basic silica gel column chromatography eluting with THF and recrystallized from MeOH/H$_2$O to give the title compound (73.6 mg, 33% yield) as a pale yellow solid: mp 200-202° C.; $^1$H NMR (300 MHz, CDCl$_3$): δ ppm 2.16-2.26 (2H, m), 2.62-2.68 (2H, m), 3.82-3.87 (2H, m), 3.90 (3H, s), 6.40 (1H, t, J=9.0 Hz), 7.10 (1H, ddd, J=1.1, 2.3, 9.0 Hz), 7.30 (1H, d, J=1.9 Hz), 7.35-7.45 (5H, m), 7.77-7.83 (3H, m). LC-MS (ESI) m/z 446 [M+H]$^+$. Anal. Calcd for C$_{24}$H$_{20}$FN$_5$O$_3$·0.25H$_2$O: C, 64.06; H, 4.59; N, 15.59. Found: C, 64.08; H, 4.57; N, 15.49.

Example 109

1-[2-Fluoro-4-(2-oxo-1,3-oxazolidin-3-yl)phenyl]-5-methoxy-3-(1-phenyl-1H-pyrazol-5-yl)pyridazin-4(1H)-one

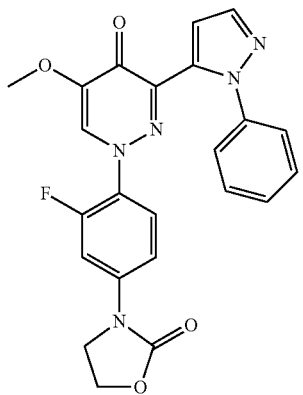 [SMILES: COc1cn(-c2ccc(N3CCOC3=O)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), 2-oxazolidone (52.2 mg, 0.6 mmol), CuI (9.5 mg, 0.05 mmol), trans-1,2-diaminocyclohexane (0.012 mL, 0.1 mmol), and K$_3$PO$_4$ (212 mg, 1.0 mmol) in 1,4-dioxane (2 mL) was refluxed for 1.5 h under Ar atmosphere. The reaction mixture was poured into water and extracted with AcOEt. The extract was washed with brine, dried over MgSO$_4$, and concentrated under reduced pressure. The residue was washed with AcOEt and recrystallized from MeOH/H$_2$O to give the title compound (159 mg, 71% yield) as a pale yellow solid: mp 218-220° C.; $^1$H NMR (300 MHz, CDCl$_3$): δ ppm 3.90 (3H, s), 4.03-4.08 (2H, m), 4.51-4.56 (2H, m), 6.42 (1H, t, J=9.0 Hz), 7.01 (1H, ddd, J=1.1, 2.3, 9.0 Hz), 7.30 (1H, d, J=1.9 Hz), 7.35-7.45 (5H, m), 7.66 (1H, dd, J=2.3, 13.6 Hz), 7.78 (21-1, d, J=1.9 Hz). LC-MS (ESI) m/z 448 [M+H]$^+$. Anal. Calcd for C$_{23}$H$_{18}$FN$_5$O$_4$: C, 61.74; H, 4.06; N, 15.65. Found: C, 61.48; H, 4.07; N, 15.54.

Example 110

4-{3-Fluoro-4-[5-methoxy-4-oxo-3-(1-phenyl-1H-pyrazol-5-yl)pyridazin-1(4H)-yl]phenyl}morpholin-3-one

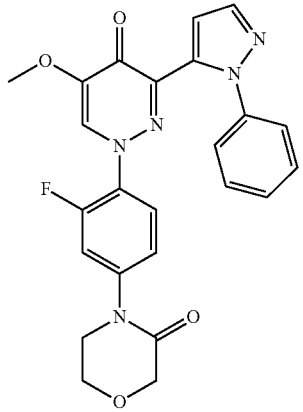 [SMILES: COc1cn(-c2ccc(N3CCOCC3=O)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), 3-morpholinone (60.7 mg, 0.6 mmol), CuI (9.5 mg, 0.05 mmol), trans-1,2-diaminocyclohexane (0.012 mL, 0.1 mmol), and K$_3$PO$_4$ (212 mg, 1.0 mmol) in 1,4-dioxane (2 mL) was refluxed for 6 h under Ar atmosphere. The reaction mixture was poured into water and extracted with AcOEt. The extract was washed with brine, dried over MgSO$_4$, and concentrated under reduced pressure. The residue was purified by basic silica gel column chromatography eluting with AcOEt and recrystallized from MeOH/H$_2$O to give the title compound (136 mg, 59% yield) as a white solid: mp 193-195° C.; $^1$H NMR (300 MHz, CDCl$_3$): δ ppm 3.75-3.79 (2H, m), 3.90 (3H, s), 4.04-4.07 (2H, m), 4.35 (2H, s), 6.41 (1H, t, J=9.0 Hz), 7.00 (1H, ddd, J=1.1, 2.3, 9.0 Hz), 7.31 (1H, d, J=2.3 Hz), 7.33-7.46 (6H, m), 7.78-7.80 (2H, m). LC-MS (ESI) m/z 462 [M+H]$^+$. Anal. Calcd for C$_{24}$H$_{20}$FN$_5$O$_4$: C, 62.47; H, 4.37; N, 15.18. Found: C, 62.31; H, 4.33; N, 15.25.

Example 111

1-[2-Fluoro-4-(1H-imidazol-1-yl)phenyl]-5-methoxy-3-(1-phenyl-1H-pyrazol-5-yl)pyridazin-4(1H)-one

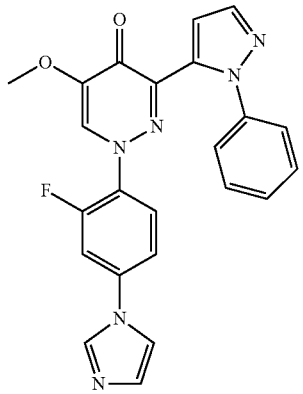 [SMILES: COc1cn(-c2ccc(-n3ccnc3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), imidazole (40.8 mg, 0.6 mmol), CuI (9.5 mg, 0.05 mmol), trans-1,2-diaminocyclohexane (0.012 mL, 0.1 mmol), and $Cs_2CO_3$. (326 mg, 1.0 mmol) in 1,4-dioxane (2 mL) was refluxed for 4 h under Ar atmosphere. The reaction mixture was poured into water and extracted with AcOEt. The extract was washed with brine, dried over $MgSO_4$, and concentrated under reduced pressure. The residue was purified by basic silica gel column chromatography eluting with AcOEt/ THF (1/0-0/1) and crystallized from MeOH to give the title compound (16.5 mg, 8% yield) as a white solid: mp 235-236° C. (dec); $^1$H NMR (300 MHz, $CDCl_3$): δ ppm 3.93 (3H, s), 6.49 (1H, t, J=8.7 Hz), 7.03 (1H, ddd, J=1.1, 2.3, 8.7 Hz), 7.22-7.27 (3H, m), 7.35 (1H, d, J=1.9 Hz), 7.38-7.49 (5H, m), 7.80 (1H, d, J=1.9 Hz), 7.82 (1H, d, J=2.6 Hz), 7.86 (1H, t, J=1.1 Hz). LC-MS (ESI) m/z 429 [M+H]$^+$. Anal. Calcd for $C_{23}H_{17}FN_6O_2$: C, 64.48; H, 4.00; N, 19.62. Found: C, 64.35; H, 3.90; N, 19.43.

Example 112

1-[4-(3,5-Dimethylisoxazol-4-yl)-2-fluorophenyl]-5-methoxy-3-(1-phenyl-1H-pyrazol-5-yl)pyridazin-4(1H)-one

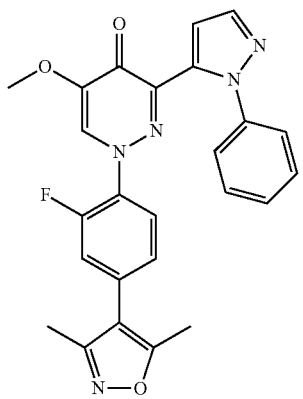 [SMILES: COc1cn(-c2ccc(-c3c(C)noc3C)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (230 mg, 0.45 mmol); 3,5-dimethylisoxazole-4-boronic acid (70 mg, 0.50 mmol), $Pd(PPh_3)_4$ (29 mg, 0.025 mmol), $Na_2CO_3$ (106 mg, 1.0 mmol), DME (4 mL), and $H_2O$ (1 mL) was refluxed for 3 h under Ar atmosphere. After cooling to room temperature, the reaction mixture was poured into water and extracted with AcOEt. The extract was washed with brine, dried over $MgSO_4$, and concentrated under reduced pressure. The residue was purified by basic silica gel column chromatography eluting with THF and recrystallized from MeOH/$H_2O$ to give the title compound (121 mg, 59% yield) as a white solid: mp 200-202° C.; $^1$H NMR (300 MHz, $CDCl_3$): δ ppm 2.27 (3H, s), 2.42 (3H, s), 3.92 (3H, s), 6.49 (1H, t, J=8.3 Hz), 6.89 (1H, ddd, J=0.8, 1.9, 8.3 Hz), 7.08 (1H, dd, J=1.9, 12.1 Hz), 7.32 (1H, d, J=1.9 Hz), 7.35-7.47 (5H, m), 7.79 (1H, d, J=1.9 Hz), 7.85 (1H, d, J=2.3 Hz). LC-MS (ESI) m/z 458 [M+H]$^+$. Anal. Calcd for $C_{25}H_{20}FN_5O_3$: C, 65.64; H, 4.41; N, 15.31. Found: C, 65.55; H, 4.32; N, 15.33.

Example 113

1-[2-Fluoro-3-(1-methyl-1H-pyrazol-4-yl)phenyl]-5-methoxy-3-(1-phenyl-1H-pyrazol-5-yl)pyridazin-4(1H)-one

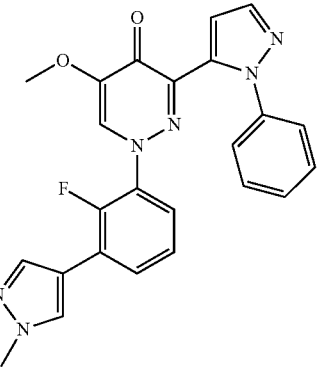

A mixture of 3-acetyl-1-[2-fluoro-3-(1-methyl-1H-pyrazol-4-yl)phenyl]-5-methoxypyridazin-4(1H)-one (243 mg, 0.708 mmol) in N,N-dimethylformamide dimethyl acetal (2.4 mL) was heated to reflux for 2 h. The mixture was concentrated in vacuo. To the residue were added AcOH (2.4 mL) and phenylhydrazine (0.139 mL, 1.42 mmol). The mixture was heated to reflux for 2 h. The mixture was diluted with 1 M HCl aqueous solution, extracted with AcOEt, washed with saturated $NaHCO_3$ aqueous solution, dried over $Na_2SO_4$, filtered, concentrated in vacuo, purified by column chromatography on basic silica gel (hexane/AcOEt=20/80 to 0/100) and recrystallized with EtOH/AcOEt/hexane to yield the title compound (193 mg, 62% yield) as a pale yellow solid: mp 218-221° C. $^1$H NMR (DMSO-$d_6$, 300 MHz): δ ppm 3.78 (3H, s), 3.91 (3H, s), 6.97 (2H, d, J=1.9 Hz), 7.13-7.50 (6H, m), 7.72-7.84 (2H, m), 7.93 (1H, s), 8.18 (1H, d, J=2.3 Hz), 8.55 (1H, d, J=1.9 Hz).

Example 114

1-[2-Fluoro-4-(1-methyl-1H-pyrazol-4-yl)phenyl]-5-methoxy-3-(1-phenyl-1H-pyrazol-5-yl)pyridazin-4(1H)-one

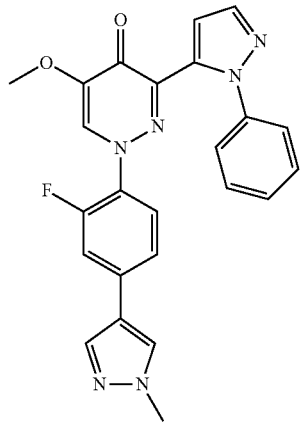 [SMILES: COc1cn(-c2ccc(-c3cnn(C)c3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (230 mg, 0.45 mmol), 1-methyl-1H-pyrazole-4-boronic acid pinacol ester (104 mg, 0.50 mmol), Pd(PPh$_3$)$_4$ (29 mg, 0.025 mmol), Na$_2$CO$_3$ (106 mg, 1.0 mmol), DME (4 mL), and H$_2$O (1 mL) was refluxed overnight under Ar atmosphere. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with THF and recrystallized from MeOH/H$_2$O to give the title compound (162 mg, 81% yield) as a white solid: mp 195-197° C.; $^1$H NMR (300 MHz, CDCl$_3$): δ ppm 3.91 (3H, s), 3.96 (3H, s), 6.38 (1H, t, J=8.3 Hz), 7.06 (1H, ddd, J=0.8, 1.9, 8.3 Hz), 7.23 (1H, dd, J=1.9, 12.8 Hz), 7.30 (1H, d, J=1.9 Hz), 7.36-7.47 (5H, m), 7.64 (1H, s), 7.74 (1H, d, J=0.8 Hz), 7.79 (1H, d, J=1.9 Hz), 7.81 (1H, d, J=2.6 Hz). LC-MS (ESI) m/z 443 [M+H]$^+$. Anal. Calcd for C$_{24}$H$_{19}$FN$_6$O$_2$: C, 65.15; H, 4.33; N, 18.99. Found: C, 65.15; H, 4.30; N, 19.02.

Example 115

1-[2-Fluoro-5-(1-methyl-1H-pyrazol-4-yl)phenyl]-5-methoxy-3-(1-phenyl-1H-pyrazol-5-yl)pyridazin-4(1H)-one

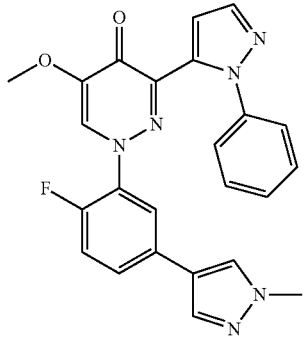

A mixture of 3-acetyl-1-[2-fluoro-5-(1-methyl-1H-pyrazol-4-yl)phenyl]-5-methoxypyridazin-4(1H)-one (200 mg, 0.585 mmol) in N,N-dimethylformamide dimethyl acetal (2.0 mL) was heated to reflux for 3 h. The mixture was concentrated in vacuo. To the residue were added AcOH (2.0 mL) and phenylhydrazine (0.115 mL, 1.17 mmol). The mixture was heated to reflux for 3 h. The mixture was diluted with 1 M HCl aqueous solution, extracted with AcOEt, washed with saturated NaHCO$_3$ aqueous solution, dried over Na$_2$SO$_4$, filtered, concentrated in vacuo, purified by column chromatography on basic silica gel (hexane/AcOEt=50/50 to 0/100) and by HPLC and recrystallized with EtOH/hexane to yield the title compound (118 mg, 46% yield) as a white solid: mp 93-102° C. $^1$H NMR (DMSO-d$_6$, 300 MHz): δ ppm 3.78 (3H, s), 3.89 (3H, s), 6.91 (1H, d, J=1.9 Hz), 7.20-7.52 (7H, m), 7.63-7.71 (1H, m), 7.78 (1H, d, J=1.9 Hz), 7.83 (1H, s), 8.10 (1H, s), 8.53 (1H, d, J=1.6 Hz). Anal. Calcd for C$_{24}$H$_{19}$FN$_6$O$_2$·1.3H$_2$O: C, 61.88; H, 4.67; N, 18.04. Found: C, 61.63; H, 4.64; N, 18.09.

Preparative HPLC was performed at the conditions described below.

Column: YMC CombiPrep Pro C18 RS (50×20 mm I.D. S-5 μm, 8 nm)

Column temp: 25° C.

Mobile phase: (A) 0.1% TFA in distilled water, (B) 0.1% TFA in acetonitrile

Gradient: 0 min (A/B=95/5)→1.00 min (A/B=95/5)→5.70 min (A/B=0/100)→7.30 min (A/B=0/100)→7.40 min (A/B=95/5)→8.00 min (A/B=95/5)

Flow rate: 20 mL/min

Detector: UV 220 nm

Concentration: 89 mg/mL

Inject volume: 100 μL

Example 116

1-{4-[1-(Difluoromethyl)-1H-pyrazol-4-yl]-2-fluorophenyl}-5-methoxy-3-(1-phenyl-1H-pyrazol-5-yl)pyridazin-4(1H)-one

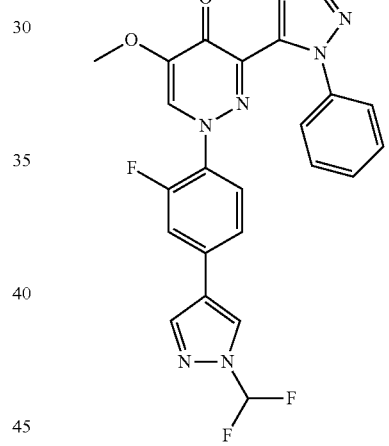

A mixture of 3-fluoro-4-[5-methoxy-4-oxo-3-(1-phenyl-1H-pyrazol-5-yl)pyridazin-1(4H)-yl]phenyl trifluoromethanesulfonate (230 mg, 0.45 mmol), 1-(difluoromethyl)-1H-pyrazole-4-boronic acid pinacol ester (122 mg, 0.50 mmol), Pd(PPh$_3$)$_4$ (17 mg, 0.015 mmol), Na$_2$CO$_3$ (106 mg, 1.0 mmol), DME (4 mL), and H$_2$O (1 mL) was refluxed for 3 h under Ar atmosphere. After cooling to room temperature, the reaction mixture was poured into water and extracted with AcOEt. The extract was washed with brine, dried over MgSO$_4$, and concentrated under reduced pressure. The residue was purified by basic silica gel column chromatography eluting with AcOEt and recrystallized from MeOH/H$_2$O to give the title compound (183 mg, 85% yield) as a white solid: mp 185-187° C.; $^1$H NMR (300 MHz, CDCl$_3$): δ ppm 3.92 (3H, s), 6.41 (1H, t, J=8.3 Hz), 7.03-7.48 (10H, m), 7.79 (1H, d, J=1.9 Hz), 7.83 (1H, d, J=2.3 Hz), 7.91 (1H, d, J=0.8 Hz). LC-MS (ESI) m/z 479 [M+H]$^+$. Anal. Calcd for C$_{24}$H$_{17}$F$_3$N$_6$O$_2$: C, 60.25; H, 3.58; N, 17.57. Found: C, 60.19; H, 3.48; N, 17.52.

Example 117

1-[2-Fluoro-4-(1,3-oxazol-2-yl)phenyl]-5-methoxy-3-(1-phenyl-1H-pyrazol-5-yl)pyridazin-4(1H)-one

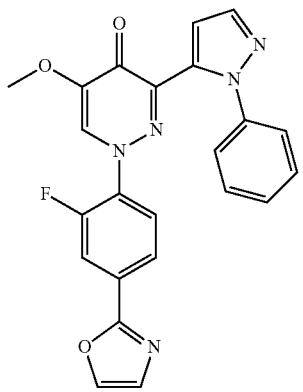 [SMILES: COc1cn(-c2ccc(-c3ncco3)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (244 mg, 0.5 mmol), 2-(tributylstannanyl)-1,3-oxazole (0.209 mL, 1.0 mmol) and Pd(PPh$_3$)$_4$ (57.8 mg, 0.05 mmol) in 1,4-dioxane (3 mL) was heated to reflux for 11 h under Ar. The mixture was diluted with NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100 and AcOEt/MeOH=100/0 to 70/30) and recrystallized with EtOH/hexane to yield the title compound (113 mg, 53% yield) as a yellow solid: mp 223-225° C. $^1$H NMR (DMSO-d$_6$, 300 MHz): δ ppm 3.79 (3H, s), 7.02 (1H, d, J=1.9 Hz), 7.16 (1H, t, J=8.3 Hz), 7.31-7.51 (6H, m), 7.77-7.83 (2H, m), 7.96 (1H, dd, J=11.5, 1.7 Hz), 8.34 (1H, s), 8.55 (1H, d, J=2.6 Hz). Anal. Calcd for C$_{23}$H$_{16}$FN$_5$O$_3$·0.1H$_2$O: C, 64.06; H, 3.79; N, 16.24. Found: C, 63.92; H, 3.67; N, 16.23.

Example 118

1-(2-Fluoro-4-pyridin-2-ylphenyl)-5-methoxy-3-(1-phenyl-1H-pyrazol-5-yl)pyridazin-4(1H)-one

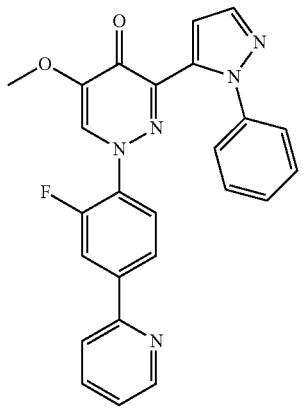 [SMILES: COc1cn(-c2ccc(-c3ccccn3)cc2F)nc(-c2ccnn2-c2ccccc2)c1=O]

A mixture of 3-fluoro-4-[5-methoxy-4-oxo-3-(1-phenyl-1H-pyrazol-5-yl)pyridazin-1(4H)-yl]phenyl trifluoromethanesulfonate (200 mg, 0.392 mmol), (2-pyridine)cyclic-triolborate lithium salt (167 mg, 0.784 mmol), 2-(di-tert-butylphosphino)biphenyl (12.9 mg, 0.0431 mmol), CuI (14.9 mg, 0.0784 mmol) and Pd(OAc)$_2$ (4.4 mg, 0.0196 mmol) in DMF (1.2 mL) was heated to 80° C. for 13 h under Ar. The mixture was diluted with NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and on silica gel (hexane/AcOEt=50/50 to 0/100) and recrystallized with AcOEt/hexane to yield the title compound (68.9 mg, 40% yield) as a pale yellow solid: mp 206-208° C.; $^1$H NMR (DMSO-d$_6$, 300 MHz): δ ppm 3.80 (3H, s), 7.01 (1H, d, J=1.9 Hz), 7.11 (1H, t, J=8.3 Hz), 7.31-7.53 (6H, m), 7.80 (1H, d, J=1.9 Hz), 7.91-8.02 (2H, m), 8.08-8.20 (2H, m), 8.55 (1H, d, J=1.9 Hz), 8.72 (1H, d, J=4.5 Hz). Anal. Calcd for C$_{25}$H$_{18}$FN$_5$O$_2$: C, 68.33; H, 4.13; N, 15.94. Found: C, 68.15; H, 4.18; N, 15.83.

Example 119

1-[4-(3,4-Difluoro-1H-pyrrol-1-yl)-2-fluorophenyl]-5-methoxy-3-(1-phenyl-1H-pyrazol-5-yl)pyridazin-4(1H)-one

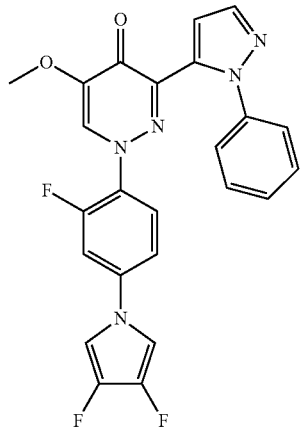 [SMILES: COc1cn(-c2ccc(-n3cc(F)c(F)c3)cc2F)nc(-c2ccnn2-c2ccccc2)c1=O]

KOtBu (236 mg, 2.1 mmol) was added portionwise at room temperature to a solution of 1-[2-fluoro-4-(3,3,4,4-tetrafluoropyrrolidin-1-yl)phenyl]-5-methoxy-3-(1-phenyl-1H-pyrazol-5-yl)pyridazin-4(1H)-one (352 mg, 0.7 mmol) in DMSO (3.5 mL). After stirring for 30 min, the reaction mixture was poured into water and extracted with AcOEt. The extract was washed with brine, dried over MgSO$_4$, and concentrated under reduced pressure. The residue was subjected to basic silica gel column chromatography eluting with hexane/AcOEt (1/1-0/1) followed by purification by preparative HPLC. Recrystallization from MeOH/H$_2$O afforded the title compound (105 mg, 32% yield) as a white solid: mp 212-214° C.; $^1$H NMR (300 MHz, CDCl$_3$): δ ppm 3.91 (3H, s), 6.42 (1H, t, J=9.0 Hz), 6.68-6.78 (2H, m), 6.87 (1H, ddd, J=1.1, 2.6, 9.0 Hz), 7.07 (1H, dd, J=2.6, 12.4 Hz), 7.33 (1H, d, J=2.3 Hz), 7.36-7.48 (5H, m), 7.78-7.79 (2H, m). LC-MS (ESI) m/z 464 [M+H]$^+$. Anal. Calcd for C$_{24}$H$_{16}$F$_3$N$_5$O$_2$: C, 62.20; H, 3.48; N, 15.11. Found: C, 62.20; H, 3.51; N, 15.01.

Preparative HPLC was performed at the conditions described below.

Column: YMC CombiPrep ODS-A (20×50 mm S-5 μm)
Column temp: 25° C.
Mobile phase: (A) 0.1% TFA in distilled water, (B) 0.1% TFA in acetonitrile
Gradient: 0.00 min (A/B=60/40)→1.00 min (A/B=60/40)→4.75 min (A/B=0/100)→7.39 min (A/B=0/100)→7.40 min (A/B=100/0)→7.50 min (A/B=100/0)
Flow rate: 25 mL/min
Detector: UV 220 nm
Concentration: 33.3 mg/mL
Inject volume: 0.300 mL
Retention time: 2.35 min Example 120

1-[2-Fluoro-4-(1H-pyrazol-1-yl)phenyl]-5-methoxy-3-(1-phenyl-1H-pyrazol-5-yl)pyridazin-4(1H)-one

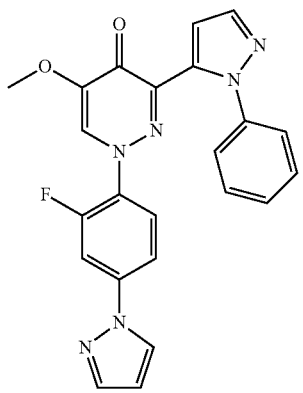 [SMILES: COc1cn(-c2ccc(-n3cccn3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (4.88 g, 10 mmol), pyrazole (0.681 g, 10 mmol), $Cu_2O$ (0.143 g, 1 mmol), salicylaldoxime (0.549 g, 4 mmol), and $Cs_2CO_3$ (6.52 g, 20 mmol) in $CH_3CN$ (100 mL) was refluxed for 5 h under Ar atmosphere. After cooling to room temperature, the reaction mixture was poured into water and extracted with AcOEt. The extract was washed with brine, dried over $MgSO_4$, and concentrated under reduced pressure. The residue was purified by basic silica gel column chromatography eluting with hexane/THF (1/2) and recrystallized from EtOH/$H_2O$ to give the title compound (1.90 g, 44% yield) as a pale yellow powder: mp 214-216° C.; $^1$H NMR (300 MHz, $CDCl_3$) δ ppm 3.92 (3H, s), 6.44 (1H, t, J=9.0 Hz), 6.53 (1H, dd, J=1.9, 2.3 Hz), 7.30 (1H, ddd, J=1.1, 2.3, 9.0 Hz), 7.34 (1H, d, J=1.9 Hz), 7.37-7.48 (5H, m), 7.61 (1H, dd, J=2.3, 12.4 Hz), 7.76 (1H, d, J=1.9 Hz), 7.79 (1H, d, J=1.9 Hz), 7.82 (1H, d, J=2.3 Hz), 7.92 (1H, d, J=2.3 Hz). LC-MS (ESI) m/z 429 [M+H]$^+$. Anal. Calcd for $C_{23}H_{17}FN_6O_2$: C, 64.48; H, 4.00; N, 19.62. Found: C, 64.41; H, 4.00; N, 19.54.

Example 121

Ethyl 1-{3-fluoro-4-[5-methoxy-4-oxo-3-(1-phenyl-1H-pyrazol-5-yl)pyridazin-1(4H)-yl]phenyl}-5-hydroxy-1H-pyrazole-4-carboxylate

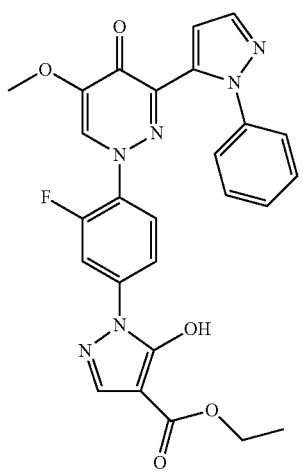 [SMILES: CCOC(=O)c1cnn(-c2ccc(-n3cc(OC)c(=O)c(-c4ccnn4-c4ccccc4)n3)c(F)c2)c1O]

A mixture of tert-butyl 1-{3-fluoro-4-[5-methoxy-4-oxo-3-(1-phenyl-1H-pyrazol-5-yl)pyridazin-1(4H)-yl]phenyl}hydrazinecarboxylate (2.02 g, 4.1 mmol), TFA (5 mL), and $CH_2Cl_2$ (10 mL) was stirred for 3 h at room temperature. The reaction mixture was concentrated under reduced pressure.

A suspension of the residue, diethyl ethoxymethylenemalonate (0.829 mL, 4.1 mmol), and $K_2CO_3$ (1.70 g, 12.3 mmol) in EtOH (20 mL) was refluxed for 3 h. After cooling to room temperature, the reaction mixture was poured into water and extracted with AcOEt. The extract was washed with brine, dried over $MgSO_4$, and concentrated under reduced pressure. The residue was washed with AcOEt and recrystallized from EtOH to give the title compound (1.43 g, 67% yield) as a pale orange solid: mp 188-193° C.; $^1$H NMR (300 MHz, $CDCl_3$): δ ppm 1.41 (3H, t, J=7.2 Hz), 3.92 (3H, s), 4.39 (2H, q, J=7.2 Hz), 6.45 (1H, t, J=9.0 Hz), 7.35 (1H, d, J=1.9 Hz), 7.37-7.48 (5H, m), 7.55 (1H, ddd, J=1.1, 2.3, 9.0 Hz), 7.77-7.82 (3H, m), 7.83 (1H, d, J=2.3 Hz). Anal. Calcd for $C_{26}H_{21}FN_6O_5$: C, 60.46; H, 4.10; N, 16.27. Found: C, 60.28; H, 4.17; N, 16.37.

Example 122

1-[2-Fluoro-4-(5-hydroxy-1H-pyrazol-1-yl)phenyl]-5-methoxy-3-(1-phenyl-1H-pyrazol-5-yl)pyridazin-4(1H)-one

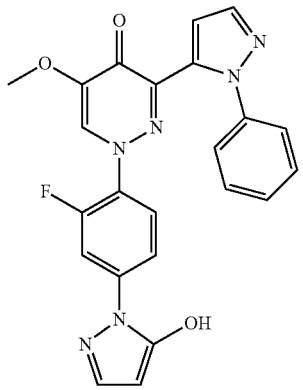 [SMILES: COc1cn(-c2ccc(-n3nccc3O)cc2F)nc(-c2ccnn2-c2ccccc2)c1=O]

A mixture of ethyl 1-{3-fluoro-4-[5-methoxy-4-oxo-3-(1-phenyl-1H-pyrazol-5-yl)pyridazin-1(4H)-yl]phenyl}-5-hydroxy-1H-pyrazole-4-carboxylate (1.41 g, 2.73 mmol), 4 M NaOH (40 mL), and EtOH (40 mL) was refluxed for 4 h. After cooling to room temperature, conc. HCl (20 mL) was added slowly. The mixture was stirred for 30 min at room temperature and then refluxed for 1 h. After cooling to room temperature, the reaction mixture was poured into water and extracted with AcOEt. The extract was washed with brine, dried over MgSO$_4$, and concentrated under reduced pressure. The residue was purified by silica gel column chromatography eluting with AcOEt/THF (2/1) and recrystallized from THF/MeOH to give the title compound (387 mg, 32% yield) as a pale yellow solid: mp 221-229° C.; $^1$H NMR (300 MHz, DMSO-d$_6$): δ ppm 3.78 (3H, s), 5.57 (1H, d, J=1.5 Hz), 6.99 (1H, d, J=1.9 Hz), 7.14 (1H, t, J=9.0 Hz), 7.31-7.51 (6H, m), 7.64-7.68 (1H, m), 7.79-7.84 (2H, m), 8.52 (1H, d, J=1.9 Hz), 12.17 (1H, brs). LC-MS (ESI) m/z 445 [M+H]$^+$.

Example 123

1-{4-[5-(Difluoromethoxy)-1H-pyrazol-1-yl]-2-fluorophenyl}-5-methoxy-3-(1-phenyl-1H-pyrazol-5-yl)pyridazin-4(1H)-one

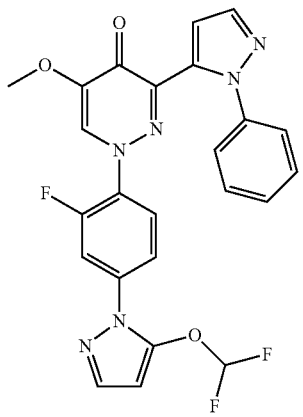 [SMILES: COc1cn(-c2ccc(-n3nccc3OC(F)F)cc2F)nc(-c2ccnn2-c2ccccc2)c1=O]

Example 124

1-{4-[2-(Difluoromethyl)-5-oxo-2,5-dihydro-1H-pyrazol-1-yl]-2-fluorophenyl}-5-methoxy-3-(1-phenyl-1H-pyrazol-5-yl)pyridazin-4(1H)-one

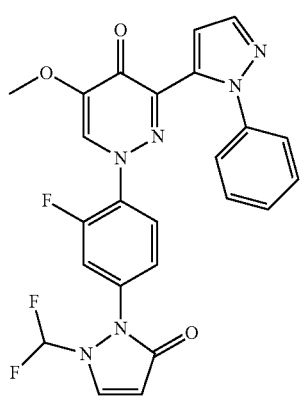 [SMILES: COc1cn(-c2ccc(-n3c(=O)ccn3C(F)F)cc2F)nc(-c2ccnn2-c2ccccc2)c1=O]

A mixture of 1-[2-fluoro-4-(5-hydroxy-1H-pyrazol-1-yl)phenyl]-5-methoxy-3-(1-phenyl-1H-pyrazol-5-yl)pyridazin-4(1H)-one (373 mg, 0.84 mmol), CF$_2$ClCO$_2$Na (256 mg, 1.68 mmol), K$_2$CO$_3$ (232 mg, 1.68 mmol), DMF (2.5 mL), and H$_2$O (0.5 mL) was stirred for 2 h at 100° C. The reaction mixture was poured into water and extracted with AcOEt. The extract was washed with brine, dried over MgSO$_4$, and concentrated under reduced pressure. The residue was purified by basic silica gel column chromatography eluting with AcOEt and recrystallized from AcOEt to give 1-{4-[5-(difluoromethoxy)-1H-pyrazol-1-yl]-2-fluorophenyl}-5-methoxy-3-(1-phenyl-1H-pyrazol-5-yl)pyridazin-4(1H)-one (168 mg, 40% yield) as a pale yellow solid: mp 177-179° C.; $^1$H NMR (300 MHz, CDCl$_3$): δ ppm 3.92 (3H, s), 6.07-6.08 (1H, m), 6.45 (1H, t, J=9.0 Hz), 6.59 (1H, t, J=71.8 Hz), 7.34-7.47 (7H, m), 7.58 (1H, dd, J=2.3, 12.4 Hz), 7.61 (1H, d, J=1.9 Hz), 7.79 (1H, d, J=1.9 Hz), 7.83 (1H, d, J=2.3 Hz). LC-MS (ESI) m/z 495 [M+H]$^+$. Anal. Calcd for C$_{24}$H$_{17}$F$_3$N$_6$O$_3$: C, 58.30; H, 3.47; N, 17.00. Found: C, 58.17; H, 3.46; N, 16.91.

Further elution followed by recrystallization from MeOH/H$_2$O afforded 1-{4-[2-(difluoromethyl)-5-oxo-2,5-dihydro-1H-pyrazol-1-yl]-2-fluorophenyl}-5-methoxy-3-(1-phenyl-1H-pyrazol-5-yl)pyridazin-4(1H)-one (63.5 mg, 15% yield) as a white solid: mp 161-163° C.; $^1$H NMR (CDCl$_3$) δ 3.91 (3H, s), 5.99 (1H, d, J=4.1 Hz), 6.40 (1H, t, J=60.7 Hz), 6.47 (1H, t, J=8.7 Hz), 7.09 (1H, ddd, J=1.1, 2.3, 8.7 Hz), 7.32 (1H, d, J=1.9 Hz), 7.36-7.47 (6H, m), 7.79-7.81 (3H, m). LC-MS (ESI) m/z 495 [M+H]$^+$. Anal. Calcd for C$_{24}$H$_{17}$F$_3$N$_6$O$_3$·0.5H$_2$O: C, 57.26; H, 3.60; N, 16.69. Found: 57.38; H, 3.52; N, 16.78.

Example 125

1-[2-(1-Methylethyl)phenyl]-3-(1-phenyl-1H-pyrazol-5-yl)pyridazin-4(1H)-one

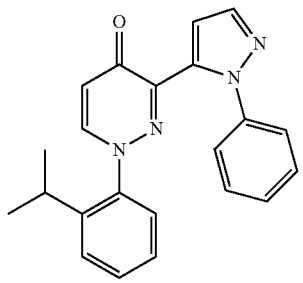 [SMILES: CC(C)c1ccccc1-n1ccc(=O)c(-c2ccnn2-c2ccccc2)n1]

3-{[2-(1-Methylethyl)phenyl]hydrazono}pentane-2,4-dione (0.98 g, 3.98 mmol) was dissolved in 10 mL of N,N-dimethylformamide dimethyl acetal, and the mixture was stirred for 4 hours at 120° C., and then concentrated under reduced pressure.

To a solution of the residue in 20 mL of methanol, phenylhydrazine (1.72 g, 15.93 mmol) was added, and the mixture was refluxed for 4 hours, and concentrated. The residue was dissolved in dichloromethane (40 mL), washed with 1 M HCl aqueous solution and brine, dried over $Na_2SO_4$, and concentrated under reduced pressure. The residue was purified by prep-HPLC to give the title compound (80 mg, 6% yield) as a yellow solid: $^1$H NMR (400 MHz, $CDCl_3$): δ 1.08 (6H, d, J=7.2 Hz), 2.62-2.70 (1H, m), 6.61 (1H, d, J=7.6 Hz), 6.85 (1H, dd, J=8.0, 1.6 Hz), 7.06 (1H, d, J=1.6 Hz), 7.16-7.21 (1H, m), 7.26-7.41 (7H, m), 7.75 (1H, d, J=1.6 Hz), 7.78 (1H, d, J=8.0 Hz); LCMS (mobile phase: from 70% water and 30% $CH_3CN$ to 5% water and 95% $CH_3CN$ in 6 min, finally under these conditions for 0.5 min.) purity is 90%, Rt=3.158 min; MS Calcd.: 356; MS Found: 357 [M+H]$^+$.

Example 126

2-[4-Oxo-3-(1-phenyl-1H-pyrazol-5-yl)pyridazin-1(4H)-yl]benzonitrile

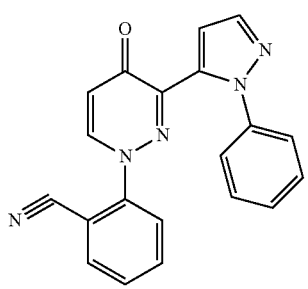 [SMILES: N#Cc1ccccc1-n1ccc(=O)c(-c2ccnn2-c2ccccc2)n1]

2-[2-(1-Acetyl-2-oxopropylidene)hydrazino]benzonitrile (4.00 g, 17.47 mmol) was dissolved in 40 mL of N,N-dimethylformamide dimethyl acetal, the mixture was stirred for 4 hours at 120° C., and then concentrated under reduced pressure.

To a solution of the residue in 80 mL of methanol, phenylhydrazine (3.77 g, 34.94 mmol) was added, and the mixture was refluxed for 4 hours at 80° C., and concentrated. The residue was dissolved in dichloromethane (80 mL), washed with 1 M HCl aqueous solution and brine, dried over $Na_2SO_4$, and concentrated under reduced pressure. The residue was purified by prep-HPLC to give the title compound (350 mg, 6% yield) as a brown solid: $^1$H NMR (400 MHz, $CDCl_3$): δ 6.68 (1H, d, J=8.0 Hz), 6.72 (1H, dd, J=8.0, 1.2 Hz), 7.32-7.40 (6H, m), 7.48-7.54 (2H, m), 7.74 (1H, dd, J=7.6, 2.0 Hz), 7.79 (1H, d, J=2.0 Hz), 8.11 (1H, d, J=7.6 Hz); LCMS (mobile phase: from 80% water and 20% $CH_3CN$ to 5% water and 95% $CH_3CN$ in 6 min, finally under these conditions for 0.5 min.) purity is >95%, Rt=2.881 min; MS Calcd.: 339; MS Found: 340 [M+H]$^+$.

Example 127

1-Biphenyl-2-yl-3-(1-phenyl-1H-pyrazol-5-yl)pyridazin-4(1H)-one

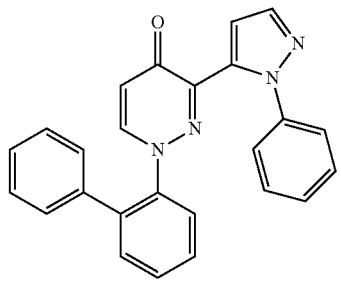 [SMILES: O=c1ccn(-c2ccccc2-c2ccccc2)nc1-c1ccnn1-c1ccccc1]

3-(Biphenyl-2-ylhydrazono)pentane-2,4-dione (420 mg, 1.50 mmol) was dissolved in 4 mL of N,N-dimethylformamide dimethyl acetal, and the mixture was stirred for 4 hours at 120° C., and then concentrated under reduced pressure.

To a solution of the residue in 10 mL of methanol, phenylhydrazine (648 mg, 6.00 mmol) was added, and the mixture was refluxed for 4 hours at 80° C., and concentrated. The residue was dissolved in dichloromethane (30 mL), washed with 1 M HCl aqueous solution and brine, dried over $Na_2SO_4$, and concentrated under reduced pressure. The residue was purified by prep-HPLC to give the title compound (184 mg, 31% yield) as a yellow solid: $^1$H NMR (400 MHz, $CDCl_3$): δ 6.25 (1H, d, J=7.6 Hz), 6.72 (1H, dd, J=8.0, 0.8 Hz), 7.05-7.08 (2H, m), 7.12 (1H, d, J=2.0 Hz), 7.27-7.45 (12H, m), 7.77 (1H, d, J=1.6 Hz); LCMS (mobile phase: from 70% water and 30% $CH_3CN$ to 5% water and 95% CH3CN in 6 min, finally under these conditions for 0.5 min.) purity is >95%, Rt=3.272 min; MS Calcd.: 390; MS Found: 391 [M+H]$^+$.

Example 128

1-(2-Ethoxyphenyl)-3-(1-phenyl-1H-pyrazol-5-yl)pyridazin-4(1H)-one

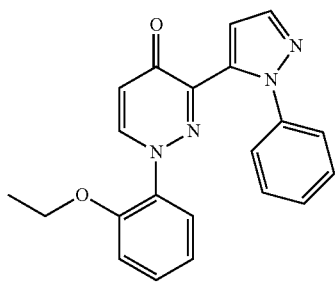 [SMILES: CCOc1ccccc1-n1ccc(=O)c(-c2ccnn2-c2ccccc2)n1]

3-[(2-Ethoxyphenyl)hydrazono]pentane-2,4-dione (2.00 g, 8.06 mmol) was dissolved in 20 mL of N,N-dimethylformamide dimethyl acetal, the mixture was stirred for 4 hours at 120° C., and then concentrated under reduced pressure.

To a solution of the residue in 60 mL of methanol, phenylhydrazine (3.48 g, 32.24 mmol) was added, and the mixture was refluxed for 4 hours at 80° C., and concentrated. The residue was dissolved in dichloromethane (80 mL), washed with 1 M HCl aqueous solution and brine, dried over Na$_2$SO$_4$, and concentrated under reduced pressure. The residue was purified by prep-HPLC to give the title compound (75 mg, 2% yield) as a brown solid: $^1$H NMR (400 MHz, CDCl$_3$): δ 1.36 (3H, t, J=6.8 Hz), 4.05 (2H, q, J=6.8 Hz), 6.32 (1H, dd, J=8.0, 1.2 Hz), 6.61 (1H, d, J=7.6 Hz), 6.78 (1H, td, J=7.6, 1.2 Hz), 6.94 (1H, dd, J=8.4, 1.2 Hz), 7.25-7.30 (2H, m), 7.39-7.43 (5H, m), 7.78 (1H, d, J=2.0 Hz), 8.06 (1H, d, J=7.6 Hz); LCMS (mobile phase: from 80% water and 20% CH3CN to 5% water and 95% CH3CN in 6 min, finally under these conditions for 0.5 min.) purity is >95%, Rt=3.375 min; MS Calcd.: 358; MS Found: 359 [M+H]$^+$.

Example 129

1-[2-(1-Methylethoxy)phenyl]-3-(1-phenyl-1H-pyrazol-5-yl)pyridazin-4(1H)-one

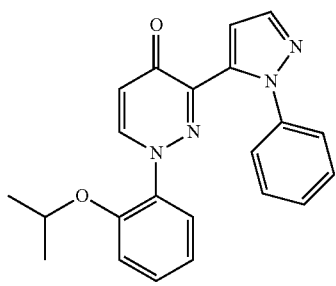 [SMILES: CC(C)Oc1ccccc1-n1ccc(=O)c(-c2ccnn2-c2ccccc2)n1]

3-{[2-(1-Methylethoxy)phenyl]hydrazono}pentane-2,4-dione (0.53 g, 2.02 mmol) was dissolved in 6 mL of N,N-dimethylformamide dimethyl acetal, and the mixture was stirred for 4 hours at 120° C., then concentrated under reduced pressure.

To a solution of the residue in 20 mL of methanol, phenylhydrazine (0.87 g, 8.08 mmol) was added, and the mixture was refluxed for 4 hours at 80° C., and concentrated. The residue was dissolved in dichloromethane (40 mL), washed with 1 M HCl aqueous solution and brine, dried over Na$_2$SO$_4$, and concentrated under reduced pressure. The residue was purified by prep-HPLC to give the title compound (7 mg, 1% yield) as a yellow solid: $^1$H NMR (400 MHz, CDCl$_3$): δ 1.26 (6H, d, J=6.0 Hz), 4.50-4.54 (1H, m), 6.37 (1H, dd, J=8.0, 1.6 Hz), 6.60 (1H, d, J=7.6 Hz), 6.79 (1H, td, J=7.6, 1.2 Hz), 6.96 (1H, dd, J=8.0, 1.2 Hz), 7.24-7.28 (2H, m), 7.36-7.42 (5H, m), 7.97 (1H, d, J=2.4 Hz), 8.04 (1H, d, J=8.0 Hz); LCMS (mobile phase: from 70% water and 30% CH3CN to 5% water and 95% CH3CN in 6 min, finally under these conditions for 0.5 min.) purity is >95%, Rt=3.151 min; MS Calcd.: 372; MS Found: 373 [M+H]$^+$.

Example 130

3-(1-Phenyl-1H-pyrazol-5-yl)-1-[2-(trifluoromethoxy)phenyl]pyridazin-4(1H)-one

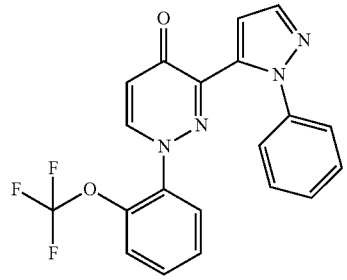 [SMILES: O=c1ccn(-c2ccccc2OC(F)(F)F)nc1-c1ccnn1-c1ccccc1]

3-{[2-(Trifluoromethoxy)phenyl]hydrazono}pentane-2,4-dione (0.43 g, 1.5 mmol) was dissolved in 20 mL of N,N-dimethylformamide dimethyl acetal, and the mixture was stirred for 4 hours at 120° C., and then concentrated under reduced pressure.

To a solution of the residue in 40 mL of methanol, phenylhydrazine (486 mg, 4.5 mmol) was added, and the mixture was refluxed for 4 hours at 80° C., and concentrated. The residue was dissolved in dichloromethane (40 mL), washed with 1 M HCl aqueous solution and brine, dried over Na$_2$SO$_4$, and concentrated under reduced pressure. The residue was purified by prep-HPLC to give the title compound (22 mg, 4% yield) as a yellow solid: $^1$H NMR (400 MHz, CDCl$_3$): δ ppm 6.67 (dt, J=8.0, 1.6 Hz, 2H), 7.23-7.31 (m, 2H), 7.36-7.46 (m, 7H), 7.81 (d, J=2.0 Hz, 1H), 7.95 (d, J=8.0 Hz, 1H); LCMS (mobile phase: from 70% water and 30% CH$_3$CN to 5% water and 95% CH$_3$CN in 6 min, finally under these conditions for 0.5 min.) purity is >95%, Rt=3.118 min; MS Calcd.: 398; MS Found: 399 [M+H]$^+$.

Example 131

1-(2-Phenoxyphenyl)-3-(1-phenyl-1H-pyrazol-5-yl)pyridazin-4(1H)-one

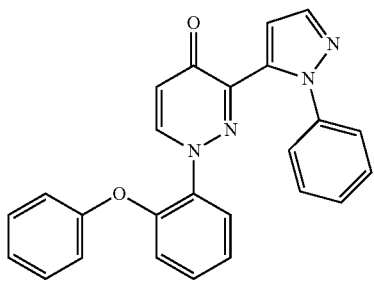 [SMILES: O=c1ccn(-c2ccccc2Oc2ccccc2)nc1-c1ccnn1-c1ccccc1]

3-[(2-Phenoxyphenyl)hydrazono]pentane-2,4-dione (1.00 g, 3.37 mmol) was dissolved in 10 mL of N,N-dimethylformamide dimethyl acetal, and the mixture was stirred for 4 hours at 120° C., then concentrated under reduced pressure.

To a solution of the residue in 30 mL of methanol, phenylhydrazine (1.46 g, 13.48 mmol) was added, and the mixture was refluxed for 4 hours at 80° C., and concentrated. The residue was dissolved in dichloromethane (30 mL), washed with 1 M HCl aqueous solution and brine, dried over $Na_2SO_4$, and concentrated under reduced pressure. The residue was purified by prep-HPLC to give the title compound (55 mg, 4% yield) as a yellow solid: $^1$H NMR (400 MHz, $CDCl_3$): δ 6.55 (2H, dd, J=8.0, 1.2 Hz), 6.86-6.89 (2H, m), 6.94-7.01 (2H, m), 7.11-7.15 (1H, m), 7.22 (1H, d, J=1.6 Hz), 7.25-7.41 (8H, m), 7.76 (1H, d, J=2.0 Hz), 8.12 (1H, d, J=7.6 Hz); LCMS (mobile phase: from 70% water and 30% CH3CN to 5% water and 95% CH3CN in 6 min, finally under these conditions for 0.5 min.) purity is >95%, Rt=3.410 min; MS Calcd.: 406; MS Found: 407 $[M+H]^+$.

Example 132

1-[2-(Methylsulfinyl)phenyl]-3-(1-phenyl-1H-pyrazol-5-yl)pyridazin-4(1H)-one

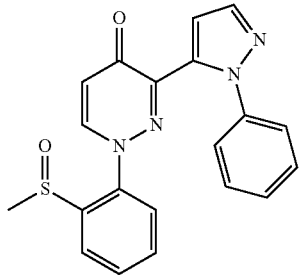 [SMILES: CS(=O)c1ccccc1-n1ccc(=O)c(-c2ccnn2-c2ccccc2)n1]

3-{[2-(Methylsulfinyl)phenyl]hydrazono}pentane-2,4-dione (0.66 g, 2.48 mmol) was dissolved in 8 mL of N,N-dimethylformamide dimethyl acetal, and the mixture was stirred for 4 hours at 120° C., then concentrated under reduced pressure.

To a solution of the residue in 15 mL of methanol, phenylhydrazine (1.07 g, 9.92 mmol) was added, and the mixture was refluxed for 4 hours at 80° C., and concentrated. The residue was dissolved in dichloromethane (40 mL), washed with 1 M HCl aqueous solution and brine, dried over $Na_2SO_4$, and concentrated under reduced pressure. The residue was purified by prep-HPLC to give the title compound (32 mg, 3% yield) as a red solid: $^1$H NMR (400 MHz, $CDCl_3$): δ 2.63 (3H, s), 6.64 (1H, d, J=7.6 Hz), 6.87 (1H, d, J=2.0 Hz), 7.22 (1H, dd, J=8.0, 1.2 Hz), 7.30-7.40 (5H, m), 7.60 (1H, td, J=8.0, 1.2 Hz), 7.70 (1H, t, J=8.0, 1.2 Hz), 7.80 (1H, d, J=1.6 Hz), 8.07 (1H, d, J=8.0 Hz), 8.20 (1H, dd, J=7.6, 1.6 Hz); LCMS (mobile phase: from 90% water and 10% CH3CN to 5% water and 95% CH3CN in 6 min, finally under these conditions for 0.5 min.) purity is 93%, Rt=2.720 min; MS Calcd.: 376; MS Found: 377 $[M+H]^+$.

Example 133

1-[2-(Methylsulfonyl)phenyl]-3-(1-phenyl-1H-pyrazol-5-yl)pyridazin-4(1H)-one

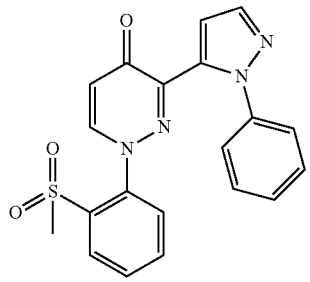 [SMILES: CS(=O)(=O)c1ccccc1-n1ccc(=O)c(-c2ccnn2-c2ccccc2)n1]

To a solution of 1-[2-(methylsulfinyl)phenyl]-3-(1-phenyl-1H-pyrazol-5-yl)pyridazin-4(1H)-one (60% purity, 300 mg, 0.80 mmol) in 20 mL of acetic acid was added 30% $H_2O_2$ aqueous solution (362 mg, 3.19 mmol), and the mixture was stirred at 40° C. for 18 h. The solvents were removed under reduced pressure, water was added, extracted with AcOEt, washed with water, $Na_2CO_3$ aqueous solution and brine, dried over $Na_2SO_4$, and then concentrated. The residue was purified by prep.-HPLC to give the title compound (20 mg, 6% yield) as a red solid: $^1$H NMR (400 MHz, $CDCl_3$): δ 2.89 (3H, s), 6.60 (1H, d, J=8.0 Hz), 6.96 (1H, d, J=2.0 Hz), 7.24-7.35 (4H, m), 7.41-7.43 (2H, m), 7.70-7.77 (3H, m), 7.92 (1H, d, J=8.0 Hz), 8.16-8.18 (1H, m); LCMS (mobile phase: from 90% water and 10% CH3CN to 5% water and 95% CH3CN in 6 min, finally under these conditions for 0.5 min.) purity is >90%, Rt=3.073 min; MS Calcd.: 392; MS Found: 393 $[M+H]^+$.

Example 134

3-(1-Phenyl-1H-pyrazol-5-yl)-1-[3-(trifluoromethoxy)phenyl]pyridazin-4(1H)-one

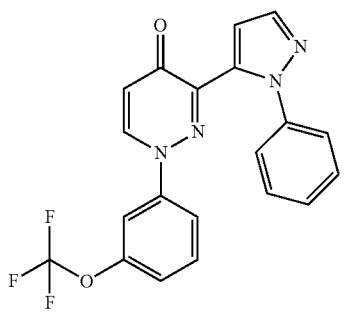 [SMILES: O=c1ccn(-c2cccc(OC(F)(F)F)c2)nc1-c1ccnn1-c1ccccc1]

3-{[3-(Trifluoromethoxy)phenyl]hydrazono}pentane-2,4-dione (0.43 g, 1.5 mmol) was dissolved in 20 mL of N,N-dimethylformamide dimethyl acetal, and the mixture was stirred for 4 hours at 120° C., and then concentrated under reduced pressure.

To a solution of the residue in 40 mL of methanol, phenylhydrazine (486 mg, 4.5 mmol,) was added, and the mixture was refluxed for 4 hours at 80° C., and concentrated. The residue was dissolved in dichloromethane (40 mL), washed with 1 M HCl aqueous solution and brine, dried over $Na_2SO_4$, and concentrated under reduced pressure. The residue was purified by prep-HPLC to give the title compound (105 mg, 18% yield) as a yellow solid: $^1$H NMR (400 MHz, $CDCl_3$): δ ppm 6.56 (t, J=2.0 Hz, 1H), 6.76 (d, J=8.0 Hz, 1H), 6.85-6.88 (m, 1H), 7.15-7.18 (m, 1H), 7.33-7.49 (m, 7H), 7.81 (d, J=2.0 Hz, 1H), 8.16 (d, J=8.0 Hz, 1H); LCMS (mobile phase: from 70% water and 30% $CH_3CN$ to 5% water and 95% $CH_3CN$ in 6 min, finally under these conditions for 0.5 min.) purity is >95%, Rt=3.450 min; MS Calcd.: 398; MS Found: 399 $[M+H]^+$.

Example 135

N-{4-[4-Oxo-3-(1-phenyl-1H-pyrazol-5-yl)pyridazin-1(4H)-yl]phenyl}acetamide

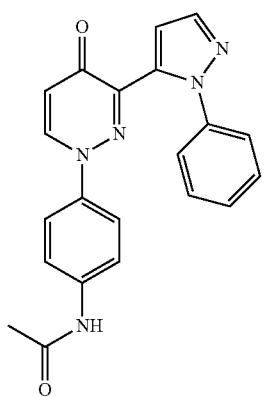 [SMILES: CC(=O)Nc1ccc(-n2ccc(=O)c(-c3ccnn3-c3ccccc3)n2)cc1]

N-{4-[2-(1-Acetyl-2-oxopropylidene)hydrazino]phenyl}acetamide (500 mg, 1.92 mmol) was dissolved in 10 mL of N,N-dimethylformamide dimethyl acetal, and the mixture was refluxed for 4 hours, then concentrated under reduced pressure.

To a solution of the residue in 20 mL of methanol, phenylhydrazine (829 mg, 7.68 mmol) was added, and the mixture was refluxed for 4 hours, and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (51 mg, 7.2% yield) as a yellow solid: $^1$H NMR (400 MHz, $CDCl_3$): δ 2.20 (3H, s), 6.70-6.77 (3H, m), 7.41-7.44 (8H, m), 7.80 (1H, d, J=2.0 Hz), 8.13 (1H, d, J=8.0 Hz); LCMS (mobile phase: from 90% water and 10% CH3CN to 5% water and 95% CH3CN in 6 min, finally under these conditions for 0.5 min.) purity is >95%, Rt=2.870 min; MS. Calcd.: 371, MS Found: 372 $[M+H]^+$.

Example 136

1-[4-(Dimethylamino)phenyl]-3-(1-phenyl-1H-pyrazol-5-yl)pyridazin-4(1H)-one

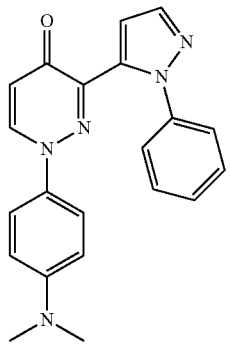 [SMILES: CN(C)c1ccc(-n2ccc(=O)c(-c3ccnn3-c3ccccc3)n2)cc1]

3-{[4-(Dimethylamino)phenyl]hydrazono}pentane-2,4-dione (500 mg, 2.02 mmol) was dissolved in 10 mL of N,N-dimethylformamide dimethyl acetal, and the mixture was refluxed for 4 hours, then concentrated under reduced pressure.

To a solution of the residue in 20 mL of methanol, phenylhydrazine (656 mg, 6.07 mmol) was added, and the mixture was refluxed for 4 hours, and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (17 mg, 2.4% yield) as a brown solid: $^1$H NMR (400 MHz, $CDCl_3$): δ 2.98 (6H, s), 6.53 (2H, d, J=9.2 Hz), 6.67-6.70 (3H, m), 7.36 (1H, d, J=1.6 Hz), 7.41-7.46 (5H, m), 7.79 (1H, d, J=2.0 Hz), 8.07 (1H, d, J=7.6 Hz); LCMS (mobile phase: from 90% water and 10% CH3CN to 5% water and 95% CH3CN in 6 min, finally under these conditions for 0.5 min.) purity is >90%, Rt=3.658 min; MS Calcd.: 357, MS Found: 358 $[M+H]^+$.

Example 137

1-[4-(4-Methylpiperazin-1-yl)phenyl]-3-(1-phenyl-1H-pyrazol-5-yl)pyridazin-4(1H)-one

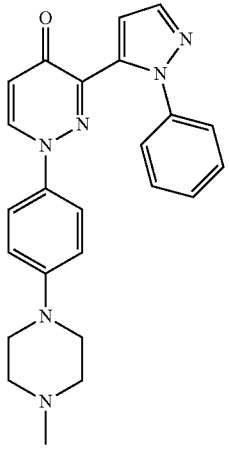 [SMILES: CN1CCN(c2ccc(-n3ccc(=O)c(-c4ccnn4-c4ccccc4)n3)cc2)CC1]

3-{[4-(4-Methylpiperazin-1-yl)phenyl]hydrazono}pentane-2,4-dione (610 mg, 2.02 mmol) was dissolved in 10 mL of N,N-dimethylformamide dimethyl acetal, and the mixture was refluxed for 4 hours, then concentrated under reduced pressure.

To a solution of the residue in 20 mL of methanol, phenylhydrazine (872 mg, 8.08 mmol) was added, and the mixture was refluxed for 4 hours, and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (11 mg, 1.3% yield) as a yellow solid: $^1$H NMR (400 MHz, $CDCl_3$): δ 2.47 (3H, s), 2.71-2.75 (4H, m), 3.28 (4H, t, J=4.8 Hz), 6.67-6.77 (5H, m), 7.37-7.44 (6H, m), 7.78 (1H, d, J=2.0 Hz), 8.07 (1H, d, J=7.6 Hz); LCMS (mobile phase: from 80% water and 20% $CH_3CN$ to 5% water and 95% $CH_3CN$ in 6 min, finally under these conditions for 0.5 min.) purity is >95%, Rt=2.522 min; MS Calcd.: 412, MS Found: 413 [M+H]$^+$.

Example 138

3-(1-Phenyl-1H-pyrazol-5-yl)-1-[4-(1H-1,2,4-triazol-1-yl)phenyl]pyridazin-4(1H)-one

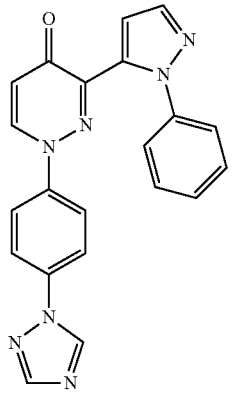 [SMILES: O=c1ccn(-c2ccc(-n3cncn3)cc2)nc1-c1ccnn1-c1ccccc1]

3-{[4-(1H-1,2,4-Triazol-1-yl)phenyl]hydrazono}pentane-2,4-dione (500 mg, 1.84 mmol) was dissolved in 10 mL of N,N-dimethylformamide dimethyl acetal, and the mixture was refluxed for 4 hours, then concentrated under reduced pressure.

To a solution of the residue in 20 mL of methanol, phenylhydrazine (795 mg, 736 mmol) was added, and the mixture was refluxed for 4 hours, and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (33 mg, 4.7% yield) as a yellow solid: $^1$H NMR (400 MHz, $CDCl_3$): δ 6.75 (1H, d, J=8.0 Hz), 6.93 (2H, dd, J=7.2, 2.0 Hz), 7.42-7.50 (6H, m), 7.62 (2H, dd, J=6.8, 2.0 Hz), 7.82 (1H, d, J=2.0 Hz), 8.14 (1H, s), 8.21 (1H, d, J=8.4 Hz), 8.57 (1H, s); LCMS (mobile phase: from 90% water and 10% CH3CN to 5% water and 95% CH3CN in 6 min, finally under these conditions for 0.5 min.) purity is >95%, Rt=2.992 min; MS Calcd.: 381, MS Found: 382 [M+H]$^+$.

Example 139

3-(1-Phenyl-1H-pyrazol-5-yl)-1-[4-(trifluoromethoxy)phenyl]pyridazin-4(1H)-one

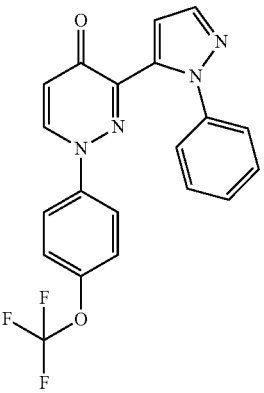 [SMILES: O=c1ccn(-c2ccc(OC(F)(F)F)cc2)nc1-c1ccnn1-c1ccccc1]

3-{[4-(Trifluoromethoxy)phenyl]hydrazono}pentane-2,4-dione (1.58 g, 6.124 mmol) was dissolved in 30 mL of N,N-dimethylformamide dimethyl acetal, and the mixture was stirred for 4 hours at 120° C., and then concentrated under reduced pressure.

To a solution of the residue in 40 mL of methanol, phenylhydrazine (2.0 g, 18.4 mmol,) was added, and the mixture was refluxed for 4 hours at 80° C., and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (15 mg, 0.5% yield) as a yellow solid: $^1$H NMR (400 MHz, $CDCl_3$): δ ppm 6.72 (d, J=8.0 Hz, 1H), 6.81 (dd, J=6.8, 2.4 Hz, 2H), 7.13 (d, J=8.0 Hz, 2H), 7.40-7.47 (m, 6H), 7.81 (d, J=1.6 Hz, 1H), 8.14 (d, J=7.6 Hz, 1H); LCMS (mobile phase: from 60% water and 40% $CH_3CN$ to 5% water and 95% $CH_3CN$ in 6 min, finally under these conditions for 0.5 min.) purity is >95%, Rt=2.860 min; MS Calcd.: 398; MS Found: 399 [M+H]$^+$

Example 140

1-[2-Fluoro-3-(trifluoromethyl)phenyl]-3-(1-phenyl-1H-pyrazol-5-yl)pyridazin-4(1H)-one

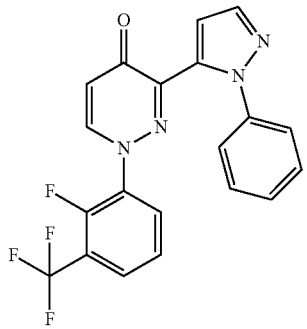 [SMILES: O=c1ccn(-c2cccc(C(F)(F)F)c2F)nc1-c1ccnn1-c1ccccc1]

3-{[2-Fluoro-3-(trifluoromethyl)phenyl]hydrazono}pentane-2,4-dione (900 mg, 3.1 mmol) was dissolved in 1 mL of N,N-dimethylformamide diisopropyl acetal and 2 mL of DMF and the mixture was stirred at 120° C. for 4 hours, and then concentrated under reduced pressure.

To a solution of the residue in 25 mL of t-BuOH, phenylhydrazine (1 g, 9.3 mmol,) was added, and the mixture was stirred for 4 hours at 60° C., and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (38 mg, 4% yield) as a yellow solid: $^1$H NMR (400 MHz, $CDCl_3$): δ ppm 6.62-6.66 (m, 1H), 6.70 (d, J=8.0 Hz, 1H), 7.15 (t, J=8.0 Hz, 1H), 7.40-7.49 (m, 6H), 7.60-7.63 (m, 1H), 7.82 (d, J=2.0 Hz, 1H), 8.06 (dd, J=8.0, 2.8 Hz, 1H); LCMS (mobile phase: from 70% water and 30% $CH_3CN$ to 5% water and 95% $CH_3CN$ in 6 min, finally under these conditions for 0.5 min.) purity is >95%, Rt=3.333 min; MS Calcd.: 400; MS Found: 401 $[M+H]^+$.

Example 141

1-(2,3-Difluorophenyl)-3-(1-phenyl-1H-pyrazol-5-yl)pyridazin-4(1H)-one

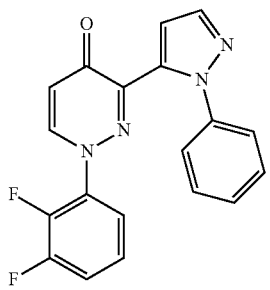 [SMILES: O=c1ccn(-c2cccc(F)c2F)nc1-c1ccnn1-c1ccccc1]

3-[(2,3-Difluorophenyl)hydrazono]pentane-2,4-dione (900 mg, 1.16 mmol) was dissolved in 3.5 mL of N,N-dimethylformamide diisopropyl acetal and 5.5 mL of DMF and the mixture was stirred at 120° C. for 4 hours, and then concentrated under reduced pressure.

To a solution of the residue in 20 mL of t-BuOH, phenylhydrazine (376 mg, 3.48 mmol,) was added, and the mixture was stirred for 4 hours at 60° C., and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (22 mg, 5% yield) as a yellow solid: $^1$H NMR (400 MHz, $CDCl_3$): δ ppm 6.23 (td, J=6.8, 2.0 Hz, 1H), 6.66 (d, J=7.6 Hz, 1H), 6.92-6.98 (m, 1H), 7.12-7.19 (m, 1H), 7.36-7.45 (m, 6H), 7.79 (d, J=2.0 Hz, 1H), 8.01 (dd, J=7.6, 2.4 Hz, 1H); LCMS (mobile phase: from 70% water and 30% $CH_3CN$ to 5% water and 95% $CH_3CN$ in 6 min, finally under these conditions for 0.5 min.) purity is >95%, Rt=2.824 min; MS Calcd.: 350; MS Found: 351 $[M+H]^+$.

Example 142

1-(2,2-Difluoro-1,3-benzodioxol-4-yl)-3-(1-phenyl-1H-pyrazol-5-yl)pyridazin-4(1H)-one

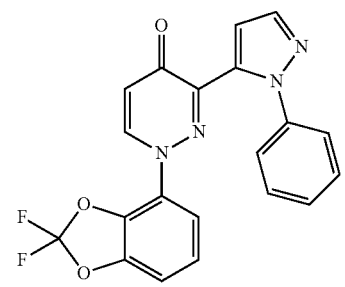 [SMILES: O=c1ccn(-c2cccc3c2OC(F)(F)O3)nc1-c1ccnn1-c1ccccc1]

A mixture of 3-[(2,2-difluoro-1,3-benzodioxol-4-yl)hydrazono]pentane-2,4-dione (3.0 g, 10 mmol) in N,N-dimethylformamide dimethyl acetal (30 mL) was refluxed for 5 h. The mixture was concentrated under reduced pressure.

A solution of the residue and phenylhydrazine (2.0 mL, 21 mmol) in AcOH (30 mL) was refluxed for 4 h. After stirring at room temperature overnight, the mixture was concentrated under reduced pressure. The residue was diluted with AcOEt, and washed with saturated $NaHCO_3$ aqueous solution and brine. The organic layer was dried over $MgSO_4$, filtered and concentrated under reduced pressure. The residue was chromatographed on silica gel (5/95-40/60 AcOEt/hexane) to give the title compound (2.1 g, 51% yield) as white crystals: mp 105-107° C.; $^1$H NMR (300 MHz, $CDCl_3$): δ ppm 6.16 (1H, dd, J=8.3, 1.1 Hz), 6.71 (1H, d, J=7.9 Hz), 6.90 (1H, d, J=8.3 Hz), 6.98 (1H, dd, J=7.9, 1.3 Hz), 7.35-7.49 (6H, m), 7.80 (1H, d, J=1.9 Hz), 8.30 (1H, d, J=7.9 Hz). LC-MS (ESI) m/z 395 $[M+H]^+$. Anal. Calcd. for $C_{20}H_{12}F_2N_4O_3$: C, 60.92; H, 3.07; N, 14.21. Found: C, 60.91; H, 3.13; N, 14.30.

Example 143

1-[2-Fluoro-4-(trifluoromethyl)phenyl]-3-(1-phenyl-1H-pyrazol-5-yl)pyridazin-4(1H)-one

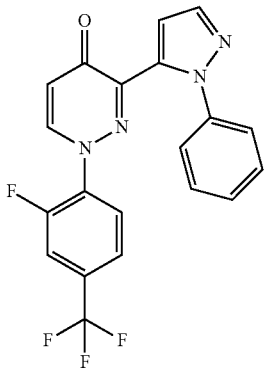 [SMILES: O=c1ccn(-c2ccc(C(F)(F)F)cc2F)nc1-c1ccnn1-c1ccccc1]

3-{[2-Fluoro-4-(trifluoromethyl)phenyl]hydrazono}pentane-2,4-dione (720 mg, 2.48 mmol) was dissolved in 1 mL of N,N-dimethylformamide diisopropyl acetal and 2 mL of DMF and the mixture was stirred at 120° C. for 4 hours, and then concentrated under reduced pressure.

To a solution of the residue in 20 mL of t-BuOH, phenylhydrazine (803 mg, 7.44 mmol,) was added, and the mixture was stirred for 4 hours at 60° C., and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (16 mg, 2% yield) as a yellow solid: $^1$H NMR (400 MHz, CDCl$_3$): δ ppm 6.43 (t, J=8.4 Hz, 1H), 6.68 (d, J=8.0 Hz, 1H), 7.23-7.25 (m, 1H), 7.38-7.49 (m, 7H), 7.80 (d, J=2.0 Hz, 1H), 8.10 (dd, J=8.0, 2.4 Hz, 1H); LCMS (mobile phase: from 70% water and 30% CH$_3$CN to 5% water and 95% CH$_3$CN in 6 min, finally under these conditions for 0.5 min.) purity is >95%, Rt=3.421 min; MS Calcd.: 400; MS Found: 401 [M+H]$^+$.

Example 144

1-[4-(Difluoromethoxy)-2-fluorophenyl]-3-(1-phenyl-1H-pyrazol-5-yl)pyridazin-4(1H)-one

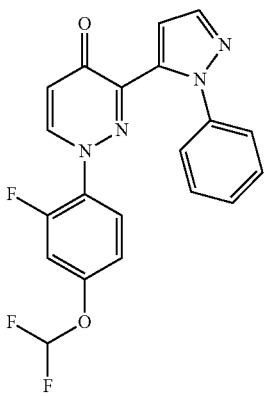 [SMILES: O=c1ccn(-c2ccc(OC(F)F)cc2F)nc1-c1ccnn1-c1ccccc1]

3-{[4-(Difluoromethoxy)-2-fluorophenyl]hydrazono}pentane-2,4-dione (300 mg, 1.04 mmol) was dissolved in 1 mL of N,N-dimethylformamide diisopropyl acetal and 2 mL of DMF and the mixture was stirred at 120° C. for 4 hours, and then concentrated under reduced pressure.

To a solution of the residue in 20 mL of t-BuOH, phenylhydrazine (337 mg, 3.12 mmol,) was added, and the mixture was stirred for 4 hours at 60° C., and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (35 mg, 9% yield) as a yellow solid: $^1$H NMR (400 MHz, CDCl$_3$): δ ppm 6.34-6.70 (m, 4H), 6.78 (d, J=9.2 Hz, 1H), 6.99 (dd, J=12.0, 2.4 Hz, 1H), 7.36-7.46 (m, 5H), 7.79 (d, J=2.0 Hz, 1H), 7.97 (dd, J=8.0, 2.4 Hz, 1H); LCMS (mobile phase: from 70% water and 30% CH$_3$CN to 5% water and 95% CH$_3$CN in 6 min, finally under these conditions for 0.5 min.) purity is >95%, Rt=3.065 min; MS Calcd.: 398; MS Found: 399 [M+H]$^+$.

Example 145

1-[2-Fluoro-4-(trifluoromethoxy)phenyl]-3-(1-phenyl-1H-pyrazol-5-yl)pyridazin-4(1H)-one

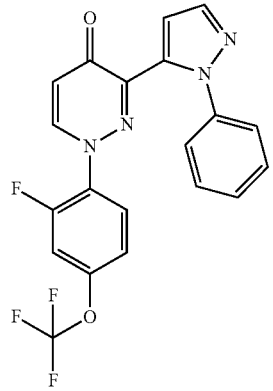 [SMILES: O=c1ccn(-c2ccc(OC(F)(F)F)cc2F)nc1-c1ccnn1-c1ccccc1]

3-{[2-Fluoro-4-(trifluoromethoxy)phenyl]hydrazono}pentane-2,4-dione (200 mg, 0.65 mmol) was dissolved in 1 mL of N,N-dimethylformamide diisopropyl acetal and 2 mL of DMF and the mixture was stirred at 120° C. for 4 hours, and then concentrated under reduced pressure.

To a solution of the residue in 20 mL of t-BuOH, phenylhydrazine (211 mg, 1.96 mmol,) was added, and the mixture was stirred for 4 hours at 60° C., and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (35 mg, 13% yield) as a yellow solid: $^1$H NMR (400 MHz, CDCl$_3$): δ ppm 6.44 (t, J=8.8 Hz, 1H), 6.69 (d, J=7.6 Hz, 1H), 6.90 (d, J=8.8 Hz, 1H), 7.11 (d, J=11.2 Hz, 1H), 7.41-7.49 (m, 6H), 7.82 (d, J=1.6 Hz, 1H), 8.02 (dd, J=8.0, 2.4 Hz, 1H); LCMS (mobile phase: from 70% water and 30% CH$_3$CN to 5% water and 95% CH$_3$CN in 6 min, finally under these conditions for 0.5 min.) purity is >95%, Rt=3.432 min; MS Calcd.: 416; MS Found: 417 [M+H]$^+$.

Example 146

1-(2,4-Difluorophenyl)-3-(1-phenyl-1H-pyrazol-5-yl)pyridazin-4(1H)-one

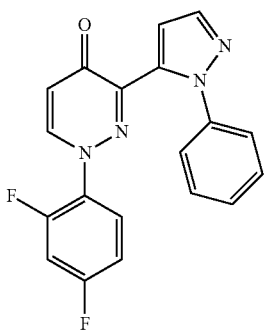 [SMILES: O=c1ccn(-c2ccc(F)cc2F)nc1-c1ccnn1-c1ccccc1]

3-[(2,4-Difluorophenyl)hydrazono]pentane-2,4-dione (550 mg, 2.29 mmol) was dissolved in 1.5 mL of N,N-dimethylformamide diisopropyl acetal and 3 mL of DMF and the mixture was stirred at 120° C. for 4 hours, and then concentrated under reduced pressure.

To a solution of the residue in 20 mL of t-BuOH, phenylhydrazine (742 mg, 6.87 mmol,) was added, and the mixture was stirred for 4 hours at 60° C., and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (42 mg, 5% yield) as a yellow solid: $^1$H NMR (400 MHz, $CDCl_3$): δ ppm 6.36-6.41 (m, 1H), 6.66 (d, J=8.0 Hz, 1H), 6.72-6.77 (m, 1H), 6.90-6.96 (m, 1H), 7.36-7.47 (m, 6H), 7.79 (d, J=2.0 Hz, 1H), 7.96 (dd, J=8.0, 2.4 Hz, 1H); LCMS [mobile phase: from 70% water (0.1% TFA) and 30% $CH_3CN$ to 5% water (0.1% TFA) and 95% $CH_3CN$ in 6 min, finally under these conditions for 0.5 min.] purity is >95%, Rt=2.829 min; MS Calcd.: 350; MS Found: 351 [M+H]$^+$.

Example 147

1-(4-Chloro-2-fluorophenyl)-3-(1-phenyl-1H-pyrazol-5-yl)pyridazin-4(1H)-one

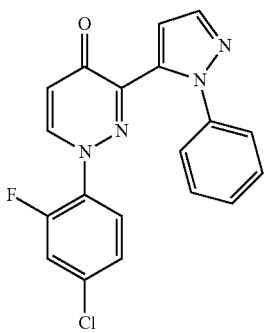 [SMILES: O=c1ccn(-c2ccc(Cl)cc2F)nc1-c1ccnn1-c1ccccc1]

3-[(4-Chloro-2-fluorophenyl)hydrazono]pentane-2,4-dione (1 g, 3.9 mmol) was dissolved in 1.76 mL of N,N-dimethylformamide diisopropyl acetal and 3 mL of DMF and the mixture was stirred at 120° C. for 4 hours, and then concentrated under reduced pressure.

To a solution of the residue in 20 mL of t-BuOH, phenylhydrazine (1.26 g, 11.7 mmol) was added, and the mixture was stirred for 4 hours at 60° C., and concentrated. The residue was dissolved in dichloromethane (20 mL), washed with 1 M HCl aqueous solution and brine, dried over $Na_2SO_4$, and concentrated under reduced pressure. The residue was purified by prep-HPLC to give the title compound (59 mg, 4% yield) as a yellow solid: $^1$H NMR (400 MHz, $CDCl_3$): δ ppm 6.27 (t, J=8.8 Hz, 1H), 6.66 (d, J=8.0 Hz, 1H), 6.96-6.99 (m, 1H), 7.20 (dd, J=10.8, 2.4 Hz, 1H), 7.37-7.48 (m, 6H), 7.79 (d, J=2.0 Hz, 1H), 7.99 (dd, J=8.0, 2.4 Hz, 1H); LCMS (mobile phase: from 50% water and 50% $CH_3CN$ to 5% water and 95% $CH_3CN$ in 6 min, finally under these conditions for 0.5 min.) purity is 93%, Rt=1.622 min; MS Calcd.: 366; MS Found: 367 [M+H]$^+$.

Example 148

1-[2-(Dimethylamino)-5-(trifluoromethyl)phenyl]-3-(1-phenyl-1H-pyrazol-5-yl)pyridazin-4(1H)-one

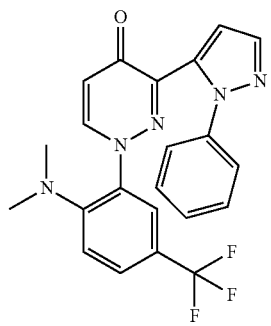 [SMILES: CN(C)c1ccc(C(F)(F)F)cc1-n1ccc(=O)c(-c2ccnn2-c2ccccc2)n1]

Example 149

1-[2-Fluoro-5-(trifluoromethyl)phenyl]-3-(1-phenyl-1H-pyrazol-5-yl)pyridazin-4(1H)-one

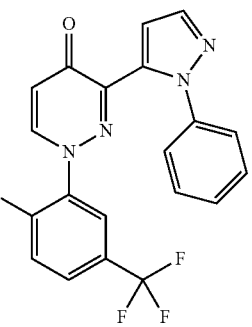

3-{[2-Fluoro-5-(trifluoromethyl)phenyl]hydrazono}pentane-2,4-dione (630 mg, 2.2 mmol) was dissolved in 4.6 mL of DMF and N,N-dimethylformamide diisopropyl acetal (1.0 mL, 1.1 equiv.), and the mixture was stirred for 4 hours at 120° C., and then concentrated under reduced pressure.

To a solution of the residue in 20 mL of toluene, phenylhydrazine (713 mg, 6.6 mmol,) was added, and the mixture was stirred for 4 hours at 60° C., and concentrated. The residue was dissolved in dichloromethane (40 mL), washed with 1 M HCl aqueous solution and brine, dried over Na$_2$SO$_4$, and concentrated under reduced pressure. The residue was purified by prep-HPLC to give 1-[2-fluoro-5-(trifluoromethyl)phenyl]-3-(1-phenyl-1H-pyrazol-5-yl)pyridazin-4 (1H)-one (43 mg, 5% yield) and 1-[2-(dimethylamino)-5-(trifluoromethyl)phenyl]-3-(1-phenyl-1H-pyrazol-5-yl)pyridazin-4(1H)-one (20 mg, 2% yield).

1-[2-Fluoro-5-(trifluoromethyl)phenyl]-3-(1-phenyl-1H-pyrazol-5-yl)pyridazin-4(1H)-one: a yellow solid; $^1$H NMR (400 MHz, CDCl$_3$): δ ppm 6.70 (d, J=8.0 Hz, 1H), 6.89-6.90 (m, 1H), 7.30-7.44 (m, 7H), 7.60-7.63 (m, 1H), 7.81 (d, J=2.4 Hz, 1H), 8.00 (dd, J=8.0, 2.8 Hz, 1H); LCMS (mobile phase: from 70% water and 30% CH$_3$CN to 5% water and 95% CH$_3$CN in 6 min, finally under these conditions for 0.5 min.) purity is >95%, Rt=3.205 min; MS Calcd.: 400; MS Found: 401 [M+H]$^+$.

1-[2-(Dimethylamino)-5-(trifluoromethyl)phenyl]-3-(1-phenyl-1H-pyrazol-5-yl)pyridazin-4(1H)-one: a white solid; $^1$H NMR (400 MHz, CDCl$_3$): δ ppm 2.57 (s, 6H), 6.66 (d, J=8.0 Hz, 1H), 6.74 (d, J=2.0 Hz, 1H), 7.04 (d, J=8.8 Hz, 1H), 7.28 (d, J=2.4 Hz, 1H), 7.34-7.37 (m, 5H), 7.49 (dd, J=8.8, 2.0 Hz, 1H), 7.79 (d, J=2.0 Hz, 1H), 7.98 (d, J=8.0 Hz, 1H); LCMS (mobile phase: from 70% water and 30% CH$_3$CN to 5% water and 95% CH$_3$CN in 6 min, finally under these conditions for 0.5 min.) purity is >95%, Rt=3.479 min; MS Calcd.: 425; MS Found: 426 [M+H]$^+$.

Example 150

1-(2,5-Difluorophenyl)-3-(1-phenyl-1H-pyrazol-5-yl)pyridazin-4(1H)-one

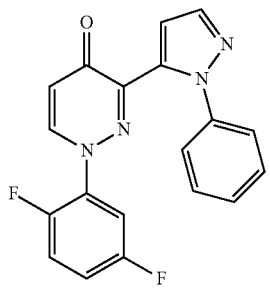 [SMILES: O=c1ccn(-c2cc(F)ccc2F)nc1-c1ccnn1-c1ccccc1]

3-[(2,5-Difluorophenyl)hydrazono]pentane-2,4-dione (1.455 g, 6.06 mmol) was dissolved in 20 mL of DMF and then 4.3 mL of N,N-dimethylformamide diisopropyl acetal was added, and the mixture was stirred for 4 hours at 120° C., and then concentrated under reduced pressure.

To a solution of the residue in 35 mL of t-BuOH, phenylhydrazine (1.96 g, 18.18 mmol,) was added, and the mixture was refluxed for 4 hours at 80° C., and concentrated. The residue was dissolved in dichloromethane (40 mL), washed with 1 M HCl aqueous solution and brine, dried over Na$_2$SO$_4$, and concentrated under reduced pressure. The residue was purified by prep-HPLC to give the title compound (66 mg, 3% yield) as a yellow solid: $^1$H NMR (400 MHz, CDCl$_3$): δ ppm 6.02-6.06 (m, 1H), 6.66 (d, J=7.6 Hz, 1H), 6.97-7.02 (m, 1H), 7.11-7.17 (m, 1H), 7.32-7.52 (m, 6H), 7.79 (d, J=2.0 Hz, 1H), 8.05 (dd, J=7.6, 2.4 Hz, 1H); LCMS [mobile phase: from 80% water (0.1% TFA) and 20% CH$_3$CN to 5% water (0.1% TFA) and 95% CH$_3$CN in 6 min, finally under these conditions for 0.5 min.] purity is >95%, Rt=3.347 min; MS Calcd.: 350; MS Found: 351 [M+H]$^+$.

Example 151

1-(2,6-Difluorophenyl)-3-(1-phenyl-1H-pyrazol-5-yl)pyridazin-4(1H)-one

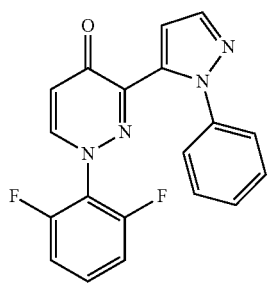 [SMILES: O=c1ccn(-c2c(F)cccc2F)nc1-c1ccnn1-c1ccccc1]

3-[(2,6-Difluorophenyl)hydrazono]pentane-2,4-dione (400 mg, 1.67 mmol) was dissolved in 1 mL of N,N-dimethylformamide di-tert-butyl acetal and 2 mL of DMF and the mixture was stirred at 120° C. for 4 hours, and then concentrated under reduced pressure.

To a solution of the residue in 20 mL of toluene, phenylhydrazine (541 mg, 5 mmol,) was added, and the mixture was stirred for 4 hours at 60° C., and concentrated. The residue was dissolved in dichloromethane (20 mL), washed with 1 M HCl aqueous solution and brine, dried over Na$_2$SO$_4$, and concentrated under reduced pressure. The residue was purified by prep-HPLC to give the title compound (30 mg, 5% yield) as a yellow solid: $^1$H NMR (400 MHz, CDCl$_3$): δ ppm 6.59 (d, J=8.0 Hz, 1H), 6.98-7.03 (m, 2H), 7.12 (d, J=2.0 Hz, 1H), 7.21-7.42 (m, 6H), 7.73-7.75 (m, 2H); LCMS (mobile phase: from 70% water and 30% CH$_3$CN to 5% water and 95% CH$_3$CN in 6 min, finally under these conditions for 0.5 min.) purity is >94%, Rt=2.497 min; MS Calcd.: 350; MS Found: 351 [M+H]$^+$.

Example 152

3-[1-(Cyclopropylmethyl)-1H-pyrazol-5-yl]-1-[3-(trifluoromethyl)phenyl]pyridazin-4(1H)-one

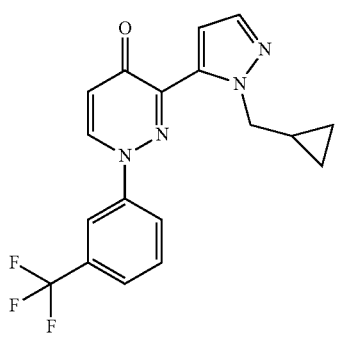 [SMILES: O=c1ccn(-c2cccc(C(F)(F)F)c2)nc1-c1ccnn1CC1CC1]

A solution of 3-[3-(dimethylamino)prop-2-enoyl]-1-[3-(trifluoromethyl)phenyl]pyridazin-4(1H)-one (675 mg, 2 mmol), cyclopropylmethylhydrazine hydrochloride (490 mg, 4 mmol), and Et₃N (0.558 mL, 4 mmol) in MeOH (20 mL) was refluxed for 2 h. After cooling to room temperature, the reaction mixture was poured into 1 M HCl aqueous solution and extracted with AcOEt. The extract was washed with brine, dried over MgSO₄, and concentrated under reduced pressure. The residue was purified by basic silica gel column chromatography eluting with AcOEt and recrystallized from hexane/AcOEt to give the title compound (315 mg, 44% yield) as a pale yellow solid: mp 155-157° C.; ¹H NMR (300 MHz, CDCl₃): δ ppm 0.35-0.44 (2H, m), 0.45-0.57 (2H, m), 1.24-1.40 (1H, m), 4.37 (2H, d, J=6.8 Hz), 6.76 (1H, d, J=7.9 Hz), 7.37 (1H, d, J=1.9 Hz), 7.61 (1H, d, J=1.9 Hz), 7.68-7.74 (2H, m), 7.78-7.83 (1H, m), 7.94 (1H, s), 8.28 (1H, d, J=7.9 Hz). Anal. Calcd for C₁₈H₁₅F₃N₄O: C, 60.00; H, 4.20; N, 15.55. Found: C, 60.07; H, 4.24; N, 15.56.

Example 153

3-(1-Benzyl-1H-pyrazol-5-yl)-1-[3-(trifluoromethyl)phenyl]pyridazin-4(1H)-one

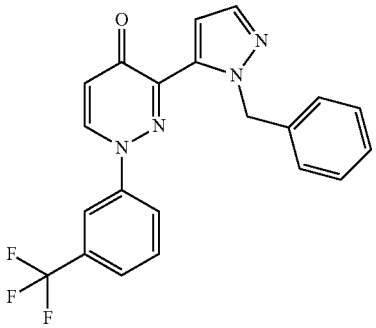 [SMILES: O=c1ccn(-c2cccc(C(F)(F)F)c2)nc1-c1ccnn1Cc1ccccc1]

A solution of 3-[3-(dimethylamino)prop-2-enoyl]-1-[3-(trifluoromethyl)phenyl]pyridazin-4(1H)-one (0.675 g, 2.0 mmol), benzylhydrazine dihydrochloride (1.56 g, 8.0 mmol), and Et₃N (2.23 mL, 16 mmol) in MeOH (20 mL) was refluxed for 3 h. After cooling to room temperature, the reaction mixture was poured into 1 M HCl aqueous solution and extracted with AcOEt. The extract was washed with brine, dried over MgSO₄, and concentrated under reduced pressure. The residue was recrystallized from hexane/AcOEt to give the title compound (375 mg, 47% yield) as a white solid: mp 156-157° C.; ¹H NMR (300 MHz, CDCl₃): δ ppm 5.75 (2H, s), 6.70 (1H, d, J=7.9 Hz), 6.84-6.91 (2H, m), 7.18-7.24 (3H, m), 7.32-7.37 (1H, m), 7.47-7.53 (2H, m), 7.64-7.67 (2H, m), 7.70 (1H, d, J=1.9 Hz), 8.15 (1H, d, J=7.9 Hz). Anal. Calcd for C₂₁H₁₅F₃N₄O: C, 63.63; H, 3.81; N, 14.14. Found: C, 63.63; H, 3.85; N, 14.16.

Example 154

3-[1-(4-Methoxybenzyl)-1H-pyrazol-5-yl]-1-[3-(trifluoromethyl)phenyl]pyridazin-4(1H)-one

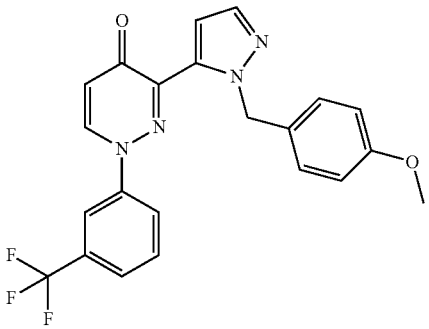 [SMILES: COc1ccc(Cn2nccc2-c2nn(-c3cccc(C(F)(F)F)c3)ccc2=O)cc1]

A solution of 3-[3-(dimethylamino)prop-2-enoyl]-1-[3-(trifluoromethyl)phenyl]pyridazin-4(1H)-one (675 mg, 2 mmol), (4-methoxybenzyl)hydrazine hydrochloride (755 mg, 4 mmol), and Et₃N (0.558 mL, 4 mmol) in MeOH (20 mL) was refluxed for 3 h. After cooling to room temperature, the reaction mixture was poured into 1 M HCl aqueous solution and extracted with AcOEt. The extract was washed with brine, dried over MgSO₄, and concentrated under reduced pressure. The residue was purified by basic silica gel column chromatography eluting with AcOEt and recrystallized from hexane/AcOEt to give the title compound (367 mg, 43% yield) as an off-white solid: mp 159-161° C.; ¹H NMR (300 MHz, CDCl₃): δ ppm 3.73 (3H, s), 5.67 (2H, s), 6.69-6.75 (3H, m), 6.81-6.86 (2H, m), 7.41 (1H, d, J=1.9 Hz), 7.45-7.51 (1H, m), 7.54-7.59 (1H, m), 7.65-7.71 (3H, m), 8.17 (1H, d, J=7.9 Hz). LC-MS (ESI) m/z 427 [M+H]⁺. Anal. Calcd for C₂₂H₁₇F₃N₄O₂: C, 61.97; H, 4.02; N, 13.14. Found: C, 61.95; H, 4.14; N, 13.08.

Example 155

3-(1-Thiophen-2-yl-1H-pyrazol-5-yl)-1-[3-(trifluoromethyl)phenyl]pyridazin-4(1H)-one

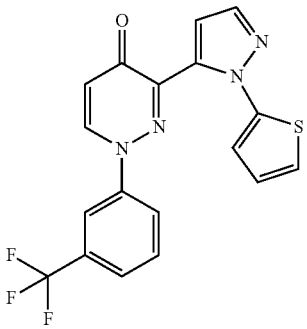 [SMILES: O=c1ccn(-c2cccc(C(F)(F)F)c2)nc1-c1ccnn1-c1cccs1]

To a mixture of copper (I) oxide (0.028 g, 0.20 mmol), salicylaldoxime (0.11 g, 0.78 mmol), Cs₂CO₃ (0.64 g, 2.0 mmol) and 3-(1H-pyrazol-5-yl)-1-[3-(trifluoromethyl)phenyl]pyridazin-4(1H)-one (0.30 g, 0.98 mmol) in MeCN (8 mL) was added 2-iodothiophene (0.16 mL, 1.5 mmol), and the mixture was stirred at 90° C. for 1 day. The mixture was diluted with AcOEt and water, and filtered. The filtrate was partitioned between AcOEt and water. The organic layer was washed with brine, dried over MgSO$_4$, filtered and concentrated under reduced pressure. The residue was chromatographed on silica gel (20/80-100/0 AcOEt/hexane) to give yellow crystals. The crystals were purified by preparative HPLC and recrystallized from AcOEt/hexane to give the title compound (11 mg, 3% yield) as off-white crystals: $^1$H NMR (300 MHz, CDCl$_3$): δ ppm 6.75 (1H, d, J=7.9 Hz), 6.95 (1H, dd, J=5.5, 3.8 Hz), 7.01 (1H, dd, J=3.8, 1.3 Hz), 7.23 (1H, dd, J=5.5, 1.3 Hz), 7.31 (1H, d, J=8.7 Hz), 7.40 (1H, brs), 7.42 (1H, d, J=1.9 Hz), 7.51-7.57 (1H, m), 7.62 (1H, d, J=7.9 Hz), 7.81 (1H, d, J=1.9 Hz), 8.21 (1H, d, J=7.9 Hz). LC-MS (ESI) m/z 389 [M+H]$^+$.

Preparative HPLC was performed at the conditions described below.

Column: Waters SunFire Column C18 (30×50 mm. S-5 μm)

Column temp: 25° C.

Mobile phase: (A) 0.1% TFA in distilled water, (B) 0.1% TFA in acetonitrile

Gradient: 0 min (A/B=90/10)→1 min (A/B=90/10)→4.75 min (A/B=0/100)→7.40 min (A/B=0/100)→7.41 min (A/B=90/10)→8.50 min (A/B=90/10)

Flow rate: 70 mL/min

Detector: UV 220 nm

Example 156

3-(1-Thiophen-3-yl-1H-pyrazol-5-yl)-1-[3-(trifluoromethyl)phenyl]pyridazin-4(1H)-one

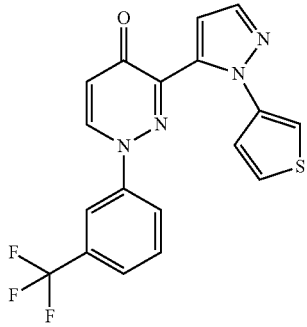 [SMILES: O=c1ccn(-c2cccc(C(F)(F)F)c2)nc1-c1ccnn1-c1ccsc1]

To a mixture of copper (I) oxide (0.028 g, 0.20 mmol), salicylaldoxime (0.11 g, 0.78 mmol), Cs$_2$CO$_3$ (0.64 g, 2.0 mmol) and 3-(1H-pyrazol-5-yl)-1-[3-(trifluoromethyl)phenyl]pyridazin-4(1H)-one (0.30 g, 0.98 mmol) in MeCN (8 mL) was added 3-iodothiophene (0.15 mL, 1.5 mmol), and the mixture was stirred at 90° C. for 2 days and at room temperature for 4 days. The mixture was diluted with AcOEt and water, and filtered. The filtrate was partitioned between AcOEt and water. The organic layer was washed with brine, dried over MgSO$_4$, filtered and concentrated under reduced pressure. The residue was chromatographed on silica gel (20/80-100/0 AcOEt/hexane) to give yellow crystals. The crystals were purified by preparative HPLC and recrystallized from AcOEt/hexane to give the title compound (7 mg, 2% yield) as off-white crystals: $^1$H NMR (300 MHz, CDCl$_3$): δ ppm 6.75 (1H, d, J=7.9 Hz), 7.12 (1H, dd, J=4.5, 1.9 Hz), 7.24 (1H, s), 7.30-7.34 (2H, m), 7.36 (1H, d, J=1.9 Hz), 7.41 (1H, s), 7.50-7.57 (1H, m), 7.59-7.64 (1H, m), 7.78 (1H, d, J=1.9 Hz), 8.23 (1H, d, J=7.9 Hz). LC-MS (ESI) m/z 389 [M+H]$^+$.

Preparative HPLC was performed at the conditions described below.

Column: Waters SunFire Column C18 (30×50 mm S-5 μm)

Column temp: 25° C.

Mobile phase: (A) 0.1% TFA in distilled water, (B) 0.1% TFA in acetonitrile

Gradient: 0 min (A/B=90/10)→1 min (A/B=90/10)→4.75 min (A/B=0/100)→7.40 min (A/B=0/100)→7.41 min (A/B=90/10)→8.50 min (A/B=90/10)

Flow rate: 70 mL/min

Detector: UV 220 nm

Example 157

3-[1-(2-methylpropyl)-1H-pyrazol-5-yl]-1-(4-morpholin-4-ylphenyl)pyridazin-4(1H)-one

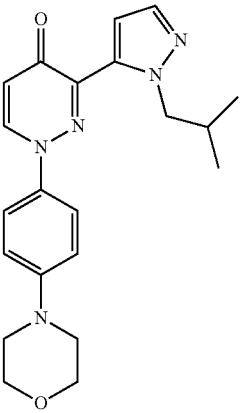 [SMILES: CC(C)Cn1nccc1-c1nn(-c2ccc(N3CCOCC3)cc2)ccc1=O]

To a solution of 3-[3-(dimethylamino)prop-2-enoyl]-1-(4-morpholin-4-ylphenyl)pyridazin-4(1H)-one (300 mg, 0.85 mmol) in 20 mL of methanol, 2-methylpropylhydrazine (300 mg, 3.39 mmol) was added, the resulting mixture was refluxed for 4 hours, then concentrated. The residue was dissolved in dichloromethane (20 mL), washed with 1 M acetic acid aqueous solution and brine, dried over anhydrous Na$_2$SO$_4$, and concentrated under reduced pressure. The residue was purified by prep-HPLC to give the title compound (48 mg, 15% yield) as a yellow solid: $^1$H NMR (400 MHz, CDCl$_3$): δ 0.83 (6H, d, J=6.8 Hz), 2.17-2.25 (1H, m), 3.25-3.27 (4H, m), 3.89-3.92 (4H, m), 4.34 (2H, d, J=7.6 Hz), 6.72 (1H, d, J=8.0 Hz), 7.00-7.04 (2H, m), 7.33 (1H, d, J=2.4 Hz), 7.45-7.49 (2H, m), 7.59 (1H, d, J=2.0 Hz), 8.15 (1H, d, J=7.6 Hz); LCMS (mobile phase: from 90% water and 10% CH3CN to 5% water and 95% CH3CN in 6 min, finally under these conditions for 0.5 min.) purity is >95%, Rt=3.396 min; MS Calcd.: 379, MS Found: 380 [M+H]$^+$.

Example 158

3-[1-(2-Hydroxyethyl)-1H-pyrazol-5-yl]-1-(4-morpholin-4-ylphenyl)pyridazin-4(1H)-one

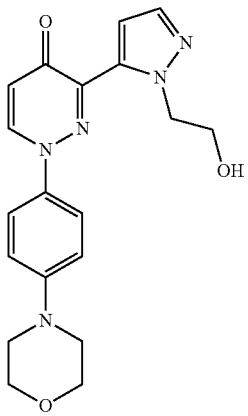 [SMILES: O=c1ccn(-c2ccc(N3CCOCC3)cc2)nc1-c1ccnn1CCO]

To a solution of 3-[3-(dimethylamino)prop-2-enoyl]-1-(4-morpholin-4-ylphenyl)pyridazin-4(1H)-one (476 mg, 1.34 mmol) in 20 mL of methanol, 2-hydroxyethylhydrazine (414 mg, 5.36 mmol) was added, the resulting mixture was refluxed for 4 hours, and then concentrated. The residue was dissolved in dichloromethane (20 mL), washed with 1 M acetic acid aqueous solution and brine, dried over anhydrous $Na_2SO_4$, and concentrated under reduced pressure. The residue was purified by prep-HPLC to give the title compound (36 mg, 7.3% yield) as a yellow solid: $^1$H NMR (400 MHz, $CDCl_3$): δ 120-3.22 (4H, m), 3.87-3.89 (4H, m), 4.03-4.05 (2H, m), 4.33-4.36 (2H, m), 6.69 (1H, d, J=7.6 Hz), 6.98 (2H, dd, J=6.8, 2.0 Hz), 7.34 (1H, d, J=2.4 Hz), 7.51-7.53 (3H, m), 8.14 (1H, d, J=7.6 Hz); LCMS (mobile phase: from 95% water and 5% CH3CN to 5% water and 95% CH3CN in 6 min, finally under these conditions for 0.5 min.) purity is >95%, Rt=2.770 min; MS Calcd.: 367, MS Found: 368 [M+H]$^+$.

Example 159

3-[1-(2,2-Dimethylpropyl)-1H-pyrazol-5-yl]-1-(4-morpholin-4-ylphenyl)pyridazin-4(1H)-one

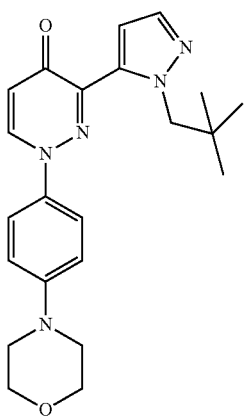 [SMILES: CC(C)(C)Cn1nccc1-c1nn(-c2ccc(N3CCOCC3)cc2)ccc1=O]

To a solution of 3-[3-(dimethylamino)prop-2-enoyl]-1-(4-morpholin-4-ylphenyl)pyridazin-4(1H)-one (300 mg, 0.85 mmol) in 20 mL of methanol, 2,2-dimethylpropylhydrazine (346 mg, 3.39 mmol) was added, the resulting mixture was refluxed for 4 hours, and then concentrated. The residue was dissolved in dichloromethane (20 mL), washed with 1 M acetic acid aqueous solution and brine, dried over anhydrous $Na_2SO_4$, and concentrated under reduced pressure. The residue was purified by prep-HPLC to give the title compound (75 mg, 22% yield) as a yellow solid: $^1$H NMR (400 MHz, $CDCl_3$): δ 0.83 (9H, s), 3.22-3.25 (4H, m), 3.88-3.90 (4H, m), 4.41 (2H, s), 6.70 (1H, d, J=7.6 Hz), 7.00 (2H, d, J=9.2 Hz), 7.08 (1H, d, J=2.0 Hz), 7.45 (2H, d, J=9.2 Hz), 7.58 (1H, d, J=2.0 Hz), 8.14 (1H, d, J=8.0 Hz); LCMS (mobile phase: from 70% water and 30% CH3CN to 5% water and 95% CH3CN in 6 min, finally under these conditions for 0.5 min.) purity is >95%, Rt=2.656 min; MS Calcd.: 393, MS Found: 394 (M$^+$+H.

Example 160

3-(1-Cyclopentyl-1H-pyrazol-5-yl)-1-(4-morpholin-4-ylphenyl)pyridazin-4(1H)-one

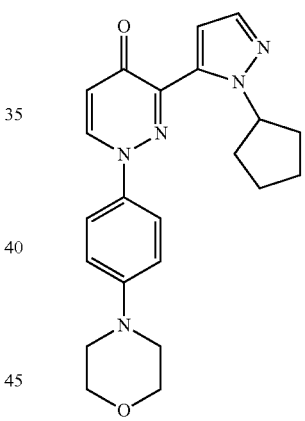

To a solution of 3-[3-(dimethylamino)prop-2-enoyl]-1-(4-morpholin-4-ylphenyl)pyridazin-4(1H)-one (300 mg, 0.85 mmol) in 20 mL of methanol, cyclopentylhydrazine (340 mg, 3.39 mmol) was added, the resulting mixture was refluxed for 4 hours, and then concentrated. The residue was dissolved in dichloromethane (20 mL), washed with 1 M acetic acid aqueous solution and brine, dried over anhydrous $Na_2SO_4$, and concentrated under reduced pressure. The residue was purified by prep-HPLC to give the title compound (30 mg, 9% yield) as a brown solid: $^1$H NMR (400 MHz, $CDCl_3$): δ 1.46-1.69 (5H, m), 1.92-1.96 (1H, m), 2.04-2.09 (1H, m), 2.14-2.19 (1H, m), 3.22-3.25 (4H, m), 3.87-3.90 (4H, m), 5.10 (1H, quintet, J=3.6 Hz), 6.71 (1H, d, J=8.0 Hz), 6.98-7.01 (2H, m), 7.04 (1H, d, J=1.6 Hz), 7.44-7.47 (2H, m), 7.60 (1H, d, J=2.0 Hz), 8.16 (1H, d, J=7.6 Hz); LCMS (mobile phase: from 90% water and 10% CH3CN to 5% water and 95% CH3CN in 6 min, finally under these conditions for 0.5 min.) purity is >95%, Rt=3.196 min; MS Calcd.: 391, MS Found: 392 [M+H]$^+$.

Example 161

3-(1-Cyclohexyl-1H-pyrazol-5-yl)-1-(4-morpholin-4-ylphenyl)pyridazin-4(1H)-one

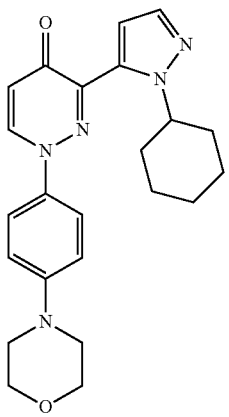 [SMILES: O=c1ccn(-c2ccc(N3CCOCC3)cc2)nc1-c1ccnn1C1CCCCC1]

3-[(4-Morpholin-4-ylphenyl)hydrazono]pentane-2,4-dione (500 mg, 1.73 mmol) was dissolved in 10 mL of N,N-dimethylformamide dimethyl acetal, and the mixture was refluxed for 4 hours, then concentrated under reduced pressure.

To a solution of the residue in 20 mL of methanol, cyclohexylhydrazine (790 mg, 6.92 mmol) was added, and the resulting mixture was refluxed for 4 hours, then concentrated. The residue was dissolved in dichloromethane (20 mL), washed with 1 M acetic acid aqueous solution and brine, dried over anhydrous $Na_2SO_4$, and concentrated under reduced pressure. The residue was purified by prep-HPLC to give the title compound (50 mg, 7.1% yield) as a yellow solid: $^1$H NMR (400 MHz, CDCl$_3$): δ 1.21-1.35 (3H, m), 1.63-1.69 (1H, m), 1.85-1.87 (2H, m), 2.00-2.06 (4H, m), 3.21-3.25 (4H, m), 3.87-3.90 (4H, m), 4.58-4.65 (1H, m), 6.70 (1H, dd, J=1.6, 8.0 Hz), 6.96-7.02 (2H, m), 7.12 (1H, d, J=1.6 Hz), 7.45-7.50 (2H, m), 7.59-7.62 (1H, m), 8.19 (1H, d, J=8.0 Hz); LCMS (mobile phase: from 80% water and 20% CH3CN to 5% water and 95% CH3CN in 6 min, finally under these conditions for 0.5 min.) purity is >95%, Rt=3.318 min; MS Calcd.: 405, MS Found: 406 [M+H]$^+$.

Example 162

1-(2-Fluoro-5-iodophenyl)-5-methoxy-3-(1-phenyl-1H-pyrazol-5-yl)pyridazin-4(1H)-one

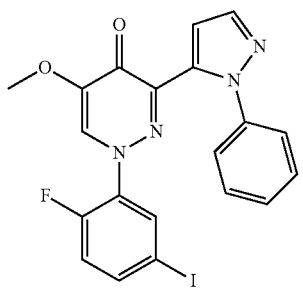 [SMILES: COc1cn(-c2cc(I)ccc2F)nc(-c2ccnn2-c2ccccc2)c1=O]

A mixture of 3-acetyl-1-(2-fluoro-5-iodophenyl)-5-methoxypyridazin-4(1H)-one (3.88 g, 10.0 mmol) in N,N-dimethylformamide dimethyl acetal (38.8 mL) was heated to reflux for 3 h. The mixture was concentrated in vacuo. To the residue were added AcOH (38.8 mL) and phenylhydrazine (1.97 mL, 20.0 mmol). The mixture was heated to reflux for 5 h. The mixture was concentrated in vacuo, diluted with 1 M HCl aqueous solution, extracted with AcOEt, washed with saturated NaHCO$_3$ aqueous solution, dried over Na$_2$SO$_4$, filtered, concentrated in vacuo, purified by column chromatography on basic silica gel (hexane/AcOEt=50/50 to 0/100) and triturated with AcOEt/hexane to yield the title compound (2.95 g, 60% yield) as a yellow solid: $^1$H NMR (DMSO-d$_6$, 300 MHz): δ ppm 3.77 (3H, s), 6.99 (1H, d, J=1.5 Hz), 7.23-7.50 (7H, m), 7.79 (1H, d, J=1.9 Hz), 7.84 (1H, ddd, J=8.7, 4.5, 2.3 Hz), 8.49 (1H, d, J=2.6 Hz).

Example 163

3-[1-(2-Fluorophenyl)-1H-pyrazol-5-yl]-1-[2-fluoro-4-(1H-pyrazol-1-yl)phenyl]-5-methoxypyridazin-4(1H)-one

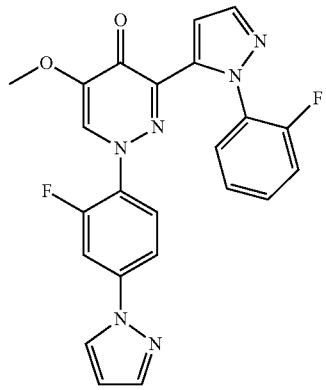 [SMILES: COc1cn(-c2ccc(-n3cccn3)cc2F)nc(-c2ccnn2-c2ccccc2F)c1=O]

A suspension of 3-acetyl-1-[2-fluoro-4-(1H-pyrazol-1-yl)phenyl]-5-methoxypyridazin-4(1H)-one (197 mg, 0.600 mmol) in N,N-dimethylformamide dimethyl acetal (2.0 mL) was stirred at 100° C. for 1 h. The reaction mixture was concentrated in vacuo. To the residue were added AcOH (2.0 mL) and 2-fluorophenylhydrazine (151 mg, 1.20 mmol). The mixture was stirred at 100° C. for 1 h. After solvent evaporated, the residue was diluted with saturated NaHCO$_3$ aqueous solution (25 mL) and extracted with AcOEt (25 mL×3). The combined organic phase was washed with brine (40 mL), dried with MgSO$_4$, and evaporated. The residue was crystallized from AcOEt to give a coarse solid, which was recrystallized from EtOH/hexane to give the title compound (125 mg, 47% yield) as a white solid: mp 202-206° C.; $^1$H NMR (300 MHz, DMSO-d$_6$): δ ppm 3.79 (3H, s), 6.64 (1H, d, J=1.9

Hz), 6.96 (1H, t, J=8.5 Hz), 7.23-7.33 (3H, m), 7.41-7.53 (2H, m), 7.71 (1H, d, J=9.1 Hz), 7.84 (2H, dd, J=4.0, 1.7 Hz), 7.94 (1H, dd, J=12.3, 2.5 Hz), 8.48 (1H, d, J=1.9 Hz), 8.65 (1H, d, J=2.6 Hz). LC-MS (ESI) m/z 447 [M+H]$^+$. Anal. Calcd for $C_{23}H_{16}F_2N_6O_2 \cdot 0.4H_2O$: C, 60.90; H, 3.73; N, 18.53. Found: C, 60.68; H, 3.69; N, 18.39.

7.44 (3H, dd, J=16.6, 10.2 Hz), 7.34-7.52 (1H, m), 7.84 (3H, dd, J=3.6, 1.7 Hz), 8.00 (1H, dd, J=12.3, 2.1 Hz), 8.56 (1H, d, J=1.9 Hz), 8.67 (1H, d, J=2.6 Hz): LC-MS (ESI) m/z 463 [M+H]$^+$. Anal. Calcd for $C_{23}H_{16}ClFN_6O_2 \cdot 0.03H_2O$: C, 59.61; H, 3.49; N, 18.14. Found: C, 59.32; H, 3.50; N, 17.92.

Example 164

3-[1-(3-Chlorophenyl)-1H-pyrazol-5-yl]-1-[2-fluoro-4-(1H-pyrazol-1-yl)phenyl]-5-methoxypyridazin-4(1H)-one

Example 165

1-[4-(3-tert-Butyl-2-oxoimidazolidin-1-yl)-2-fluorophenyl]-5-methoxy-3-(1-phenyl-1H-pyrazol-5-yl)pyridazin-4(1H)-one

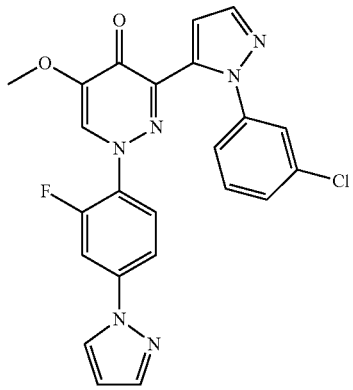 [SMILES: COc1cn(-c2ccc(-n3cccn3)cc2F)nc(-c2ccnn2-c2cccc(Cl)c2)c1=O]

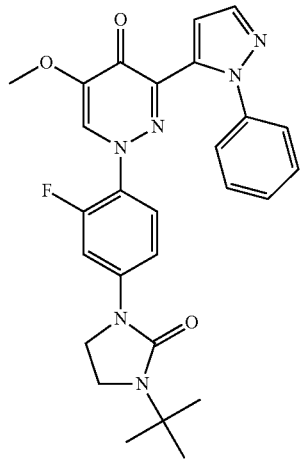 [SMILES: COc1cn(-c2ccc(N3CCN(C(C)(C)C)C3=O)cc2F)nc(-c2ccnn2-c2ccccc2)c1=O]

A suspension of 3-acetyl-1-[2-fluoro-4-(1H-pyrazol-1-yl)phenyl]-5-methoxypyridazin-4(1H)-one (393 mg, 1.20 mmol) in N,N-dimethylformamide dimethyl acetal (4.0 mL) was stirred at 100° C. for 1 h. The reaction mixture was concentrated in vacuo. To the residue were added AcOH (4 mL) and 3-chlorophenylhydrazine hydrochloride (429 mg, 2.40 mmol). The mixture was stirred at 100° C. for 1 h. After solvent evaporated, the residue was diluted with saturated NaHCO$_3$ aqueous solution (25 mL) and extracted with AcOEt (25 mL×3). The combined organic phase was washed with brine (40 mL), dried with MgSO$_4$, and evaporated. The residue was crystallized from AcOEt to give a coarse solid, which was recrystallized from EtOH/hexane to give the title compound (242 mg, 44% yield) as an orange solid: mp 186-190° C.; $^1$H NMR (300 MHz, DMSO-d$_6$): δ ppm 3.80 (3H, s), 6.64 (1H, d, J=1.9 Hz), 7.05 (1H, d, J=1.9 Hz), 7.27-7.34 (1H, m), A suspension of 1-(2-fluoro-4-iodophenyl)-5-methoxy-3-(1-phenyl-1H-pyrazol-5-yl)pyridazin-4(1H)-one (488 mg, 1.0 mmol), 1-tert-butylimidazolidin-2-one (171 mg, 1.2 mmol), CuI (19 mg, 0.1 mmol), trans-1,2-diaminocyclohexane (0.024 mL, 0.2 mmol), and K$_3$PO$_4$ (425 mg, 2.0 mmol) in toluene (5 mL) was stirred at 80° C. for 24 h under N$_2$ atmosphere. After cooling to room temperature, the reaction mixture was purified by silica gel column chromatography eluting with hexane/AcOEt (1/1), AcOEt only and then AcOEt/MeOH (10/1) and recrystallized from AcOEt to give the title compound (198 mg, 39% yield) as a white solid: mp 238-239° C.; $^1$H NMR (300 MHz, DMSO-d$_6$): δ ppm 1.36 (9H, s), 3.29 (3H, s), 3.44-3.59 (2H, m), 3.64-3.76 (2H, m), 6.92-7.03 (2H, m), 7.23-7.51 (6H, m), 7.70 (1H, dd, J=14.1, 2.4 Hz), 7.78 (1H, d, J=1.9 Hz), 8.43 (1H, d, J=1.9 Hz). LC-MS (ESI) m/z 503 [M+H]$^+$. Anal. Calcd for $C_{27}H_{27}FN_6O_3$: C, 64.53; H, 5.42; N, 16.72. Found: C, 64.31; H, 5.38; N, 16.58.

Example 166

1-[2-Fluoro-4-(2-oxoimidazolidin-1-yl)phenyl]-5-methoxy-3-(1-phenyl-1H-pyrazol-5-yl)pyridazin-4(1H)-one

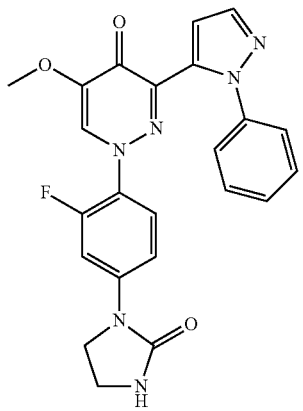 [SMILES: COc1cn(-c2ccc(N3CCNC3=O)cc2F)nc(-c2ccnn2-c2ccccc2)c1=O]

A mixture of 1-[4-(3-tert-butyl-2-oxoimidazolidin-1-yl)-2-fluorophenyl]-5-methoxy-3-(1-phenyl-1H-pyrazol-5-yl)pyridazin-4(1H)-one (503 mg, 1.0 mmol) in trifluoroacetic acid (3.0 mL) was stirred at 80° C. for 1 h. After cooling to room temperature, the reaction mixture was evaporated. The residue was recrystallized from AcOEt/MeOH to give the title compound (334 mg, 75% yield) as a pale yellow solid: mp 259-260° C.; $^1$H NMR (300 MHz, DMSO-$d_6$): δ ppm 3.40-3.50 (2H, m), 3.77 (3H, s), 3.82-3.93 (2H, m), 6.95 (1H, d, J=2.3 Hz), 7.01 (1H, t, J=9.0 Hz), 7.23-7.49 (7H, m), 7.73 (1H, dd, J=14.1, 2.4 Hz), 7.78 (1H, d, J=1.9 Hz), 8.44 (1H, d, J=1.9 Hz). LC-MS (ESI) m/z 447 [M+H]$^+$. Anal. Calcd for $C_{23}H_{19}FN_6O_3 \cdot 0.75H_2O$: C, 60.06; H, 4.49; N, 18.27. Found: C, 60.05; H, 4.26; N, 18.16.

Example 167

1-{4-[3-(Difluoromethyl)-2-oxoimidazolidin-1-yl]-2-fluorophenyl}-5-methoxy-3-(1-phenyl-1H-pyrazol-5-yl)pyridazin-4(1H)-one

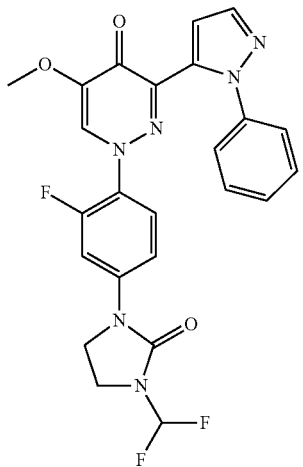 [SMILES: COc1cn(-c2ccc(N3CCN(C(F)F)C3=O)cc2F)nc(-c2ccnn2-c2ccccc2)c1=O]

A mixture of 1-[2-fluoro-4-(2-oxoimidazolidin-1-yl)phenyl]-5-methoxy-3-(1-phenyl-1H-pyrazol-5-yl)pyridazin-4(1H)-one (100 mg, 0.22 mmol), sodium chlorodifluoroacetate (40 mg, 0.26 mmol), and 18-crown-6 (12 mg, 0.044 mmol) in acetonitrile (10 mL) was stirred at 90° C. for 20 h. After cooling to room temperature, to the reaction mixture was added silica gel. This mixture was evaporated, and purified by silica gel column chromatography eluting with AcOEt/MeOH (1/0 to 10/1) to give the title compound (2.5 mg, 2.3% yield) as a pale yellow powder: $^1$H NMR (300 MHz, DMSO-$d_6$): δ ppm 1.11-1.40 (4H, m), 3.61-3.86 (4H, m), 6.96 (1H, d, J=1.9 Hz), 7.01-7.15 (1H, m), 7.16-7.50 (6H, m), 7.71 (1H, dd, J=13.6, 2.3 Hz), 7.79 (1H, d, J=2.3 Hz), 8.47 (1H, d, J=1.9 Hz). LC-MS (ESI) m/z 497 [M+H]$^+$.

Example 168

1-[3-(3,6-Dihydro-2H-pyran-4-yl)-2-fluorophenyl]-5-methoxy-3-(1-phenyl-1H-pyrazol-5-yl)pyridazin-4(1H)-one

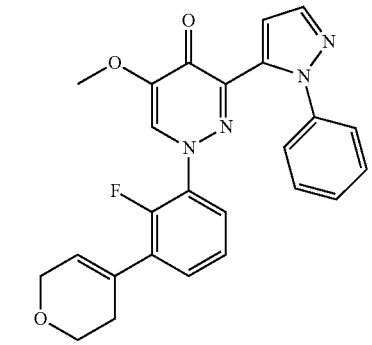 [SMILES: COc1cn(-c2cccc(C3=CCOCC3)c2F)nc(-c2ccnn2-c2ccccc2)c1=O]

A mixture of 1-(3-bromo-2-fluorophenyl)-5-methoxy-3-(1-phenyl-1H-pyrazol-5-yl)pyridazin-4(1H)-one (441 mg, 1.0 mmol), 4-(4,4,5,5-tetramethyl-1,3,2-dioxaborolan-2-yl)-3,6-dihydro-2H-pyran (231 mg, 1.1 mmol), Pd(PPh$_3$)$_4$ (57.8 mg, 0.05 mmol) and Na$_2$CO$_3$ (233 mg, 2.2 mmol) in DME (8.8 mL) and water (2.2 mL) was heated to reflux for 15 h under N$_2$. The mixture was diluted with NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and recrystallized with EtOH/hexane to yield the title compound (380 mg, 85% yield) as a white solid: mp 138-141° C. $^1$H NMR (DMSO-$d_6$, 300 MHz): δ ppm 2.42 (2H, brs), 3.74-3.89 (5H, m), 4.21-4.29 (2H, m), 6.15 (1H, brs), 6.92-7.10 (2H, m), 7.17-7.59 (7H, m), 7.78 (1H, d, J=1.9 Hz), 8.52 (1H, s). Anal. Calcd for $C_{25}H_{21}FN_4O_3$: C, 67.56; H, 4.76; N, 12.61. Found: C, 67.42; H, 4.83; N, 12.44.

Example 169

1-[2-Fluoro-3-(tetrahydro-2H-pyran-4-yl)phenyl]-5-methoxy-3-(1-phenyl-1H-pyrazol-5-yl)pyridazin-4(1H)-one

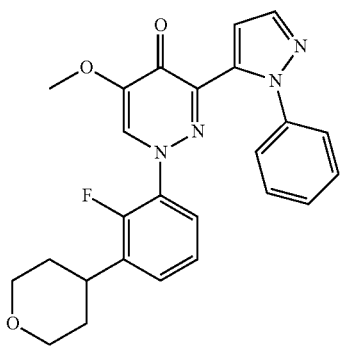 [SMILES: COc1cn(-c2cccc(C3CCOCC3)c2F)nc(-c2ccnn2-c2ccccc2)c1=O]

A mixture of 1-[3-(3,6-dihydro-2H-pyran-4-yl)-2-fluorophenyl]-5-methoxy-3-(1-phenyl-1H-pyrazol-5-yl)pyridazin-4(1H)-one (190 mg, 0.427 mmol) and Pd/C (10% Pd, 50% wet, 19 mg) in MeOH (10 mL) was stirred at room temperature for 16 h under $H_2$. The mixture was filtered through a pad of Celite, concentrated in vacuo, purified by column chromatography on basic silica gel (hexane/AcOEt=50/50 to 0/100) and recrystallized with EtOH/hexane to yield the title compound (152 mg, 79% yield) as a pale yellow solid: $^1$H NMR (DMSO-$d_6$, 300 MHz): δ ppm 1.60-1.85 (4H, m), 3.39-3.56 (3H, m), 3.77 (3H, s), 3.91-4.04 (2H, m), 6.92-7.04 (2H, m), 7.21 (1H, t, J=8.1 Hz), 7.27-7.54 (6H, m), 7.78 (1H, d, J=1.9 Hz), 8.49 (1H, d, J=1.9 Hz).

Example 170

1-(2-Fluoro-3-morpholin-4-ylphenyl)-5-methoxy-3-(1-phenyl-1H-pyrazol-5-yl)pyridazin-4(1H)-one

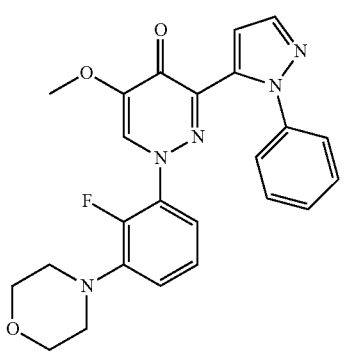 [SMILES: COc1cn(-c2cccc(N3CCOCC3)c2F)nc(-c2ccnn2-c2ccccc2)c1=O]

A mixture of 1-(3-bromo-2-fluorophenyl)-5-methoxy-3-(1-phenyl-1H-pyrazol-5-yl)pyridazin-4(1H)-one (221 mg, 0.5 mmol), morpholine (0.0525 mL, 0.6 mmol), NaOt-Bu (67.3 mg, 0.7 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 18 h under Ar. The mixture was diluted with NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and recrystallized with AcOEt/hexane and EtOH/hexane to yield the title compound (139 mg, 59% yield) as a pale yellow solid: mp 187-189° C. $^1$H NMR (DMSO-$d_6$, 300 MHz): δ ppm 2.97-3.08 (4H, m), 3.70-3.80 (7H, m), 6.61-6.72 (1H, m), 6.96 (1H, d, J=1.5 Hz), 7.06-7.17 (2H, m), 7.26-7.47 (5H, m), 7.78 (1H, d, J=1.9 Hz), 8.50 (1H, d, J=1.9 Hz). Anal. Calcd for C$_{24}$H$_{22}$FN$_5$O$_3$: C, 64.42; H, 4.96; N, 15.65. Found: C, 64.47; H, 4.99; N, 15.55.

Example 171

1-[3-(3,3-Difluoroazetidin-1-yl)-2-fluorophenyl]-5-methoxy-3-(1-phenyl-1H-pyrazol-5-yl)pyridazin-4(1H)-one

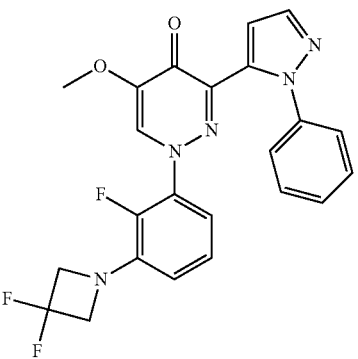 [SMILES: COc1cn(-c2cccc(N3CC(F)(F)C3)c2F)nc(-c2ccnn2-c2ccccc2)c1=O]

A mixture of 1-(3-bromo-2-fluorophenyl)-5-methoxy-3-(1-phenyl-1H-pyrazol-5-yl)pyridazin-4(1H)-one (177 mg, 0.4 mmol), 3,3-difluoroazetidine hydrochloride (62.2 mg, 0.48 mmol), NaOt-Bu (99.9 mg, 1.04 mmol), Xantphos (99.9 mg, 0.173 mmol) and Pd$_2$(dba)$_3$ (39.7 mg, 0.043 mmol) in 1,4-dioxane (2 mL) was heated to 90° C. for 16 h under N$_2$. The mixture was diluted with saturated NaHCO$_3$ aqueous solution, extracted with AcOEt, dried over Na$_2$SO$_4$, filtered, concentrated in vacuo and purified by column chromatography on basic silica gel (hexane/AcOEt=50/50 to 0/100) to yield the title compound (58.8 mg, 32% yield) as a pale yellow solid: $^1$H NMR (DMSO-$d_6$, 300 MHz): δ ppm 3.77 (3H, s), 4.42 (4H, t, J=12.6 Hz), 6.43-6.82 (1H, m), 6.90-7.49 (8H, m), 7.79 (1H, s), 8.39-8.60 (1H, m).

Example 172

1-[3-(3,3-Difluoropyrrolidin-1-yl)-2-fluorophenyl]-5-methoxy-3-(1-phenyl-1H-pyrazol-5-yl)pyridazin-4(1H)-one

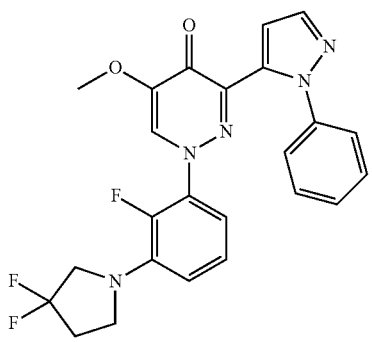 [SMILES: COc1cn(-c2cccc(N3CCC(F)(F)C3)c2F)nc(-c2ccnn2-c2ccccc2)c1=O]

A mixture of 1-(3-bromo-2-fluorophenyl)-5-methoxy-3-(1-phenyl-1H-pyrazol-5-yl)pyridazin-4(1H)-one (221 mg, 0.5 mmol), 3,3-difluoropyrrolidine hydrochloride (86.1 mg, 0.6 mmol), NaOt-Bu (125 mg, 1.3 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 24 h under N$_2$. The mixture was diluted with saturated. NaHCO$_3$ aqueous solution, extracted with AcOEt, dried over Na$_2$SO$_4$, filtered, concentrated in vacuo and purified by column chromatography on basic silica gel (hexane/AcOEt=50/50 to 0/100) to yield the title compound (119 mg, 51% yield) as a pale yellow solid: $^1$H NMR (DMSO-d$_6$, 300 MHz): δ ppm 2.42-2.50 (2H, m), 3.56 (2H, t, J=7.4 Hz), 3.71-3.88 (5H, m), 6.43-6.54 (1H, m), 6.84-7.13 (3H, m), 7.27-7.49 (5H, m), 7.78 (1H, d, J=1.9 Hz), 8.47 (1H, d, J=2.3 Hz). Anal. Calcd for C$_{24}$H$_{20}$F$_3$N$_5$O$_2$.0.2H$_2$O: C, 61.20; H, 4.37; N, 14.87. Found: C, 61.36; H, 4.45; N, 14.56.

Example 173

5-Methoxy-3-(1-phenyl-1H-pyrazol-5-yl)-1-pyridin-3-ylpyridazin-4(1H)-one

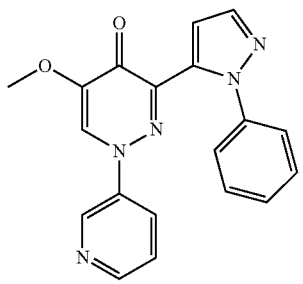 [SMILES: COc1cn(-c2cccnc2)nc(-c2ccnn2-c2ccccc2)c1=O]

A mixture of 3-acetyl-5-methoxy-1-pyridin-3-ylpyridazin-4(1H)-one (0.21 g, 0.86 mmol) in N,N-dimethylformamide dimethyl acetal (10 mL, 75 mmol) was heated to reflux. MeOH (10 mL) was added to the mixture. After refluxing for 2 h, the mixture was concentrated under reduced pressure.

A solution of the residue and phenylhydrazine (0.17 mL, 1.7 mmol) in AcOH (10 mL) was refluxed for 3 h. After stirring at room temperature overnight, the mixture was concentrated under reduced pressure. The residue was diluted with AcOEt, and washed with saturated NaHCO$_3$ aqueous solution and brine. The organic layer was dried over MgSO$_4$, filtered and concentrated under reduced pressure. The residue was chromatographed on basic silica gel (30/70-100/0 AcOEt/hexane) to give brown crystals. The crystals were recrystallized from 2-propanolheptane to give the title compound (70 mg, 24% yield) as beige crystals: mp 210-212° C.; $^1$H NMR (300 MHz, DMSO-d$_6$): δ ppm 3.88 (3H, s), 7.16 (1H, d, J=1.9 Hz), 7.35-7.50 (6H, m), 7.54-7.59 (1H, m), 7.81 (1H, d, J=1.9 Hz), 8.46 (1H, d, J=2.6 Hz), 8.54 (1H, dd, J=4.7, 1.3 Hz), 8.65 (1H, s). LC-MS (ESI) m/z 346 [M+H]$^+$. Anal. Calcd. for C$_{19}$H$_{15}$N$_5$O$_2$: C, 66.08; H, 4.38; N, 20.28. Found: C, 65.85; H, 4.34; N, 20.11.

Example 174

1-{2-Fluoro-3-[3-(trifluoromethyl)pyrrolidin-1-yl]phenyl}-5-methoxy-3-(1-phenyl-1H-pyrazol-5-yl)pyridazin-4(1H)-one

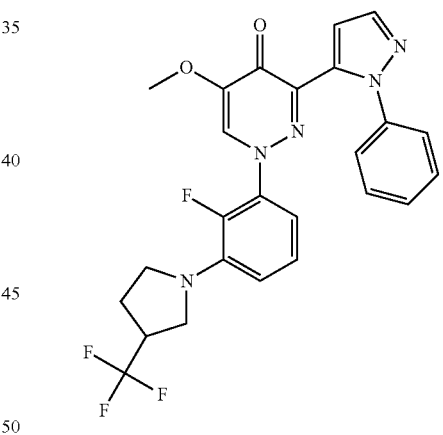

A mixture of 1-(3-bromo-2-fluorophenyl)-5-methoxy-3-(1-phenyl-1H-pyrazol-5-yl)pyridazin-4(1H)-one (300 mg, 0.68 mmol), 3-(trifluoromethyl)pyrrolidine hydrochloride (143 mg, 0.82 mmol), NaOt-Bu (170 mg, 1.8 mmol), Xantphos (31 mg, 0.054 mmol) and Pd$_2$(dba)$_3$ (12 mg, 0.014 mmol) in 1,4-dioxane (4 mL) was heated at 90° C. for 14 h under Ar. The mixture was extracted with AcOEt, dried over Na$_2$SO$_4$, filtered, concentrated in vacuo and purified by column chromatography on basic silica gel (hexane/AcOEt=10/90 to 0/100) to yield the title compound (131 mg, 39% yield) as a white amorphous solid: $^1$H NMR (300 MHz, CDCl$_3$): δ ppm 2.09-2.40 (2H, m), 3.05 (1H, s), 3.38-3.75 (4H, m), 3.83-3.99 (3H, m), 5.88-6.07 (1H, m), 6.65 (1H, td, J=8.3, 1.5 Hz), 6.80-6.95 (1H, m), 7.22 (1H, d, J=2.3 Hz), 7.30-7.49 (5H, m), 7.72 (1H, d, J=2.6 Hz), 7.74-7.80 (1H, m); MS Calcd.: 499; MS Found: 500 [M+H]$^+$.

Example 175

1-{2-Fluoro-4-[3-(trifluoromethyl)pyrrolidin-1-yl]phenyl}-5-methoxy-3-(1-phenyl-1H-pyrazol-5-yl)pyridazin-4(1H)-one

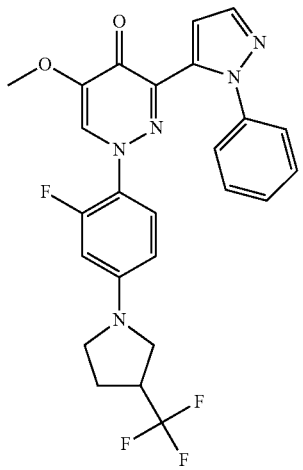 [SMILES: COc1cn(-c2ccc(N3CCC(C(F)(F)F)C3)cc2F)nc(-c2ccnn2-c2ccccc2)c1=O]

A mixture of 1-(2-fluoro-4-iodophenyl)-5-methoxy-3-(1-phenyl-1H-pyrazol-5-yl)pyridazin-4(1H)-one (300 mg, 0.61 mmol), 3-(trifluoromethyl)pyrrolidine hydrochloride (130 mg, 0.74 mmol), NaOt-Bu (154 mg, 1.6 mmol), Xantphos (28 mg, 0.049 mmol) and Pd$_2$(dba)$_3$ (11 mg, 0.012 mmol) in 1,4-dioxane (4 mL) was heated to 90° C. for 12 h under Ar. The mixture was extracted with AcOEt, dried over Na$_2$SO$_4$, filtered, concentrated in vacuo and purified by column chromatography on basic silica gel (hexane/AcOEt=10/90 to 0/100) to yield the title compound (138 mg, 45% yield) as a pale green solid: $^1$H NMR (300 MHz, CDCl$_3$): δ ppm 2.17-2.42 (2H, m), 3.01-3.21 (1H, m), 3.30-3.63 (4H, m), 3.89 (3H, s), 6.11 (1H, dd, J=8.9, 2.4 Hz), 6.20-6.37 (2H, m), 7.24 (1H, d, J=1.9 Hz), 7.33-7.47 (5H, m), 7.71 (1H, d, J=2.3 Hz), 7.77 (1H, d, J=1.9 Hz); MS Calcd.: 499; MS Found: 500 [M+H]$^+$.

Example 176

1-[2-Fluoro-3-(3,3,4,4-tetrafluoropyrrolidin-1-yl)phenyl]-5-methoxy-3-(1-phenyl-1H-pyrazol-5-yl)pyridazin-4(1H)-one

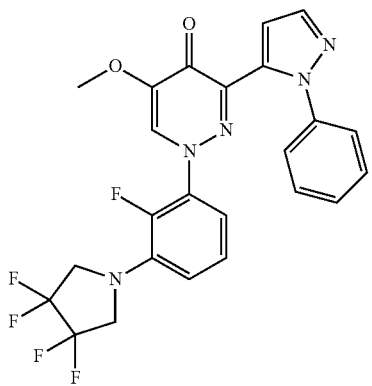 [SMILES: COc1cn(-c2cccc(N3CC(F)(F)C(F)(F)C3)c2F)nc(-c2ccnn2-c2ccccc2)c1=O]

A suspension of 1-(3-bromo-2-fluorophenyl)-5-methoxy-3-(1-phenyl-1H-pyrazol-5-yl)pyridazin-4(1H)-one (221 mg, 0.500 mmol), 3,3,4,4-tetrafluoropyrrolidine hydrochloride (108 mg, 0.600 mmol), sodium tert-butoxide (125 mg, 1.300 mmol), Xantphos (23 mg, 0.040 mmol), and tris(dibenzylideneacetone)dipalladium(0) (9 mg, 0.010 mmol) in 1,4-dioxane (2.5 mL) was stirred at 90° C. under Ar atmosphere. The reaction mixture was poured into 5% NaHCO$_3$ aqueous solution (20 mL) and extracted with AcOEt (20 mL×3). The combined organic phase was washed with brine (40 mL), dried with MgSO$_4$, and evaporated. The residue was purified by silica gel column chromatography (AcOEt/hexane=60%-100%) to give the title compound (95.4 mg, 38% yield) as an amorphous solid: $^1$H NMR (300 MHz, CDCl$_3$): δ ppm 3.84-3.96 (7H, m), 6.11 (1H, t, J=7.5 Hz), 6.60 (1H, td, J=8.3, 1.5 Hz), 6.90-6.98 (1H, m), 7.25 (1H, d, J=1.9 Hz), 7.33-7.41 (5H, m), 7.70 (1H, d, J=2.6 Hz), 7.78 (1H, d, J=1.9 Hz). LC-MS (ESI) m/z 504 [M+H]$^+$.

Example 177

1-(2-Fluoro-3-pyridin-3-ylphenyl)-5-methoxy-3-(1-phenyl-1H-pyrazol-5-yl)pyridazin-4(1H)-one

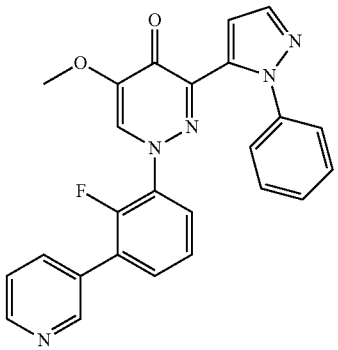 [SMILES: COc1cn(-c2cccc(-c3cccnc3)c2F)nc(-c2ccnn2-c2ccccc2)c1=O]

A solution of 1-(3-bromo-2-fluorophenyl)-5-methoxy-3-(1-phenyl-1H-pyrazol-5-yl)pyridazin-4(1H)-one (177 mg, 0.400 mmol), 3-pyridineboronic acid (54.1 mg, 0.440 mmol), tetrakis(triphenylphosphine)palladium(0) (23 mg, 0.020 mmol) and Na$_2$CO$_3$ (93 mg, 0.88 mmol) in DME (3.6 mL) and water (0.9 mL) was stirred at 85° C. for 5 h under Ar atmosphere. The mixture was poured into 5% NaHCO$_3$ aqueous solution (20 mL) and extracted with AcOEt (20 mL×3). The combined organic phase was washed with brine (30 mL), dried with MgSO$_4$, and evaporated. The residue was purified by basic silica gel column chromatography (MeOH/AcOEt=0%-10%) and crystallized from AcOEt to give the title compound (84.8 mg, 48% yield) as a colorless solid: mp 147-153° C.; $^1$H NMR (300 MHz, DMSO-d$_6$): δ ppm 3.78 (3H, s), 7.01 (1H, d, J=1.9 Hz), 7.04-7.17 (1H, m), 7.28-7.51 (6H, m), 7.56 (1H, dd, J=7.7, 5.1 Hz), 7.63-7.75 (1H, m), 7.79 (1H, d, J=1.9 Hz), 8.03 (1H, dd, J=7.9, 1.9 Hz), 8.58-8.68 (2H, m), 8.81 (1H, s). LC-MS (ESI) m/z 440 [M+H]$^+$. Anal. Calcd for C$_{25}$H$_{18}$FN$_5$O$_2$: C, 68.33; H, 4.13; N, 15.94. Found: C, 68.04; H, 4.03; N, 15.80.

Example 178

1-[2-fluoro-4-(3-methyl-2-oxoimidazolidin-1-yl) phenyl]-5-methoxy-3-(1-phenyl-1H-pyrazol-5-yl) pyridazin-4(1H)-one

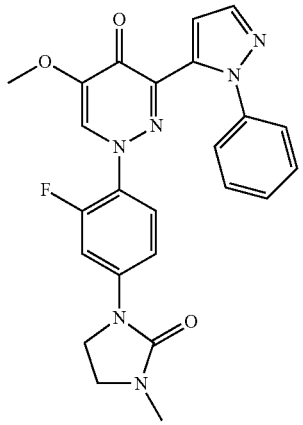 [SMILES: COc1cn(-c2ccc(N3CCN(C)C3=O)cc2F)nc(-c2ccnn2-c2ccccc2)c1=O]

A mixture of 1-[2-fluoro-4-(2-oxoimidazolidin-1-yl)phenyl]-5-methoxy-3-(1-phenyl-1H-pyrazol-5-yl)pyridazin-4 (1H)-one (40 mg, 0.09 mmol), iodomethane (0.02 mL, 0.36 mmol), and sodium hydride (60% in oil) (7.0 mg, 0.18 mmol) in DMF (4.0 mL) was stirred at 0° C. for 2 h. The reaction mixture was quenched with H$_2$O, and extracted with AcOEt. The organic layer was dried over MgSO$_4$, and concentrated under reduced pressure. The residue was recrystallized from $^i$Pr$_2$O/AcOEt to give the title compound (24 mg, 59% yield) as a white solid: mp 208-209° C.; $^1$H NMR (300 MHz, DMSO-d$_6$): δ ppm 2.79 (3H, s), 3.42-3.58 (2H, m), 3.77 (3H, s), 3.78-3.86 (2H, m), 6.95 (1H, d, J=1.9 Hz), 7.01 (1H, t, J=9.0 Hz), 7.22-7.51 (6H, m), 7.73 (1H, dd, J=14.1, 2.4 Hz), 7.78 (1H, d, J=1.9 Hz), 8.44 (1H, d, J=1.9 Hz). LC-MS (ESI) m/z 461 [M+H]$^+$. Anal. Calcd for C$_{24}$H$_{21}$FN$_6$O$_3$·0.75H$_2$O: C, 60.06; H, 4.49; N, 18.27. Found: C, 60.05; H, 4.26; N, 18.16.

Example 179

1-[4-(2,5-Dihydro-1H-pyrrol-1-yl)-2-fluorophenyl]-5-methoxy-3-(1-phenyl-1H-pyrazol-5-yl)pyridazin-4 (1H)-one

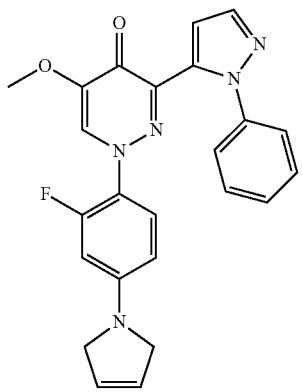 [SMILES: COc1cn(-c2ccc(N3CC=CC3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.5 mmol), 3-pyrroline (0.046 mL, 0.6 mmol), Pd$_2$(dba)$_3$ (18.3 mg, 0.02 mmol), Xantphos (46.3 mg, 0.08 mmol), and NaOtBu (67.3 mg, 0.7 mmol) in 1,4-dioxane (2.5 mL) was stirred for 2 h at 90° C. under Ar atmosphere. The reaction mixture was poured into water and extracted with AcOEt. The extract was washed with brine, dried over MgSO$_4$, and concentrated under reduced pressure. The residue was purified by basic silica gel column chromatography eluting with hexane/THF (1/2) and recrystallized from MeOH/H$_2$O to give the title compound (109 mg, 51% yield) as a yellow solid: mp 204-207° C.; $^1$H NMR (300 MHz, CDCl$_3$): δ ppm 3.89 (3H, s), 4.09 (4H, s), 5.97 (2H, t, J=4.1 Hz), 6.07 (1H, dd, J=2.6, 9.0 Hz), 6.19 (1H, dd, J=2.6, 14.3 Hz), 6.32 (1H, t, J=9.0 Hz), 7.24 (1H, d, J=1.9 Hz), 7.33-7.45 (5H, m), 7.72 (1H, d, J=2.3 Hz), 7.77 (1H, d, J=1.9 Hz). LC-MS (ESI) m/z 430 [M+H]$^+$. Anal. Calcd for C$_{24}$H$_{20}$FN$_5$O$_2$: C, 67.12; H, 4.69; N, 16.31. Found: C, 67.03; H, 4.76; N, 16.16.

Example 180

1-[4-(4-Chloro-1H-pyrazol-1-yl)-2-fluorophenyl]-5-methoxy-3-(1-phenyl-1H-pyrazol-5-yl)pyridazin-4 (1H)-one

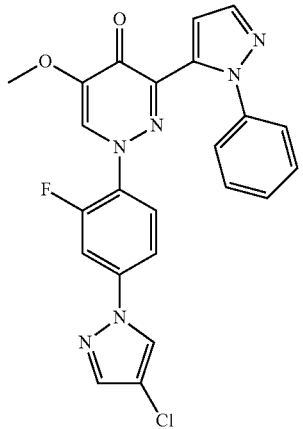 [SMILES: COc1cn(-c2ccc(-n3cc(Cl)cn3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (488 mg, 1.0 mmol), 4-chloro-1H-pyrazole (103 mg, 1.0 mmol), Cu$_2$O (14.3 mg, 0.1 mmol), salicylaldoxime (54.9 mg, 0.4 mmol), and Cs$_2$CO$_3$ (652 mg, 2.0 mmol) in CH$_3$CN (10 mL) was refluxed overnight under Ar atmosphere. After cooling to room temperature, the reaction mixture was poured into water and extracted with AcOEt. The extract was washed with brine, dried over MgSO$_4$, and concentrated under reduced pressure. The residue was subjected to basic silica gel column chromatography eluting with AcOEt followed by purification by preparative HPLC. Recrystallization from MeOH/H$_2$O gave the title compound (68.1 mg, 15% yield) as a pale yellow powder: mp 190-192° C.; $^1$H NMR (300 MHz, CDCl$_3$): δ ppm 3.92 (3H, s), 6.43 (1H, t, J=9.0 Hz), 7.23 (1H, ddd, J=1.1, 2.3, 9.0 Hz), 7.35 (1H, d, J=1.9 Hz), 7.36-7.48 (5H, m), 7.57 (1H, dd, J=2.6, 12.4 Hz), 7.68 (1H, s), 7.79 (1H, d, J=1.9 Hz), 7.82 (1H, d, J=2.3 Hz), 7.92 (1H, d, J=0.8 Hz). LC-MS (ESI) m/z 463 [M+H]$^+$. Anal. Calcd for $C_{23}H_{16}ClFN_6O_2$: C, 59.68; H, 3.48; N, 18.16. Found: C, 59.81; H, 3.50; N, 18.14.

Preparative HPLC was performed at the conditions described below.

Column: CHIRALPAK AS CC001 (50 mm ID×500 mL)

Column temp: 30° C.

Mobile phase: MeOH

Flow rate: 60 mL/min

Detector: UV 220 nm

Concentration: 111 mg/mL

Inject volume: 1 mL

Retention time: 18.8 min

Example 181

1-[5-(3,3-Difluoroazetidin-1-yl)-2-fluorophenyl]-5-methoxy-3-(1-phenyl-1H-pyrazol-5-yl)pyridazin-4(1H)-one

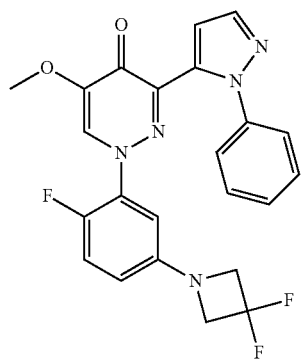 [SMILES: COc1cn(-c2cc(N3CC(F)(F)C3)ccc2F)nc(-c2ccnn2-c2ccccc2)c1=O]

A mixture of 1-(2-fluoro-5-iodophenyl)-5-methoxy-3-(1-phenyl-1H-pyrazol-5-yl)pyridazin-4(1H)-one (244 mg, 0.5 mmol), 3,3-difluoroazetidine hydrochloride (77.7 mg, 0.6 mmol), NaOtBu (125 mg, 1.3 mmol), Xantphos (46.3 mg, 0.08 mmol) and Pd$_2$(dba)$_3$ (18.3 mg, 0.02 mmol) in 1,4-dioxane (2.5 mL) was heated to 90° C. for 13 h under Ar. The mixture was diluted with saturated NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and recrystallized with EtOH/hexane to yield the title compound (92 mg, 41% yield) as a white solid: $^1$H NMR (DMSO-d$_6$, 300 MHz): δ ppm 3.77 (3H, s), 4.25 (4H, t, J=12.2 Hz), 6.48 (1H, dd, J=6.4, 3.0 Hz), 6.63-6.72 (1H, m), 6.90 (1H, d, J=1.5 Hz), 7.25-7.48 (6H, m), 7.79 (1H, d, J=1.9 Hz), 8.45 (1H, d, J=1.9 Hz). Anal. Calcd for $C_{23}H_{18}F_3N_5O_2$: C, 60.93; H, 4.00; N, 15.45. Found: C, 60.97; H, 3.94; N, 15.47.

Example 182

1-[2-Fluoro-5-(2-oxopyrrolidin-1-yl)phenyl]-5-methoxy-3-(1-phenyl-1H-pyrazol-5-yl)pyridazin-4(1H)-one

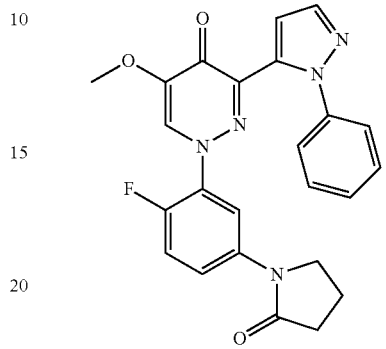

A mixture of 1-(2-fluoro-5-iodophenyl)-5-methoxy-3-(1-phenyl-1H-pyrazol-5-yl)pyridazin-4(1H)-one (244 mg, 0.5 mmol), pyrrolidin-2-one (0.0456 mL, 0.6 mmol), K$_3$PO$_4$ (212 mg, 1.0 mmol), trans-1,2-diaminocyclohexane (0.012 mL, 0.1 mmol) and CuI (9.5 mg, 0.05 mmol) in 1,4-dioxane (2 mL) was heated to reflux for 13 h under Ar. The mixture was diluted with saturated NaHCO$_3$ aqueous solution, extracted with AcOEt, dried over Na$_2$SO$_4$, filtered, concentrated in vacuo, purified by column chromatography on basic silica gel (hexane/AcOEt=50/50 to 0/100) and recrystallized with AcOEt/hexane to yield the title compound (126 mg, 57% yield) as a white solid: mp 171-174° C. $^1$H NMR (DMSO-d$_6$, 300 MHz): δ ppm 2.02-2.19 (2H, m), 2.47-2.58 (2H, m), 3.69-3.87 (5H, m), 6.92 (1H, d, J=1.9 Hz), 7.22-7.58 (7H, m), 7.74-7.89 (2H, m), 8.51 (1H, d, J=1.9 Hz). Anal. Calcd for $C_{24}H_{20}FN_5O_3$: C, 64.71; H, 4.53; N, 15.72. Found: C, 64.59; H, 4.45; N, 15.67.

Example 183

1-[2-Fluoro-5-(1H-pyrazol-1-yl)phenyl]-5-methoxy-3-(1-phenyl-1H-pyrazol-5-yl)pyridazin-4(1H)-one

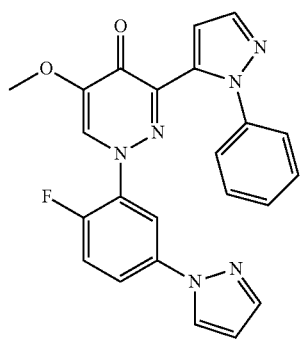 [SMILES: COc1cn(-c2cc(-n3cccn3)ccc2F)nc(-c2ccnn2-c2ccccc2)c1=O]

A mixture of 1-(2-fluoro-5-iodophenyl)-5-methoxy-3-(1-phenyl-1H-pyrazol-5-yl)pyridazin-4(1H)-one (244 mg, 0.5 mmol), pyrazole (34.0 mg, 0.5 mmol), 2-hydroxybenzaldehyde oxime (27.4 mg, 0.2 mmol), $Cu_2O$ (7.2 mg, 0.05 mmol) and $Cs_2CO_3$ (326 mg, 1.0 mmol) in acetonitrile (1 mL) was heated to reflux for 14 h under Ar. The mixture was diluted with saturated $NaHCO_3$ aqueous solution, extracted with AcOEt, dried over $Na_2SO_4$, filtered, concentrated in vacuo, purified by column chromatography on basic silica gel (hexane/AcOEt=50/50 to 0/100) and on silica gel (hexane/AcOEt=50/50 to 0/100) and recrystallized with AcOEt/hexane to yield the title compound (8.3 mg, 4% yield) as a white solid: mp 186-187° C. $^1H$ NMR (DMSO-$d_6$, 300 MHz): δ ppm 3.78 (3H, s), 6.59-6.66 (1H, m), 6.95 (1H, d, J=1.9 Hz), 7.17-7.27 (1H, m), 7.30-7.42 (4H, m), 7.56-7.67 (1H, m), 7.76-7.90 (3H, m), 7.93-8.02 (1H, m), 8.47 (1H, d, J=2.6 Hz), 8.59 (1H, d, J=1.9 Hz). Anal. Calcd for $C_{23}H_{17}FN_6O_2$: C, 64.48; H, 4.00; N, 19.62. Found: C, 64.21; H, 4.08; N, 19.42.

Example 184

1-[2-Fluoro-3-(2-oxopyrrolidin-1-yl)phenyl]-5-methoxy-3-(1-phenyl-1H-pyrazol-5-yl)pyridazin-4(1H)-one

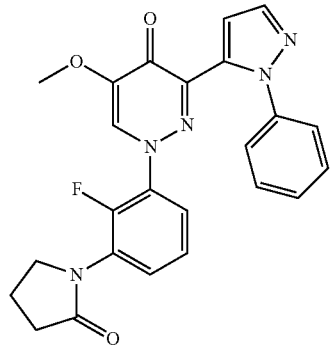 [SMILES: COc1cn(-c2cccc(N3CCCC3=O)c2F)nc(-c2ccnn2-c2ccccc2)c1=O]

A suspension of 1-(3-bromo-2-fluorophenyl)-5-methoxy-3-(1-phenyl-1H-pyrazol-5-yl)pyridazin-4(1H)-one (221 mg, 0.5 mmol), 2-pyrrolidinone (46 μL, 0.60 mmol), N,N'-dimethylethylenediamine (22 μL, 0.20 mmol), CuI (19 mg, 0.10 mmol), and $K_3PO_4$ (212 mg, 1.00 mmol) in 1,4-dioxane (2.0 mL) was stirred at 90° C. under Ar atmosphere. The reaction mixture was poured into 5% $NaHCO_3$ aqueous solution (20 mL) and extracted with AcOEt (20 mL×3). The combined organic phase was washed with brine (40 mL), dried with $MgSO_4$, and evaporated. The residue was purified by basic silica gel column chromatography (AcOEt/hexane=50%-100%) to give the title compound (89.4 mg, 40% yield) as an amorphous solid: $^1H$ NMR (300 MHz, $CDCl_3$): δ ppm 2.26 (2H, q, J=7.7 Hz), 2.59 (2H, t, J=8.1 Hz), 3.80 (2H, t, J=7.0 Hz), 3.89 (3H, s), 6.36 (1H, dd, J=15.5, 1.9 Hz), 7.03 (1H, t, J=8.3 Hz), 7.30 (1H, d, J=1.9 Hz), 7.34-7.49 (6H, m), 7.73-7.83 (2H, m). LC-MS (ESI) m/z 446 [M+H]$^+$. Anal. Calcd for $C_{24}H_{20}FN_5O_3$.$0.2H_2O$: C, 64.19; H, 4.58; N, 15.59. Found: C, 64.00; H, 4.51; N, 15.56.

Example 185

1-[2-Fluoro-3-(2-oxopiperidin-1-yl)phenyl]-5-methoxy-3-(1-phenyl-1H-pyrazol-5-yl)pyridazin-4(1H)-one

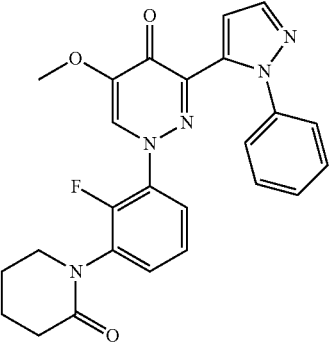 [SMILES: COc1cn(-c2cccc(N3CCCCC3=O)c2F)nc(-c2ccnn2-c2ccccc2)c1=O]

A suspension of 1-(3-bromo-2-fluorophenyl)-5-methoxy-3-(1-phenyl-1H-pyrazol-5-yl)pyridazin-4(1H)-one (221 mg, 0.500 mmol), 2-piperidone (59.5 mg, 0.600 mmol), N,N'-dimethylethylenediamine (0.022 mL, 0.200 mmol), CuI (19 mg, 0.10 mmol) and $K_3PO_4$ (212 mg, 1.00 mmol) in 1,4-dioxane (2.0 mL) was stirred at 90° C. under Ar atmosphere. The reaction mixture was poured into 5% $NaHCO_3$ aqueous solution (20 mL) and extracted with AcOEt (20 mL×3). The combined organic phase was washed with brine (40 mL), dried with $MgSO_4$, and evaporated. The residue was purified by basic silica gel column chromatography (AcOEt/hexane=50%-100%) to give the title compound (52.3 mg, 23% yield) as an amorphous solid: $^1H$ NMR (300 MHz, $CDCl_3$): δ ppm 1.97 (4H, t, J=3.4 Hz), 2.54-2.63 (2H, m), 3.56 (2H, brs), 3.88 (3H, s), 6.36 (1H, dd, J=15.5, 1.9 Hz), 7.03 (1H, dd, J=16.2, 1.5 Hz), 7.22 (1H, dd, J=14.7, 1.9 Hz), 7.29 (1H, d, J=2.3 Hz), 7.35-7.44 (2H, m), 7.40 (3H, d, J=4.5 Hz), 7.78 (1H, d, J=1.9 Hz), 7.82 (1H, d, J=2.6 Hz). LC-MS (ESI) m/z 460 [M+H]$^+$. Anal. Calcd for $C_{25}H_{22}FN_5O_3$.$0.5H_2O$: C, 64.34; H, 4.93; N, 15.00. Found: C, 64.12; H, 4.73; N, 15.13.

Example 186

1-[2-Fluoro-4-(4-hydroxy-4-methylpiperidin-1-yl) phenyl]-5-methoxy-3-(1-phenyl-1H-pyrazol-5-yl) pyridazin-4(1H)-one

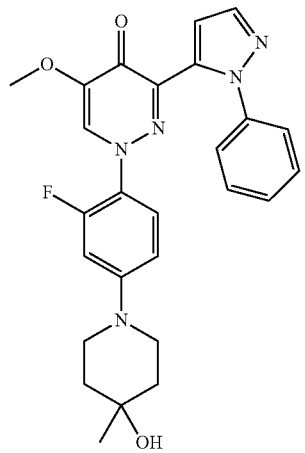 [SMILES: COc1cn(-c2ccc(N3CCC(C)(O)CC3)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.500 mmol), 4-methylpiperidin-4-ol hydrochloride (91 mg, 0.60 mmol), sodium tert-butoxide (187 mg, 1.95 mmol), Xantphos (23 mg, 0.040 mmol), and tris(dibenzylideneacetone)dipalladium(0) (9 mg, 0.010 mmol) in 1,4-dioxane (2.5 mL) was stirred at 90° C. under Ar atmosphere. The reaction mixture was poured into 5% NaHCO$_3$ aqueous solution (20 mL) and extracted with AcOEt (20 mL×3). The combined organic phase was washed with brine (40 mL), dried with MgSO$_4$, and evaporated. The residue was purified by basic silica gel column chromatography (MeOH/AcOEt=0%-20%). The residue was recrystallized from AcOEt/hexane to give the title compound (76.2 mg, 32% yield) as a pale yellow solid: $^1$H NMR (300 MHz, DMSO-d$_6$): δ ppm 1.14 (3H, s), 1.39-1.60 (4H, m), 3.20 (2H, ddd, J=13.2, 8.7, 5.3 Hz), 3.40-3.52 (2H, m), 3.76 (3H, s), 4.36 (1H, s), 6.70 (1H, dd, J=9.0, 2.6 Hz), 6.91 (2H, d, J=1.9 Hz), 6.79-6.94 (1H, m), 7.32 (1H, d, J=1.9 Hz), 7.29 (1H, s), 7.35-7.47 (3H, m), 7.77 (1H, d, J=1.9 Hz), 8.37 (1H, d, J=1.9 Hz). LC-MS (ESI) m/z 476 [M+H]$^+$. Anal. Calcd for C$_{26}$H$_{26}$FN$_5$O$_3$: C, 65.67; H, 5.51; N, 14.73. Found: C, 65.53; H, 5.50; N, 14.66.

Example 187

1-(4-Bromo-2,5-difluorophenyl)-5-methoxy-3-(1-phenyl-1H-pyrazol-5-yl)pyridazin-4(1H)-one

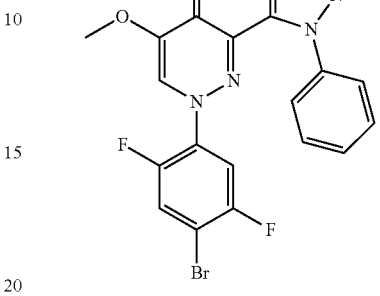

A mixture of 3-acetyl-1-(4-bromo-2,5-difluorophenyl)-5-methoxypyridazin-4(1H)-one (3.57 g, 10 mmol) and N,N-dimethylformamide dimethyl acetal (16 mL) was stirred at 100° C. for 5 h. After cooling to room temperature, the reaction mixture was concentrated under reduced pressure. The residue was dissolved in AcOH (20 mL) and added phenylhydrazine (2.0 mL, 20 mmol). This mixture was stirred at 130° C. for 3 h. After cooling to room temperature, the reaction mixture was concentrated under reduced pressure. The residue was purified by silica gel column chromatography eluting with hexane/AcOEt (1/0 to 0/1) and recrystallized from $^i$Pr$_2$O/AcOEt to give the title compound (1.05 g, 23% yield) as a pale yellow solid: mp 211-213° C.; $^1$H NMR (300 MHz, DMSO-d$_6$): δ ppm 3.77 (3H, s), 7.02 (1H, d, J=1.9 Hz), 7.09 (1H, dd, J=8.9, 6.6 Hz), 7.22-7.62 (5H, m), 7.80 (1H, d, J=1.9 Hz), 8.07 (1H, dd, J=10.2, 6.0 Hz), 8.49 (1H, d, J=2.3 Hz). LC-MS (ESI) m/z 460 [M+H]$^+$. Anal. Calcd for C$_{20}$H$_{13}$BrF$_2$N$_4$O$_2$: C, 52.31; H, 2.85; N, 12.20. Found: C, 52.51; H, 2.95; N, 12.20.

Example 188

1-[2,5-Difluoro-4-(2-oxopyrrolidin-1-yl)phenyl]-5-methoxy-3-(1-phenyl-1H-pyrazol-5-yl)pyridazin-4(1H)-one

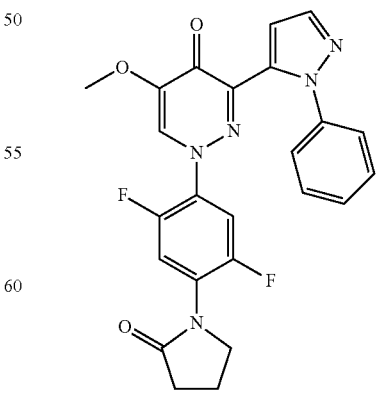

A suspension of 1-(4-bromo-2,5-difluorophenyl)-5-methoxy-3-(1-phenyl-1H-pyrazol-5-yl)pyridazin-4(1H)-one (200 mg, 0.44 mmol), pyrrolidin-2-one (0.040 mL, 0.53 mmol), CuI (17 mg, 0.088 mmol), N,N'-dimethylethane-1,2-diamine (0.019 mL, 0.18 mmol), and K$_3$PO$_4$ (187 mg, 0.88 mmol) in 1,4-dioxane (4.0 mL) was stirred at 80° C. for 14 h under N$_2$ atmosphere. After cooling to rt, the reaction mixture was purified by silica gel column chromatography eluting with hexane/AcOEt (1/0 to 0/1) then AcOEt/MeOH (10/1) and recrystallized from AcOEt to give the title compound (12 mg, 6% yield) as a pale brown solid: $^1$H NMR (300 MHz, DMSO-d$_6$): δ ppm 2.06-2.23 (2H, m), 3.29 (3H, s), 3.69-3.91 (4H, m), 7.27-7.42 (2H, m), 7.43-7.56 (2H, m), 7.78 (1H, dd, J=11.3, 6.4 Hz), 7.85-7.91 (2H, m), 7.95 (1H, dd, J=10.5, 7.2 Hz), 8.57 (1H, d, J=2.3 Hz), 8.60 (1H, d, J=1.5 Hz). LC-MS (ESI) m/z 464 [M+H]$^+$.

Example 189

1-[4-(4,4-Dimethyl-2-oxopyrrolidin-1-yl)-2-fluorophenyl]-5-methoxy-3-(1-phenyl-1H-pyrazol-5-yl)pyridazin-4(1H)-one

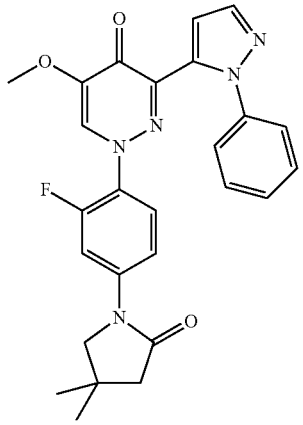 [SMILES: COc1cn(-c2ccc(N3CC(C)(C)CC3=O)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (244 mg, 0.500 mmol), 4,4-dimethyl-2-pyrrolidinone (67.9 mg, 0.600 mmol), trans-1,2-diaminocyclohexane (0.012 mL, 0.10 mmol), CuI (9.5 mg, 0.050 mmol), and K$_3$PO$_4$ (212 mg, 1.00 mmol) in 1,4-dioxane (2.0 mL) was stirred at 110° C. under Ar atmosphere. The reaction mixture was poured into 5% NaHCO$_3$ aqueous solution (20 mL) and extracted with AcOEt (20 mL×3). The combined organic phase was washed with brine (40 mL), dried with MgSO$_4$, and evaporated. The residue was purified by basic silica gel column chromatography (AcOEt/hexane=50%-100%) and silica gel column chromatography (AcOEt/hexane=50%-100%) to give the title compound (142.8 mg, 60% yield): $^1$H NMR (300 MHz, DMSO-d$_6$): δ ppm 1.16 (6H, s), 2.39-2.44 (2H, m), 3.58-3.63 (2H, m), 3.77 (3H, s), 6.94-6.98 (1H, m), 6.98-7.08 (1H, m), 7.29-7.35 (2H, m), 7.35-7.49 (4H, m), 7.68-7.88 (2H, m), 8.37-8.55 (1H, m). LC-MS (ESI) m/z 474 [M+H]$^+$. Anal. Calcd for C$_{26}$H$_{24}$FN$_5$O$_3$.0.2H$_2$O: C, 65.45; H, 5.16; N, 14.68. Found: C, 65.17; H, 5.16; N, 14.55.

Example 190

1-[4-(5,5-Dimethyl-2-oxo-1,3-oxazolidin-3-yl)-2-fluorophenyl]-5-methoxy-3-(1-phenyl-1H-pyrazol-5-yl)pyridazin-4(1H)-one

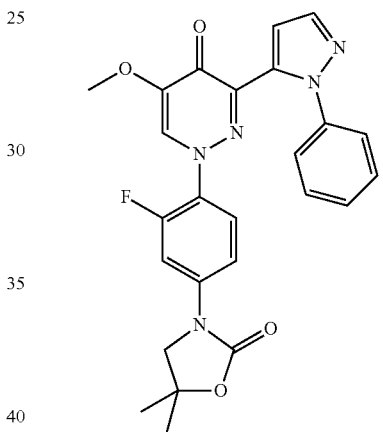

A suspension of 1-(2-fluoro-4-iodophenyl)-5-methoxy-3-(1-phenyl-1H-pyrazol-5-yl)pyridazin-4(1H)-one (244 mg, 0.500 mmol), 5,5-dimethyl-1,3-oxazolidin-2-one (69.1 mg, 0.600 mmol), trans-1,2-diaminocyclohexane (0.012 mL, 0.100 mmol), CuI (9.5 mg, 0.050 mmol), and K$_3$PO$_4$ (212 mg, 1.00 mmol) in 1,4-dioxane (2.0 mL) was stirred at 110° C. under Ar atmosphere. The reaction mixture was poured into 5% NaHCO$_3$ aqueous solution (20 mL) and extracted with AcOEt (20 mL×3). The combined organic phase was washed with brine (40 mL), dried with MgSO$_4$, and evaporated. The residue was purified by basic silica gel column chromatography (MeOH/AcOEt=0%-10%) to give the title compound (157.4 mg, 66% yield): $^1$H NMR (300 MHz, DMSO-d$_6$): δ ppm 1.49 (6H, s), 3.78 (3H, s), 3.89 (2H, s), 6.97 (1H, d, J=1.9 Hz), 7.05 (1H, t, J=9.0 Hz), 7.31 (1H, d, J=8.7 Hz), 7.31 (1H, t, J=1.7 Hz), 7.33 (1H, s), 7.37-7.48 (3H, m), 7.68 (1H, dd, J=13.4, 2.5 Hz), 7.79 (1H, d, J=1.9 Hz), 8.46 (1H, d, J=2.3 Hz). LC-MS (ESI) m/z 476 [M+H]$^+$. Anal. Calcd for C$_{25}$H$_{22}$FN$_5$O$_4$: C, 63.15; H, 4.66; N, 14.73. Found: C, 63.09; H, 4.70; N, 14.85.

Example 191

6-{3-Fluoro-4-[5-methoxy-4-oxo-3-(1-phenyl-1H-pyrazol-5-yl)pyridazin-1(4H)-yl]phenyl}-4-oxa-6-azaspiro[2.4]heptan-5-one

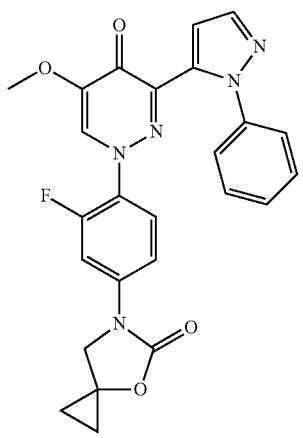 [SMILES: COc1cn(-c2ccc(N3CC4(CC4)OC3=O)cc2F)nc(-c2ccnn2-c2ccccc2)c1=O]

A suspension of 1-(2-fluoro-4-iodophenyl)-5-methoxy-3-(1-phenyl-1H-pyrazol-5-yl)pyridazin-4(1H)-one (0.24 g, 0.50 mmol), 4-oxa-6-azaspiro[2.4]heptan-5-one (0.068 g, 0.60 mmol), trans-1,2-diaminocyclohexane (0.024 mL, 0.20 mmol), CuI (0.019 g, 0.10 mmol), and $K_3PO_4$ (0.21 g, 1.0 mmol) in 1,4-dioxane (3 mL) was stirred at 110° C. under Ar atmosphere for 2 h. The mixture was diluted with AcOEt and filtered through a basic-silica gel pad, and then the silica gel was washed with AcOEt. The filtrate was concentrated under reduced pressure. The residue was chromatographed on basic silica gel (0/100-3/97 MeOH/AcOEt) to give white crystals. The crystals were recrystallized from AcOEt/hexane to give the title compound (0.17 g, 72% yield) as a white solid: mp 200-201° C.; $^1$H NMR (300 MHz, CDCl$_3$): δ ppm 0.85-0.92 (2H, m), 1.33-1.40 (2H, m), 3.90 (3H, s), 4.08 (2H, s), 6.39 (1H, t, J=8.9 Hz), 6.96 (1H, ddd, J=8.9, 2.5, 1.4 Hz), 7.30 (1H, d, J=1.9 Hz), 7.35-7.45 (5H, m), 7.68 (1H, dd, J=13.7, 2.5 Hz), 7.77-7.79 (2H, m). LC-MS (ESI) m/z 474 [M+H]$^+$. Anal. Calcd. for $C_{25}H_{20}FN_5O_4 \cdot H_2O$: C, 62.94; H, 4.31; N, 14.68. Found: C, 62.83; H, 4.42; N, 14.77.

Example 192

5-Methoxy-1-[2-methoxy-4-(1H-pyrazol-1-yl)phenyl]-3-(1-phenyl-1H-pyrazol-5-yl)pyridazin-4(1H)-one

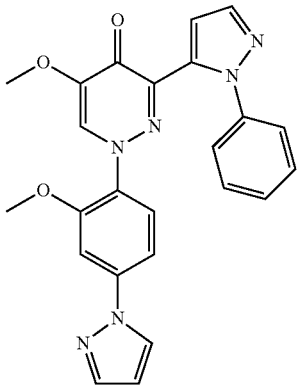 [SMILES: COc1cc(-n2cccn2)ccc1-n1cc(OC)c(=O)c(-c2ccnn2-c2ccccc2)n1]

A mixture of 3-acetyl-5-methoxy-1-[2-methoxy-4-(1H-pyrazol-1-yl)phenyl]pyridazin-4(1H)-one (1.50 g, 4.41 mmol), N,N-dimethylformamide dimethyl acetal (15 mL), and MeOH (15 mL) was refluxed for 3 h. After cooling to room temperature, the reaction mixture was concentrated under reduced pressure.

A solution of the residue and phenylhydrazine (0.868 mL, 8.82 mmol) in AcOH (15 mL) was refluxed for 2 h. After cooling to room temperature, the reaction mixture was poured into 1 M HCl aqueous solution and extracted with AcOEt. The extract was washed with 1 M NaOH aqueous solution and brine, dried over MgSO$_4$, and concentrated under reduced pressure. The residue was purified by basic silica gel column chromatography eluting with AcOEt and crystallized from hexane/AcOEt to give the title compound (0.921 g, 47% yield) as an off-white solid: mp 133-135° C.; $^1$H NMR (300 MHz, CDCl$_3$): δ ppm 3.90 (3H, s), 3.93 (3H, s), 6.39 (1H, d, J=8.7 Hz), 6.52 (1H, dd, J=1.9, 2.6 Hz), 6.99 (1H, dd, J=2.3, 8.7 Hz), 7.26 (1H, d, J=1.9 Hz), 7.36-7.46 (5H, m), 7.49 (1H, d, J=2.3 Hz), 7.75 (1H, d, J=1.9 Hz), 7.77 (1H, d, J=1.9 Hz), 7.86 (1H, s), 7.94 (1H, d, J=2.6 Hz). LC-MS (ESI) m/z 441 [M+H]$^+$. Anal. Calcd for $C_{24}H_{20}N_6O_3$: C, 65.45; H, 4.58; N, 19.08. Found: C, 65.37; H, 4.65; N, 18.88.

Example 193

6-Methoxy-3-(1-phenyl-1H-pyrazol-5-yl)-1-[3-(trifluoromethyl)phenyl]pyridazin-4(1H)-one

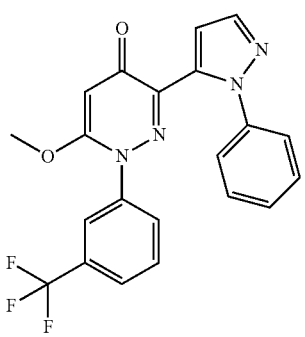 [SMILES: COc1cc(=O)c(-c2ccnn2-c2ccccc2)nn1-c1cccc(C(F)(F)F)c1]

To a solution 6-hydroxy-3-(1-phenyl-1H-pyrazol-5-yl)-1-[3-(trifluoromethyl)phenyl]pyridazin-4(1H)-one (0.23 g, 0.58 mmol) in MeOH (10 mL) was added dropwise trimethylsilyldiazomethane (2 M solution in diethylether, 8.0 mL, 16.0 mmol) at 0° C., and the mixture was stirred at 0° C. for 1 h. The mixture was concentrated under reduced pressure. The residue was purified by silica gel column chromatography eluting with AcOEt/hexane (20/80-100/0) and recrystallized from AcOEt/hexane to give the title compound (0.023 g, 10% yield) as white crystals: mp 139-141° C.; $^1$H NMR (300 MHz, CDCl$_3$): δ ppm 3.90 (3H, s), 6.14 (1H, s), 6.97-7.02 (1H, m), 7.13 (1H, s), 7.22 (1H, d, J=1.9 Hz), 7.31-7.44 (6H, m), 7.56-7.61 (1H, m), 7.76 (1H, d, J=1.9 Hz). LC-MS (ESI) m/z 413 [M+H]$^+$. Anal. Calcd for C$_{21}$H$_{15}$F$_3$N$_4$O$_2$: C, 61.17; H, 3.67; N, 13.59. Found: C, 61.19; H, 3.71; N, 13.69.

Example 194

1-(2,3-Difluoro-4-morpholin-4-ylphenyl)-5-methoxy-3-(1-phenyl-1H-pyrazol-5-yl)pyridazin-4(1H)-one

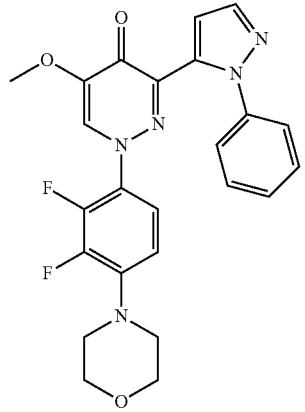 [SMILES: COc1cn(-c2ccc(N3CCOCC3)c(F)c2F)nc(-c2ccnn2-c2ccccc2)c1=O]

A mixture of 3-acetyl-1-(2,3-difluoro-4-morpholin-4-ylphenyl)-5-methoxypyridazin-4(1H)-one (200 mg, 0.55 mmol) and N,N-dimethylformamide dimethyl acetal (2.0 mL) was stirred at 120° C. for 2.5 h. After cooling to room temperature, the reaction mixture was concentrated under reduced pressure. The residue was dissolved in AcOH (2.0 mL) and phenylhydrazine (0.11 mL, 1.1 mmol) was added. This mixture was stirred at room temperature for 1 h, and then the reaction mixture was concentrated under reduced pressure. The residue was purified by silica gel column chromatography eluting with AcOEt/MeOH (1/0 to 10/1) and recrystallized from $^i$Pr$_2$O/AcOEt to give the title compound (141 mg, 55% yield) as a yellow solid: mp 182-183° C.; $^1$H NMR (300 MHz, DMSO-d$_6$): δ ppm 2.98-3.22 (4H, m), 3.62-3.87 (7H, m), 6.78-6.92 (2H, m), 6.95 (1H, d, J=1.9 Hz), 7.21-7.54 (5H, m), 7.78 (1H, d, J=1.9 Hz), 8.48 (1H, d, J=1.9 Hz). LC-MS (ESI) m/z 466 [M+H]$^+$. Anal. Calcd for C$_{24}$H$_{21}$F$_2$N$_5$O$_3$: C, 61.93; H, 4.55; N, 15.05. Found: C, 61.90; H, 4.58; N, 14.87.

Example 195

1-(2,5-Difluoro-4-morpholin-4-ylphenyl)-5-methoxy-3-(1-phenyl-1H-pyrazol-5-yl)pyridazin-4(1H)-one

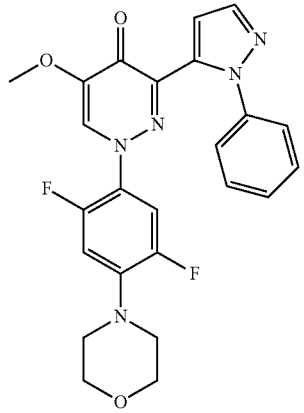 [SMILES: COc1cn(-c2cc(F)c(N3CCOCC3)cc2F)nc(-c2ccnn2-c2ccccc2)c1=O]

A mixture of 3-acetyl-1-(2,5-difluoro-4-morpholin-4-ylphenyl)-5-methoxypyridazin-4(1H)-one (340 mg, 0.93 mmol) and N,N-dimethylformamide dimethyl acetal (3.4 mL) was stirred at 120° C. for 2.5 h. After cooling to room temperature, the reaction mixture was concentrated under reduced pressure. The residue was dissolved in AcOH (3.4 mL) and phenylhydrazine (0.18 mL, 1.9 mmol) was added. This mixture was stirred at room temperature for 1 h. The reaction mixture was diluted with AcOEt, and washed with saturated NaHCO$_3$ aqueous solution and brine. The organic layer was dried over MgSO$_4$, and concentrated under reduced pressure. The residue was recrystallized from AcOEt/MeOH to give the title compound (156 mg, 36% yield) as a pale orange solid: mp 211-212° C.; $^1$H NMR (300 MHz, DMSO-d$_6$): δ ppm 2.99-3.15 (4H, m), 3.60-3.88 (7H, m), 6.85 (1H, dd, J=12.8, 7.2 Hz), 6.99 (1H, d, J=2.3 Hz), 7.09 (1H, dd, J=12.8, 7.6 Hz), 7.24-7.50 (5H, m), 7.79 (1H, d, J=1.9 Hz), 8.43 (1H, d, J=2.3 Hz). LC-MS (ESI) m/z 466 [M+H]$^+$. Anal. Calcd for C$_{24}$H$_{21}$F$_2$N$_5$O$_3$·0.5H$_2$O: C, 60.75; H, 4.67; N, 14.76. Found: C, 60.98; H, 4.71; N, 14.63.

Test Example 1

PDE Enzyme Inhibition

Human PDE10A enzyme was generated from Sf9 or COS-7 cells transfected with the full-length gene. Cloned enzyme was extracted from homogenized cell pellets. The extracted enzyme from Sf9 cells was partially purified using His-tag affinity column. The enzyme was stored at −70° C. until use. PDE activity was measured using a SPA (Scintillation Proximity Assay) (GE Healthcare). To evaluate the inhibitory activity, 10 μL of serial diluted compounds were incubated with 20 μL of PDE enzyme in assay buffer (50 mM HEPES-NaOH, 8.3 mM MgCl$_2$, 1.7 mM EGTA, 0.1% BSA (pH 7.4)) for 30 min. at room temperature. Final concentration of DMSO in the assay was 1 percent as compounds were tested in duplicate in 96-well half-area plates (Corning). To start the reaction, 10 μL of substrate [3H] cGMP (25 or 50 nM; enclosed in SPA kits from GE Healthcare or purchased from PerkinElmer, respectively) was added for a final assay volume of 40 μL. After 60 min incubation at room temperature, yttrium SPA beads containing Zinc sulphate were added (20 μL at 6 mg/mL) to terminate the PDE reaction. After being settled for 60 min., assay plates were counted in a scintillation counter (PerkinElmer) to allow calculation of inhibition rate and $IC_{50}$. Inhibition rate was calculated on the basis of 0% control wells with DMSO and 100% control wells without enzyme. The results are shown in Tables 1 and 2.

TABLE 1

| Example No. | $IC_{50}$ | Percent inhibition (1 μM) |
|---|---|---|
| 10 | B | 98 |
| 13 | B | 96 |
| 15 | B | 97 |
| 16 | B | 97 |
| 17 | B | 97 |
| 23 | A | 102 |
| 26 | B | 97 |
| 30 | B | 87 (at 0.1 μM) |
| 32 | B | 89 |
| 36 | A | 90 (at 0.1 μM) |
| 39 | A | 98 |
| 46 | B | 97 |
| 48 | A | 100 |
| 49 | A | 98 |
| 52 | A | 99 |
| 54 | A | 100 |
| 57 | A | 101 |
| 59 | B | 96 |
| 64 | B | 94 |

A: less than 10 nM
B: 10-200 nM

TABLE 2

| Example No. | $IC_{50}$ | Percent inhibition (0.1 μM) |
|---|---|---|
| 102 | A | 103 |
| 103 | A | 99 |
| 104 | A | 99 |
| 106 | A | 100 |
| 107 | A | 104 |
| 108 | A | 103 |
| 109 | A | 99 |
| 111 | A | 97 |
| 113 | A | 99 |
| 114 | A | 102 |
| 116 | A | 99 |
| 119 | A | 100 |
| 120 | A | 100 |
| 123 | A | 99 |
| 124 | A | 97 |
| 163 | A | 101 |
| 164 | A | 101 |
| 178 | A | 92 |
| 179 | A | 96 |
| 180 | A | 96 |
| 186 | A | 100 |
| 189 | A | 100 |
| 190 | A | 100 |
| 192 | A | 101 |

A: less than 10 nM
B: 10-200 nM

Test Example 2

Animals

Male ICR mice were supplied by CLEA Japan, Inc (Japan). After arrival to the vivarium, animals were allowed a minimum of 1 week for acclimation. They were housed under a 12:12-h light/dark cycle in a temperature- and humidity-controlled laboratory and allowed food and water ad libitum. The care and use of the animals and the experimental protocols used in this research were approved by the Experimental Animal Care and Use Committee of Takeda Pharmaceutical Company, Ltd (Osaka, Japan).

Drug Administration

The compounds were suspended in 0.5% methylcellulose in saline or distilled water, and administered by intraperitoneally (i.p.) or orally (p.o.), respectively. Methamphetamine (Dainippon Sumitomo Pharma Co., Ltd.) and MK-801 (Sigma-Aldrich, St Louis, Mo.) were dissolved in saline, and administered subcutaneously (s.c.). All drugs were dosed in a volume of 20 mL/kg body weight for mice.

Measurement of Striatal Tissue Cyclic Nucleotides

Male ICR mice were sacrificed by focused microwave irradiation of the brain at 30 min after administration of the compound. Striatum were isolated and homogenized in 0.5 N HCl followed by centrifugation. Supernatant concentrations of cyclic nucleotides were measured using enzyme immunoassay kits (Cayman Chemical, Ann Arbor, Mich.). All data were represented as means plus the standard errors of the means (n=5-7) and analyzed using a williams' test with significance set at $\#P<0.025$.

Inhibition of Methamphetamine (MAP)- or MK-801-Induced Hyperlocomotion

The widely used animal models of psychosis have been the measurement of the extent of hyperlocomotion induced by psychostimulants (e.g., amphetamine, cocaine, methamphetamine, MK-801 and phencyclidine) in rodents (Psychopharmacology 1999, vol. 145: 237-250). The compounds were tested for its ability to antagonize either MAP- or MK-801-induced hyperlocomotion in mice. Male ICR mice were habituated in the locomotor chambers with infrared sensors (BrainScienceIdea Co., Ltd. Japan) to the experiment. After the habituation, animals were treated with either vehicle or the compounds (3-100 mg/kg, i.p. or 1 mg/kg, p.o.), and MK-801 (0.3 mg/kg, s.c.) or MAP (2 mg/kg, s.c.) was administrated 30 or 60 min after i.p. or p.o., respectively. Locomotion activities were measured, and accumulated counts (30 or 60 min before and 90 min after administration of stimulants) were calculated in each treatment group. All data were represented as means plus the standard errors of the means (n=5-8) and analyzed using a williams' test with significance set at $\#P<0.025$ or Dunnett's t-test with significance set at $*P<0.025$.

Improvement of MK-801-Induced Prepulse Inhibition (PPI) Deficits.

PPI is a measure of sensorimotor gating and is one of a few neuropsychological measures in which humans and rodents can be evaluated in a similar fashion (Psychopharmacology (Berl) 2001, vol. 156: 117-154). We evaluated whether compound could reverse PPI deficits induced by MK-801 using male ICR mice. Compounds and MK-801 (0.3 mg/kg, s.c.) were administered 30 min and 20 min, respectively, before testing. Experiments employed eight SR-LAB acoustic startle chambers (San Diego Instruments, San Diego, Calif.), each consisting of a clear, Plexiglas cylinder mounted on a platform and housed in ventilated, sound-attenuating external chambers. Placement of mice inside the cylinders allowed the whole-body startle responses induced by the acoustic stimuli to be measured via the transduction of movement into analog signals by a piezoelectric unit attached to the platform. A loudspeaker inside each chamber provided continuous background noise and the various acoustic stimuli. Test sessions consisted of placement of individual animals into the startle chambers and initiation of the background noise (70 dB). After a 5-min acclimation period, each subject was presented with 54 trials with variable inter-trial intervals (7-23 sec). The trials consisted of the following three types: 1) a pulse only trial of 118 dB presented for 40 ms during which time the startle response was recorded for 40 ms beginning with the onset of the 118 dB, 2) two prepulse trial types consisting of a 118 dB presented for 40 ms which was preceded 100 ms earlier by a 20 ms burst of 76 or 82 dB during which the startle response was recorded for 40 ms beginning with the onset of the 118 dB, and 3) a no stimulus trial in which only background noise was present. Percent of PPI was calculated separately for each of the 2 prepulse dB levels using the following traditional formula: [((average maximum startle on pulse only trials−average maximum startle on prepulse trials)/average maximum startle on pulse only trials)×100]. All data were represented as means plus the standard errors of the means (n=8-11) and dose-dependency was analyzed using a williams' test with significance set at #P<0.025. *P<0.05, Student's t-test as compared to control group. $P<0.05, Student's t-test as compared to MK-801-treated group. Results are shown in FIG. 1 to FIG. 4.

Figure 1B:
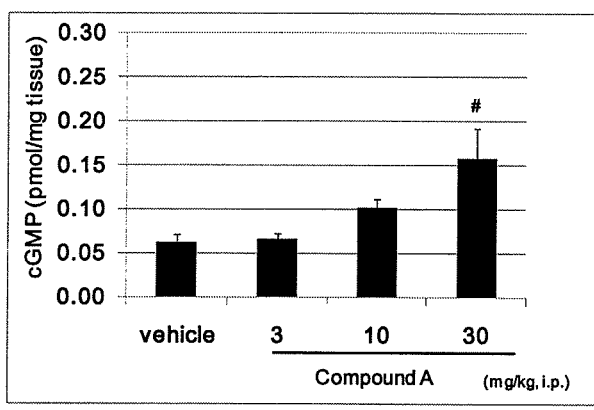

The graphs of FIG. 1 shows dose-dependent elevation of cAMP (FIG. 1A) and cGMP (FIG. 1B) contents in the mouse striatum by compound A. Thirty min after administration of the compound A, striatum was isolated from mice and then cAMP and cGMP contents were measured using EIA kits.

Figure 2A:
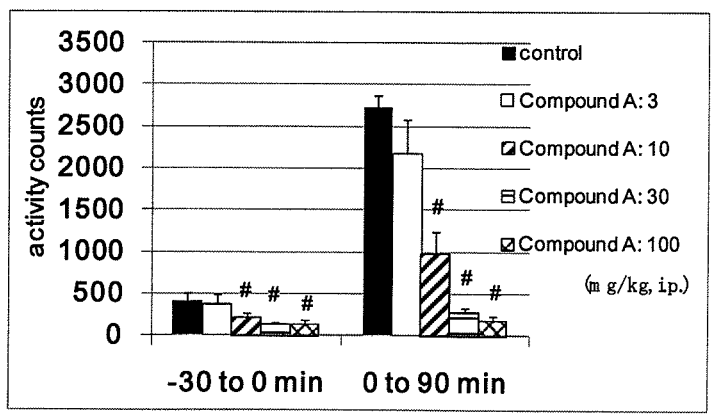
FIG. 2. Graphs showing dose-dependent inhibition of methamphetamine (MAP)- or MK-801-induced hyperlocomotion by compound A. The compound A decreased spontaneous locomotion (−30-0 min). All data were represented as means plus the standard errors of the means (n=5-8) and analyzed using a williams' test with significance set at #P<0.025. The phrase (mg/kg, i.p.) means (milligram per kilogram, intraperitoneal treatment).
Figure 2B:
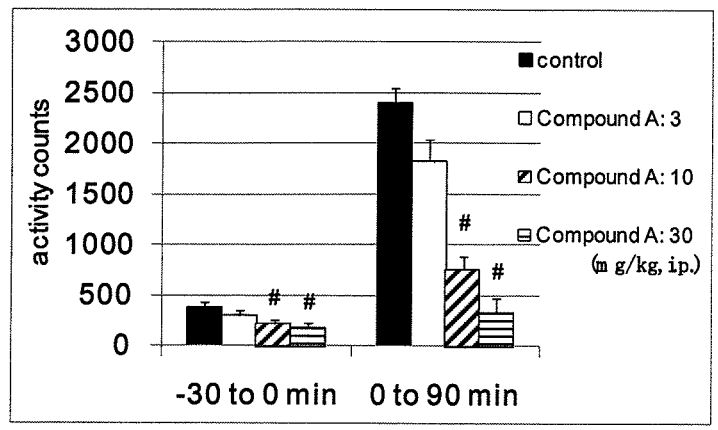

The graphs of FIG. 2 shows dose-dependent inhibition of methamphetamine (MAP)- or MK-801-induced hyperlocomotion by compound A. The compound A decreased spontaneous locomotion (−30-0 min). By administered 30 min before MAP (FIG. 2A) or MK-801 (FIG. 2B) treatment, compound A produced a dose-dependent inhibition of stimulant-induced hyperlocomotion (0-90 min).

Figure 3:
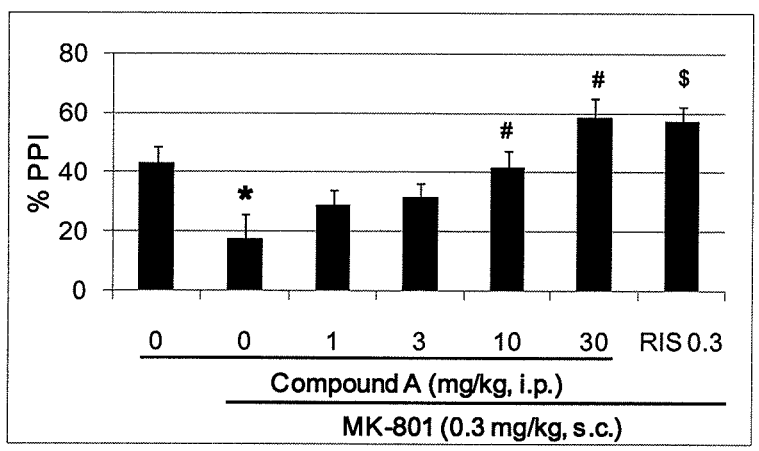
FIG. 3. A graph showing reversal of MK-801-induced PPI deficits at 82 dB prepulse by compound A. All data were represented as means plus the standard errors of the means (n=8-11) and dose-dependency was analyzed using a williams' test with significance set at #P<0.025. *P<0.05, Student's t-test as compared to control group. $P<0.05, Student's t-test as compared to MK-801-treated group. The phrase (mg/kg, i.p.) means (milligram per kilogram, intraperitoneal treatment).

The graph of FIG. 3 shows reversal of MK-801-induced PPI deficits at 82 dB prepulse by compound A. By intraperitoneally administered 30 min before testing, compounds produced a dose-dependent reversal of MK-801-induced PPI deficits. Risperidone (RIS, 0.3 mg/kg) also significantly reversed MK-801-induced PPI deficits.

Figure 4:
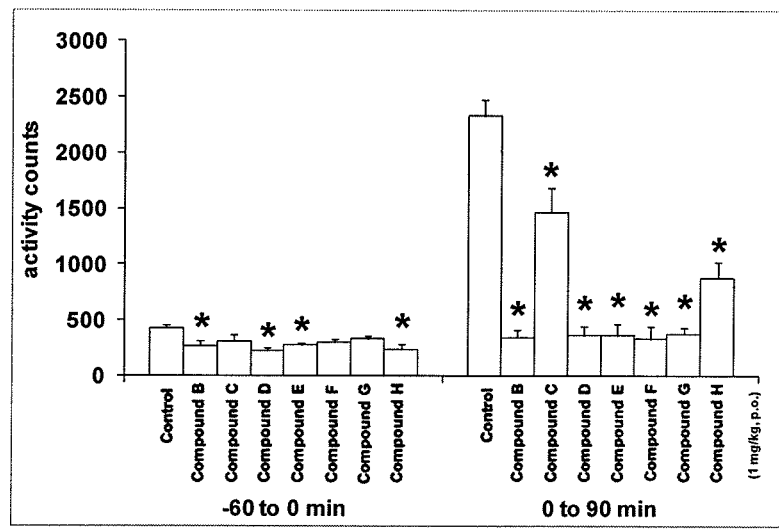
FIG. 4 A graph showing inhibition of MK-801-induced hyperlocomotion by compounds in mice. All data were represented as means plus the standard errors of the means (n=5-8) and analyzed using Dunnett's t-test with significance set at *P<0.025.

The graph of FIG. 4. shows inhibition of MK-801-induced hyperlocomotion by compounds in mice. By orally administered 60 min before MK-801 (0.3 mg/kg, s.c.) treatment, compounds produced significant inhibition of stimulant-induced hyperlocomotion (0-90 min).

Compounds in figures (FIG. 1 to FIG. 4) correspond to the following example.

Compound A (Example 10)
Compound B (Example 104)
Compound C (Example 108)
Compound D (Example 120)
Compound E (Example 163)
Compound F (Example 164)
Compound G (Example 180)
Compound H (Example 192)

Formulation Example 1

| | |
|---|---|
| (1) Compound of the Example 1 | 10.0 g |
| (2) Lactose | 70.0 g |
| (3) Cornstarch | 50.0 g |
| (4) Soluble starch | 7.0 g |
| (5) Magnesium stearate | 3.0 g |

After 10.0 g of the compound in Embodiment 1 and 3.0 g of magnesium stearate were granulated in 70 ml aqueous solution of soluble starch (7.0 g as soluble starch) and then dried, the resulting mixture was mixed with 70.0 g of lactose and 50.0 g of cornstarch (lactose, cornstarch, soluble starch and magnesium stearate were all products in compliance with Japanese Pharmacopoeia $14^{th}$ Edition). The mixture was compressed to obtain a tablet.

INDUSTRIAL APPLICABILITY

The medicine of the present invention can be used as a medicine for preventing and treating psychiatric disorders such as schizophrenia.

CITATION LIST

Patent Literature

Patent Literature 1
WO2006072828
Patent Literature 2
WO2008001182

What is claimed is:
1. 1-[4-(4-chloro-1H-pyrazol-1-yl)-2-fluorophenyl]-5-methoxy-3-(1-phenyl-1H-pyrazol-5-yl)pyridazin-4(1H)-one, or a salt thereof.

* * * * *